US012012411B2

(12) United States Patent
Bardiot et al.

(10) Patent No.: US 12,012,411 B2
(45) Date of Patent: Jun. 18, 2024

(54) VIRAL REPLICATION INHIBITORS

(71) Applicant: Katholieke Universiteit Leuven, Leuven (BE)

(72) Inventors: Dorothée Bardiot, Leuven (BE); Gunter Carlens, Leuven (BE); Kai Dallmeier, Leuven (BE); Suzanne Kaptein, Leuven (BE); Michael McNaughton, Leuven (BE); Arnaud Marchand, Leuven (BE); Johan Neyts, Leuven (BE); Wim Smets, Leuven (BE); Mohamed Koukni, Leuven (BE)

(73) Assignee: Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 17/538,532

(22) Filed: Nov. 30, 2021

(65) Prior Publication Data

US 2022/0106321 A1 Apr. 7, 2022

Related U.S. Application Data

(60) Continuation of application No. 16/515,272, filed on Jul. 18, 2019, now Pat. No. 11,279,704, which is a
(Continued)

(30) Foreign Application Priority Data

Sep. 26, 2011 (GB) ..................................... 1116559

(51) Int. Cl.
C07D 487/04 (2006.01)
C07D 209/14 (2006.01)
C07D 401/06 (2006.01)
C07D 401/08 (2006.01)
C07D 401/12 (2006.01)
C07D 401/14 (2006.01)
C07D 403/06 (2006.01)
C07D 403/08 (2006.01)
C07D 403/10 (2006.01)
C07D 403/12 (2006.01)
C07D 405/06 (2006.01)
C07D 405/12 (2006.01)
C07D 409/06 (2006.01)
C07D 409/08 (2006.01)
C07D 409/12 (2006.01)
C07D 413/06 (2006.01)
C07D 413/08 (2006.01)
C07D 413/12 (2006.01)
C07D 417/14 (2006.01)
C07D 471/04 (2006.01)
C07D 495/04 (2006.01)
C07D 498/04 (2006.01)
C07D 513/04 (2006.01)

(52) U.S. Cl.
CPC ......... *C07D 487/04* (2013.01); *C07D 209/14* (2013.01); *C07D 401/06* (2013.01); *C07D 401/08* (2013.01); *C07D 401/12* (2013.01); *C07D 401/14* (2013.01); *C07D 403/06* (2013.01); *C07D 403/08* (2013.01); *C07D 403/10* (2013.01); *C07D 403/12* (2013.01); *C07D 405/06* (2013.01); *C07D 405/12* (2013.01); *C07D 409/06* (2013.01); *C07D 409/08* (2013.01); *C07D 409/12* (2013.01); *C07D 413/06* (2013.01); *C07D 413/08* (2013.01); *C07D 413/12* (2013.01); *C07D 417/14* (2013.01); *C07D 471/04* (2013.01); *C07D 495/04* (2013.01); *C07D 498/04* (2013.01); *C07D 513/04* (2013.01)

(58) Field of Classification Search
CPC .................................................... C07D 487/04
See application file for complete search history.

(56) References Cited

U.S. PATENT DOCUMENTS 7,601,735 B2 10/2009 Tyms et al.
8,299,056 B2 10/2012 Bahmanyar et al.
(Continued)

FOREIGN PATENT DOCUMENTS

WO 2001060826 A2 8/2001
WO 2002089780 A2 11/2002
(Continued)

OTHER PUBLICATIONS

Opposition filed in Ecuadorian Patent Application No. SENADI-2019-83621 (English language translation).
(Continued)

*Primary Examiner* — Shawquia Jackson
(74) *Attorney, Agent, or Firm* — Burns & Levinson, LLP; Shawn P. Foley; Chris Lorenc

(57) ABSTRACT

The present invention relates to a series of novel compounds, methods to prevent or treat viral infections in animals by using the novel compounds and to said novel compounds for use as a medicine, more preferably for use as a medicine to treat or prevent viral infections, particularly infections with RNA viruses, more particularly infections with viruses belonging to the family of the Flaviviridae, and yet more particularly infections with the Dengue virus. The present invention furthermore relates to pharmaceutical compositions or combination preparations of the novel compounds, to the compositions or preparations for use as a medicine, more preferably for the prevention or treatment of viral infections. The invention also relates to processes for preparation of the compounds.

18 Claims, 1 Drawing Sheet
Specification includes a Sequence Listing.

Related U.S. Application Data division of application No. 14/346,777, filed as application No. PCT/EP2012/069007 on Sep. 26, 2012, now Pat. No. 10,550,123.

(60) Provisional application No. 61/626,410, filed on Sep. 26, 2011.

(56) References Cited

U.S. PATENT DOCUMENTS

| | | |
|---|---|---|
| 8,884,030 B2 | 11/2014 | Canales et al. |
| 8,993,604 B2 | 3/2015 | Byrd et al. |
| 9,029,376 B2 | 5/2015 | Byrd et al. |
| 9,522,923 B2 | 12/2016 | Richards et al. |
| 9,944,598 B2 | 4/2018 | Kesteleyn et al. |
| 10,029,984 B2 | 7/2018 | Kesteleyn et al. |
| 10,064,870 B2 | 9/2018 | Rajagopalan et al. |
| 10,071,961 B2 | 9/2018 | Vandyck et al. |
| 10,117,850 B2 | 11/2018 | Griffioen et al. |
| 10,206,902 B2 | 2/2019 | Kesteleyn et al. |
| 10,323,026 B2 | 6/2019 | Ikeda et al. |
| 2005/0239821 A1 | 10/2005 | Neyts et al. |
| 2006/0194835 A1 | 8/2006 | Dugourd et al. |
| 2006/0211698 A1 | 9/2006 | Botyanszki et al. |
| 2008/0318338 A1 | 12/2008 | Kamal et al. |
| 2010/0048589 A1 | 2/2010 | Colburn et al. |
| 2012/0136006 A1 | 5/2012 | Colburn et al. |
| 2014/0213586 A1 | 7/2014 | Bardiot et al. |
| 2016/0297810 A1 | 10/2016 | Bardiot et al. |
| 2017/0002006 A1 | 1/2017 | Corte et al. |
| 2017/0096429 A1 | 4/2017 | Corte et al. |
| 2017/0281633 A1 | 10/2017 | Boylan et al. |
| 2017/0281766 A1 | 10/2017 | Wiltzius |
| 2017/0283500 A1 | 10/2017 | Wiltzius et al. |
| 2017/0298017 A1 | 10/2017 | Kesteleyn et al. |
| 2018/0256544 A1 | 9/2018 | Kesteleyn et al. |
| 2018/0256545 A1 | 9/2018 | Kesteleyn et al. |
| 2018/0346419 A1 | 12/2018 | Kesteleyn et al. |
| 2019/0104738 A1 | 4/2019 | Narine et al. |
| 2019/0112266 A1 | 4/2019 | Kesteleyn et al. |
| 2019/0183931 A1 | 6/2019 | Bakker et al. |

FOREIGN PATENT DOCUMENTS

| | | |
|---|---|---|
| WO | 2003050295 A2 | 6/2003 |
| WO | 2005095403 A2 | 10/2005 |
| WO | 2006071618 A1 | 7/2006 |
| WO | 2006136305 A1 | 12/2006 |
| WO | 2007017093 A1 | 2/2007 |
| WO | 2007026920 A2 | 3/2007 |
| WO | 2009149054 A1 | 12/2009 |
| WO | 2010021878 A1 | 2/2010 |
| WO | 2010027500 A1 | 3/2010 |
| WO | 2010091413 A1 | 8/2010 |
| WO | 2011031669 A1 | 3/2011 |
| WO | 2011037643 A2 | 3/2011 |
| WO | 2011088303 A1 | 7/2011 |
| WO | 2013045516 A1 | 4/2013 |
| WO | 2014154682 A1 | 10/2014 |
| WO | 2016050841 A1 | 4/2016 |
| WO | 2016053455 A1 | 4/2016 |
| WO | 2016113371 A1 | 7/2016 |
| WO | 2017046255 A1 | 3/2017 |
| WO | 2017046258 A1 | 3/2017 |
| WO | 2017079216 A1 | 5/2017 |
| WO | 2017167951 A1 | 5/2017 |
| WO | 2017167832 A1 | 10/2017 |
| WO | 2017167950 | 10/2017 |
| WO | 2017167950 A1 | 10/2017 |
| WO | 2017167951 A1 | 10/2017 |
| WO | 2017167952 A1 | 10/2017 |
| WO | 2017167953 A1 | 10/2017 |
| WO | 2017171100 A1 | 10/2017 |
| WO | 2017173206 A1 | 10/2017 |
| WO | 2017173256 A1 | 10/2017 |
| WO | 2017173384 A1 | 10/2017 |
| WO | 2017173410 S | 10/2017 |
| WO | 2018178238 | 10/2018 |
| WO | 2018178240 | 10/2018 |
| WO | 2018215315 | 11/2018 |
| WO | 2018215316 | 11/2018 |

OTHER PUBLICATIONS

Opposition filed in Ecuadorian Patent Application No. SENADI-2019-83640 (English language translation).
Naziroglu et al., entitled "Synthesis and application of L-proline and R-phenylglycine derived organocatalysts for direct asymmetric Michael addition of cyclohexanone to nitroalkenes," Turk J Chem, 36 (2012), 659-670.
Aripo Office Action dated Feb. 10, 2016 in connection with African Patent Application No. AP/P/2014/007535.
Eurasian Office Action dated May 2016 in connection with Eurasian Patent Application No. 201490654, 1 page.
Summons to attend oral proceedings pursuant to Rule (115(1) EPC in connection with European Patent Application No. 12775463.8, Jul. 6, 2016.
New Zealand First Office Action dated Jul. 19, 2014 in connection with case No. 721700.
New Zealand Further Examination Report dated Jul. 19, 2016 in connection with case No. 622588.
Singapore Written Opinion dated Jul. 5, 2016 in connection with Singapore Patent Application No. Sep. 26, 2012.
Duan et al., entitled "Syntheses and Photochromic Studies of Dithienylethene-Containing Imidazolium Derivatives and Their Reactivity towards Nucleophiles," Chem. Eur. J. 2010, 16, 13199-13209.
STN International, RN 1316109-81-5, 1297049-96-7, 1297011-10-9, 1296377-78-0, 1295540-00-9, 1295460-37-5, 1294813-77-6, 1294288-37-1, 1293697-77-4, 1287503-18-7, 1287040-60-1, 1286579-37-0, 1277962-26-1, 1252467-88-1, 1181884-55-8, 1134766-19-0, 1118870-48-6, 1062132-16-4, 1030212-41-9, 1015662-06-2, 1014535-82-0, 1014493-63-0, 1012956-97-6, 1011162-23-4, 1011120-58-3, 1011119-79-1, 1011113-94-2, 931000-99-6, 920834-07-7, 878619-92-2, File Registry [online], Aug. 11, 2011, ED Mar. 30, 2006-Aug. 11, 2011.
Examination Report on Israeli Patent Application No. 231492, 3 pages, with Annex to Report, 1 page, dated Nov. 30, 2015.
Registry No. 1277962-26-1, entered in STN on Apr. 10, 2011.
Registry No. 924715-04-8, entered in STN on Mar. 4, 2007.
Registry No. 1386766-68-2, entered in STN on Aug. 6, 2012.
Registry No. 1388775-15-2, entered in STN on Aug. 9, 2012.
Registry No. 1388908-86-8, entered in STN on Aug. 14, 2012.
Registry No. 1386200-09-4, entered in STN on Aug. 3, 2012.
Registry No. 1388629-42-2, entered in STN on Aug. 9, 2012.
Japanese Office Action dated Jun. 2, 2020 from Japanese Patent Appln. No. JP2017-243354 (English language translation).
ACS on STN Registry No. 931079-09-3, Apr. 20, 2007.
ACS on STN Registry No. 931007-71-5, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.
ACS Registry No. 1295460-37-5, entered STN: May 16, 2011, "Registry Copyright 2015 ACS on STN," p. 19.
ACS Registry 1252467-88-1, entered STN: Nov. 10, 2010, "Registry Copyright 2015 ACS on STN," p. 20.

(56) References Cited

OTHER PUBLICATIONS

Database Pubchem [online] NCBI; Jul. 30, 2007, Pubchem CID: 16307180, 12 pages.
Database Pubchem [online] NCBI; Dec. 4, 2007, Pubchem CID: 18190680, 11 pages.
Database Pubchem [online] NCBI; Jul. 20, 2009, Pubchem CID: 42916879, 12 pages.
Database Pubchem [online] NCBI; Jul. 30, 2006, Pubchem CID: 8377731, 9 pages.
Database Pubchem [online] NCBI; Jul. 30, 2006, Pubchem CID: 8377750, 9 pages.
Database Pubchem [online] NCBI; Jul. 30, 2006, Pubchem CID: 8377765, 9 pages.
Database Pubchem [online] NCBI; Jul. 30, 2006, Pubchem CID: 8377782, 9 pages.
Database Pubchem [online] NCBI; Jul. 30, 2006, Pubchem CID: 8377825, 9 pages.
Database Pubchem [online] NCBI; Jul. 30, 2006, Pubchem CID: 8377845, 10 pages.
Database Pubchem [online] NCBI; Jul. 30, 2006, Pubchem CID: 8377864, 9 pages.
Database Pubchem [online] NCBI; Jul. 30, 2006, Pubchem CID: 8377894, 10 pages.
Database Pubchem [online] NCBI; Jul. 30, 2006, Pubchem CID: 8377913, 10 pages.
Database Pubchem [online] NCBI; Jul. 30, 2006, Pubchem CID: 8377936, 9 pages.
Database Pubchem [online] NCBI; Jul. 30, 2006, Pubchem CID: 8377950, 10 pages.
Database Pubchem [online] NCBI; Jul. 30, 2006, Pubchem CID: 8377957, 9 pages.
Database Pubchem [online] NCBI; Jul. 30, 2006, Pubchem CID: 8378071, 9 pages.
Database Pubchem [online] NCBI; Jul. 30, 2006, Pubchem CID: 8378972, 10 pages.
Database Pubchem [online] NCBI; Jul. 30, 2006, Pubchem CID: 9292530, 9 pages.
Database Pubchem [online] NCBI; Jul. 30, 2006, Pubchem CID: 9329202, 10 pages.
Database Pubchem [online] NCBI; Jul. 31, 2006, Pubchem CID: 9356704, 10 pages.
Database Pubchem [online] NCBI; Jul. 31, 2006, Pubchem CID: 9461840, 9 pages.
Database Pubchem [online] NCBI; Jul. 30, 2007, Pubchem CID: 16267760, 12 pages.
Database Pubchem [online] NCBI; Jul. 30, 2007, Pubchem CID: 16340406, 12 pages.
Database Pubchem [online] NCBI; Jul. 30, 2007, Pubchem CID: 16343459, 10 pages.
Database Pubchem [online] NCBI; Jul. 30, 2007, Pubchem CID: 16366089, 12 pages.
Database Pubchem [online] NCBI; Dec. 4, 2007, Pubchem CID: 18226977, 10 pages.
Database Pubchem [online] NCBI; Feb. 29, 2008, Pubchem CID: 24614828, 12 pages.
Database Pubchem [online] NCBI; Feb. 29, 2008, Pubchem CID: 24614964, 12 pages.
Database Pubchem [online] NCBI; Feb. 29, 2008, Pubchem CID: 24652310, 11 pages.
Database Pubchem [online] NCBI; May 28, 2009, Pubchem CID: 26654475, 9 pages.
Database Pubchem [online] NCBI; May 29, 2009, Pubchem CID: 31392427, 9 pages.
Database Pubchem [online] NCBI; May 30, 2009, Pubchem CID: 39912467, 9 pages.
Database Pubchem [online] NCBI; Nov. 25, 2010, Pubchem CID: 47065408, 12 pages.
Database Pubchem [online] NCBI; May 20, 2011, Pubchem CID: 52708600, 9 pages.
Database Pubchem [online] NCBI; May 20, 2011, Pubchem CID: 52764912, 9 pages.
Database Pubchem [online] NCBI; May 20, 2011, Pubchem CID: 52886897, 9 pages.
Database Pubchem [online] NCBI; Sep. 17, 2005, Database accession No. CID 4793342, 4 pages.
Database Pubchem [online] NCBI; Sep. 17, 2005, Database accession No. CID 4796066, 4 pages.
Database Pubchem [online] NCBI; Sep. 17, 2005, Database accession No. CID 4849237, 4 pages.
Database Pubchem [online] NCBI; Sep. 17, 2005, Database accession No. CID 4793878, 4 pages.
PubChem [online] Jul. 30, 2006 PubChem CID 8377731, 12 pages.
The PCT International Search Report dated Nov. 29, 2012 in connection with PCT International Patent Application No. PCT/EP2012/69007, 4 pages.
Columbian Office Action dated Oct. 28, 2015 in connection with Colombian Patent Application No. 14-89597-8.
Declaration of Neil Thomas Simpkin BA regarding certified English-language translation dated Jan. 19, 2015, 1 page.
Opposition in connection with patent family member, Costa Rican Patent Application No. 14-089.597 dated Nov. 14, 2014, 15 pages.
Invitation to Respond to Written Opinion dated Jan. 8, 2015, from the Intellectual Property Office of Singapore in connection with patent family member Singapore Application No. 11201400927W, 9 pages.
Japanese Office Action dated Oct. 23, 2018, in connection with Japanese Patent Application No. JP-2017-243354.
Li et al., entitled "Thiazolium-derived N-heterocyclic carbene-catalyzed cross-coupling of aldehydes with unactived imines," Chem. Commun, 2007, 852-854.
"Solvation," Wikipedia, at internet address: https://en.wikipedia.org/wiki/Solvation, web page last edited on Mar. 13, 2019, 6 pages.
Examination Report dated Jan. 7, 2020, from Indian Patent Appln. No. 201727014547.
Communication Euroopean Search Report dated Nov. 19, 2019, in connection with European Patent Application No. 19183201.3.
N.C.B.I.: qHTS for inhibitors of binding or entry into cells for Marburg Virus, Pubchem Bioassay Record Aid 540276, Jul. 2011, 13 pages, XP55641386, Retrieved from the Internet: https://pubchem.ncbi.nlm.nih.gov/bioassay/540276.
Prasad et al., Intrinsic Rotation and Molecular Structure, Chirality 15: S143-S149 (2003).
Prevention, Dengue, Centers for Disease Control and Prevention (Sep. 27, 2012) https://www.cdc.gov/dengue/prevention/index.html, internet.
Linda et al., Bioisosterism: A Useful Strategy for Molecular Modification and Drug Design, Current Medicinal Chemistry, Bentham Science Publishers Ltd. (2005) 12, pp. 23-49.
Stansfield et al., Development of carboxylic acid replacements in indole-N-acetamide inhibitors of hepatitis C virus NS5B polymerase, Bioorganic & Medicinal Chemistry Letters 17 (2007) 5143-5149. ScienceDirect (2007) www.sciencedirect.com, internet.
Boltromeyuk V.V., Obshchaya khimiya (General Chemistry), Minsk, Vysheyshaya shkola, 2012, p. 65 (translation).
Banker et al., (1996) Modern Pharmaceuticals, 3rd Edition, Revised and Expanded, p. 596.
Wolff et al., Burger's Medicinal Chemistry and Drug Discovery, 5th Ed. part 1, p. 975-977 (1995).
Bergman et al., Synthesis and reactions of some 3-(2-haloacyl)indoles. Tetrahedron 29: 971-976, 1973.
PCT Notification Concerning Transmittal of International Preliminary Report on Patentability and Written Opinion of the International Searching Authority dated Apr. 10, 2014 in connection with PCT International Patent Application No. PCT/EP2012/069007, 9 pages.
Office Action dated Jun. 4, 2015 in connection with Columbian Patent Application No. 14-89597-5, 26 pages.
Registry No. 1241127-58-1, entered in STN on Sep. 15, 2010.
Registry No. 1062257-51-5, entered in STN on Oct. 16, 2008.
Registry No. 1062132-16-4, entered in STN on Oct. 16, 2008.
Registry No. 1030735-63-7, entered in STN on Jun. 26, 2008.
Registry No. 1030232-46-2, entered in STN on Jun. 24, 2008.

(56) References Cited

OTHER PUBLICATIONS

Registry No. 1014493-63-0, entered in STN on Apr. 14, 2008.
Database Pubchem [online] NCBI; Jul. 31, 2006, Pubchem CID: 9356705, 3 pages.
Database Pubchem [online] NCBI; May 29, 2009, Pubchem CID: 31392243, 1 page.
Database Pubchem [online] NCBI; May 29, 2009, Pubcchem CID: 37329396, 2 pages.
Office Action dated Jun. 25, 2018 that issued in connection with patent family member Peruvian Patent Application.
English translation of an Office Action dated May 4, 2018 that issued in connection with patent family member Eurasian Patent Application No. 201490654.
English translation of an Office Action dated Jun. 22, 2018 issued in connection with patent family member Uzbekistan Patent Application.
English translation of an Office Action dated Jun. 28, 2018 that issued in connection with patent family member Chilean Divisional Patent Application No. 201601580.
Canadian Office Action dated May 2, 2018 that issued in connection with patent family member Canadian Patent App. No. 2,848,604.
New Zealand Further Examination Report dated Jan. 19, 2018 in connection with New Zealand Patent Application No. 721700.
Registry No. 1219356-85-0 entered STN Apr. 15, 2010.
Registry No. 1041392-09-9 entered STN Aug. 17, 2008.
Registry No. 1036730-78-5 entered STN Jul. 28, 2008.
Japanese Office Action dated Apr. 21, 2016 in connection with Japanese Patent Application No. 2014-531279.

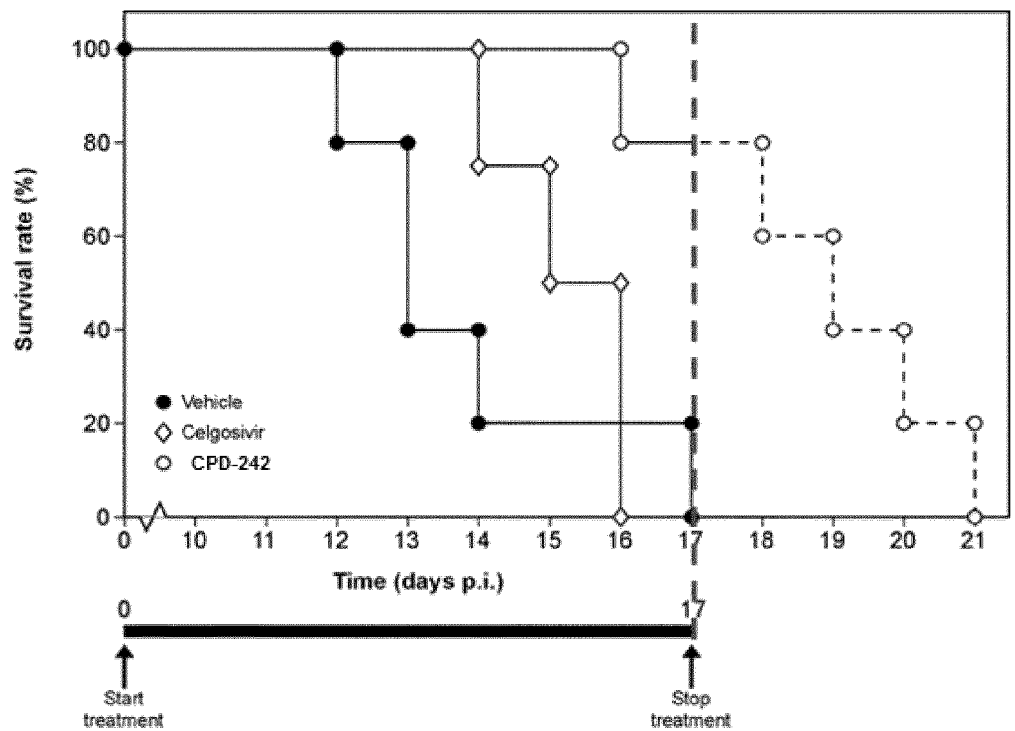

VIRAL REPLICATION INHIBITORS

RELATED APPLICATIONS

This application is a continuation of U.S. patent application Ser. No. 16/515,272, filed Jul. 18, 2019, which is a divisional application of U.S. patent application Ser. No. 14/346,777, filed Mar. 24, 2014, now U.S. Pat. No. 10,550,123, which is the U.S. national stage entry under 35 U.S.C. § 371 of PCT International Patent Application No. PCT/EP2012/069007, filed Sep. 26, 2012, which claims priority to Great Britain Application No. 1116559.4, filed Sep. 26, 2011 and U.S. Provisional Patent Application No. 61/626,410, filed Sep. 26, 2011, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 20, 2021 is named "56570-03028_ST25.txt" and is 4 KB in size.

FIELD OF THE INVENTION

The present invention relates to a series of novel compounds, methods to prevent or treat viral infections in animals by using the novel compounds and to said novel compounds for use as a medicine, more preferably for use as a medicine to treat or prevent viral infections, particularly infections with RNA viruses, more particularly infections with viruses belonging to the family of the Flaviviridae, and yet more particularly infections with the Dengue virus. The present invention furthermore relates to pharmaceutical compositions or combination preparations of the novel compounds, to the compositions or preparations for use as a medicine, more preferably for the prevention or treatment of viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known (DENV-1, −2, −3, and −4). Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalisation and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control dengue disease, the only available methods at present are mosquito eradication strategies to control the vector. Although progress is being made in the development of vaccines for dengue, many difficulties are encountered. These include the existence of a phenomenon referred to as antibody-dependent enhancement (ADE).

Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titres. In both primary and secondary infections, higher viral titres are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyperendemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north. According to the United States (US) Centers for Disease Control and Prevention (CDC), both mosquitoes are currently omnipresent in southern Texas. The spread north of dengue-carrying mosquitoes is not confined to the US, but has also been observed in Europe.

Despite large efforts over the past 3 decades, there is currently no vaccine available to protect against dengue virus disease. The main problem is to develop a vaccine that offers protection against all four serotypes (a tetravalent vaccine) to the same extent. Furthermore, today, specific antiviral drugs for the treatment or prevention of dengue fever virus infection are not available. Clearly, there is still a great need for therapeutics for the prevention or treatment of viral infections in animals, more in particular in humans and especially for viral infections caused by Flaviviruses, more in particular Dengue virus. Therapeutics with good potency, no or low levels of less side-effects, a broad spectrum activity against multiple Dengue virus serotypes, a low toxicity and/or good pharmacokinetic or -dynamic properties are very welcome. The present invention provides novel compounds which show activity against Flaviviruses, including Dengue virus. The prior art does not lead a person skilled in the art to the compounds of the present invention, nor to their use as antiviral compounds.

SUMMARY OF THE INVENTION

The present invention is based on the unexpected finding that at least one of the above-mentioned problems can be solved by a novel class of compounds.

The present invention provides new compounds which have been shown to possess antiviral activity. The present invention furthermore demonstrates that these compounds efficiently inhibit proliferation of viruses, especially Flaviviruses, more specifically Dengue virus (DENV) and Yellow Fever virus (YFV). Therefore, these compounds constitute a useful class of new potent compounds that can be used in the treatment and/or prevention of viral infections in animals, mammals and humans, more specifically for the treatment and/or prevention of infections with viruses belonging to the family of the Flaviviruses, and yet more particularly infections with Dengue viruses or yellow fever virus.

The present invention furthermore relates to the use of such compounds as medicines and to their use for the manufacture of medicaments for treating and/or preventing viral infections, in particular with viruses belonging to the family of the Flaviviruses, and yet more particularly infections with Dengue viruses or yellow fever virus, in animals or mammals, more in particular in humans. The invention also relates to methods for the preparation of all such compounds and to pharmaceutical compositions comprising them in an effective amount.

The present invention also relates to a method of treatment or prevention of viral infections in humans by the administration of one or more such compounds, optionally in combination with one or more other medicines, to a patient in need thereof. Particularly, the present invention also relates to a method of treatment or prevention of viral infections, especially Flaviviral infections, in humans by the administration of an effective amount of one or more such compounds or a pharmaceutically acceptable salt thereof, optionally in combination with one or more other medicines, to a patient in need thereof. More particularly, the present invention also relates to a method of treatment or prevention of infections by the Dengue virus or yellow fever virus in humans by the administration of an effective amount of one or more such compounds or a pharmaceutically acceptable salt thereof, optionally in combination with one or more other medicines, to a patient in need thereof.

One aspect of the invention is the provision of new compounds of formula (A),

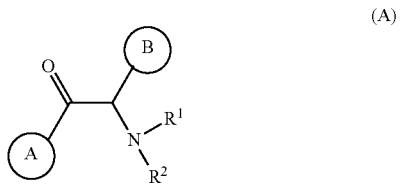

(A)

wherein,
cycle A is a heterocycle, which can be unsubstituted or substituted with one or more $Z^1$;
cycle B is selected from aryl; and heterocycle; wherein said aryl and heterocycle can be unsubstituted or substituted with one or more $Z^{1a}$;
$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;
and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;
$R^2$ is selected from hydrogen; alkyl; alkenyl; alkynyl; heteroalkyl; heteroalkenyl; and heteroalkynyl;
and wherein said alkyl, alkenyl, alkynyl, heteroalkyl, heteroalkenyl, and heteroalkynyl, can be unsubstituted or substituted with one or more $Z^{1c}$,
each Z, $Z^{1a}$, $Z^{1b}$, and $Z^{1c}$ is independently selected from the group consisting of halogen; hydroxyl; sulfhydryl; —$OZ^2$; =O; —$SZ^2$; =S; —$S(O)Z^2$; —$S(O)_2Z^3$; —$S(O)_2NZ^4Z^5$; trifluoromethyl; trifluoromethoxy; nitro; —$NZ^4Z^5$; —$NZ^4S(O)_2Z^2$; —$NZ^4C(O)Z^2$; —$NZ^4C(O)NZ^4Z^5$; cyano; —$C(O)Z^3$; —$C(O)OZ^2$; —$C(O)NZ^4Z^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;
and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —$OCF_3$, cyano, nitro, —C(O)OH or $NH_2$;
each $Z^2$ is independently selected from alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —$OCF_3$, cyano, nitro, —C(O)OH or $NH_2$;
each $Z^3$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —$OCF_3$, cyano, nitro, —C(O)OH or $NH_2$;
each $Z^4$ and $Z^5$ is independently selected from hydrogen; alkyl; alkenyl; alkynyl; heteroalkyl; heteroalkenyl; heteroalkynyl; aryl; heterocycle; arylalkyl; arylalkenyl;

arylalkynyl; arylheteroalkyl; arylheteroalkenyl; aryl-heteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein Z$^4$ and Z$^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —OCF$_3$, cyano, nitro, —C(O)OH or —NH$_2$; and isomers (in particular stereo-isomers or tautomers), solvates, salts (in particular pharmaceutically acceptable salts) or prodrugs thereof.

DETAILED DESCRIPTION OF THE FIGURES

FIG. 1: Kaplan Meier plot of dengue virus induced mortality/euthanasia in AG129 mice and the effect of treatment with Celgosivir and CPD-242. The red dotted line indicates end of treatment.

DETAILED DESCRIPTION OF THE INVENTION

The present invention will be described with respect to particular embodiments but the invention is not limited thereto.

A first embodiment of the present invention relates to a compound according to formula (D),

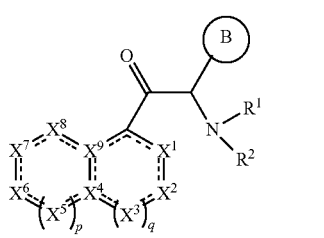

(D)

wherein
each dotted line represents an optional double bond whereby maximally 6 non-adjacent dotted lines can form a double bond;
each of X$^1$, X$^2$, X$^3$, X$^5$, X$^6$, X$^7$ and X$^8$ is independently selected from CR$^3$; NR$^4$; O; and S;
each of X$^4$ and X$^9$ is independently selected from C; CH; and N;
p is 0; 1; or 2;
q is 0; 1; or 2;
cycle B is selected from aryl; and heterocycle; wherein said aryl and heterocycle can be unsubstituted or substituted with one or more Z$^{1a}$; provided that cycle B is not unsubstituted phenyl;

R$^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;

and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more Z$^{1b}$;

R$^2$ is selected from hydrogen; alkyl; alkenyl; alkynyl; heteroalkyl; heteroalkenyl; and heteroalkynyl;
and wherein said alkyl, alkenyl, alkynyl, heteroalkyl, heteroalkenyl, and heteroalkynyl, can be unsubstituted or substituted with one or more Z$^{1c}$;

each R$^3$ is independently selected from hydrogen and Z$^1$;
each R$^4$ is independently selected from hydrogen; hydroxyl; sulfhydryl; —S(O)Z$^2$; —S(O)$_2$Z$^3$; —S(O)$_2$NZ$^4$Z$^5$; trifluoromethyl; —C(O)Z$^3$; —C(O)OZ$^2$; —C(O)NZ$^4$Z$^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each Z$^1$, Z$^{1a}$, Z$^{1b}$, and Z$^{1c}$ is independently selected from the group consisting of halogen; hydroxyl; sulfhydryl; —OZ$^2$; =O; —SZ$^2$; =S; —S(O)Z$^2$; —S(O)$_2$Z$^3$; —S(O)$_2$NZ$^4$Z$^5$; trifluoromethyl; trifluoromethoxy; nitro; —NZ$^4$Z$^5$; —NZ$^4$S(O)$_2$Z$^2$; —NZ$^4$C(O)Z$^2$; —NZ$^4$C(O)NZ$^4$Z$^5$; cyano; —C(O)Z$^3$; —C(O)OZ$^2$; —C(O)NZ$^4$Z$^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $Z^2$ is independently selected from alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; or heterocycle-heteroalkynyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —OCF$_3$, cyano, nitro, —C(O)OH or —NH$_2$; and isomers (in particular stereo-isomers or tautomers), solvates, salts (in particular pharmaceutically acceptable salts) or prodrugs thereof.

In a second embodiment, the compounds have a structure according to formula (D3),

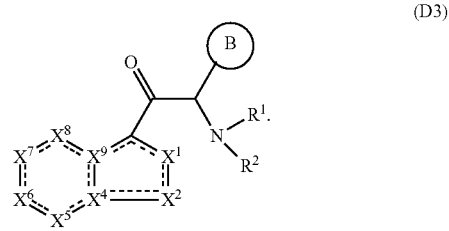

(D3)

In a third embodiment, the compounds have a structure according to formula (F1)

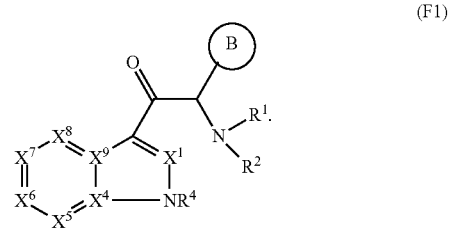

(F1)

In a fourth embodiment, the present invention relates to a compound of formula (D) for use as a medicine,

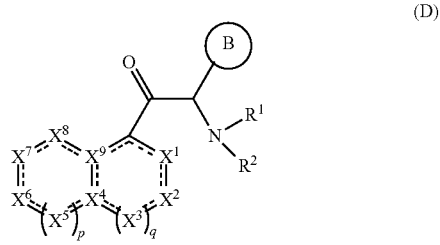

(D)

wherein
each dotted line represents an optional double bond whereby maximally 6 non-adjacent dotted lines can form a double bond;
each of $X^1$, $X^2$, $X^3$, $X^5$, $X^6$, $X^7$ and $X^8$ is independently selected from CR$^3$; NR$^4$; O; and S;
each of $X^4$ and $X^9$ is independently selected from C; CH; and N;
p is 0; 1; or 2;
q is 0; 1; or 2;
cycle B is selected from aryl; and heterocycle; wherein said aryl and heterocycle can be unsubstituted or substituted with one or more $Z^{1a}$;
$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;

and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;

$R^2$ is selected from hydrogen; alkyl; alkenyl; alkynyl; heteroalkyl; heteroalkenyl; and heteroalkynyl;
and wherein said alkyl, alkenyl, alkynyl, heteroalkyl, heteroalkenyl, and heteroalkynyl, can be unsubstituted or substituted with one or more $Z^{1c}$;

each $R^3$ is independently selected from hydrogen and $Z^1$;
each $R^4$ is independently selected from hydrogen; hydroxyl; sulfhydryl; —S(O)$Z^2$; —S(O)$_2Z^3$; —S(O)$_2NZ^4Z^5$; trifluoromethyl; —C(O)$Z^3$; —C(O)O$Z^2$; —C(O)N$Z^4Z^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;
and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $Z^1$, $Z^{1a}$, $Z^{1b}$, and $Z^{1c}$ is independently selected from the group consisting of halogen; hydroxyl; sulfhydryl; —O$Z^2$; =O; —S$Z^2$; =S; —S(O)$Z^2$; —S(O)$_2Z^3$; —S(O)$_2NZ^4Z^5$; trifluoromethyl; trifluoromethoxy; nitro; —N$Z^4Z^5$; —N$Z^4$S(O)$_2Z^2$; —N$Z^4$C(O)$Z^2$; —N$Z^4$C(O)N$Z^4Z^5$; cyano; —C(O)$Z^3$; —C(O)O$Z^2$; —C(O)N$Z^4Z^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;
and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

each $Z^2$ is independently selected from alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^3$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;

each $Z^4$ and $Z^5$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —OCF$_3$, cyano, nitro, —C(O)OH or NH$_2$;
and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —OCF$_3$, cyano, nitro, —C(O)OH or —NH$_2$; and isomers (in particular stereo-isomers or tautomers), solvates, salts (in particular pharmaceutically acceptable salts) or prodrugs thereof.

A fifth embodiment relates to a compound of formula (A) for use as a medicament for the prevention or treatment of a viral infection in an animal (including a human)

(A)

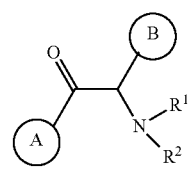

wherein,
cycle A is a heterocycle, which can be unsubstituted or substituted with one or more $Z^1$;
cycle B is selected from aryl; and heterocycle; wherein said aryl and heterocycle can be unsubstituted or substituted with one or more $Z^{1a}$;
$R^1$ is selected from cycloalkyl; cycloalkenyl; cycloalkynyl; aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl;
and wherein said cycloalkyl; cycloalkenyl; cycloalkynyl; aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$;
$R^2$ is selected from hydrogen; alkyl; alkenyl; alkynyl; heteroalkyl; heteroalkenyl; and heteroalkynyl;
and wherein said alkyl, alkenyl, alkynyl, heteroalkyl, heteroalkenyl, and heteroalkynyl, can be unsubstituted or substituted with one or more $Z^{1c}$;
each $Z^1$, $Z^{1a}$, $Z^{1b}$, and $Z^{1c}$ is independently selected from the group consisting of halogen; hydroxyl; sulfhydryl; —$OZ^2$; =O; —$SZ^2$; =S; —$S(O)Z^2$; —$S(O)_2Z^3$; —$S(O)_2NZ^4Z^5$; trifluoromethyl; trifluoromethoxy; nitro; —$NZ^4Z^5$; —$NZ^4S(O)_2Z^2$; —$NZ^4C(O)Z^2$; —$NZ^4C(O)NZ^4Z^5$; cyano; —$C(O)Z^3$; —$C(O)OZ^2$; —$C(O)NZ^4Z^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;
and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —$OCF_3$, cyano, nitro, —C(O)OH or $NH_2$;
each $Z^2$ is independently selected from alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —$OCF_3$, cyano, nitro, —C(O)OH or $NH_2$;

each $Z^3$ is independently selected from hydroxyl; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —$OCF_3$, cyano, nitro, —C(O)OH or $NH_2$;
each $Z^4$ and $Z^5$ is independently selected from hydrogen; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl; heterocycle-heteroalkenyl; or heterocycle-heteroalkynyl;
wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, hydroxyl, =O, halogen, —SH, =S, trifluoromethyl, —O-alkyl, —$OCF_3$, cyano, nitro, —C(O)OH or $NH_2$;
and wherein $Z^4$ and $Z^5$ can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —C(O)OH or —$NH_2$; and isomers (in particular stereo-isomers or tautomers), solvates, salts (in particular pharmaceutically acceptable salts) or prodrugs thereof.

A sixth embodiment relates to a compound of formula (B) for use as a medicament for the prevention or treatment of a viral infection in an animal (including a human)

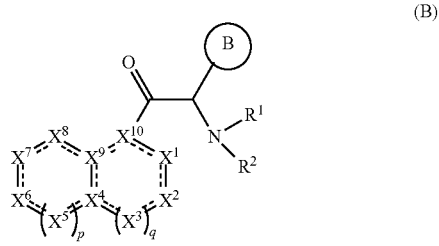
(B)

wherein
each dotted line represents an optional double bond whereby maximally 6 non-adjacent dotted lines can form a double bond;
each of $X^1$, $X^2$, $X^3$, $X^5$, $X^6$, $X^7$ and $X^8$ is independently selected from $CR^3$; $NR^4$; O; and S;

each of $X^4$ and $X^9$ is independently selected from C; CH; and N;

$X^{10}$ is selected from C; CH; and N; whereby minimally 5 of $X^1$ to $X^{10}$ are selected from $CR^3$, C or CH;

p is 0; 1; or 2;

q is 0; 1; or 2;

each $R^3$ is independently selected from hydrogen and $Z^1$;

each $R^4$ is independently selected from hydrogen; hydroxyl; sulfhydryl; —S(O)$Z^2$; —S(O)$_2Z^3$; —S(O)$_2NZ^4Z^5$; trifluoromethyl; —C(O)$Z^3$; —C(O)O$Z^2$; —C(O)N$Z^4Z^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$.

In a seventh embodiment, the present invention relates to a compound of formula (C) for use as a medicament for the prevention or treatment of a viral infection in an animal (including a human),

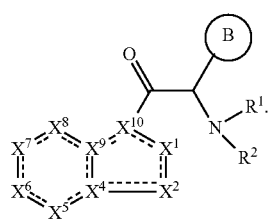

(C)

In an eighth embodiment, the present invention relates to the compounds and uses thereof according to the previous embodiments, wherein $R^2$ is hydrogen.

In a ninth embodiment, the present invention relates to the compounds and uses thereof according to the previous embodiments, wherein $R^1$ is selected from aryl and heterocycle, wherein said aryl and heterocycle can be unsubstituted or substituted with one or more $Z^{1b}$.

The present invention further relates to the compounds according to the previous embodiments, for use as a medicine for the prevention or treatment of a viral infection of an animal.

In one embodiment, the viral infection is an infection with Flavivirus.

In a further embodiment, the Flavivirus is Dengue virus.

The present invention further relates to a pharmaceutical composition comprising the compounds according to the fourth to ninth embodiments in combination with a pharmaceutically acceptable carrier.

The present invention further relates to a method for the prevention or treatment of a viral infection in an animal comprising administering said animal (including a human) in need for such prevention or treatment an effective dose of the compounds according to any one of the previous embodiments.

The present invention further relates a method for the preparation of the compounds according to the first three embodiments, comprising the steps of:

reacting an heterocycle under Friedel Craft conditions to obtain a ketone derivative having a methylene adjacent to the carbonyl;

reacting the previously obtained ketone under halogenation conditions to obtain an alpha-halogenoketone;

substitute the previously obtained alpha-halogenoketone with amines to obtain the desired compounds of the invention.

One aspect of the invention is the provision of compounds of formula (A),

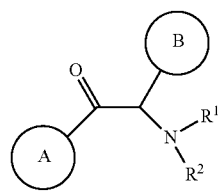

(A)

wherein, cycle A is a heterocycle optionally substituted with one, two, or three $Z^1$; preferably cycle A is a heterocycle optionally substituted with one or two $Z^1$; more preferably cycle A is a heterocycle selected from

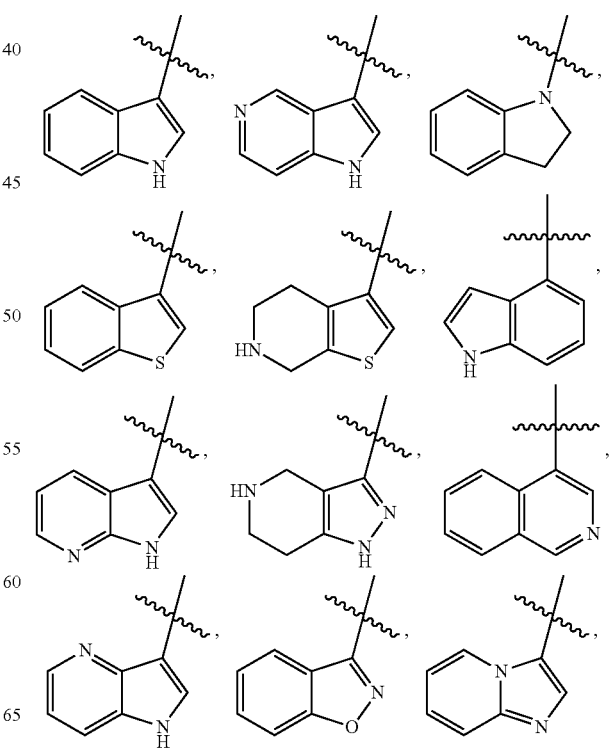

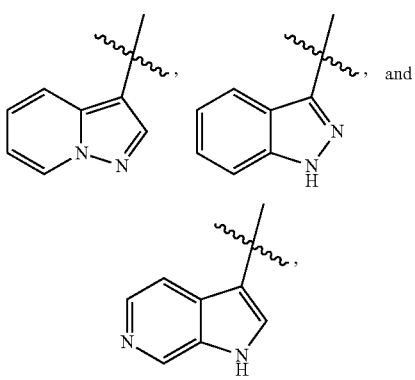
wherein the wavy line (∿) indicates the point of attachment to the carbonyl of the main formula (A), and wherein the depicted heterocycles may be optionally substituted with one or two $Z^1$;
cycle B is selected from aryl and heterocycle, wherein said aryl and heterocycle are optionally substituted with one, two, or three $Z^{1a}$; preferably cycle B is selected from
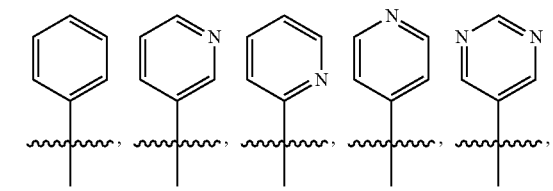
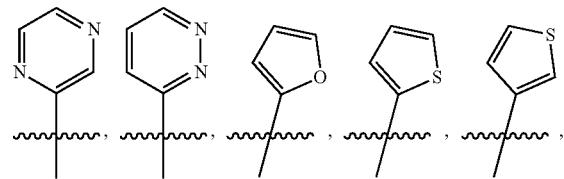
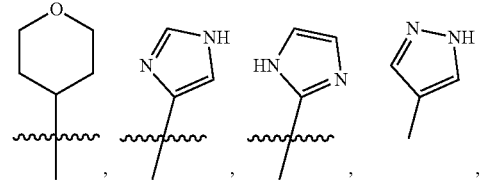
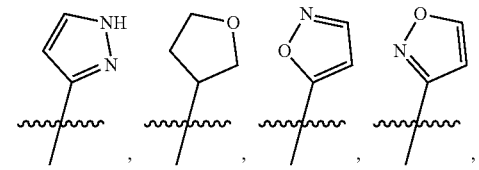
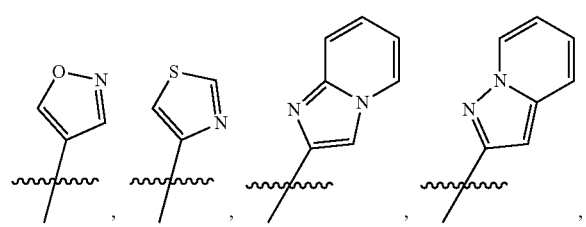
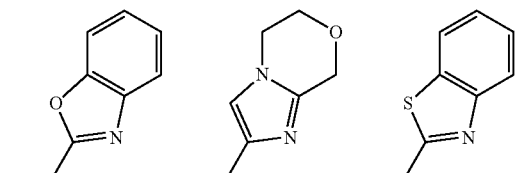
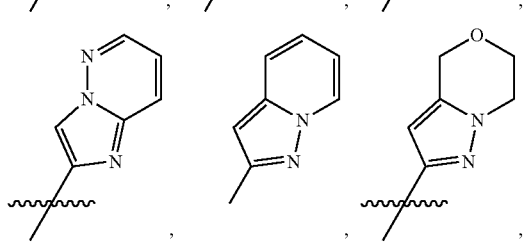
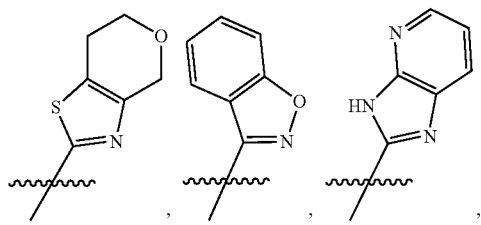
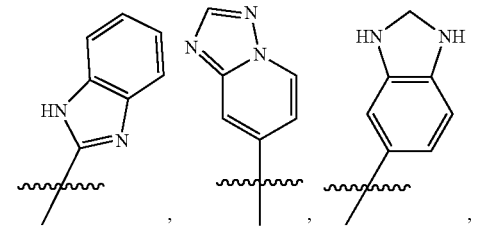
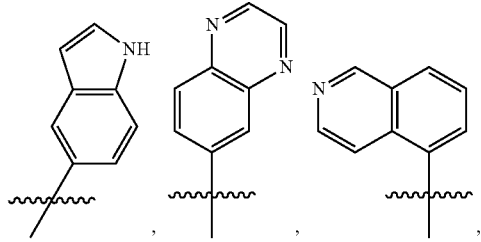
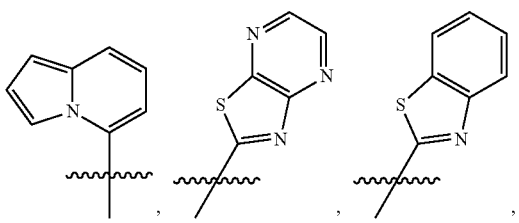
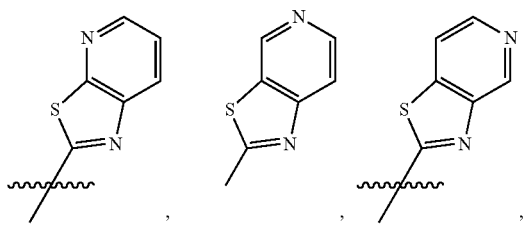

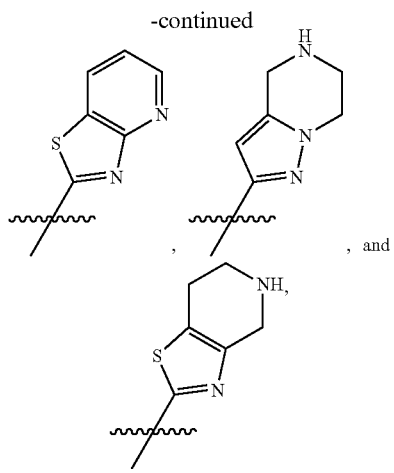

wherein the wavy line ( ~~~ ) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylheteroC$_{1-6}$alkyl, arylheteroC$_{2-6}$alkenyl, arylheteroC$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylheteroC$_{1-6}$alkyl, arylheteroC$_{2-6}$alkenyl, arylheteroC$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three $Z^{1b}$; preferably said $C_{1-6}$ alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl, are optionally substituted with one, two, or three $Z^{1c}$; preferably said $C_{1-6}$alkyl is optionally substituted with one, two, or three $Z^{1c}$;

each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, aryl$C_{1-6}$alkyl, aryl$C_{2-6}$alkenyl, aryl$C_{2-6}$alkynyl, arylheteroC$_{1-6}$alkyl, arylheteroC$_{2-6}$alkenyl, arylheteroC$_{2-6}$alkynyl, heterocycle-$C_{1-6}$alkyl, heterocycle-$C_{2-6}$alkenyl, heterocycle-$C_{2-6}$alkynyl, heterocycle-heteroC$_{1-6}$ alkyl, heterocycle-heteroC$_{2-6}$alkenyl, and heterocycle-heteroC$_{2-6}$alkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)$_2Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, heteroC$_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —O$Z^2$, —O—C(=O)$Z^3$, =O, —S(=O)$_2Z^3$, —S(=O)$_2$N$Z^4Z^5$, trifluoromethyl, trifluoromethoxy, —N$Z^4Z^5$, —N$Z^4$C(=O)$Z^2$, —N$Z^4$C(=O)—O$Z^2$, cyano, —C(=O)$Z^3$, —C(=O)O$Z^2$, —C(=O)N$Z^4Z^5$, $C_{1-6}$alkyl, heteroC$_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, aryl$C_{1-6}$alkyl, aryl$C_{2-6}$alkenyl, aryl$C_{2-6}$alkynyl, arylheteroC$_{1-6}$alkyl, arylheteroC$_{2-6}$alkenyl, arylheteroC$_{2-6}$alkynyl, heterocycle-$C_{1-6}$alkyl, heterocycle-$C_{2-6}$alkenyl, heterocycle-$C_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$ alkyl; preferably said $C_{1-6}$alkyl, heteroC$_{1-6}$alkyl, aryl, heterocycle, and heterocycle-$C_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, aryl$C_{1-6}$alkyl, aryl$C_{2-6}$alkenyl, aryl$C_{2-6}$alkynyl, arylheteroC$_{1-6}$alkyl, arylheteroC$_{1-6}$alkenyl, arylheteroC$_{1-6}$alkynyl, heterocycle-$C_{1-6}$alkyl, heterocycle-$C_{2-6}$alkenyl, heterocycle-$C_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from $C_{1-6}$alkyl, aryl, heterocycle, and heterocycle-$C_{1-6}$alkyl; more preferably $Z^2$ is independently selected from $C_{1-6}$alkyl, aryl, and heterocycle-$C_{1-6}$alkyl;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, aryl$C_{1-6}$alkyl, aryl$C_{2-6}$alkenyl, aryl$C_{2-6}$alkynyl, arylheteroC$_{1-6}$alkyl, arylheteroC$_{2-6}$alkenyl, arylheteroC$_{2-6}$alkynyl, heterocycle-$C_{1-6}$alkyl, heterocycle-$C_{2-6}$alkenyl, heterocycle-$C_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, difluoromethyl, —O—C$_{1-6}$alkyl, —OCF$_3$, —S(=O)$_2$C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; preferably said C$_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, —N(CH$_3$)$_2$, pyrrolidinyl, piperidinyl, and piperazinyl; more preferably said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, —N(CH$_3$)$_2$, pyrrolidinyl, piperidinyl, and piperazinyl;

each $Z^3$ is independently selected from hydroxyl, C$_{1-6}$alkyl, C$_{2-6}$alkenyl, C$_{2-6}$alkynyl, heteroC$_{1-6}$ alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$ alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^3$ is independently selected from hydroxyl, C$_{1-6}$alkyl, aryl, and heterocycle; more preferably $Z^3$ is independently selected from hydroxyl, C$_{1-6}$alkyl, and heterocycle;
wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;

each $Z^4$ and $Z^5$ is independently selected from hydrogen, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, C$_{3-7}$cycloalkyl, heterocycle, arylC$_{1-6}$ alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each $Z^4$ and $Z^5$ is independently selected from hydrogen, C$_{1-6}$alkyl, aryl, C$_{3-7}$cycloalkyl, and heterocycle; more preferably each $Z^4$ and $Z^5$ is independently selected from hydrogen, C$_{1-6}$alkyl, and C$_{3-7}$cycloalkyl;
wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH or —NH$_2$;
and wherein $Z^4$ and $Z^5$ can be taken together in order to form a (5-, 6-, or 7-membered) heterocycle which is optionally substituted with C$_{1-6}$alkyl, C$_{2-6}$alkenyl, C$_{2-6}$alkynyl, hydroxyl, halogen, —SH, trifluoromethyl, —O—C$_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof.

One aspect of the invention relates to compounds of formula (A),

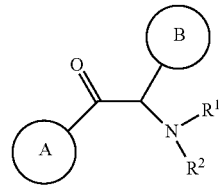

(A)

wherein,
cycle A is a heterocycle optionally substituted with one, two, or three $Z^1$; preferably cycle A is a heterocycle optionally substituted with one or two $Z^1$; more preferably cycle A is a heterocycle selected from

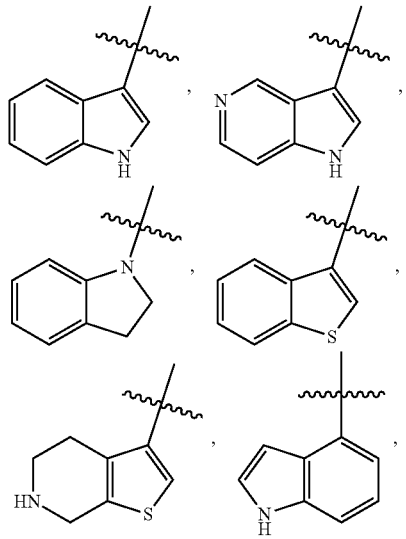

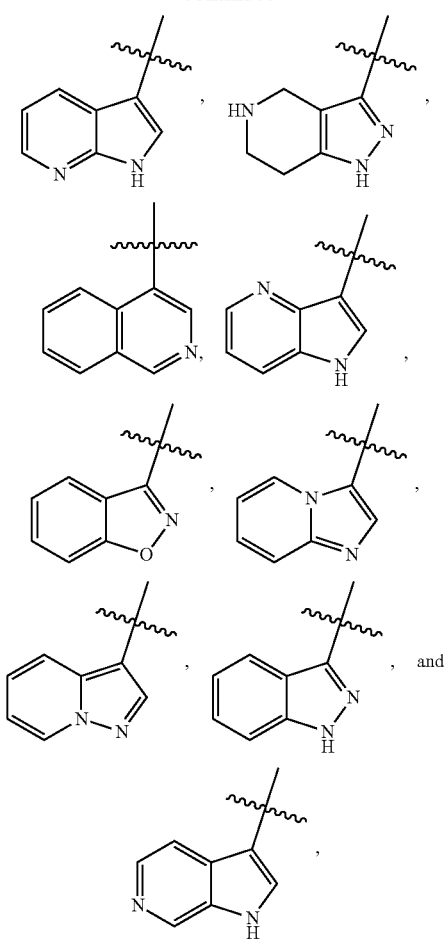
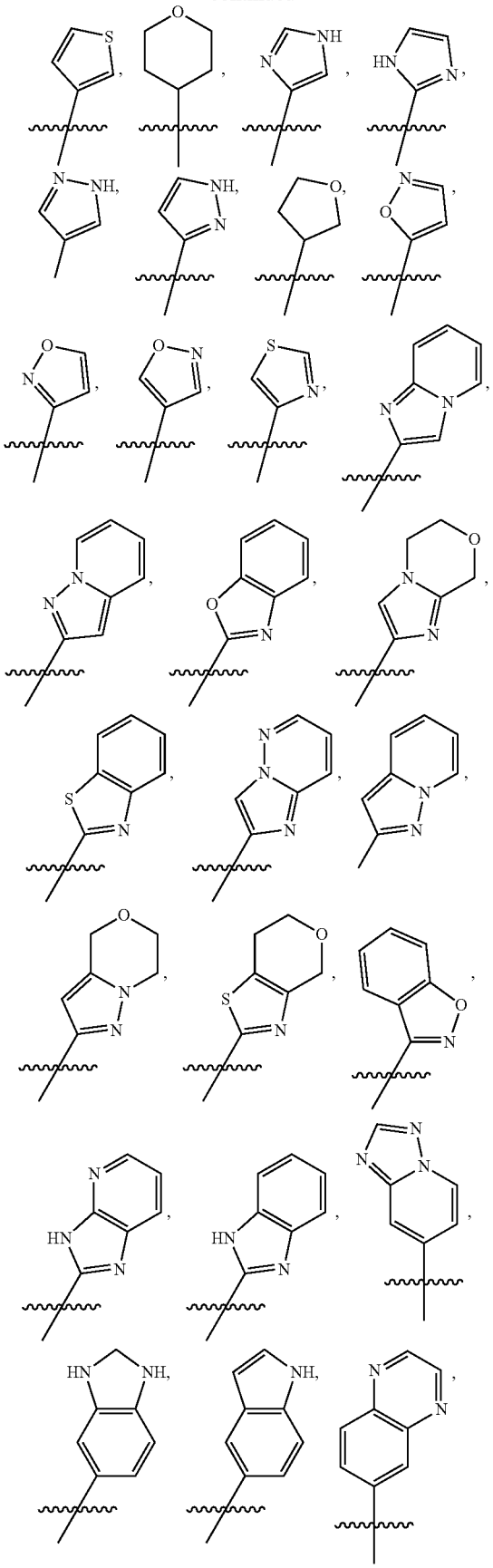
wherein the wavy line (⁓) indicates the point of attachment to the carbonyl of the main formula ⁓(A), and wherein the depicted heterocycles may be optionally substituted with one or two $Z^1$;
cycle B is selected from aryl and heterocycle, wherein said aryl and heterocycle are optionally substituted with one, two, or three $Z^a$; preferably cycle B is selected from
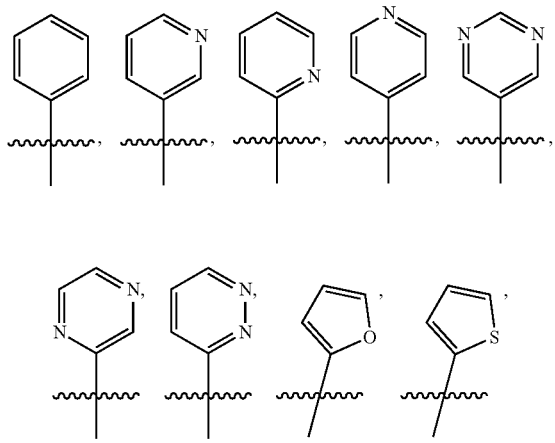

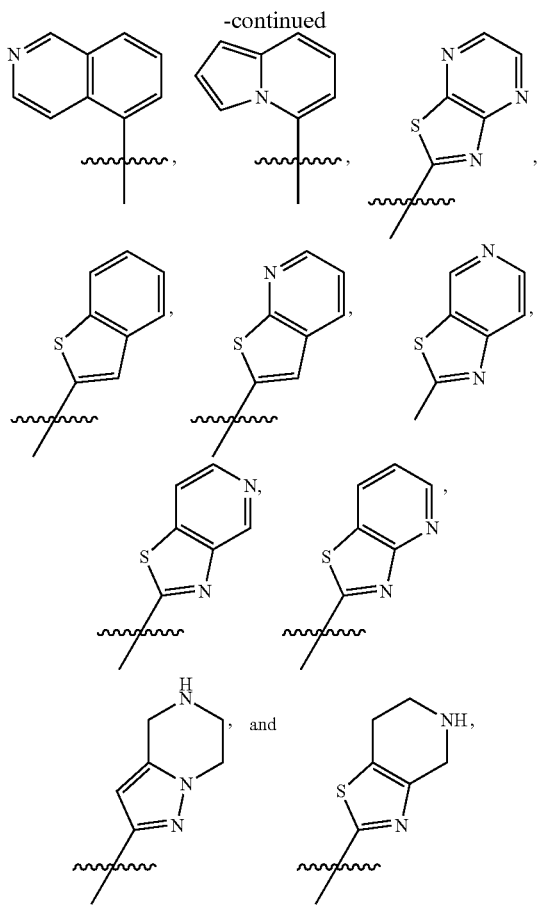

wherein the wavy line (∿) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl, are optionally substituted with one, two, or three $Z^{1c}$; preferably said $C_{1-6}$alkyl is optionally substituted with one, two, or three $Z^{1c}$;

each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —O$Z^2$, —O—C(=O)$Z^3$, =O, —S(=O)$_2Z^3$, —S(=O)$_2$N$Z^4Z^5$, trifluoromethyl, trifluoromethoxy, —N$Z^4Z^5$, —N$Z^4$C(=O)$Z^2$, —N$Z^4$C(=O)—O$Z^2$, cyano, —C(=O)$Z^3$, —C(=O)O$Z^2$, —C(=O)N$Z^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$ alkyl; preferably said $C_{1-6}$alkyl, hetero$C_{1-6}$alkyl, aryl, heterocycle, and heterocycle-$C_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said $C_{1-6}$alkyl, aryl, and heterocycle are optionally substituted with one, two, or three substituents selected from hydroxyl, =O, —O—C(O) Me, cyano, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{1-6}$alkenyl, arylheteroC$_{1-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from $C_{1-6}$alkyl, aryl, heterocycle, and heterocycle-C$_{1-6}$alkyl; more preferably $Z^2$ is independently selected from $C_{1-6}$alkyl, aryl, and heterocycle-C$_{1-6}$alkyl;
  wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—C$_{1-6}$alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; preferably said $C_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, heteroC$_{1-6}$ alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^3$ is independently selected from hydroxyl, $C_{1-6}$alkyl, aryl, and heterocycle; more preferably $Z^3$ is independently selected from hydroxyl, $C_{1-6}$alkyl, and heterocycle;
  wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two or three substituents selected from $C_{1-6}$alkyl, $C_{2-6}$alkenyl, $C_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said $C_{1-6}$alkyl, aryl, and heterocycle are optionally substituted with one, two, or three substituents selected from $C_{1-6}$alkyl and —N(CH$_3$)$_2$; more preferably said $C_{1-6}$alkyl and heterocycle are optionally substituted with one, two, or three substituents selected from $C_{1-6}$alkyl and —N(CH$_3$)$_2$;

each $Z^4$ and $Z^5$ is independently selected from hydrogen, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, $C_{3-7}$cycloalkyl, heterocycle, arylC$_{1-6}$ alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each $Z^4$ and $Z^5$ is independently selected from hydrogen, $C_{1-6}$alkyl, aryl, $C_{3-7}$cycloalkyl, and heterocycle; more preferably each $Z^4$ and $Z^5$ is independently selected from hydrogen, $C_{1-6}$alkyl, and $C_{3-7}$cycloalkyl;
  wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—C$_{1-6}$alkyl, —OCF$_3$, cyano, nitro, or —NH$_2$;
and wherein $Z^4$ and $Z^5$ can be taken together in order to form a (5-, 6-, or 7-membered) heterocycle which is optionally substituted with $C_{1-6}$alkyl, $C_{2-6}$alkenyl, $C_{2-6}$alkynyl, hydroxyl, halogen, —SH, trifluoromethyl, —O—C$_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof; with the proviso that compound of formula (A) is not N-(5-(2-(7-ethyl-1H-indol-3-yl)-2-oxo-1-phenylethylamino)-2-methoxyphenyl)-methanesulfonamide (CAS nr. 1294288-37-1);

3-(2-(1H-indol-3-yl)-2-oxo-1-phenylethylamino)benzenesulfonamide (CAS nr. 1211427-21-2);

2-(3,4-dihydro-2H-benzo[b][1,4]dioxepin-7-ylamino)-1-(1H-indol-3-yl)-2-phenylethanone (CAS nr. 1090733-87-1);

1-(1H-indol-3-yl)-2-phenyl-2-(pyridin-3-ylmethylamino)ethanone (CAS nr. 875860-58-5); or 2-(benzo[d][1,3]dioxol-5-ylmethylamino)-1-(1H-indol-3-yl)-2-phenylethanone (CAS nr. 920816-95-1).

One aspect of the invention relates to the compounds of formula (A) for use as a medicine, (A)

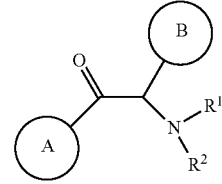

wherein,
cycle A is a heterocycle optionally substituted with one, two, or three $Z^1$; preferably cycle A is a heterocycle optionally substituted with one or two $Z^1$; more preferably cycle A is a heterocycle selected from

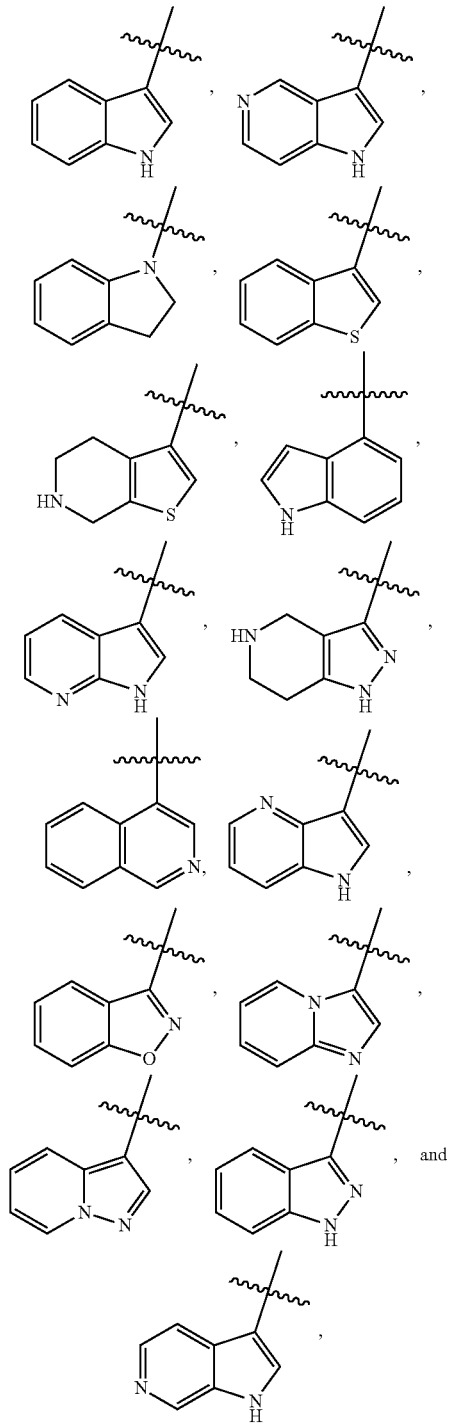

wherein the wavy line ($\sim$) indicates of attachment to the carbonyl of the main formula (A), and wherein the depicted heterocycles may be optionally substituted with one or two $Z^1$;

cycle B is selected from aryl and heterocycle, wherein said aryl and heterocycle are optionally substituted with one, two, or three $Z^{1a}$; preferably cycle B is selected from

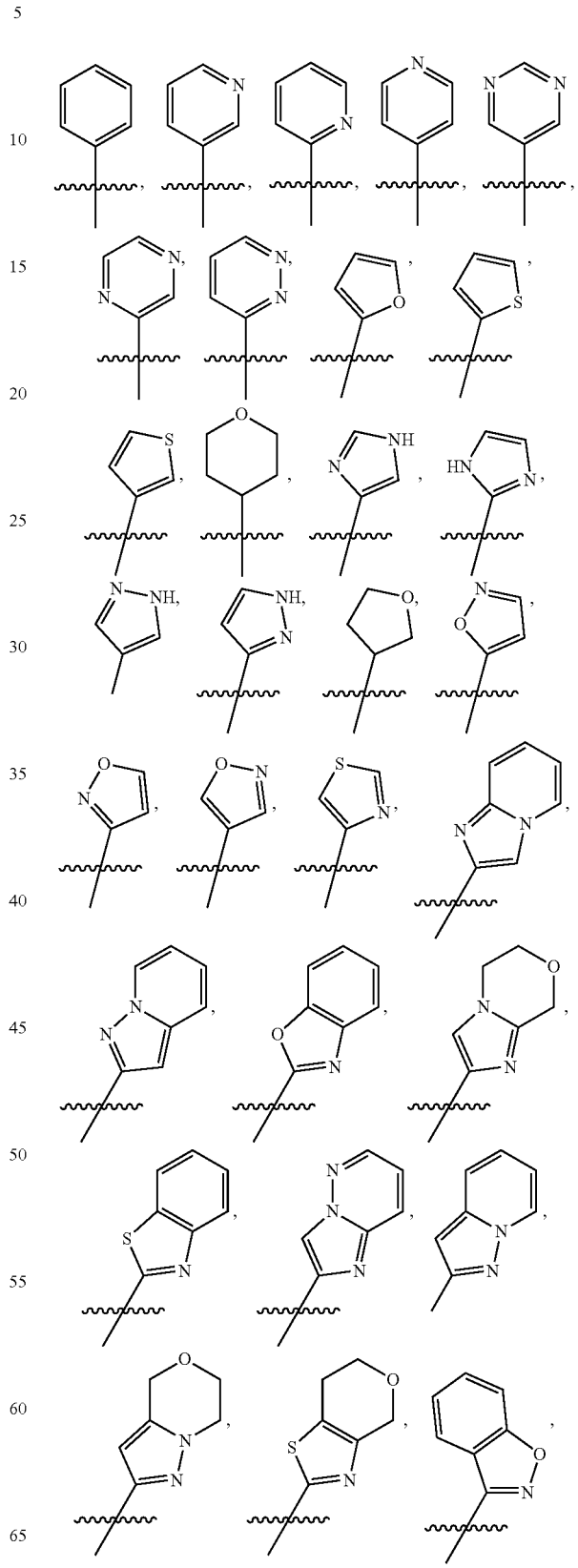

-continued

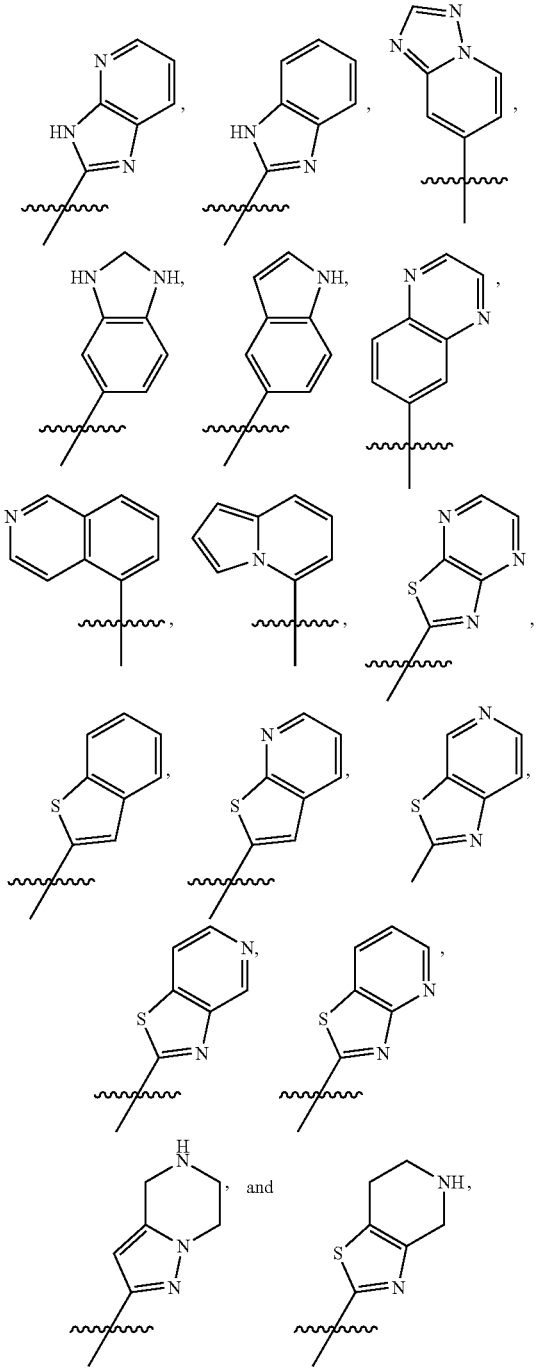

wherein the wavy line (⌇) indicates the point of attachment to the carbon atom of the main formula (A), and wherein the depicted cycles may be optionally substituted with one, two, or three $Z^{1a}$;

R$^1$ is selected from $C_{1-6}$alkyl, $C_{3-7}$cycloalkyl, $C_{3-7}$cycloalkenyl, $C_{3-7}$cycloalkynyl, aryl, heterocycle, arylC$_{1-6}$alkyl, arylC$_{2-6}$alkenyl, arylC$_{2-6}$alkynyl, heterocycle-C$_{1-6}$alkyl, heterocycle-C$_{2-6}$alkenyl, heterocycle-C$_{2-6}$alkynyl, arylheteroC$_{1-6}$alkyl, arylheteroC$_{2-6}$alkenyl, arylheteroC$_{2-6}$alkynyl, heterocycle-heteroC$_{1-6}$alkyl, heterocycle-heteroC$_{2-6}$alkenyl, and heterocycle-heteroC$_{2-6}$alkynyl; preferably R$^1$ is selected from $C_{1-6}$alkyl, $C_{3-7}$cycloalkyl, aryl, heterocycle; and wherein said $C_{1-6}$alkyl, $C_{3-7}$cycloalkyl, $C_{3-7}$cycloalkenyl, $C_{3-7}$cycloalkynyl, aryl, heterocycle, arylC$_{1-6}$alkyl, arylC$_{2-6}$alkenyl, arylC$_{2-6}$alkynyl, heterocycle-C$_{1-6}$alkyl, heterocycle-C$_{2-6}$alkenyl, heterocycle-C$_{2-6}$alkynyl, arylheteroC$_{1-6}$alkyl, arylheteroC$_{2-6}$alkenyl, arylheteroC$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

R$^2$ is selected from hydrogen, —C(O)Z$^3$, $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl; preferably R$^2$ is selected from hydrogen, —C(O)Z$^3$, and $C_{1-6}$alkyl; and wherein said $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl, are optionally substituted with one, two, or three $Z^{1c}$; preferably said $C_{1-6}$alkyl is optionally substituted with one, two, or three $Z^{1c}$;

each $Z^1$, $Z^{1a}$, $Z^{1b}$, and $Z^{1c}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)—OZ$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$ alkyl, heterocycle-heteroC$_{2-6}$alkenyl, and heterocycle-heteroC$_{2-6}$alkynyl; preferably each $Z^1$, $Z^{1a}$, $Z^{1b}$, and $Z^{1c}$ is independently selected from the group consisting of halogen, hydroxyl, sulfhydryl, —OZ$^2$, —O—C(=O)Z$^3$, =O, —SZ$^2$, =S, —S(=O)Z$^2$, —S(=O)$_2$Z$^3$, —S(=O)$_2$NZ$^4$Z$^5$, trifluoromethyl, trifluoromethoxy, nitro, —NZ$^4$Z$^5$, —NZ$^4$S(=O)$_2$Z$^2$, —NZ$^4$C(=O)Z$^2$, —NZ$^4$C(=O)—OZ$^2$, —NZ$^4$C(=O)NZ$^4$Z$^5$, cyano, —C(=O)Z$^3$, —C(=O)OZ$^2$, —C(=O)NZ$^4$Z$^5$, —C(=O)H, $C_{1-6}$alkyl, heteroC$_{1-6}$alkyl, aryl, heterocycle, and heterocycle-C$_{1-6}$alkyl; more preferably each $Z^1$, $Z^{1a}$, $Z^{1b}$, and $Z^c$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, $C_{1-6}$alkyl, heteroC$_{1-6}$alkyl, aryl, heterocycle, and heterocycle-C$_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)

$OC_{1-6}$alkyl, —$NH_2$, —$NHCH_3$; —$N(CH_3)_2$, —NH—C(=O)O—$C_{1-4}$alkyl, morpholinyl, —$S(O)_2C_{1-4}$alkyl, and —O—$C_{1-6}$ alkyl; preferably said $C_{1-6}$alkyl, hetero$C_{1-6}$alkyl, aryl, heterocycle, and heterocycle-$C_{1-6}$ alkyl, are optionally substituted with one, two, or three substituents selected from hydroxyl, =O, halogen, —SH, =S, trifluoromethyl, —$OCF_3$, —O—C(O)Me, cyano, nitro, —C(O)OH, —C(O)O$C_{1-6}$alkyl, —$NH_2$, —$NHCH_3$; —$N(CH_3)_2$, —NH—C(=O)O—$C_{1-4}$alkyl, morpholinyl, —$S(O)_2C_{1-4}$alkyl, and —O—$C_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)O$C_{1-6}$alkyl, —$NH_2$, —$NHCH_3$; —$N(CH_3)_2$, —NH—C(=O)O—$C_{1-4}$alkyl, morpholinyl, —$S(O)_2C_{1-4}$alkyl, and —O—$C_{1-6}$alkyl;

each $Z^2$ is independently selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{1-6}$alkenyl, arylhetero$C_{1-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $Z^2$ is independently selected from $C_{1-6}$alkyl, aryl, heterocycle, and heterocycle-$C_{1-6}$alkyl; more preferably $Z^2$ is independently selected from $C_{1-6}$alkyl, aryl, and heterocycle-$C_{1-6}$alkyl;
  wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—$C_{1-6}$alkyl, —$OCF_3$, —$S(=O)_2C_{1-4}$alkyl, cyano, nitro, —C(=O)OH, —C(=O)O—$C_{1-4}$alkyl, —$NH_2$, and —$N(CH_3)_2$, pyrrolidinyl, piperidinyl, and piperazinyl; preferably said $C_{1-6}$alkyl, aryl, heterocycle, and heterocycle-$C_{1-6}$alkyl, are optionally substituted with one, two, or three substituents selected from hydroxyl, =O, halogen, —SH, =S, trifluoromethyl, difluoromethyl, —O—$C_{1-6}$ alkyl, —$OCF_3$, —$S(=O)_2C_{1-4}$alkyl, cyano, nitro, —C(=O)OH, —C(=O)O—$C_{1-4}$alkyl, —$NH_2$, and —$N(CH_3)_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—$C_{1-6}$alkyl, —$S(=O)_2C_{1-4}$alkyl, —C(=O)OH, —C(=O)O—$C_{1-4}$alkyl, —$NH_2$, and —$N(CH_3)_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, hetero$C_{1-6}$ alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $Z^3$ is independently selected from hydroxyl, $C_{1-6}$alkyl, aryl, and heterocycle; more preferably $Z^3$ is independently selected from hydroxyl, $C_{1-6}$alkyl, and heterocycle;
  wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —$OCF_3$, cyano, nitro, —C(=O)OH, —$NH_2$, and —$N(CH_3)_2$; preferably said $C_{1-6}$alkyl, aryl, and heterocycle are optionally substituted with one, two, or three substituents selected from $C_{1-6}$alkyl and —$N(CH_3)_2$; more preferably said $C_{1-6}$alkyl and heterocycle are optionally substituted with one, two, or three substituents selected from $C_{1-6}$alkyl and —$N(CH_3)_2$;

each $Z^4$ and $Z^5$ is independently selected from hydrogen, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, $C_{3-7}$cycloalkyl, heterocycle, aryl$C_{1-6}$ alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably each $Z^4$ and $Z^5$ is independently selected from hydrogen, $C_{1-6}$alkyl, aryl, $C_{3-7}$cycloalkyl, and heterocycle; more preferably each $Z^4$ and $Z^5$ is independently selected from hydrogen, $C_{1-6}$alkyl, and $C_{3-7}$cycloalkyl;
  wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —$OCF_3$, cyano, nitro, or —$NH_2$;
  and wherein $Z^4$ and $Z^5$ can be taken together in order to form a (5-, 6-, or 7-membered) heterocycle which is optionally substituted with $C_{1-6}$alkyl, $C_{2-6}$alkenyl, $C_{2-6}$alkynyl, hydroxyl, halogen, —SH, trifluoromethyl, —O—$C_{1-6}$alkyl, —$OCF_3$, cyano, nitro, —C(=O)OH, or —$NH_2$;

and isomers (in particular stereo-isomers or tautomers), solvates, salts (in particular pharmaceutically acceptable salts) or prodrugs thereof.

One aspect of the invention relates to the compounds of formula (A) for use in the prevention or treatment of a flavivirus infection in an animal, mammal or human, preferably an infection with dengue virus or yellow fever virus,

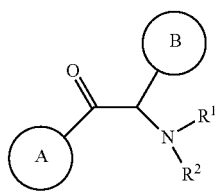
(A)

wherein,
cycle A is a heterocycle optionally substituted with one, two, or three $Z^1$; preferably cycle A is a heterocycle optionally substituted with one or two $Z^1$; more preferably cycle A is a heterocycle selected from

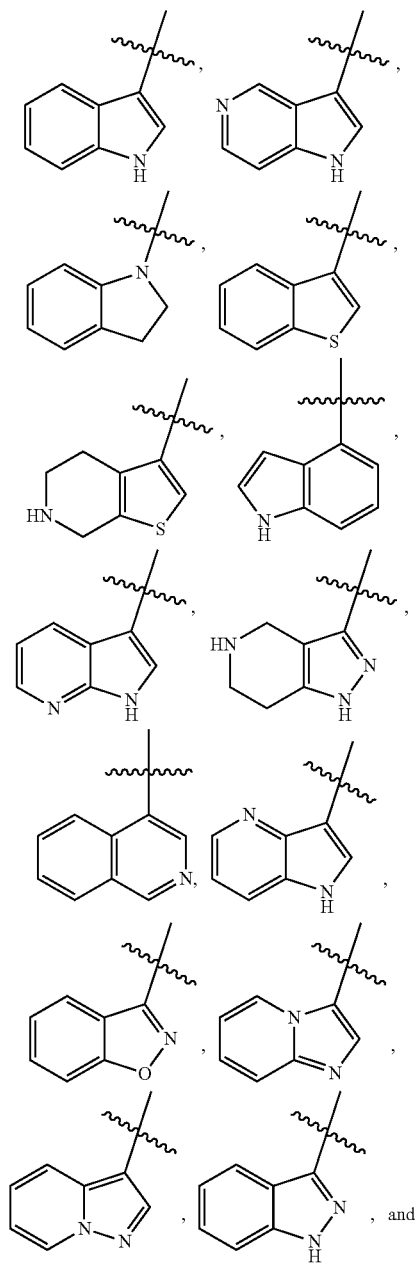

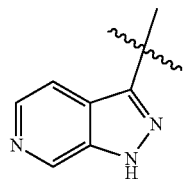

wherein the wavy line (∿) indicates the point of attachment to the carbonyl of the main formula (A), and wherein the depicted heterocycles may be optionally substituted with one or two $Z^1$;

cycle B is selected from aryl and heterocycle, wherein said aryl and heterocycle are optionally substituted with one, two, or three $Z^{1a}$; preferably cycle B is selected from

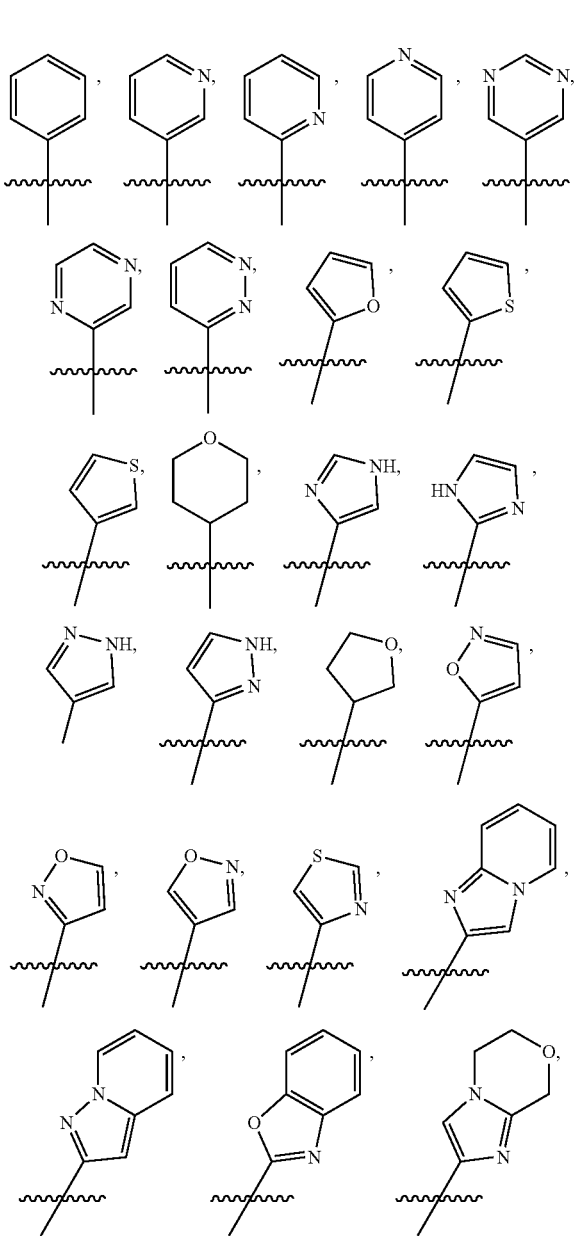

-continued

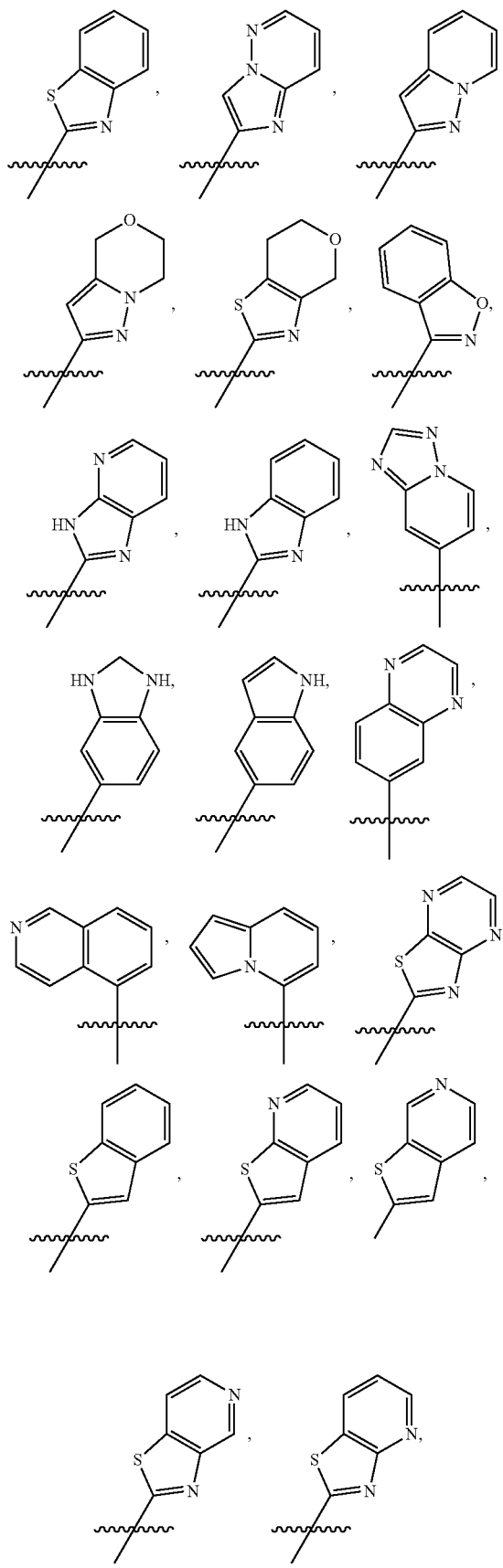

-continued

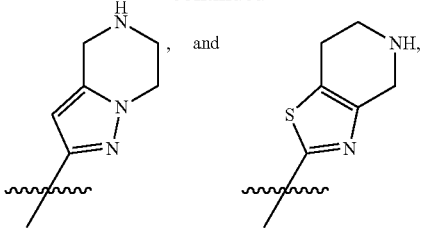

wherein the wavy line (∿) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$ alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl; preferably $R^2$ is selected from hydrogen, —C(O)$Z^3$, and $C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl, are optionally substituted with one, two, or three $Z^{1c}$; preferably said $C_{1-6}$alkyl is optionally substituted with one, two, or three $Z^{1c}$;

each Z, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)$Z^3$, —C(=O)O$Z^2$, —C(=O)N$Z^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O)N$Z^4Z^5$, cyano, —C(=O)Z$^3$, —C(=O)OZ$^2$, —C(=O)NZ$^4$Z$^5$, —C(=O)H, C$_{1-6}$alkyl, heteroC$_{1-6}$alkyl, aryl, heterocycle, and heterocycle-C$_{1-6}$alkyl; more preferably each Z$^1$, Z$^{1a}$, Z$^{1b}$, and Z$^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, C$_{1-6}$alkyl, heteroC$_{1-6}$alkyl, aryl, heterocycle, and heterocycle-C$_{1-6}$alkyl;

and wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$ alkyl; preferably said C$_{1-6}$alkyl, heteroC$_{1-6}$alkyl, aryl, heterocycle, and heterocycle-C$_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said C$_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl;

each Z$^2$ is independently selected from C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably Z$^2$ is independently selected from C$_{1-6}$alkyl, aryl, heterocycle, and heterocycle-C$_{1-6}$alkyl; more preferably Z$^2$ is independently selected from C$_{1-6}$alkyl, aryl, and heterocycle-C$_{1-6}$alkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; preferably said C$_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; more preferably said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;

each Z$^3$ is independently selected from hydroxyl, C$_{1-6}$alkyl, C$_{2-6}$alkenyl, C$_{2-6}$alkynyl, heteroC$_{1-6}$ alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$ alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably Z$^3$ is independently selected from hydroxyl, C$_{1-6}$alkyl, aryl, and heterocycle; more preferably Z$^3$ is independently selected from hydroxyl, C$_{1-6}$alkyl, and heterocycle;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;

each Z$^4$ and Z$^5$ is independently selected from hydrogen, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, C$_{3-7}$cycloalkyl, heterocycle, arylC$_{1-6}$ alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each Z$^4$ and Z$^5$ is independently selected from hydrogen, C$_{1-6}$alkyl, aryl, C$_{3-7}$cycloalkyl, and heterocycle; more preferably each Z$^4$ and Z$^5$ is independently selected from hydrogen, C$_{1-6}$alkyl, and C$_{3-7}$cycloalkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —OCF$_3$, cyano, nitro, —C(=O)OH or —NH$_2$;

and wherein $Z^4$ and $Z^5$ can be taken together in order to form a (5-, 6-, or 7-membered) heterocycle which is optionally substituted with $C_{1-6}$alkyl, $C_{2-6}$alkenyl, $C_{2-6}$alkynyl, hydroxyl, halogen, —SH, trifluoromethyl, —O—$C_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof.

One aspect of the invention relates to the compounds of formula (A) for use in the prevention or treatment of a flavivirus infection in an animal, mammal or human, preferably an infection with dengue virus or yellow fever virus,

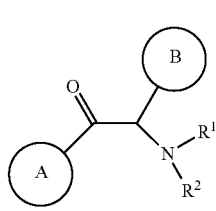

(A)

wherein,
cycle A is a heterocycle optionally substituted with one, two, or three $Z^1$; preferably cycle A is a heterocycle optionally substituted with one or two $Z^1$; more preferably cycle A is a heterocycle selected from

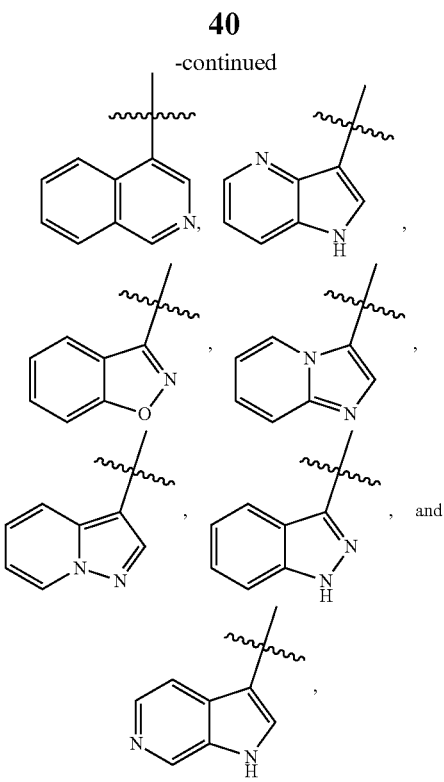

wherein the wavy line (〜) indicates the point of attachment to the carbonyl of the main formula (A), and wherein the depicted heterocycles may be optionally substituted with one or two $Z^1$;

cycle B is selected from aryl and heterocycle, wherein said aryl and heterocycle are optionally substituted with one, two, or three $Z^{1a}$; preferably cycle B is selected from

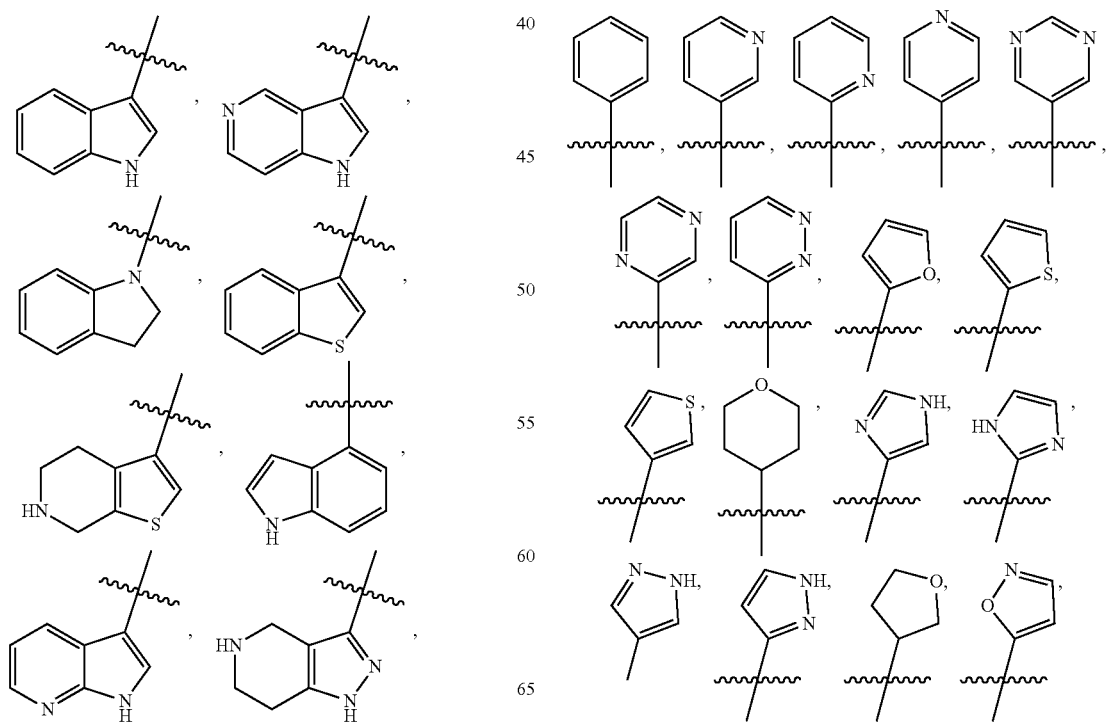

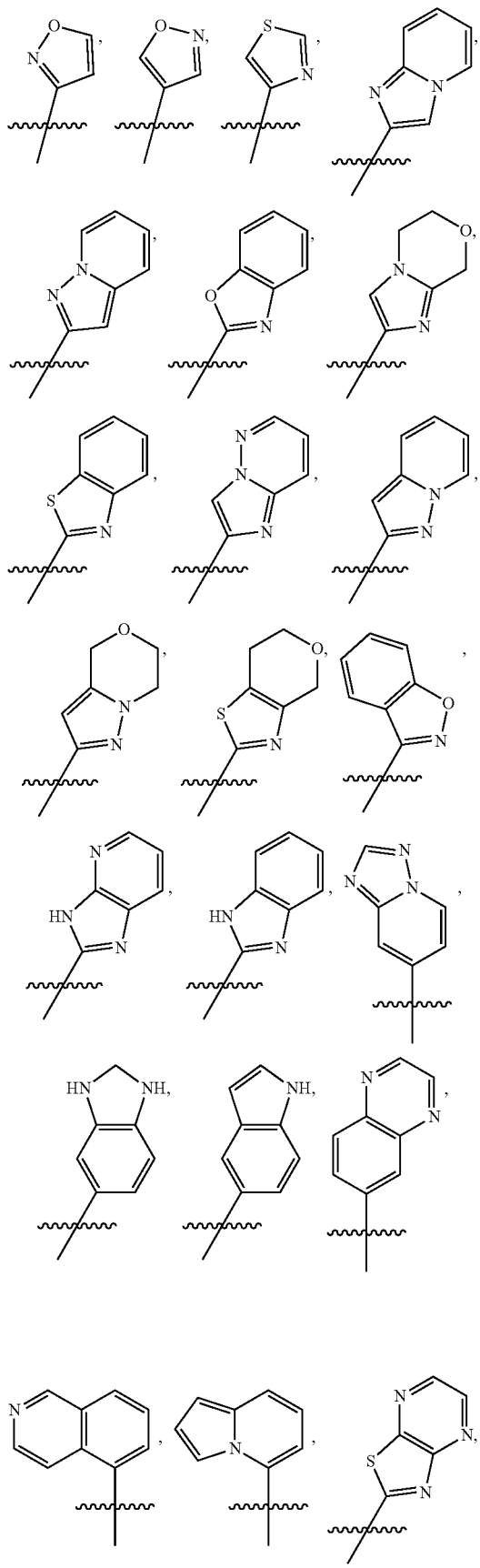
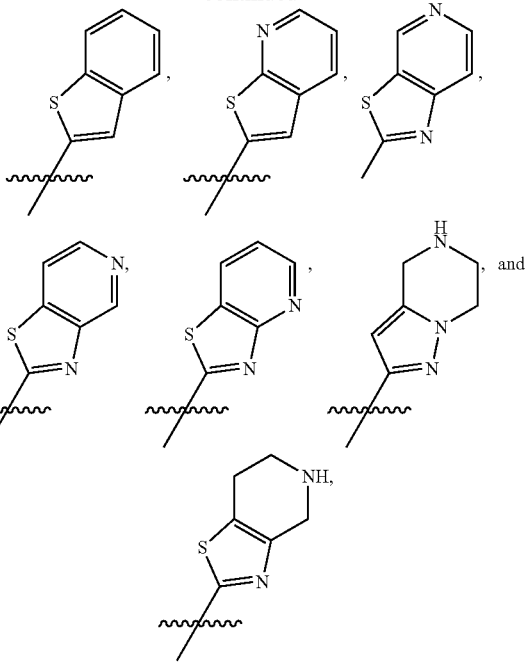

wherein the wavy line (∿) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle; and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl; preferably $R^2$ is selected from hydrogen, —C(O)$Z^3$, and $C_{1-6}$alkyl; and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl, are optionally substituted with one, two, or three $Z^{1c}$; preferably said $C_{1-6}$alkyl is optionally substituted with one, two, or three $Z^{1c}$;

each $Z^1$, $Z^{1a}$, $Z^{1b}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2NZ^4Z^5$, trifluoromethyl, trifluoromethoxy, nitro, —$NZ^4Z^5$, —$NZ^4S(=O)_2Z^2$, —$NZ^4C(=O)Z^2$, —$NZ^4C(=O)$—$OZ^2$, —$NZ^4C(=O)$ $NZ^4Z^5$, cyano, —C(=O)$Z^3$, —C(=O)O$Z^2$, —C(=O)$NZ^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$ alkyl, heterocycle-hetero$C_{2-6}$alkenyl, and heterocycle-hetero$C_{2-6}$alkynyl; preferably each $Z^1$, $Z^{1a}$, $Z^{1b}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2NZ^4Z^5$, trifluoromethyl, trifluoromethoxy, nitro, —$NZ^4Z^5$, —$NZ^4$S(=O)$_2Z^2$, —$NZ^4$C(=O)$Z^2$, —$NZ^4$C(=O)—$OZ^2$, —$NZ^4$C(=O)$NZ^4Z^5$, cyano, —C(=O)$Z^3$, —C(=O)$OZ^2$, —C(=O)$NZ^4Z^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, $Z^{1b}$, and $Z^{1c}$ is independently selected from the group consisting of halogen, hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)—$OZ^2$, cyano, —C(=O)$Z^3$, —C(=O)$OZ^2$, —C(=O)$NZ^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —$OCF_3$, —O—C(O)Me, cyano, nitro, —C(O)OH, —C(O)O$C_{1-6}$alkyl, —$NH_2$, —$NHCH_3$; —N($CH_3$)$_2$, —NH—C(=O)O—$C_{1-4}$alkyl, morpholinyl, —S(O)$_2C_{1-4}$alkyl, and —O—$C_{1-6}$ alkyl; preferably said $C_{1-6}$alkyl, hetero$C_{1-6}$alkyl, aryl, heterocycle, and heterocycle-$C_{1-6}$ alkyl, are optionally substituted with one, two, or three substituents selected from hydroxyl, =O, halogen, —SH, =S, trifluoromethyl, —$OCF_3$, —O—C(O)Me, cyano, nitro, —C(O)OH, —C(O)O$C_{1-6}$alkyl, —$NH_2$, —$NHCH_3$; —N($CH_3$)$_2$, —NH—C(=O)O—$C_{1-4}$alkyl, morpholinyl, —S(O)$_2C_{1-4}$alkyl, and —O—$C_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)O$C_{1-6}$alkyl, —$NH_2$, —$NHCH_3$; —N($CH_3$)$_2$, —NH—C(=O)O—$C_{1-4}$alkyl, morpholinyl, —S(O)$_2C_{1-4}$alkyl, and —O—$C_{1-6}$alkyl;

each $Z^2$ is independently selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{1-6}$alkyl, arylhetero$C_{1-6}$alkyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $Z^2$ is independently selected from $C_{1-6}$alkyl, aryl, heterocycle, and heterocycle-$C_{1-6}$alkyl; more preferably $Z^2$ is independently selected from $C_{1-6}$alkyl, aryl, and heterocycle-$C_{1-6}$alkyl;

wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—$C_{1-6}$alkyl, —$OCF_3$, —S(=O)$_2C_{1-4}$alkyl, cyano, nitro, —C(=O)OH, —C(=O)O—$C_{1-4}$alkyl, —$NH_2$, and —N($CH_3$)$_2$, pyrrolidinyl, piperidinyl, and piperazinyl; preferably said $C_{1-6}$alkyl, aryl, heterocycle, and heterocycle-$C_{1-6}$alkyl, are optionally substituted with one, two, or three substituents selected from hydroxyl, =O, halogen, —SH, =S, trifluoromethyl, difluoromethyl, —O—$C_{1-6}$ alkyl, —$OCF_3$, —S(=O)$_2C_{1-4}$alkyl, cyano, nitro, —C(=O)OH, —C(=O)O—$C_{1-4}$alkyl, —$NH_2$, and —N($CH_3$)$_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—$C_{1-6}$alkyl, —S(=O)$_2C_{1-4}$alkyl, —C(=O)OH, —C(=O)O—$C_{1-4}$alkyl, —$NH_2$, and —N($CH_3$)$_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, hetero$C_{1-6}$ alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $Z^3$ is independently selected from hydroxyl, $C_{1-6}$alkyl, aryl, and heterocycle; more preferably $Z^3$ is independently selected from hydroxyl, $C_{1-6}$alkyl, and heterocycle;

wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —$OCF_3$, cyano, nitro, —C(=O)OH, —$NH_2$, and —N($CH_3$)$_2$; preferably said $C_{1-6}$alkyl, aryl, and heterocycle are optionally substituted with one, two, or three substituents selected from $C_{1-6}$alkyl and —N($CH_3$)$_2$; more preferably said $C_{1-6}$alkyl and heterocycle are optionally substituted with one, two, or three substituents selected from $C_{1-6}$alkyl and —N($CH_3$)$_2$;

each $Z^4$ and $Z^5$ is independently selected from hydrogen, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, $C_{3-7}$cycloalkyl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably each $Z^4$ and $Z^5$ is independently selected from hydrogen, $C_{1-6}$alkyl, aryl, $C_{3-7}$cycloalkyl, and heterocycle; more preferably each $Z^4$ and $Z^5$ is independently selected from hydrogen, $C_{1-6}$alkyl, and $C_{3-7}$cycloalkyl;

wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —OCF$_3$, cyano, nitro, or —NH$_2$;

and wherein $Z^4$ and $Z^5$ can be taken together in order to form a (5-, 6-, or 7-membered) heterocycle which is optionally substituted with $C_{1-6}$alkyl, $C_{2-6}$alkenyl, $C_{2-6}$alkynyl, hydroxyl, halogen, —SH, trifluoromethyl, —O—$C_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof.

In a particular embodiment of this aspect of the invention, the compounds have a structure according to formula (B),

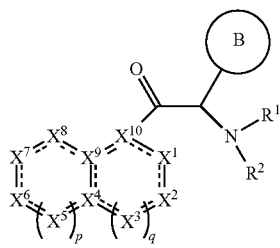

(B)

wherein cycle B, $R^1$, $R^2$, $Z^1$, $Z^2$, $Z^3$, $Z^4$, and $Z^5$ are as defined in any one of the embodiments with formula (A), and each dotted line represents an optional double bond whereby maximally 6 non-adjacent dotted lines can form a double bond;
each of $X^1$, $X^2$, $X^3$, $X^5$, $X^6$, $X^7$ and $X^8$ is independently selected from $CR^3$; $NR^4$; O; and S;
each of $X^4$ and $X^9$ is independently selected from C; CH; and N;
$X^{10}$ is selected from C; CH; and N; whereby minimally 5 of $X^1$ to $X^{10}$ are selected from $CR^3$, C or CH;
p is 0; 1; or 2;
q is 0; 1; or 2;
each $R^3$ is independently selected from hydrogen and $Z^1$;

each $R^4$ is independently selected from hydrogen; hydroxyl; sulfhydryl; —S(O)$Z^2$; —S(O)$_2Z^3$; —S(O)$_2NZ^4Z^5$; trifluoromethyl; —C(O)$Z^3$; —C(O)O$Z^2$; —C(O)N$Z^4Z^5$; —C(O)H; alkyl; alkenyl; alkynyl; heteroalkyl; heteroalkenyl; heteroalkynyl; aryl; heterocycle; arylalkyl; arylalkenyl; arylalkynyl; arylheteroalkyl; arylheteroalkenyl; arylheteroalkynyl; heterocycle-alkyl; heterocycle-alkenyl; heterocycle-alkynyl; heterocycle-heteroalkyl, heterocycle-heteroalkenyl; or heterocycle-heteroalkynyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, or heterocycle-heteroalkynyl can be unsubstituted or substituted with one or more substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(O)OH or NH$_2$;

and isomers (in particular stereo-isomers or tautomers), solvates, salts (in particular pharmaceutically acceptable salts) or prodrugs thereof.

In a particular embodiment of this aspect of the invention, the compounds, for use in the prevention or treatment of a flavivirus infection in an animal, mammal or human; for use as a medicine; or per se; have a structure according to formula (B),

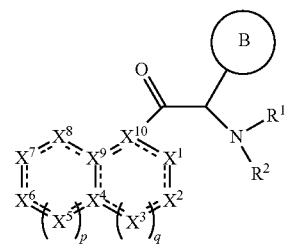

(B)

wherein
each dotted line represents an optional double bond whereby maximally 6 non-adjacent dotted lines can form a double bond;
each of $X^1$, $X^2$, $X^3$, $X^5$, $X^6$, $X^7$, and $X^8$ is independently selected from $CR^3$, N, $NR^4$, O, and S;
each of $X^4$ and $X^9$ is independently selected from C, CH, and N;
$X^{10}$ is selected from C, CH, and N;
whereby at least five of $X^1$ to $X^{10}$ are selected from $CR^3$, C, and CH; and at least one of $X^1$ to $X^{10}$ is a heteroatom;
p is 0, 1, or 2;
q is 0, 1, or 2;
preferably the moiety

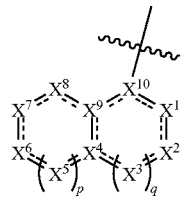

is selected from
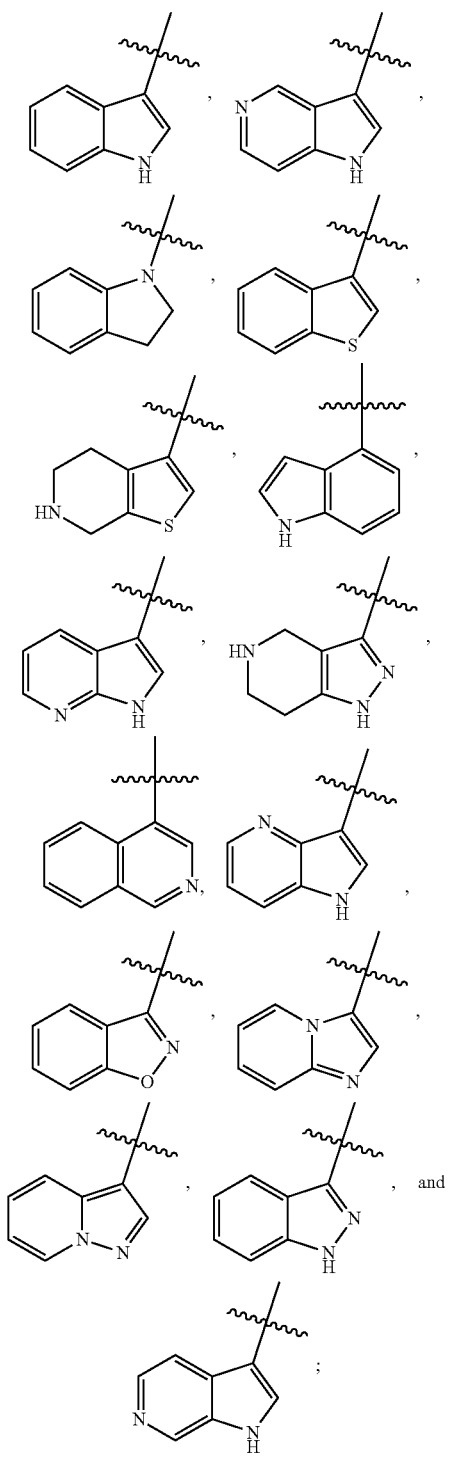
wherein the wavy line (⁓) indicates the point of attachment to the carbonyl of the main formula (B); wherein said moiety is optionally substituted with one or two $Z^1$;
cycle B is selected from aryl and heterocycle, wherein said aryl and heterocycle are optionally substituted with one, two, or three $Z^{1a}$; preferably cycle B is selected from
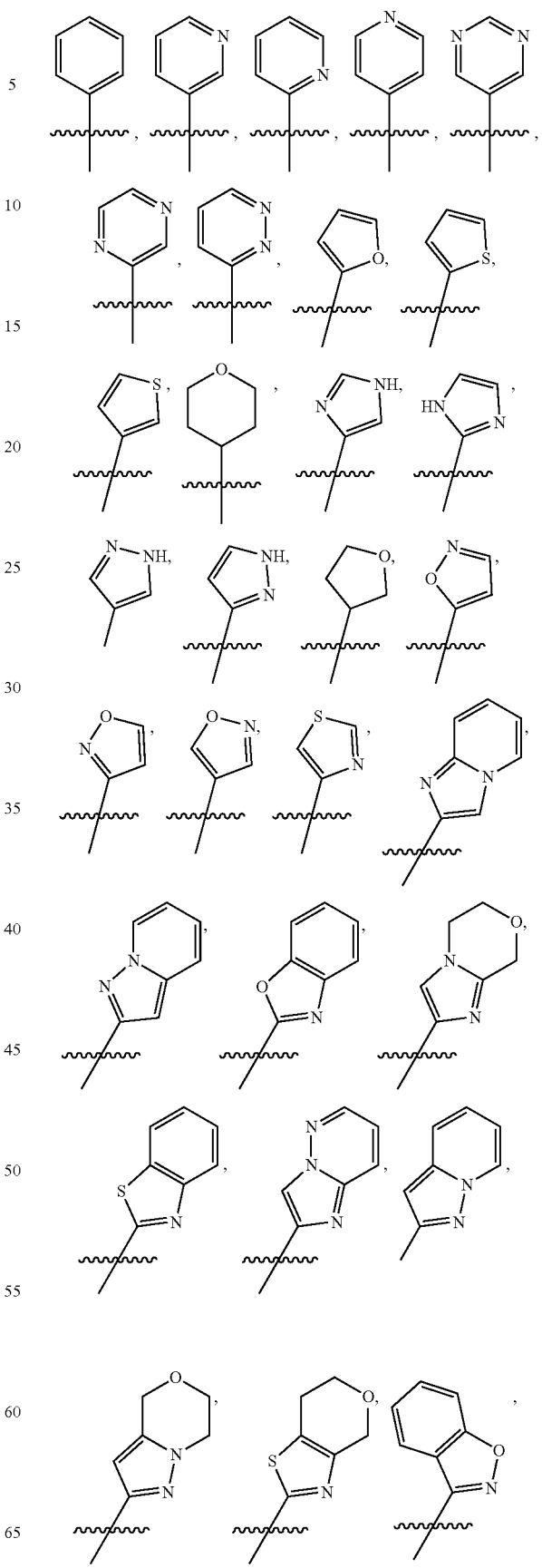

-continued

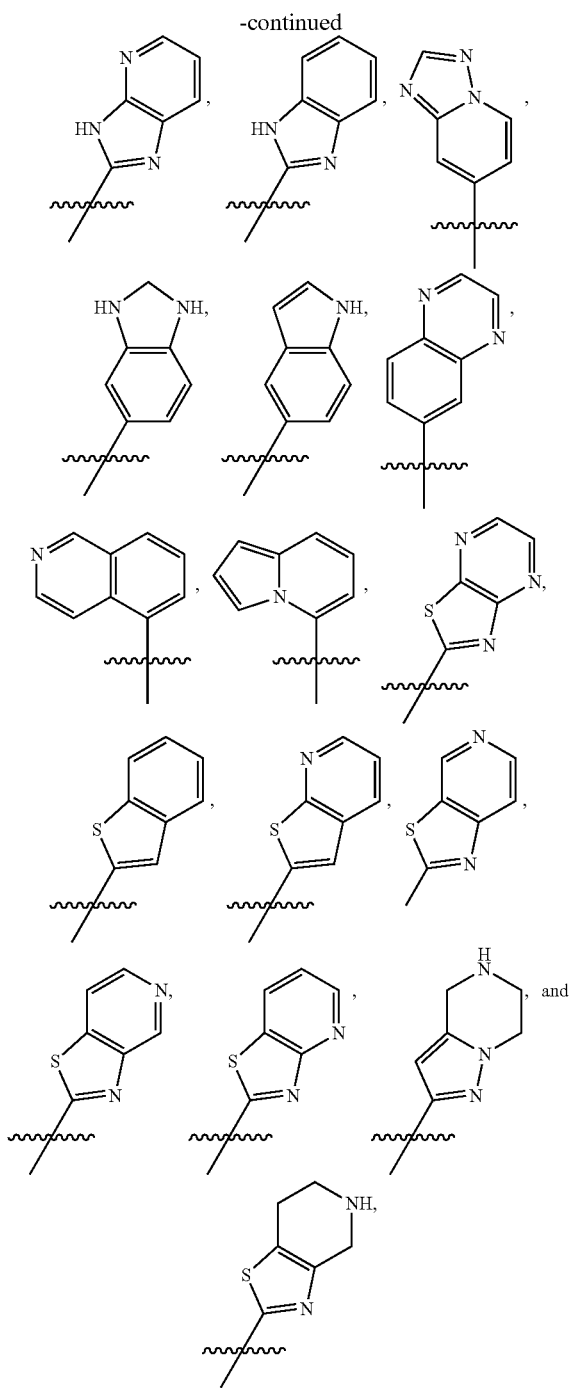

wherein the wavy line (∿) indicates the point of attachment to the carbon atom of the main formula (B), and wherein the depicted cycles may be optionally substituted with one, two, or three $Z^{1a}$;

$R^1$ is selected from alkyl, cycloalkyl, cycloalkenyl, cycloalkynyl, aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl, and heterocycle-heteroalkynyl; preferably $R^1$ is selected from alkyl, cycloalkyl, aryl, heterocycle;

and wherein said alkyl, cycloalkyl, cycloalkenyl, cycloalkynyl, aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl, and heterocycle-heteroalkynyl, are optionally substituted with one, two, or three $Z^{1b}$; preferably said alkyl, cycloalkyl, aryl, and heterocycle, are optionally substituted with one, two, or three $Z^{1b}$;

$R^2$ is selected from hydrogen, —C(O)$Z^3$, alkyl, alkenyl, alkynyl, heteroalkyl, heteroalkenyl, and heteroalkynyl; preferably $R^2$ is selected from hydrogen, —C(O)$Z^3$, and alkyl;

and wherein said alkyl, alkenyl, alkynyl, heteroalkyl, heteroalkenyl, and heteroalkynyl, are optionally substituted with one, two, or three $Z^{1c}$; preferably said alkyl is optionally substituted with one, two, or three $Z^{1c}$;

each $R^3$ is independently selected from hydrogen and $Z^1$;

each $R^4$ is independently selected from hydrogen, hydroxyl, sulfhydryl, —S(=O)$Z^2$, —S(=O)$_2Z^3$, —S(=O)$_2$N$Z^4Z^5$, trifluoromethyl, —C(=O)$Z^3$, —C(=O)O$Z^2$, —C(=O)N$Z^4Z^5$, —C(=O)H, alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl; preferably $R^4$ is independently selected from hydrogen, —S(=O)$_2Z^3$, —C(=O)O$Z^2$, alkyl, and heteroalkyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl are optionally substituted with one, two, or three substituents selected from alkyl, alkenyl, alkynyl, heteroalkyl, heteroalkenyl, heteroalkynyl, hydroxyl, =O, halogen, —SH, =S, trifluoromethyl, —OCF$_3$, cyano, nitro, —C(=O) OH, —C(O)Oalkyl, and —N(CH$_3$)$_2$, —NH$_2$, —NH—C(=O)O—C$_{1-4}$alkyl, —O-alkyl;

each Z, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O) $Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)—O$Z^2$, —N$Z^4$C(=O) N$Z^4Z^5$, cyano, —C(=O)$Z^3$, —C(=O)O$Z^2$, —C(=O) N$Z^4Z^5$, —C(=O)H, alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$N$Z^4Z^5$, trifluoromethyl, trifluoromethoxy, nitro, —N$Z^4Z^5$, —N$Z^4$S(=O)$_2Z^2$, —N$Z^4$C(=O)$Z^2$, —N$Z^4$C(=O)$_2Z^2$, —N$Z^4$C(=O) N$Z^4Z^5$, cyano, —C(=O)$Z^3$, —C(=O)O$Z^2$, —C(=O) N$Z^4Z^5$, —C(=O)H, alkyl, heteroalkyl, aryl, heterocycle, and heterocycle-alkyl; more preferably each $Z^1$, $Z^{1a}$, $Z^{1b}$, and $Z^{1c}$ is independently selected from the group consisting of halogen, hydroxyl, —OZ$^2$, —O—C(=O)Z$^3$, =O, —S(=O)$_2$Z$^3$, —S(=O)$_2$NZ$^4$Z$^5$, trifluoromethyl, trifluoromethoxy, —NZ$^4$Z$^5$, —NZ$^4$C(=O)Z$^2$, —NZ$^4$C(=O)—OZ$^2$, cyano, —C(=O)Z$^3$, —C(=O)OZ$^2$, —C(=O)NZ$^4$Z$^5$, alkyl, heteroalkyl, aryl, heterocycle, and heterocycle-alkyl;

and wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl, are optionally substituted with one, two, or three substituents selected from alkyl, alkenyl, alkynyl, heteroalkyl, heteroalkenyl, heteroalkynyl, hydroxyl, =O, halogen, —SH, =S, trifluoromethyl, —OCF$_3$, —O—C(O)Me, cyano, nitro, —C(O)OH, —C(O)Oalkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O-alkyl; preferably said alkyl, heteroalkyl, aryl, heterocycle, and heterocycle-alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)Oalkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O-alkyl; more preferably said alkyl, aryl, and heterocycle are optionally substituted with one, two, or three substituents selected from hydroxyl, =O, —O—C(O)Me, cyano, —C(O)OH, —C(O)O-alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O-alkyl;

each Z$^2$ is independently selected from alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl; preferably Z$^2$ is independently selected from alkyl, aryl, heterocycle, and heterocycle-alkyl; more preferably Z$^2$ is independently selected from alkyl, aryl, and heterocycle-alkyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl, are optionally substituted with one, two, or three substituents selected from alkyl, alkenyl, alkynyl, hydroxyl, =O, halogen, —SH, =S, trifluoromethyl, difluoromethyl, —O-alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; preferably said alkyl, aryl, heterocycle, and heterocycle-alkyl, are optionally substituted with one, two, or three substituents selected from hydroxyl, =O, halogen, —SH, =S, trifluoromethyl, difluoromethyl, —O-alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; more preferably said alkyl, and aryl, are optionally substituted with one, two, or three substituents selected from hydroxyl, halogen, difluoromethyl, —O-alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;

each Z$^3$ is independently selected from hydroxyl, alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl; preferably Z$^3$ is independently selected from hydroxyl, alkyl, aryl, and heterocycle; more preferably Z$^3$ is independently selected from hydroxyl, alkyl, and heterocycle;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl, are optionally substituted with one, two, or three substituents selected from alkyl, alkenyl, alkynyl, hydroxyl, =O, halogen, —SH, =S, trifluoromethyl, —O-alkyl, —OCF$_3$, cyano, nitro, —C(=O)OH, —NH$_2$, and —N(CH$_3$)$_2$; preferably said alkyl, aryl, and heterocycle are optionally substituted with one, two, or three substituents selected from alkyl and —N(CH$_3$)$_2$; more preferably said alkyl and heterocycle are optionally substituted with one, two, or three substituents selected from alkyl and —N(CH$_3$)$_2$;

each Z$^4$ and Z$^5$ is independently selected from hydrogen, alkyl, alkenyl, alkynyl, heteroalkyl, heteroalkenyl, heteroalkynyl, aryl, cycloalkyl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl; preferably each Z$^4$ and Z$^5$ is independently selected from hydrogen, alkyl, aryl, cycloalkyl, and heterocycle; more preferably each Z$^4$ and Z$^5$ is independently selected from hydrogen, alkyl, and cycloalkyl;

wherein said alkyl, alkenyl, alkynyl, heteroalkyl, heteroalkenyl, heteroalkynyl, aryl, heterocycle, arylalkyl, arylalkenyl, arylalkynyl, arylheteroalkyl, arylheteroalkenyl, arylheteroalkynyl, heterocycle-alkyl, heterocycle-alkenyl, heterocycle-alkynyl, heterocycle-heteroalkyl, heterocycle-heteroalkenyl, and heterocycle-heteroalkynyl, are optionally substituted with one, two, or three substituents selected from alkyl, alkenyl, alkynyl, hydroxyl, =O, halogen, —SH, =S, trifluoromethyl, —O-alkyl, —OCF$_3$, cyano, nitro, —C(=O)OH or —NH$_2$;

and wherein Z$^4$ and Z$^5$ can be taken together in order to form a (5-, 6-, or 7-membered) heterocycle which is optionally substituted with alkyl, alkenyl, alkynyl, hydroxyl, halogen, —SH, trifluoromethyl, —O-alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof;

with the proviso that the compound per se of formula (B) is not

N-(5-(2-(7-ethyl-1H-indol-3-yl)-2-oxo-1-phenylethyl-
amino)-2-methoxyphenyl)-methanesulfonamide (CAS nr. 1294288-37-1);
3-(2-(1H-indol-3-yl)-2-oxo-1-phenylethylamino)benzene-
sulfonamide (CAS nr. 1211427-21-2);
2-(3,4-dihydro-2H-benzo[b][1,4]dioxepin-7-ylamino)-1-
(1H-indol-3-yl)-2-phenylethanone (CAS nr. 1090733-87-1);
1-(1H-indol-3-yl)-2-phenyl-2-(pyridin-3-ylmethylamino)
ethanone (CAS nr. 875860-58-5); or
2-(benzo[d][1,3]dioxol-5-ylmethylamino)-1-(1H-indol-3-
yl)-2-phenylethanone (CAS nr. 920816-95-1).

In a particular embodiment of this aspect of the invention, the compounds, for use in the prevention or treatment of a flavivirus infection in an animal, mammal or human; for use as a medicine; or per se; have a structure according to formula (B),

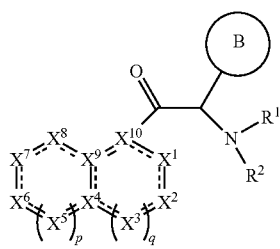

wherein
each dotted line represents an optional double bond whereby maximally 6 non-adjacent dotted lines can form a double bond;
each of $X^1$, $X^2$, $X^3$, $X^5$, $X^6$, $X^7$, and $X^8$ is independently selected from $CR^3$, N, $NR^4$, O, and S;
each of $X^4$ and $X^9$ is independently selected from C, CH, and N;
$X^{10}$ is selected from C, CH, and N;
whereby at least five of $X^1$ to $X^{10}$ are selected from $CR^3$, C, and CH; and at least one of $X^1$ to $X^{10}$ is a heteroatom;
p is 0, 1, or 2;
q is 0, 1, or 2;
preferably the moiety

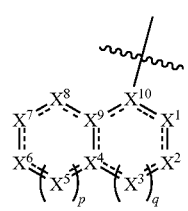

is selected from

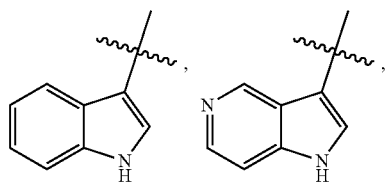

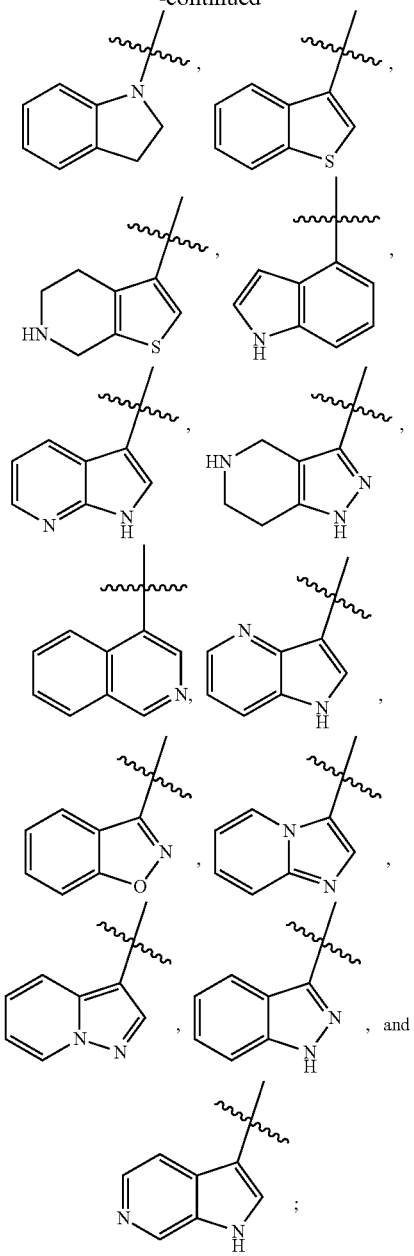

wherein the wavy line (∿) indicates the point of attachment to the carbonyl of the main formula (B); wherein said moiety is optionally substituted with one or two $Z^1$;
cycle B is selected from aryl and heterocycle, wherein said aryl and heterocycle are optionally substituted with one, two, or three $Z^{1a}$; preferably cycle B is selected from

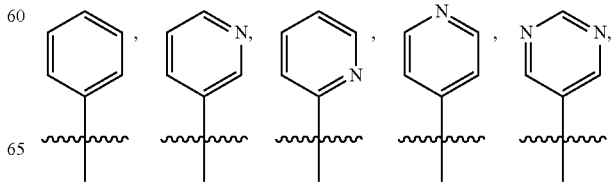

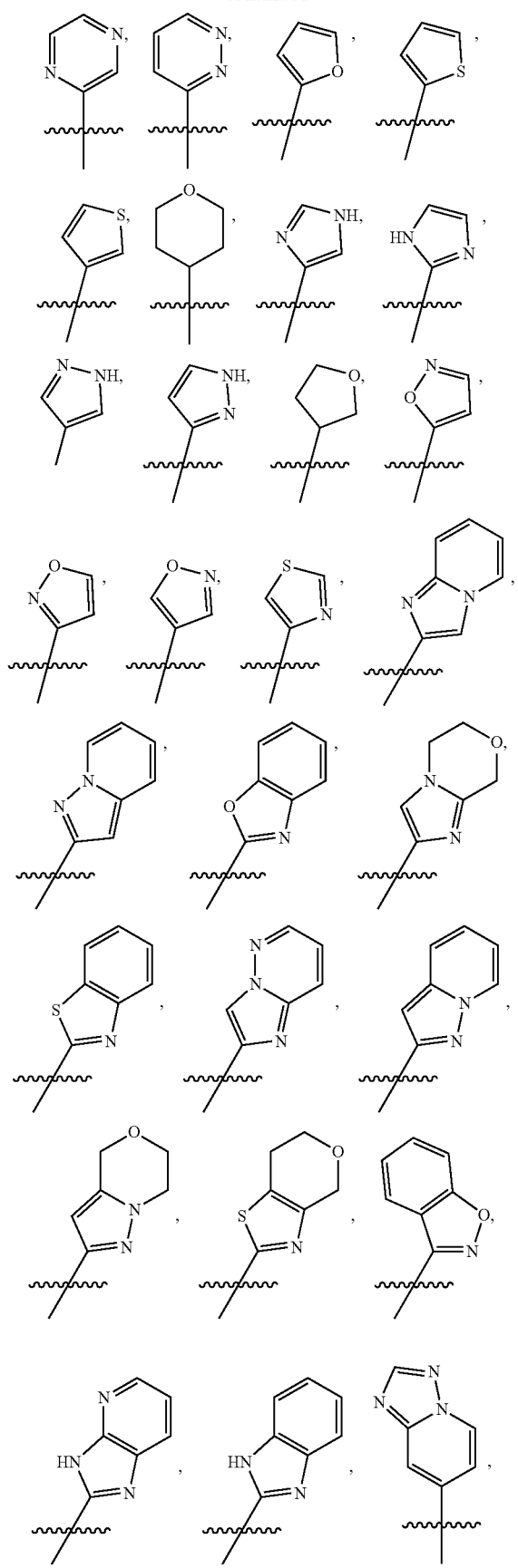
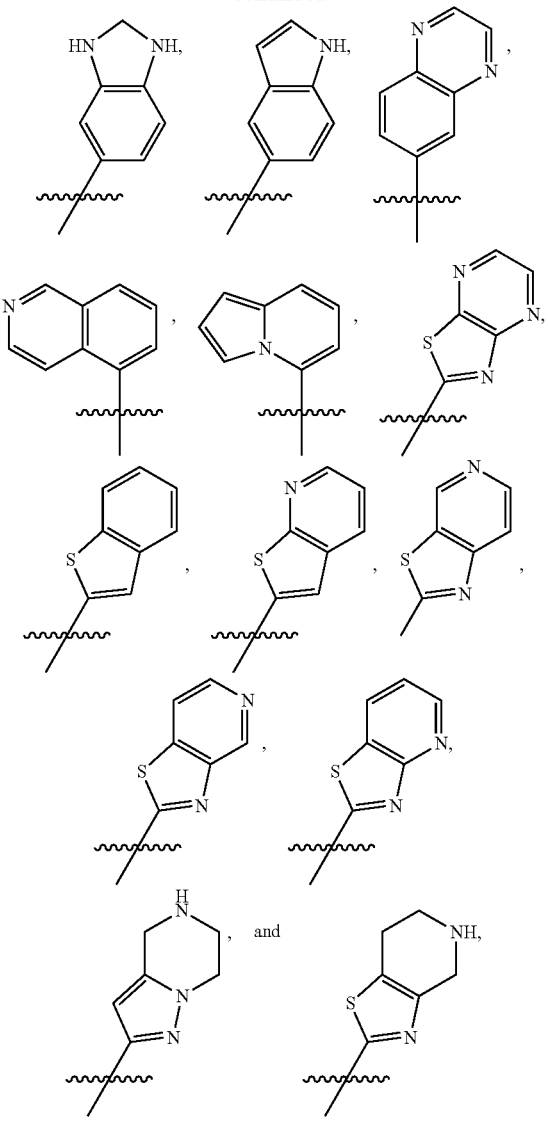

wherein the wavy line (∿) indicates the point of attachment to the carbon atom of the main formula (B), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle;

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$;

$R^2$ is selected from hydrogen, —C(O)$Z^3$, $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl; preferably $R^2$ is selected from hydrogen, —C(O)$Z^3$, and $C_{1-6}$alkyl; and wherein said $C_{1-6}$alkyl, $C_{2-6}$alkenyl, $C_{2-6}$alkynyl, heteroC$_{1-6}$alkyl, heteroC$_{2-6}$alkenyl, and heteroC$_{2-6}$alkynyl, are optionally substituted with one, two, or three $Z^{1c}$; preferably said $C_{1-6}$alkyl is optionally substituted with one, two, or three $Z^{1c}$;

each $R^3$ is independently selected from hydrogen and $Z^1$;

each $R^4$ is independently selected from hydrogen, hydroxyl, sulfhydryl, —S(=O)$Z^2$, —S(=O)$_2Z^3$, —S(=O)$_2$NZ$^4Z^5$, trifluoromethyl, —C(=O)$Z^3$, —C(=O)O$Z^2$, —C(=O)NZ$^4Z^5$, —C(=O)H, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $R^4$ is independently selected from hydrogen, —S(=O)$_2Z^3$, —C(=O)O$Z^2$, $C_{1-6}$alkyl, and heteroC$_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, cyano, nitro, —C(=O)OH, —C(O)OC$_{1-6}$alkyl, and —N(CH$_3$)$_2$, —NH$_2$, —NH—C(=O)O—C$_{1-4}$alkyl, —O—C$_{1-6}$alkyl;

each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$NZ$^4Z^5$, trifluoromethyl, trifluoromethoxy, nitro, —NZ$^4Z^5$, —NZ$^4$S(=O)$_2Z^2$, —NZ$^4$C(=O)$Z^2$, —NZ$^4$C(=O)—O$Z^2$, —NZ$^4$C(=O)NZ$^4Z^5$, cyano, —C(=O)$Z^3$, —C(=O)O$Z^2$, —C(=O)NZ$^4Z^5$, —C(=O)H, $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$ alkyl, heterocycle-heteroC$_{2-6}$alkenyl, and heterocycle-heteroC$_{2-6}$alkynyl; preferably each $Z^1$, $Z^{1a}$, $Z^{1b}$, and $Z^{1c}$ is independently selected from the group consisting of halogen, hydroxyl, sulfhydryl, —O$Z^2$, —O—C(=O)$Z^3$, =O, —S$Z^2$, =S, —S(=O)$Z^2$, —S(=O)$_2Z^3$, —S(=O)$_2$NZ$^4Z^5$, trifluoromethyl, trifluoromethoxy, nitro, —NZ$^4Z^5$, —NZ$^4$S(=O)$_2Z^2$, —NZ$^4$C(=O)$Z^2$, —NZ$^4$C(=O)$_2Z^2$, —NZ$^4$C(=O)NZ$^4Z^5$, cyano, —C(=O)$Z^3$, —C(=O)O$Z^2$, —C(=O)NZ$^4Z^5$, —C(=O)H, $C_{1-6}$alkyl, heteroC$_{1-6}$alkyl, aryl, heterocycle, and heterocycle-C$_{1-6}$alkyl; more preferably each $Z^1$, $Z^{1a}$, $Z^{1b}$, and $Z^{1c}$ is independently selected from the group consisting of halogen, hydroxyl, —O$Z^2$, —O—C(=O)$Z^3$, =O, —S(=O)$_2Z^3$, —S(=O)$_2$NZ$^4Z^5$, trifluoromethyl, trifluoromethoxy, —NZ$^4Z^5$, —NZ$^4$C(=O)$Z^2$, —NZ$^4$C(=O)—O$Z^2$, cyano, —C(=O)$Z^3$, —C(=O)O$Z^2$, —C(=O)NZ$^4Z^5$, $C_{1-6}$alkyl, heteroC$_{1-6}$alkyl, aryl, heterocycle, and heterocycle-C$_{1-6}$alkyl;

and wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; preferably said $C_{1-6}$alkyl, heteroC$_{1-6}$alkyl, aryl, heterocycle, and heterocycle-C$_{1-6}$ alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)OC$_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)OC$_{1-6}$alkyl, —NH$_2$, —NHCH$_3$; —N(CH$_3$)$_2$, —NH—C(=O)O—C$_{1-4}$ alkyl, morpholinyl, —S(O)$_2$C$_{1-4}$alkyl, and —O—C$_{1-6}$alkyl;

each $Z^2$ is independently selected from $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from $C_{1-6}$alkyl, aryl, heterocycle, and heterocycle-C$_{1-6}$alkyl; more preferably $Z^2$ is independently selected from $C_{1-6}$alkyl, aryl, and heterocycle-C$_{1-6}$alkyl;

wherein said $C_{1-6}$alkyl, $C_{2-6}$alkenyl, $C_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, difluoromethyl, —O—C$_{1-6}$alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; preferably said $C_{1-6}$alkyl, aryl, heterocycle, and heterocycle-$C_{1-6}$alkyl, are optionally substituted with one, two, or three substituents selected from hydroxyl, =O, halogen, —SH, =S, trifluoromethyl, difluoromethyl, —O—$C_{1-6}$alkyl, —OCF$_3$, —S(=O)$_2$C$_{1-4}$alkyl, cyano, nitro, —C(=O)OH, —C(=O)O—$C_{1-4}$alkyl, —NH$_2$, and —N(CH$_3$)$_2$, pyrrolidinyl, piperidinyl, and piperazinyl; more preferably said $C_{1-6}$alkyl, and aryl, are optionally substituted with one, two, or three substituents selected from hydroxyl, halogen, difluoromethyl, —O—$C_{1-6}$alkyl, —S(=O)$_2$C$_{1-4}$alkyl, —C(=O)OH, —C(=O)O—$C_{1-4}$alkyl, —NH$_2$, and —N(CH$_3$)$_2$, pyrrolidinyl, piperidinyl, and piperazinyl;

each $Z^3$ is independently selected from hydroxyl, $C_{1-6}$alkyl, $C_{2-6}$alkenyl, $C_{2-6}$alkynyl, hetero$C_{1-6}$ alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$ alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $Z^3$ is independently selected from hydroxyl, $C_{1-6}$alkyl, aryl, and heterocycle; more preferably $Z^3$ is independently selected from hydroxyl, $C_{1-6}$alkyl, and heterocycle;
wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —OCF$_3$, cyano, nitro, —C(=O)OH, —NH$_2$, and —N(CH$_3$)$_2$; preferably said $C_{1-6}$alkyl, aryl, and heterocycle are optionally substituted with one, two, or three substituents selected from $C_{1-6}$alkyl and —N(CH$_3$)$_2$; more preferably said $C_{1-6}$alkyl and heterocycle are optionally substituted with one, two, or three substituents selected from $C_{1-6}$alkyl and —N(CH$_3$)$_2$;

each $Z^4$ and $Z^5$ is independently selected from hydrogen, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, $C_{3-7}$cycloalkyl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably each $Z^4$ and $Z^5$ is independently selected from hydrogen, $C_{1-6}$alkyl, aryl, $C_{3-7}$cycloalkyl, and heterocycle; more preferably each $Z^4$ and $Z^5$ is independently selected from hydrogen, $C_{1-6}$alkyl, and $C_{3-7}$cycloalkyl;
wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hydroxyl, =O, halogen, —SH, =S, trifluoromethyl, —O—$C_{1-6}$alkyl, —OCF$_3$, cyano, nitro, —C(=O)OH or —NH$_2$;

and wherein $Z^4$ and $Z^5$ can be taken together in order to form a (5-, 6-, or 7-membered) heterocycle which is optionally substituted with $C_{1-6}$alkyl, $C_{2-6}$alkenyl, $C_{2-6}$alkynyl, hydroxyl, halogen, —SH, trifluoromethyl, —O—$C_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof;

with the proviso that the compound per se of formula (B) is not

N-(5-(2-(7-ethyl-1H-indol-3-yl)-2-oxo-1-phenylethylamino)-2-methoxyphenyl)-methanesulfonamide (CAS nr. 1294288-37-1);

3-(2-(1H-indol-3-yl)-2-oxo-1-phenylethylamino)benzenesulfonamide (CAS nr. 1211427-21-2);

2-(3,4-dihydro-2H-benzo[b][1,4]dioxepin-7-ylamino)-1-(1H-indol-3-yl)-2-phenylethanone (CAS nr. 1090733-87-1);

1-(1H-indol-3-yl)-2-phenyl-2-(pyridin-3-ylmethylamino)ethanone (CAS nr. 875860-58-5); or 2-(benzo[d][1,3]dioxol-5-ylmethylamino)-1-(1H-indol-3-yl)-2-phenylethanone (CAS nr. 920816-95-1).

In another particular embodiment, the compounds have a structure according to formula (C),

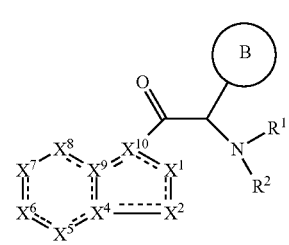

(C)

wherein cycle B, $R^1$, $R^2$, the dotted lines, $X^1$, $X^2$, $X^4$, $X^5$, $X^6$, $X^7$, $X^8$, $X^9$ and $X^{10}$ are as defined in any one of the embodiments with formula (A) and (B).

In another particular embodiment, the compounds have a structure according to formula (D), (D1), (D2), (D3), (D4), or (D5),

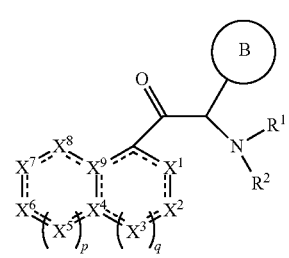

(D)

-continued (D1) 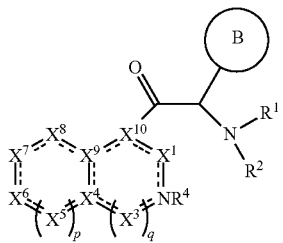

(D2) 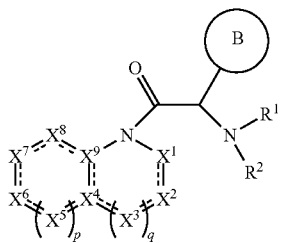

(D3) 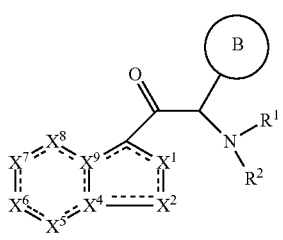

(D4) 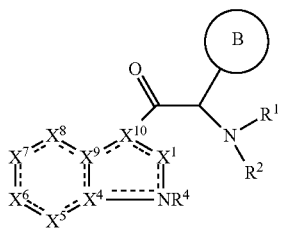

(D5) 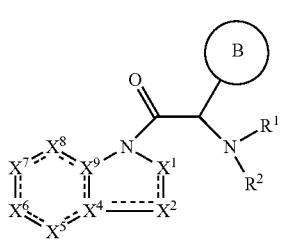

wherein cycle B, $R^1$, $R^2$, the dotted lines, $X^1$, $X^2$, $X^4$, $X^5$, $X^6$, $X^7$, $X^8$, $X^9$ and $X^{10}$ are as defined in any one of the embodiments with formula (A) and (B).

In another particular embodiment, the compounds have a structure according to formula (D),

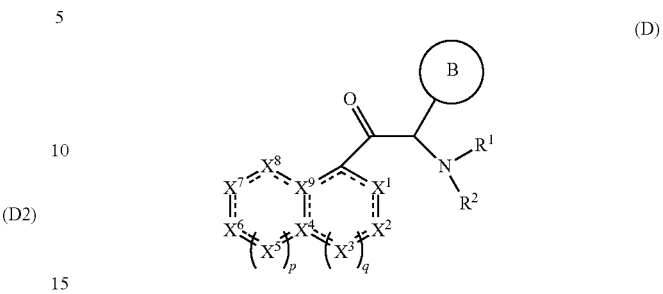

(D)

wherein
- each dotted line represents an optional double bond whereby maximally 6 non-adjacent dotted lines can form a double bond;
- each of $X^1$, $X^2$, $X^3$, $X^5$, $X^6$, $X^7$, and $X^8$ is independently selected from $CR^3$, N, $NR^4$, O, and S;
- each of $X^4$ and $X^9$ is independently selected from C, CH, and N;
- whereby at least five of $X^1$ to $X^9$ are selected from $CR^3$, C, and CH; and at least one of $X^1$ to $X^9$ is a heteroatom;
- p is 0, 1, or 2;
- q is 0, 1, or 2;
- preferably the moiety

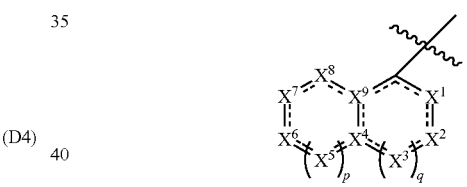

is selected from

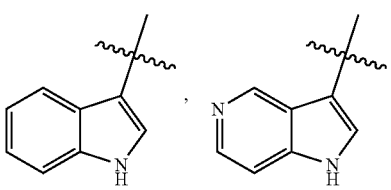

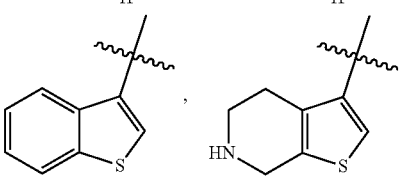

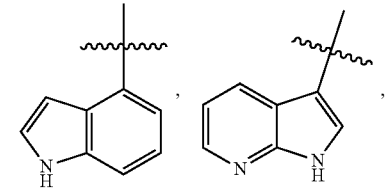

-continued
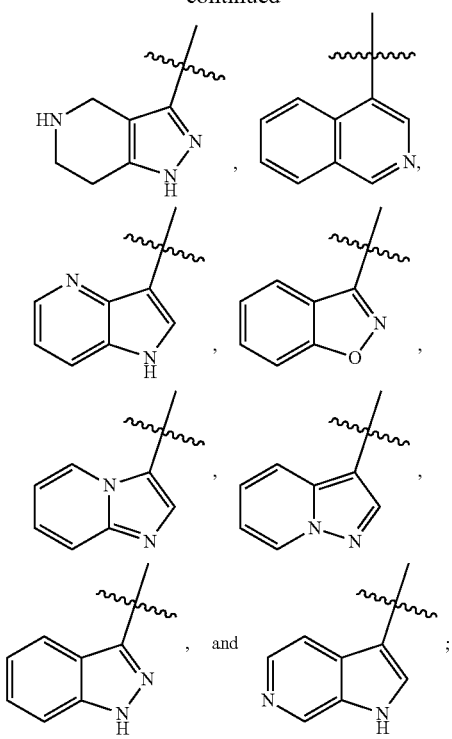
wherein said moiety is optionally substituted with one or two $Z^1$;
cycle B is selected from aryl and heterocycle, wherein said aryl and heterocycle are optionally substituted with one, two, or three $Z^{1a}$; preferably cycle B is selected from
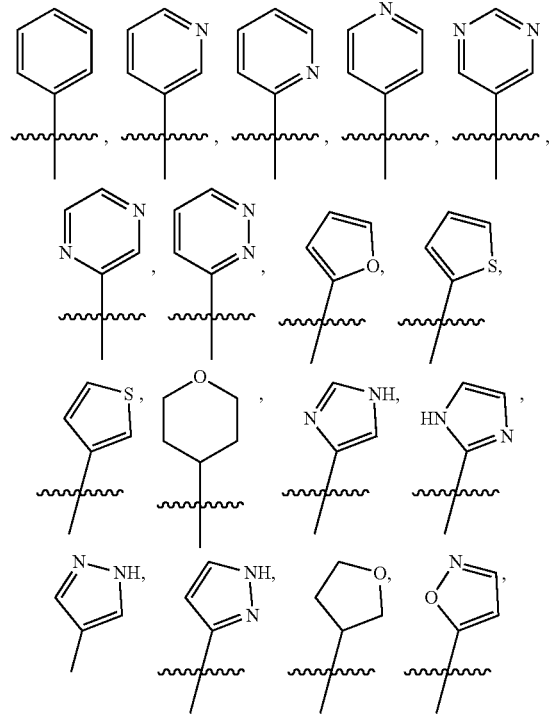
-continued
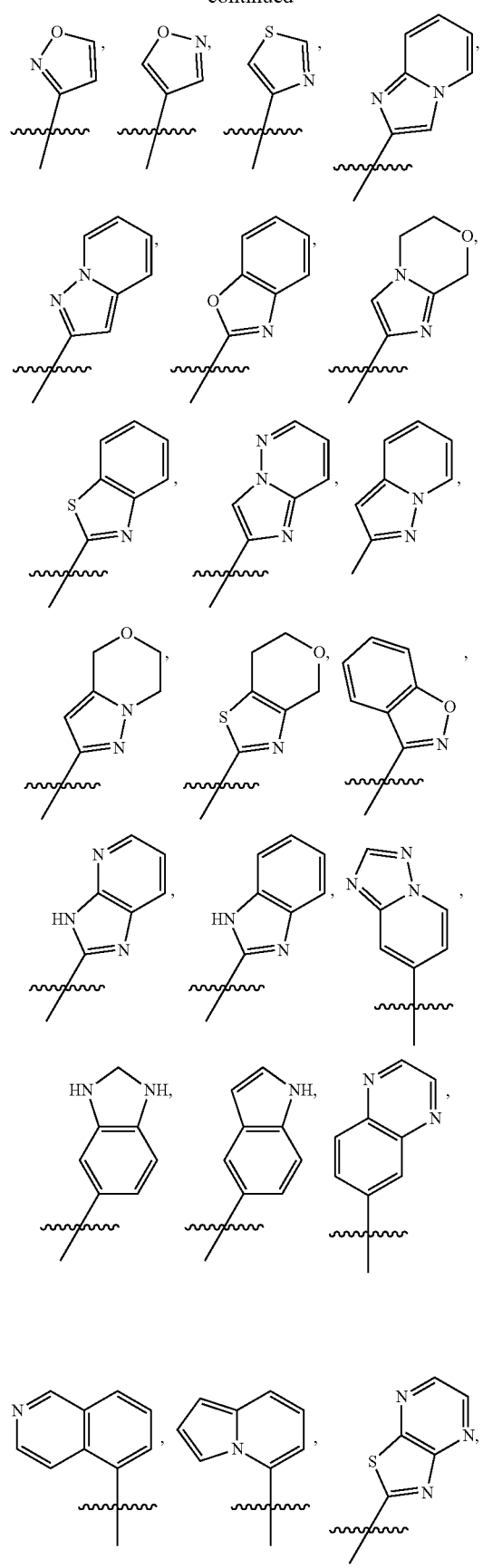

-continued

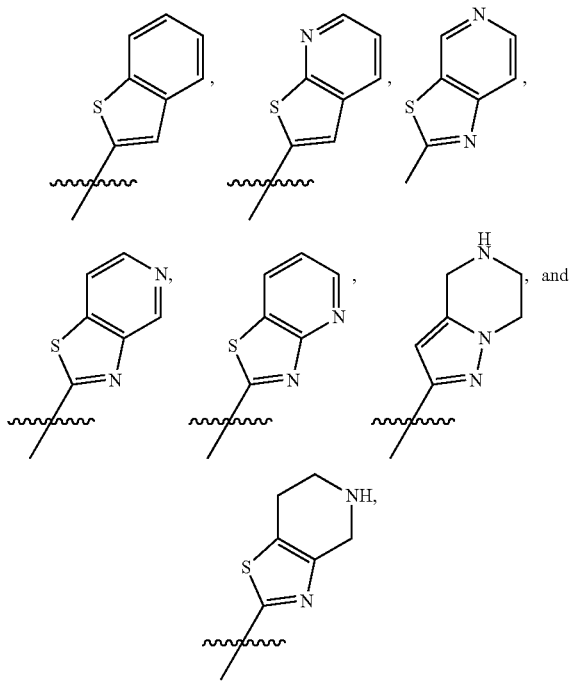

wherein the wavy line ( ~~~ ) indicates the point of attachment to the carbon atom of the main formula (A), and wherein the depicted cycles may be optionally substituted with one, two, or three $Z^{1a}$;

$R^1$ is selected from $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^1$ is selected from $C_{1-6}$alkyl, $C_{3-7}$cycloalkyl, aryl, heterocycle; more preferably R $C_{1-6}$alkyl, or a moiety selected from

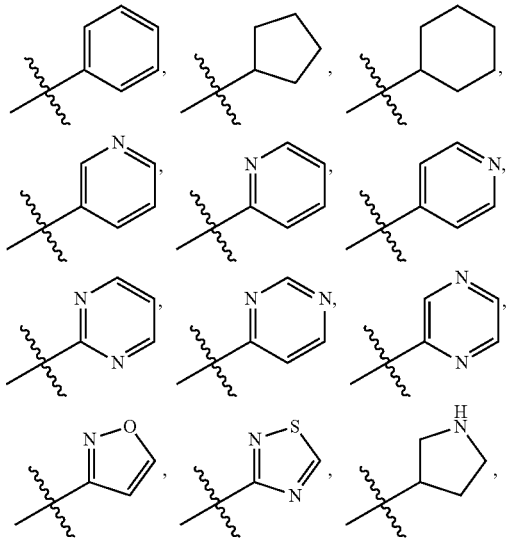

-continued

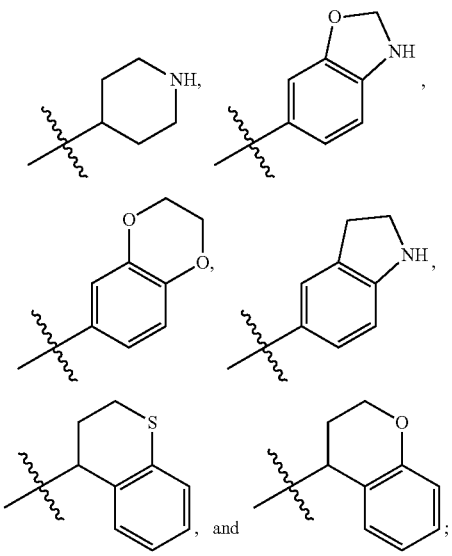

and wherein said $C_{1-6}$alkyl, $C_{3-7}$cycloalkyl, $C_{3-7}$cycloalkenyl, $C_{3-7}$cycloalkynyl, aryl, heterocycle, aryl$C_{1-6}$alkyl, aryl$C_{2-6}$alkenyl, aryl$C_{2-6}$alkynyl, heterocycle-$C_{1-6}$alkyl, heterocycle-$C_{2-6}$alkenyl, heterocycle-$C_{2-6}$alkynyl, arylhetero$C_{1-6}$alkyl, arylhetero$C_{2-6}$alkenyl, arylhetero$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three $Z^{1b}$; preferably said $C_{1-6}$alkyl, $C_{3-7}$cycloalkyl, aryl, and heterocycle, are optionally substituted with one, two, or three $Z^{1b}$; more preferably said moiety selected from

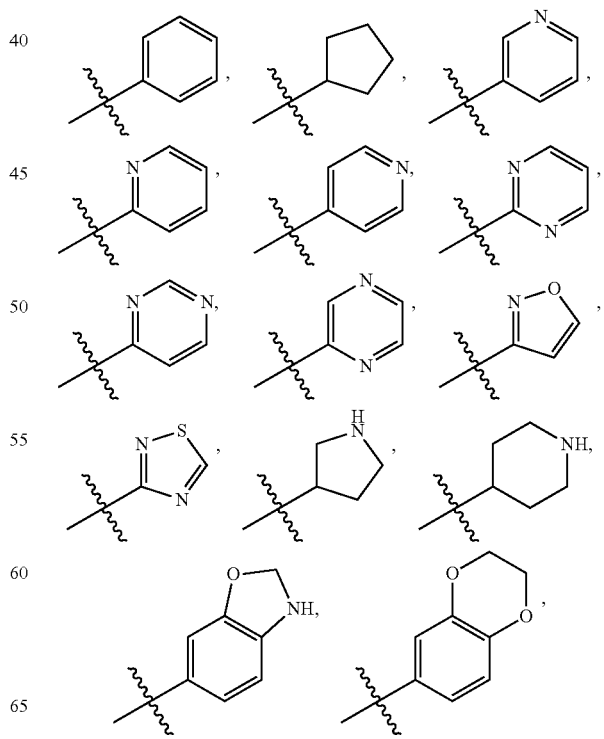

-continued are optionally substituted with one, two, or three $Z^{1b}$;
$Z^{1b}$, is selected from the group consisting of halogen, hydroxyl, —$OZ^2$, =O, —S(=O)$_2Z^3$, —S(=O)$_2NZ^4Z^5$, trifluoromethyl, trifluoromethoxy, —$NZ^4Z^5$, —$NZ^4C(=O)Z^2$, cyano, —C(=O)$Z^3$, —C(=O)$OZ^2$, —C(=O)$NZ^4Z^5$, $C_{1-6}$alkyl, aryl, and heterocycle;

and wherein said $C_{1-6}$alkyl, aryl, and heterocycle are optionally substituted with one, two, or three substituents selected from hydroxyl, =O, —O—C(O)Me, cyano, —C(O)OH, —NHCH$_3$; —N(CH$_3$)$_2$, —S(O)$_2C_{1-4}$alkyl, and —O—$C_{1-6}$alkyl;

$R^2$ is selected from hydrogen, —C(O)$Z^3$, $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl; preferably $R^2$ is selected from hydrogen, —C(O)$Z^3$, and $C_{1-6}$alkyl; and wherein said $C_{1-6}$alkyl, $C_{2-6}$alkenyl, $C_{2-6}$alkynyl, hetero$C_{1-6}$alkyl, hetero$C_{2-6}$alkenyl, and hetero$C_{2-6}$alkynyl, are optionally substituted with one, two, or three $Z^{1c}$; preferably said $C_{1-6}$alkyl is optionally substituted with one, two, or three $Z^{1c}$;

each $R^3$ is independently selected from hydrogen and $Z^1$;

each $R^4$ is independently selected from hydrogen, hydroxyl, sulfhydryl, —S(=O)$Z^3$, —S(=O)$_2Z^3$, —S(=O)$_2NZ^4Z^5$, trifluoromethyl, —C(=O)$Z^3$, —C(=O)$OZ^2$, —C(=O)$NZ^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably $R^4$ is independently selected from hydrogen, —S(=O)$_2Z^3$, —C(=O)$OZ^2$, $C_{1-6}$alkyl, and hetero$C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl are optionally substituted with one, two, or three substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF$_3$, cyano, nitro, —C(=O)OH, —C(O)O$C_{1-6}$alkyl, and —N(CH$_3$)$_2$, —NH$_2$, —NH—C(=O)O—$C_{1-4}$alkyl, —O—$C_{1-6}$alkyl; preferably said $C_{1-6}$alkyl is optionally substituted with one, two, or three substituents selected from —C(=O)OH, —C(O)O$C_{1-6}$alkyl, and —N(CH$_3$)$_2$, —NH$_2$, —NH—C(=O)O—$C_{1-4}$alkyl, —O—$C_{1-6}$alkyl;

each $Z^1$, $Z^{1a}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2NZ^4Z^5$, trifluoromethyl, trifluoromethoxy, nitro, —$NZ^4Z^5$, —$NZ^4S(=O)_2Z^2$, —$NZ^4C(=O)Z^2$, —$NZ^4C(=O)$—$OZ^2$, —$NZ^4C(=O)NZ^4Z^5$, cyano, —C(=O)$Z^3$, —C(=O)$OZ^2$, —C(=O)$NZ^4Z^5$, —C(=O)H, $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl; preferably each $Z^1$, $Z^{1a}$, and $Z^{1c}$ is independently selected from the group consisting of halogen, hydroxyl, sulfhydryl, —$OZ^2$, —O—C(=O)$Z^3$, =O, —$SZ^2$, =S, —S(=O)$Z^2$, —S(=O)$_2Z^3$, —S(=O)$_2NZ^4Z^5$, trifluoromethyl, trifluoromethoxy, nitro, —$NZ^4Z^5$, —$NZ^4S(=O)_2Z^2$, —$NZ^4C(=O)Z^2$, —$NZ^4C(=O)_2Z^2$, —$NZ^4C(=O)NZ^4Z^5$, cyano, —C(=O)$Z^3$, —C(=O)$OZ^2$, —C(=O)$NZ^4Z^5$, —C(=O)H, $C_{1-6}$alkyl, hetero$C_{1-6}$alkyl, aryl, heterocycle, and heterocycle-$C_{1-6}$alkyl; more preferably each $Z^1$, $Z^{1a}$, and $Z^{1c}$ is independently selected from the group consisting of halogen, hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4C(=O)Z^2$, —$NZ^4C(=O)$—$OZ^2$, cyano, —C(=O)$Z^3$, —C(=O)$OZ^2$, —C(=O)$NZ^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, aryl, heterocycle, aryl$C_{1-6}$alkyl, aryl$C_{2-6}$alkenyl, aryl$C_{2-6}$alkynyl, arylhetero$C_{1-6}$alkyl, arylhetero$C_{2-6}$alkenyl, arylhetero$C_{2-6}$alkynyl, heterocycle-$C_{1-6}$alkyl, heterocycle-$C_{2-6}$alkenyl, heterocycle-$C_{2-6}$alkynyl, heterocycle-hetero$C_{1-6}$alkyl, heterocycle-hetero$C_{2-6}$alkenyl, and heterocycle-hetero$C_{2-6}$alkynyl, are optionally substituted with one, two, or three substituents selected from $C_{1-6}$alkyl, $C_{2-6}$alkenyl, $C_{2-6}$alkynyl, hetero$C_{1-6}$alkyl, hetero$C_{2-6}$alkenyl, hetero$C_{2-6}$alkynyl, hydroxyl, =O, halogen, —SH, =S, trifluoromethyl, —OCF$_3$, —O—C(O)Me, cyano, nitro, —C(O)OH, —C(O)O$C_{1-6}$alkyl, —NH$_2$, —NHCH$_3$; —N(CH$_3$)$_2$, —NH—C(=O)O—$C_{1-4}$alkyl, morpholinyl, —S(O)$_2C_{1-4}$alkyl, and —O—$C_{1-6}$ alkyl; preferably said $C_{1-6}$alkyl, hetero$C_{1-6}$alkyl, aryl, heterocycle, and heterocycle-$C_{1-6}$alkyl, are optionally substituted with one, two, or three substituents selected from hydroxyl, =O, halogen, —SH, =S, trifluoromethyl, —OCF$_3$, —O—C(O)Me, cyano, nitro, —C(O)OH, —C(O)O$C_{1-6}$alkyl, —NH$_2$, —NHCH$_3$; —N(CH$_3$)$_2$, —NH—C(=O)O—$C_{1-4}$alkyl, morpholinyl, —S(O)$_2C_{1-4}$alkyl, and —O—$C_{1-6}$alkyl; more preferably said $C_{1-6}$alkyl, aryl, and heterocycle are optionally substituted with one, two, or three substituents selected from hydroxyl, =O, —O—C(O)Me, cyano, —C(O)OH, —C(O)O$C_{1-6}$alkyl, —NH$_2$, —NHCH$_3$; —N(CH$_3$)$_2$, —NH—C(=O)O—C$_{1-4}$alkyl, morpholinyl, —S(O)$_2$C$_{1-4}$alkyl, and —O—C$_{1-6}$alkyl;

each $Z^2$ is independently selected from C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{1-6}$alkenyl, arylheteroC$_{1-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^2$ is independently selected from C$_{1-6}$alkyl, aryl, heterocycle, and heterocycle-C$_{1-6}$alkyl; more preferably $Z^2$ is independently selected from C$_{1-6}$alkyl, aryl, and heterocycle-C$_{1-6}$alkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, difluoromethyl, —O—C$_{1-6}$alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; preferably said C$_{1-6}$alkyl, aryl, heterocycle, and heterocycle-C$_{1-6}$alkyl, are optionally substituted with one, two, or three substituents selected from hydroxyl, =O, halogen, —SH, =S, trifluoromethyl, difluoromethyl, —O—C$_{1-6}$ alkyl, —OCF$_3$, —S(=O)$_2$C$_{1-4}$alkyl, cyano, nitro, —C(=O)OH, —C(=O)O—C$_{1-4}$alkyl, —NH$_2$, and —N(CH$_3$)$_2$, pyrrolidinyl, piperidinyl, and piperazinyl; more preferably said C$_{1-6}$alkyl, and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, and —N(CH$_3$)$_2$, pyrrolidinyl, piperidinyl, and piperazinyl;

each $Z^3$ is independently selected from hydroxyl, C$_{1-6}$alkyl, C$_{2-6}$alkenyl, C$_{2-6}$alkynyl, heteroC$_{1-6}$ alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$ alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably $Z^3$ is independently selected from hydroxyl, C$_{1-6}$alkyl, aryl, and heterocycle; more preferably $Z^3$ is independently selected from hydroxyl, C$_{1-6}$alkyl, and heterocycle;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, —C(=O)OH, —NH$_2$, and —N(CH$_3$)$_2$; preferably said C$_{1-6}$alkyl, aryl, and heterocycle are optionally substituted with one, two, or three substituents selected from C$_{1-6}$alkyl and —N(CH$_3$)$_2$; more preferably said C$_{1-6}$alkyl and heterocycle are optionally substituted with one, two, or three substituents selected from C$_{1-6}$alkyl and —N(CH$_3$)$_2$;

each $Z^4$ and $Z^5$ is independently selected from hydrogen, C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, C$_{3-7}$cycloalkyl, heterocycle, arylC$_{1-6}$ alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl; preferably each $Z^4$ and $Z^5$ is independently selected from hydrogen, C$_{1-6}$alkyl, aryl, C$_{3-7}$cycloalkyl, and heterocycle; more preferably each $Z^4$ and $Z^5$ is independently selected from hydrogen, C$_{1-6}$alkyl, and C$_{3-7}$cycloalkyl;

wherein said C$_{1-6}$alkyl, C$_{2-6}$alkenyl, C$_{2-6}$alkynyl, heteroC$_{1-6}$alkyl, heteroC$_{2-6}$alkenyl, heteroC$_{2-6}$alkynyl, aryl, heterocycle, arylC$_{1-6}$alkyl, arylC$_{2-6}$alkenyl, arylC$_{2-6}$alkynyl, arylheteroC$_{1-6}$alkyl, arylheteroC$_{2-6}$alkenyl, arylheteroC$_{2-6}$alkynyl, heterocycle-C$_{1-6}$alkyl, heterocycle-C$_{2-6}$alkenyl, heterocycle-C$_{2-6}$alkynyl, heterocycle-heteroC$_{1-6}$alkyl, heterocycle-heteroC$_{2-6}$alkenyl, and heterocycle-heteroC$_{2-6}$alkynyl, are optionally substituted with one, two, or three substituents selected from C$_{1-6}$alkyl, C$_{2-6}$alkenyl, C$_{2-6}$alkynyl, hydroxyl, =O, halogen, —SH, =S, trifluoromethyl, —O—C$_{1-6}$alkyl, —OCF$_3$, cyano, nitro, or —NH$_2$;

and wherein $Z^4$ and $Z^5$ can be taken together in order to form a (5-, 6-, or 7-membered) heterocycle which is optionally substituted with C$_{1-6}$alkyl, C$_{2-6}$alkenyl, C$_{2-6}$alkynyl, hydroxyl, halogen, —SH, trifluoromethyl, —O—C$_{1-6}$alkyl, —OCF$_3$, cyano, nitro, —C(=O)OH, or —NH$_2$;

and isomers (in particular stereo-isomers or tautomers), solvates, salts (in particular pharmaceutically acceptable salts) or prodrugs thereof;

with the proviso that compound of formula (D) is not

N-(5-(2-(7-ethyl-1H-indol-3-yl)-2-oxo-1-phenylethylamino)-2-methoxyphenyl)-methanesulfonamide (CAS nr. 1294288-37-1);

3-(2-(1H-indol-3-yl)-2-oxo-1-phenylethylamino)benzenesulfonamide (CAS nr. 1211427-21-2);

2-(3,4-dihydro-2H-benzo[b][1,4]dioxepin-7-ylamino)-1-(1H-indol-3-yl)-2-phenylethanone (CAS nr. 1090733-87-1);

1-(1H-indol-3-yl)-2-phenyl-2-(pyridin-3-ylmethylamino) ethanone (CAS nr. 875860-58-5); or 2-(benzo[d][1,3]dioxol-5-ylmethylamino)-1-(1H-indol-3-yl)-2-phenylethanone (CAS nr. 920816-95-1).

In one embodiment, the compound per se of the invention is not any one of the following:

N-(5-(2-(7-ethyl-1H-indol-3-yl)-2-oxo-1-phenylethylamino)-2-methoxyphenyl)-methanesulfonamide (CAS nr. 1294288-37-1);

3-(2-(1H-indol-3-yl)-2-oxo-1-phenylethylamino)benzenesulfonamide (CAS nr. 1211427-21-2);

2-(3,4-dihydro-2H-benzo[b][1,4]dioxepin-7-ylamino)-1-(1H-indol-3-yl)-2-phenylethanone (CAS nr. 1090733-87-1);

1-(1H-indol-3-yl)-2-phenyl-2-(pyridin-3-ylmethylamino)
 ethanone (CAS nr. 875860-58-5); or
2-(benzo[d][1,3]dioxol-5-ylmethylamino)-1-(1H-indol-3-
 yl)-2-phenylethanone (CAS nr. 920816-95-1).
 In another embodiment, the compound per se of the
invention is not any one of the following:
1-(7-ethyl-1H-indol-3-yl)-2-[(1-methyl-1H-pyrazol-3-yl)
 amino]-2-phenyl-ethanone (CAS nr. 1296377-78-0);
N-[4-[[2-(1H-indol-3-yl)-2-oxo-1-phenylethyl]amino]phe-
 nyl]-2-methyl-propanamide (CAS nr. 1294813-77-6);
N-[4-[[2-(7-ethyl-1H-indol-3-yl)-2-oxo-1-phenylethyl]
 amino]-2-methoxyphenyl]-acetamide (CAS nr. 1287503-
 18-7);
1-(7-ethyl-1H-indol-3-yl)-2-phenyl-2-[(3,4,5-trimethoxy-
 phenyl)amino]-ethanone (CAS nr. 1287040-60-1);
2-[(1-acetyl-2,3-dihydro-1H-indol-5-yl)amino]-1-(7-ethyl-
 1H-indol-3-yl)-2-phenyl-ethanone (CAS nr. 1286579-37-
 0);
3,4-dihydro-6-[[2-(1H-indol-3-yl)-2-oxo-1-phenylethyl]
 amino]-2(1H)-quinolinone (CAS nr. 1277962-26-1);
1-(1H-indol-3-yl)-2-phenyl-2-(m-tolylamino)ethanone
 (CAS nr. 1252467-88-1);
2-(4-ethoxy-3-(hydroxymethyl)phenylamino)-1-(1H-indol-
 3-yl)-2-phenylethanone (CAS nr. 1241127-58-1);
2-[(1-acetyl-4-piperidinyl)amino]-1-(1H-indol-3-yl)-2-phe-
 nyl-ethanone (CAS nr. 1210169-39-3);
1-(1H-indol-3-yl)-2-[(6-methoxy-3-pyridinyl)amino]-2-
 phenyl-ethanone (CAS nr. 1181884-55-8);
1-(1H-indol-3-yl)-2-[(1-methyl-1H-pyrazol-3-yl)amino]-2-
 phenyl-ethanone (CAS nr. 1134766-19-0);
3-[[2-(1H-indol-3-yl)-2-oxo-1-phenylethyl]amino]-benz-
 amide (CAS nr. 1062257-51-5);
N-[4-[[2-(1H-indol-3-yl)-2-oxo-1-phenylethyl]amino]phe-
 nyl]-2,2-dimethyl-propanamide (CAS nr. 1062132-16-4);
N-[3-[[2-(1H-indol-3-yl)-2-oxo-1-phenylethyl]amino]phe-
 nyl]-acetamide (CAS nr. 1030735-63-7);
2-[(3,5-dimethoxyphenyl)amino]-1-(1H-indol-3-yl)-2-phe-
 nyl-ethanone (CAS nr. 1030232-46-2);
1-(1H-indol-3-yl)-2-phenyl-2-(phenylamino)-ethanone
 (CAS nr. 1030214-83-5);
1-(1H-indol-3-yl)-2-[[6-(4-morpholinyl)-3-pyridinyl]
 amino]-2-phenyl-ethanone (CAS nr. 1030212-41-9);
2-(3-(difluoromethoxy)-4-methoxyphenylamino)-1-(1H-in-
 dol-3-yl)-2-phenylethanone (CAS nr. 1015662-06-2);
1-(1H-indol-3-yl)-2-phenyl-2-[(3,4,5-trimethoxyphenyl)
 amino]-ethanone (CAS nr. 1014535-82-0);
2-[(4-fluorophenyl)amino]-1-(1H-indol-3-yl)-2-phenyl-
 ethanone (CAS nr. 1014493-63-0);
2-[(4-ethoxy-3-methoxyphenyl)amino]-1-(1H-indol-3-yl)-
 2-phenyl-ethanone (CAS nr. 1014422-80-0);
N-[4-[[2-(1H-indol-3-yl)-2-oxo-1-phenylethyl]amino]phe-
 nyl]-acetamide (CAS nr. 1013712-88-3);
1-(7-ethyl-1H-indol-3-yl)-2-[[3-(hydroxymethyl)phenyl]
 amino]-2-phenyl-ethanone (CAS nr. 1012956-97-6);
N-[2-chloro-4-[[2-(1H-indol-3-yl)-2-oxo-1-phenylethyl]
 amino]phenyl]-acetamide (CAS nr. 1011120-58-3);
1-[4-[[2-(1H-indol-3-yl)-2-oxo-1-phenylethyl]amino]-2-
 methoxyphenyl]-2-pyrrolidinone (CAS nr. 1011119-79-
 1);
N-cyclopropyl-4-[[2-(1H-indol-3-yl)-2-oxo-1-phenylethyl]
 amino]-benzamide (CAS nr. 1011113-94-2);
2-[(1-acetyl-2,3-dihydro-1H-indol-5-yl)amino]-1-(1H-in-
 dol-3-yl)-2-phenyl-ethanone (CAS nr. 949443-90-7);
1-(1H-indol-3-yl)-2-phenyl-2-[(1-propyl-4-piperidinyl)
 amino]-ethanone (CAS nr. 941047-24-1);
2-(cyclopentylamino)-1-(1H-indol-3-yl)-2-phenyl-ethanone
 (CAS nr. 931079-25-3);

1-(1H-indol-3-yl)-2-[(4-methylphenyl)amino]-2-phenyl-
 ethanone (CAS nr. 931016-79-4);
2-(cyclopropylamino)-1-(1H-indol-3-yl)-2-phenyl-ethanone
 (CAS nr. 931000-99-6);
1-[4-[[2-(1H-indol-3-yl)-2-oxo-1-phenylethyl]amino]phe-
 nyl]-2-pyrrolidinone (CAS nr. 924713-83-7);
2-[(3,4-dihydro-2H-1-benzothiopyran-4-yl)amino]-1-(1H-
 indol-3-yl)-2-phenyl-ethanone (CAS nr. 924713-60-0);
2-[(3,4-dimethoxyphenyl)amino]-1-(1H-indol-3-yl)-2-phe-
 nyl-ethanone (CAS nr. 924712-67-4);
1-[3-[[2-(1H-indol-3-yl)-2-oxo-1-phenylethyl]amino]phe-
 nyl]-2-pyrrolidinone (CAS nr. 920952-63-2);
2-ethoxy-5-[[2-(1H-indol-3-yl)-2-oxo-1-phenylethyl]
 amino]-N,N-dimethyl-benzenesulfonamide (CAS nr.
 920883-17-6);
6-[[2-(1H-indol-3-yl)-2-oxo-1-phenylethyl]amino]-2-
 methyl-2H-1,4-benzoxazin-3(4H)-one (CAS nr. 920834-
 07-7);
2-[(3,4-dihydro-2H-1-benzopyran-4-yl)amino]-1-(1H-in-
 dol-3-yl)-2-phenyl-ethanone (CAS nr. 920819-87-0);
3-[[2-(1H-indol-3-yl)-2-oxo-1-phenylethyl]amino]-N-
 methyl-benzamide (CAS nr. 920672-79-3);
4-[[2-(1H-indol-3-yl)-2-oxo-1-phenylethyl]amino]-benze-
 neacetonitrile (CAS nr. 920669-36-9);
1-(1H-indol-3-yl)-2-[(4-methoxyphenyl)amino]-2-phenyl-
 ethanone (CAS nr. 920601-77-0);
1-(1H-indol-3-yl)-2-phenyl-2-(1,1-dioxotetrahydrothi-
 ophen-3-ylamino)ethanone (CAS nr. 878619-92-2);
N-cyclopropyl-3-[[2-(1H-indol-3-yl)-2-oxo-1-phenylethyl]
 amino]-benzamide (CAS nr. 878577-28-7);
2-[[3-(hydroxymethyl)phenyl]amino]-1-(1H-indol-3-yl)-2-
 phenyl-ethanone (CAS nr. 875166-36-2);
2-[(2,3-dihydro-1,4-benzodioxin-6-yl)amino]-1-(1H-indol-
 3-yl)-2-phenyl-ethanone (CAS nr. 874669-99-5);
1-(1H-indol-3-yl)-2-(methyl((tetrahydrofuran-2-yl)methyl)
 amino)-2-phenylethanone;
N-(4-(2-(1H-indol-3-yl)-2-oxo-1-phenylethylamino)phe-
 nyl)isobutyramide;
2-((benzo[d][1,3]dioxol-5-ylmethyl)(methyl)amino)-1-(1H-
 indol-3-yl)-2-phenylethanone;
3-(3-(2-(7-ethyl-1H-indol-3-yl)-2-oxo-1-phenylethylamino)
 propyl)-1,3-diazaspiro[4.4]nonane-2,4-dione;
1-(7-ethyl-1H-indol-3-yl)-2-((2-methoxypyridin-3-yl)meth-
 ylamino)-2-phenylethanone;
3-(3-(2-(1H-indol-3-yl)-2-oxo-1-phenylethylamino)pro-
 pyl)-1,3-diazaspiro[4.4]nonane-2,4-dione;
1-(1H-indol-3-yl)-2-(methyl(2,3,4-trimethoxybenzyl)
 amino)-2-phenylethanone;
2-(2-(1H-indol-3-yl)-2-oxo-1-phenylethylamino)-N-(3,4-
 difluorophenyl)acetamide;
1-(1H-indol-3-yl)-2-(morpholino(phenyl)methylamino)-2-
 phenylethanone;
2-(4-(dimethylamino)benzylamino)-1-(1H-indol-3-yl)-2-
 phenylethanone;
2-(2-(furan-2-yl)ethylamino)-1-(1H-indol-3-yl)-2-phenyle-
 thanone;
3-(2-(1H-indol-3-yl)-2-oxo-1-phenylethylamino)-1-(pyrro-
 lidin-1-yl)propan-1-one;
2-(1-(2,3-dihydrobenzo[b][1,4]dioxin-6-yl)ethylamino)-1-
 (1H-indol-3-yl)-2-phenylethanone;
2-((2-(1H-indol-3-yl)-2-oxo-1-phenylethyl)(methyl)
 amino)-N-(4-methoxyphenyl)acetamide;
2-(2-(2-fluorophenoxy)ethylamino)-1-(1H-indol-3-yl)-2-
 phenylethanone;
2-((2,3-dimethoxybenzyl)(methyl)amino)-1-(1H-indol-3-
 yl)-2-phenylethanone;

2-((3,4-dimethoxybenzyl)(methyl)amino)-1-(1H-indol-3-yl)-2-phenylethanone;
1-(1H-indol-3-yl)-2-phenyl-2-(2-(thiophen-2-yl)ethylamino)ethanone;
2-(1-(furan-2-yl)ethylamino)-1-(1H-indol-3-yl)-2-phenylethanone;
1-(1H-indol-3-yl)-2-(2-methoxybenzylamino)-2-phenylethanone;
1-(1H-indol-3-yl)-2-(methyl(thiophen-2-ylmethyl)amino)-2-phenylethanone;
1-(1H-indol-3-yl)-2-phenyl-2-((tetrahydrofuran-2-yl)methylamino)ethanone;
2-(benzo[d][1,3]dioxol-5-ylmethylamino)-1-(1H-indol-3-yl)-2-phenylethanone;
1-(1H-indol-3-yl)-2-(3-methoxybenzylamino)-2-phenylethanone;
2-(2-(dimethylamino)-1-phenylethylamino)-1-(1H-indol-3-yl)-2-phenylethanone;
1-(1H-indol-3-yl)-2-(methyl(thiophen-3-ylmethyl)amino)-2-phenylethanone;
1-(1H-indol-3-yl)-2-phenyl-2-(1-(thiophen-2-yl)ethylamino)ethanone;
2-(3,4-dimethoxyphenethylamino)-1-(1H-indol-3-yl)-2-phenylethanone;
1-(1H-indol-3-yl)-2-(1-(2-methoxyphenyl)ethylamino)-2-phenylethanone;
1-(1H-indol-3-yl)-2-(4-methoxybenzylamino)-2-phenylethanone;
1-(1H-indol-3-yl)-2-phenyl-2-(pyridin-2-ylmethylamino)ethanone;
2-(benzylamino)-1-(1H-indol-3-yl)-2-phenylethanone;
2-(furan-2-ylmethylamino)-1-(1H-indol-3-yl)-2-phenylethanone;
2-(2-(1H-indol-3-yl)-2-oxo-1-phenylethylamino)-N-(2,6-dimethylphenyl)acetamide;
1-(1H-indol-3-yl)-2-phenyl-2-(pyridin-3-ylmethylamino)ethanone;
2-((2,3-dihydrobenzo[b][1,4]dioxin-2-yl)methylamino)-1-(1H-indol-3-yl)-2-phenylethanone;
1-(1H-indol-3-yl)-2-phenyl-2-(thiophen-2-ylmethylamino)ethanone; or
2-(furan-2-ylmethylamino)-1-(1H-indol-3-yl)-2-phenylethanone.

In another particular embodiment, the compounds have a structure according to formula (E), (E1), or (E2),

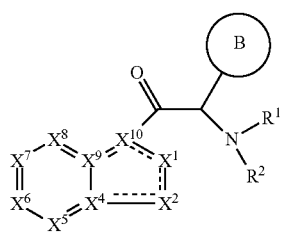

(E)

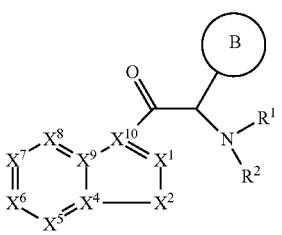

(E1)

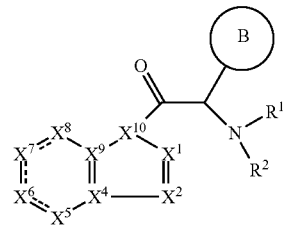

(E2)

wherein cycle B, $R^1$, $R^2$, the dotted lines, $X^1$, $X^2$, $X^4$, $X^5$, $X^6$, $X^7$, $X^8$, $X^9$ and $X^{10}$ are as defined in any one of the embodiments with formula (A) and (B).

In another particular embodiment, the compounds have a structure according to formula (F) or (F1),

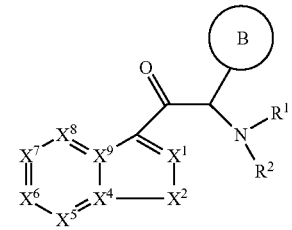

(F)

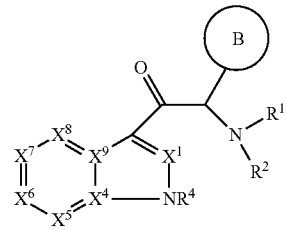

(F1)

wherein cycle B, $R^1$, $R^2$, the dotted lines, $X^1$, $X^4$, $X^5$, $X^6$, $X^7$, $X^8$, $X^9$ and $Z^4$ are as defined in any one of the embodiments with formula (A) and (B).

In another particular embodiment, the compounds have a structure according to formula (G),

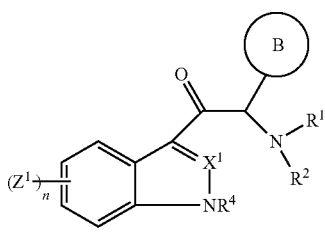

(G)

wherein cycle B, $R^1$, $R^2$, $X^1$, $Z^1$, and $R^4$ are as defined in any one of the embodiments with formula (A) and (B) and wherein n is selected from 0; 1; 2 and 3.

In another particular embodiment, the compounds have a structure according to formula (H),

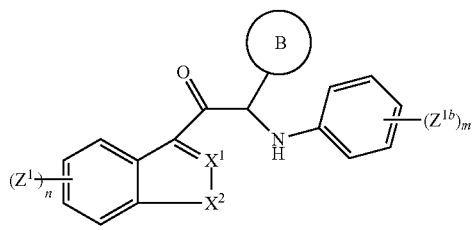

wherein
cycle B, each $Z^1$ independently, and each $Z^{1b}$ independently, are as described in any one of the embodiments with formula (A); preferably $Z^{1b}$ is located in meta or para; preferably cycle B is not an unsubstituted phenyl;
m is selected from 0, 1, 2, and 3;
n is selected from 0, 1, 2, and 3; and
$X^1$ and $X^2$, are as described in any one of the embodiments with formula (B).

In another particular embodiment, the compounds have a structure according to formula (I),

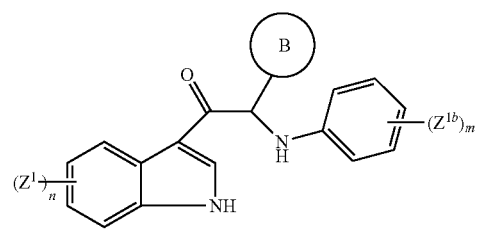

wherein
cycle B, each $Z^1$ independently, and each $Z^{1b}$ independently, are as described in any one of the embodiments with formula (A);
preferably cycle B is selected from aryl and heteroaryl; more preferably cycle B is selected from

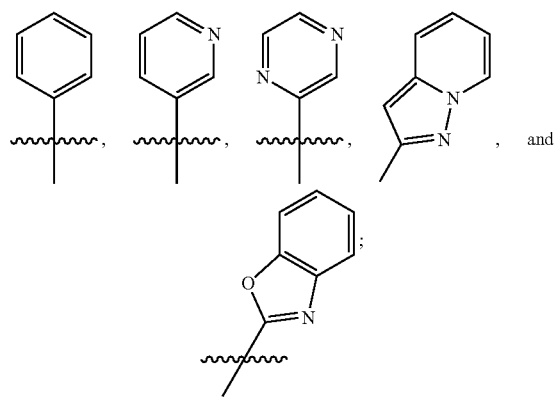

wherein said aryl, heteroaryl, and the depicted cycles may optionally be substituted with halogen, $C_{1-4}$alkyl, or $C_{1-4}$alkoxy; more preferably said aryl is substituted with halogen, $C_{1-4}$alkyl, or $C_{1-4}$alkoxy;
preferably $Z^1$ is hydrogen, halogen, or $C_{1-4}$alkyl;
preferably $Z^{1b}$ is $C_{1-4}$alkoxy, —$OCH_2CH_2OH$, hydrogen, —$CH_2$—OH;
m is selected from 0, 1, 2, and 3; preferably m is selected from 1 and 2;
n is selected from 0, 1, 2, and 3; preferably n is selected from 0 and 1.

In another particular embodiment, the compounds have a structure according to formula (J),

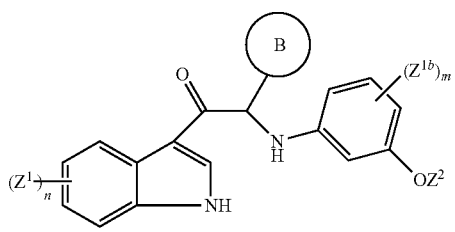

wherein
$Z^1$ is hydrogen, halogen, or $C_{1-4}$alkyl;
n is selected from 0 and 1;
cycle B is aryl and heteroaryl; more preferably cycle B is selected from

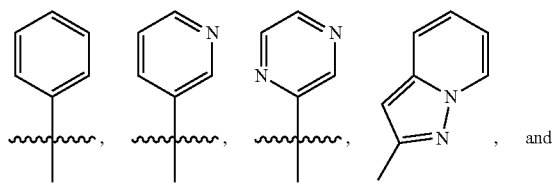

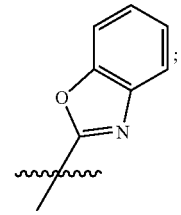

wherein said aryl, heteroaryl, and the depicted cycles may optionally be substituted with halogen, $C_{1-4}$alkyl, or $C_{1-4}$alkoxy; more preferably said aryl is substituted with halogen, $C_{1-4}$alkyl, or $C_{1-4}$alkoxy;
$Z^{1b}$ is $C_{1-4}$alkoxy, —$OCH_2CH_2OH$, —$CH_2$—OH;
m is selected from 0 and 1; and
$Z^2$ is $C_{1-4}$alkyl.

The compounds of the present invention present at least one asymmetric center at the carbon atom substituted with cycle B, as shown below with an asterisk on formula (A). This asymmetric center can occur in its R or S configuration. In one preferred embodiment, said asymmetric center is in the R configuration. In another preferred embodiment, said asymmetric center is in the S configuration.

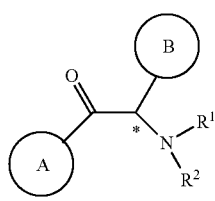

In a particular embodiment, cycle A is a heteroaryl which can be unsubstituted or substituted with one or more $Z^1$. In another particular embodiment, cycle A is selected from unsubstituted or substituted with one or more $Z^1$ indolyl, benzothienyl, pyrrolopyridinyl, pyridinimidazolyl, indazolyl, tetrahydropyridinthienyl, pyrazolepyridinyl and indolinyl. In a more particular embodiment, cycle A is selected from unsubstituted or substituted with one or more $Z^1$ indolyl and indolinyl. Yet more in particular, cycle A is selected from unsubstituted or substituted with one or more $Z^1$ indol-3-yl and indolin-1-yl.

In a particular embodiment of the invention, cycle A is not selected from indolin-1-yl.

In another particular embodiment, cycle B is selected from unsubstituted or substituted with one or more $Z^{1a}$ phenyl; pyridyl, pyridazinyl, pyrimidinyl, pyrazinyl, triazinyl, oxazolyl, imidazolyl, thiazolyl, isoxazolyl, pyrazolyl, isothiazolyl, furyl, thienyl, pyrrolyl, benzofuranyl, indolyl, quinolinyl, isoquinolinyl, benzimidazolyl, pyridinimidazolyl, pyridinpyrolyl, pyrazolepyridinyl, benzpyrolyl, triazinyl, purinyl, quinoxalinyl, quinazolinyl, dihydroimidazooxazinyl and pteridinyl. In yet another particular embodiment, cycle B is selected from unsubstituted or substituted with one or more $Z^{1a}$ phenyl; and pyridyl.

In another particular embodiment, cycle B is a heterocycle which can be unsubstituted or substituted with one or more $Z^{1a}$. In another particular embodiment, cycle B is selected from unsubstituted or substituted with one or more $Z^{1a}$ aryl and heteroaryl. In a more particular embodiment cycle B is a heteroaryl which can be unsubstituted or substituted with one or more $Z^{1a}$.

In a yet more particular embodiment, cycle B is selected from unsubstituted or substituted with one or more $Z^{1a}$ pyridyl, pyridazinyl, pyrimidinyl, pyrazinyl, triazinyl, oxazolyl, imidazolyl, thiazolyl, isoxazolyl, pyrazolyl, isothiazolyl, furyl, thienyl, pyrrolyl, benzofuranyl, indolyl, quinolinyl, isoquinolinyl, benzimidazolyl, pyridinimidazolyl, pyridinpyrolyl, pyrazolepyridinyl, benzpyrolyl, triazinyl, purinyl, quinoxalinyl, quinazolinyl, and pteridinyl.

In a still more particular embodiment, cycle B is selected from unsubstituted or substituted with one or more $Z^{1a}$ pyridyl, pyrazinyl, pyrimidyl, imidazolyl, isoxazolyl, pyrazolyl, furyl, thienyl, isoquinolinyl, benzimidazolyl, pyridinimidazolyl, benzopyrolyl, pyrazolepyridinyl and quinoxalinyl.

In a particular embodiment, cycle B is not an unsubstituted phenyl.

In another particular embodiment, $R^2$ is selected from hydrogen and unsubstituted or substituted with one or more $Z^{1c}$ alkyl. In another particular embodiment, $R^2$ is selected from hydrogen and alkyl (more in particular $C_{1-3}$alkyl). In yet another particular embodiment, $R^2$ is selected from hydrogen, methyl, ethyl, and propyl.

In another embodiment, $R^1$ is selected from aryl; heterocycle; arylalkyl; arylalkenyl; arylalkynyl; heterocycle-alkyl; heterocycle-alkenyl; heterocycle-alkynyl; arylheteroalkyl; arylheteroalkenyl; arylheteroalkynyl; heterocycle-heteroalkyl; heterocycle-heteroalkenyl; heterocycle-heteroalkynyl; and wherein said aryl, heterocycle, arylalkyl, arylalkenyl, arylalkynyl, heterocycle-alkyl, heterocycle-alkenyl, heterocycle-alkynyl, arylheteroalkyl, arylheteroalkenyl, arylheteroalkynyl, heterocycle-heteroalkyl, heterocycle-heteroalkenyl and heterocycle-heteroalkynyl can be unsubstituted or substituted with one or more $Z^{1b}$.

In another embodiment, $R^1$ is selected from aryl; heterocycle; W-aryl; and W-heterocycle; wherein said aryl, heterocycle, W-aryl, and W-heterocycle can be unsubstituted or substituted with one or more $Z^{1b}$; and wherein W is selected from $C_{1-3}$alkyl, $C_{1-3}$alkenyl, $C_{1-3}$alkynyl, $C_{1-3}$ heteroalkyl, $C_{1-3}$ heteroalkenyl and $C_{1-3}$ heteroalkynyl.

In another particular embodiment, $R^1$ is selected from aryl; heterocycle; W-aryl; and W-heterocycle; wherein said aryl, heterocycle, W-aryl, and W-heterocycle can be unsubstituted or substituted with one or more $Z^{1b}$; and wherein W is selected from $C_{1-3}$alkyl.

In yet another particular embodiment, $R^1$ is selected from aryl; heterocycle; —$CH_2$-aryl; and —$CH_2$-heterocycle; wherein said aryl, heterocycle, —$CH_2$-aryl and —$CH_2$-heterocycle can be unsubstituted or substituted with one or more $Z^{1b}$. In another embodiment, $R^1$ is selected from aryl; and heterocycle; wherein said aryl and heterocycle can be unsubstituted or substituted with one or more $Z^{1b}$. In yet a more particular embodiment, $R^1$ is selected from phenyl and pyridine, unsubstituted or substituted with one or more $Z^{1b}$. In still a more particular embodiment, $R^1$ is selected from phenyl and

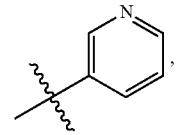 [SMILES: *c1cccnc1]

unsubstituted or substituted with one or more $Z^{1b}$

A very particular embodiment of the invention relates to the compounds selected from:

2-((3-ethoxyphenyl)amino)-1-(1H-indol-3-yl)-2-phenylethanone;

2-((4-chloro-3-methoxyphenyl)amino)-1-(1H-indol-3-yl)-2-phenylethanone;

1-(1H-indol-3-yl)-2-phenyl-2-((3-(trifluoromethoxy)phenyl)amino)ethanone;

2-((3-chlorophenyl)amino)-1-(1H-indol-3-yl)-2-phenylethanone;

2-((3,4-difluorophenyl)amino)-1-(1H-indol-3-yl)-2-phenylethanone;

2-((3-fluorophenyl)amino)-1-(1H-indol-3-yl)-2-phenylethanone;

1-(1H-indol-3-yl)-2-phenyl-2-((3-(trifluoromethyl)phenyl)amino)ethanone;

1-(1H-indol-3-yl)-2-((3-methoxyphenyl)amino)-2-phenylethanone;

2-((3,5-difluorophenyl)amino)-1-(1H-indol-3-yl)-2-phenylethanone;

2-((3,5-dimethoxyphenyl)amino)-1-(2-methyl-1H-indol-3-yl)-2-phenylethanone;

1-(6-chloro-1H-indol-3-yl)-2-((3,5-dimethoxyphenyl)amino)-2-phenylethanone;

1-(1H-indol-3-yl)-2-((3-methoxy-5-(trifluoromethyl)phenyl)amino)-2-phenylethanone;

2-((3-fluoro-5-methoxyphenyl)amino)-1-(1H-indol-3-yl)-2-phenylethanone;

1-(1H-indol-3-yl)-2-phenyl-2-(pyridin-3-ylamino)ethanone;
1-(1H-indol-3-yl)-2-phenyl-2-(pyridin-4-ylamino)ethanone;
1-(1H-indol-3-yl)-2-((3-methoxyphenyl)(methyl)amino)-2-phenylethanone;
1-(1H-indol-3-yl)-2-((3-methoxyphenyl)amino)-2-(pyridin-3-yl)ethanone;
1-(1H-indol-3-yl)-2-((3-methoxyphenyl)amino)-2-(pyridin-4-yl)ethanone;
1-(1H-indol-3-yl)-2-((3-methoxyphenyl)amino)-2-(4-(methylsulfonyl)phenyl)ethanone;
1-(1H-indol-3-yl)-2-((5-methylisoxazol-3-yl)amino)-2-phenylethanone;
2-(furan-2-yl)-1-(1H-indol-3-yl)-2-((3-methoxyphenyl)amino)ethanone;
1-(1H-indol-3-yl)-2-((3-methoxyphenyl)amino)-2-(thiophen-2-yl)ethanone;
1-(1H-indol-3-yl)-2-((3-methoxyphenyl)amino)-2-(5-methylisoxazol-3-yl)ethanone;
1-(1H-indol-3-yl)-2-((3-methoxyphenyl)amino)-2-(1-methyl-1H-imidazol-2-yl)ethanone;
1-(1H-indol-3-yl)-2-((3-methoxyphenyl)amino)-2-(thiophen-3-yl)ethanone;
2-(1H-imidazol-2-yl)-1-(1H-indol-3-yl)-2-((3-methoxyphenyl)amino)ethanone;
1-(1H-indol-3-yl)-2-((3-methoxyphenyl)amino)-2-(pyrimidin-5-yl)ethanone;
2-(imidazo[1,2-a]pyridin-2-yl)-1-(1H-indol-3-yl)-2-((3-methoxyphenyl)amino)ethanone;
2-((2-hydroxypyridin-4-yl)amino)-1-(1H-indol-3-yl)-2-phenylethanone;
1-(1H-indol-3-yl)-2-phenyl-2-((pyridin-2-ylmethyl)amino)ethanone;
1-(1H-indol-3-yl)-2-phenyl-2-((thiophen-2-ylmethyl)amino)ethanone;
2-((furan-2-ylmethyl)amino)-1-(1H-indol-3-yl)-2-phenylethanone;
3-((2-(1H-indol-3-yl)-2-oxo-1-phenylethyl)amino)benzonitrile;
4-(2-(1H-indol-3-yl)-1-((3-methoxyphenyl)amino)-2-oxoethyl)benzonitrile;
1-(1H-indol-3-yl)-2-((3-methoxyphenyl)amino)-2-(quinoxalin-6-yl)ethanone;
1-(1H-indol-3-yl)-2-((2-methoxyphenyl)amino)-2-phenylethanone;
2-((2,5-dimethoxyphenyl)amino)-1-(1H-indol-3-yl)-2-phenylethanone;
2-((2,3-dimethoxyphenyl)amino)-1-(1H-indol-3-yl)-2-phenylethanone;
3-(2-(1H-indol-3-yl)-1-((3-methoxyphenyl)amino)-2-oxoethyl)benzonitrile;
1-(1H-indol-3-yl)-2-((3-methoxyphenyl)amino)-2-(1-methyl-1H-pyrazol-4-yl)ethanone;
1-(1H-indol-3-yl)-2-((3-methoxyphenyl)amino)-2-(pyrazolo[1,5-a]pyridin-7-yl)ethanone;
1-(1H-indol-3-yl)-2-((3-(methylsulfonyl)phenyl)amino)-2-phenylethanone;
1-(1H-indol-3-yl)-2-((2-methoxypyridin-4-yl)amino)-2-phenylethanone;
2-((3-ethylphenyl)amino)-1-(1H-indol-3-yl)-2-phenylethanone;
1-(1H-indol-3-yl)-2-(isoquinolin-5-yl)-2-((3-methoxyphenyl)amino)ethanone;
1-(1H-indol-3-yl)-2-((3-methoxyphenyl)amino)-2-(4-(pyrimidin-5-yl)phenyl)ethanone;
2-((3-methoxyphenyl)amino)-1-(1-methyl-1H-indol-3-yl)-2-phenylethanone;
1-(1H-indol-3-yl)-2-phenyl-2-(quinoxalin-6-ylamino)ethanone;
3-((2-(1H-indol-3-yl)-2-oxo-1-phenylethyl)amino)-N,N-dimethylbenzamide;
3-((2-(1H-indol-3-yl)-2-oxo-1-phenylethyl)amino)-N-methylbenzenesulfonamide;
1-(4-chloro-1H-indol-3-yl)-2-((3-methoxyphenyl)amino)-2-phenylethanone;
1-(1H-indol-3-yl)-2-((3-methoxyphenyl)amino)-2-(3-(pyrimidin-5-yl)phenyl)ethanone;
1-(1H-indol-3-yl)-2-((3-methoxyphenyl)amino)-2-(6-methoxypyridin-3-yl)ethanone;
6-((2-(1H-indol-3-yl)-2-oxo-1-phenylethyl)amino)benzo[d]oxazol-2(3H)-one;
2-((3-(1H-1,2,4-triazol-1-yl)phenyl)amino)-1-(1H-indol-3-yl)-2-phenylethanone;
1-(1H-indol-3-yl)-2-((3-(oxazol-5-yl)phenyl)amino)-2-phenylethanone;
5-(2-(1H-indol-3-yl)-1-((3-methoxyphenyl)amino)-2-oxoethyl)-1,3-dimethyl-1H-benzo[d]imidazol-2(3H)-one;
4-(2-(1H-indol-3-yl)-1-((2-methoxypyridin-4-yl)amino)-2-oxoethyl)benzonitrile;
1-(1H-indol-3-yl)-2-((4-methoxy-6-methylpyrimidin-2-yl)amino)-2-phenylethanone;
2-(6-hydroxypyridin-3-yl)-1-(1H-indol-3-yl)-2-((3-methoxyphenyl)amino)ethanone;
2-(imidazo[1,2-a]pyridin-2-yl)-1-(1H-indol-3-yl)-2-((2-methoxypyridin-4-yl)amino)ethanone;
3-((2-(1H-indol-3-yl)-2-oxo-1-phenylethyl)amino)benzamide;
1-(1H-indol-3-yl)-2-((4-methoxypyridin-2-yl)amino)-2-phenylethanone;
1-(1H-indol-3-yl)-2-((5-methoxypyridin-3-yl)amino)-2-phenylethanone;
ethyl 3-((2-(1H-indol-3-yl)-2-oxo-1-phenylethyl)amino)benzoate;
1-(6-chloro-1H-indol-3-yl)-2-(imidazo[1,2-a]pyridin-2-yl)-2-((2-methoxypyridin-4-yl)amino)ethanone;
1-(1H-indol-3-yl)-2-((5-methoxy-1,2,4-thiadiazol-3-yl)amino)-2-phenylethanone;
3-((2-(1H-indol-3-yl)-2-oxo-1-phenylethyl)amino)benzoic acid;
1-(1H-indol-3-yl)-2-((6-methoxypyrimidin-4-yl)amino)-2-phenylethanone;
1-(6-chloro-1H-indol-3-yl)-2-((2-methoxypyridin-4-yl)amino)-2-phenylethanone;
1-(1H-indol-3-yl)-2-((2-methoxypyridin-4-yl)amino)-2-(pyridin-3-yl)ethanone;
1-(6-fluoro-1H-indol-3-yl)-2-((2-methoxypyridin-4-yl)amino)-2-phenylethanone;
1-(6-methoxy-1H-indol-3-yl)-2-((2-methoxypyridin-4-yl)amino)-2-phenylethanone;
1-(6-methoxy-1H-indol-3-yl)-2-((3-methoxyphenyl)amino)-2-phenylethanone;
1-(5-methoxy-1H-indol-3-yl)-2-((2-methoxypyridin-4-yl)amino)-2-phenylethanone;
methyl 3-(2-((2-methoxypyridin-4-yl)amino)-2-phenylacetyl)-1H-indole-6-carboxylate;
2-(6,8-dihydro-5H-imidazo[2,1-c][1,4]oxazin-2-yl)-1-(1H-indol-3-yl)-2-((3-methoxyphenyl)amino)ethanone;
2-(5-fluoroimidazo[1,2-a]pyridin-2-yl)-1-(1H-indol-3-yl)-2-((2-methoxypyridin-4-yl)amino)ethanone;
1-(1H-indol-3-yl)-2-((2-methoxypyridin-4-yl)amino)-2-(thiazol-4-yl)ethanone;
1-(1H-indol-3-yl)-2-((3-methoxyphenyl)amino)-2-(pyrazolo[1,5-a]pyridin-2-yl)ethanone;

1-(7-chloro-1H-indol-3-yl)-2-((3-methoxyphenyl)amino)-2-phenylethanone;
methyl 3-(2-((3-methoxyphenyl)amino)-2-phenylacetyl)-1H-indole-6-carboxylate;
1-(5-chloro-1H-indol-3-yl)-2-((3-methoxyphenyl)amino)-2-phenylethanone;
2-((2,6-dimethoxypyrimidin-4-yl)amino)-1-(1H-indol-3-yl)-2-phenylethanone;
1-(1H-indol-3-yl)-2-((3-methoxyphenyl)amino)-2-(8-methylimidazo[1,2-a]pyridin-2-yl)ethanone;
1-(1H-indol-3-yl)-2-((4-methoxypyrimidin-2-yl)amino)-2-phenylethanone;
2-(4-fluorophenyl)-1-(1H-indol-3-yl)-2-((2-methoxypyridin-4-yl)amino)ethanone;
2-(3-fluorophenyl)-1-(1H-indol-3-yl)-2-((2-methoxypyridin-4-yl)amino)ethanone;
1-(5-methoxy-1H-indol-3-yl)-2-((3-methoxyphenyl)amino)-2-phenylethanone;
3-(2-((2-methoxypyridin-4-yl)amino)-2-phenylacetyl)-1H-indole-6-carbonitrile;
3-(2-((3-methoxyphenyl)amino)-2-phenylacetyl)-1H-indole-6-carbonitrile;
2-(6,8-dihydro-5H-imidazo[2,1-c][1,4]oxazin-2-yl)-1-(1H-indol-3-yl)-2-((2-methoxypyridin-4-yl)amino)ethanone;
1-(1H-indol-3-yl)-2-((3-methoxyphenyl)amino)-2-(7-methylimidazo[1,2-a]pyridin-2-yl)ethanone;
1-(1H-indol-3-yl)-2-(1H-indol-5-yl)-2-((2-methoxypyridin-4-yl)amino)ethanone;
1-(1H-indol-3-yl)-2-((3-methoxyphenyl)amino)-2-(6-methylimidazo[1,2-a]pyridin-2-yl)ethanone;
1-(5-chloro-1H-indol-3-yl)-2-((2-methoxypyridin-4-yl)amino)-2-phenylethanone;
2-((2-methoxypyridin-4-yl)amino)-1-(1-methyl-1H-indol-3-yl)-2-phenylethanone;
1-(7-chloro-1H-indol-3-yl)-2-((2-methoxypyridin-4-yl)amino)-2-phenylethanone;
1-(1H-indol-3-yl)-2-((3-methoxyphenyl)amino)-2-(3-methylisoxazol-5-yl)ethanone;
1-(1H-indol-3-yl)-2-((3-methoxyphenyl)amino)-2-(1-methyl-1H-imidazol-4-yl)ethanone;
1-(1-(2-hydroxyethyl)-1H-indol-3-yl)-2-((3-methoxyphenyl)amino)-2-phenylethanone;
1-(1-(2-aminoethyl)-1H-indol-3-yl)-2-((3-methoxyphenyl)amino)-2-phenylethanone;
2-(3-(2-((3-methoxyphenyl)amino)-2-phenylacetyl)-1H-indol-1-yl)acetic acid;
2-(1-ethyl-1H-pyrazol-5-yl)-1-(1H-indol-3-yl)-2-((3-methoxyphenyl)amino)ethanone;
1-(1H-indol-3-yl)-2-((2-methoxypyridin-4-yl)amino)-2-(5-methylisoxazol-3-yl)ethanone;
2-(5-fluoroimidazo[1,2-a]pyridin-2-yl)-1-(1H-indol-3-yl)-2-((3-methoxyphenyl)amino)ethanone;
2-(6-fluoroimidazo[1,2-a]pyridin-2-yl)-1-(1H-indol-3-yl)-2-((3-methoxyphenyl)amino)ethanone;
2-((3-methoxyphenyl)amino)-1-(1-(methylsulfonyl)-1H-indol-3-yl)-2-phenylethanone;
2-(4-(2-(dimethylamino)ethoxy)phenyl)-1-(1H-indol-3-yl)-2-((3-methoxyphenyl)amino)ethanone;
ethyl 2-(3-(2-((3-methoxyphenyl)amino)-2-phenylacetyl)-1H-indol-1-yl)acetate;
1-(1-(2-(dimethylamino)ethyl)-1H-indol-3-yl)-2-((3-methoxyphenyl)amino)-2-phenylethanone;
N-(2-(1H-indol-3-yl)-2-oxo-1-phenylethyl)-2-(dimethylamino)-N-(3-methoxyphenyl)acetamide;
1-(6-chloro-1H-indol-3-yl)-2-((3-methoxyphenyl)amino)-2-(5-methylisoxazol-3-yl)ethanone;
2-((3-methoxyphenyl)amino)-1-(1-methyl-1H-indol-3-yl)-2-(5-methylisoxazol-3-yl)ethanone;
1-(6-chloro-1H-indol-3-yl)-2-((3-methoxyphenyl)amino)-2-phenylethanone;
1-(5-fluoro-1H-indol-3-yl)-2-((3-methoxyphenyl)amino)-2-phenylethanone;
4-(2-(7-chloro-1H-indol-3-yl)-1-((3-methoxyphenyl)amino)-2-oxoethyl)benzonitrile;
2-((2-methoxypyridin-4-yl)amino)-1-(1-(methylsulfonyl)-1H-indol-3-yl)-2-phenylethanone;
2-((3-methoxyphenyl)amino)-1-(6-methyl-1H-indol-3-yl)-2-phenylethanone;
1-(6-fluoro-1H-indol-3-yl)-2-((3-methoxyphenyl)amino)-2-phenylethanone;
2-(4-((dimethylamino)methyl)phenyl)-1-(1H-indol-3-yl)-2-((3-methoxyphenyl)amino)ethanone;
1-(1H-indol-3-yl)-2-((3-methoxyphenyl)amino)-2-(4-methyl-1H-imidazol-5-yl)ethanone;
3-(2-((3-methoxyphenyl)amino)-2-phenylacetyl)-1H-indole-5-carbonitrile;
2-(4-(hydroxymethyl)phenyl)-1-(1H-indol-3-yl)-2-((3-methoxyphenyl)amino)ethanone;
1-(1-(3-hydroxypropyl)-1H-indol-3-yl)-2-((3-methoxyphenyl)amino)-2-phenylethanone;
3-(2-((3-methoxyphenyl)amino)-2-phenylacetyl)-N,N-dimethyl-1H-indole-5-sulfonamide;
2-((3-methoxyphenyl)amino)-1-(5-methyl-1H-indol-3-yl)-2-phenylethanone;
2-((3,5-dimethoxyphenyl)amino)-1-(5-fluoro-1H-indol-3-yl)-2-phenylethanone;
4-(2-(1H-indol-3-yl)-1-((3-methoxyphenyl)amino)-2-oxoethyl)-2-fluorobenzonitrile;
4-(2-(1H-indol-3-yl)-1-((3-methoxyphenyl)amino)-2-oxoethyl)-3,5-difluorobenzonitrile;
1-(6-hydroxy-1H-indol-3-yl)-2-((3-methoxyphenyl)amino)-2-phenylethanone;
3-(2-((3-methoxyphenyl)amino)-2-phenylacetyl)-1H-indole-6-carboxylic acid;
1-(1-(2-methoxyethyl)-1H-indol-3-yl)-2-((3-methoxyphenyl)amino)-2-phenylethanone;
1-(5-fluoro-1-methyl-1H-indol-3-yl)-2-((3-methoxyphenyl)amino)-2-phenylethanone;
1-(1H-indol-3-yl)-2-((3-methoxyphenyl)amino)-2-(m-tolyl)ethanone;
1-(1H-indol-3-yl)-2-((3-methoxyphenyl)amino)-2-(p-tolyl)ethanone;
1-(6-(hydroxymethyl)-1H-indol-3-yl)-2-((3-methoxyphenyl)amino)-2-phenylethanone;
1-(6-(2-hydroxyethoxy)-1H-indol-3-yl)-2-((3-methoxyphenyl)amino)-2-phenylethanone;
methyl 3-(2-((3-methoxyphenyl)amino)-2-phenylacetyl)-1H-indole-5-carboxylate;
3-(2-((3-methoxyphenyl)amino)-2-phenylacetyl)-1H-indole-5-carboxylic acid;
2-(2-fluorophenyl)-1-(1H-indol-3-yl)-2-((3-methoxyphenyl)amino)ethanone;
1-(5-fluoro-1-(2-(methoxymethoxy)ethyl)-1H-indol-3-yl)-2-((3-methoxyphenyl)amino)-2-phenylethanone;
1-(5-fluoro-1-(2-hydroxyethyl)-1H-indol-3-yl)-2-((3-methoxyphenyl)amino)-2-phenylethanone;
2-((3,5-dimethoxyphenyl)amino)-1-(1-(2-(methoxymethoxy)ethyl)-1H-indol-3-yl)-2-phenylethanone;
2-((3,5-dimethoxyphenyl)amino)-1-(1-(2-hydroxyethyl)-1H-indol-3-yl)-2-phenylethanone;
2-(4-fluorophenyl)-1-(1H-indol-3-yl)-2-((3-methoxyphenyl)amino)ethanone;

1-(6-chloro-1H-indol-3-yl)-2-(imidazo[1,2-a]pyridin-2-yl)-2-((3-methoxyphenyl)amino)ethanone;
1-(5-fluoro-1H-indol-3-yl)-2-((3-methoxyphenyl)amino)-2-(pyridin-3-yl)ethanone;
1-(6-fluoro-1H-indol-3-yl)-2-((3-methoxyphenyl)amino)-2-(pyridin-3-yl)ethanone;
1-(7-fluoro-1H-indol-3-yl)-2-((3-methoxyphenyl)amino)-2-(pyridin-3-yl)ethanone;
1-(5-fluoro-1H-indol-3-yl)-2-((3-methoxyphenyl)amino)-2-(6-methoxypyridin-3-yl)ethanone;
1-(7-fluoro-1H-indol-3-yl)-2-((3-methoxyphenyl)amino)-2-(6-methoxypyridin-3-yl)ethanone;
2-(3,5-dimethoxyphenyl)amino)-1-(5-fluoro-1-(3-hydroxypropyl)-1H-indol-3-yl)-2-phenylethanone;
1-(6-fluoro-1H-indol-3-yl)-2-((5-methoxypyridin-3-yl)amino)-2-phenylethanone;
1-(1H-indol-3-yl)-2-(6-methoxypyridin-3-yl)-2-((5-methoxypyridin-3-yl)amino)ethanone;
4-(2-(1H-indol-3-yl)-1-((5-methoxypyridin-3-yl)amino)-2-oxoethyl)benzonitrile;
1-(benzo[b]thiophen-3-yl)-2-((3-methoxyphenyl)amino)-2-phenylethanone;
2-((3-methoxyphenyl)amino)-2-phenyl-1-(1H-pyrrolo[2,3-b]pyridin-3-yl)ethanone;
2-((3-methoxyphenyl)amino)-2-phenyl-1-(1H-pyrrolo[3,2-b]pyridin-3-yl)ethanone;
1-(imidazo[1,2-a]pyridin-3-yl)-2-((3-methoxyphenyl)amino)-2-phenylethanone;
2-((3-methoxyphenyl)amino)-2-phenyl-1-(pyrazolo[1,5-a]pyridin-3-yl)ethanone;
1-(1H-indazol-3-yl)-2-((3-methoxyphenyl)amino)-2-phenylethanone;
1-(benzo[b]thiophen-3-yl)-2-(imidazo[1,2-a]pyridin-2-yl)-2-((2-methoxypyridin-4-yl)amino)ethanone;
2-((3-methoxyphenyl)amino)-2-phenyl-1-(1H-pyrrolo[2,3-c]pyridin-3-yl)ethanone;
2-((3-methoxyphenyl)amino)-2-phenyl-1-(1H-pyrrolo[3,2-c]pyridin-3-yl)ethanone;
2-((3-methoxyphenyl)amino)-1-(6-methyl-4,5,6,7-tetrahydrothieno[2,3-c]pyridin-3-yl)-2-phenylethanone;
2-((3-methoxyphenyl)amino)-1-(1-methyl-1H-indazol-3-yl)-2-phenylethanone;
1-(indolin-1-yl)-2-((3-methoxyphenyl)amino)-2-phenylethanone;
tert-butyl (2-(3-(2-((3-methoxyphenyl)amino)-2-phenylacetyl)-1H-indol-1-yl)ethyl)carbamate;
1-(7-fluoro-1H-indol-3-yl)-2-((3-methoxyphenyl)amino)-2-phenylethanone;
2-((3,5-dimethoxyphenyl)amino)-1-(5-fluoro-1H-indol-3-yl)-2-(6-methoxypyridin-3-yl)ethanone;
2-((2-fluoropyridin-4-yl)amino)-1-(1H-indol-3-yl)-2-phenylethanone;
2-((3-methoxyphenyl)amino)-2-phenyl-1-(1-((tetrahydrofuran-3-yl)sulfonyl)-1H-indol-3-yl)ethanone;
2-((3-methoxyphenyl)amino)-1-(1-((1-methyl-1H-imidazol-4-yl)sulfonyl)-1H-indol-3-yl)-2-phenylethanone;
2-((3,5-dimethoxyphenyl)amino)-1-(1-(3-hydroxypropyl)-1H-indol-3-yl)-2-phenylethanone;
1-(1-(ethylsulfonyl)-1H-indol-3-yl)-2-((3-methoxyphenyl)amino)-2-phenylethanone;
1-(5-fluoro-1-(methylsulfonyl)-1H-indol-3-yl)-2-((3-methoxyphenyl)amino)-2-phenylethanone;
1-(6-fluoro-1H-indol-3-yl)-2-((3-methoxyphenyl)amino)-2-(6-methoxypyridin-3-yl)ethanone;
2-(6-fluoropyridin-3-yl)-1-(1H-indol-3-yl)-2-((3-methoxyphenyl)amino)ethanone;

1-(1H-indol-3-yl)-2-((3-methoxyphenyl)amino)-2-(2-methoxypyridin-3-yl)ethanone;
2-((3-methoxyphenyl)amino)-1-(1-(2-morpholinoethyl)-1H-indol-3-yl)-2-phenylethanone;
2-((3-methoxyphenyl)amino)-2-phenyl-1-(1-(piperidin-4-ylsulfonyl)-1H-indol-3-yl)ethanone;
4-((2-(1H-indol-3-yl)-2-oxo-1-phenylethyl)amino)-2-methoxybenzonitrile;
1-(5-(hydroxymethyl)-1H-indol-3-yl)-2-((3-methoxyphenyl)amino)-2-phenylethanone;
tert-butyl 3-(2-((3-methoxyphenyl)amino)-2-phenylacetyl)-1-methyl-6,7-dihydro-1H-pyrazolo[4,3-c]pyridine-5(4H)-carboxylate;
2-((3-methoxyphenyl)amino)-1-(1-methyl-4,5,6,7-tetrahydro-1H-pyrazolo[4,3-c]pyridin-3-yl)-2-phenylethanone hydrochloride;
1-(7-methoxy-1H-indol-3-yl)-2-((3-methoxyphenyl)amino)-2-phenylethanone;
1-(1,5-dimethyl-4,5,6,7-tetrahydro-1H-pyrazolo[4,3-c]pyridin-3-yl)-2-((3-methoxyphenyl)amino)-2-phenylethanone;
2-((3-methoxyphenyl)amino)-1-(7-methyl-1H-indol-3-yl)-2-phenylethanone;
2-((3-methoxyphenyl)amino)-1-(6-methyl-1H-pyrrolo[2,3-b]pyridin-3-yl)-2-phenylethanone;
1-(1H-indol-3-yl)-2-((3-methoxyphenyl)amino)-2-(6-methylpyridin-3-yl)ethanone;
1-(5-fluoro-1H-pyrrolo[2,3-b]pyridin-3-yl)-2-((3-methoxyphenyl)amino)-2-phenylethanone;
1-(5-((dimethylamino)methyl)-1H-indol-3-yl)-2-((3-methoxyphenyl)amino)-2-phenylethanone;
2-((3-methoxyphenyl)amino)-1-(5-(methylsulfonyl)-1H-indol-3-yl)-2-phenylethanone;
1-(4-fluoro-1H-indol-3-yl)-2-((3-methoxyphenyl)amino)-2-phenylethanone;
1-(4-methoxy-1H-indol-3-yl)-2-((3-methoxyphenyl)amino)-2-phenylethanone;
2-((3,5-dimethoxyphenyl)amino)-1-(6-methyl-1H-pyrrolo[2,3-b]pyridin-3-yl)-2-phenylethanone;
4-(1-((3,5-dimethoxyphenyl)amino)-2-(1H-indol-3-yl)-2-oxoethyl)benzonitrile;
2-((3,5-dimethoxyphenyl)amino)-1-(5-fluoro-1H-pyrrolo[2,3-b]pyridin-3-yl)-2-phenylethanone;
2-((3,5-dimethoxyphenyl)amino)-2-(4-fluorophenyl)-1-(1H-indol-3-yl)ethanone;
2-((3,5-dimethoxyphenyl)amino)-1-(1H-indol-3-yl)-2-(pyridin-3-yl)ethanone;
2-((3-methoxyphenyl)amino)-1-(6-morpholino-1H-indol-3-yl)-2-phenylethanone;
2-(imidazo[1,2-b]pyridazin-2-yl)-1-(1H-indol-3-yl)-2-((3-methoxyphenyl)amino)ethanone;
2-(6-(dimethylamino)pyridin-3-yl)-1-(1H-indol-3-yl)-2-((3-methoxyphenyl)amino)ethanone;
1-(1H-indol-3-yl)-2-((3-methoxyphenyl)amino)-2-(2-methoxypyrimidin-5-yl)ethanone;
1-(5-fluoro-1H-indol-3-yl)-2-(6-methoxypyridin-3-yl)-2-((5-methoxypyridin-3-yl)amino)ethanone;
1-(6-fluoro-1H-indol-3-yl)-2-(6-methoxypyridin-3-yl)-2-((5-methoxypyridin-3-yl)amino)ethanone;
2-((3-(2-(dimethylamino)ethoxy)-5-methoxyphenyl)amino)-1-(1H-indol-3-yl)-2-phenylethanone;
1-(1-(2-(tert-butoxy)ethyl)-6-fluoro-1H-indol-3-yl)-2-((3-methoxyphenyl)amino)-2-phenylethanone;
1-(6-fluoro-1-(2-hydroxyethyl)-1H-indol-3-yl)-2-((3-methoxyphenyl)amino)-2-phenylethanone;
2-((5-ethoxypyridin-3-yl)amino)-1-(1H-indol-3-yl)-2-phenylethanone;

1-(1H-indol-3-yl)-2-((5-isopropoxypyridin-3-yl)amino)-2-phenylethanone;
2-((5-ethylpyridin-3-yl)amino)-1-(1H-indol-3-yl)-2-phenylethanone;
1-(1H-indol-3-yl)-2-((3-methoxyphenyl)amino)-2-(5-methoxypyrazin-2-yl)ethanone;
2-(6-ethoxypyridin-3-yl)-1-(1H-indol-3-yl)-2-((3-methoxyphenyl)amino)ethanone;
2-((3-methoxyphenyl)amino)-1-(4-methyl-1H-indol-3-yl)-2-phenylethanone;
1-(1H-indol-3-yl)-2-((6-methoxypyrazin-2-yl)amino)-2-phenylethanone;
2-((3-(2-(tert-butoxy)ethoxy)-5-methoxyphenyl)amino)-1-(1H-indol-3-yl)-2-phenylethanone;
2-((3-ethoxy-5-methoxyphenyl)amino)-1-(1H-indol-3-yl)-2-phenylethanone;
2-((3-(2-hydroxyethoxy)-5-methoxyphenyl)amino)-1-(1H-indol-3-yl)-2-phenylethanone;
2-((5,6-dimethoxypyridin-3-yl)amino)-1-(1H-indol-3-yl)-2-phenylethanone;
2-((6-(dimethylamino)-5-methoxypyridin-3-yl)amino)-1-(1H-indol-3-yl)-2-phenylethanone;
2-((6-ethoxy-5-methoxypyridin-3-yl)amino)-1-(1H-indol-3-yl)-2-phenylethanone;
2-((5-methoxypyridin-3-yl)amino)-1-(1-methyl-1H-indazol-3-yl)-2-phenylethanone;
4-(1-((3-methoxyphenyl)amino)-2-(1-methyl-1H-indazol-3-yl)-2-oxoethyl)benzonitrile;
1-(1H-indol-3-yl)-2-((5-methoxy-6-(methylamino)pyridin-3-yl)amino)-2-phenylethanone;
2-((3-(hydroxymethyl)-5-methoxyphenyl)amino)-1-(1H-indol-3-yl)-2-phenylethanone;
2-((3-((dimethylamino)methyl)-5-methoxyphenyl)amino)-1-(1H-indol-3-yl)-2-phenylethanone;
2-((3-methoxyphenyl)amino)-2-(6-methoxypyridin-3-yl)-1-(1-methyl-1H-indazol-3-yl)ethanone;
2-((3,5-dimethoxyphenyl)amino)-1-(1-methyl-1H-indazol-3-yl)-2-phenylethanone;
1-(6-methoxy-1-methyl-1H-indazol-3-yl)-2-((3-methoxyphenyl)amino)-2-phenylethanone;
2-(1,5-dimethyl-1H-pyrazol-3-yl)-1-(1H-indol-3-yl)-2-((3-methoxyphenyl)amino)ethanone;
1-(1H-indol-3-yl)-2-(6-isopropoxypyridin-3-yl)-2-((3-methoxyphenyl)amino)ethanone;
2-((5-(difluoromethoxy)pyridin-3-yl)amino)-1-(1H-indol-3-yl)-2-phenylethanone;
1-(5-fluoro-1-methyl-1H-indazol-3-yl)-2-((3-methoxyphenyl)amino)-2-phenylethanone;
1-(1H-indol-3-yl)-2-((3-methoxyphenyl)amino)-2-(6-(methylamino)pyridin-3-yl)ethanone;
2-((3-methoxyphenyl)amino)-2-(5-methoxypyrazin-2-yl)-1-(1-methyl-1H-indazol-3-yl)ethanone;
2-((3-methoxyphenyl)amino)-1-(1-methyl-1H-indazol-3-yl)-2-(pyrazolo[1,5-a]pyridin-2-yl)ethanone;
1-(1H-indol-3-yl)-2-((3-methoxyphenyl)amino)-2-(pyrazin-2-yl)ethanone;
3-(2-((3-methoxyphenyl)amino)-2-phenylacetyl)-1-methyl-1H-indazole-5-carbonitrile;
2-((6-methoxypyrazin-2-yl)amino)-1-(1-methyl-1H-indazol-3-yl)-2-phenylethanone;
1-(1H-indol-3-yl)-2-((6-methoxypyridin-2-yl)amino)-2-phenylethanone;
2-((3-(hydroxymethyl)-5-methoxyphenyl)amino)-1-(1-methyl-1H-indazol-3-yl)-2-phenylethanone;
2-((3,5-dimethoxyphenyl)amino)-1-(1-methyl-1H-indazol-3-yl)-2-(pyridin-3-yl)ethanone;
1-(1H-indol-3-yl)-2-((6-methoxypyrazin-2-yl)amino)-2-(pyridin-3-yl)ethanone;
1-(6-fluoro-1-methyl-1H-indazol-3-yl)-2-((3-methoxyphenyl)amino)-2-phenylethanone;
2-((3-(hydroxymethyl)-5-methoxyphenyl)amino)-1-(1H-indol-3-yl)-2-(pyridin-3-yl)ethanone;
2-((3-(hydroxymethyl)-5-methoxyphenyl)amino)-1-(1H-indol-3-yl)-2-(6-methoxypyridin-3-yl)ethanone;
1-(1H-indol-3-yl)-2-((6-methoxypyrazin-2-yl)amino)-2-(6-methoxypyridin-3-yl)ethanone;
1-(6-fluoro-1H-indol-3-yl)-2-((3-(hydroxymethyl)-5-methoxyphenyl)amino)-2-phenylethanone;
3-(2-((3-methoxyphenyl)amino)-2-phenylacetyl)-1-methyl-1H-indazole-6-carbonitrile;
1-(6-fluoro-1H-indol-3-yl)-2-((6-methoxypyrazin-2-yl)amino)-2-phenylethanone;
2-((3-(hydroxymethyl)-5-methoxyphenyl)amino)-1-(1H-indol-3-yl)-2-(5-methoxypyrazin-2-yl)ethanone;
2-((3-(hydroxymethyl)-5-methoxyphenyl)amino)-1-(1H-indol-3-yl)-2-(pyrazolo[1,5-a]pyridin-2-yl)ethanone;
1-(1H-indol-3-yl)-2-((6-methoxypyrazin-2-yl)amino)-2-(pyrazolo[1,5-a]pyridin-2-yl)ethanone;
2-((3-(2-hydroxyethoxy)-5-methoxyphenyl)amino)-1-(1H-indol-3-yl)-2-(6-methoxypyridin-3-yl)ethanone;
2-((3-(2-hydroxyethoxy)-5-methoxyphenyl)amino)-1-(1H-indol-3-yl)-2-(5-methoxypyrazin-2-yl)ethanone;
2-((3,5-dimethoxyphenyl)amino)-1-(1H-indol-3-yl)-2-(pyrazolo[1,5-a]pyridin-2-yl)ethanone;
2-((3,5-dimethoxyphenyl)amino)-1-(1H-indol-3-yl)-2-(5-methoxypyrazin-2-yl)ethanone;
1-(5-fluoro-1H-indol-3-yl)-2-((3-methoxyphenyl)amino)-2-(5-methoxypyrazin-2-yl)ethanone;
1-(5-fluoro-1H-indol-3-yl)-2-((3-(hydroxymethyl)-5-methoxyphenyl)amino)-2-phenylethanone;
1-(6-fluoro-1H-indol-3-yl)-2-((3-methoxyphenyl)amino)-2-(5-methoxypyrazin-2-yl)ethanone;
2-((3-(2-hydroxyethoxy)-5-methoxyphenyl)amino)-1-(1-methyl-1H-indazol-3-yl)-2-phenylethanone;
(−)-1-(1H-indol-3-yl)-2-((5-methoxypyridin-3-yl)amino)-2-phenylethanone;
(+)-1-(1H-indol-3-yl)-2-((5-methoxypyridin-3-yl)amino)-2-phenylethanone;
1-(1H-indol-3-yl)-2-((3-methoxyphenyl)amino)-2-(pyridin-2-yl)ethanone;
1-(1H-indol-4-yl)-2-((3-methoxyphenyl)amino)-2-phenylethanone;
1-(1-(2-hydroxyethyl)-1H-indazol-3-yl)-2-((3-methoxyphenyl)amino)-2-phenylethanone;
2-((3-(2-(tert-butoxy)ethoxy)-5-methoxyphenyl)amino)-1-(1-methyl-1H-indol-3-yl)-2-phenylethanone;
2-((3-(2-hydroxyethoxy)-5-methoxyphenyl)amino)-1-(1-methyl-1H-indol-3-yl)-2-phenylethanone;
3-methoxy-5-((2-(1-methyl-1H-indol-3-yl)-2-oxo-1-phenylethyl)amino)benzyl acetate;
2-((3-(hydroxymethyl)-5-methoxyphenyl)amino)-1-(1-methyl-1H-indol-3-yl)-2-phenylethanone;
1-(isoquinolin-4-yl)-2-((3-methoxyphenyl)amino)-2-phenylethanone;
1-(1H-indol-3-yl)-2-((3-methoxyphenyl)amino)-2-(5-methylpyridin-3-yl)ethanone;
1-(1H-indol-3-yl)-2-((3-methoxyphenyl)amino)-2-(5-methoxypyridin-2-yl)ethanone;
2-(6,7-dihydro-4H-pyrazolo[5,1-c][1,4]oxazin-2-yl)-1-(1H-indol-3-yl)-2-((3-methoxyphenyl)amino)ethanone;
1-(1H-indol-3-yl)-2-((3-methoxyphenyl)amino)-2-(5-methoxypyridin-3-yl)ethanone;

2-(4-fluorophenyl)-2-((3-(hydroxymethyl)-5-methoxyphenyl)amino)-1-(1H-indol-3-yl)ethanone;
5-(2-(1H-indol-3-yl)-1-((3-methoxyphenyl)amino)-2-oxoethyl)picolinonitrile;
1-(1H-indol-3-yl)-2-((3-methoxyphenyl)amino)-2-(6-(trifluoromethyl)pyridin-3-yl)ethanone;
1-(6-fluoro-1H-indol-3-yl)-2-((3-(2-hydroxyethoxy)-5-methoxyphenyl)amino)-2-phenylethanone;
1-(1H-indol-3-yl)-2-((3-methoxyphenyl)amino)-2-(pyridazin-3-yl)ethanone;
2-((3-(hydroxymethyl)-5-methoxyphenyl)amino)-1-(7-methyl-1H-indol-3-yl)-2-phenylethanone;
2-((2,6-dimethoxypyridin-4-yl)amino)-1-(1H-indol-3-yl)-2-phenylethanone;
2-((3-(hydroxymethyl)-5-methoxyphenyl)amino)-1-(1H-indol-3-yl)-2-(6-methylpyridin-3-yl)ethanone;
2-(5-fluoropyridin-3-yl)-1-(1H-indol-3-yl)-2-((3-methoxyphenyl)amino)ethanone;
(−)-1-(5-fluoro-1H-indol-3-yl)-2-(6-methoxypyridin-3-yl)-2-((5-methoxypyridin-3-yl)amino)ethanone;
(+)-1-(5-fluoro-1H-indol-3-yl)-2-(6-methoxypyridin-3-yl)-2-((5-methoxypyridin-3-yl)amino)ethanone;
(−)-1-(1H-indol-3-yl)-2-((3-methoxyphenyl)amino)-2-(pyrazolo[1,5-a]pyridin-2-yl)ethanone;
(+)-1-(1H-indol-3-yl)-2-((3-methoxyphenyl)amino)-2-(pyrazolo[1,5-a]pyridin-2-yl)ethanone;
(−)-2-((3,5-dimethoxyphenyl)amino)-1-(1H-indol-3-yl)-2-phenylethanone;
(+)-2-((3,5-dimethoxyphenyl)amino)-1-(1H-indol-3-yl)-2-phenylethanone;
2-(benzo[d]oxazol-2-yl)-1-(1H-indol-3-yl)-2-((3-methoxyphenyl)amino)ethanone;
2-((3-methoxyphenyl)amino)-1-(7-methyl-1H-indol-3-yl)-2-(pyrazolo[1,5-a]pyridin-2-yl)ethanone;
1-(benzo[d]isoxazol-3-yl)-2-((3-methoxyphenyl)amino)-2-phenylethanone;
2-((3-(2-hydroxyethoxy)-5-methoxyphenyl)amino)-1-(7-methyl-1H-indol-3-yl)-2-phenylethanone;
2-((3-methoxyphenyl)amino)-2-(6-methoxypyridin-3-yl)-1-(7-methyl-1H-indol-3-yl)ethanone;
2-(6-fluoropyridin-3-yl)-2-((3-(hydroxymethyl)-5-methoxyphenyl)amino)-1-(1H-indol-3-yl)ethanone;
1-(5-fluoro-1H-indol-3-yl)-2-((3-(hydroxymethyl)-5-methoxyphenyl)amino)-2-(pyridin-3-yl)ethanone;
2-((3,5-dimethoxyphenyl)amino)-1-(1H-indol-3-yl)-2-(6-methoxypyridin-3-yl)ethanone;
2-((3-(2-hydroxyethoxy)-5-methoxyphenyl)amino)-1-(1H-indol-3-yl)-2-(pyrazolo[1,5-a]pyridin-2-yl)ethanone;
2-((3,5-dimethoxyphenyl)amino)-1-(7-methyl-1H-indol-3-yl)-2-phenylethanone;
2-((3,5-dimethoxyphenyl)amino)-1-(1-methyl-1H-indol-3-yl)-2-phenylethanone;
2-((3,5-dimethoxyphenyl)amino)-1-(7-(2-hydroxyethyl)-1H-indol-3-yl)-2-phenylethanone;
2-((3,5-dimethoxyphenyl)amino)-2-(4-fluorophenyl)-1-(1-methyl-1H-indazol-3-yl)ethanone;
2-((3,5-dimethoxyphenyl)amino)-2-(4-fluorophenyl)-1-(7-methyl-1H-indol-3-yl)ethanone;
2-((3-(2-(tert-butoxy)ethoxy)-5-methoxyphenyl)amino)-1-(1H-indol-3-yl)-2-(pyridin-3-yl)ethanone;
2-((3-(2-hydroxyethoxy)-5-methoxyphenyl)amino)-1-(1H-indol-3-yl)-2-(pyridin-3-yl)ethanone;
1-(6-fluoro-1H-indol-3-yl)-2-((3-(hydroxymethyl)-5-methoxyphenyl)amino)-2-(pyridin-3-yl)ethanone;
2-((2-fluoro-3,5-dimethoxyphenyl)amino)-1-(1H-indol-3-yl)-2-phenylethanone;
2-((3,5-dimethoxyphenyl)amino)-1-(1H-indol-3-yl)-2-(6-methylpyridin-3-yl)ethanone;
2-((4,6-dimethoxypyrimidin-2-yl)amino)-1-(1H-indol-3-yl)-2-phenylethanone;
1-(1H-indol-3-yl)-2-((3-methoxyphenyl)amino)-2-(o-tolyl)ethanone;
2-((3-(2-(tert-butoxy)ethoxy)-5-methoxyphenyl)amino)-2-(4-fluorophenyl)-1-(1H-indol-3-yl)ethanone;
2-(4-fluorophenyl)-2-((3-(2-hydroxyethoxy)-5-methoxyphenyl)amino)-1-(1H-indol-3-yl)ethanone;
2-((3,5-dimethoxyphenyl)amino)-1-(5-(hydroxymethyl)-1H-indol-3-yl)-2-phenylethanone;
2-((3,5-dimethoxyphenyl)amino)-1-(4-(hydroxymethyl)-1H-indol-3-yl)-2-phenylethanone;
2-((3,5-dimethoxyphenyl)amino)-1-(5-(3-hydroxypropyl)-1H-indol-3-yl)-2-phenylethanone;
2-((3-(2-(tert-butoxy)ethoxy)-5-methoxyphenyl)amino)-1-(5-fluoro-1H-indol-3-yl)-2-phenylethanone;
1-(5-fluoro-1H-indol-3-yl)-2-((3-(2-hydroxyethoxy)-5-methoxyphenyl)amino)-2-phenylethanone;
2-((4-fluoro-3-methoxyphenyl)amino)-1-(1H-indol-3-yl)-2-phenylethanone;
2-((3,5-dimethoxyphenyl)amino)-1-(4-(3-hydroxypropyl)-1H-indol-3-yl)-2-phenylethanone;
2-((3,5-dimethoxyphenyl)amino)-1-(7-(2-hydroxyethyl)-1-methyl-1H-indol-3-yl)-2-phenylethanone;
2-((3-hydroxy-5-methoxyphenyl)amino)-1-(1H-indol-3-yl)-2-phenylethanone;
2-((3,5-dimethoxyphenyl)amino)-1-(1-methyl-1H-indol-3-yl)-2-(pyridin-3-yl)ethanone;
2-((3-(3-hydroxypropoxy)-5-methoxyphenyl)amino)-1-(1H-indol-3-yl)-2-phenylethanone;
2-((3,5-dimethoxyphenyl)amino)-1-(7-(hydroxymethyl)-1H-indol-3-yl)-2-phenylethanone;
2-(3-(2-((5-methoxypyridin-3-yl)amino)-2-phenylacetyl)-1H-indol-7-yl)ethyl acetate;
1-(7-(2-hydroxyethyl)-1H-indol-3-yl)-2-((5-methoxypyridin-3-yl)amino)-2-phenylethanone;
2-((3,5-dimethoxyphenyl)amino)-1-(7-(2-(dimethylamino)ethyl)-1H-indol-3-yl)-2-phenylethanone;
2-((3-hydroxyphenyl)amino)-1-(1H-indol-3-yl)-2-phenylethanone;
ethyl 4-(3-((2-(1H-indol-3-yl)-2-oxo-1-phenylethyl)amino)-5-methoxyphenoxy)butanoate;
2-((3-(2-(tert-butoxy)ethoxy)-5-methoxyphenyl)amino)-1-(1H-indol-3-yl)-2-(p-tolyl)ethanone;
2-((3-(2-hydroxyethoxy)-5-methoxyphenyl)amino)-1-(1H-indol-3-yl)-2-(p-tolyl)ethanone;
2-((3,5-dimethoxyphenyl)amino)-1-(5-(2-hydroxyethyl)-1H-indol-3-yl)-2-phenylethanone;
2-((3,5-dimethoxyphenyl)amino)-2-(4-fluorophenyl)-1-(7-(2-hydroxyethyl)-1H-indol-3-yl)ethanone;
3-(3-(2-((5-methoxypyridin-3-yl)amino)-2-phenylacetyl)-1H-indol-5-yl)propyl acetate;
1-(5-(3-hydroxypropyl)-1H-indol-3-yl)-2-((5-methoxypyridin-3-yl)amino)-2-phenylethanone;
2-(3-fluorophenyl)-2-((3-(2-hydroxyethoxy)-5-methoxyphenyl)amino)-1-(1H-indol-3-yl)ethanone;
2-(3-(2-(5-methoxypyrazin-2-yl)-2-((5-methoxypyridin-3-yl)amino)acetyl)-1H-indol-7-yl)ethyl acetate;
1-(7-(2-hydroxyethyl)-1H-indol-3-yl)-2-(5-methoxypyrazin-2-yl)-2-((5-methoxypyridin-3-yl)amino)ethanone;
2-(3-(2-((5-methoxypyridin-3-yl)amino)-2-(pyrazolo[1,5-a]pyridin-2-yl)acetyl)-1H-indol-7-yl)ethyl acetate;

1-(7-(2-hydroxyethyl)-1H-indol-3-yl)-2-((5-methoxypyridin-3-yl)amino)-2-(pyrazolo[1,5-a]pyridin-2-yl)ethanone;

2-(3-(2-(5-fluoropyridin-3-yl)-2-((5-methoxypyridin-3-yl)amino)acetyl)-1H-indol-7-yl)ethyl acetate;

2-(5-fluoropyridin-3-yl)-1-(7-(2-hydroxyethyl)-1H-indol-3-yl)-2-((5-methoxypyridin-3-yl)amino)ethanone;

2-(3-(2-((5-methoxypyridin-3-yl)amino)-2-phenylacetyl)-1H-indol-5-yl)ethyl acetate;

1-(5-(2-hydroxyethyl)-1H-indol-3-yl)-2-((5-methoxypyridin-3-yl)amino)-2-phenylethanone;

2-(3-(2-(5-methoxypyrazin-2-yl)-2-((5-methoxypyridin-3-yl)amino)acetyl)-1H-indol-5-yl)ethyl acetate;

1-(5-(2-hydroxyethyl)-1H-indol-3-yl)-2-(5-methoxypyrazin-2-yl)-2-((5-methoxypyridin-3-yl)amino)ethanone;

2-(3-(2-((5-methoxypyridin-3-yl)amino)-2-(pyrazolo[1,5-a]pyridin-2-yl)acetyl)-1H-indol-5-yl)ethyl acetate;

1-(5-(2-hydroxyethyl)-1H-indol-3-yl)-2-((5-methoxypyridin-3-yl)amino)-2-(pyrazolo[1,5-a]pyridin-2-yl)ethanone;

2-(3-(2-(4-fluorophenyl)-2-((5-methoxypyridin-3-yl)amino)acetyl)-1H-indol-7-yl)ethyl acetate;

2-(4-fluorophenyl)-1-(7-(2-hydroxyethyl)-1H-indol-3-yl)-2-((5-methoxypyridin-3-yl)amino)ethanone;

4-(3-((2-(1H-indol-3-yl)-2-oxo-1-phenylethyl)amino)-5-methoxyphenoxy)butanoic acid;

2-(3-(2-((3,5-dimethoxyphenyl)amino)-2-(pyrazolo[1,5-a]pyridin-2-yl)acetyl)-1H-indol-5-yl)ethyl acetate;

2-((3,5-dimethoxyphenyl)amino)-1-(5-(2-hydroxyethyl)-1H-indol-3-yl)-2-(pyrazolo[1,5-a]pyridin-2-yl)ethanone;

3-(3-(2-((5-methoxypyridin-3-yl)amino)-2-(pyrazolo[1,5-a]pyridin-2-yl)acetyl)-1H-indol-5-yl)propyl acetate;

1-(5-(3-hydroxypropyl)-1H-indol-3-yl)-2-((5-methoxypyridin-3-yl)amino)-2-(pyrazolo[1,5-a]pyridin-2-yl)ethanone;

3-(3-(2-(5-methoxypyrazin-2-yl)-2-((5-methoxypyridin-3-yl)amino)acetyl)-1H-indol-5-yl)propyl acetate;

1-(5-(3-hydroxypropyl)-1H-indol-3-yl)-2-(5-methoxypyrazin-2-yl)-2-((5-methoxypyridin-3-yl)amino)ethanone;

2-((3,5-dimethoxyphenyl)amino)-1-(7-(2-(methylsulfonyl)ethyl)-1H-indol-3-yl)-2-phenylethanone;

2-((3,5-dimethoxyphenyl)amino)-2-(4-fluorophenyl)-1-(5-(3-hydroxypropyl)-1H-indol-3-yl)ethanone;

3-(3-(2-(4-fluorophenyl)-2-((5-methoxypyridin-3-yl)amino)acetyl)-1H-indol-5-yl)propyl acetate;

2-(4-fluorophenyl)-1-(5-(3-hydroxypropyl)-1H-indol-3-yl)-2-((5-methoxypyridin-3-yl)amino)ethanone;

2-((3,5-dimethoxyphenyl)amino)-2-(4-fluorophenyl)-1-(5-(2-hydroxyethyl)-1H-indol-3-yl)ethanone;

4-(3-((1-(4,6-dimethylpyridin-3-yl)-2-(1H-indol-3-yl)-2-oxoethyl)amino)-5-methoxyphenyl)butanoic acid;

2-(6-(hydroxymethyl)pyridin-3-yl)-1-(1H-indol-3-yl)-2-((3-methoxy-5-(2-(methylsulfonyl)ethyl)phenyl)amino)ethanone;

2-((3,5-dimethoxyphenyl)amino)-1-(5-fluoro-7-(2-hydroxyethyl)-1H-indol-3-yl)-2-(tetrahydrofuran-3-yl)ethanone;

2-((3,5-dimethoxyphenyl)amino)-1-(5-((methylsulfonyl)methyl)-1H-indol-3-yl)-2-(tetrahydro-2H-pyran-4-yl)ethanone;

2-((3,5-dimethoxyphenyl)amino)-1-(5-(3-(dimethylamino)propyl)-1H-indol-3-yl)-2-(3,5-dimethylisoxazol-4-yl)ethanone;

2-([1,2,4]triazolo[1,5-a]pyridin-7-yl)-1-(7-(3-aminopropyl)-1H-indol-3-yl)-2-((3,5-dimethoxyphenyl)amino)ethanone;

2-(benzo[d]isoxazol-3-yl)-2-((3,5-dimethoxyphenyl)amino)-1-(7-(3-hydroxypropyl)-1H-indol-3-yl)ethanone;

3-(3-(2-((3,5-dimethoxyphenyl)amino)-2-(5-phenylisoxazol-3-yl)acetyl)-1H-indol-5-yl)propanoic acid;

1-(5-(2-aminoethyl)-1H-indol-3-yl)-2-((3,5-dimethoxyphenyl)amino)-2-(5-methyl-1-phenyl-1H-pyrazol-3-yl)ethanone;

1-methyl-4-((2-(5-(2-(methylsulfonyl)ethyl)-1H-indol-3-yl)-2-oxo-1-phenylethyl)amino)pyrrolidin-2-one;

1-(1H-indol-3-yl)-2-((3-methoxy-5-((methylamino)methyl)phenyl)amino)-2-(3-methyl-3H-imidazo[4,5-b]pyridin-2-yl)ethanone;

2-(6,7-dihydro-4H-pyrano[3,4-d]thiazol-2-yl)-2-((3-(2-hydroxyethyl)-5-methoxyphenyl)amino)-1-(1H-indol-3-yl)ethanone;

2-((3-(2-aminoethoxy)-5-methoxyphenyl)amino)-1-(1H-indol-3-yl)-2-(1-methyl-1H-benzo[d]imidazol-2-yl)ethanone;

2-(benzo[d]thiazol-2-yl)-1-(1H-indol-3-yl)-2-((3-methoxy-5-(2-(pyrrolidin-1-yl)ethoxy)phenyl)amino)ethanone;

2-((3-(difluoromethoxy)phenyl)amino)-1-(1H-indol-3-yl)-2-(thiazolo[4,5-b]pyrazin-2-yl)ethanone;

2-(3-((1-(benzo[b]thiophen-2-yl)-2-(1H-indol-3-yl)-2-oxoethyl)amino)-5-methoxyphenyl)acetic acid;

2-((3-(3-aminopropoxy)-5-methoxyphenyl)amino)-1-(1H-indol-3-yl)-2-(thieno[2,3-b]pyridin-2-yl)ethanone;

1-(5-(aminomethyl)-1H-indol-3-yl)-2-((3,5-dimethoxyphenyl)amino)-2-(thiazolo[5,4-c]pyridin-2-yl)ethanone;

1-(7-(aminomethyl)-1H-indol-3-yl)-2-((3,5-dimethoxyphenyl)amino)-2-(thiazolo[4,5-c]pyridin-2-yl)ethanone;

1-(5-(2-aminoethyl)-1H-indol-3-yl)-2-((3,5-dimethoxyphenyl)amino)-2-(thiazolo[4,5-b]pyridin-2-yl)ethanone;

1-(1H-indol-3-yl)-2-((3-methoxy-5-(2-(methylsulfonyl)ethoxy)phenyl)amino)-2-(5-methyl-4,5,6,7-tetrahydropyrazolo[1,5-a]pyrazin-2-yl)ethanone;

2-((3,5-dimethoxyphenyl)amino)-1-(1H-indol-3-yl)-2-(5-methyl-4,5,6,7-tetrahydrothiazolo[4,5-c]pyridin-2-yl)ethanone;

2-((3,5-dimethoxyphenyl)amino)-1-(7-(2-hydroxyethyl)-1H-indol-3-yl)-2-(p-tolyl)ethanone;

2-(4-fluorophenyl)-2-((3-(2-hydroxyethoxy)-5-methoxyphenyl)amino)-1-(7-(2-hydroxyethyl)-1H-indol-3-yl)ethanone;

2-((3-(2-hydroxyethoxy)-5-methoxyphenyl)amino)-1-(5-(2-hydroxyethyl)-1H-indol-3-yl)-2-phenylethanone;

2-((3,5-dimethoxyphenyl)amino)-1-(5-(2-(dimethylamino)ethyl)-1H-indol-3-yl)-2-(4-fluorophenyl)ethanone;

2-((3,5-dimethoxyphenyl)amino)-2-(4-fluorophenyl)-1-(5-(2-hydroxyethyl)-1-methyl-1H-indazol-3-yl)ethanone;

2-(4-fluorophenyl)-2-((3-(2-hydroxyethoxy)-5-methoxyphenyl)amino)-1-(1-methyl-1H-indazol-3-yl)ethanone;

2-((3,5-dimethoxyphenyl)amino)-1-(5-(2-hydroxyethyl)-1-methyl-1H-indazol-3-yl)-2-(pyrazolo[1,5-a]pyridin-2-yl)ethanone;

2-(4-fluorophenyl)-1-(1H-indol-3-yl)-2-((3-methoxy-5-((methylsulfonyl)methyl)phenyl)amino)ethanone;

2-((3,5-dimethoxyphenyl)amino)-2-(3-methylpyridin-2-yl)-1-(7-((methylsulfonyl)methyl)-1H-indol-3-yl)ethanone; and 3-(3-(2-(6-cyanopyridin-2-yl)-2-((3,5-dimethoxyphenyl)amino)acetyl)-1H-indol-5-yl)propanoic acid.

Another aspect of the invention relates to the compounds described in the first aspect with the formulas (A), (B), (C), (D), (D1), (D2), (D3), (D4), (D5), (E), (E1), (E2), (F), (F1) and (G) and all embodiments thereof, for use as a medicine.

Another aspect of the invention relates to the compounds described in the first aspect with the formulas (A), (B), (C), (D), (D1), (D2), (D3), (D4), (D5), (E), (E1), (E2), (F), (F1), (G), (H), (1), (J), and all embodiments thereof, for use as a medicine.

Yet another aspect of the invention relates to the compounds described herein for use as a medicine for the prevention or treatment of a flavivirus infection in an animal, mammal or human. In a particular embodiment, flavivirus infection is an infection with dengue virus. The present invention also relates to the use of the compounds herein described for the manufacture of a medicament, in a particular embodiment said medicament is for the prevention or treatment of a flavivirus infection in an animal, mammal or human.

Another aspect of the present invention relates to a pharmaceutical composition comprising the compounds described herein above and all embodiments thereof in combination with a pharmaceutically acceptable carrier. The pharmaceutical composition comprises compounds selected from the formulas (A), (B), (C), (D), (D1), (D2), (D3), (D4), (D5), (E), (E1), (E2), (F), (F1) and (G) and all embodiments thereof.

Another aspect of the present invention relates to a pharmaceutical composition comprising an effective amount of the compounds described herein above and all embodiments thereof in combination with a pharmaceutically acceptable carrier. The pharmaceutical composition comprises compounds selected from the formulas (A), (B), (C), (D), (D1), (D2), (D3), (D4), (D5), (E), (E1), (E2), (F), (F1), (G), (H), (1), (J), and all embodiments thereof.

Yet another aspect of the present invention relates to a method for the prevention or treatment of a flavivirus infection in an animal, mammal or human comprising administering to an animal, mammal or human in need for such prevention or treatment an effective dose of the compounds of the first aspect described herein and the embodiments thereof.

Still another aspect relates to a method for the preparation of the compounds of the invention, comprising the step of reacting an imine with an aldehyde under umpolung conditions in the presence of a thiazolium catalyst to obtain the desired compounds of the invention.

In another embodiment, the invention relates to a method for the preparation of the compounds of the invention, comprising the steps of
reacting an heterocycle under Friedel Craft conditions to obtain a ketone derivative having a methylene adjacent to the carbonyl,
reacting the previously obtained ketone under halogenation conditions to obtain an alpha-halogenoketone,
substitute the previously obtained alpha-halogenoketone with amines to obtain the desired compounds of the invention.

In another embodiment, the invention relates to a method for the preparation of the compounds of the invention, comprising the steps of
reacting a heterocyclicamine with 2-halogeno-acetic acid halide to obtain an alpha-halogenoamide derivative,
substitute the previously obtained alpha-halogenoamide with amines to obtain the desired compounds of the invention.

In another embodiment, the invention relates to a method for the preparation of the compounds of the invention, comprising the steps of
reacting an aldehyde with an imine in the presence of a catalyst to obtain a beta-aminoketone derivative as desired compound.

One embodiment of the invention relates to a method for the preparation of the compounds of the invention, comprising the step of
reacting compound of formula (X1) with the amine $R^1R^2NH$ in a suitable solvent, wherein cycle A, cycle B, $R^1$, and $R^2$ have the meaning according to any one of the embodiments presented herein, and LG is a leaving group as known by the skilled in the art, preferably selected from chlorine, bromine, and iodine; or

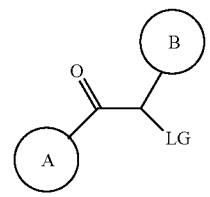

(X1)

reacting the imine of formula (X2) with an aldehyde of formula (X3) in the presence of a catalyst and a suitable solvent to obtain compound of formula (A1), wherein cycle A, cycle B, and $R^1$, have the meaning according to any one of the embodiments presented herein, and provided that in cycle A of formulae (X3) and (A1), a carbon atom is binding to the carbonyl.

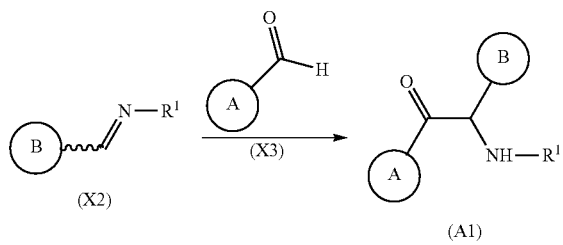

The term "treat" or "treating" as used herein is intended to refer to administration of a compound or composition of the invention to a subject for the purpose of effecting a therapeutic or prophylactic benefit through inhibition of a viral infection. Treating includes reversing, ameliorating, alleviating, inhibiting the progress of, lessening the severity of, or preventing a disease, disorder, or condition, or one or more symptoms of such disease, disorder or condition mediated through the inhibition of the viral infection. The term "subject" refers to an animal or mammalian patient in need of such treatment, such as a human.

It is to be noticed that the term "comprising", used in the claims, should not be interpreted as being restricted to the means listed thereafter; it does not exclude other elements or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments. Where an indefinite or definite article is used when referring to a singular noun e.g. "a" or "an", "the", this includes a plural of that noun unless something else is specifically stated.

Similarly it should be appreciated that in the description of exemplary embodiments of the invention, various features of the invention are sometimes grouped together in a single embodiment, Figure, or description thereof for the purpose of streamlining the disclosure and aiding in the understanding of one or more of the various inventive aspects.

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "leaving group" or "LG" as used herein means a chemical group which is susceptible to be displaced by a nucleophile or cleaved off or hydrolyzed in basic or acidic conditions. In a particular embodiment, a leaving group is selected from a halogen atom (e.g., Cl, Br, I) or a sulfonate (e.g., mesylate, tosylate, triflate).

The term "protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

The term "hydrocarbyl", "$C_{1-18}$ hydrocarbyl", "hydrocarbyl group" or "$C_{1-18}$ hydrocarbyl group" as used herein refers to $C_1$-$C_{18}$ normal, secondary, tertiary, unsaturated or saturated, non-aromatic, acyclic or cyclic, hydrocarbons and combinations thereof. This term therefore comprises alkyl, alkenyl, alkynyl, cycloalkyl, cycloalkenyl and cycloalkynyl.

The terminology "heterohydrocarbyl", "hetero $C_{1-18}$ hydrocarbyl", "heterohydrocarbyl group", "hetero $C_{1-18}$ hydrocarbyl group" or "hydrocarbyl group which optionally includes one or more heteroatoms, said heteroatoms being selected from the atoms consisting of O, S, and N" as used herein, refers to a hydrocarbyl group where one or more carbon atoms are replaced by an oxygen, nitrogen or sulphur atom(s) and thus includes heteroalkyl, heteroalkenyl, heteroalkynyl and non-aromatic heterocycle. This term therefore comprises as an example alkoxy, alkenyloxy, $C_w$alkyl-O—$C_{18-w}$alkyl, $C_w$alkenyl-O-alkyl, $C_w$alkyl-NH—$C_{18-w}$alkenyl, among others, wherein w is selected from any number between 1 and 18.

The term "alkyl" or "$C_{1-18}$ alkyl" as used herein means $C_1$-$C_{18}$ normal, secondary, or tertiary, linear or cyclic (or a combination of linear and cyclic), branched or straight hydrocarbon with no site of unsaturation. Examples are methyl, ethyl, 1-propyl (n-propyl), 2-propyl (iPr), 1-butyl, 2-methyl-1-propyl(i-Bu), 2-butyl (s-Bu), 2-dimethyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, cyclopropylethylene, methylcyclopropylene, 2,3-dimethyl-2-butyl, cyclopentylmethylene, 3,3-dimethyl-2-butyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons, yet more in particular to $C_{1-3}$ hydrocarbons as further defined herein above. A preferred alkyl is $C_{1-6}$alkyl. Another preferred alkyl is $C_{1-4}$alkyl.

The term "acyclic alkyl" or "linear alkyl" as used herein means $C_1$-$C_{18}$ non-cyclic normal, secondary, or tertiary, linear, branched or straight, hydrocarbon with no site of unsaturation. Examples are methyl, ethyl, 1-propyl, 2-propyl (iPr), 1-butyl, 2-methyl-1-propyl(i-Bu), 2-butyl (s-Bu), 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-icosyl.

The term "cycloalkyl" or "$C_{3-18}$ cycloalkyl" as used herein and unless otherwise stated means a saturated hydrocarbon monovalent radical having from 3 to 18 carbon atoms consisting of or comprising a $C_{3-10}$ monocyclic or $C_{7-18}$ polycyclic saturated hydrocarbon, such as for instance cyclopropyl, cyclopropylmethylene, cyclobutyl, cyclopentyl, cyclopentylmethylene, cyclopropylethylene, methylcyclopropylene, cyclohexyl, cycloheptyl, cyclooctyl, isopropoylcyclooctyl, cyclooctylmethylene, norbornyl, fenchyl, trimethyltricycloheptyl, decalinyl, adamantyl and the like. For the avoidance of doubt and as an example, cyclopentylmethylene refers to

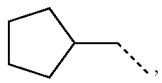

whereby the methyl group on the cyclopentyl is coupled to another group. Furthermore, for the avoidance of doubt and as an example, methylcyclopropylene refers to

whereby the cyclopropyl of the methylcyclopropyl is coupled to another group. A preferred cycloalkyl is $C_{3-7}$cycloalkyl.

The term "alkenyl" or "$C_{2-18}$alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$), cyclopentenyl (—C$_5$H$_7$), cyclohexenyl (—C$_6$H$_9$), cyclopentenylpropylene, methylcyclohexenylene and 5-hexenyl (—CH$_2$CH$_2$CH$_2$CH$_2$CH=CH$_2$). The double bond may be in the cis or trans configuration. In a particular embodiment, the term alkenyl refers to $C_{1-12}$ hydrocarbons, yet more in particular to $C_{1-6}$ hydrocarbons as further defined herein above. A preferred alkenyl is $C_{2-6}$alkenyl.

The term "acyclic alkenyl" or "linear alkenyl" as used herein refers to $C_2$-$C_{18}$ non-cyclic normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$) and 5-hexenyl (—CH$_2$CH$_2$CH$_2$CH$_2$CH=CH$_2$). The double bond may be in the cis or trans configuration.

The term "cycloalkenyl" as used herein refers to a non-aromatic hydrocarbon radical having from 3 to 18 carbon atoms with at least one site (usually 1 to 3, preferably 1) of unsaturation, namely a carbon-carbon, sp2 double bond and consisting of or comprising a $C_{3-10}$ monocyclic or $C_{7-8}$ polycyclic hydrocarbon. Examples include, but are not limited to: cyclopentenyl (—C$_5$H$_7$), cyclopentenylpropylene, methylcyclohexenylene and cyclohexenyl (—C$_6$H$_9$). The double bond may be in the cis or trans configuration.

The term "alkynyl" or "$C_{2-18}$alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: ethynyl (—C≡CH), 3-ethyl-cyclohept-1-ynylene, 4-cyclohept-1-yn-methylene and 1-propynyl (propargyl, —CH$_2$C≡CH). In a particular embodiment, the term alkenyl refers to $C_{1-12}$ hydrocarbons, yet more in particular to $C_{1-6}$ hydrocarbons as further defined herein above. A preferred alkynyl is $C_{2-6}$alkynyl.

The term "acyclic alkynyl" or "linear alkynyl" as used herein refers to $C_2$-$C_{18}$ non-cyclic normal, secondary, tertiary, linear, branched or straight hydrocarbon with at least one site (usually 1 to 3, preferably 1) of unsaturation, namely a carbon-carbon, sp triple bond. Examples include, but are not limited to: ethynyl (—C≡CH) and 1-propynyl (propargyl, —CH$_2$C≡CH).

The term "cycloalkynyl" as used herein refers to a non-aromatic hydrocarbon radical having from 3 to 18 carbon atoms with at least one site (usually 1 to 3, preferably 1) of unsaturation, namely a carbon-carbon, sp triple bond and consisting of or comprising a $C_{3-10}$ monocyclic or $C_{7-18}$ polycyclic hydrocarbon. Examples include, but are not limited to: cyclohept-1-yne, 3-ethyl-cyclohept-1-ynylene, 4-cyclohept-1-yn-methylene and ethylene-cyclohept-1-yne.

The term "alkylene" as used herein each refer to a saturated, branched or straight chain hydrocarbon radical of 1-18 carbon atoms (more in particular $C_{1-12}$ or $C_{1-6}$ carbon atoms), and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The term "alkenylene" as used herein each refer to a branched or straight chain hydrocarbon radical of 2-18 carbon atoms (more in particular $C_{2-12}$ or $C_{2-6}$ carbon atoms) with at least one site (usually 1 to 3, preferably 1) of unsaturation, namely a carbon-carbon, sp2 double bond, and having two monovalent radical centers derived by the removal of two hydrogen atoms from the same or two different carbon atoms of a parent alkene.

The term "alkynylene" as used herein each refer to a branched or straight chain hydrocarbon radical of 2-18 carbon atoms (more in particular $C_{2-12}$ or $C_{2-6}$ carbon atoms) with at least one site (usually 1 to 3, preferably 1) of unsaturation, namely a carbon-carbon, sp triple bond, and having two monovalent radical centers derived by the removal of two hydrogen atoms from the same or two different carbon atoms of a parent alkyne.

The term "heteroalkyl" as used herein refers to an acyclic alkyl wherein one or more carbon atoms are replaced by an oxygen, nitrogen or sulphur atom, with the proviso that said chain may not contain two adjacent O atoms or two adjacent S atoms. This means that one or more —CH$_3$ of said acyclic alkyl can be replaced by —NH$_2$ and/or that one or more —CH$_2$— of said acyclic alkyl can be replaced by —NH—, —O— or —S—. The S atoms in said chains may be optionally oxidized with one or two oxygen atoms, to afford sulfoxides and sulfones, respectively. Furthermore, the heteroalkyl groups in the compounds of the present invention can contain an oxo or thio group at any carbon or heteroatom that will result in a stable compound. Exemplary heteroalkyl groups include, but are not limited to, alcohols, alkyl ethers, primary, secondary, and tertiary alkyl amines, amides, ketones, esters, alkyl sulfides, and alkyl sulfones.

The term "heteroalkenyl" as used herein refers to an acyclic alkenyl wherein one or more carbon atoms are replaced by an oxygen, nitrogen or sulphur atom, with the proviso that said chain may not contain two adjacent O atoms or two adjacent S atoms. This means that one or more —CH$_3$ of said acyclic alkenyl can be replaced by —NH$_2$, that one or more —CH$_2$— of said acyclic alkenyl can be replaced by —NH—, —O— or —S— and/or that one or more —CH= of said acyclic alkynyl can be replaced by —N=. The S atoms in said chains may be optionally oxidized with one or two oxygen atoms, to afford sulfoxides and sulfones, respectively. Furthermore, the heteroalkyl groups in the compounds of the present invention can contain an oxo or thio group at any carbon or heteroatom that will result in a stable compound. The term heteroalkenyl thus comprises imines, —O-alkenyl, —NH-alkenyl, —N(alkenyl)$_2$, —N(alkyl)(alkenyl), and —S-alkenyl.

The term "heteroalkynyl" as used herein refers to an acyclic alkynyl wherein one or more carbon atoms are replaced by an oxygen, nitrogen or sulphur atom, with the proviso that said chain may not contain two adjacent O atoms or two adjacent S atoms. This means that one or more —CH$_3$ of said acyclic alkynyl can be replaced by —NH$_2$, that one or more —CH$_2$— of said acyclic alkynyl can be replaced by —NH—, —O— or —S—, that one or more —CH= of said acyclic alkynyl can be replaced by —N= and/or that one or more ≡CH of said acyclic alkynyl can be replaced by ≡N. The S atoms in said chains may be optionally oxidized with one or two oxygen atoms, to afford sulfoxides and sulfones, respectively. Furthermore, the heteroalkynyl groups in the compounds of the present invention can contain an oxo or thio group at any carbon or heteroatom that will result in a stable compound. The term heteroalkynyl thus comprises —O-alkynyl, —NH-alkynyl, —N(alkynyl)$_2$, —N(alkyl)(alkynyl), —N(alkenyl)(alkynyl), and —S—alkynyl.

The term "heteroalkylene" as used herein refers to an alkylene wherein one or more carbon atoms are replaced by an oxygen, nitrogen or sulphur atom, with the proviso that said chain may not contain two adjacent O atoms or two adjacent S atoms. This means that one or more —CH$_3$ of said alkylene can be replaced by —NH$_2$ and/or that one or more —CH$_2$— of said alkylene can be replaced by —NH—, —O— or —S—. The S atoms in said chains may be optionally oxidized with one or two oxygen atoms, to afford sulfoxides and sulfones, respectively. Furthermore, the heteroalkylene groups in the compounds of the present invention can contain an oxo or thio group at any carbon or heteroatom that will result in a stable compound.

The term "heteroalkenylene" as used herein refers to an alkenylene wherein one or more carbon atoms are replaced by an oxygen, nitrogen or sulphur atom, with the proviso that said chain may not contain two adjacent O atoms or two adjacent S atoms. This means that one or more —CH$_3$ of said alkenylene can be replaced by —NH$_2$, that one or more —CH$_2$— of said alkenylene can be replaced by —NH—, —O— or —S— and/or that one or more —CH= of said alkynylene can be replaced by —N=. The S atoms in said chains may be optionally oxidized with one or two oxygen atoms, to afford sulfoxides and sulfones, respectively. Furthermore, the heteroalkenylene groups in the compounds of the present invention can contain an oxo or thio group at any carbon or heteroatom that will result in a stable compound.

The term "heteroalkynylene" as used herein refers to an alkynylene wherein one or more carbon atoms are replaced by an oxygen, nitrogen or sulphur atom, with the proviso that said chain may not contain two adjacent O atoms or two adjacent S atoms. This means that one or more —CH$_3$ of said alkynylene can be replaced by —NH$_2$, that one or more —CH$_2$— of said alkynylene can be replaced by —NH—, —O— or —S—, that one or more —CH= of said alkynylene can be replaced by —N= and/or that one or more ≡CH of said alkynylene can be replaced by ≡N. The S atoms in said chains may be optionally oxidized with one or two oxygen atoms, to afford sulfoxides and sulfones, respectively. Furthermore, the heteroalkynylene groups in the compounds of the present invention can contain an oxo or thio group at any carbon or heteroatom that will result in a stable compound.

The term "aryl" as used herein means an aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. The term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like. Particular aryl groups are phenyl and naphthyl, especially phenyl.

The term "arylalkyl" or "arylalkyl-" as used herein refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethyl, and the like. The arylalkyl group comprises 6 to 20 carbon atoms, e.g. the alkyl moiety of the arylalkyl group is 1 to 6 carbon atoms and the aryl moiety is 5 to 14 carbon atoms.

The term "arylalkenyl" or "arylalkenyl-" as used herein refers to an acyclic alkenyl radical in which one of the hydrogen atoms bonded to a carbon atom, is replaced with an aryl radical. The arylalkenyl group comprises 6 to 20 carbon atoms, e.g. the alkenyl moiety of the arylalkenyl group is 1 to 6 carbon atoms and the aryl moiety is 5 to 14 carbon atoms.

The term "arylalkynyl" or "arylalkynyl-" as used herein refers to an acyclic alkynyl radical in which one of the hydrogen atoms bonded to a carbon atom, is replaced with an aryl radical. The arylalkynyl group comprises 6 to 20 carbon atoms, e.g. the alkynyl moiety of the arylalkynyl group is 1 to 6 carbon atoms and the aryl moiety is 5 to 14 carbon atoms.

The term "arylheteroalkyl" or "arylheteroalkyl-" as used herein refers to a heteroalkyl radical in which one of the hydrogen atoms bonded to a carbon atom, typically a terminal or sp3 carbon atom, is replaced with an aryl radical. The arylheteroalkyl group comprises 6 to 20 carbon atoms, e.g. the heteroalkyl moiety of the arylheteroalkyl group is 1 to 6 carbon atoms and the aryl moiety is 5 to 14 carbon atoms.

The term "arylheteroalkenyl" or "arylheteroalkenyl-" as used herein refers to a heteroalkenyl radical in which one of the hydrogen atoms bonded to a carbon atom, is replaced with an aryl radical. The arylheteroalkenyl group comprises 6 to 20 carbon atoms, e.g. the heteroalkenyl moiety of the arylheteroalkenyl group is 1 to 6 carbon atoms and the aryl moiety is 5 to 14 carbon atoms.

The term "arylheteroalkynyl" or "arylheteroalkynyl-" as used herein refers to a heteroalkynyl radical in which one of the hydrogen atoms bonded to a carbon atom, is replaced with an aryl radical. The arylheteroalkynyl group comprises 6 to 20 carbon atoms, e.g. the heteroalkynyl moiety of the arylheteroalkynyl group is 1 to 6 carbon atoms and the aryl moiety is 5 to 14 carbon atoms.

The term "heterocycle" as used herein means a saturated, unsaturated or aromatic ring system of 3 to 18 atoms including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, ß-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

The term "heteroaryl" means an aromatic ring system of 5 to 18 atoms including at least one N, O, S, or P and thus refers to aromatic heterocycles. Examples of heteroaryl include but are not limited to pyridyl, pyridazinyl, pyrimidinyl, pyrazinyl, s-triazinyl, oxazolyl, imidazolyl, thiazolyl, isoxazolyl, pyrazolyl, isothiazolyl, furyl, thienyl, and pyrrolyl.

The term "non-aromatic heterocycle" as used herein means a saturated or unsaturated non-aromatic ring system of 3 to 18 atoms including at least one N, O, S, or P.

The term "heterocycle-alkyl" or "heterocycle-alkyl-" as used herein refers to an acyclic alkyl radical in which one of the hydrogen atoms bonded to a carbon atom, typically a terminal or sp3 carbon atom, is replaced with a heterocycle radical. An example of a heterocycle-alkyl group is 2-pyridyl-methylene. The heterocycle-alkyl group comprises 6 to 20 atoms, e.g. the alkyl moiety of the heterocycle-alkyl group is 1 to 6 carbon atoms and the heterocycle moiety is 3 to 14 atoms.

The term "heterocycle-alkenyl" or "heterocycle-alkenyl-" as used herein refers to an acyclic alkenyl radical in which one of the hydrogen atoms bonded to a carbon atom, is replaced with an heterocycle radical. The heterocycle-alkenyl group comprises 6 to 20 atoms, e.g. the alkenyl moiety of the heterocycle-alkenyl group is 1 to 6 carbon atoms and the heterocycle moiety is 3 to 14 atoms.

The term "heterocycle-alkynyl" or "heterocycle-alkynyl-" as used herein refers to an acyclic alkynyl radical in which one of the hydrogen atoms bonded to a carbon atom, is replaced with a heterocycle radical. The heterocycle-alkynyl group comprises 6 to 20 atoms, e.g. the alkynyl moiety of the heterocycle-alkynyl group is 1 to 6 carbon atoms and the heterocycle moiety is 3 to 14 atoms.

The term "heterocycle-heteroalkyl" or "heterocycle-heteroalkyl-" as used herein refers to a heteroalkyl radical in which one of the hydrogen atoms bonded to a carbon atom, typically a terminal or sp3 carbon atom, is replaced with a heterocycle radical. The heterocycle-heteroalkyl group comprises 6 to 20 atoms, e.g. the heteroalkyl moiety of the heterocycle-heteroalkyl group is 1 to 6 carbon atoms and the heterocycle moiety is 3 to 14 atoms.

The term "heterocycle-heteroalkenyl" or "heterocycle-heteroalkenyl-" as used herein refers to a heteroalkenyl radical in which one of the hydrogen atoms bonded to a carbon atom, is replaced with an heterocycle radical. The heterocycle-heteroalkenyl group comprises 6 to 20 atoms, e.g. the heteroalkenyl moiety of the heterocycle-heteroalkenyl group is 1 to 6 carbon atoms and the heterocycle moiety is 3 to 14 atoms.

The term "heterocycle-heteroalkynyl" or "heterocycle-heteroalkynyl-" as used herein refers to a heteroalkynyl radical in which one of the hydrogen atoms bonded to a carbon atom, is replaced with a heterocycle radical. The heterocycle-heteroalkynyl group comprises 6 to 20 atoms, e.g. the heteroalkynyl moiety of the heterocycle-heteroalkynyl group is 1 to 6 carbon atoms and the heterocycle moiety is 3 to 14 atoms.

The term "heteroaryl-alkyl" or "heteroaryl-alkyl-" as used herein refers to an acyclic alkyl radical in which one of the hydrogen atoms bonded to a carbon atom, typically a terminal or sp3 carbon atom, is replaced with a heteraryl radical. An example of a heteroaryl-alkyl group is 2-pyridyl-methylene. The heteroaryl-alkyl group comprises 6 to 20 atoms, e.g. the alkyl moiety of the heteroaryl-alkyl group is 1 to 6 carbon atoms and the heteroaryl moiety is 5 to 14 atoms.

The term "heteroaryl-alkenyl" or "heteroaryl-alkenyl-" as used herein refers to an acyclic alkenyl radical in which one of the hydrogen atoms bonded to a carbon atom, is replaced with an heteroaryl radical. The heteroaryl-alkenyl group comprises 6 to 20 atoms, e.g. the alkenyl moiety of the heteroaryl-alkenyl group is 1 to 6 carbon atoms and the heteroaryl moiety is 5 to 14 atoms.

The term "heteroaryl-alkynyl" or "heteroaryl-alkynyl-" as used herein refers to an acyclic alkynyl radical in which one of the hydrogen atoms bonded to a carbon atom, is replaced with a heteroaryl radical. The heteroaryl-alkynyl group comprises 6 to 20 atoms, e.g. the alkynyl moiety of the heteroaryl-alkynyl group is 1 to 6 carbon atoms and the heteroaryl moiety is 5 to 14 atoms.

The term "heteroaryl-heteroalkyl" or "heteroaryl-heteroalkyl-" as used herein refers to a heteroalkyl radical in which one of the hydrogen atoms bonded to a carbon atom, typically a terminal or sp3 carbon atom, is replaced with a heterocycle radical. The heteroaryl-heteroalkyl group comprises 6 to 20 atoms, e.g. the heteroalkyl moiety of the heteroaryl-heteroalkyl group is 1 to 6 carbon atoms and the heteroaryl moiety is 5 to 14 atoms.

The term "heteroaryl-heteroalkenyl" or "heteroaryl-heteroalkenyl-" as used herein refers to a heteroalkenyl radical in which one of the hydrogen atoms bonded to a carbon atom, is replaced with an heteroaryl radical. The heteroaryl-heteroalkenyl group comprises 6 to 20 atoms, e.g. the heteroalkenyl moiety of the heteroaryl-heteroalkenyl group is 1 to 6 carbon atoms and the heteroaryl moiety is 5 to 14 atoms.

The term "heteroaryl-heteroalkynyl" or "heteroaryl-heteroalkynyl-" as used herein refers to a heteroalkynyl radical in which one of the hydrogen atoms bonded to a carbon atom, is replaced with a heteroaryl radical. The heteroaryl-heteroalkynyl group comprises 6 to 20 atoms, e.g. the heteroalkynyl moiety of the heteroaryl-heteroalkynyl group is 1 to 6 carbon atoms and the heteroaryl moiety is 5 to 14 atoms.

The term "non-aromatic heterocycle-alkyl" or "non-aromatic heterocycle-alkyl-" as used herein refers to an acyclic alkyl radical in which one of the hydrogen atoms bonded to a carbon atom, typically a terminal or sp3 carbon atom, is replaced with a non-aromatic heterocycle radical. The non-aromatic heterocycle-alkyl group comprises 6 to 20 atoms, e.g. the alkyl moiety of the non-aromatic heterocycle-alkyl group is 1 to 6 carbon atoms and the non-aromatic heterocycle moiety is 3 to 14 atoms.

The term "non-aromatic heterocycle-alkenyl" or "non-aromatic heterocycle-alkenyl-" as used herein refers to an acyclic alkenyl radical in which one of the hydrogen atoms bonded to a carbon atom, is replaced with an non-aromatic heterocycle radical. The non-aromatic heterocycle-alkenyl group comprises 6 to 20 atoms, e.g. the alkenyl moiety of the non-aromatic heterocycle-alkenyl group is 1 to 6 carbon atoms and the non-aromatic heterocycle moiety is 3 to 14 atoms.

The term "non-aromatic heterocycle-alkynyl" or "non-aromatic heterocycle-alkynyl-" as used herein refers to an acyclic alkynyl radical in which one of the hydrogen atoms bonded to a carbon atom, is replaced with a non-aromatic heterocycle radical. The non-aromatic heterocycle-alkynyl group comprises 6 to 20 atoms, e.g. the alkynyl moiety of the non-aromatic heterocycle-alkynyl group is 1 to 6 carbon atoms and the non-aromatic heterocycle moiety is 3 to 14 atoms.

The term "non-aromatic heterocycle-heteroalkyl" or "non-aromatic heterocycle-heteroalkyl-" as used herein refers to a heteroalkyl radical in which one of the hydrogen atoms bonded to a carbon atom, typically a terminal or sp3 carbon atom, is replaced with a heterocycle radical. The non-aromatic heterocycle-heteroalkyl group comprises 6 to 20 atoms, e.g. the heteroalkyl moiety of the non-aromatic heterocycle-heteroalkyl group is 1 to 6 carbon atoms and the non-aromatic heterocycle moiety is 3 to 14 atoms.

The term "non-aromatic heterocycle-heteroalkenyl" or "non-aromatic heterocycle-heteroalkenyl-" as used herein refers to a heteroalkenyl radical in which one of the hydrogen atoms bonded to a carbon atom, is replaced with an non-aromatic heterocycle radical. The non-aromatic heterocycle-heteroalkenyl group comprises 6 to 20 atoms, e.g. the heteroalkenyl moiety of the non-aromatic heterocycle-heteroalkenyl group is 1 to 6 carbon atoms and the non-aromatic heterocycle moiety is 3 to 14 atoms.

The term "non-aromatic heterocycle-heteroalkynyl" or "non-aromatic heterocycle-heteroalkynyl-" as used herein refers to a heteroalkynyl radical in which one of the hydrogen atoms bonded to a carbon atom, is replaced with a non-aromatic heterocycle radical. The non-aromatic heterocycle-heteroalkynyl group comprises 6 to 20 atoms, e.g. the heteroalkynyl moiety of the non-aromatic heterocycle-heteroalkynyl group is 1 to 6 carbon atoms and the non-aromatic heterocycle moiety is 3 to 14 atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl. By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or ß-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cyclo-alkoxy", "aryloxy", "arylalkyloxy", "heterocycleoxy", "alkylthio", "cycloalkylthio", "arylthio", "arylalkylthio" and "heterocyclethio" refer to substituents wherein an alkyl group, respectively a cycloalkyl, aryl, arylalkyl or heterocycle (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl. A preferred alkoxy is $C_{1-6}$alkoxy; another preferred alkoxy is $C_{1-4}$alkoxy.

As used herein and unless otherwise stated, the term halogen means any atom selected from the group consisting of fluorine (F), chlorine (Cl), bromine (Br) and iodine (I).

As used herein with respect to a substituting group, and unless otherwise stated, the terms "substituted" such as in "substituted alkyl", "substituted alkenyl", substituted alkynyl", "substituted aryl", "substituted heterocycle", "substituted arylalkyl", "substituted heterocycle-alkyl" and the like refer to the chemical structures defined herein, and wherein the said hydrocarbyl, heterohydrocarbyl group and/or the said aryl or heterocycle may be optionally substituted with one or more substituents (preferable 1, 2, 3, 4, 5 or 6), meaning that one or more hydrogen atoms are each independently replaced with a substituent. Typical substituents include, but are not limited to and in a particular embodiment said substituents are being independently selected from the group consisting of halogen, amino, hydroxyl, sulfhydryl, alkyl, alkoxy, alkenyl, alkenyloxy, alkynyl, alkynyloxy, cycloalkyl, cycloalkenyl, cycloalkynyl, heteroalkyl, heteroalkenyl, heteroalkynyl, aryl, heterocycle, arylalkyl, arylalkenyl, arylalkynyl, heterocycle-alkyl, heterocycle-alkenyl and heterocycle-alkynyl, —X, —Z, —O⁻, —OZ, =O, —SZ, —S⁻, =S, —NZ$_2$, —N⁺$_3$, =NZ, =N—OZ, —CX$_3$ (e.g. trifluoromethyl), —CN, —OCN, —SCN, —N=C≡O, —N=C=S, —NO, —NO$_2$, =N$_2$, —N$_3$, —NZC(O)Z, —NZC(S)Z, —NZC(O)O—, —NZC(O)OZ, —NZC(S)OZ, —NZC(O)NZZ, NZC(NZ)Z, NZC(NZ)NZZ, —C(O)NZZ, —C(NZ)Z, —S(O)$_2$O⁻, —S(O)$_2$OZ, —S(O)$_2$Z, —OS(O)$_2$OZ, —OS(O)$_2$Z, —OS(O)$_2$O⁻, —S(O)$_2$NZ, —S(O)Z, —OP(O)(OZ)$_2$, —P(O)(OZ)$_2$, —P(O)(O⁻)$_2$, —P(O)(OZ)(O⁻), —P(O)(OH)$_2$, —C(O)Z, —C(O)X, —C(S)Z, —C(O)OZ, —C(O)O⁻, —C(S)OZ, —C(O)SZ, —C(S)SZ, —C(O)NZZ, —C(S)NZZ, —C(NZ)NZZ, —OC(O)Z, —OC(S)Z, —OC(O)O⁻, —OC(O)OZ, —OC(S)OZ, wherein each X is independently a halogen selected from F, Cl, Br, or I; and each Z is independently —H, alkyl, alkenyl, alkynyl, heteroalkyl, heteroalkenyl, heteroalkynyl, aryl, heterocycle, protecting group or prodrug moiety, while two Z bonded to a nitrogen atom can be taken together with the nitrogen atom to which they are bonded to form a heterocycle. Alkyl(ene), alkenyl(ene), and alkynyl(ene) groups may also be similarly substituted.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

The term "heteroatom(s)" as used herein means an atom selected from nitrogen, which can be quaternized; oxygen; and sulfur, including sulfoxide and sulfone.

The term "hydroxy" as used herein means —OH.

The term "carbonyl" as used herein means carbon atom bonded to oxygen with a double bond, i.e., C=O.

The term "amino" as used herein means the —NH$_2$ group.

The compounds of the invention are employed for the treatment or prophylaxis of viral infections, more particularly Flaviviral infections.

Flavivirus is a genus of the family Flaviviridae. This genus includes the West Nile virus, dengue virus, tick-borne encephalitis virus, yellow fever virus, and several other viruses which may cause encephalitis. Flaviviruses share a common size (40-65 nm), symmetry (enveloped, icosahedral nucleocapsid), nucleic acid (positive-sense, single stranded RNA approximately 10,000-11,000 bases), and appearance in the electron microscope. These viruses are transmitted by the bite from an infected arthropod (mosquito or tick).

The compounds of the invention are particularly active against dengue virus replication. For dengue virus, four distinct, but closely related serotypes are known (DENV-1, -2, -3, and -4). Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalisation and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control dengue disease, the only available methods at present are mosquito eradication strategies to control the vector. Although progress is being made in the development of vaccines for dengue, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titres. In both primary and secondary infections, higher viral titres are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyperendemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

When using one or more compounds of the invention and of the formulae as defined herein:
the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.
the therapeutically effective amount of the preparation of the compound(s), especially for the treatment of viral infections in humans and other mammals, preferably is a flaviviral replication inhibiting amount of the formulae as defined herein and corresponds to an amount which ensures a plasma level of between 1 μg/ml and 100 mg/ml, optionally of 10 mg/ml.

The present invention further relates to a method for preventing or treating viral infections in a subject or patient by administering to the patient in need thereof a therapeutically effective amount of the compounds of the present invention. The therapeutically effective amount of the compound(s), especially for the treatment of viral infections in humans and other mammals, preferably is a flaviviral replication inhibiting amount. The suitable dosage is usually in the range of 0.001 mg to 60 mg, optionally 0.01 mg to 10 mg, optionally 0.1 mg to 1 mg per day per kg bodyweight for humans. Depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in Adv. Enzyme Reg. (1984) 22:27. Briefly, this principle states that interactions (synergism, additivity, antagonism) between two drugs can be quantified using the combination index (hereinafter referred as C1) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x + FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-viral activity or that stimulate the immune response.

The invention thus relates to a pharmaceutical composition or combined preparation having synergistic effects against a viral infection and containing:
Either:
A)
(a) a combination of two or more of the compounds of the present invention, and
(b) optionally one or more pharmaceutical excipients or pharmaceutically acceptable carriers, for simultaneous, separate or sequential use in the treatment or prevention of a flaviviral infection
or
B)
(c) one or more anti-viral agents and/or immune stimulating agents, and
(d) at least one of the compounds of the present invention, and
(e) optionally one or more pharmaceutical excipients or pharmaceutically acceptable carriers, for simultaneous, separate or sequential use in the treatment or prevention of a flaviviral infection.

Suitable anti-viral agents for inclusion into the synergistic antiviral compositions or combined preparations of this invention include ribavirin.

Suitable immune stimulating agents for inclusion into the synergistic antiviral compositions or combined preparations of this invention include interferon.

The pharmaceutical composition or combined preparation with synergistic activity against viral infection according to this invention may contain the compounds of the present invention over a broad content range depending on the contemplated use and the expected effect of the preparation. Generally, the content of the compound of the invention for inclusion into the synergistic antiviral compositions of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of Flaviviral infections, more preferably Dengue viral infections. The invention therefore relates to the use of a composition comprising:
(a) one or more compounds of the formulae described herein, and
(b) one or more Picornaviral enzyme inhibitors as biologically active agents in respective proportions such as to provide a synergistic effect against a Flaviviral infection, particularly an Dengueviral infection in a mammal, for instance in the form of a combined preparation for simultaneous, separate or sequential use in viral infection therapy.

More generally, the invention relates to the compounds of formula (A), (B), (C), (D-1), (D-2), (E), (F), and (G) and all embodiments thereof being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

More generally, the invention relates to the compounds of formula (A), (B), (C), (D-1), (D-2), (E), (F), (G), (H), (1), (J), and all embodiments thereof being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formulae herein are able to form. Therefore, the compounds of this invention optionally comprise salts of the compounds herein, especially pharmaceutically acceptable non-toxic salts containing, for example, $Na^+$, $Li^+$, $K^+$, $NH4^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived from a physiologically acceptable acid or base, are within the scope of the present invention.

Preferable anions to form pharmaceutically acceptable acid addition salts are acetate, benzenesulfonate, benzoate, bicarbonate, bitartrate, bromide, calcium edetate, camsyiate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like.

Preferable cations to form pharmaceutically acceptable basic salts are benzathine, chloroprocaine, choline, diethanolamine, ethylenediamine, meglumine, procaine, and the like; and those formed with metallic cations such as aluminum, calcium, lithium, magnesium, potassium, sodium, zinc, and the like.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and stereochemical forms, which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center) of the basic molecular structure, as well as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula (1) may easily be determined by those skilled in the art while using well-known methods such as, for example, X-ray diffraction.

The compounds of the invention may be formulated with conventional carriers and excipients, which will be selected in accordance with standard practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents, may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone, it is preferable to present them as pharmaceutical formulations. The formulations, both for veterinary and for human use, of the present invention comprise at least one active ingredient, as above described, together with one or more pharmaceutically acceptable carriers therefore and optionally other. therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound.

Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulphatesulphate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this invention relates to various precursor or "prodrug" forms of the compounds of the present invention. It may be desirable to formulate the compounds of the present invention in the form of a chemical species which itself is not significantly biologically-active, but which when delivered to the animal will undergo a chemical reaction catalyzed by the normal function of the body of the animal, inter alia, enzymes present in the stomach or in blood serum, said chemical reaction having the effect of releasing a compound as defined herein. The term "pro-drug" thus relates to these species which are converted in vivo into the active pharmaceutical ingredient.

The prodrugs of the present invention can have any form suitable to the formulator, for example, esters are non-limiting common pro-drug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a pro-drug in a form other than an easily hydrolysable precursor, inter alia an ester, an amide, and the like, may be used. The counterpart of the active pharmaceutical ingredient in the pro-drug can have different structures such as an amino acid or peptide structure, alkyl chains, sugar moieties and others as known in the art.

For the purpose of the present invention the term "therapeutically suitable prodrug" is defined herein as "a compound modified in such a way as to be transformed in vivo to the therapeutically active form, whether by way of a single or by multiple biological transformations, when in contact with the tissues of the animal, mammal or human to which the pro-drug has been administered, and without undue toxicity, irritation, or allergic response, and achieving the intended therapeutic outcome".

More specifically the term "prodrug", as used herein, relates to an inactive or significantly less active derivative of a compound of the invention, which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds of the invention optionally are bound covalently to an insoluble matrix and used for affinity chromatography (separations, depending on the nature of the groups of the compounds, for example compounds with pendant aryl are useful in hydrophobic affinity separations.

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of the present invention may be prepared according to the general procedure outlined in the following schemes.

Scheme 1: all B, $R^1$, $R^2$, $X^1$, $X^2$, $X^3$, $X^4$, $X^5$, $X^6$, $X^7$, $X^8$, $X^9$, $X^{10}$, p, q and LG are as described for the compounds of the present invention and its embodiments and formulae.

Derivatives of general formula 1 (commercially available or synthesized by procedures known to the skilled in the art) may be reacted with intermediates of formula 2 (commercially available or synthesized by procedures known to the skilled in the art) wherein LG is independently selected from chlorine, bromine and iodine (more preferably chlorine) in an aprotic solvent (e.g. toluene, dichloromethane, dichloroethane and the like) at a temperature raising from 0 to 100° C. to provide intermediates of formula 3. In case of $X^{10}$=C or CH, a catalyst (e.g. $AlCl_3$, $Et_2AlCl$, $ZrCl_4$ and the like) or a base (e.g. pyridine, DBN, DMAP and the like) might be required. More information can be found in the following references: Tetrahedron 29, 971-976, 1973; Org. Lett., Vol. 12, No. 24, 2010; J. Org. Chem. 2011, 76, 4753-4758. In case of $X^{10}$=N, compounds of formula 1 can be converted in compounds of formula 3 by reaction with intermediates of formula 2 following standard amide bond conditions. The leaving group (LG) from intermediates of formula 3 may then be displaced by amines of formula $R^1R^2NH$ (commercially available or synthesized) following procedures known to the skilled in the art or as set forth in the examples below to provide the desired compounds of formula 4.

Alternatively, the compounds of the present invention may also be prepared according to the general procedure depicted in the following scheme.

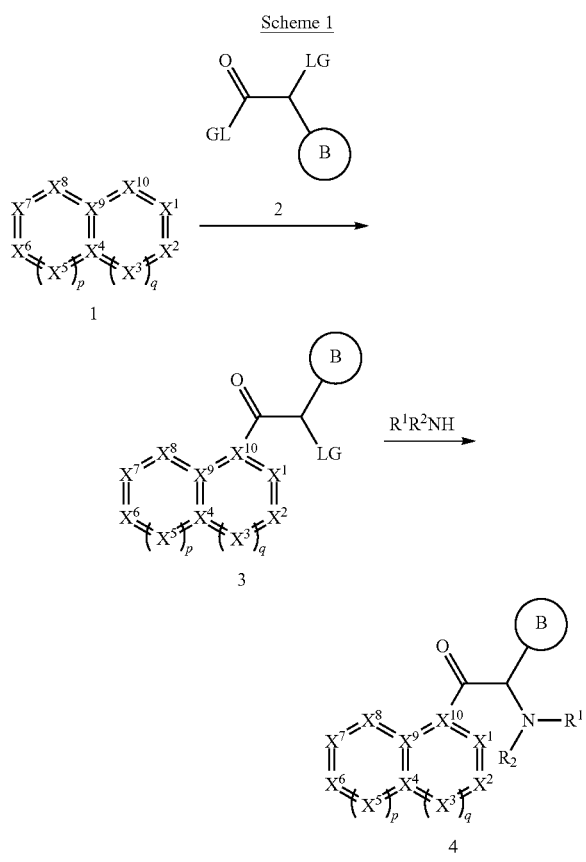

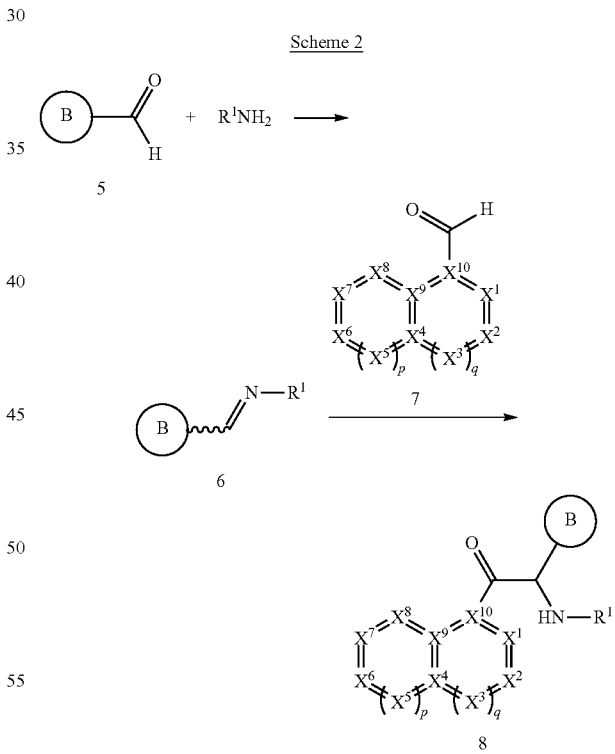

Scheme 2: all B, $R^1$, $X^1$, $X^2$, $X^3$, $X^4$, $X^5$, $X^6$, $X^7$, $X^3$, $X^9$, $X^{10}$, p and q are as described for the compounds of the present invention and its embodiments and formulae Aldehydes of general formula 5 may be reacted with amines of formula $R^1NH_2$ to provide imines of general formula 6 which may be reacted with intermediates of formula 7 (commercially available or synthesized by procedures known to the skilled in the art or as set forth in the examples below), wherein $X^{10}$ is a carbon atom, in the presence of a catalyst such as 3-benzyl-5-(2-hydroxyethyl)-4-methylthiazol-3-ium chloride to provide the desired compounds of formula 8. More detailed information can be found in Chem. Commun., 2007, 852-854.

In another embodiment, compounds of the present invention may also be synthesized according to the general procedure outlined in the following scheme.

derivatives (preferably Weinreb amide derivatives) as known to the skilled in the art. These intermediates of formula 10 may be converted into intermediates of formula 3 wherein LG is an halogen such as chlorine, bromine or iodine following reactions known to the skilled in the art or as set forth in the examples below. Intermediates of formula 10, wherein B is only selected from aryl or heteroaryl, may be prepared by α-arylation of ketone of formula 12 with

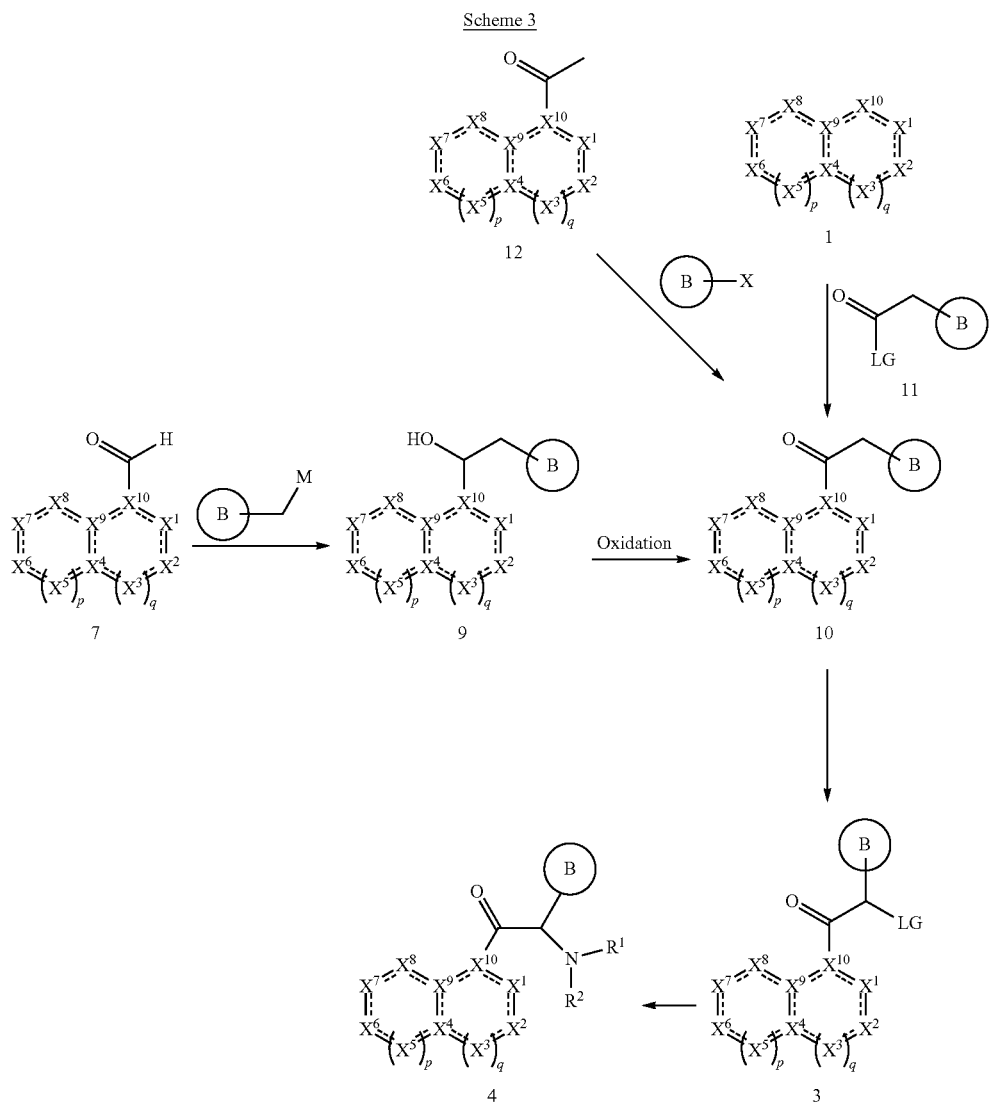

Scheme 3 all B, $R^1$, $R^2$, $X^1$, $X^2$, $X^3$, $X^4$, $X^5$, $X^6$, $X^7$, $X^8$, $X^9$, $X^{10}$, p, q and LG are as described for the compounds of the present invention and its embodiments and formulae.

Derivatives of general formula 1, wherein $X^{10}$ is only selected from C or CH (commercially available or synthesized by procedures known to the skilled in the art) may be reacted with intermediates of formula 11 (commercially available or synthesized by procedures known to the skilled in the art) wherein LG is a leaving group such as chlorine, bromine and iodine, under Friedel Crafts conditions to provide intermediates of formula 10. Alternatively, intermediates of formula 10 may also be prepared by condenstation of grignard or organolithium derivatives with an amide halogenoaryl or halogenoheteroaryl in the presence of a catalyst (e.g. $Pd_2dba_3$, $Pd(OAc)_2$, $Pd(dba)$ and the like), a ligand (e.g. BINAP, Xantphos, $PtBu_3$ and the like) and a base (e.g. NaOtBu, $K_3PO_4$ and the like). More information can be found in the following references: J. Am. Chem. Soc. 1997, 11108-11109 and J. Am. Chem. Soc. 1999, 1473-1478. Alternatively, intermediates of formula 9 may also be obtained from aldehydes of formula 7, wherein $X^{10}$ is only selected from C or CH, and reagents of general formula 8, wherein M is Li or MgCl or MgBr, followed by an oxidation reaction known to the skilled in the art. Compounds of interest having a general formula 4 may be obtained from intermediates 3 as described in Scheme 1.

Abbreviations used in the description, particularly in the schemes and examples, are as follows:
BOC tert-Butyloxycarbonyl
DBU 1,8-Diazabicyclo[5,4,0]undec-7-ene
DBN 1,5-Diazabicyclo[4.3.0]non-5-ene
DIPEA Diisopropylethylamine
DMAP 4-Dimethylaminopyridine
DMF N,N-Dimethylformamide
DMSO Dimethylsulfoxide
ee Enantiomeric excess
eq Equivalent
h Hour
HATU O-(7-Azabenzotriazol-1-yl)-N,N,N,N-tetramethyl-uronium hexafluorophosphate
HPLC High performance liquid chromatography
min Minute
NMP N-Methyl-2-pyrrolidone
TBDMSCl tert-Butyldimethylchlorosilane
THF Tetrahydrofuran
TLC Thin layer chromatography
$t_r$ retention time

EXAMPLES

The following examples are provided for the purpose of illustrating the present invention and by no means should be interpreted to limit the scope of the present invention.

Part A represents the preparation of the compounds (intermediates and final compounds) whereas Part B represents the pharmacological examples.

TABLE 1

Structures of example compounds of the invention and their respective codes.

| Code | Structure |
| --- | --- |
| CPD-001 | 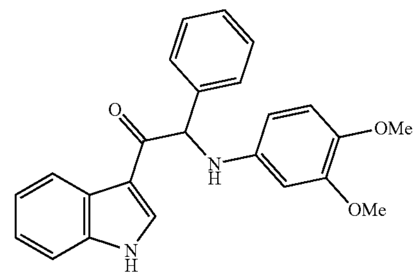 [SMILES: COc1ccc(NC(C(=O)c2c[nH]c3ccccc23)c2ccccc2)cc1OC] |
| CPD-002 | 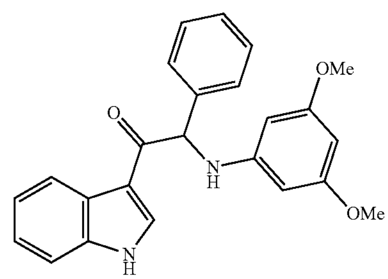 [SMILES: COc1cc(NC(C(=O)c2c[nH]c3ccccc23)c2ccccc2)cc(OC)c1] |
| CPD-003 | 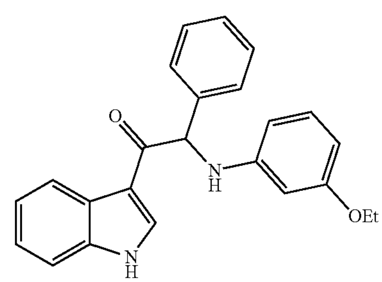 [SMILES: CCOc1cccc(NC(C(=O)c2c[nH]c3ccccc23)c2ccccc2)c1] |
| CPD-004 | 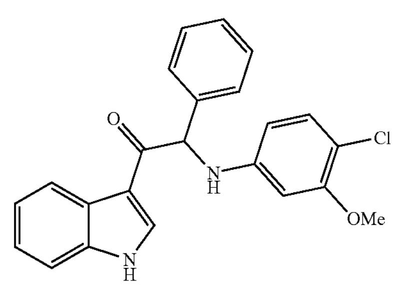 [SMILES: COc1cc(NC(C(=O)c2c[nH]c3ccccc23)c2ccccc2)ccc1Cl] |

TABLE 1-continued
Structures of example compounds of the invention and their respective codes.
| Code | Structure |
|---|---|
| CPD-005 | 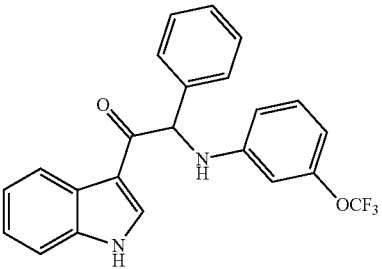 [SMILES: O=C(c1c[nH]c2ccccc12)C(Nc1cccc(OC(F)(F)F)c1)c1ccccc1] |
| CPD-006 | 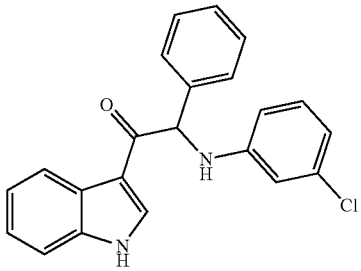 [SMILES: O=C(c1c[nH]c2ccccc12)C(Nc1cccc(Cl)c1)c1ccccc1] |
| CPD-007 | 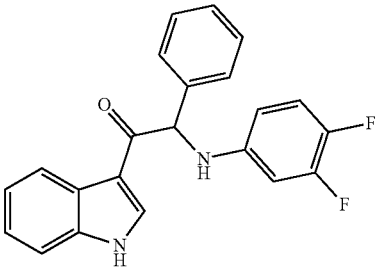 [SMILES: O=C(c1c[nH]c2ccccc12)C(Nc1ccc(F)c(F)c1)c1ccccc1] |
| CPD-008 | 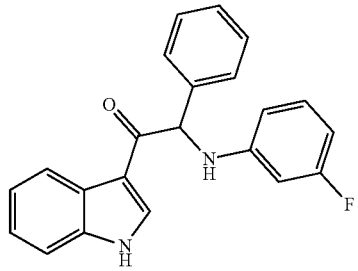 [SMILES: O=C(c1c[nH]c2ccccc12)C(Nc1cccc(F)c1)c1ccccc1] |
| CPD-009 | 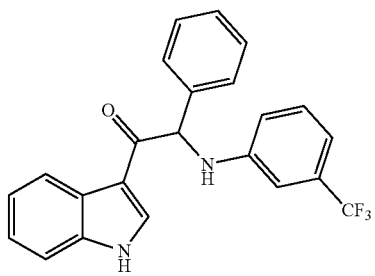 |

TABLE 1-continued
Structures of example compounds of the invention and their respective codes.
| Code | Structure |
|---|---|
| CPD-010 | 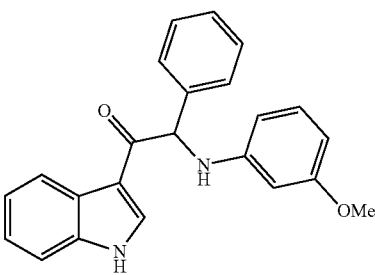 [SMILES: COc1cccc(NC(C(=O)c2c[nH]c3ccccc23)c2ccccc2)c1] |
| CPD-011 | 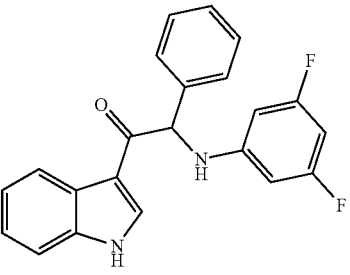 [SMILES: O=C(c1c[nH]c2ccccc12)C(Nc1cc(F)cc(F)c1)c1ccccc1] |
| CPD-012 | 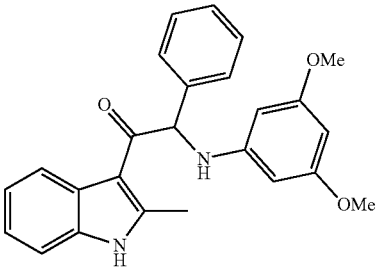 [SMILES: COc1cc(NC(C(=O)c2c(C)[nH]c3ccccc23)c2ccccc2)cc(OC)c1] |
| CPD-013 | 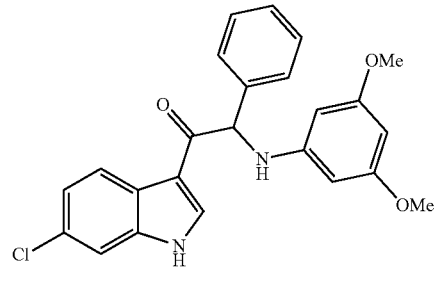 [SMILES: COc1cc(NC(C(=O)c2c[nH]c3cc(Cl)ccc23)c2ccccc2)cc(OC)c1] |
| CPD-014 | 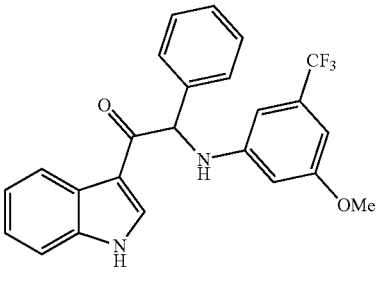 [SMILES: COc1cc(NC(C(=O)c2c[nH]c3ccccc23)c2ccccc2)cc(C(F)(F)F)c1] |

TABLE 1-continued
Structures of example compounds of the invention and their respective codes.
| Code | Structure |
| --- | --- |
| CPD-015 | 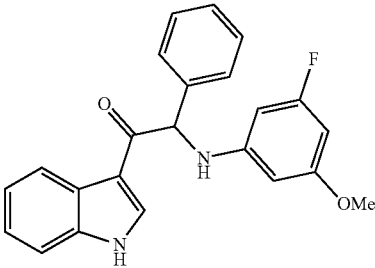 [SMILES: COc1cc(F)cc(NC(C(=O)c2c[nH]c3ccccc23)c2ccccc2)c1] |
| CPD-016 | 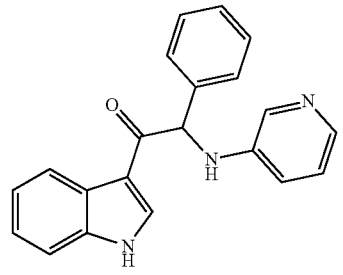 [SMILES: O=C(c1c[nH]c2ccccc12)C(Nc1cccnc1)c1ccccc1] |
| CPD-017 | 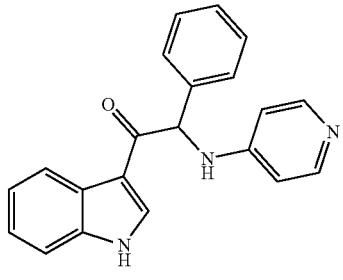 [SMILES: O=C(c1c[nH]c2ccccc12)C(Nc1ccncc1)c1ccccc1] |
| CPD-018 | 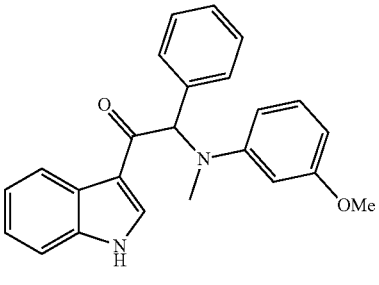 [SMILES: COc1cccc(N(C)C(C(=O)c2c[nH]c3ccccc23)c2ccccc2)c1] |
| CPD-019 | 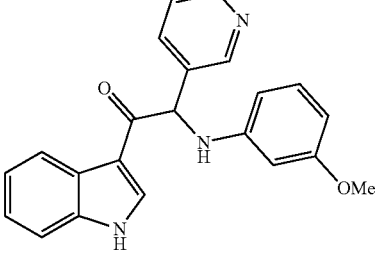 |

TABLE 1-continued
Structures of example compounds of the invention and their respective codes.
| Code | Structure |
|---|---|
| CPD-020 | 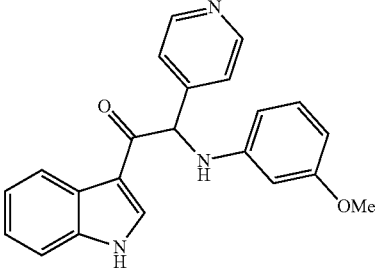 [SMILES: COc1cccc(NC(C(=O)c2c[nH]c3ccccc23)c2ccncc2)c1] |
| CPD-021 | 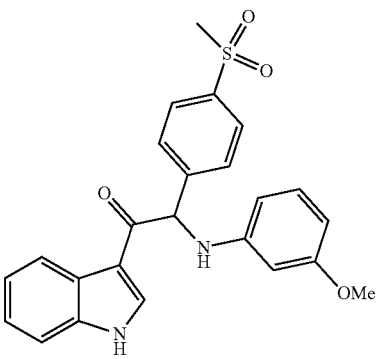 [SMILES: COc1cccc(NC(C(=O)c2c[nH]c3ccccc23)c2ccc(S(C)(=O)=O)cc2)c1] |
| CPD-022 | 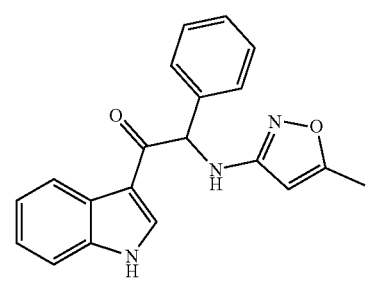 [SMILES: Cc1cc(NC(C(=O)c2c[nH]c3ccccc23)c2ccccc2)no1] |
| CPD-023 | 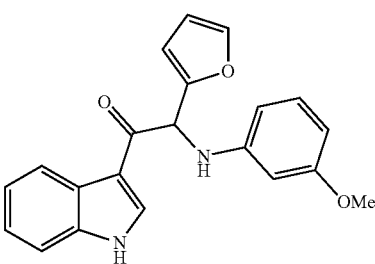 [SMILES: COc1cccc(NC(C(=O)c2c[nH]c3ccccc23)c2ccco2)c1] |
| CPD-024 | 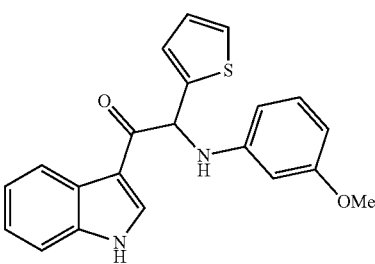 [SMILES: COc1cccc(NC(C(=O)c2c[nH]c3ccccc23)c2cccs2)c1] |

TABLE 1-continued
Structures of example compounds of the invention and their respective codes.
| Code | Structure |
|---|---|
| CPD-025 | 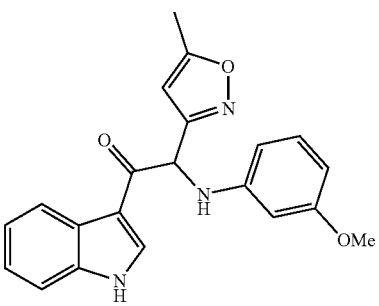 [SMILES: COc1cccc(NC(C(=O)c2c[nH]c3ccccc23)c2cc(C)on2)c1] |
| CPD-026 | 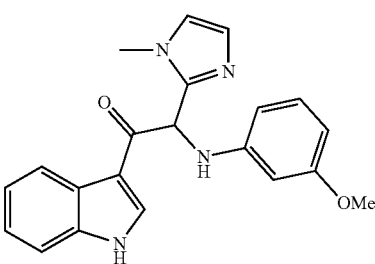 [SMILES: COc1cccc(NC(C(=O)c2c[nH]c3ccccc23)c2nccn2C)c1] |
| CPD-027 | 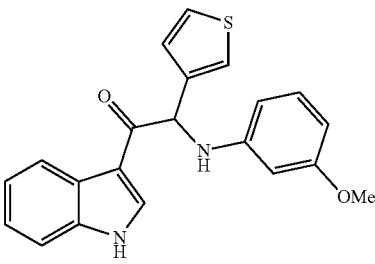 [SMILES: COc1cccc(NC(C(=O)c2c[nH]c3ccccc23)c2ccsc2)c1] |
| CPD-028 | 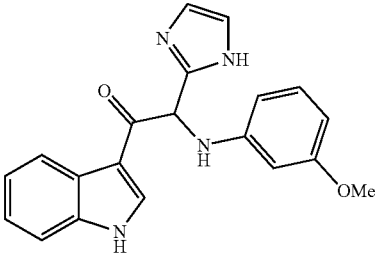 [SMILES: COc1cccc(NC(C(=O)c2c[nH]c3ccccc23)c2ncc[nH]2)c1] |
| CPD-029 | 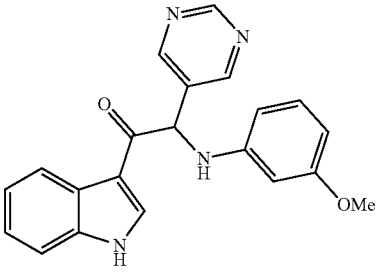 [SMILES: COc1cccc(NC(C(=O)c2c[nH]c3ccccc23)c2cncnc2)c1] |

TABLE 1-continued
Structures of example compounds of the invention and their respective codes.
| Code | Structure |
| --- | --- |
| CPD-030 | 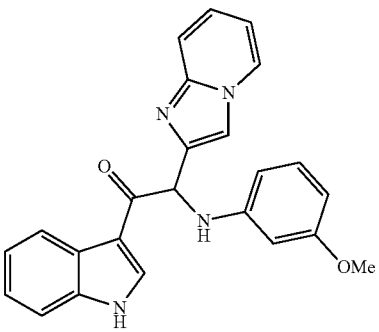 [SMILES: COc1cccc(NC(C(=O)c2c[nH]c3ccccc23)c2cn3ccccc3n2)c1] |
| CPD-031 | 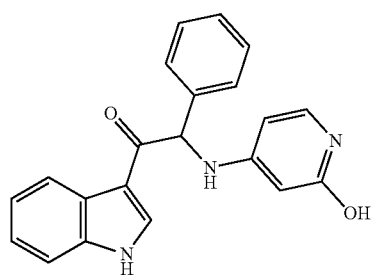 [SMILES: O=C(c1c[nH]c2ccccc12)C(Nc1ccnc(O)c1)c1ccccc1] |
| CPD-032 | 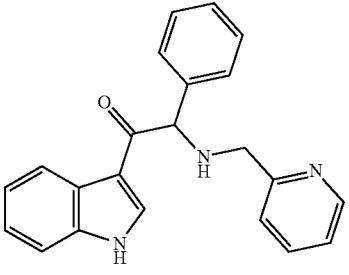 [SMILES: O=C(c1c[nH]c2ccccc12)C(NCc1ccccn1)c1ccccc1] |
| CPD-033 | 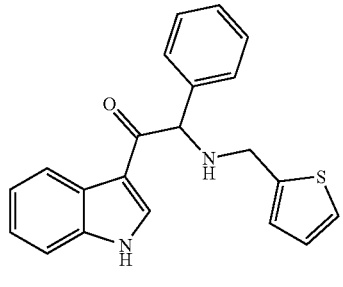 [SMILES: O=C(c1c[nH]c2ccccc12)C(NCc1cccs1)c1ccccc1] |
| CPD-034 | 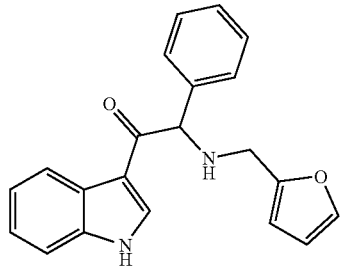 [SMILES: O=C(c1c[nH]c2ccccc12)C(NCc1ccco1)c1ccccc1] |

TABLE 1-continued
Structures of example compounds of the invention and their respective codes.
| Code | Structure |
|---|---|
| CPD-035 | 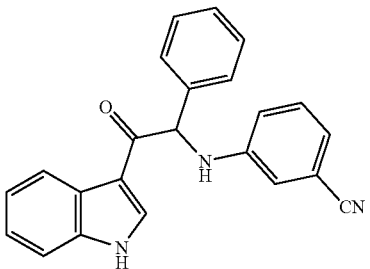 [SMILES: N#Cc1cccc(NC(C(=O)c2c[nH]c3ccccc23)c2ccccc2)c1] |
| CPD-036 | 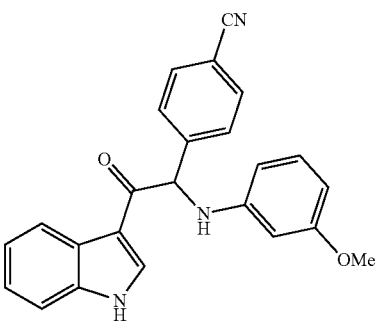 [SMILES: COc1cccc(NC(C(=O)c2c[nH]c3ccccc23)c2ccc(C#N)cc2)c1] |
| CPD-037 | 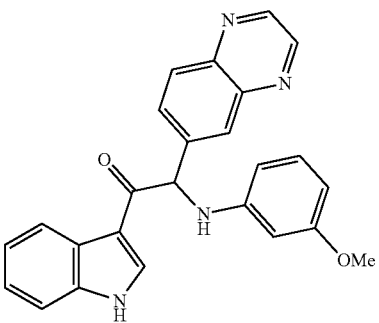 [SMILES: COc1cccc(NC(C(=O)c2c[nH]c3ccccc23)c2ccc3nccnc3c2)c1] |
| CPD-038 | 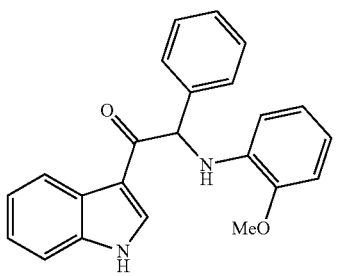 [SMILES: COc1ccccc1NC(C(=O)c1c[nH]c2ccccc12)c1ccccc1] |
| CPD-039 | 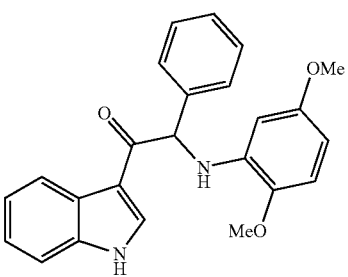 [SMILES: COc1ccc(OC)c(NC(C(=O)c2c[nH]c3ccccc23)c2ccccc2)c1] |

TABLE 1-continued
Structures of example compounds of the invention and their respective codes.
| Code | Structure |
|---|---|
| CPD-040 | 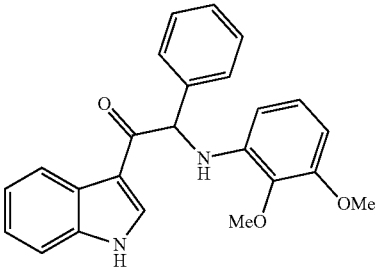 [SMILES: COc1cccc(NC(C(=O)c2c[nH]c3ccccc23)c2ccccc2)c1OC] |
| CPD-041 | 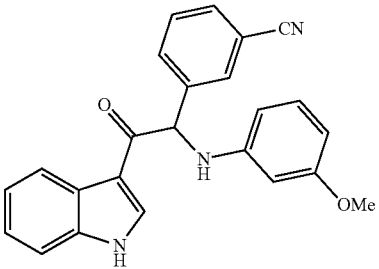 [SMILES: COc1cccc(NC(C(=O)c2c[nH]c3ccccc23)c2cccc(C#N)c2)c1] |
| CPD-042 | 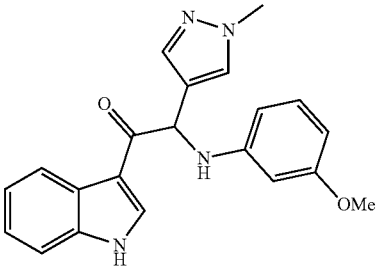 [SMILES: COc1cccc(NC(C(=O)c2c[nH]c3ccccc23)c2cnn(C)c2)c1] |
| CPD-043 | 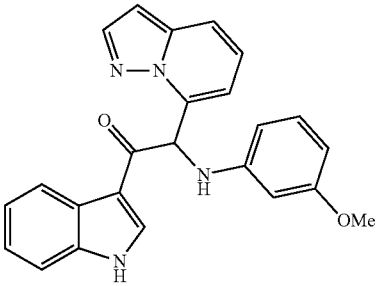 [SMILES: COc1cccc(NC(C(=O)c2c[nH]c3ccccc23)c2cccc3ccnn23)c1] |
| CPD-044 | 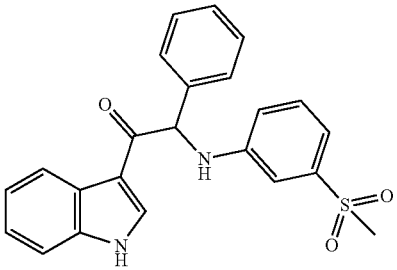 [SMILES: CS(=O)(=O)c1cccc(NC(C(=O)c2c[nH]c3ccccc23)c2ccccc2)c1] |

TABLE 1-continued
Structures of example compounds of the invention and their respective codes.
| Code | Structure |
|---|---|
| CPD-045 | 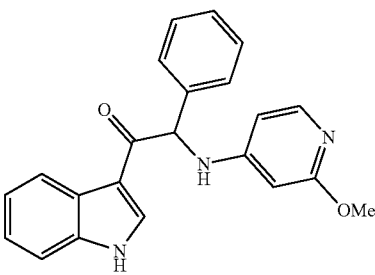 [SMILES: COc1cc(NC(C(=O)c2c[nH]c3ccccc23)c2ccccc2)ccn1] |
| CPD-046 | 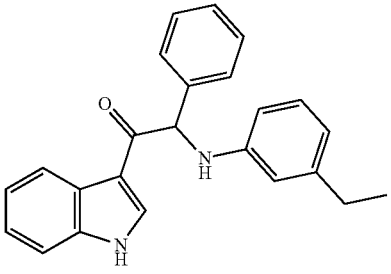 [SMILES: CCc1cccc(NC(C(=O)c2c[nH]c3ccccc23)c2ccccc2)c1] |
| CPD-047 | 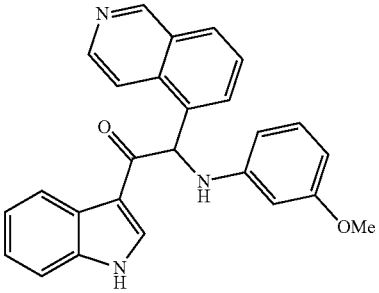 [SMILES: COc1cccc(NC(C(=O)c2c[nH]c3ccccc23)c2cccc3cnccc23)c1] |
| CPD-048 | 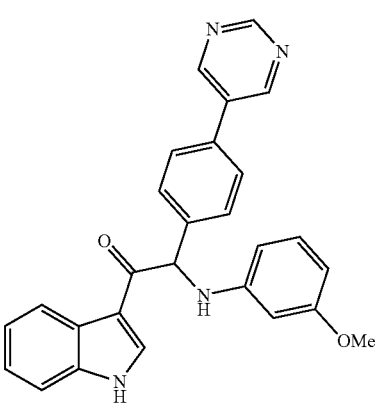 [SMILES: COc1cccc(NC(C(=O)c2c[nH]c3ccccc23)c2ccc(-c3cncnc3)cc2)c1] |
| CPD-049 | 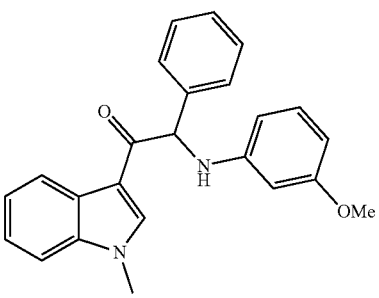 [SMILES: COc1cccc(NC(C(=O)c2cn(C)c3ccccc23)c2ccccc2)c1] |

TABLE 1-continued
Structures of example compounds of the invention and their respective codes.
| Code | Structure |
|---|---|
| CPD-050 | 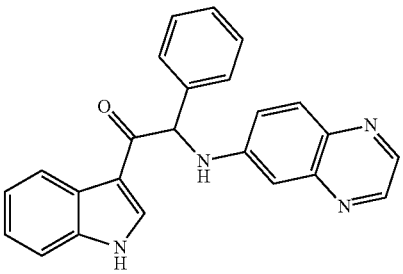 [SMILES: O=C(c1c[nH]c2ccccc12)C(Nc1ccc2nccnc2c1)c1ccccc1] |
| CPD-051 | 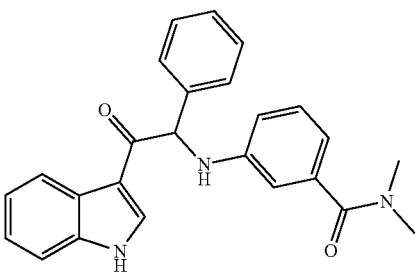 [SMILES: CN(C)C(=O)c1cccc(NC(C(=O)c2c[nH]c3ccccc23)c2ccccc2)c1] |
| CPD-052 | 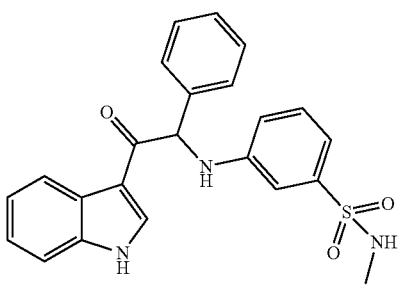 [SMILES: CNS(=O)(=O)c1cccc(NC(C(=O)c2c[nH]c3ccccc23)c2ccccc2)c1] |
| CPD-053 | 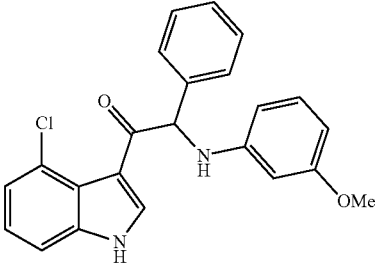 [SMILES: COc1cccc(NC(C(=O)c2c[nH]c3cccc(Cl)c23)c2ccccc2)c1] |
| CPD-054 | 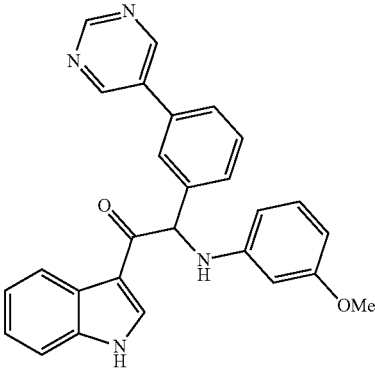 [SMILES: COc1cccc(NC(C(=O)c2c[nH]c3ccccc23)c2cccc(-c3cncnc3)c2)c1] |

TABLE 1-continued
Structures of example compounds of the invention and their respective codes.
| Code | Structure |
|------|-----------|
| CPD-055 | 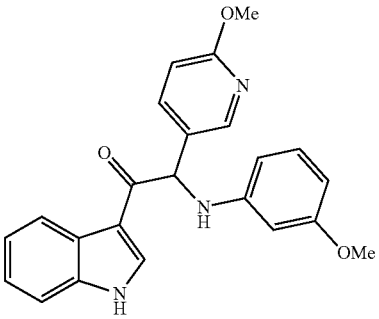 |
| CPD-056 | 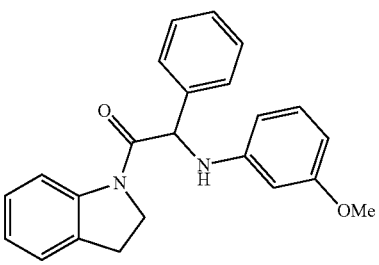 [SMILES: COc1cccc(NC(C(=O)N2CCc3ccccc32)c2ccccc2)c1] |
| CPD-057 | 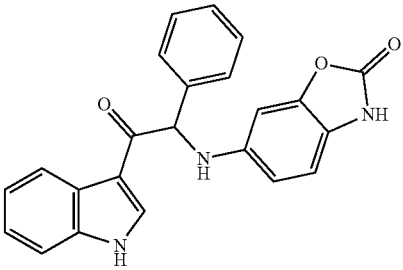 [SMILES: O=C(c1c[nH]c2ccccc12)C(Nc1ccc2[nH]c(=O)oc2c1)c1ccccc1] |
| CPD-058 | 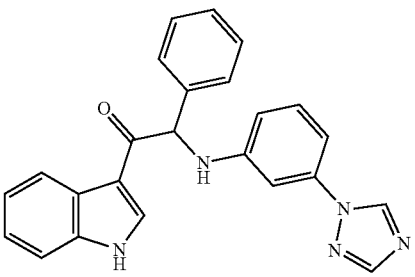 [SMILES: O=C(c1c[nH]c2ccccc12)C(Nc1cccc(-n2cncn2)c1)c1ccccc1] |
| CPD-059 | 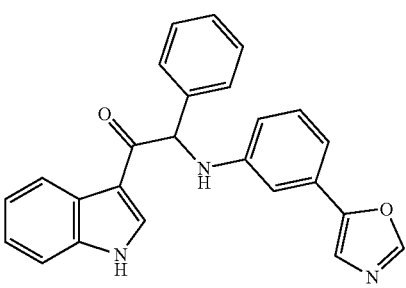 [SMILES: O=C(c1c[nH]c2ccccc12)C(Nc1cccc(-c2cnco2)c1)c1ccccc1] |

TABLE 1-continued
Structures of example compounds of the invention and their respective codes.
| Code | Structure |
|---|---|
| CPD-060 | 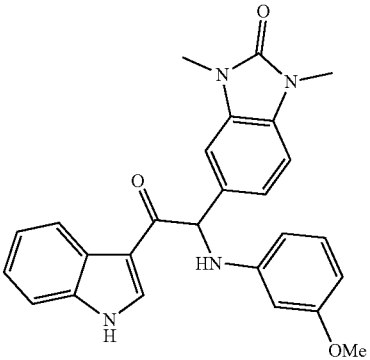 [SMILES: COc1cccc(NC(C(=O)c2c[nH]c3ccccc23)c2ccc3c(c2)n(C)c(=O)n3C)c1] |
| CPD-061 | 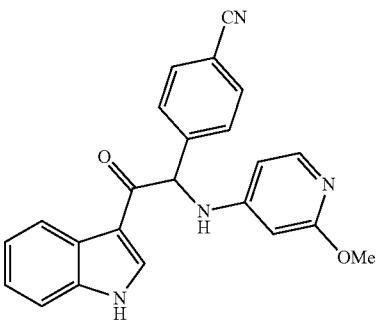 [SMILES: COc1cc(NC(C(=O)c2c[nH]c3ccccc23)c2ccc(C#N)cc2)ccn1] |
| CPD-062 | 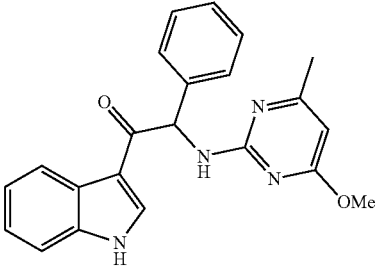 [SMILES: COc1cc(C)nc(NC(C(=O)c2c[nH]c3ccccc23)c2ccccc2)n1] |
| CPD-063 | 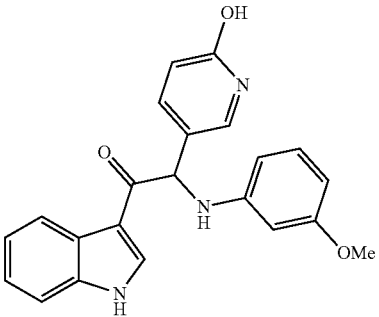 [SMILES: COc1cccc(NC(C(=O)c2c[nH]c3ccccc23)c2ccc(O)nc2)c1] |

TABLE 1-continued

Structures of example compounds of the invention and their respective codes.

| Code | Structure |
| --- | --- |
| CPD-064 | *(structure)* |
| CPD-065 | *(structure)* |
| CPD-066 | *(structure)* |
| CPD-067 | *(structure)* |
| CPD-068 | *(structure)* |

TABLE 1-continued
Structures of example compounds of the invention and their respective codes.
| Code | Structure |
|---|---|
| CPD-069 | 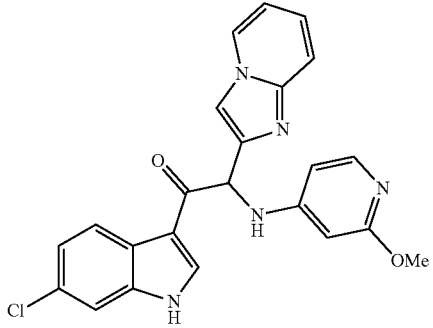 [SMILES: COc1cc(NC(C(=O)c2c[nH]c3cc(Cl)ccc23)c2cn3ccccc3n2)ccn1] |
| CPD-070 | 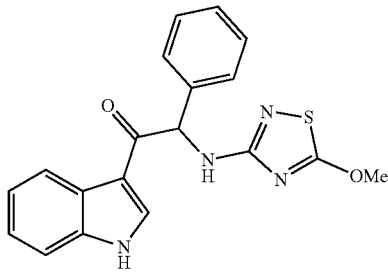 [SMILES: COc1nc(NC(C(=O)c2c[nH]c3ccccc23)c2ccccc2)ns1] |
| CPD-071 | 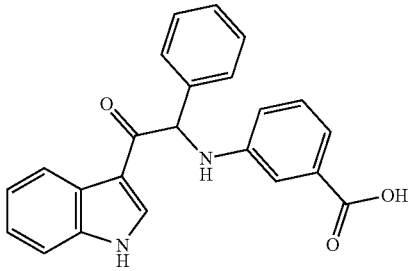 [SMILES: O=C(O)c1cccc(NC(C(=O)c2c[nH]c3ccccc23)c2ccccc2)c1] |
| CPD-072 | 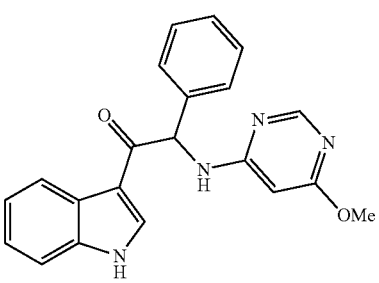 [SMILES: COc1cc(NC(C(=O)c2c[nH]c3ccccc23)c2ccccc2)ncn1] |
| CPD-073 | 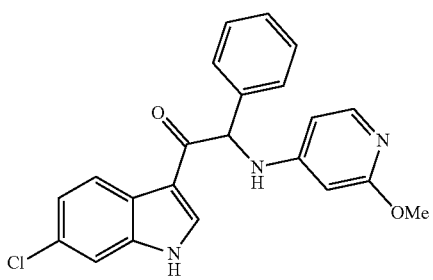 |

TABLE 1-continued
Structures of example compounds of the invention and their respective codes.
| Code | Structure |
|---|---|
| CPD-074 | 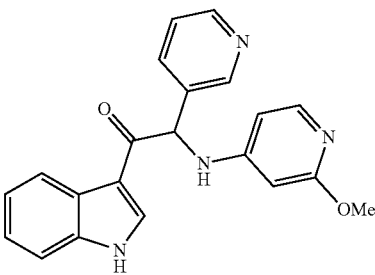 |
| CPD-075 | 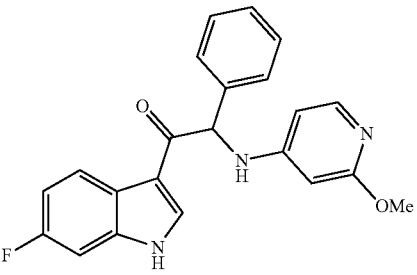 [SMILES: COc1cc(NC(C(=O)c2c[nH]c3cc(F)ccc23)c2ccccc2)ccn1] |
| CPD-076 | 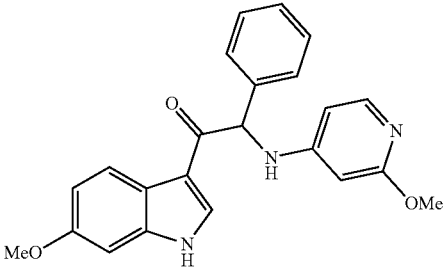 [SMILES: COc1ccc2c(C(=O)C(Nc3ccnc(OC)c3)c3ccccc3)c[nH]c2c1] |
| CPD-077 | 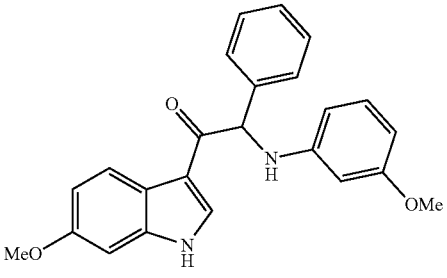 [SMILES: COc1cccc(NC(C(=O)c2c[nH]c3cc(OC)ccc23)c2ccccc2)c1] |
| CPD-078 | 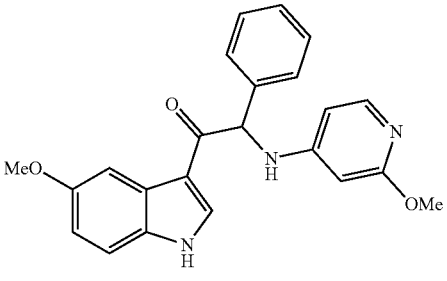 |

TABLE 1-continued
Structures of example compounds of the invention and their respective codes.
| Code | Structure |
|---|---|
| CPD-079 | 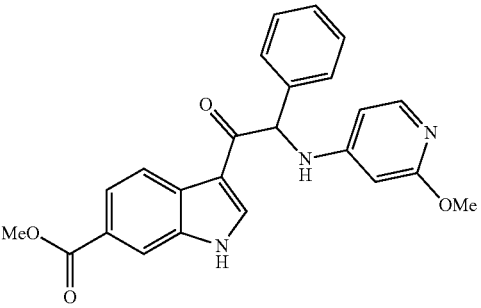 [SMILES: COC(=O)c1ccc2c(C(=O)C(Nc3ccnc(OC)c3)c3ccccc3)c[nH]c2c1] |
| CPD-080 | 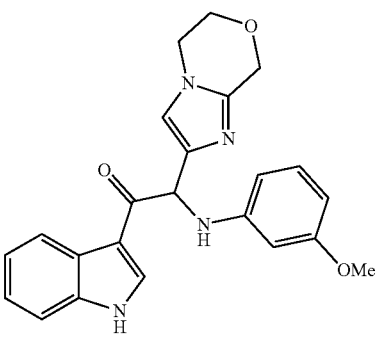 [SMILES: COc1cccc(NC(C(=O)c2c[nH]c3ccccc23)c2cn3c(n2)COCC3)c1] |
| CPD-081 | 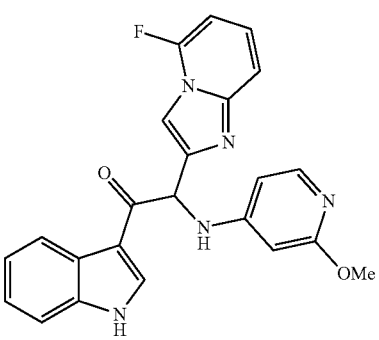 [SMILES: COc1cc(NC(C(=O)c2c[nH]c3ccccc23)c2cn3c(F)cccc3n2)ccn1] |
| CPD-082 | 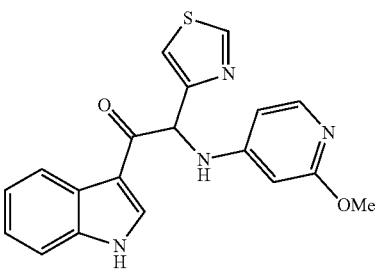 [SMILES: COc1cc(NC(C(=O)c2c[nH]c3ccccc23)c2cscn2)ccn1] |

TABLE 1-continued

Structures of example compounds of the invention and their respective codes.

| Code | Structure |
| --- | --- |
| CPD-083 | 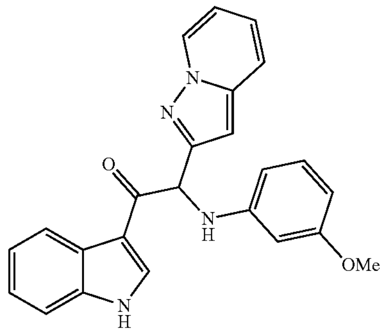 [SMILES: COc1cccc(NC(C(=O)c2c[nH]c3ccccc23)c2cc3ccccn3n2)c1] |
| CPD-084 | 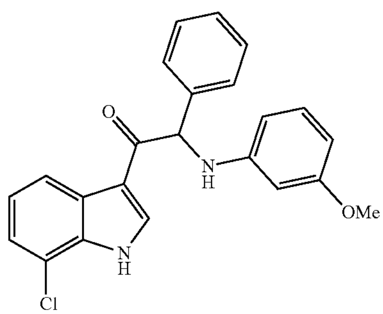 [SMILES: COc1cccc(NC(C(=O)c2c[nH]c3c(Cl)cccc23)c2ccccc2)c1] |
| CPD-085 | 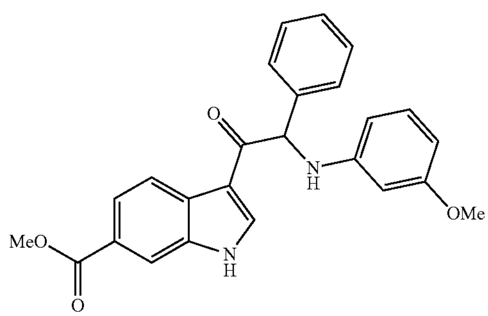 [SMILES: COC(=O)c1ccc2c(C(=O)C(Nc3cccc(OC)c3)c3ccccc3)c[nH]c2c1] |
| CPD-086 | 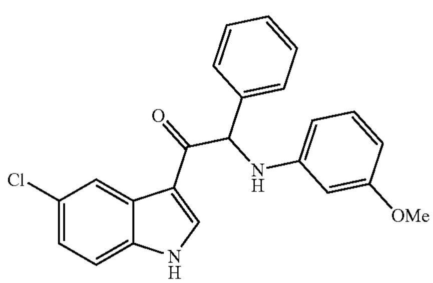 |
| CPD-087 | 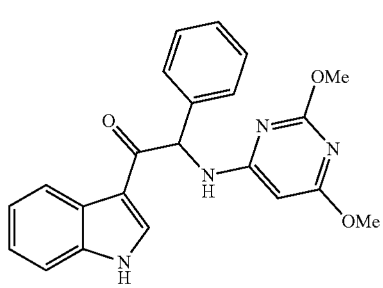 [SMILES: COc1cc(NC(C(=O)c2c[nH]c3ccccc23)c2ccccc2)nc(OC)n1] |

TABLE 1-continued
Structures of example compounds of the invention and their respective codes.
| Code | Structure |
|------|-----------|
| CPD-088 | 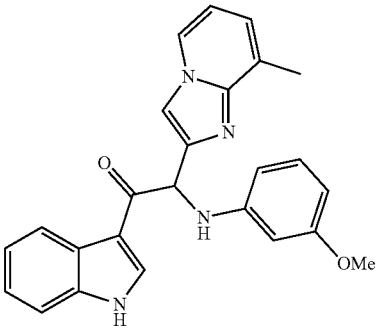 [SMILES: COc1cccc(NC(C(=O)c2c[nH]c3ccccc23)c2cn3cccc(C)c3n2)c1] |
| CPD-089 | 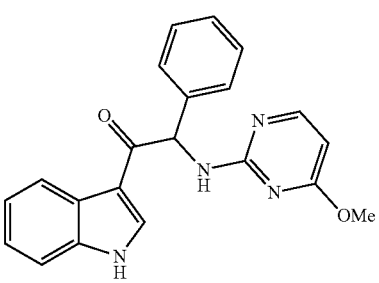 [SMILES: COc1ccnc(NC(C(=O)c2c[nH]c3ccccc23)c2ccccc2)n1] |
| CPD-090 | 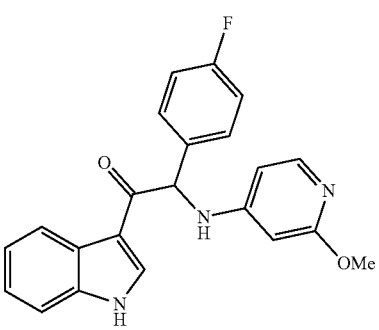 [SMILES: COc1cc(NC(C(=O)c2c[nH]c3ccccc23)c2ccc(F)cc2)ccn1] |
| CPD-091 | 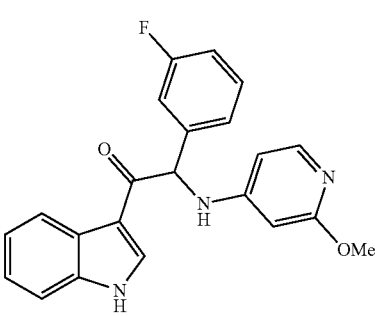 [SMILES: COc1cc(NC(C(=O)c2c[nH]c3ccccc23)c2cccc(F)c2)ccn1] |
| CPD-092 | 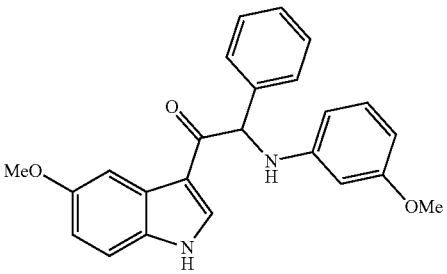 [SMILES: COc1cccc(NC(C(=O)c2c[nH]c3ccc(OC)cc23)c2ccccc2)c1] |

TABLE 1-continued
Structures of example compounds of the invention and their respective codes.
| Code | Structure |
|---|---|
| CPD-093 | 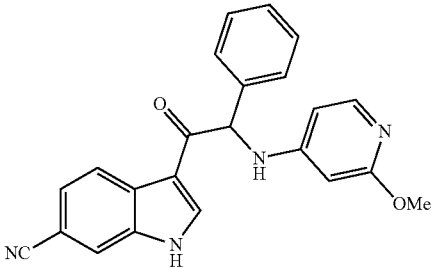 [SMILES: COc1cc(NC(C(=O)c2c[nH]c3cc(C#N)ccc23)c2ccccc2)ccn1] |
| CPD-094 | 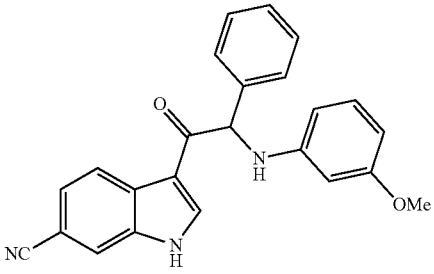 [SMILES: COc1cccc(NC(C(=O)c2c[nH]c3cc(C#N)ccc23)c2ccccc2)c1] |
| CPD-095 | 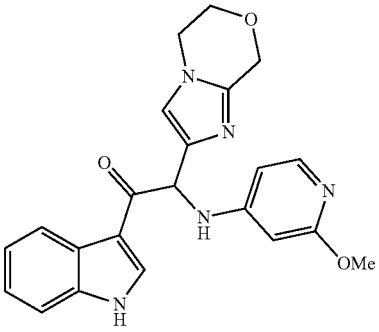 [SMILES: COc1cc(NC(C(=O)c2c[nH]c3ccccc23)c2cn3c(n2)COCC3)ccn1] |
| CPD-096 | 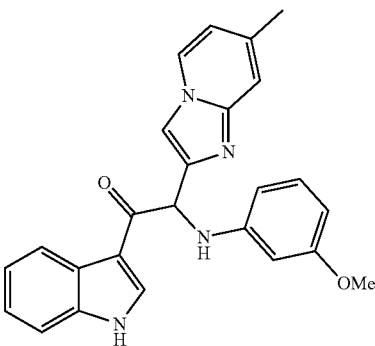 [SMILES: COc1cccc(NC(C(=O)c2c[nH]c3ccccc23)c2cn3ccc(C)cc3n2)c1] |

TABLE 1-continued
Structures of example compounds of the invention and their respective codes.
| Code | Structure |
|---|---|
| CPD-097 | 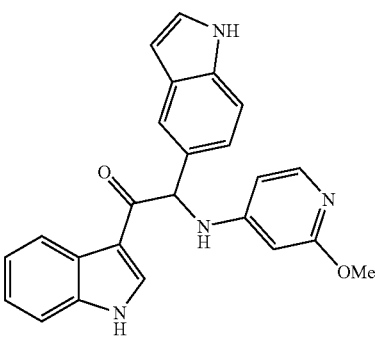 [SMILES: COc1cc(NC(C(=O)c2c[nH]c3ccccc23)c2ccc3[nH]ccc3c2)ccn1] |
| CPD-098 | 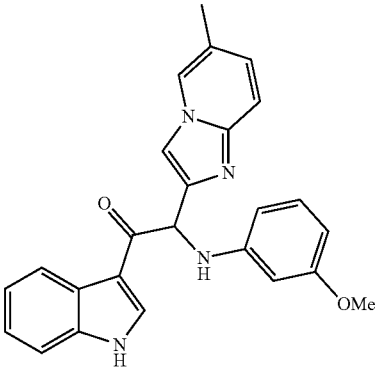 [SMILES: COc1cccc(NC(C(=O)c2c[nH]c3ccccc23)c2cn3cc(C)ccc3n2)c1] |
| CPD-099 | 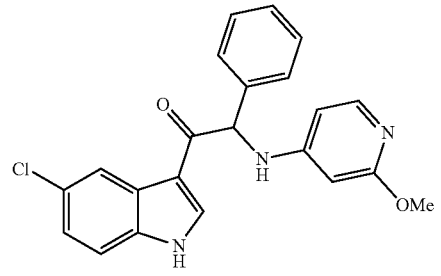 [SMILES: COc1cc(NC(C(=O)c2c[nH]c3ccc(Cl)cc23)c2ccccc2)ccn1] |
| CPD-100 | 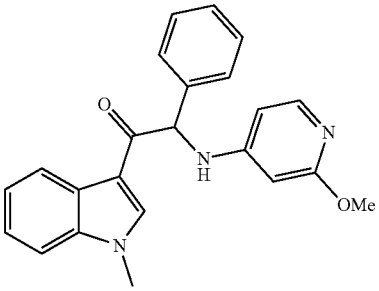 [SMILES: COc1cc(NC(C(=O)c2cn(C)c3ccccc23)c2ccccc2)ccn1] |

TABLE 1-continued
Structures of example compounds of the invention and their respective codes.
| Code | Structure |
|---|---|
| CPD-101 | 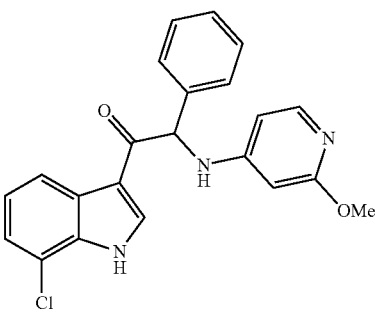 [SMILES: COc1cc(NC(C(=O)c2c[nH]c3c(Cl)cccc23)c2ccccc2)ccn1] |
| CPD-102 | 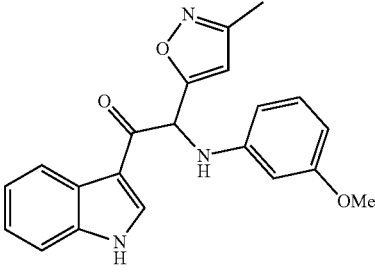 [SMILES: COc1cccc(NC(C(=O)c2c[nH]c3ccccc23)c2cc(C)no2)c1] |
| CPD-103 | 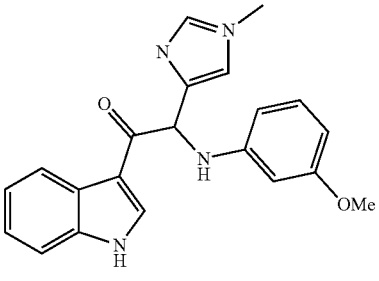 |
| CPD-104 | 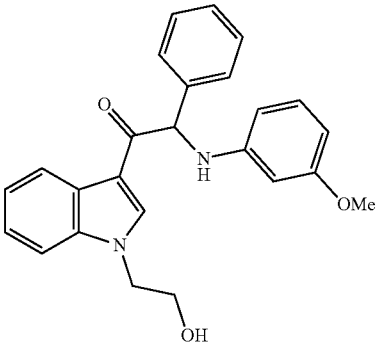 [SMILES: COc1cccc(NC(C(=O)c2cn(CCO)c3ccccc23)c2ccccc2)c1] |

TABLE 1-continued
Structures of example compounds of the invention and their respective codes.
| Code | Structure |
|---|---|
| CPD-105 | 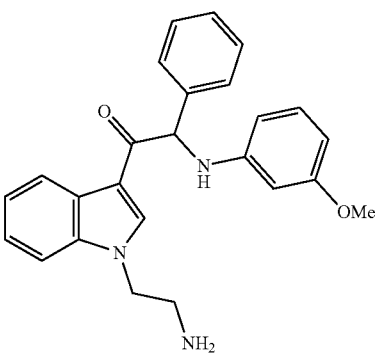 [SMILES: COc1cccc(NC(C(=O)c2cn(CCN)c3ccccc23)c2ccccc2)c1] |
| CPD-106 | 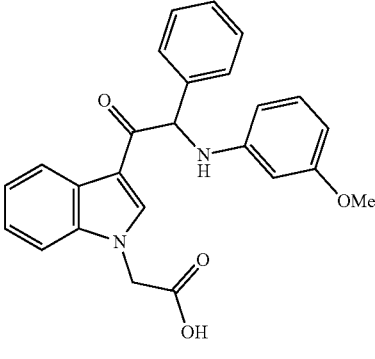 [SMILES: COc1cccc(NC(C(=O)c2cn(CC(=O)O)c3ccccc23)c2ccccc2)c1] |
| CPD-107 | 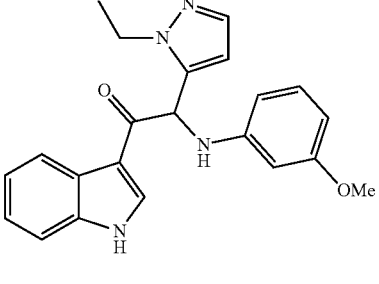 [SMILES: CCn1nccc1C(Nc1cccc(OC)c1)C(=O)c1c[nH]c2ccccc12] |
| CPD-108 | 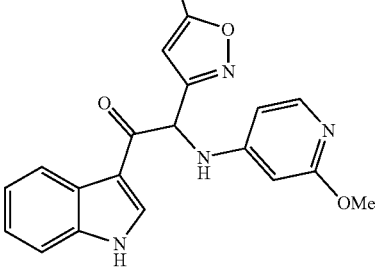 |

TABLE 1-continued

Structures of example compounds of the invention and their respective codes.

| Code | Structure |
|------|-----------|
| CPD-109 | 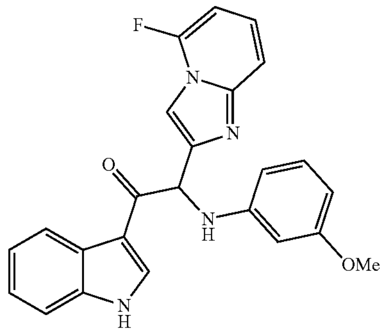 [SMILES: COc1cccc(NC(C(=O)c2c[nH]c3ccccc23)c2cn3c(F)cccc3n2)c1] |
| CPD-110 | 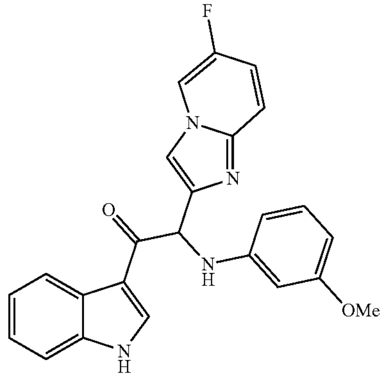 [SMILES: COc1cccc(NC(C(=O)c2c[nH]c3ccccc23)c2cn3cc(F)ccc3n2)c1] |
| CPD-111 | 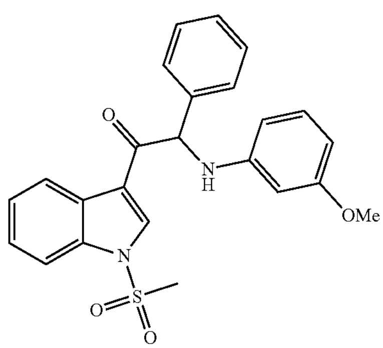 [SMILES: COc1cccc(NC(C(=O)c2cn(S(C)(=O)=O)c3ccccc23)c2ccccc2)c1] |
| CPD-112 | 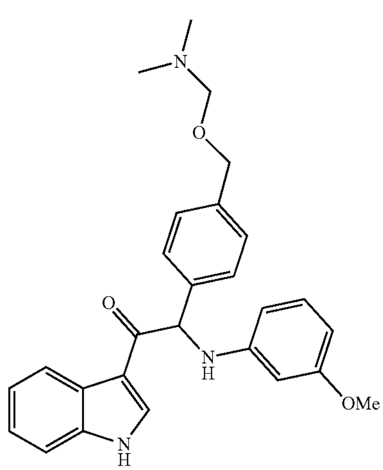 [SMILES: COc1cccc(NC(C(=O)c2c[nH]c3ccccc23)c2ccc(COCN(C)C)cc2)c1] |

TABLE 1-continued
Structures of example compounds of the invention and their respective codes.
| Code | Structure |
|---|---|
| CPD-113 | 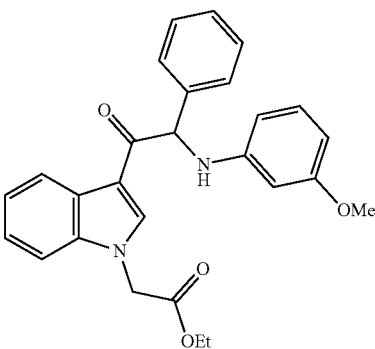 [SMILES: CCOC(=O)Cn1cc(C(=O)C(Nc2cccc(OC)c2)c2ccccc2)c2ccccc21] |
| CPD-114 | 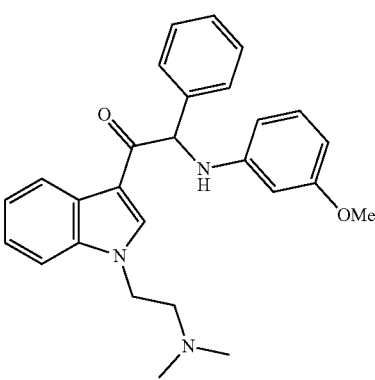 [SMILES: COc1cccc(NC(C(=O)c2cn(CCN(C)C)c3ccccc23)c2ccccc2)c1] |
| CPD-115 | 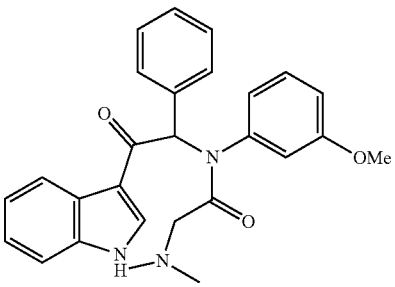 [SMILES: COc1cccc(N2C(=O)CN(C)n3cc(c4ccccc43)C(=O)C2c2ccccc2)c1] |
| CPD-116 | 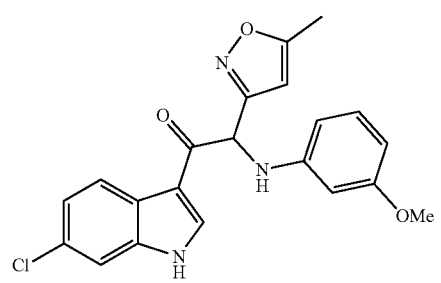 [SMILES: COc1cccc(NC(C(=O)c2c[nH]c3cc(Cl)ccc23)c2cc(C)on2)c1] |

TABLE 1-continued

Structures of example compounds of the invention and their respective codes.

| Code | Structure |
|---|---|
| CPD-117 | *(structure: 1-methylindole-3-yl C(O)-CH(NH-3-methoxyphenyl)-(5-methylisoxazol-3-yl))* |
| CPD-118 | *(structure: 6-chloro-1H-indol-3-yl C(O)-CH(NH-3-methoxyphenyl)-phenyl)* |
| CPD-119 | *(structure: 5-fluoro-1H-indol-3-yl C(O)-CH(NH-3-methoxyphenyl)-phenyl)* |
| CPD-120 | *(structure: 7-chloro-1H-indol-3-yl C(O)-CH(NH-3-methoxyphenyl)-(4-cyanophenyl))* |
| CPD-121 | *(structure: 1-(methylsulfonyl)indol-3-yl C(O)-CH(NH-(2-methoxypyridin-4-yl))-phenyl)* |

TABLE 1-continued
Structures of example compounds of the invention and their respective codes.
| Code | Structure |
| --- | --- |
| CPD-122 | 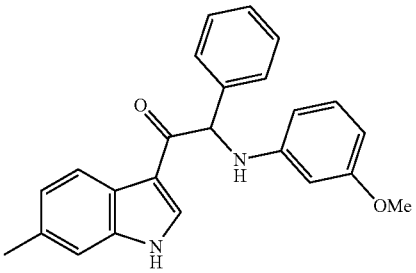 [SMILES: COc1cccc(NC(C(=O)c2c[nH]c3cc(C)ccc23)c2ccccc2)c1] |
| CPD-123 | 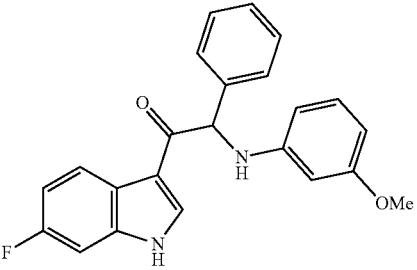 [SMILES: COc1cccc(NC(C(=O)c2c[nH]c3cc(F)ccc23)c2ccccc2)c1] |
| CPD-124 | 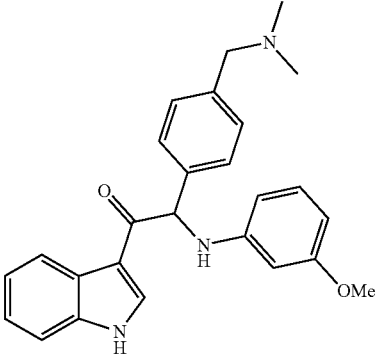 [SMILES: COc1cccc(NC(C(=O)c2c[nH]c3ccccc23)c2ccc(CN(C)C)cc2)c1] |
| CPD-125 | 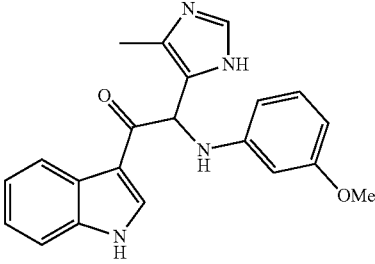 [SMILES: COc1cccc(NC(C(=O)c2c[nH]c3ccccc23)c2[nH]cnc2C)c1] |
| CPD-126 | 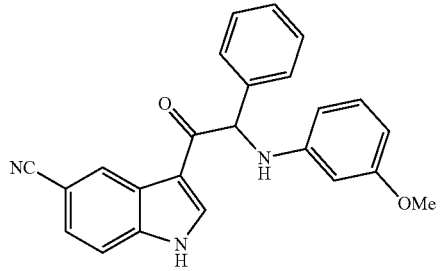 [SMILES: COc1cccc(NC(C(=O)c2c[nH]c3ccc(C#N)cc23)c2ccccc2)c1] |

TABLE 1-continued

Structures of example compounds of the invention and their respective codes.

| Code | Structure |
| --- | --- |
| CPD-127 | 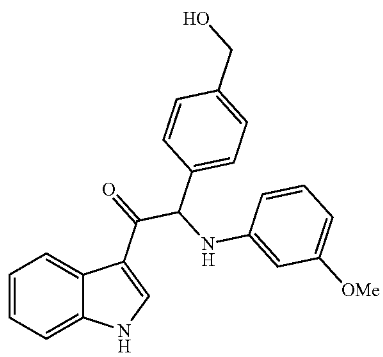 [SMILES: COc1cccc(NC(C(=O)c2c[nH]c3ccccc23)c2ccc(CO)cc2)c1] |
| CPD-128 | 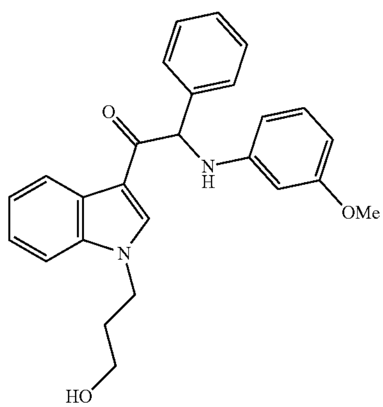 [SMILES: COc1cccc(NC(C(=O)c2cn(CCCO)c3ccccc23)c2ccccc2)c1] |
| CPD-129 | 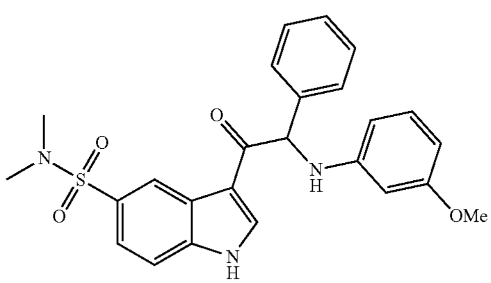 [SMILES: COc1cccc(NC(C(=O)c2c[nH]c3ccc(S(=O)(=O)N(C)C)cc23)c2ccccc2)c1] |
| CPD-130 | 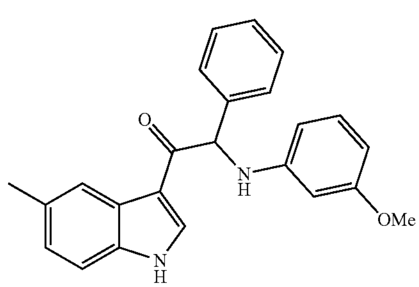 [SMILES: COc1cccc(NC(C(=O)c2c[nH]c3ccc(C)cc23)c2ccccc2)c1] |

TABLE 1-continued

Structures of example compounds of the invention and their respective codes.

| Code | Structure |
|---|---|
| CPD-131 | 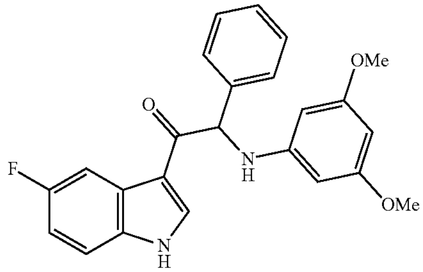 [SMILES: COc1cc(NC(C(=O)c2c[nH]c3ccc(F)cc23)c2ccccc2)cc(OC)c1] |
| CPD-132 | 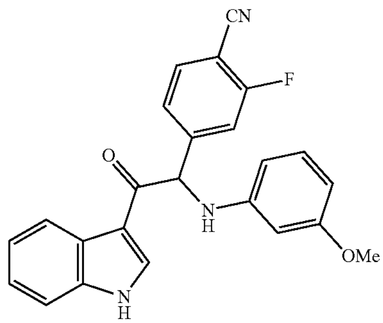 [SMILES: COc1cccc(NC(C(=O)c2c[nH]c3ccccc23)c2ccc(C#N)c(F)c2)c1] |
| CPD-133 | 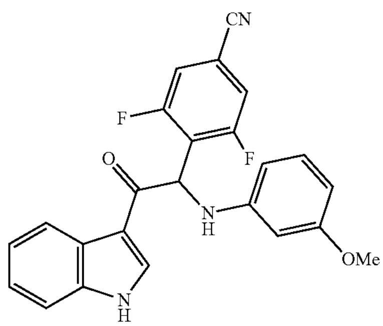 [SMILES: COc1cccc(NC(C(=O)c2c[nH]c3ccccc23)c2c(F)cc(C#N)cc2F)c1] |
| CPD-134 | 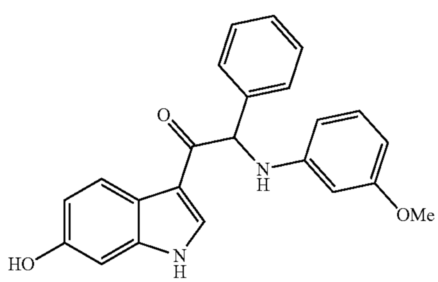 [SMILES: COc1cccc(NC(C(=O)c2c[nH]c3cc(O)ccc23)c2ccccc2)c1] |
| CPD-135 | 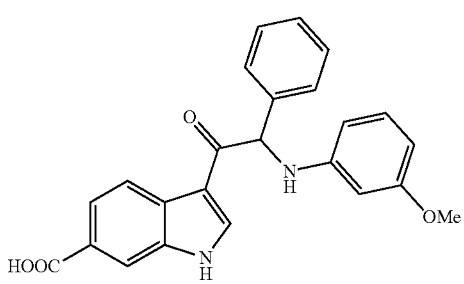 [SMILES: COc1cccc(NC(C(=O)c2c[nH]c3cc(C(=O)O)ccc23)c2ccccc2)c1] |

TABLE 1-continued

Structures of example compounds of the invention and their respective codes.

| Code | Structure |
|---|---|
| CPD-136 | 1-(1-(2-methoxyethyl)-1H-indol-3-yl)-2-((3-methoxyphenyl)amino)-2-phenylethan-1-one |
| CPD-137 | 1-(5-fluoro-1-methyl-1H-indol-3-yl)-2-((3-methoxyphenyl)amino)-2-phenylethan-1-one |
| CPD-138 | 1-(1H-indol-3-yl)-2-((3-methoxyphenyl)amino)-2-(m-tolyl)ethan-1-one |
| CPD-139 | 1-(1H-indol-3-yl)-2-((3-methoxyphenyl)amino)-2-(p-tolyl)ethan-1-one |
| CPD-140 | 1-(6-(hydroxymethyl)-1H-indol-3-yl)-2-((3-methoxyphenyl)amino)-2-phenylethan-1-one |

TABLE 1-continued

Structures of example compounds of the invention and their respective codes.

| Code | Structure |
| --- | --- |
| CPD-141 | 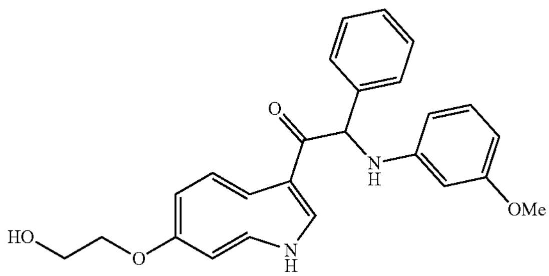 [SMILES: COc1cccc(NC(C(=O)c2cccc(OCCO)cc[nH]c2)c2ccccc2)c1] |
| CPD-142 | 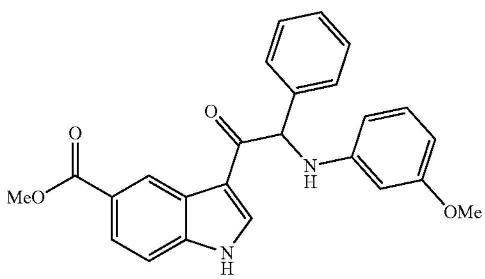 [SMILES: COC(=O)c1ccc2[nH]cc(C(=O)C(Nc3cccc(OC)c3)c3ccccc3)c2c1] |
| CPD-143 | 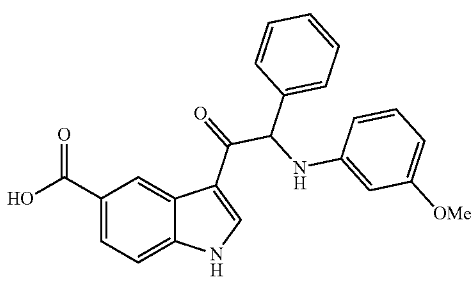 [SMILES: COc1cccc(NC(C(=O)c2c[nH]c3ccc(C(=O)O)cc23)c2ccccc2)c1] |
| CPD-144 | 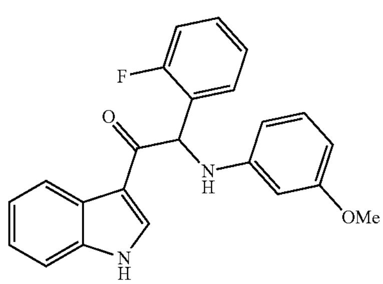 [SMILES: COc1cccc(NC(C(=O)c2c[nH]c3ccccc23)c2ccccc2F)c1] |

TABLE 1-continued
Structures of example compounds of the invention and their respective codes.
| Code | Structure |
|------|-----------|
| CPD-145 | 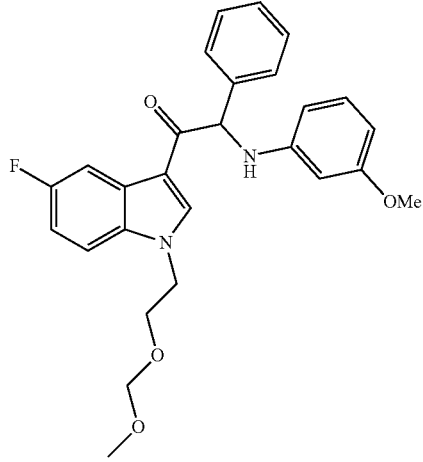 [SMILES: COCOCCn1cc(C(=O)C(Nc2cccc(OC)c2)c2ccccc2)c2cc(F)ccc21] |
| CPD-146 | 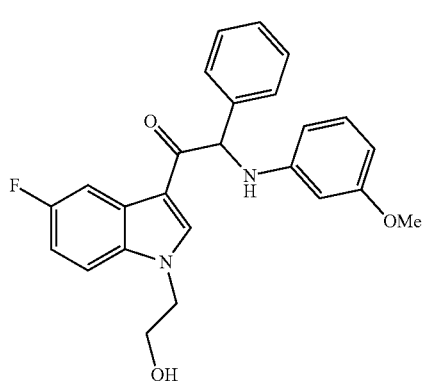 [SMILES: COc1cccc(NC(C(=O)c2cn(CCO)c3ccc(F)cc23)c2ccccc2)c1] |
| CPD-147 | 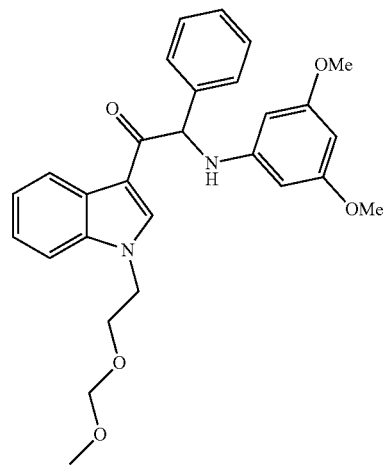 [SMILES: COCOCCn1cc(C(=O)C(Nc2cc(OC)cc(OC)c2)c2ccccc2)c2ccccc21] |

TABLE 1-continued
Structures of example compounds of the invention and their respective codes.
| Code | Structure |
| --- | --- |
| CPD-148 | 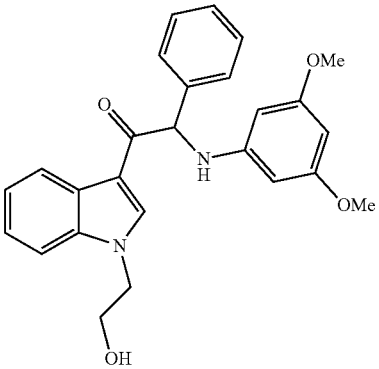 [SMILES: COc1cc(NC(C(=O)c2cn(CCO)c3ccccc23)c2ccccc2)cc(OC)c1] |
| CPD-149 | 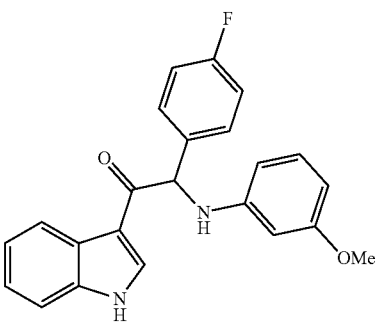 [SMILES: COc1cccc(NC(C(=O)c2c[nH]c3ccccc23)c2ccc(F)cc2)c1] |
| CPD-150 | 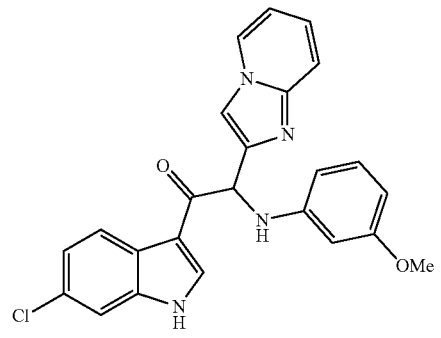 [SMILES: COc1cccc(NC(C(=O)c2c[nH]c3cc(Cl)ccc23)c2cn3ccccc3n2)c1] |
| CPD-151 | 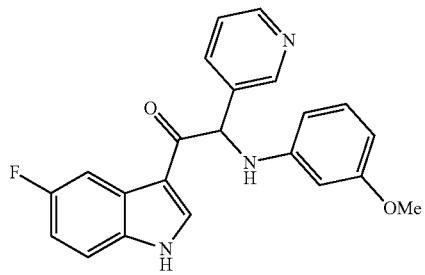 [SMILES: COc1cccc(NC(C(=O)c2c[nH]c3ccc(F)cc23)c2cccnc2)c1] |

TABLE 1-continued
Structures of example compounds of the invention and their respective codes.
| Code | Structure |
|---|---|
| CPD-152 | 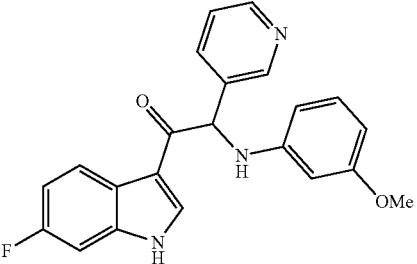 [SMILES: COc1cccc(NC(C(=O)c2c[nH]c3cc(F)ccc23)c2cccnc2)c1] |
| CPD-153 | 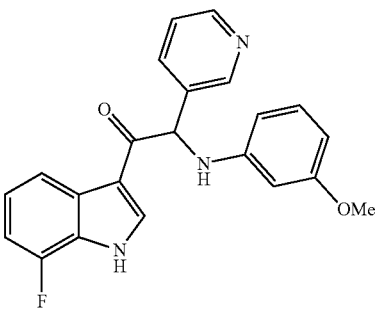 [SMILES: COc1cccc(NC(C(=O)c2c[nH]c3c(F)cccc23)c2cccnc2)c1] |
| CPD-154 | 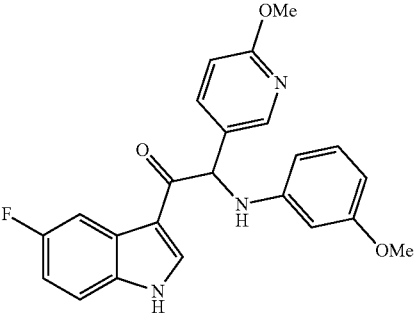 [SMILES: COc1cccc(NC(C(=O)c2c[nH]c3ccc(F)cc23)c2ccc(OC)nc2)c1] |
| CPD-155 | 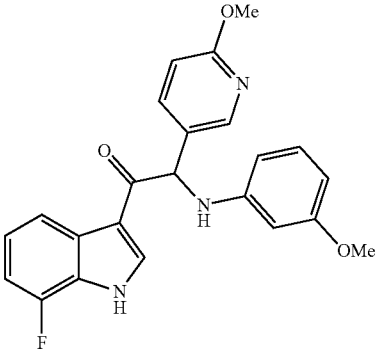 [SMILES: COc1cccc(NC(C(=O)c2c[nH]c3c(F)cccc23)c2ccc(OC)nc2)c1] |

TABLE 1-continued

Structures of example compounds of the invention and their respective codes.

| Code | Structure |
| --- | --- |
| CPD-156 | 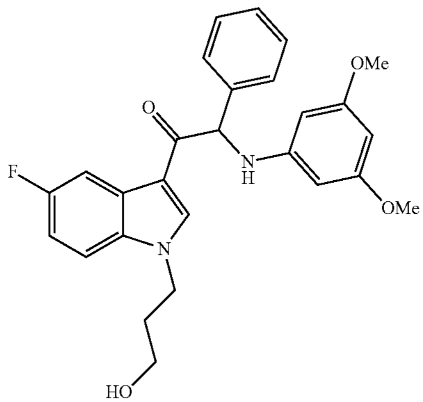 [SMILES: COc1cc(NC(C(=O)c2cn(CCCO)c3ccc(F)cc23)c2ccccc2)cc(OC)c1] |
| CPD-157 | 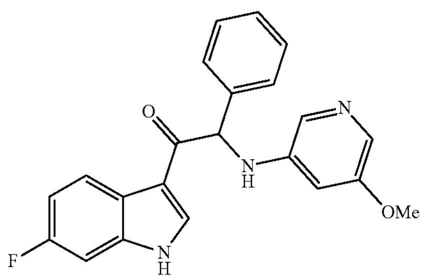 [SMILES: COc1cncc(NC(C(=O)c2c[nH]c3cc(F)ccc23)c2ccccc2)c1] |
| CPD-158 | 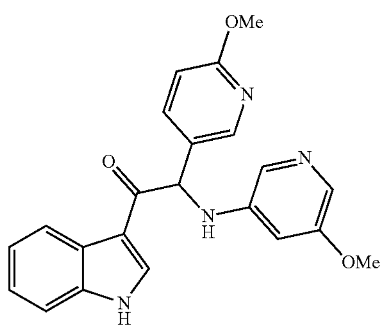 [SMILES: COc1cncc(NC(C(=O)c2c[nH]c3ccccc23)c2ccc(OC)nc2)c1] |
| CPD-159 | 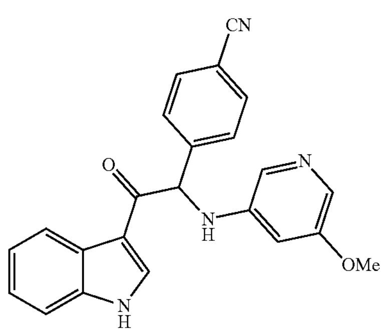 [SMILES: COc1cncc(NC(C(=O)c2c[nH]c3ccccc23)c2ccc(C#N)cc2)c1] |

TABLE 1-continued
Structures of example compounds of the invention and their respective codes.
| Code | Structure |
|---|---|
| CPD-160 | 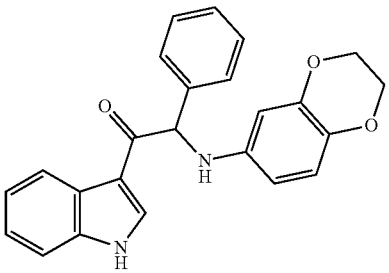 [SMILES: O=C(c1c[nH]c2ccccc12)C(Nc1ccc2c(c1)OCCO2)c1ccccc1] |
| CPD-161 | 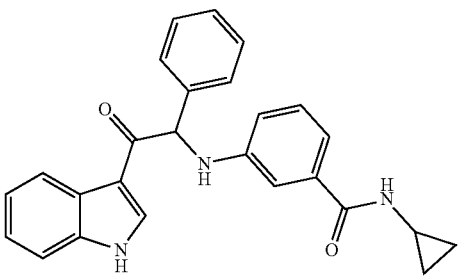 [SMILES: O=C(NC1CC1)c1cccc(NC(C(=O)c2c[nH]c3ccccc23)c2ccccc2)c1] |
| CPD-162 | 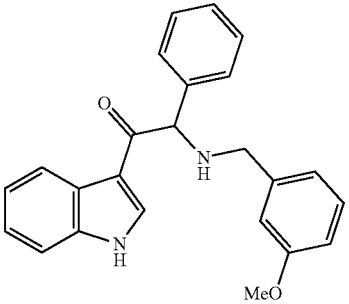 [SMILES: COc1cccc(CNC(C(=O)c2c[nH]c3ccccc23)c2ccccc2)c1] |
| CPD-163 | 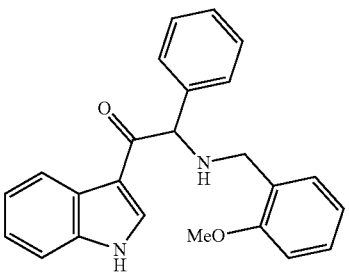 [SMILES: COc1ccccc1CNC(C(=O)c1c[nH]c2ccccc12)c1ccccc1] |
| CPD-164 | 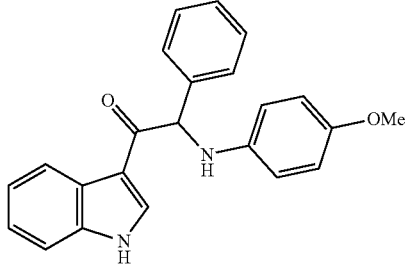 [SMILES: COc1ccc(NC(C(=O)c2c[nH]c3ccccc23)c2ccccc2)cc1] |

TABLE 1-continued

Structures of example compounds of the invention and their respective codes.

| Code | Structure |
|------|-----------|
| CPD-165 | 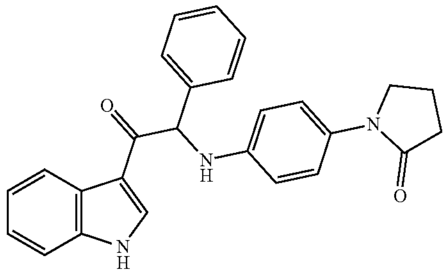 [SMILES: O=C(c1c[nH]c2ccccc12)C(Nc1ccc(N2CCCC2=O)cc1)c1ccccc1] |
| CPD-166 | 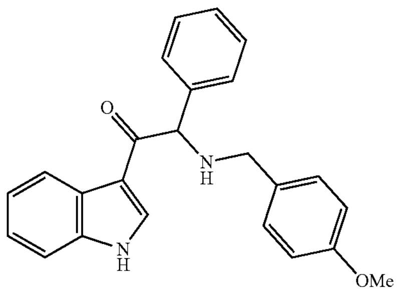 [SMILES: COc1ccc(CNC(C(=O)c2c[nH]c3ccccc23)c2ccccc2)cc1] |
| CPD-167 | 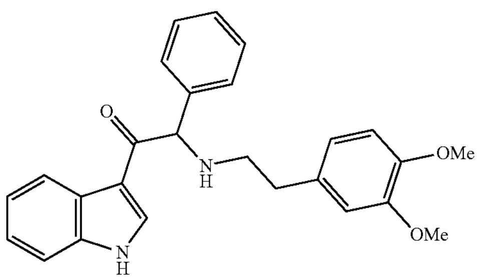 [SMILES: COc1ccc(CCNC(C(=O)c2c[nH]c3ccccc23)c2ccccc2)cc1OC] |
| CPD-168 | 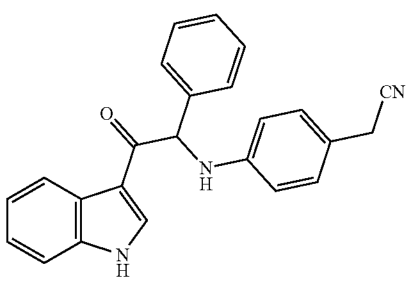 [SMILES: N#CCc1ccc(NC(C(=O)c2c[nH]c3ccccc23)c2ccccc2)cc1] |
| CPD-169 | 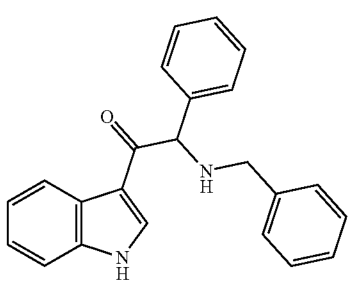 [SMILES: O=C(c1c[nH]c2ccccc12)C(NCc1ccccc1)c1ccccc1] |

TABLE 1-continued
Structures of example compounds of the invention and their respective codes.
| Code | Structure |
|------|-----------|
| CPD-170 | 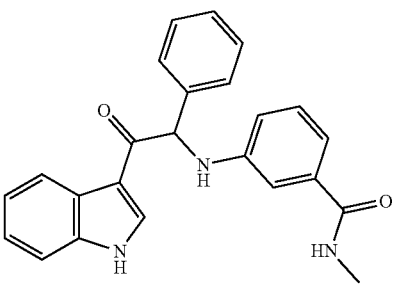 [SMILES: CNC(=O)c1cccc(NC(C(=O)c2c[nH]c3ccccc23)c2ccccc2)c1] |
| CPD-171 | 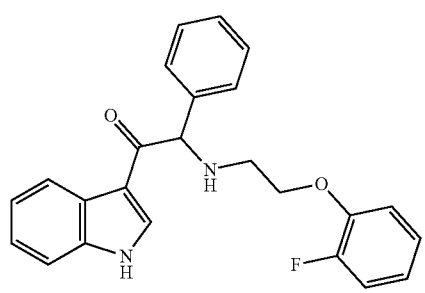 [SMILES: O=C(c1c[nH]c2ccccc12)C(NCCOc1ccccc1F)c1ccccc1] |
| CPD-172 | 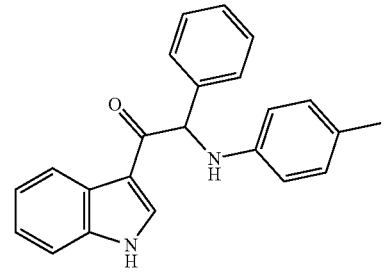 [SMILES: Cc1ccc(NC(C(=O)c2c[nH]c3ccccc23)c2ccccc2)cc1] |
| CPD-173 | 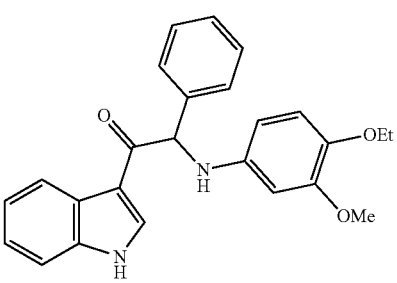 [SMILES: CCOc1ccc(NC(C(=O)c2c[nH]c3ccccc23)c2ccccc2)cc1OC] |
| CPD-174 | 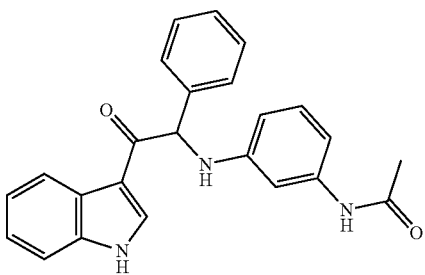 [SMILES: CC(=O)Nc1cccc(NC(C(=O)c2c[nH]c3ccccc23)c2ccccc2)c1] |

TABLE 1-continued

Structures of example compounds of the invention and their respective codes.

| Code | Structure |
|------|-----------|
| CPD-175 | 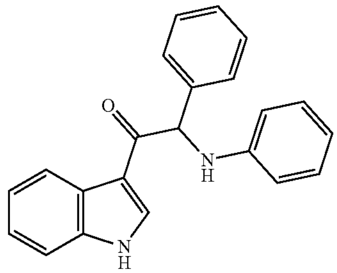 [SMILES: O=C(c1c[nH]c2ccccc12)C(Nc1ccccc1)c1ccccc1] |
| CPD-176 | 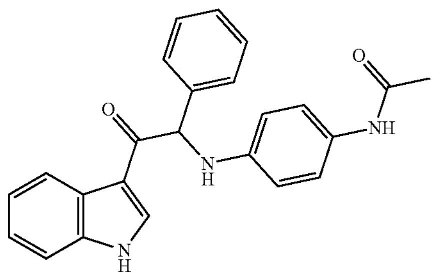 [SMILES: CC(=O)Nc1ccc(NC(C(=O)c2c[nH]c3ccccc23)c2ccccc2)cc1] |
| CPD-177 | 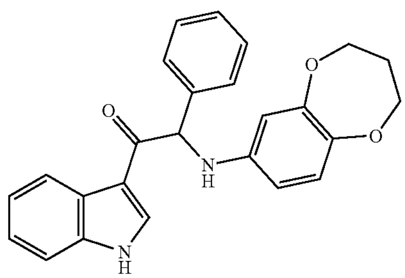 [SMILES: O=C(c1c[nH]c2ccccc12)C(Nc1ccc2c(c1)OCCCO2)c1ccccc1] |
| CPD-178 | 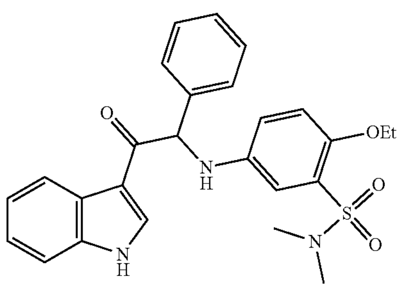 [SMILES: CCOc1ccc(NC(C(=O)c2c[nH]c3ccccc23)c2ccccc2)cc1S(=O)(=O)N(C)C] |
| CPD-179 | 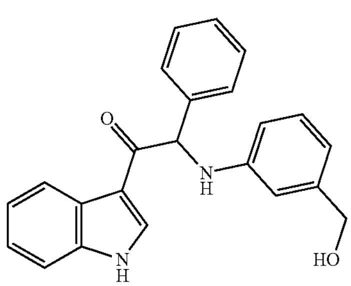 [SMILES: O=C(c1c[nH]c2ccccc12)C(Nc1cccc(CO)c1)c1ccccc1] |

TABLE 1-continued
Structures of example compounds of the invention and their respective codes.
| Code | Structure |
|---|---|
| CPD-180 | 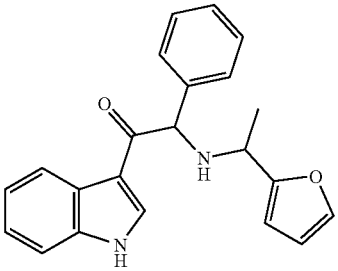 [SMILES: CC(NC(C(=O)c1c[nH]c2ccccc12)c1ccccc1)c1ccco1] |
| CPD-181 | 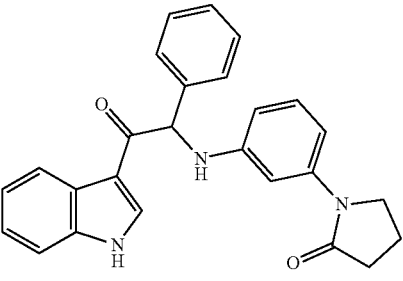 [SMILES: O=C(c1c[nH]c2ccccc12)C(Nc1cccc(N2CCCC2=O)c1)c1ccccc1] |
| CPD-182 | 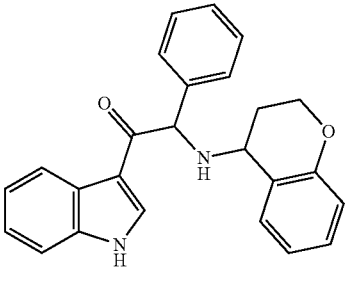 [SMILES: O=C(c1c[nH]c2ccccc12)C(NC1CCOc2ccccc21)c1ccccc1] |
| CPD-183 | 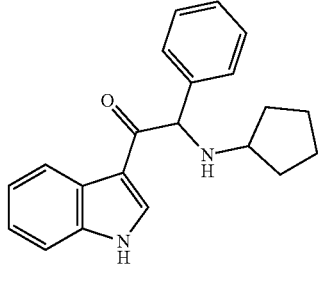 [SMILES: O=C(c1c[nH]c2ccccc12)C(NC1CCCC1)c1ccccc1] |
| CPD-184 | 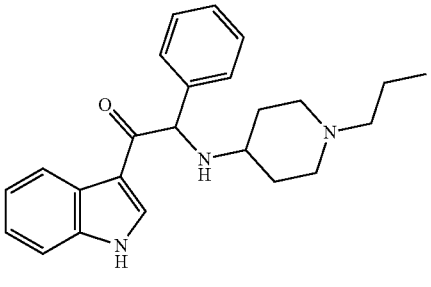 [SMILES: CCCN1CCC(NC(C(=O)c2c[nH]c3ccccc23)c2ccccc2)CC1] |

TABLE 1-continued

Structures of example compounds of the invention and their respective codes.

| Code | Structure |
| --- | --- |
| CPD-185 | 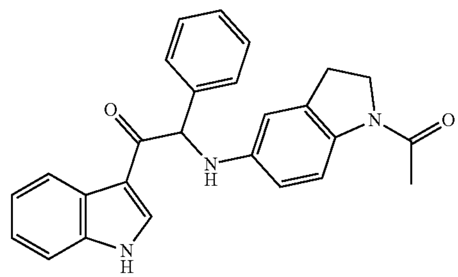 [SMILES: CC(=O)N1CCc2cc(NC(C(=O)c3c[nH]c4ccccc34)c3ccccc3)ccc21] |
| CPD-186 | 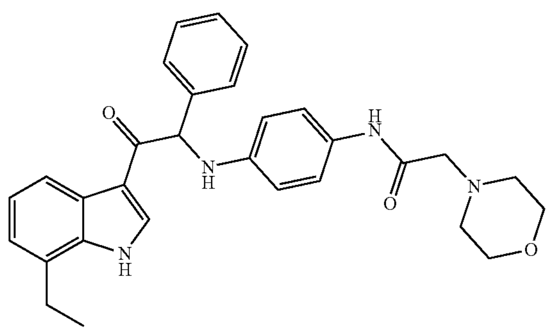 [SMILES: CCc1cccc2c(C(=O)C(Nc3ccc(NC(=O)CN4CCOCC4)cc3)c3ccccc3)c[nH]c12] |
| CPD-187 | 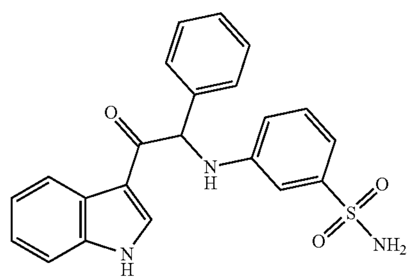 [SMILES: NS(=O)(=O)c1cccc(NC(C(=O)c2c[nH]c3ccccc23)c2ccccc2)c1] |
| CPD-188 | 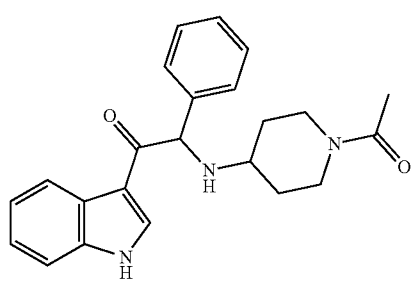 [SMILES: CC(=O)N1CCC(NC(C(=O)c2c[nH]c3ccccc23)c2ccccc2)CC1] |
| CPD-189 | 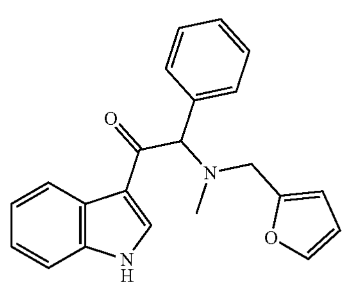 [SMILES: CN(Cc1ccco1)C(C(=O)c1c[nH]c2ccccc12)c1ccccc1] |

TABLE 1-continued

Structures of example compounds of the invention and their respective codes.

| Code | Structure |
|---|---|
| CPD-190 | 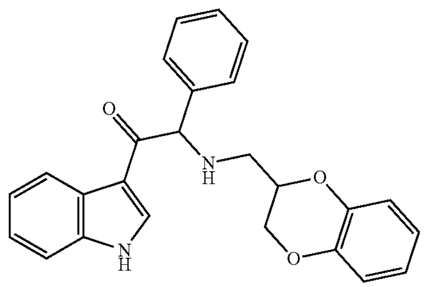 [SMILES: O=C(c1c[nH]c2ccccc12)C(NCC1COc2ccccc2O1)c1ccccc1] |
| CPD-191 | 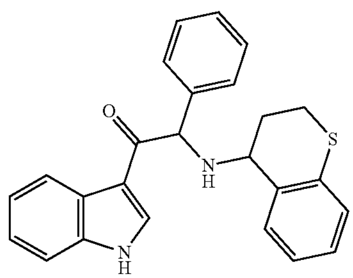 [SMILES: O=C(c1c[nH]c2ccccc12)C(NC1CCSc2ccccc21)c1ccccc1] |
| CPD-192 | 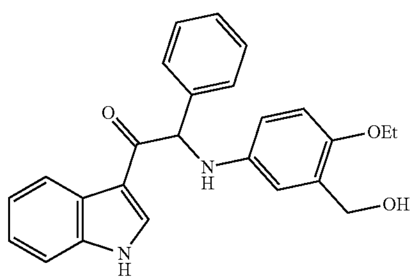 [SMILES: CCOc1ccc(NC(C(=O)c2c[nH]c3ccccc23)c2ccccc2)cc1CO] |
| CPD-193 | 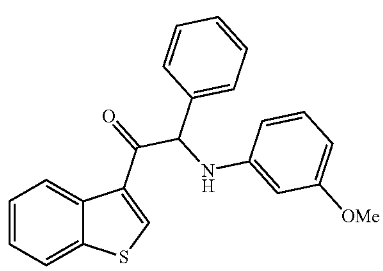 [SMILES: COc1cccc(NC(C(=O)c2csc3ccccc23)c2ccccc2)c1] |
| CPD-194 | 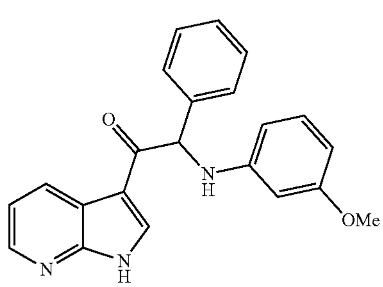 [SMILES: COc1cccc(NC(C(=O)c2c[nH]c3ncccc23)c2ccccc2)c1] |

TABLE 1-continued
Structures of example compounds of the invention and their respective codes.
| Code | Structure |
| --- | --- |
| CPD-195 | 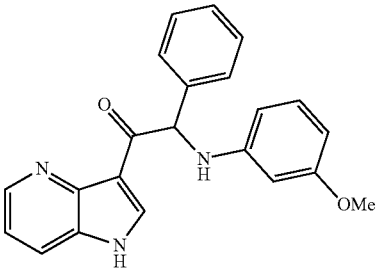 [SMILES: COc1cccc(NC(C(=O)c2c[nH]c3cccnc23)c2ccccc2)c1] |
| CPD-196 | 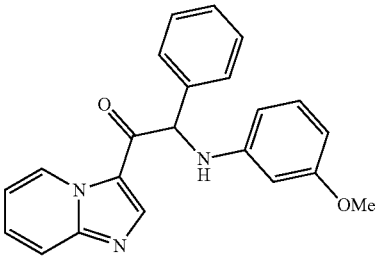 [SMILES: COc1cccc(NC(C(=O)c2cnc3ccccn23)c2ccccc2)c1] |
| CPD-197 | 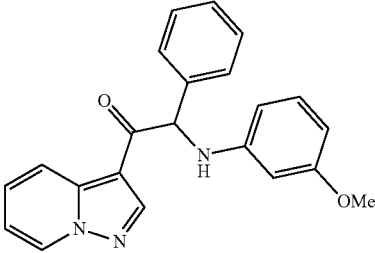 [SMILES: COc1cccc(NC(C(=O)c2cnn3ccccc23)c2ccccc2)c1] |
| CPD-198 | 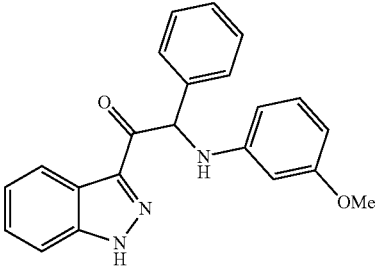 [SMILES: COc1cccc(NC(C(=O)c2n[nH]c3ccccc23)c2ccccc2)c1] |
| CPD-199 | 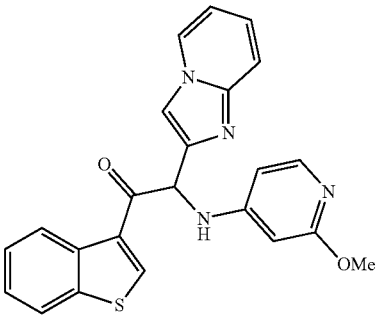 [SMILES: COc1cc(NC(C(=O)c2csc3ccccc23)c2cn3ccccc3n2)ccn1] |

TABLE 1-continued
Structures of example compounds of the invention and their respective codes.
| Code | Structure |
|---|---|
| CPD-200 | 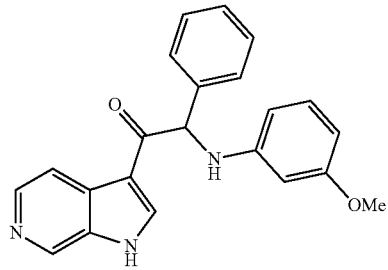 [SMILES: COc1cccc(NC(C(=O)c2c[nH]c3cnccc23)c2ccccc2)c1] |
| CPD-201 | 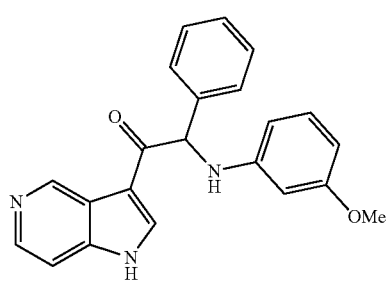 [SMILES: COc1cccc(NC(C(=O)c2c[nH]c3ccncc23)c2ccccc2)c1] |
| CPD-202 | 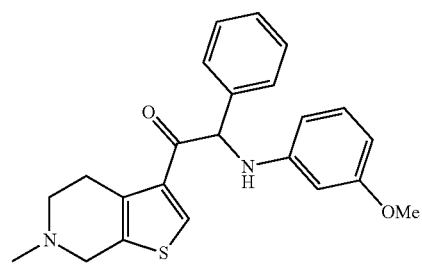 [SMILES: COc1cccc(NC(C(=O)c2csc3c2CCN(C)C3)c2ccccc2)c1] |
| CPD-203 | 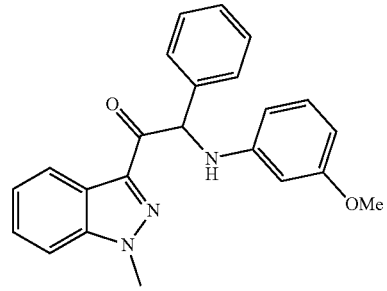 [SMILES: COc1cccc(NC(C(=O)c2nn(C)c3ccccc23)c2ccccc2)c1] |

TABLE 1-continued

Structures of example compounds of the invention and their respective codes.

| Code | Structure |
|------|-----------|
| CPD-204 | 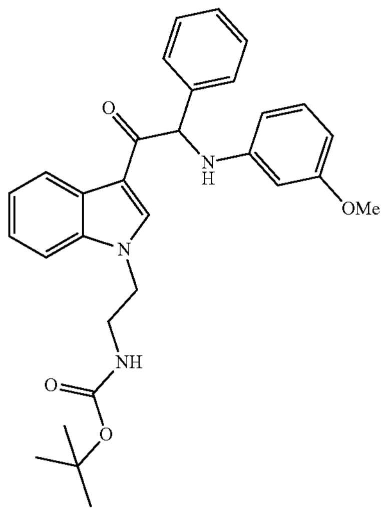 [SMILES: COc1cccc(NC(C(=O)c2cn(CCNC(=O)OC(C)(C)C)c3ccccc23)c2ccccc2)c1] |
| CPD-205 | 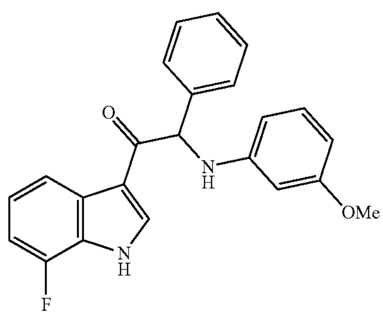 [SMILES: COc1cccc(NC(C(=O)c2c[nH]c3c(F)cccc23)c2ccccc2)c1] |
| CPD-206 | 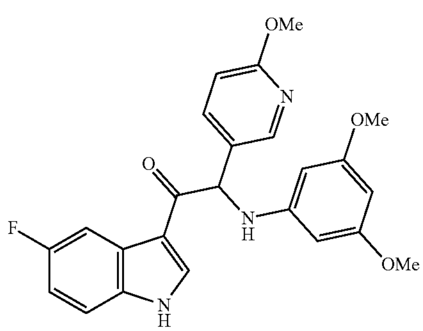 [SMILES: COc1cc(NC(C(=O)c2c[nH]c3ccc(F)cc23)c2ccc(OC)nc2)cc(OC)c1] |
| CPD-207 | 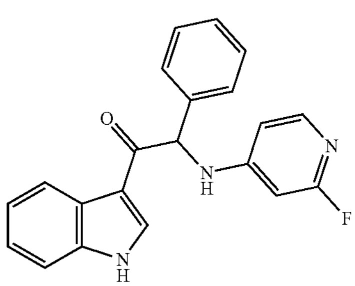 [SMILES: O=C(c1c[nH]c2ccccc12)C(Nc1ccnc(F)c1)c1ccccc1] |

TABLE 1-continued

Structures of example compounds of the invention and their respective codes.

| Code | Structure |
|---|---|
| CPD-208 | (structure) |
| CPD-209 | (structure) |
| CPD-210 | (structure) |
| CPD-211 | (structure) |

TABLE 1-continued
Structures of example compounds of the invention and their respective codes.
| Code | Structure |
| --- | --- |
| CPD-212 | 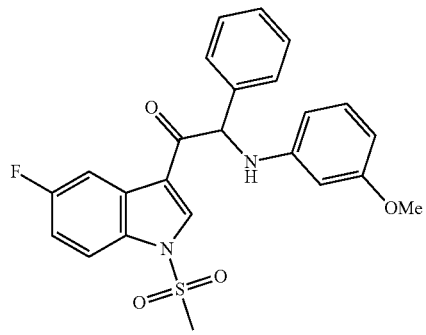 [SMILES: COc1cccc(NC(C(=O)c2cn(S(C)(=O)=O)c3ccc(F)cc23)c2ccccc2)c1] |
| CPD-213 | 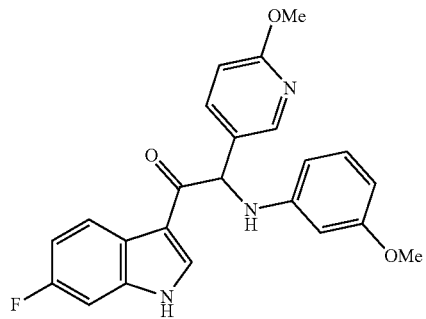 [SMILES: COc1cccc(NC(C(=O)c2c[nH]c3cc(F)ccc23)c2ccc(OC)nc2)c1] |
| CPD-214 | 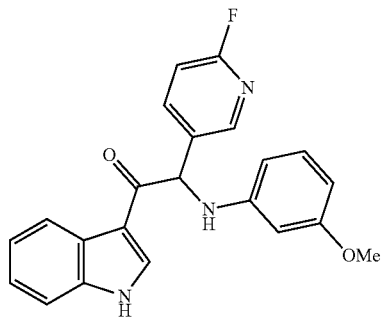 [SMILES: COc1cccc(NC(C(=O)c2c[nH]c3ccccc23)c2ccc(F)nc2)c1] |
| CPD-215 | 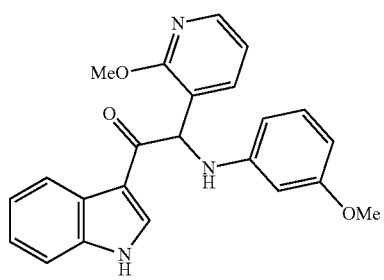 [SMILES: COc1cccc(NC(C(=O)c2c[nH]c3ccccc23)c2cccnc2OC)c1] |

TABLE 1-continued
Structures of example compounds of the invention and their respective codes.
| Code | Structure |
|------|-----------|
| CPD-216 | 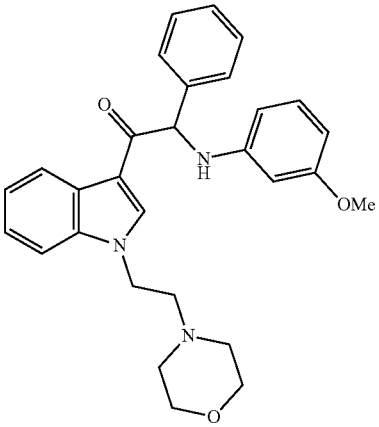 [SMILES: COc1cccc(NC(C(=O)c2cn(CCN3CCOCC3)c3ccccc23)c2ccccc2)c1] |
| CPD-217 | 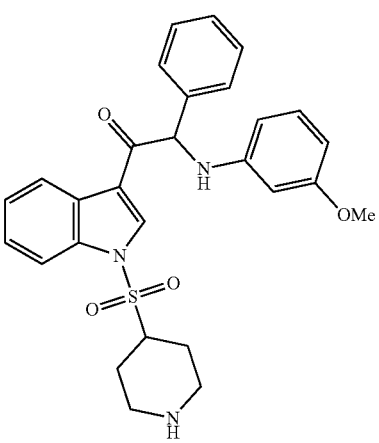 [SMILES: COc1cccc(NC(C(=O)c2cn(S(=O)(=O)C3CCNCC3)c3ccccc23)c2ccccc2)c1] |
| CPD-218 | 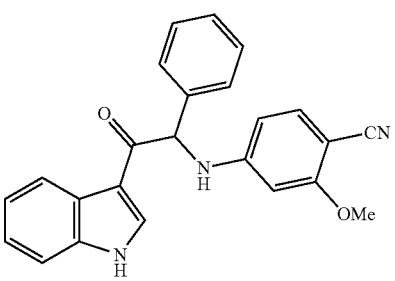 [SMILES: COc1cc(NC(C(=O)c2c[nH]c3ccccc23)c2ccccc2)ccc1C#N] |
| CPD-219 | 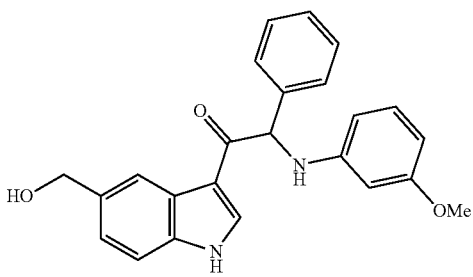 [SMILES: COc1cccc(NC(C(=O)c2c[nH]c3ccc(CO)cc23)c2ccccc2)c1] |

TABLE 1-continued

Structures of example compounds of the invention and their respective codes.

| Code | Structure |
| --- | --- |
| CPD-220 | *tert-butyl 3-[2-(3-methoxyphenylamino)-2-phenylacetyl]-1-methyl-1,4,6,7-tetrahydropyrazolo[4,3-c]pyridine-5-carboxylate* |
| CPD-221 | 1-(1-methyl-4,5,6,7-tetrahydro-1H-pyrazolo[4,3-c]pyridin-3-yl)-2-(3-methoxyphenylamino)-2-phenylethanone · HCl |
| CPD-222 | 1-(7-methoxy-1H-indol-3-yl)-2-(3-methoxyphenylamino)-2-phenylethanone |
| CPD-223 | 1-(1,5-dimethyl-4,5,6,7-tetrahydro-1H-pyrazolo[4,3-c]pyridin-3-yl)-2-(3-methoxyphenylamino)-2-phenylethanone |
| CPD-224 | 1-(7-methyl-1H-indol-3-yl)-2-(3-methoxyphenylamino)-2-phenylethanone |

TABLE 1-continued

Structures of example compounds of the invention and their respective codes.

| Code | Structure |
| --- | --- |
| CPD-225 | 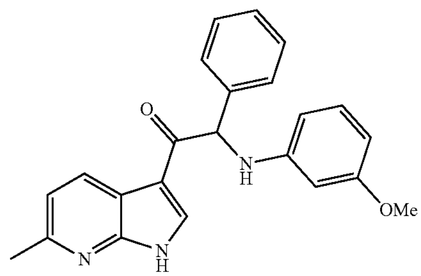 [SMILES: COc1cccc(NC(C(=O)c2c[nH]c3nc(C)ccc23)c2ccccc2)c1] |
| CPD-226 | 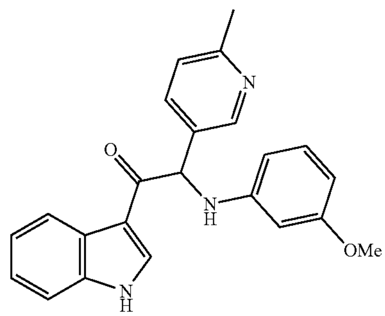 [SMILES: COc1cccc(NC(C(=O)c2c[nH]c3ccccc23)c2ccc(C)nc2)c1] |
| CPD-227 | 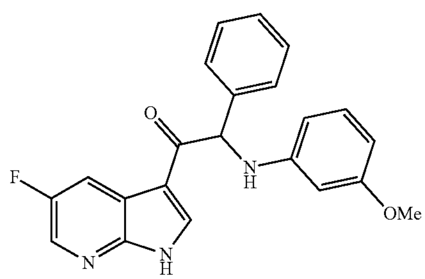 [SMILES: COc1cccc(NC(C(=O)c2c[nH]c3ncc(F)cc23)c2ccccc2)c1] |
| CPD-228 | 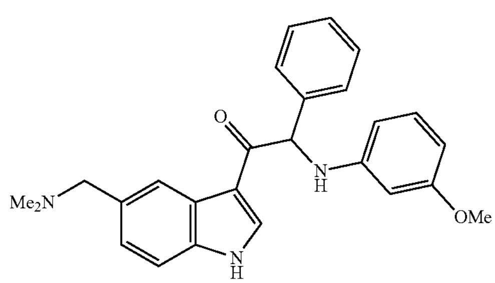 [SMILES: COc1cccc(NC(C(=O)c2c[nH]c3ccc(CN(C)C)cc23)c2ccccc2)c1] |
| CPD-229 | 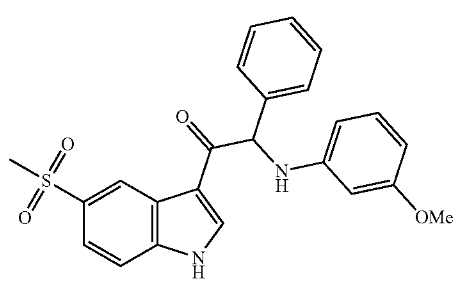 [SMILES: COc1cccc(NC(C(=O)c2c[nH]c3ccc(S(C)(=O)=O)cc23)c2ccccc2)c1] |

TABLE 1-continued

Structures of example compounds of the invention and their respective codes.

| Code | Structure |
| --- | --- |
| CPD-230 | 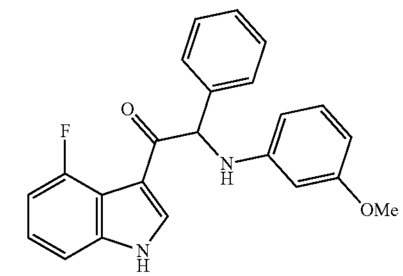 [SMILES: COc1cccc(NC(C(=O)c2c[nH]c3cccc(F)c23)c2ccccc2)c1] |
| CPD-231 | 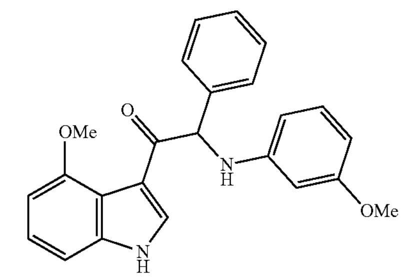 [SMILES: COc1cccc(NC(C(=O)c2c[nH]c3cccc(OC)c23)c2ccccc2)c1] |
| CPD-232 | 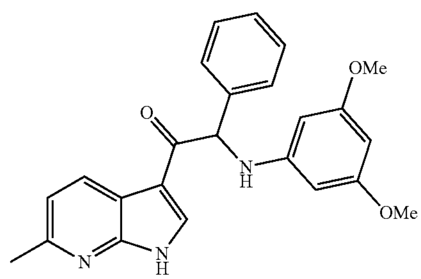 [SMILES: COc1cc(NC(C(=O)c2c[nH]c3nc(C)ccc23)c2ccccc2)cc(OC)c1] |
| CPD-233 | 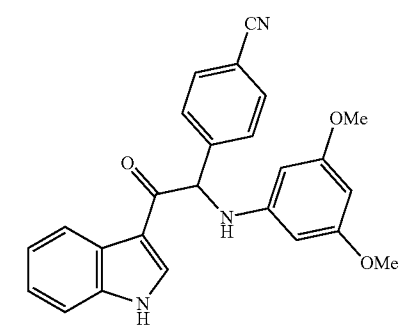 [SMILES: COc1cc(NC(C(=O)c2c[nH]c3ccccc23)c2ccc(C#N)cc2)cc(OC)c1] |
| CPD-234 | 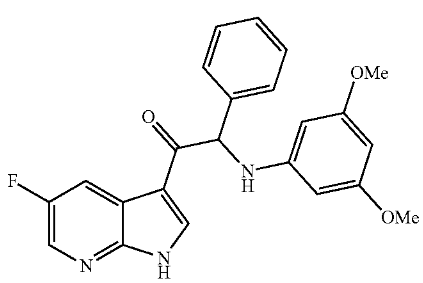 [SMILES: COc1cc(NC(C(=O)c2c[nH]c3ncc(F)cc23)c2ccccc2)cc(OC)c1] |

TABLE 1-continued
Structures of example compounds of the invention and their respective codes.
| Code | Structure |
|---|---|
| CPD-235 | 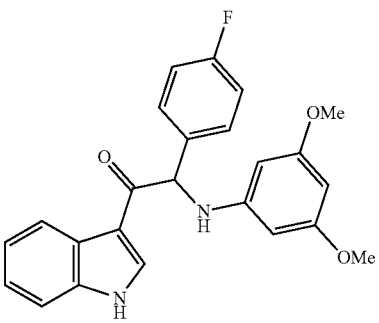 [SMILES: COc1cc(NC(C(=O)c2c[nH]c3ccccc23)c2ccc(F)cc2)cc(OC)c1] |
| CPD-236 | 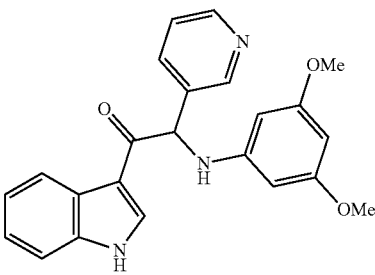 [SMILES: COc1cc(NC(C(=O)c2c[nH]c3ccccc23)c2cccnc2)cc(OC)c1] |
| CPD-237 | 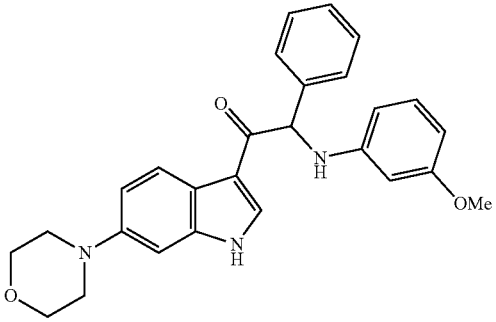 [SMILES: COc1cccc(NC(C(=O)c2c[nH]c3cc(N4CCOCC4)ccc23)c2ccccc2)c1] |
| CPD-238 | 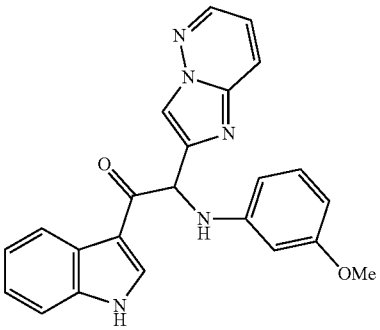 [SMILES: COc1cccc(NC(C(=O)c2c[nH]c3ccccc23)c2cn3ncccc3n2)c1] |

TABLE 1-continued
Structures of example compounds of the invention and their respective codes.
| Code | Structure |
|---|---|
| CPD-239 | 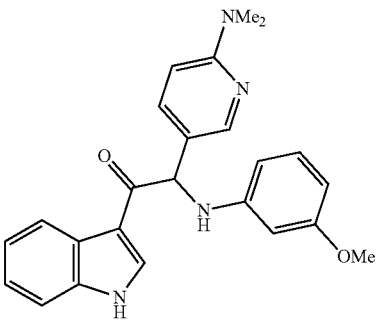 [SMILES: COc1cccc(NC(C(=O)c2c[nH]c3ccccc23)c2ccc(N(C)C)nc2)c1] |
| CPD-240 | 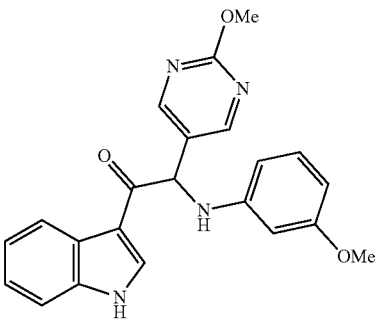 [SMILES: COc1cccc(NC(C(=O)c2c[nH]c3ccccc23)c2cnc(OC)nc2)c1] |
| CPD-241 | 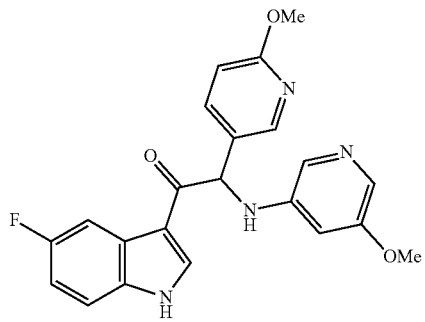 [SMILES: COc1cncc(NC(C(=O)c2c[nH]c3ccc(F)cc23)c2ccc(OC)nc2)c1] |
| CPD-242 | 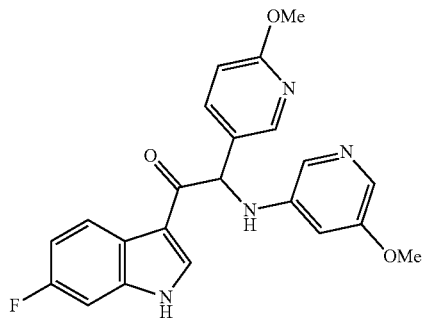 [SMILES: COc1cncc(NC(C(=O)c2c[nH]c3cc(F)ccc23)c2ccc(OC)nc2)c1] |
| CPD-243 | 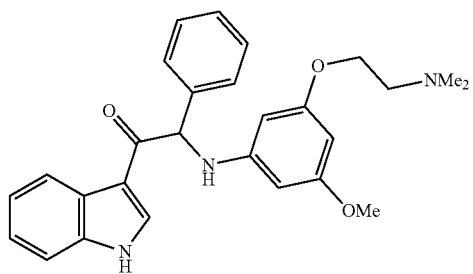 [SMILES: COc1cc(NC(C(=O)c2c[nH]c3ccccc23)c2ccccc2)cc(OCCN(C)C)c1] |

TABLE 1-continued
Structures of example compounds of the invention and their respective codes.
| Code | Structure |
|------|-----------|
| CPD-244 | 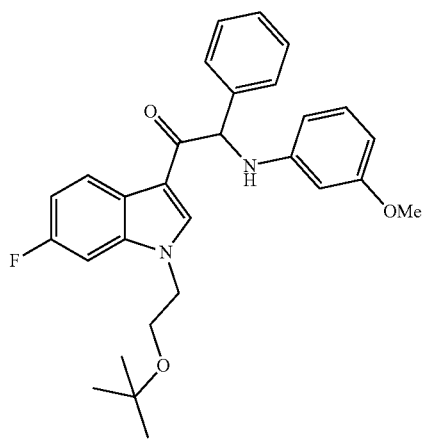 [SMILES: COc1cccc(NC(C(=O)c2cn(CCOC(C)(C)C)c3cc(F)ccc23)c2ccccc2)c1] |
| CPD-245 | 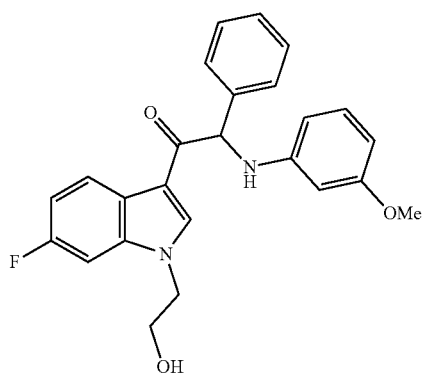 [SMILES: COc1cccc(NC(C(=O)c2cn(CCO)c3cc(F)ccc23)c2ccccc2)c1] |
| CPD-246 | 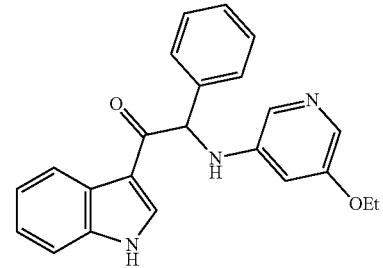 [SMILES: CCOc1cncc(NC(C(=O)c2c[nH]c3ccccc23)c2ccccc2)c1] |
| CPD-247 | 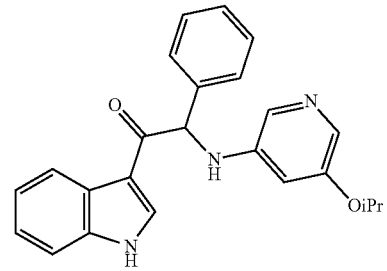 [SMILES: CC(C)Oc1cncc(NC(C(=O)c2c[nH]c3ccccc23)c2ccccc2)c1] |

TABLE 1-continued

Structures of example compounds of the invention and their respective codes.

| Code | Structure |
| --- | --- |
| CPD-248 | 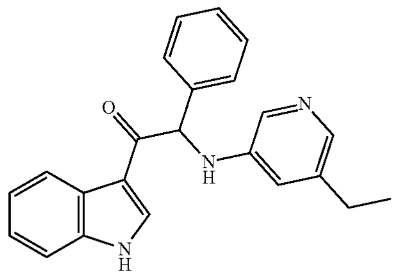 [SMILES: CCc1cncc(NC(C(=O)c2c[nH]c3ccccc23)c2ccccc2)c1] |
| CPD-249 | 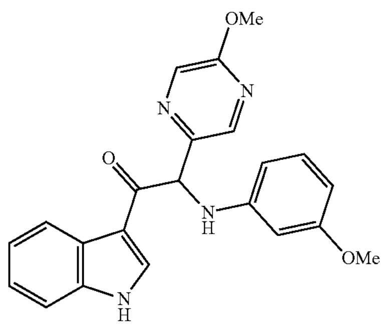 [SMILES: COc1cccc(NC(C(=O)c2c[nH]c3ccccc23)c2cnc(OC)cn2)c1] |
| CPD-250 | 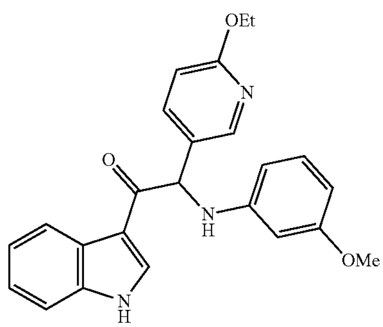 [SMILES: CCOc1ccc(C(Nc2cccc(OC)c2)C(=O)c2c[nH]c3ccccc23)cn1] |
| CPD-251 | 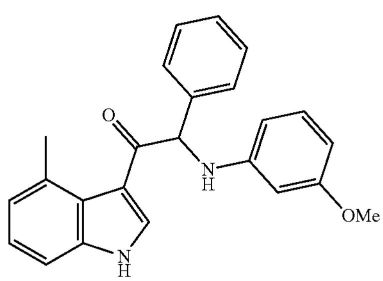 [SMILES: COc1cccc(NC(C(=O)c2c[nH]c3cccc(C)c23)c2ccccc2)c1] |
| CPD-252 | 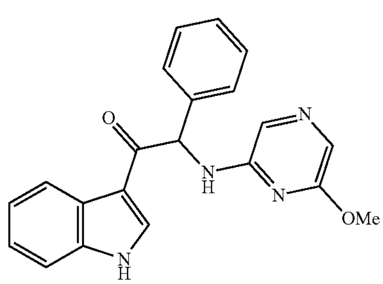 [SMILES: COc1cncc(NC(C(=O)c2c[nH]c3ccccc23)c2ccccc2)n1] |

TABLE 1-continued
Structures of example compounds of the invention and their respective codes.
| Code | Structure |
|---|---|
| CPD-253 | 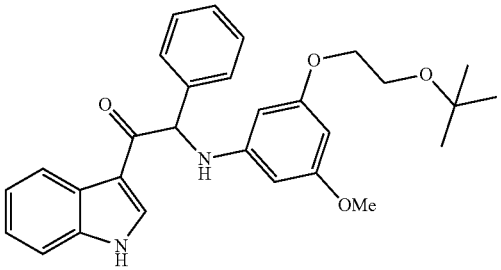 [SMILES: COc1cc(NC(C(=O)c2c[nH]c3ccccc23)c2ccccc2)cc(OCCOC(C)(C)C)c1] |
| CPD-254 | 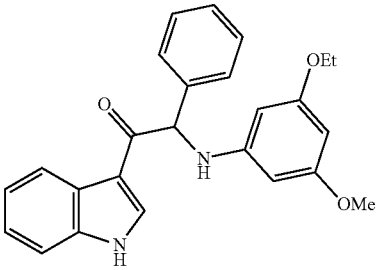 [SMILES: CCOc1cc(NC(C(=O)c2c[nH]c3ccccc23)c2ccccc2)cc(OC)c1] |
| CPD-255 | 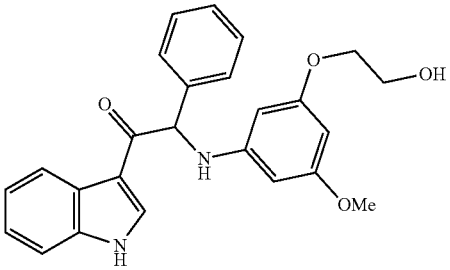 [SMILES: COc1cc(NC(C(=O)c2c[nH]c3ccccc23)c2ccccc2)cc(OCCO)c1] |
| CPD-256 | 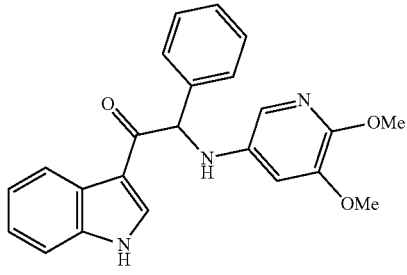 |
| CPD-257 | 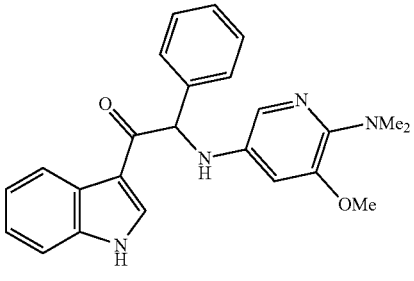 [SMILES: COc1cc(NC(C(=O)c2c[nH]c3ccccc23)c2ccccc2)cnc1N(C)C] |

TABLE 1-continued
Structures of example compounds of the invention and their respective codes.
| Code | Structure |
|---|---|
| CPD-258 | 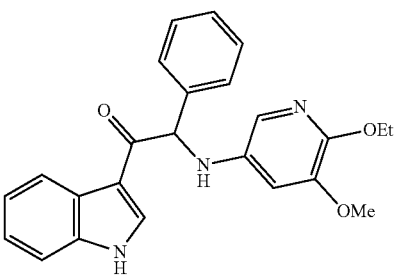 [SMILES: CCOc1ncc(NC(C(=O)c2c[nH]c3ccccc23)c2ccccc2)cc1OC] |
| CPD-259 | 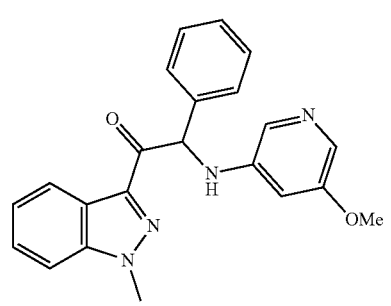 [SMILES: COc1cncc(NC(C(=O)c2nn(C)c3ccccc23)c2ccccc2)c1] |
| CPD-260 | 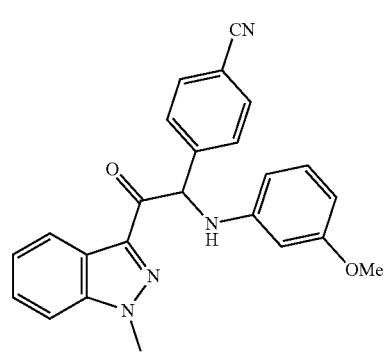 [SMILES: COc1cccc(NC(C(=O)c2nn(C)c3ccccc23)c2ccc(C#N)cc2)c1] |
| CPD-261 | 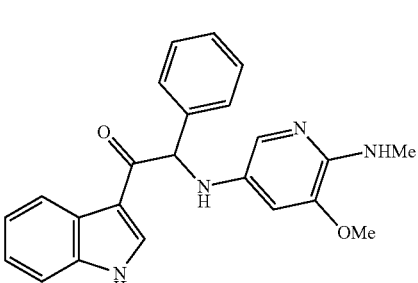 |
| CPD-262 | 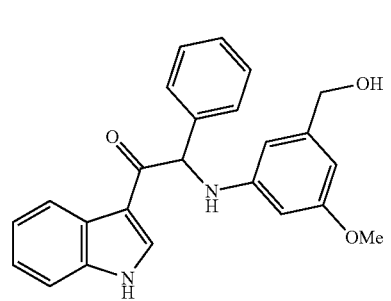 [SMILES: COc1cc(CO)cc(NC(C(=O)c2c[nH]c3ccccc23)c2ccccc2)c1] |

TABLE 1-continued
Structures of example compounds of the invention and their respective codes.
| Code | Structure |
| --- | --- |
| CPD-263 | 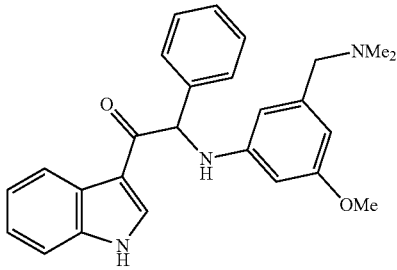 [SMILES: COc1cc(CN(C)C)cc(NC(C(=O)c2c[nH]c3ccccc23)c2ccccc2)c1] |
| CPD-264 | 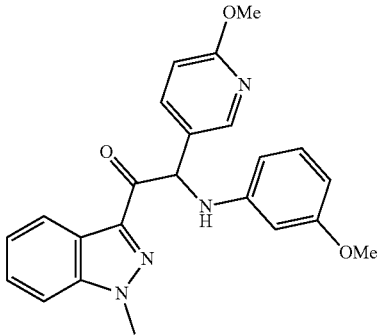 [SMILES: COc1cccc(NC(C(=O)c2nn(C)c3ccccc23)c2ccc(OC)nc2)c1] |
| CPD-265 | 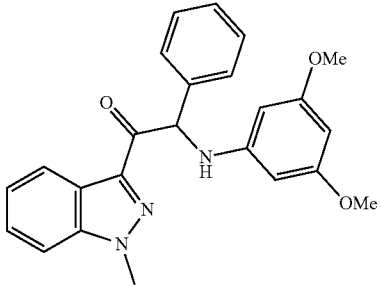 [SMILES: COc1cc(NC(C(=O)c2nn(C)c3ccccc23)c2ccccc2)cc(OC)c1] |
| CPD-266 | 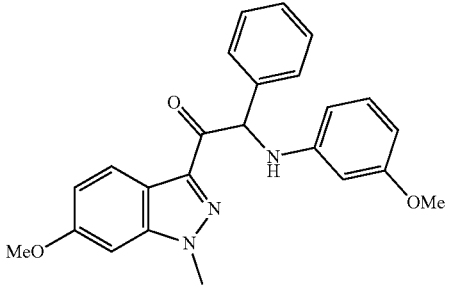 [SMILES: COc1cccc(NC(C(=O)c2nn(C)c3cc(OC)ccc23)c2ccccc2)c1] |
| CPD-267 | 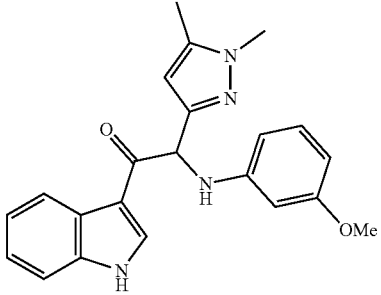 [SMILES: COc1cccc(NC(C(=O)c2c[nH]c3ccccc23)c2cc(C)n(C)n2)c1] |

TABLE 1-continued
Structures of example compounds of the invention and their respective codes.
| Code | Structure |
| --- | --- |
| CPD-268 | 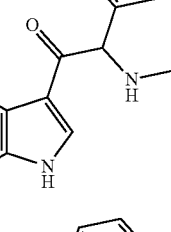 |
| CPD-269 | 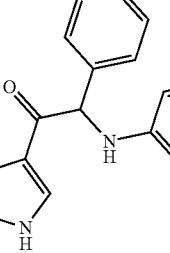 |
| CPD-270 | 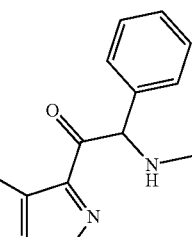 |
| CPD-271 | 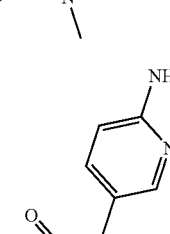 |
| CPD-272 | 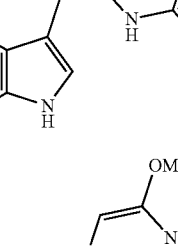 |

TABLE 1-continued
Structures of example compounds of the invention and their respective codes.
| Code | Structure |
|---|---|
| CPD-273 | 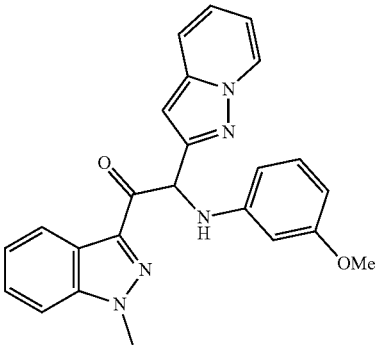 [SMILES: COc1cccc(NC(C(=O)c2nn(C)c3ccccc23)c2cc3ccccn3n2)c1] |
| CPD-274 | 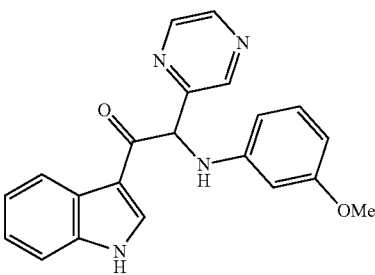 [SMILES: COc1cccc(NC(C(=O)c2c[nH]c3ccccc23)c2cnccn2)c1] |
| CPD-275 | 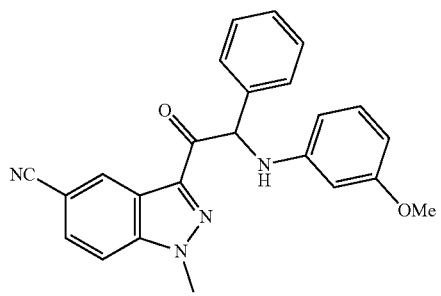 [SMILES: COc1cccc(NC(C(=O)c2nn(C)c3ccc(C#N)cc23)c2ccccc2)c1] |
| CPD-276 | 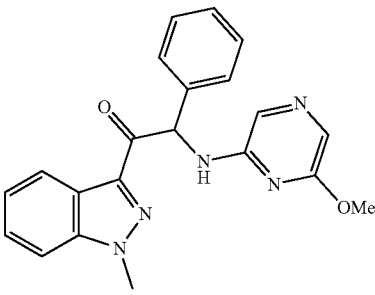 [SMILES: COc1cncc(NC(C(=O)c2nn(C)c3ccccc23)c2ccccc2)n1] |
| CPD-277 | 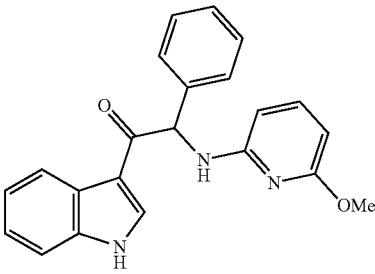 [SMILES: COc1cccc(NC(C(=O)c2c[nH]c3ccccc23)c2ccccc2)n1] |

TABLE 1-continued
Structures of example compounds of the invention and their respective codes.
| Code | Structure |
| --- | --- |
| CPD-278 | 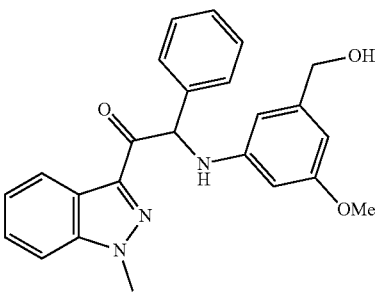 [SMILES: COc1cc(CO)cc(NC(C(=O)c2nn(C)c3ccccc23)c2ccccc2)c1] |
| CPD-279 | 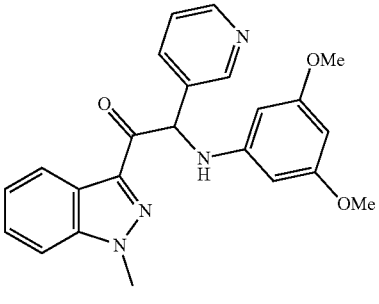 [SMILES: COc1cc(NC(C(=O)c2nn(C)c3ccccc23)c2cccnc2)cc(OC)c1] |
| CPD-280 | 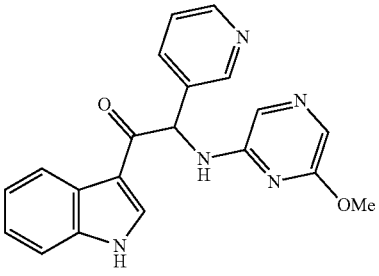 [SMILES: COc1cncc(NC(C(=O)c2c[nH]c3ccccc23)c2cccnc2)n1] |
| CPD-281 | 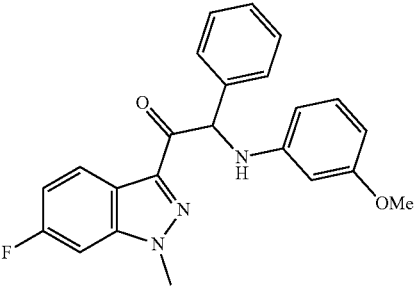 [SMILES: COc1cccc(NC(C(=O)c2nn(C)c3cc(F)ccc23)c2ccccc2)c1] |
| CPD-282 | 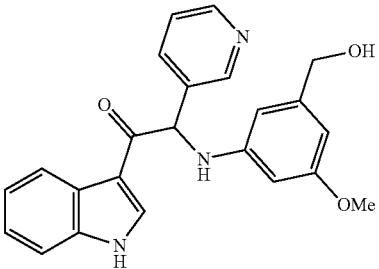 [SMILES: COc1cc(CO)cc(NC(C(=O)c2c[nH]c3ccccc23)c2cccnc2)c1] |

TABLE 1-continued
Structures of example compounds of the invention and their respective codes.
| Code | Structure |
|---|---|
| CPD-283 | 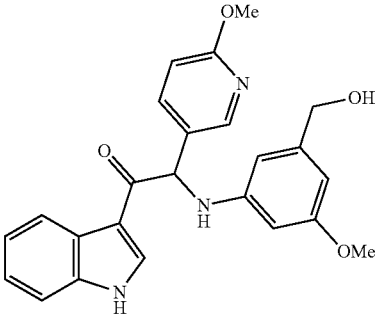 [SMILES: COc1cc(CO)cc(NC(C(=O)c2c[nH]c3ccccc23)c2ccc(OC)nc2)c1] |
| CPD-284 | 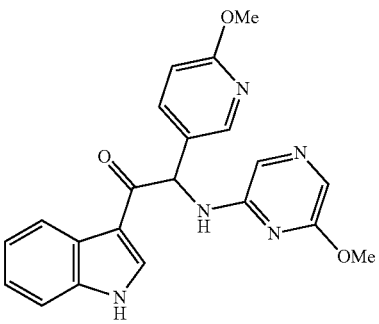 [SMILES: COc1ccc(C(Nc2cncc(OC)n2)C(=O)c2c[nH]c3ccccc23)cn1] |
| CPD-285 | 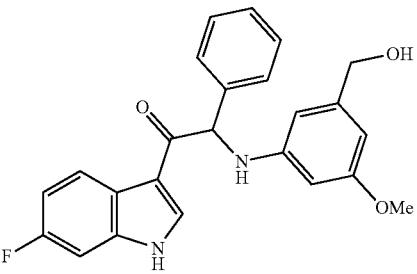 [SMILES: COc1cc(CO)cc(NC(C(=O)c2c[nH]c3cc(F)ccc23)c2ccccc2)c1] |
| CPD-286 | 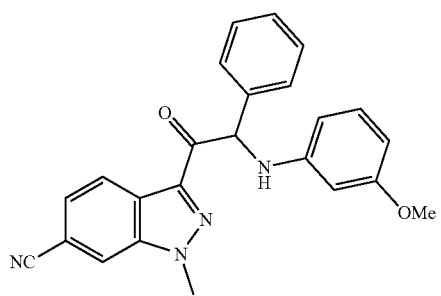 [SMILES: COc1cccc(NC(C(=O)c2nn(C)c3cc(C#N)ccc23)c2ccccc2)c1] |
| CPD-287 | 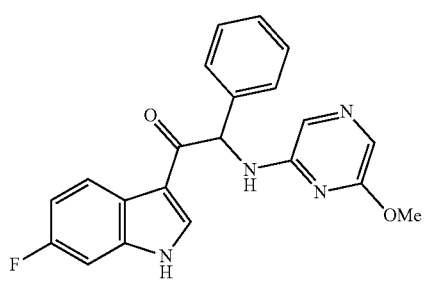 [SMILES: COc1cncc(NC(C(=O)c2c[nH]c3cc(F)ccc23)c2ccccc2)n1] |

TABLE 1-continued
Structures of example compounds of the invention and their respective codes.
| Code | Structure |
|---|---|
| CPD-288 | 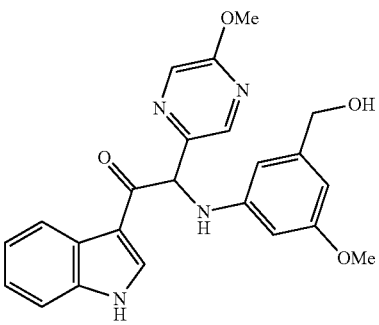 [SMILES: COc1cc(CO)cc(NC(C(=O)c2c[nH]c3ccccc23)c2cnc(OC)cn2)c1] |
| CPD-289 | 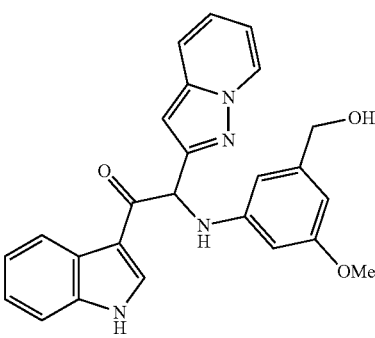 [SMILES: COc1cc(CO)cc(NC(C(=O)c2c[nH]c3ccccc23)c2cc3ccccn3n2)c1] |
| CPD-290 | 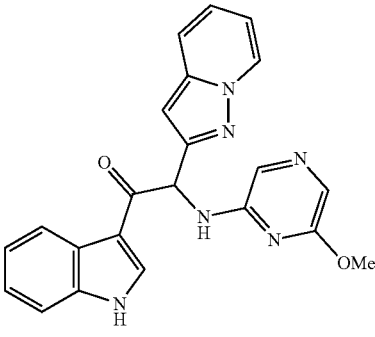 [SMILES: COc1cncc(NC(C(=O)c2c[nH]c3ccccc23)c2cc3ccccn3n2)n1] |
| CPD-291 | 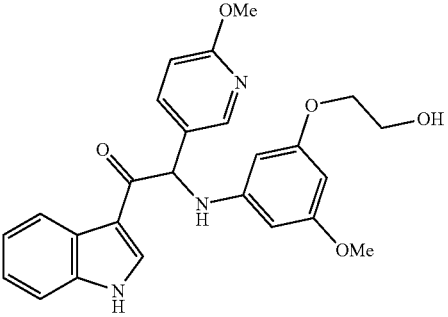 [SMILES: COc1cc(NC(C(=O)c2c[nH]c3ccccc23)c2ccc(OC)nc2)cc(OCCO)c1] |

TABLE 1-continued

Structures of example compounds of the invention and their respective codes.

| Code | Structure |
|---|---|
| CPD-292 | 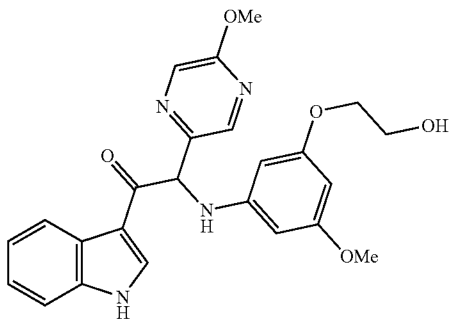 [SMILES: COc1cc(NC(C(=O)c2c[nH]c3ccccc23)c2cnc(OC)cn2)cc(OCCO)c1] |
| CPD-293 | 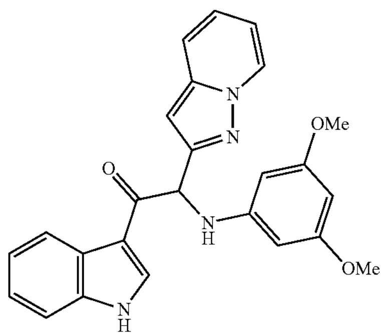 [SMILES: COc1cc(NC(C(=O)c2c[nH]c3ccccc23)c2cc3ccccn3n2)cc(OC)c1] |
| CPD-294 | 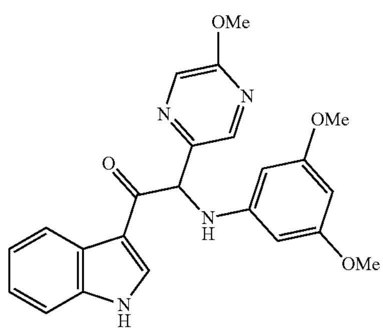 [SMILES: COc1cc(NC(C(=O)c2c[nH]c3ccccc23)c2cnc(OC)cn2)cc(OC)c1] |
| CPD-295 | 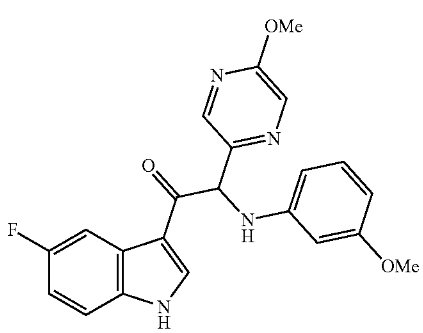 [SMILES: COc1cccc(NC(C(=O)c2c[nH]c3ccc(F)cc23)c2cnc(OC)cn2)c1] |

TABLE 1-continued

Structures of example compounds of the invention and their respective codes.

| Code | Structure |
| --- | --- |
| CPD-296 | (5-fluoro-1H-indol-3-yl)-C(=O)-CH(Ph)-NH-(3-methoxy-5-(hydroxymethyl)phenyl) |
| CPD-297 | (6-fluoro-1H-indol-3-yl)-C(=O)-CH(5-methoxypyrazin-2-yl)-NH-(3-methoxyphenyl) |
| CPD-298 | (1-methyl-1H-indazol-3-yl)-C(=O)-CH(Ph)-NH-(3-methoxy-5-(2-hydroxyethoxy)phenyl) |
| CPD-299 | (1H-indol-3-yl)-C(=O)-CH(Ph)-NH-(5-methoxypyridin-3-yl); enantiomer 1, $t_r$ = 6.7 min |
| CPD-300 | (1H-indol-3-yl)-C(=O)-CH(Ph)-NH-(5-methoxypyridin-3-yl); enantiomer 2 |

TABLE 1-continued
Structures of example compounds of the invention and their respective codes.
| Code | Structure |
|---|---|
| | $t_r$ = 12.1 min |
| CPD-301 | 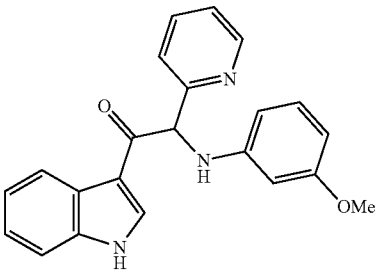 [SMILES: COc1cccc(NC(C(=O)c2c[nH]c3ccccc23)c2ccccn2)c1] |
| CPD-302 | 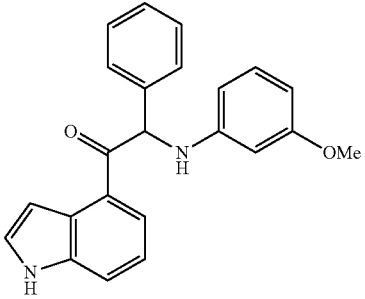 [SMILES: COc1cccc(NC(C(=O)c2cccc3[nH]ccc23)c2ccccc2)c1] |
| CPD-303 | 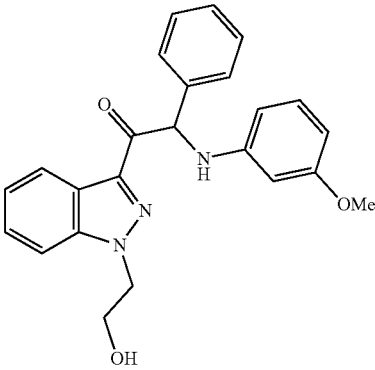 [SMILES: COc1cccc(NC(C(=O)c2nn(CCO)c3ccccc23)c2ccccc2)c1] |
| CPD-304 | 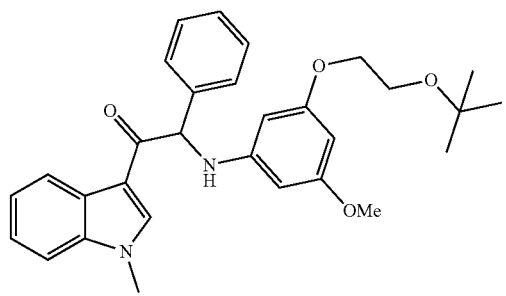 [SMILES: COc1cc(NC(C(=O)c2cn(C)c3ccccc23)c2ccccc2)cc(OCCOC(C)(C)C)c1] |

TABLE 1-continued
Structures of example compounds of the invention and their respective codes.
| Code | Structure |
|---|---|
| CPD-305 | 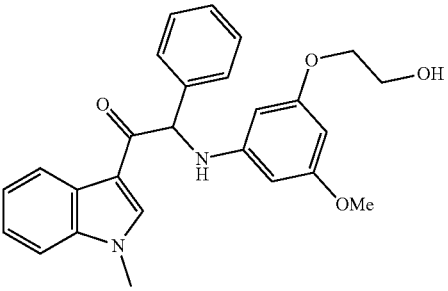 [SMILES: COc1cc(NC(C(=O)c2cn(C)c3ccccc23)c2ccccc2)cc(OCCO)c1] |
| CPD-306 | 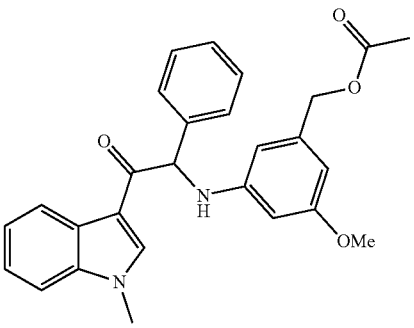 [SMILES: COc1cc(COC(C)=O)cc(NC(C(=O)c2cn(C)c3ccccc23)c2ccccc2)c1] |
| CPD-307 | 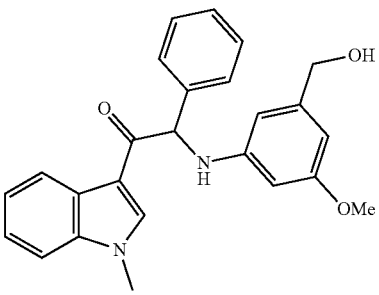 [SMILES: COc1cc(CO)cc(NC(C(=O)c2cn(C)c3ccccc23)c2ccccc2)c1] |
| CPD-308 | 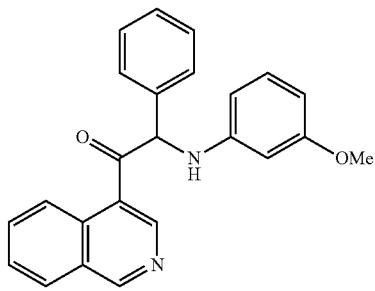 [SMILES: COc1cccc(NC(C(=O)c2cncc3ccccc23)c2ccccc2)c1] |
| CPD-309 | 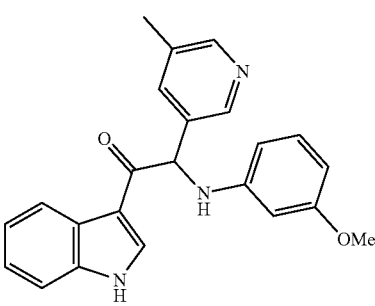 [SMILES: COc1cccc(NC(C(=O)c2c[nH]c3ccccc23)c2cncc(C)c2)c1] |

TABLE 1-continued
Structures of example compounds of the invention and their respective codes.
| Code | Structure |
| --- | --- |
| CPD-310 | 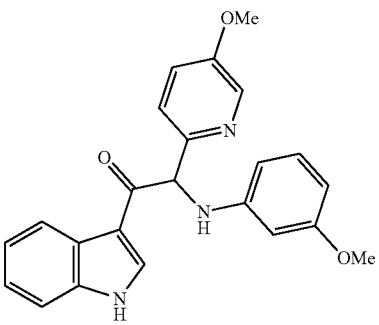 [SMILES: COc1ccc(C(Nc2cccc(OC)c2)C(=O)c2c[nH]c3ccccc23)nc1] |
| CPD-311 | 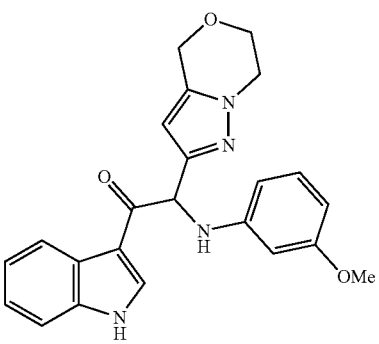 [SMILES: COc1cccc(NC(C(=O)c2c[nH]c3ccccc23)c2cc3n(n2)CCOC3)c1] |
| CPD-312 | 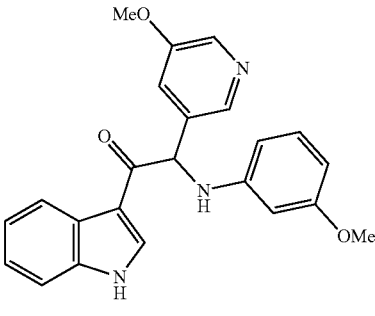 [SMILES: COc1cccc(NC(C(=O)c2c[nH]c3ccccc23)c2cncc(OC)c2)c1] |
| CPD-313 | 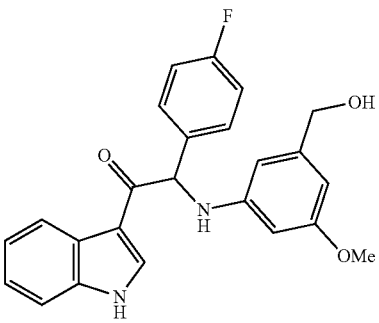 [SMILES: COc1cc(CO)cc(NC(C(=O)c2c[nH]c3ccccc23)c2ccc(F)cc2)c1] |

TABLE 1-continued
Structures of example compounds of the invention and their respective codes.
| Code | Structure |
| --- | --- |
| CPD-314 | 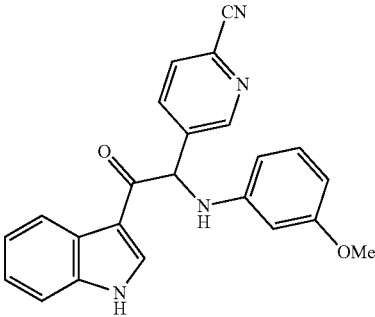 [SMILES: COc1cccc(NC(C(=O)c2c[nH]c3ccccc23)c2ccc(C#N)nc2)c1] |
| CPD-315 | 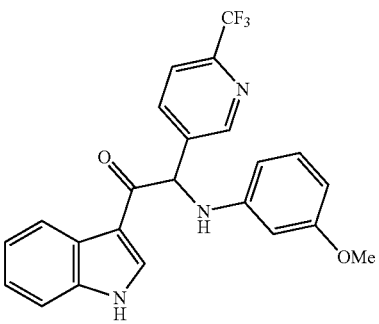 [SMILES: COc1cccc(NC(C(=O)c2c[nH]c3ccccc23)c2ccc(C(F)(F)F)nc2)c1] |
| CPD-316 | 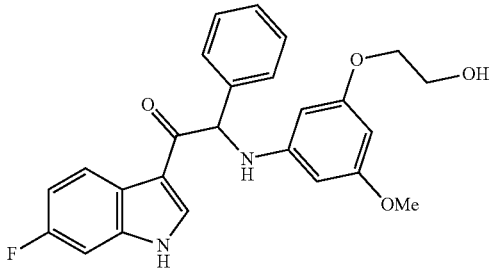 [SMILES: COc1cc(NC(C(=O)c2c[nH]c3cc(F)ccc23)c2ccccc2)cc(OCCO)c1] |
| CPD-317 | 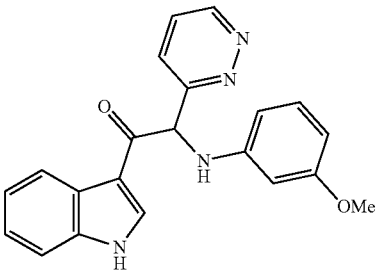 [SMILES: COc1cccc(NC(C(=O)c2c[nH]c3ccccc23)c2cccnn2)c1] |
| CPD-318 | 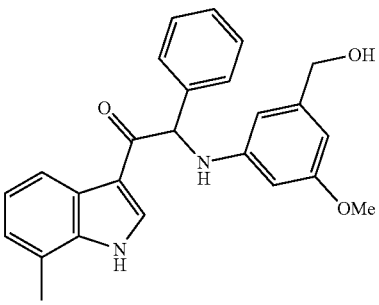 [SMILES: COc1cc(CO)cc(NC(C(=O)c2c[nH]c3c(C)cccc23)c2ccccc2)c1] |

TABLE 1-continued

Structures of example compounds of the invention and their respective codes.

| Code | Structure |
| --- | --- |
| CPD-319 | 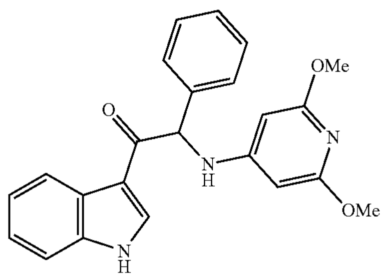 [SMILES: COc1cc(NC(C(=O)c2c[nH]c3ccccc23)c2ccccc2)cc(OC)n1] |
| CPD-320 | 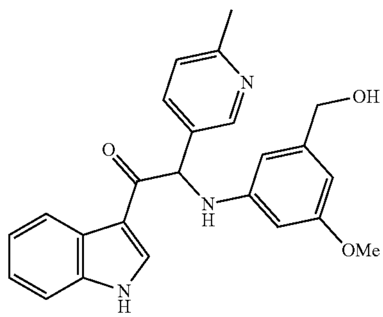 [SMILES: COc1cc(CO)cc(NC(C(=O)c2c[nH]c3ccccc23)c2ccc(C)nc2)c1] |
| CPD-321 | 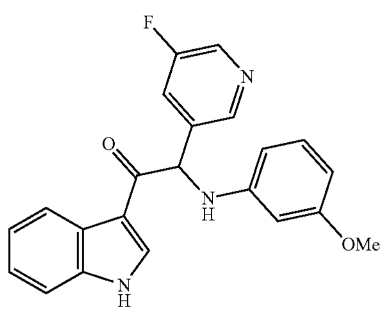 [SMILES: COc1cccc(NC(C(=O)c2c[nH]c3ccccc23)c2cncc(F)c2)c1] |
| CPD-322 | | enantiomer 1

$t_r$ = 9.7 min

TABLE 1-continued
Structures of example compounds of the invention and their respective codes.
| Code | Structure |
|---|---|
| CPD-323 | 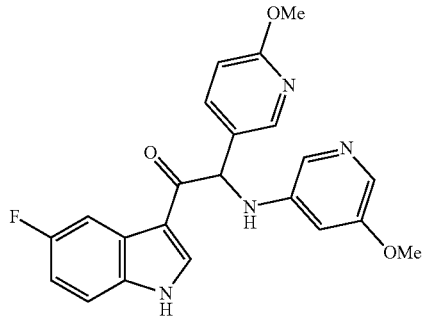 [SMILES: COc1cncc(NC(C(=O)c2c[nH]c3ccc(F)cc23)c2ccc(OC)nc2)c1]<br>enantiomer 2<br>$t_r$ = 12.5 min |
| CPD-324 | 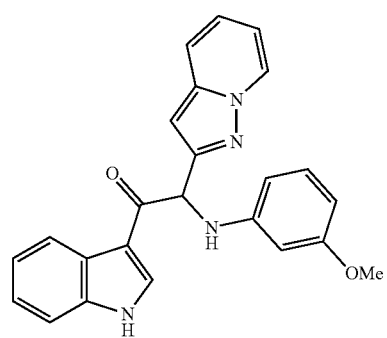 [SMILES: COc1cccc(NC(C(=O)c2c[nH]c3ccccc23)c2cc3ccccn3n2)c1]<br>enantiomer 1<br>$t_r$ = 9.3 min |
| CPD-325 | 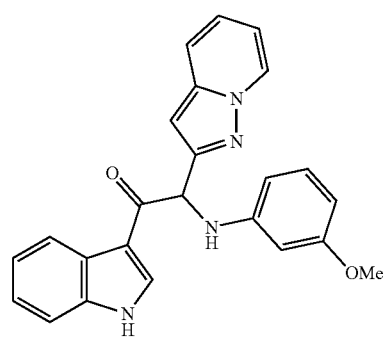 [SMILES: COc1cccc(NC(C(=O)c2c[nH]c3ccccc23)c2cc3ccccn3n2)c1]<br>enantiomer 2<br>$t_r$ = 12.9 min |
| CPD-326 | 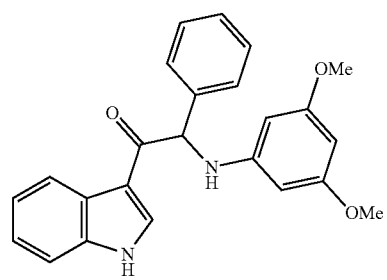 [SMILES: COc1cc(NC(C(=O)c2c[nH]c3ccccc23)c2ccccc2)cc(OC)c1]<br>enantiomer 1<br>$t_r$ = 8.1 min |

TABLE 1-continued
Structures of example compounds of the invention and their respective codes.
| Code | Structure |
|---|---|
| CPD-327 | 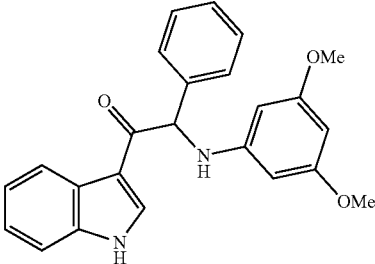 [SMILES: COc1cc(NC(C(=O)c2c[nH]c3ccccc23)c2ccccc2)cc(OC)c1]<br>enantiomer 2<br>$t_r$ = 17.9 min |
| CPD-328 | 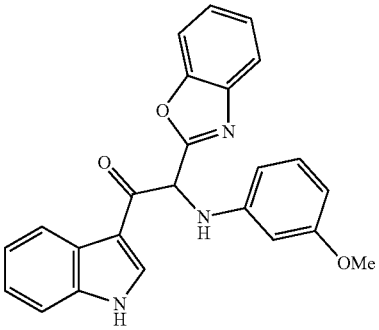 [SMILES: COc1cccc(NC(C(=O)c2c[nH]c3ccccc23)c2nc3ccccc3o2)c1] |
| CPD-329 | 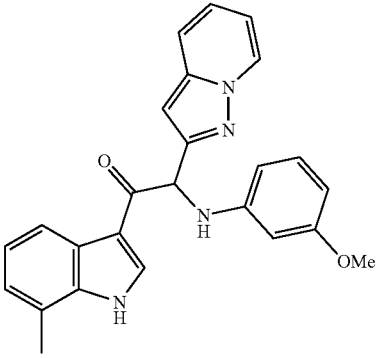 [SMILES: COc1cccc(NC(C(=O)c2c[nH]c3c(C)cccc23)c2cc3ccccn3n2)c1] |
| CPD-330 | 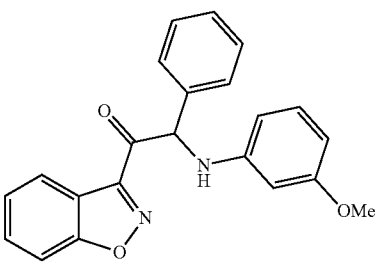 [SMILES: COc1cccc(NC(C(=O)c2noc3ccccc23)c2ccccc2)c1] |

TABLE 1-continued

Structures of example compounds of the invention and their respective codes.

| Code | Structure |
| --- | --- |
| CPD-331 | 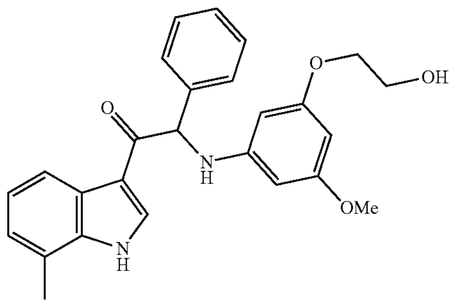 [SMILES: COc1cc(NC(C(=O)c2c[nH]c3c(C)cccc23)c2ccccc2)cc(OCCO)c1] |
| CPD-332 | 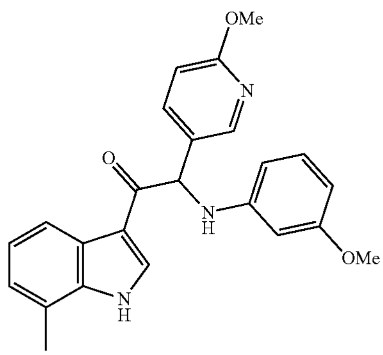 [SMILES: COc1cccc(NC(C(=O)c2c[nH]c3c(C)cccc23)c2ccc(OC)nc2)c1] |
| CPD-333 | 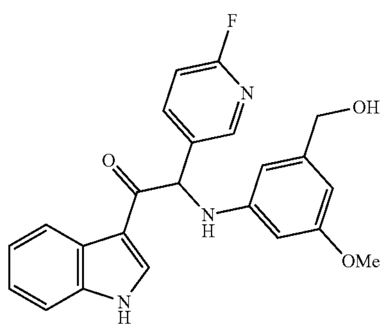 [SMILES: COc1cc(CO)cc(NC(C(=O)c2c[nH]c3ccccc23)c2ccc(F)nc2)c1] |
| CPD-334 | 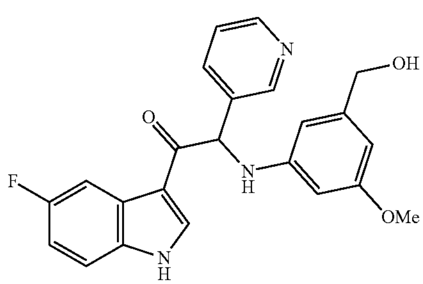 [SMILES: COc1cc(CO)cc(NC(C(=O)c2c[nH]c3ccc(F)cc23)c2cccnc2)c1] |

TABLE 1-continued
Structures of example compounds of the invention and their respective codes.
| Code | Structure |
|---|---|
| CPD-335 | 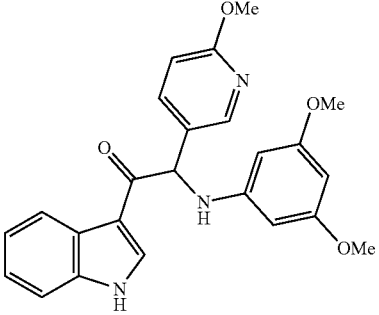 [SMILES: COc1cc(NC(C(=O)c2c[nH]c3ccccc23)c2ccc(OC)nc2)cc(OC)c1] |
| CPD-336 | 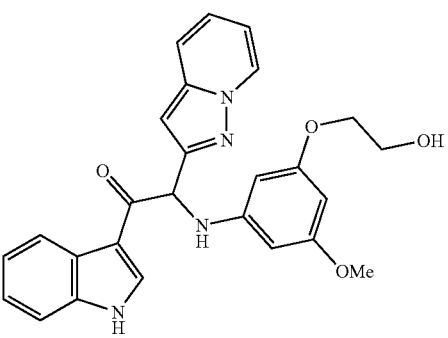 [SMILES: COc1cc(NC(C(=O)c2c[nH]c3ccccc23)c2cc3ccccn3n2)cc(OCCO)c1] |
| CPD-337 | 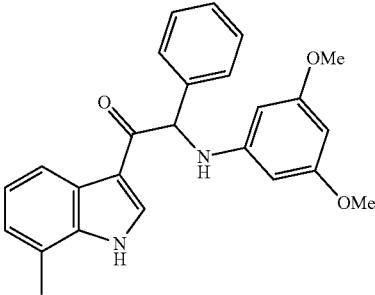 [SMILES: COc1cc(NC(C(=O)c2c[nH]c3c(C)cccc23)c2ccccc2)cc(OC)c1] |
| CPD-338 | 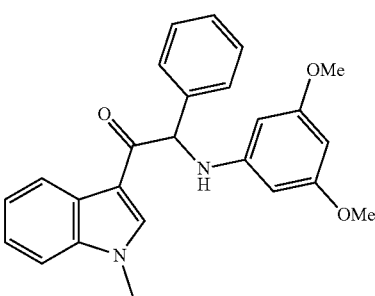 |

TABLE 1-continued

Structures of example compounds of the invention and their respective codes.

| Code | Structure |
|---|---|
| CPD-339 | 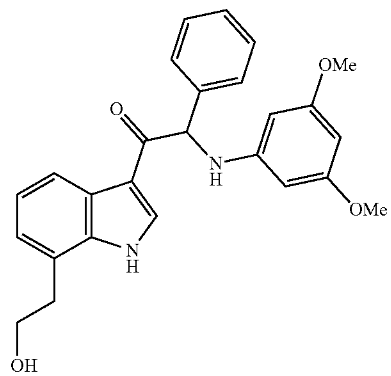 [SMILES: COc1cc(NC(C(=O)c2c[nH]c3c(CCO)cccc23)c2ccccc2)cc(OC)c1] |
| CPD-340 | 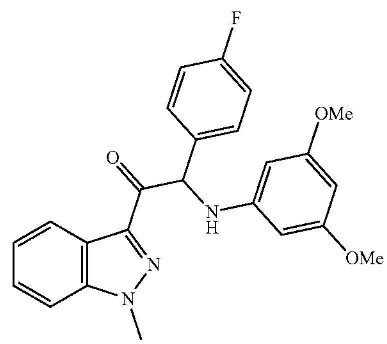 [SMILES: COc1cc(NC(C(=O)c2nn(C)c3ccccc23)c2ccc(F)cc2)cc(OC)c1] |
| CPD-341 | 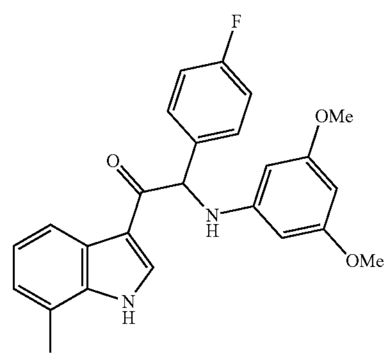 [SMILES: COc1cc(NC(C(=O)c2c[nH]c3c(C)cccc23)c2ccc(F)cc2)cc(OC)c1] |
| CPD-342 | 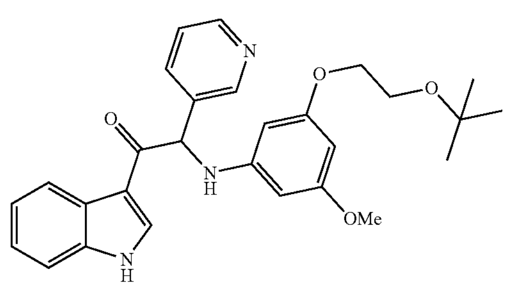 [SMILES: COc1cc(NC(C(=O)c2c[nH]c3ccccc23)c2cccnc2)cc(OCCOC(C)(C)C)c1] |

TABLE 1-continued
Structures of example compounds of the invention and their respective codes.
| Code | Structure |
|---|---|
| CPD-343 | 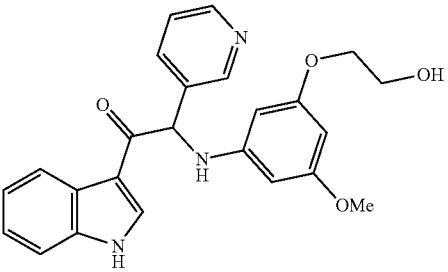 [SMILES: COc1cc(NC(C(=O)c2c[nH]c3ccccc23)c2cccnc2)cc(OCCO)c1] |
| CPD-344 | 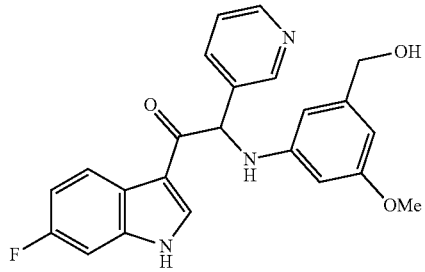 [SMILES: COc1cc(CO)cc(NC(C(=O)c2c[nH]c3cc(F)ccc23)c2cccnc2)c1] |
| CPD-345 | 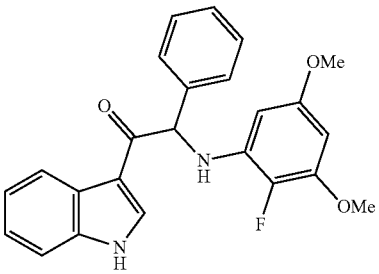 [SMILES: COc1cc(NC(C(=O)c2c[nH]c3ccccc23)c2ccccc2)c(F)c(OC)c1] |
| CPD-346 | 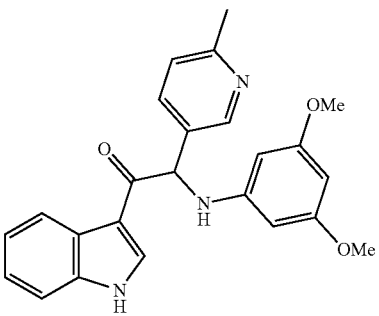 [SMILES: COc1cc(NC(C(=O)c2c[nH]c3ccccc23)c2ccc(C)nc2)cc(OC)c1] |
| CPD-347 | 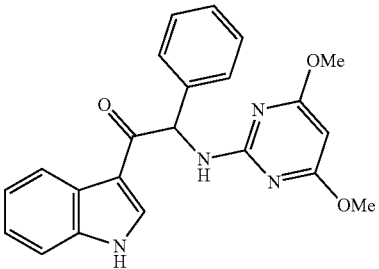 [SMILES: COc1cc(OC)nc(NC(C(=O)c2c[nH]c3ccccc23)c2ccccc2)n1] |

TABLE 1-continued
Structures of example compounds of the invention and their respective codes.
| Code | Structure |
|---|---|
| CPD-348 | 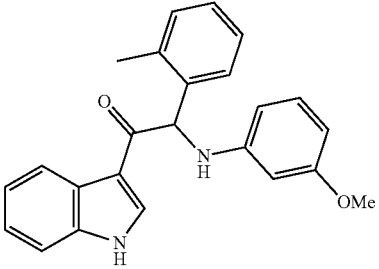 [SMILES: COc1cccc(NC(C(=O)c2c[nH]c3ccccc23)c2ccccc2C)c1] |
| CPD-349 | 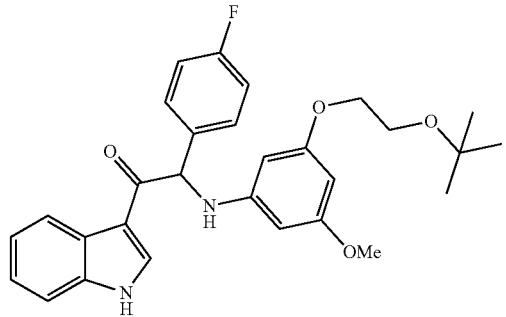 [SMILES: COc1cc(NC(C(=O)c2c[nH]c3ccccc23)c2ccc(F)cc2)cc(OCCOC(C)(C)C)c1] |
| CPD-350 | 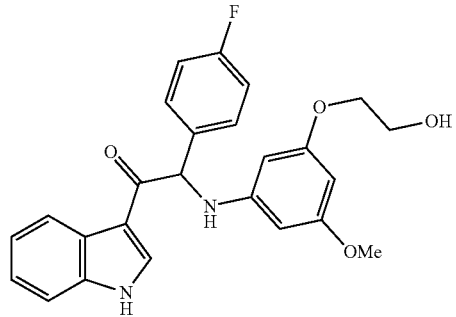 [SMILES: COc1cc(NC(C(=O)c2c[nH]c3ccccc23)c2ccc(F)cc2)cc(OCCO)c1] |
| CPD-351 | 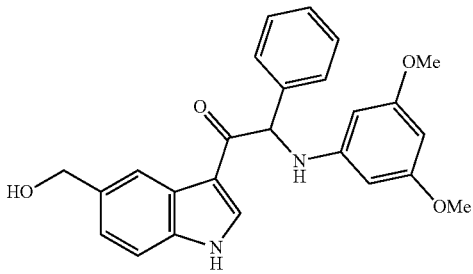 [SMILES: COc1cc(NC(C(=O)c2c[nH]c3ccc(CO)cc23)c2ccccc2)cc(OC)c1] |
| CPD-352 | 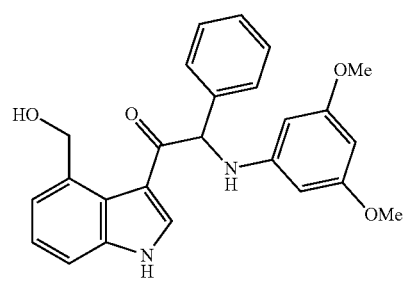 [SMILES: COc1cc(NC(C(=O)c2c[nH]c3cccc(CO)c23)c2ccccc2)cc(OC)c1] |

TABLE 1-continued
Structures of example compounds of the invention and their respective codes.
| Code | Structure |
|---|---|
| CPD-353 | 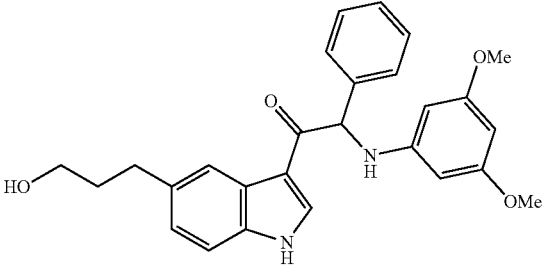 [SMILES: COc1cc(NC(C(=O)c2c[nH]c3ccc(CCCO)cc23)c2ccccc2)cc(OC)c1] |
| CPD-354 | 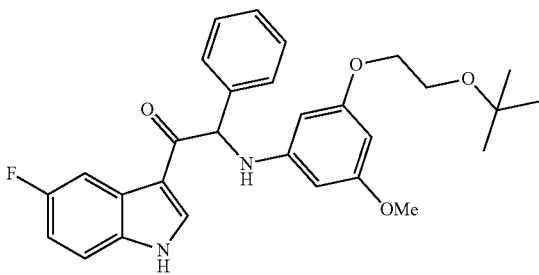 [SMILES: COc1cc(NC(C(=O)c2c[nH]c3ccc(F)cc23)c2ccccc2)cc(OCCOC(C)(C)C)c1] |
| CPD-355 | 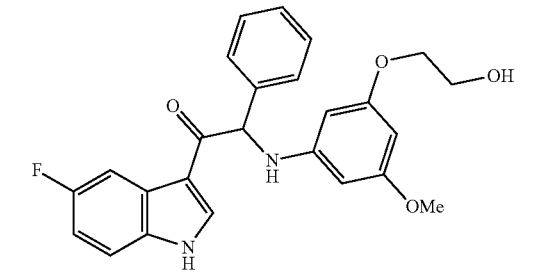 [SMILES: COc1cc(NC(C(=O)c2c[nH]c3ccc(F)cc23)c2ccccc2)cc(OCCO)c1] |
| CPD-356 | 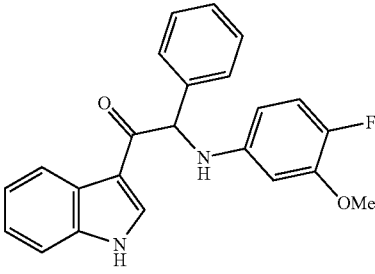 [SMILES: COc1cc(NC(C(=O)c2c[nH]c3ccccc23)c2ccccc2)ccc1F] |
| CPD-357 | 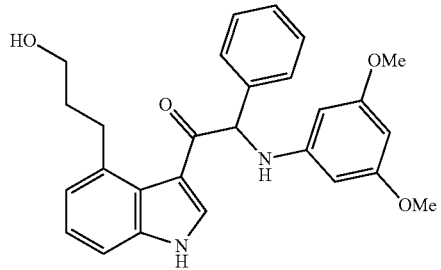 [SMILES: COc1cc(NC(C(=O)c2c[nH]c3cccc(CCCO)c23)c2ccccc2)cc(OC)c1] |

TABLE 1-continued
Structures of example compounds of the invention and their respective codes.
| Code | Structure |
|---|---|
| CPD-358 | 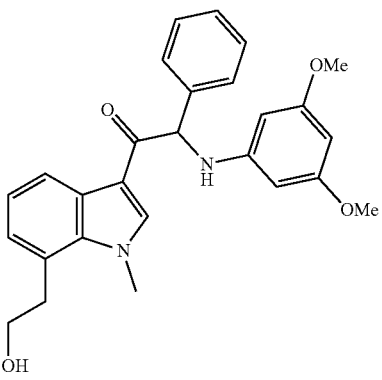 [SMILES: COc1cc(NC(C(=O)c2cn(C)c3c(CCO)cccc23)c2ccccc2)cc(OC)c1] |
| CPD-359 | 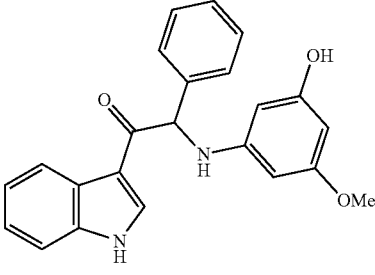 [SMILES: COc1cc(O)cc(NC(C(=O)c2c[nH]c3ccccc23)c2ccccc2)c1] |
| CPD-360 | 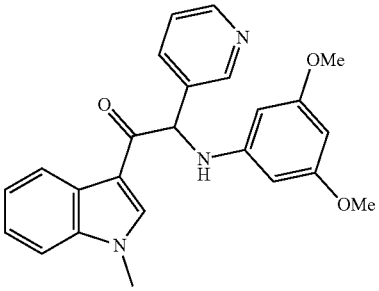 [SMILES: COc1cc(NC(C(=O)c2cn(C)c3ccccc23)c2cccnc2)cc(OC)c1] |
| CPD-361 | 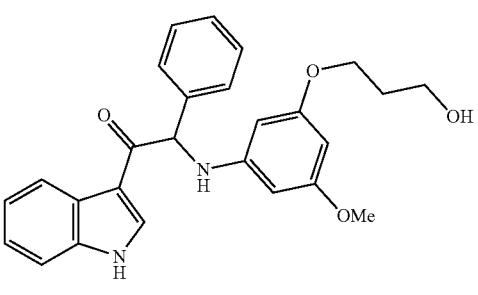 [SMILES: COc1cc(NC(C(=O)c2c[nH]c3ccccc23)c2ccccc2)cc(OCCCO)c1] |
| CPD-362 | 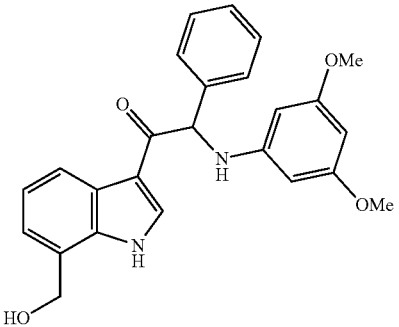 [SMILES: COc1cc(NC(C(=O)c2c[nH]c3c(CO)cccc23)c2ccccc2)cc(OC)c1] |

TABLE 1-continued
Structures of example compounds of the invention and their respective codes.
| Code | Structure |
|---|---|
| CPD-363 | 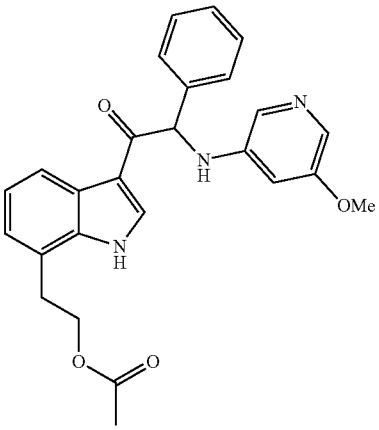 [SMILES: COc1cncc(NC(C(=O)c2c[nH]c3c(CCOC(C)=O)cccc23)c2ccccc2)c1] |
| CPD-364 | 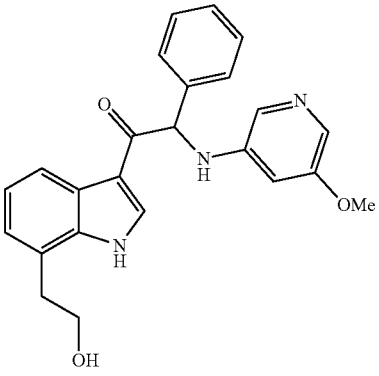 [SMILES: COc1cncc(NC(C(=O)c2c[nH]c3c(CCO)cccc23)c2ccccc2)c1] |
| CPD-365 | 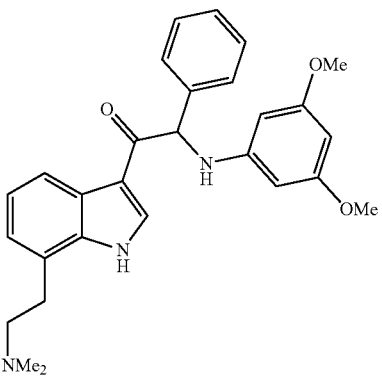 [SMILES: COc1cc(NC(C(=O)c2c[nH]c3c(CCN(C)C)cccc23)c2ccccc2)cc(OC)c1] |
| CPD-366 | 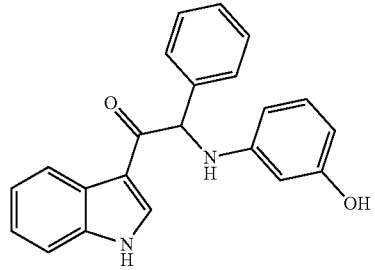 [SMILES: O=C(c1c[nH]c2ccccc12)C(Nc1cccc(O)c1)c1ccccc1] |

TABLE 1-continued
Structures of example compounds of the invention and their respective codes.
| Code | Structure |
| --- | --- |
| CPD-367 | 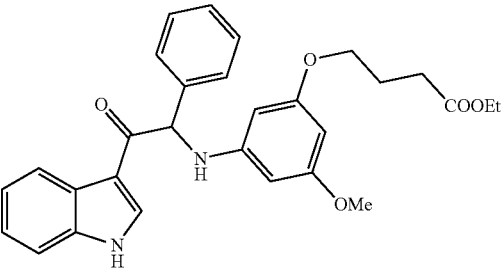 [SMILES: CCOC(=O)CCCOc1cc(NC(C(=O)c2c[nH]c3ccccc23)c2ccccc2)cc(OC)c1] |
| CPD-368 | 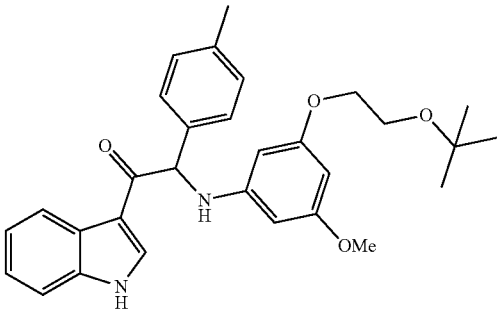 [SMILES: COc1cc(NC(C(=O)c2c[nH]c3ccccc23)c2ccc(C)cc2)cc(OCCOC(C)(C)C)c1] |
| CPD-369 | 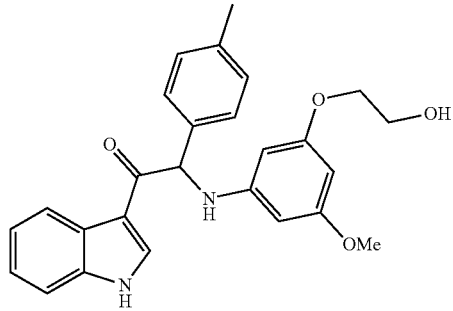 [SMILES: COc1cc(NC(C(=O)c2c[nH]c3ccccc23)c2ccc(C)cc2)cc(OCCO)c1] |
| CPD-370 | 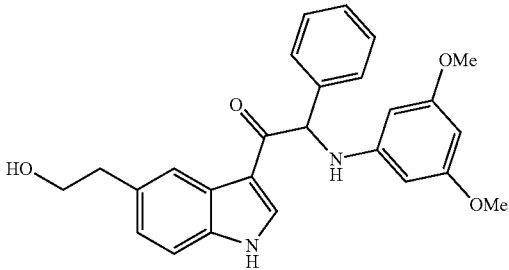 [SMILES: COc1cc(NC(C(=O)c2c[nH]c3ccc(CCO)cc23)c2ccccc2)cc(OC)c1] |

TABLE 1-continued

Structures of example compounds of the invention and their respective codes.

| Code | Structure |
|------|-----------|
| CPD-371 | 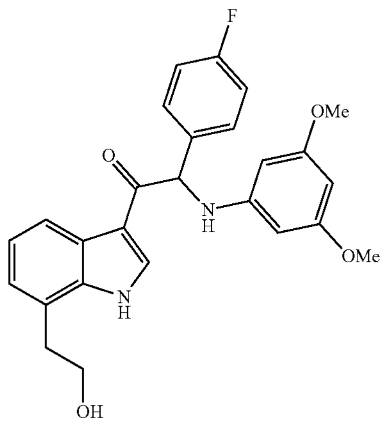 [SMILES: COc1cc(NC(C(=O)c2c[nH]c3c(CCO)cccc23)c2ccc(F)cc2)cc(OC)c1] |
| CPD-372 | 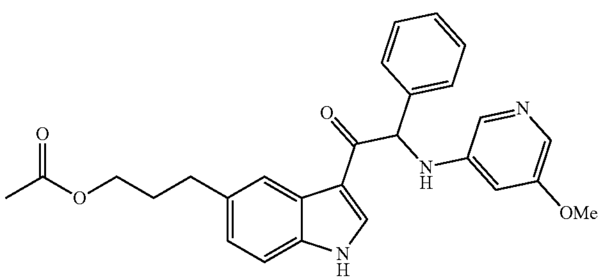 [SMILES: COc1cncc(NC(C(=O)c2c[nH]c3ccc(CCCOC(C)=O)cc23)c2ccccc2)c1] |
| CPD-373 | 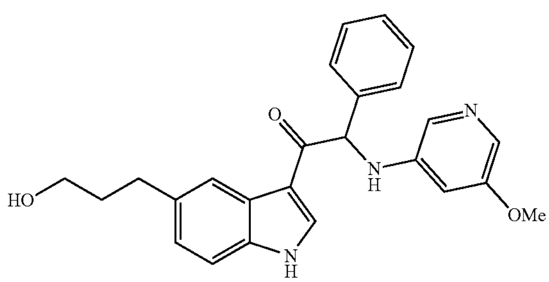 [SMILES: COc1cncc(NC(C(=O)c2c[nH]c3ccc(CCCO)cc23)c2ccccc2)c1] |
| CPD-374 | 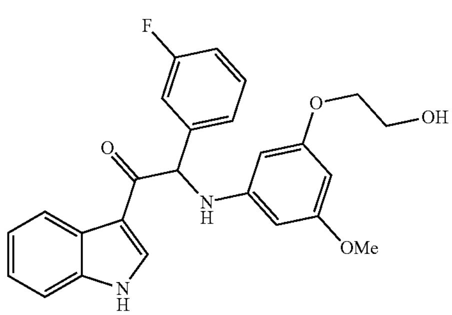 [SMILES: COc1cc(NC(C(=O)c2c[nH]c3ccccc23)c2cccc(F)c2)cc(OCCO)c1] |

TABLE 1-continued

Structures of example compounds of the invention and their respective codes.

| Code | Structure |
| --- | --- |
| CPD-375 | 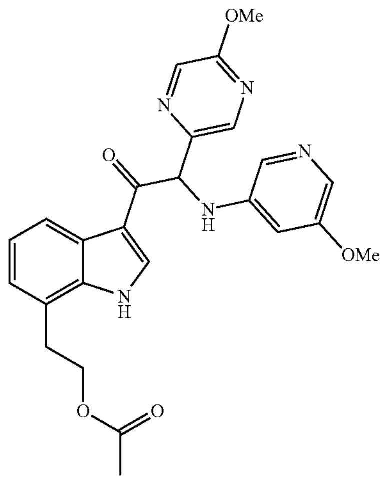 [SMILES: COc1cncc(NC(C(=O)c2c[nH]c3c(CCOC(C)=O)cccc23)c2cnc(OC)cn2)c1] |
| CPD-376 | 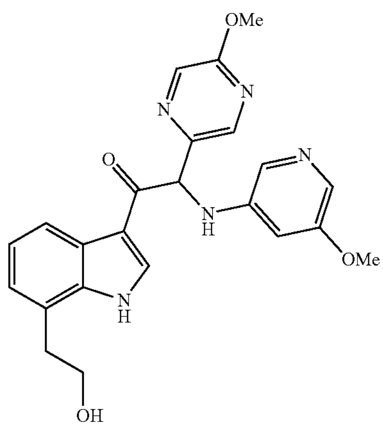 [SMILES: COc1cncc(NC(C(=O)c2c[nH]c3c(CCO)cccc23)c2cnc(OC)cn2)c1] |
| CPD-377 | 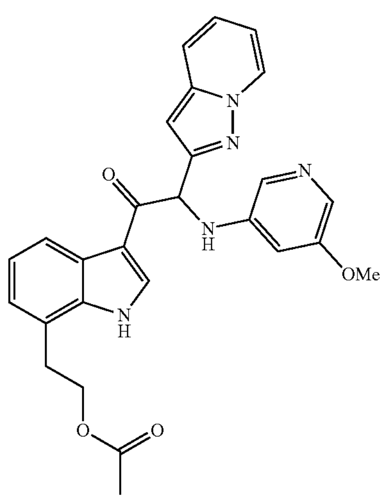 [SMILES: COc1cncc(NC(C(=O)c2c[nH]c3c(CCOC(C)=O)cccc23)c2cc3ccccn3n2)c1] |

285 286
TABLE 1-continued
Structures of example compounds of the invention and their respective codes.
| Code | Structure |
|---|---|
| CPD-378 | 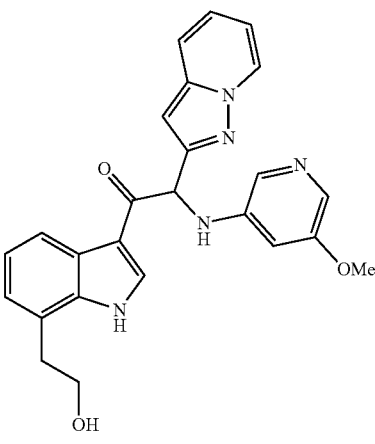 [SMILES: COc1cncc(NC(C(=O)c2c[nH]c3c(CCO)cccc23)c2cc3ccccn3n2)c1] |
| CPD-379 | 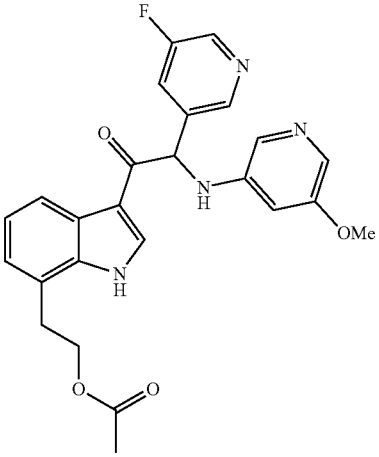 [SMILES: COc1cncc(NC(C(=O)c2c[nH]c3c(CCOC(C)=O)cccc23)c2cncc(F)c2)c1] |
| CPD-380 | 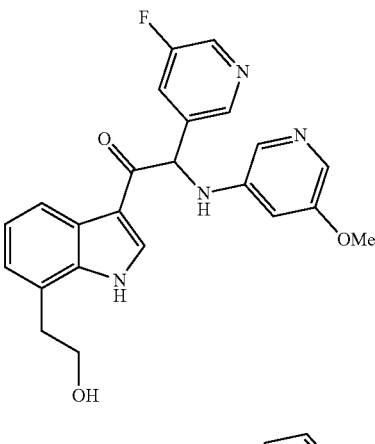 |
| CPD-381 | 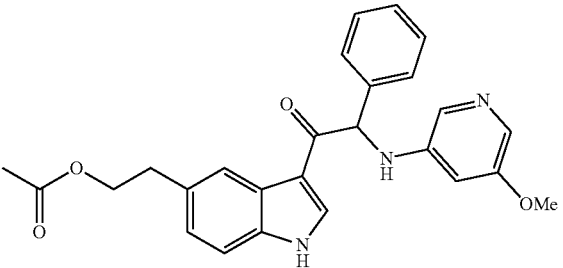 [SMILES: COc1cncc(NC(C(=O)c2c[nH]c3ccc(CCOC(C)=O)cc23)c2ccccc2)c1] |

TABLE 1-continued
Structures of example compounds of the invention and their respective codes.
| Code | Structure |
|---|---|
| CPD-382 | 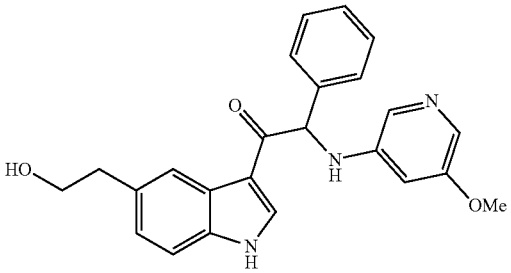 [SMILES: COc1cncc(NC(C(=O)c2c[nH]c3ccc(CCO)cc23)c2ccccc2)c1] |
| CPD-383 | 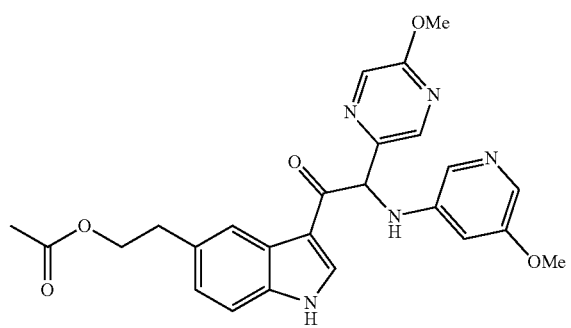 [SMILES: COc1cncc(NC(C(=O)c2c[nH]c3ccc(CCOC(C)=O)cc23)c2cnc(OC)cn2)c1] |
| CPD-384 | 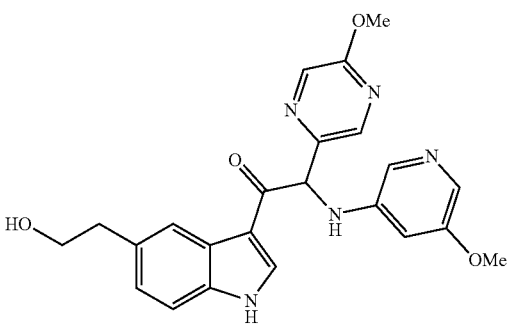 [SMILES: COc1cncc(NC(C(=O)c2c[nH]c3ccc(CCO)cc23)c2cnc(OC)cn2)c1] |
| CPD-385 | 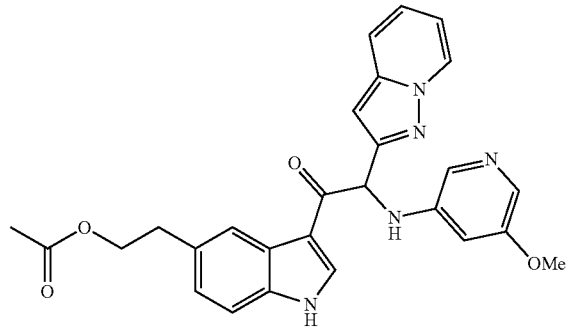 [SMILES: COc1cncc(NC(C(=O)c2c[nH]c3ccc(CCOC(C)=O)cc23)c2cc3ccccn3n2)c1] |

TABLE 1-continued
Structures of example compounds of the invention and their respective codes.
| Code | Structure |
|---|---|
| CPD-386 | 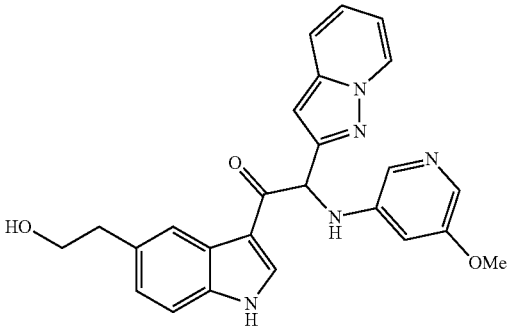 [SMILES: COc1cncc(NC(C(=O)c2c[nH]c3ccc(CCO)cc23)c2cc3ccccn3n2)c1] |
| CPD-387 | 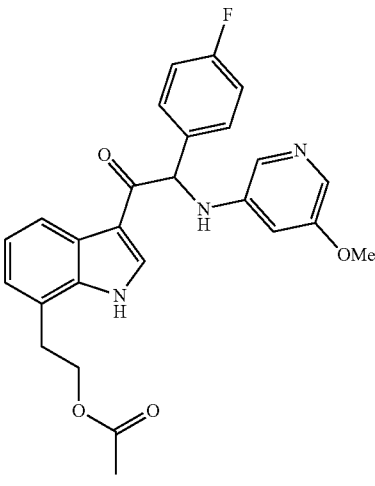 [SMILES: COc1cncc(NC(C(=O)c2c[nH]c3c(CCOC(C)=O)cccc23)c2ccc(F)cc2)c1] |
| CPD-388 | 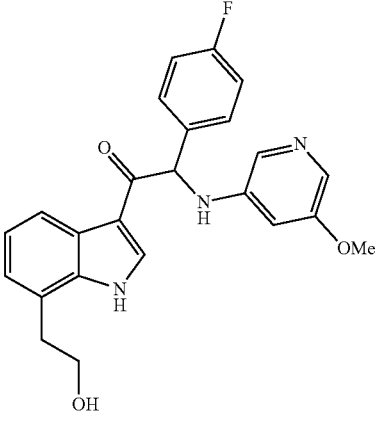 [SMILES: COc1cncc(NC(C(=O)c2c[nH]c3c(CCO)cccc23)c2ccc(F)cc2)c1] |
| CPD-389 | 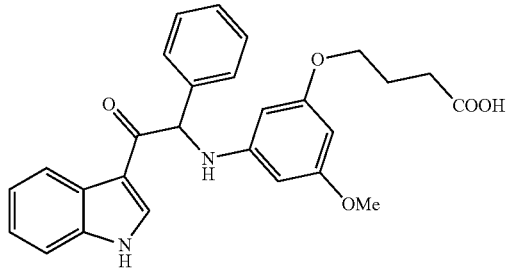 [SMILES: COc1cc(NC(C(=O)c2c[nH]c3ccccc23)c2ccccc2)cc(OCCCC(=O)O)c1] |

TABLE 1-continued
Structures of example compounds of the invention and their respective codes.
| Code | Structure |
|---|---|
| CPD-390 | 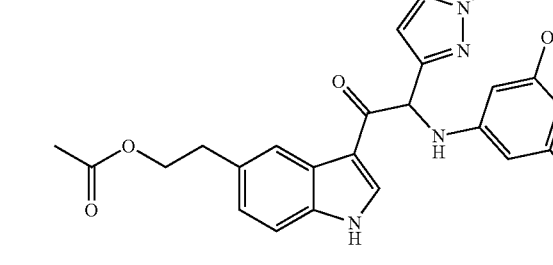 |
| CPD-391 | 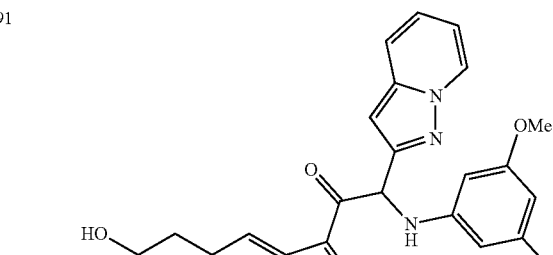 |
| CPD-392 | 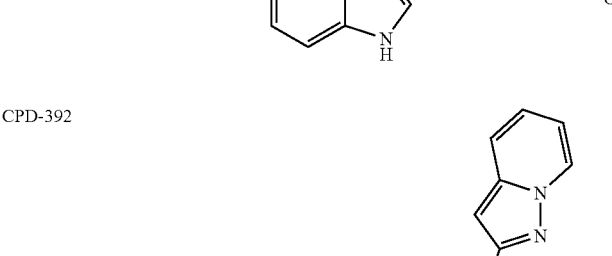 |
| CPD-393 | 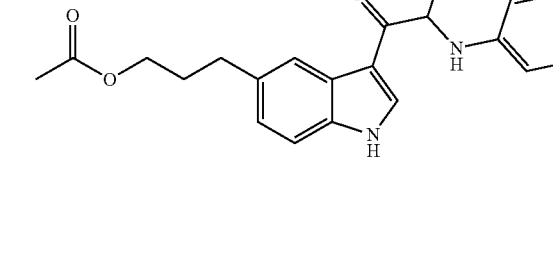 |

TABLE 1-continued
Structures of example compounds of the invention and their respective codes.
| Code | Structure |
|---|---|
| CPD-394 | 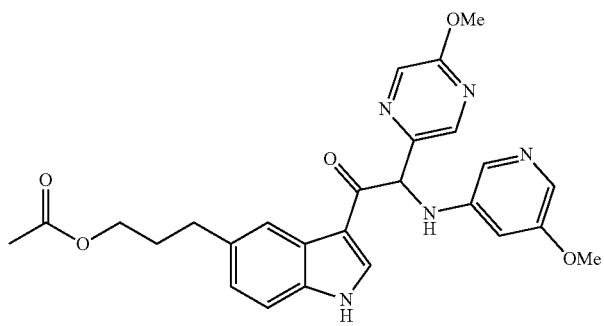 [SMILES: COc1cncc(NC(C(=O)c2c[nH]c3ccc(CCCOC(C)=O)cc23)c2cnc(OC)cn2)c1] |
| CPD-395 | 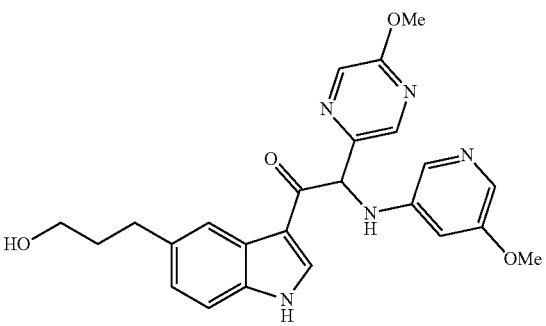 [SMILES: COc1cncc(NC(C(=O)c2c[nH]c3ccc(CCCO)cc23)c2cnc(OC)cn2)c1] |
| CPD-396 | 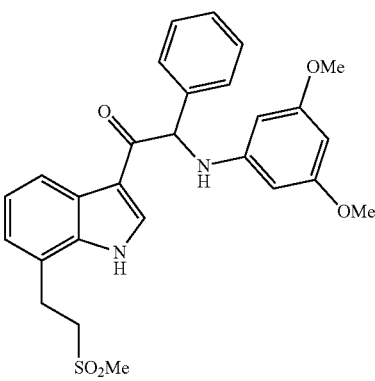 [SMILES: COc1cc(NC(C(=O)c2c[nH]c3c(CCS(C)(=O)=O)cccc23)c2ccccc2)cc(OC)c1] |
| CPD-397 | 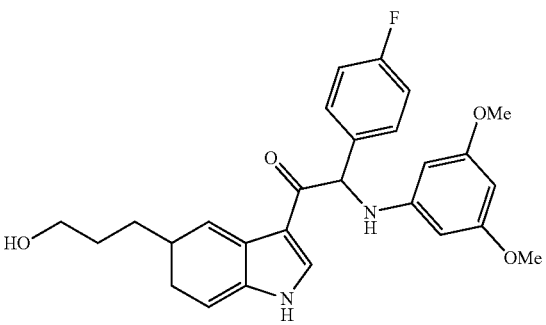 [SMILES: COc1cc(NC(C(=O)c2c[nH]c3c2=CC(CCCO)CC=3)c2ccc(F)cc2)cc(OC)c1] |

TABLE 1-continued
Structures of example compounds of the invention and their respective codes.
| Code | Structure |
|---|---|
| CPD-398 | 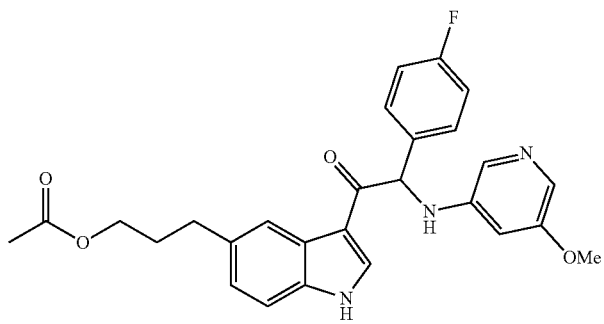 [SMILES: COc1cncc(NC(C(=O)c2c[nH]c3ccc(CCCOC(C)=O)cc23)c2ccc(F)cc2)c1] |
| CPD-399 | 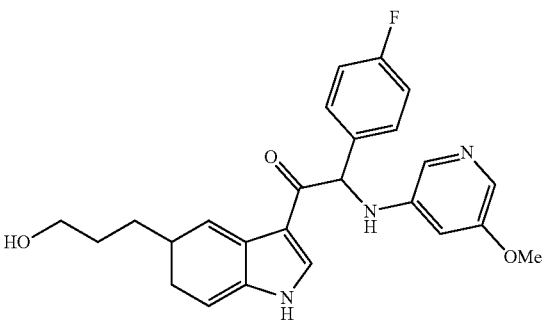 [SMILES: COc1cncc(NC(C(=O)c2c[nH]c3c2=CC(CCCO)CC=3)c2ccc(F)cc2)c1] |
| CPD-400 | 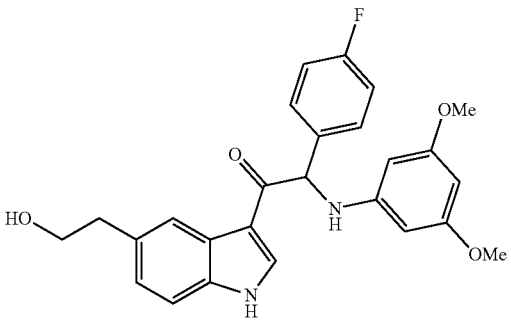 [SMILES: COc1cc(NC(C(=O)c2c[nH]c3ccc(CCO)cc23)c2ccc(F)cc2)cc(OC)c1] |
| CPD-401 | 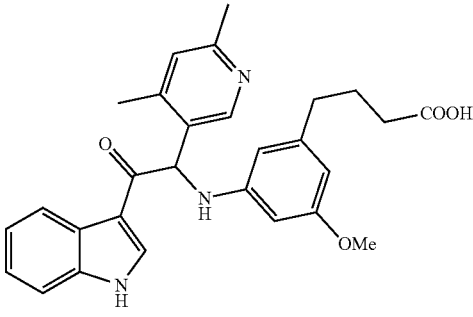 [SMILES: COc1cc(CCCC(=O)O)cc(NC(C(=O)c2c[nH]c3ccccc23)c2cnc(C)cc2C)c1] |

TABLE 1-continued

Structures of example compounds of the invention and their respective codes.

| Code | Structure |
|------|-----------|
| CPD-402 | 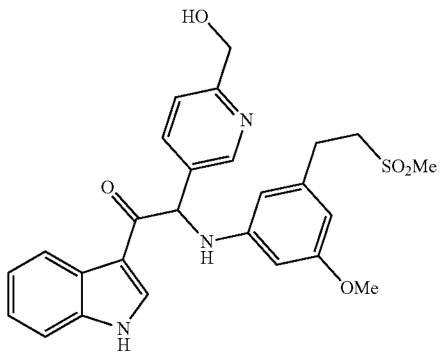 [SMILES: COc1cc(CCS(C)(=O)=O)cc(NC(C(=O)c2c[nH]c3ccccc23)c2ccc(CO)nc2)c1] |
| CPD-403 | 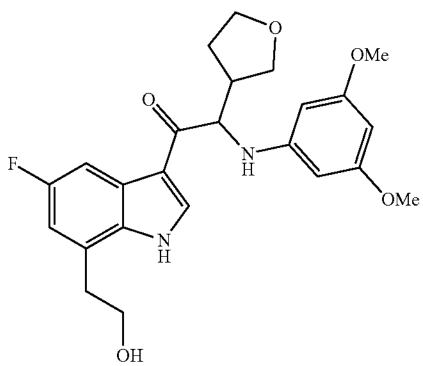 [SMILES: COc1cc(NC(C(=O)c2c[nH]c3c(CCO)cc(F)cc23)C2CCOC2)cc(OC)c1] |
| CPD-404 | 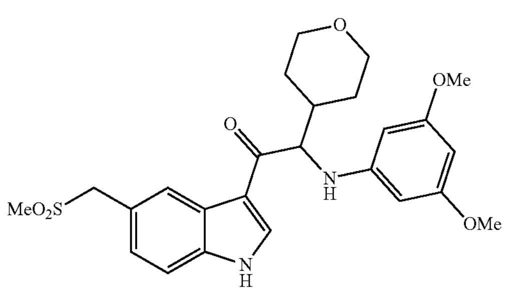 [SMILES: COc1cc(NC(C(=O)c2c[nH]c3ccc(CS(C)(=O)=O)cc23)C2CCOCC2)cc(OC)c1] |
| CPD-405 | 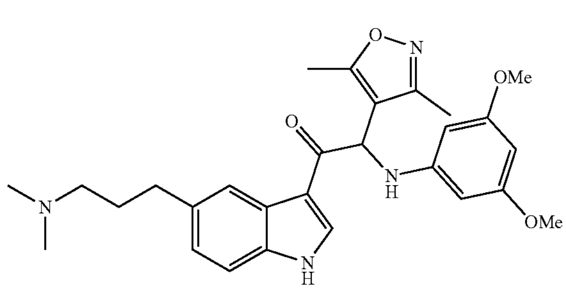 [SMILES: COc1cc(NC(C(=O)c2c[nH]c3ccc(CCCN(C)C)cc23)c2c(C)noc2C)cc(OC)c1] |

TABLE 1-continued
Structures of example compounds of the invention and their respective codes.
| Code | Structure |
|---|---|
| CPD-406 | 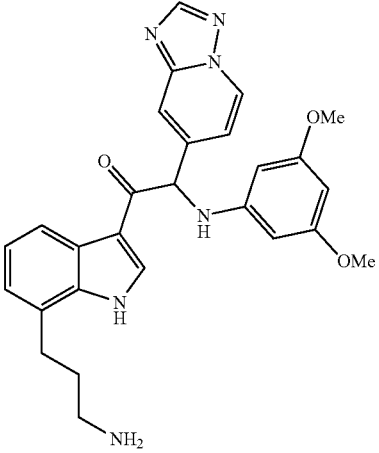 [SMILES: COc1cc(NC(C(=O)c2c[nH]c3c(CCCN)cccc23)c2ccn3ncnc3c2)cc(OC)c1] |
| CPD-407 | 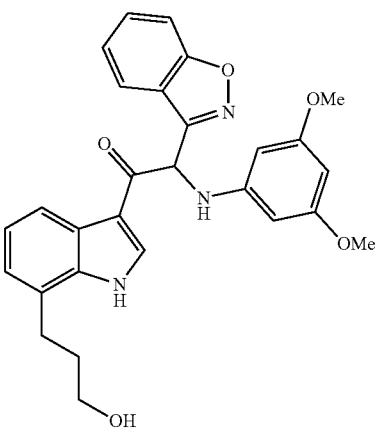 [SMILES: COc1cc(NC(C(=O)c2c[nH]c3c(CCCO)cccc23)c2noc3ccccc23)cc(OC)c1] |
| CPD-408 | 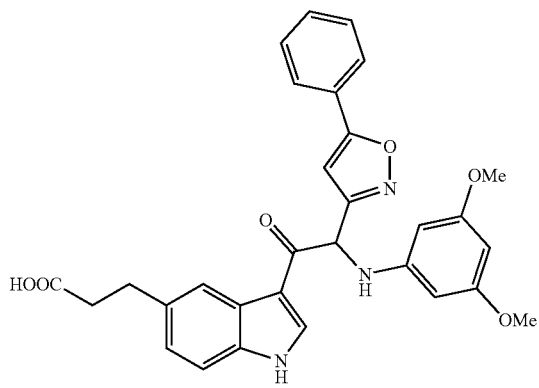 [SMILES: COc1cc(NC(C(=O)c2c[nH]c3ccc(CCC(=O)O)cc23)c2cc(-c3ccccc3)on2)cc(OC)c1] |

TABLE 1-continued

Structures of example compounds of the invention and their respective codes.

| Code | Structure |
| --- | --- |
| CPD-409 | 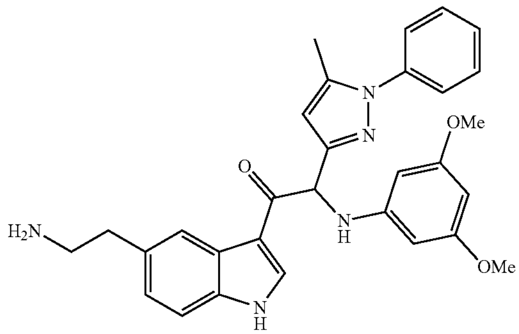 [SMILES: COc1cc(NC(C(=O)c2c[nH]c3ccc(CCN)cc23)c2cc(C)n(-c3ccccc3)n2)cc(OC)c1] |
| CPD-410 | 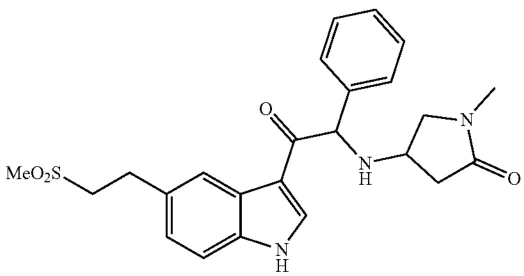 [SMILES: CN1CC(NC(C(=O)c2c[nH]c3ccc(CCS(C)(=O)=O)cc23)c2ccccc2)CC1=O] |
| CPD-411 | 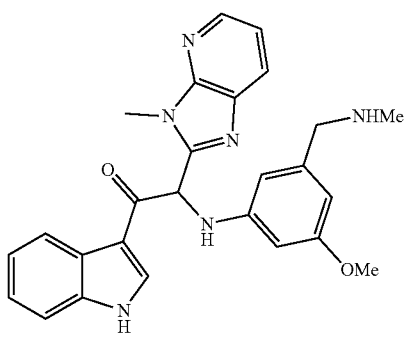 [SMILES: CNCc1cc(NC(C(=O)c2c[nH]c3ccccc23)c2nc3cccnc3n2C)cc(OC)c1] |
| CPD-412 | 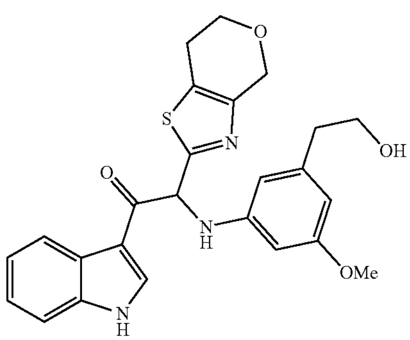 [SMILES: COc1cc(CCO)cc(NC(C(=O)c2c[nH]c3ccccc23)c2nc3c(s2)CCOC3)c1] |

TABLE 1-continued
Structures of example compounds of the invention and their respective codes.
| Code | Structure |
|---|---|
| CPD-413 | 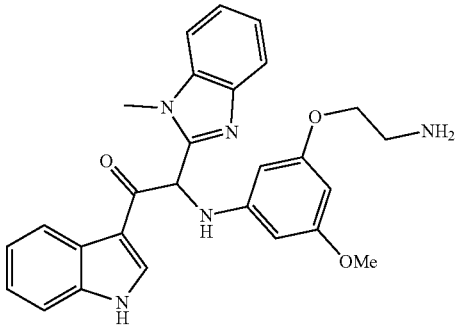 [SMILES: COc1cc(NC(C(=O)c2c[nH]c3ccccc23)c2nc3ccccc3n2C)cc(OCCN)c1] |
| CPD-414 | 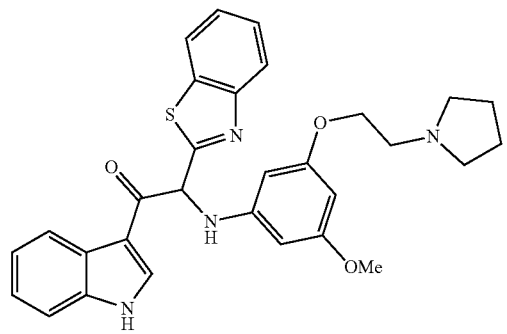 [SMILES: COc1cc(NC(C(=O)c2c[nH]c3ccccc23)c2nc3ccccc3s2)cc(OCCN2CCCC2)c1] |
| CPD-415 | 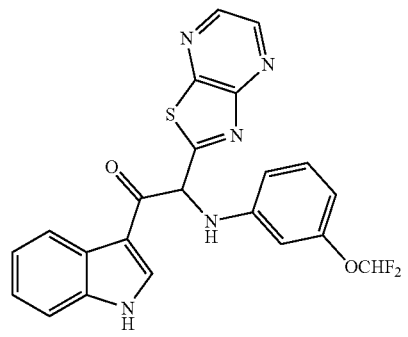 [SMILES: O=C(c1c[nH]c2ccccc12)C(Nc1cccc(OC(F)F)c1)c1nc2nccnc2s1] |
| CPD-416 | 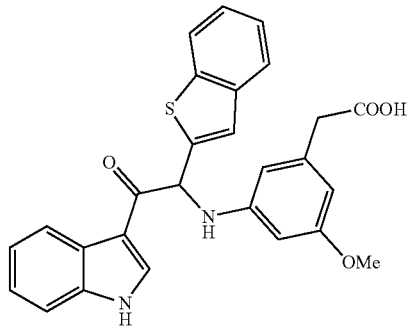 [SMILES: COc1cc(CC(=O)O)cc(NC(C(=O)c2c[nH]c3ccccc23)c2cc3ccccc3s2)c1] |

TABLE 1-continued
Structures of example compounds of the invention and their respective codes.
| Code | Structure |
|------|-----------|
| CPD-417 | 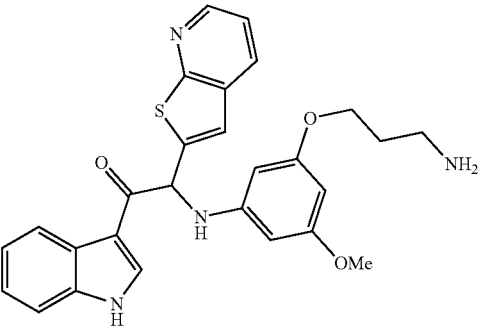 [SMILES: COc1cc(NC(C(=O)c2c[nH]c3ccccc23)c2cc3cccnc3s2)cc(OCCCN)c1] |
| CPD-418 | 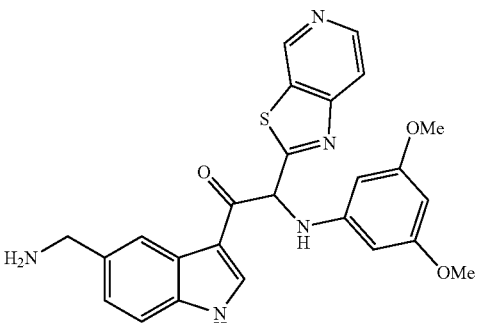 |
| CPD-419 | 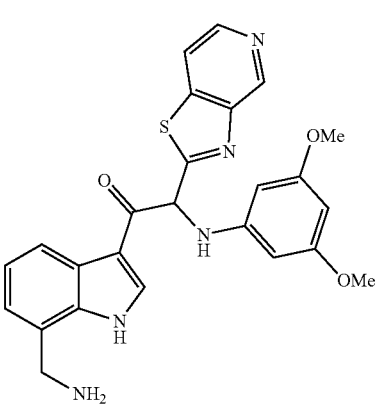 [SMILES: COc1cc(NC(C(=O)c2c[nH]c3c(CN)cccc23)c2nc3cnccc3s2)cc(OC)c1] |
| CPD-420 | 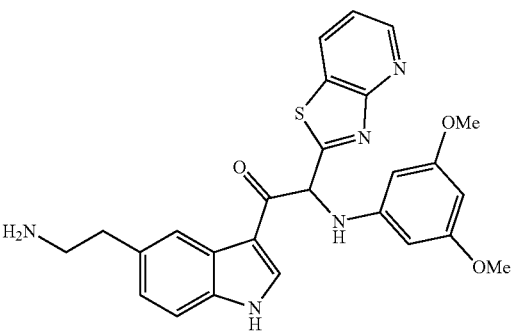 [SMILES: COc1cc(NC(C(=O)c2c[nH]c3ccc(CCN)cc23)c2nc3ncccc3s2)cc(OC)c1] |

TABLE 1-continued
Structures of example compounds of the invention and their respective codes.
| Code | Structure |
|---|---|
| CPD-421 | 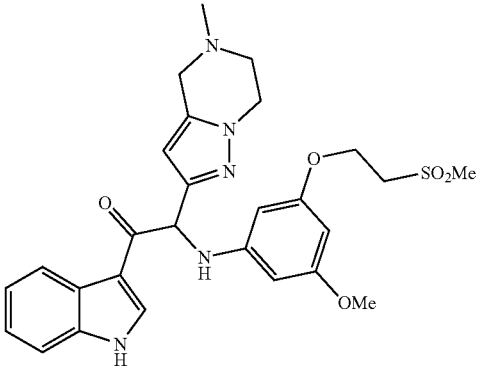 [SMILES: COc1cc(NC(C(=O)c2c[nH]c3ccccc23)c2cc3n(n2)CCN(C)C3)cc(OCCS(C)(=O)=O)c1] |
| CPD-422 | 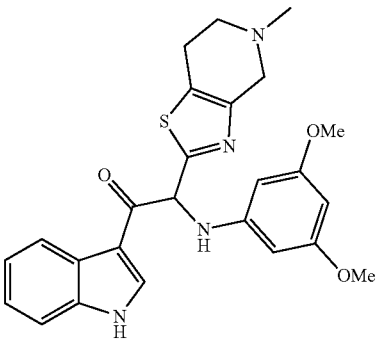 [SMILES: COc1cc(NC(C(=O)c2c[nH]c3ccccc23)c2nc3c(s2)CCN(C)C3)cc(OC)c1] |
| CPD-423 | 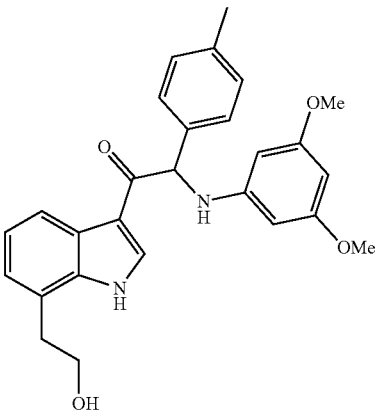 [SMILES: COc1cc(NC(C(=O)c2c[nH]c3c(CCO)cccc23)c2ccc(C)cc2)cc(OC)c1] |
| CPD-424 | 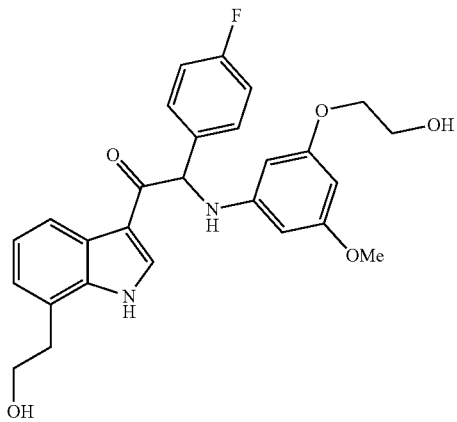 [SMILES: COc1cc(NC(C(=O)c2c[nH]c3c(CCO)cccc23)c2ccc(F)cc2)cc(OCCO)c1] |

TABLE 1-continued

Structures of example compounds of the invention and their respective codes.

| Code | Structure |
| --- | --- |
| CPD-425 | 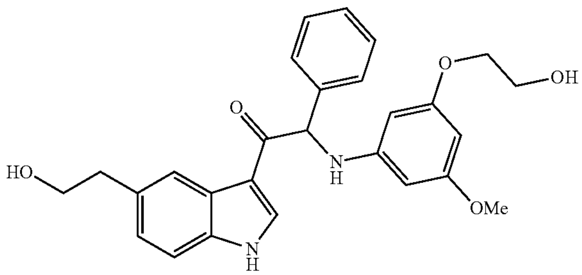 [SMILES: COc1cc(NC(C(=O)c2c[nH]c3ccc(CCO)cc23)c2ccccc2)cc(OCCO)c1] |
| CPD-426 | 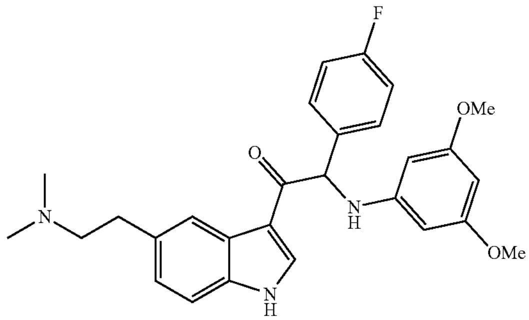 [SMILES: COc1cc(NC(C(=O)c2c[nH]c3ccc(CCN(C)C)cc23)c2ccc(F)cc2)cc(OC)c1] |
| CPD-427 | 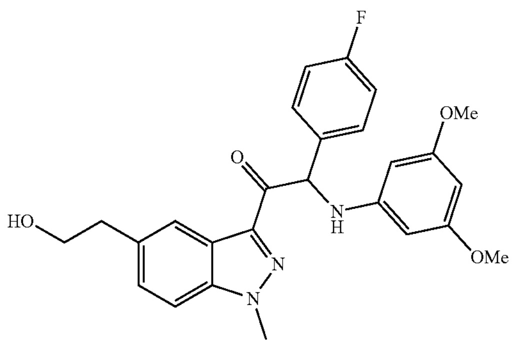 [SMILES: COc1cc(NC(C(=O)c2nn(C)c3ccc(CCO)cc23)c2ccc(F)cc2)cc(OC)c1] |
| CPD-428 | 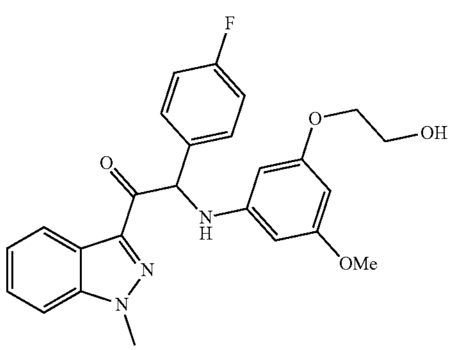 [SMILES: COc1cc(NC(C(=O)c2nn(C)c3ccccc23)c2ccc(F)cc2)cc(OCCO)c1] |

TABLE 1-continued
Structures of example compounds of the invention and their respective codes.
| Code | Structure |
|---|---|
| CPD-429 | 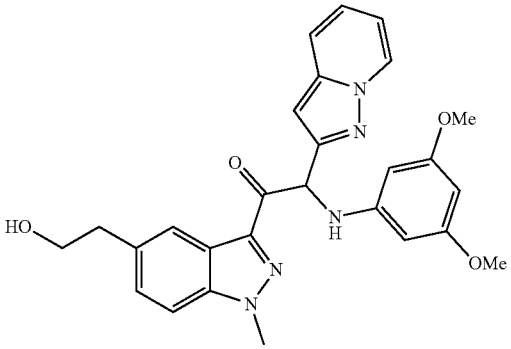 [SMILES: COc1cc(NC(C(=O)c2nn(C)c3ccc(CCO)cc23)c2cc3ccccn3n2)cc(OC)c1] |
| CPD-430 | 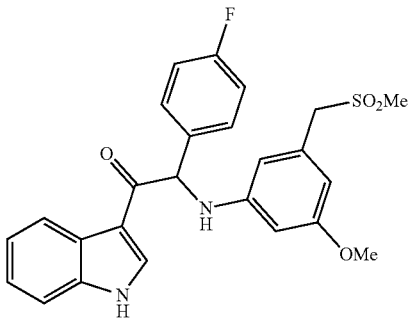 [SMILES: COc1cc(CS(C)(=O)=O)cc(NC(C(=O)c2c[nH]c3ccccc23)c2ccc(F)cc2)c1] |
| CPD-431 | 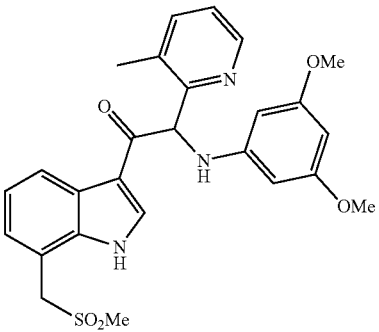 [SMILES: COc1cc(NC(C(=O)c2c[nH]c3c(CS(C)(=O)=O)cccc23)c2ncccc2C)cc(OC)c1] |
| CPD-432 | 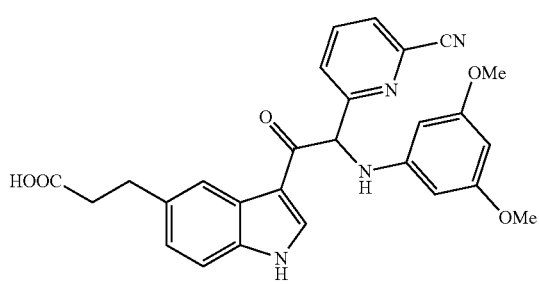 [SMILES: COc1cc(NC(C(=O)c2c[nH]c3ccc(CCC(=O)O)cc23)c2cccc(C#N)n2)cc(OC)c1] |

Part A

All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a XBridge Prep O18 column (19×100 mm; 5 μm) equipped with a XBridge C18 guard column (19×10 mm; 5 μm) or with a SunFire Prep C18 ODB column (19×100 mm; 5 μm) equipped with a SunFire O18 guard column (19×10 mm; 5 μM).

Elutions were carried out with the methods described in the following tables, and detection wavelengths were fixed at 210 and 254 nm.

Method 1

| Time (min) | Flow Rate (mL/min) | Solvent A (%) | Solvent B (%) |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

Solvent A: Formic Acid LC-MS grade 0.1% in milliQ water
Solvent B: Acetonitrile HPLC grade.

Method 2

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Formic Acid LC-MS grade 0.1% in milliQ water
Solvent B: Acetonitrile HPLC grade.

Method 3

| Time (min) | Flow Rate (mL/min) | Solvent A (%) | Solvent B (%) |
|---|---|---|---|
| 0 | 20 | 95 | 5 |
| 2.00 | 20 | 95 | 5 |
| 8.00 | 20 | 50 | 50 |
| 9.00 | 20 | 10 | 90 |
| 11.80 | 20 | 10 | 90 |
| 12.00 | 20 | 95 | 5 |
| 16.00 | 20 | 95 | 5 |

Solvent A: Formic Acid LC-MS grade 0.1% in milliQ water
Solvent B: Acetonitrile HPLC grade.

Method 4

| Time (min) | Flow Rate (mL/min) | Solvent A (%) | Solvent B (%) |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

-continued

| Time (min) | Flow Rate (mL/min) | Solvent A (%) | Solvent B (%) |
|---|---|---|---|

Solvent A: Ammonium Acetate puriss p.a. for HPLC 10 mM in milliQ water, adjusted at pH10 with Ammonium Hydroxyde puriss p.a. for HPLC
Solvent B: Acetonitrile HPLC grade.

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Ammonium Acetate puriss p.a. for HPLC 10 mM in milliQ water, adjusted at pH10 with Ammonium Hydroxyde puriss p.a. for HPLC
Solvent B: Acetonitrile HPLC grade.

All the enantiomer separations mentioned in this experimental part have been carried out with the following system: a Waters 2489 UV/Visible Detector, a Waters 2545 Binary Gradient Module, a Waters Fraction Collector III and a Waters Dual Flex Injector. The separations were performed with a ChiralPak IC column (20×250 mm; 5 μm) equipped with a ChiralPak IC guard column (10×20 mm; 5 μM). Elutions were carried out with the isocratic methods described below, and detection wavelengths were fixed at 210 and 254 nm.

Method 6:
Eluant: Acetonitrile/diethylamine: 100/0.1
Flow rate: 20 mL/min
Method 7:
Eluant: n-heptane/dichloromethane/ethanol/diethylamine: 50/50/1/0.1
Flow rate: 20 mL/min General Procedures Used in the Synthesis of Compounds of the Invention:

General Procedure A:

To a solution of an appropriate indole and pyridine in toluene heated at 55° C. was added dropwise α-chlorophenylacetyl chloride. The reaction mixture was heated at 55° C. for 2 h. After cooling to room temperature, water and methanol were added. After 1 h at room temperature, the precipitate was filtered, washed with water and dried to afford the desired compound. In case of no precipitation, the reaction mixture was diluted with ethyl acetate and washed with water. The phases were separated. The organic layer was washed with brine, dried over sodium sulfate and concentrated under reduced pressure. The residue was purified by flash chromatography on silica gel or by precipitation to give the desired compound.

General Procedure B:

A mixture of 2-chloro-1-(1H-indol-3-yl)-2-phenylethanone, an amine and triethylamine in DMF was heated at 100° C. overnight in a sealed tube. The solvent was evaporated under vacuum. The residue was partitioned between ethyl acetate and a 5% hydrochloric acid solution. The phases were separated. The organic phase was washed with water, dried over magnesium sulfate, filtered and concentrated under reduced pressure. The residue was purified by flash chromatography on silica gel followed by recrystallization.

General Procedure C:

A mixture of an α-halogenoketone, an amine and a base (DIPEA or triethylamine) in a solvent (e.g. DMF, ethanol, acetonitrile, dioxane or THF) was irradiated in a microwave oven at 100° C. to 200° C. (more in particular at 120 to 200° C.) for 5 to 180 min. (more in particular for 15 to 120 min). The reaction mixture was concentrated under reduced pressure and the residue was purified by flash chromatography on silica gel.

General Procedure D:

A mixture of an α-halogenoketone, an amine and PS-DIPEA in acetonitrile was irradiated in a microwave oven at 200° C. for 30 minutes. The reaction mixture was concentrated under reduced pressure and the residue was purified by flash chromatography on silica gel. Further purification by preparative HPLC was undertaken to furnish the product.

General Procedure E:

A mixture of an α-halogenoketone and an aniline in acetonitrile was irradiated in a microwave oven at 100 to 200° C. (more in particular at 130 to 150° C.) for 5 to 120 min (more in particular for 15 to 30 min). The reaction mixture was then concentrated. The residue was partitioned between ethyl acetate and a 1N hydrochloric acid solution. The phases were separated. The organic phase was washed with a saturated sodium hydrogencarbonate solution, water and brine, dried over sodium sulfate, filtered and concentrated. The residue was purified by flash chromatography on silica gel.

General Procedure F:

To a solution of an appropriate indole, azaindole or alternative heterocycles (1.0 eq) and di-tert-butyl dicarbonate (1 eq. to 2 eq., more in particular 1.2 eq) in acetonitrile was added DMAP (0.1 to 0.5 eq. more in particular 0.1 eq). The reaction mixture was stirred overnight at room temperature. The reaction mixture was concentrated under reduced pressure. The residue was dissolved in dichloromethane and washed with a saturated sodium bicarbonate solution. The phases were separated. The aqueous phase was extracted with dichloromethane. The organic phases were combined, washed with a saturated ammonium chloride solution, water and brine, dried over magnesium sulfate, filtered and concentrated under reduced pressure. The BOC-protected compound was used in the next step without further purification.

General Procedure G:

To a mixture of an aldehyde (1.0 eq) and magnesium sulfate (1.3 eq) in ethanol was added an amine (1.0 eq). The reaction mixture was stirred overnight at room temperature and filtered. The filtrate was concentrated under reduced pressure to give quantitatively the imine which was used without further purification in the next step.

General Procedure H:

To a mixture of an aldehyde (1.0 eq) and magnesium sulfate (1.3 eq) in ethanol was added an amine (1.0 eq). The mixture was heated overnight at 80° C. and filtered. The filtrate was concentrated under reduced pressure to give quantitatively the imine which was used without further purification in the next step.

General Procedure I:

A mixture of an aldehyde (1.0 eq) and an amine (1.0 eq) was heated in a sealed tube at 60° C. for 6 h. The crude material was dried under vacuum over phosphorus(V) oxide to give quantitatively the imine which was used in the next step without further purification.

General Procedure J:

A mixture of an aldehyde (1.0 eq), magnesium sulfate (100 mg) and an amine (1.0 eq) in ethanol was heated at 80° C. overnight. The reaction mixture was filtered. The formation of the imine was quantitative and the filtrate containing the imine was used in the next step without purification.

General Procedure K:

To a solution of 3-benzyl-5-(2-hydroxyethyl)-4-methyl-thiazol-3-ium chloride in ethanol was added triethylamine and the mixture was stirred at 70° C. for 5 min. To the resulting yellow solution were added an aldehyde and a solution of an imine in ethanol. The reaction mixture was stirred in a sealed tube at 50-70° C. for 18-170 h, after which the reaction mixture was irradiated in a microwave oven at 160° C. for 4 min. The reaction mixture was concentrated under reduced pressure and the crude material was purified by flash chromatography on silica gel or precipitation.

General Procedure L:

To a solution of 3-benzyl-5-(2-hydroxyethyl)-4-methyl-thiazol-3-ium chloride in ethanol was added triethylamine and the mixture was stirred at 70° C. for 5 min. To the resulting yellow solution were added an aldehyde and a solution of an imine in ethanol. The reaction mixture was stirred in a sealed tube at 50-70° C. for 18-120 h. The reaction mixture was concentrated under reduced pressure and the crude material was purified by flash chromatography on silica gel or precipitation.

General Procedure M:

To a solution of an appropriate indole in DMF were added an alkyl halide and potassium carbonate. The reaction mixture was stirred at room temperature for 1-20 hours. Water was added. The resulting precipitate was filtered, dried and recrystallized to afford the desired compound. In case of no precipitation, the reaction mixture was extracted with ethyl acetate. The organic layer was dried over magnesium sulfate, evaporated under reduced pressure and purified by flash chromatography.

General Procedure N:

To a solution of an alcohol (1.0 eq) in THF (e.g. 3.5 mL/mmol) were added DBU (1 eq. to 2 eq., more in particular 1.0 eq) and TBDMSCl (1 eq. to 2 eq., more in particular 2.0 eq). After 4 h at room temperature, the reaction mixture was diluted with ethyl acetate and washed with water. The phases were separated. The organic phase was washed with brine, dried over sodium sulfate, filtered and concentrated under reduced pressure. The residue was purified by flash chromatography on silica gel.

General Procedure O:

To a solution of an indole in dichloromethane cooled to 0° C. was added dropwise a 1M diethylaluminium chloride solution in hexane. After 30 min at 0° C., a solution of an acyl chloride in dichloromethane was added. The reaction mixture was stirred at 0° C. for 2 to 3 h and poured into a mixture ice/buffer (pH 7) solution. Alternatively, a saturated sodium bicarbonate solution or a 1M Rochelle salt solution was added to the reaction mixture. The phases were separated. The organic phase was washed with a saturated sodium bicarbonate solution, water and brine, dried over sodium sulfate, filtered and concentrated under reduced pressure. The residue was purified by flash chromatography on silica gel or by precipitation.

General Procedure P:

To a solution of a α-methylketone in THF cooled to 0° C. was added a solution of phenyltrimethylammonium tribromide in THF. The reaction mixture was stirred at 0° C. for 1 h and at room temperature for 2 to 20 h. The reaction mixture was filtered and the solid was washed with ethyl acetate. The filtrate was concentrated under reduced pressure. The residue was partitioned between ethyl acetate and water. The phases were separated. The organic phase was washed with brine, dried over sodium sulfate, filtered and concentrated under reduced pressure. The residue was purified by flash chromatography on silica gel or by precipitation.

General Procedure Q:

To a solution of an alcohol in dichloromethane were added DMAP and acetic anhydride. The reaction was stirred at room temperature for 15 to 60 min. The reaction mixture was diluted with dichloromethane and washed with a saturated sodium bicarbonate solution. The organic phase was washed with water and brine, dried over sodium sulfate, filtered and concentrated under reduced pressure. The residue was purified by flash chromatography on silica gel.

General Procedure R:

To a solution of oxalyl chloride in anhydrous dichloromethane cooled to 0° C. was added DMF. After 30 min at 0° C. an indole was added and the reaction mixture was stirred at room temperature for 1 h. The reaction mixture was concentrated under reduced pressure. The residue was taken up in THE and a 20% ammonium acetate solution. The mixture was refluxed for 30 min. After cooling to room temperature, the reaction mixture was diluted with ethyl acetate. The phases were separated and the organic phase was washed with a sodium bicarbonate solution, dried over sodium sulfate, filtered and concentrated under reduced pressure The residue was purified by flash chromatography on silica gel.

General Procedure S:

To a solution of an ester in a mixture of THE and methanol was added potassium carbonate. The reaction mixture was stirred at 20-45° C. for 3 to 5 h. The reaction mixture was filtered and the filtrate was concentrated under reduced pressure. The residue was purified by flash chromatography on silica gel.

Example 1: Preparation of 2-((3,4-dimethoxyphenyl)amino)-1-(1H-indol-3-yl)-2-phenylethanone Step 1: 2-Chloro-1-(1H-indol-3-yl)-2-phenylethanone was prepared according to general procedure A from indole (1.000 g; 8.536 mmol), pyridine (0.690 mL; 8.531 mmol) and α-chlorophenylacetyl chloride (1.610 g; 8.565 mmol) in toluene (22 mL). Purification by precipitation furnished 1.294 g (56%) of the desired compound as a white solid. ESI/APCI(+): 270, 272 (M+H); 292, 294 (M+Na). ESI/APCI(−): 268, 270 (M−H).

Step 2: 2-((3,4-Dimethoxyphenyl)amino)-1-(1H-indol-3-yl)-2-phenylethanone was prepared according to general procedure B from 2-chloro-1-(1H-indol-3-yl)-2-phenylethanone (0.125 g; 0.463 mmol), 4-aminoveratrole (0.142 g; 0.927 mmol) and triethylamine (0.200 mL; 1.443 mmol) in DMF (2 mL). Purification by flash chromatography on silica gel using a gradient of ethyl acetate (10% to 100%) in heptane followed by recrystallization from ethanol furnished 0.014 g (8%) of the desired compound as a beige solid. ESI/APCI(+): 387 (M+H); 409 (M+Na). ESI/APCI(−): 385 (M−H). $^1$H NMR (DMSO-$d_6$) δ 8.87 (1H, br s); 8.15 (1H, m); 7.61-7.64 (2H, m); 7.45 (1H, d); 7.13-7.30 (4H, m); 6.60-6.65 (2H, m); 6.24 (1H, m); 5.97-6.07 (2H, m); 3.65 (3H, s); 3.57 (3H, s).

Example 2: Preparation of 2-((3,5-dimethoxyphenyl)amino)-1-(1H-indol-3-yl)-2-phenylethanone 2-((3,5-Dimethoxyphenyl)amino)-1-(1H-indol-3-yl)-2-phenylethanone was prepared according to general procedure B from 2-chloro-1-(1H-indol-3-yl)-2-phenylethanone (0.054 g; 0.200 mmol), 3,5-dimethoxyaniline (0.068 g; 0.444 mmol) and triethylamine (0.100 mL; 0.717 mmol) in DMF (2 mL). Purification by flash chromatography on silica gel using a gradient of ethyl acetate (10% to 100%) in heptane followed by recrystallization from ethanol furnished 0.005 g (6%) of the desired compound as a beige solid. ESI/APCI(+): 387 (M+H). ESI/APCI(−): 385 (M−H). $^1$H NMR (DMSO-$d_6$) δ 12.12 (1H, br s); 8.88 (1H, s); 8.16 (1H, m); 7.61-7.64 (2H, m); 7.45 (1H, m); 7.14-7.31 (5H, m); 6.35 (1H, m); 6.03-6.08 (3H, m); 5.70 (1H, s); 3.61 (6H, s).

Example 3: Preparation of 2-((3-ethoxyphenyl)amino)-1-(1H-indol-3-yl)-2-phenylethanone 2-((3-Ethoxyphenyl)amino)-1-(1H-indol-3-yl)-2-phenylethanone was prepared according to general procedure C from 2-chloro-1-(1H-indol-3-yl)-2-phenylethanone (0.050 g; 0.185 mmol), 3-ethoxyaniline (0.100 mL; 0.751 mmol) and DIPEA (0.100 mL; 0.574 mmol) in DMF (2 mL), irradiated in a microwave oven at 180° C. for 15 min. Purification by flash chromatography on silica gel using a gradient of ethyl acetate (10% to 40%) in heptane furnished 0.010 g (15%) of the desired compound as a beige solid. ESI/APCI(+): 371 (M+H); 393 (M+Na). ESI/APCI(−): 369 (M−H). $^1$H NMR (CDCl$_3$) δ 8.56 (1H, br s); 8.41 (1H, m); 8.01 (1H, d); 7.53-7.55 (2H, m); 7.40 (1H, m); 7.20-7.32 (5H, m); 7.01 (1H, m); 6.29 (1H, d); 6.20-6.24 (2H, m); 5.72 (1H, m); 5.52 (1H, m); 3.94 (2H, q); 1.35 (3H, t).

Example 4: Preparation of 2-((4-chloro-3-methoxyphenyl)amino)-1-(1H-indol-3-yl)-2-phenylethanone 2-((4-Chloro-3-methoxyphenyl)amino)-1-(1H-indol-3-yl)-2-phenylethanone was prepared according to general procedure C from 2-chloro-1-(1H-indol-3-yl)-2-phenylethanone (0.104 g; 0.386 mmol), 3-methoxy-4-chloroaniline (0.105 g; 0.666 mmol) and DIPEA (0.200 mL; 1.148 mmol) in DMF (2 mL), irradiated in a microwave oven at 180° C. for 30 min. Purification by flash chromatography on silica gel using a gradient of ethyl acetate (10% to 40%) in heptane furnished 0.027 g (18%) of the desired compound as a white solid. ESI/APCI(+): 391, 393 (M+H); 413, 415 (M+Na). ESI/APCI(−): 389, 391 (M−H). $^1$H NMR (CDCl$_3$) δ 8.65 (1H, br s); 8.40 (1H, m); 7.95-8.11 (2H, m); 7.50-7.53 (2H, m); 7.24-7.53 (5H, m); 7.05 (1H, d); 6.18-6.28 (2H, m); 5.70 (1H, s); 3.79 (3H, s).

Example 5: Preparation of 1-(1H-indol-3-yl)-2-phenyl-2-((3-(trifluoromethoxy)phenyl)amino)ethanone 1-(1H-Indol-3-yl)-2-phenyl-2-((3-(trifluoromethoxy)phenyl)amino)ethanone was prepared according to general procedure C from 2-chloro-1-(1H-indol-3-yl)-2-phenylethanone (0.050 g; 0.185 mmol), 3-(trifluoromethoxy)aniline (0.100 mL; 0.751 mmol) and DIPEA (0.100 mL; 0.574 mmol) in DMF (2 mL), irradiated in a microwave oven at 180° C. for 15 min. Purification by flash chromatography on silica gel using a gradient of ethyl acetate (10% to 40%) in heptane furnished 0.009 g (12%) of the desired compound as a beige solid. ESI/APCI(+): 371 (M+H); 393 (M+Na). ESI/APCI(−): 369 (M−H). $^1$H NMR (CDCl$_3$) δ 8.56 (1H, br s); 8.41 (1H, m); 8.01 (1H, d); 7.53-7.55 (2H, m); 7.40 (1H, m); 7.20-7.32 (5H, m); 7.01 (1H, m); 6.29 (1H, d); 6.20-6.24 (2H, m); 5.72 (1H, m); 5.52 (1H, m); 3.94 (2H, q); 1.35 (3H, t).

Example 6: Preparation of 2-((3-chlorophenyl)amino)-1-(1H-indol-3-yl)-2-phenylethanone 2-((3-Chlorophenyl)amino)-1-(1H-indol-3-yl)-2-phenylethanone was prepared according to general procedure C from 2-chloro-1-(1H-indol-3-yl)-2-phenylethanone (0.105 g; 0.389 mmol), 3-chloroaniline (0.200 mL; 1.890 mmoL) and DIPEA (0.200 mL; 1.148 mmoL) in DMF (2 mL), irradiated in a microwave oven at 180° C. for 30 min. Purification by flash chromatography on silica gel using a gradient of ethyl acetate (10% to 40%) in heptane followed by recrystallization from methanol furnished 0.005 g (4%) of the desired compound as a white solid. ESI/APCI(+): 361, 363 (M+H); 383, 385 (M+Na). ESI/APCI(−): 359, 361 (M−H). $^1$H NMR (CDCl$_3$) δ 8.59 (1H, br s); 8.40 (1H, m); 8.02 (1H, d); 7.51-7.53 (2H, m); 7.21-7.38 (6H, m); 7.02 (1H, m); 6.54-6.65 (3H, m); 5.70 (1H, s).

Example 7: Preparation of 2-((3,4-difluorophenyl) amino)-1-(1H-indol-3-yl)-2-phenylethanone 2-((3,4-Difluorophenyl)amino)-1-(1H-indol-3-yl)-2-phenylethanone was prepared according to general procedure C from 2-chloro-1-(1H-indol-3-yl)-2-phenylethanone (0.105 g; 0.389 mmol), 3,4-difluoroaniline (0.200 mL; 2.017 mmol) and DIPEA (0.200 mL; 1.148 mmol) in DMF (2 mL), irradiated in a microwave oven at 180° C. for 30 min. Purification by flash chromatography on silica gel using a gradient of ethyl acetate (10% to 40%) in heptane followed by purification by preparative HPLC (XBridge column, method 1) furnished 0.025 g (18%) of the desired compound as an amorphous solid. ESI/APCI(+): 363 (M+H); 385 (M+Na). ESI/APCI(−): 361 (M−H). $^1$H NMR (CDCl$_3$) δ 8.59 (1H, br s); 8.40 (1H, m); 8.00 (1H, d); 7.49-7.52 (2H, m); 7.23-7.41 (6H, m); 6.71 (1H, m); 6.32-6.46 (2H, m); 5.30-5.64 (2H, m).

Example 8: Preparation of 2-((3-fluorophenyl) amino)-1-(1H-indol-3-yl)-2-phenylethanone 2-((3-Fluorophenyl)amino)-1-(1H-indol-3-yl)-2-phenylethanone was prepared according to general procedure C from 2-chloro-1-(1H-indol-3-yl)-2-phenylethanone (0.103 g; 0.382 mmol), 3-fluoroaniline (0.200 mL; 2.081 mmoL) and DIPEA (0.200 mL; 1.148 mmol) in ethanol (2 mL), irradiated in a microwave oven at 180° C. for 30 min. Purification by flash chromatography on silica gel using a gradient of ethyl acetate (10% to 40%) in heptane furnished 0.030 g (23%) of the desired compound as a beige solid. ESI/APCI(+): 345 (M+H); 367 (M+Na). ESI/APCI(−): 343 (M−H). $^1$H NMR (CDCl$_3$) δ 8.59 (1H, br s); 8.40 (1H, m); 8.01 (1H, d); 7.51-7.54 (2H, m); 7.22-7.41 (6H, m); 7.04 (1H, m); 6.46 (1H, d); 6.31-6.37 (2H, m); 5.69 (1H, s); 5.30 (1H, s).

Example 9: Preparation of 1-(1H-indol-3-yl)-2-phenyl-2-((3-(trifluoromethyl)phenyl)amino)ethanone 1-(1H-Indol-3-yl)-2-phenyl-2-((3-(trifluoromethyl)phenyl)amino)ethanone was prepared according to general procedure C from 2-chloro-1-(1H-indol-3-yl)-2-phenylethanone (0.104 g; 0.386 mmol), 3-(trifluoromethyl)aniline (0.100 mL; 0.801 mmol) and DIPEA (0.200 mL; 1.148 mmol) in ethanol (2 mL), irradiated in a microwave oven at 180° C. for 30 min. Purification by flash chromatography on silica gel using a gradient of ethyl acetate (10% to 40%) in heptane furnished 0.028 g (18%) of the desired compound as a beige solid. ESI/APCI(+): 395 (M+H). ESI/APCI(−): 393 (M−H). $^1$H NMR (CDCl$_3$) δ 8.59 (1H, br s); 8.41 (1H, m); 8.01 (1H, d); 7.51-7.54 (2H, m); 7.17-7.41 (7H, m); 6.80-6.90 (3H, m); 5.83 (1H, s); 5.73 (1H, s).

Example 10: Preparation of 1-(1H-indol-3-yl)-2-((3-methoxyphenyl)amino)-2-phenylethanone 1-(1H-Indol-3-yl)-2-((3-methoxyphenyl)amino)-2-phenylethanone has been prepared according to 2 different procedures described hereunder as method A and method B.

Method A: 1-(1H-Indol-3-yl)-2-((3-methoxyphenyl) amino)-2-phenylethanone was prepared according to general procedure C from 2-chloro-1-(1H-indol-3-yl)-2-phenylethanone (0.103 g; 0.382 mmol), 3-methoxyaniline (0.100 mL; 0.894 mmol) and DIPEA (0.100 mL; 0.574 mmol) in ethanol (2 mL), irradiated in a microwave oven at 180° C. for 30 min. Purification by flash chromatography on silica gel using a gradient of ethyl acetate (10% to 40%) in heptane furnished 0.050 g (37%) of the desired compound as a white solid. ESI/APCI(+): 357 (M+H); 379 (M+Na). ESI/APCI(−): 355 (M−H). $^1$H NMR (CDCl$_3$) δ 8.67 (1H, br s); 8.41 (1H, m); 7.98 (1H, d); 7.50-7.53 (2H, m); 7.20-7.39 (6H, m); 7.01 (1H, m); 6.23-6.25 (2H, m); 5.70 (1H, s); 5.52 (1H, br s); 3.72 (3H, s).

Method B:

Step 1: 1-(1H-Indol-3-yl)-2-phenylethanone was prepared according to general procedure O from a solution of 1H-indole (2.500 g; 21.34 mmol) in dichloromethane (80 mL), a 1M diethylaluminium chloride solution in hexane (32.00 mL; 32.00 mmol) and a solution of phenylacetyl chloride (4.300 mL; 32.27 mmol) in dichloromethane (80 mL). Purification by precipitation from ethyl acetate furnished 3.240 g (65%) of the desired compound as a white solid. ESI/APCI(+): 236 (M+H). ESI/APCI(−): 234 (M−H).

Step 2: 2-Bromo-1-(1H-indol-3-yl)-2-phenylethanone was prepared according to general procedure P from a solution of 1-(1H-indol-3-yl)-2-phenylethanone (3.240 g: 13.77 mmol) in THF (140 mL) and a solution of phenyltrimethylammonium tribromide (5.700 g; 15.16 mmol) in THF (70 mL). The reaction mixture was stirred at 0° C. for 1 h and at room temperature for 4 h. Purification by precipitation from ethyl acetate yielded 3.690 g (85%) of the desired product as a white solid. ESI/APCI(+): 314, 316 (M+H); 336, 338 (M+Na). ESI/APCI(−): 312, 314 (M−H). $^1$H NMR (DMSO-d$_6$) δ 12.21 (1H, br s); 8.67 (1H, s); 8.20 (1H, m); 7.68 (1H, d); 7.0-7.4 (7H, m); 6.84 (1H, s).

Step 3: 1-(1H-Indol-3-yl)-2-((3-methoxyphenyl)amino)-2-phenylethanone was prepared according to general procedure E from 2-bromo-1-(1H-indol-3-yl)-2-phenylethanone (0.032 g; 0.102 mmol) and m-anisidine (0.063 mL; 0.563 mmol) in acetonitrile (0.5 mL), irradiated in a microwave oven at 100° C. for 15 min. Purification by flash chromatography on silica gel using a gradient of ethyl acetate (20% to 60%) in heptane furnished 0.030 g (83%) of the desired product as a white powder.

Example 11: Preparation of 2-((3,5-difluorophenyl) amino)-1-(1H-indol-3-yl)-2-phenylethanone 2-((3,5-Difluorophenyl)amino)-1-(1H-indol-3-yl)-2-phenylethanone was prepared according to general procedure C from 2-chloro-1-(1H-indol-3-yl)-2-phenylethanone (0.103 g; 0.382 mmol), 3,5-difluoroaniline (0.117 g; 0.906 mmol) and DIPEA (0.100 mL; 0.574 mmol) in ethanol (2 mL), irradiated in a microwave oven at 180° C. for 30 min. Purification by flash chromatography on silica gel using a gradient of ethyl acetate (10% to 40%) in heptane furnished 0.008 g (6%) of the desired compound as a beige solid. ESI/APCI(+): 363 (M+H); 385 (M+Na). ESI/APCI(−): 361 (M−H). $^1$H NMR (CDCl$_3$) δ 8.63 (1H, br s); 8.38 (1H, m);

7.99 (1H, d); 7.51-7.54 (2H, m); 7.23-7.41 (7H, m); 6.08-6.18 (2H, m); 5.88 (1H, br s); 5.65 (1H, m).

Example 12: Preparation of 2-((3,5-dimethoxyphenyl)amino)-1-(2-methyl-1H-indol-3-yl)-2-phenylethanone Step 1: To a solution of 2-methylindole (0.098 g; 0.747 mmol) and pyridine (0.070 mL; 0.865 mmol) in toluene (2 mL) heated at 55° C. was added dropwise α-chlorophenylacetyl chloride (0.120 mL; 0.762 mmol). A brownish oil separated after the addition. The mixture was heated for 4 h at 55° C. and then water was added. The phases were separated. The aqueous phase was extracted with ethyl acetate. The organic phases were combined, washed with brine, dried over sodium sulfate, filtered and concentrated under reduced pressure. The residue was purified by flash chromatography on silica gel using a gradient of ethyl acetate (10% to 40%) in heptane to provide 0.068 g (32%) of 2-chloro-1-(2-methyl-1H-indol-3-yl)-2-phenylethanone as a beige foam. ESI/APCI(+) 284 (M+H); 306 (M+Na). ESI/APCI(−): 282 (M−H).

Step 2: 2-((3,5-Dimethoxyphenyl)amino)-1-(2-methyl-1H-indol-3-yl)-2-phenylethanone was prepared according to general procedure C from 2-chloro-1-(2-methyl-1H-indol-3-yl)-2-phenylethanone (0.068 g; 0.240 mmol), 3,5-dimethoxyaniline (0.173 g; 1.129 mmol) and DIPEA (0.250 mL; 1.435 mmol) in ethanol (2 mL), irradiated in a microwave oven at 180° C. for 30 min. Purification by flash chromatography on silica gel using a gradient of ethyl acetate (10% to 40%) in heptane furnished 0.029 g (30%) of the desired compound as a beige solid. ESI/APCI(+): 401 (M+H); 423 (M+Na). ESI/APCI(−): 399 (M−H). $^1$H NMR (CDCl$_3$) δ 8.40 (1H, br s); 8.10 (1H, d); 7.46-7.47 (2H, m); 7.20-7.32 (6H, m); 6.04 (1H, d); 5.85-5.89 (3H, m); 5.43 (1H, br s); 3.73 (6H, s); 2.68 (3H, s).

Example 13: Preparation of 1-(6-chloro-1H-indol-3-yl)-2-((3,5-dimethoxyphenyl)amino)-2-phenylethanone Step 1: To a solution of 6-chloroindole (0.103 g; 0.679 mmol) and pyridine (0.060 mL; 0.742 mmol) in toluene (2 mL) heated at 55° C. was added dropwise α-chlorophenylacetyl chloride (0.100 mL; 0.635 mmol). A brownish oil separated after the addition. The mixture was stirred for 18 hours at 55° C. and then water was added. The phases were separated. The aqueous phase was extracted with ethyl acetate. The organic phases were combined, washed with brine, dried over sodium sulfate and concentrated. The residue was purified by flash chromatography on silica gel using a gradient of ethyl acetate (20% to 60%) in heptane to provide 0.073 g (35%) of 2-chloro-1-(6-chloro-1H-indol-3-yl)-2-phenylethanone as a brown solid. ESI/APCI(+): 304, 306 (M+H); 326, 328 (M+Na). ESI/APCI(−): 302, 304 (M−H).

Step 2: 1-(6-Chloro-1H-indol-3-yl)-2-((3,5-dimethoxyphenyl)amino)-2-phenylethanone was prepared according to general procedure C from 2-chloro-1-(6-chloro-1H-indol-3-yl)-2-phenylethanone (0.073 g; 0.240 mmol), 3,5-dimethoxyaniline (0.100 g; 0.653 mmol) and DIPEA (0.200 mL; 1.148 mmol) in ethanol (2 mL), irradiated in a microwave oven at 180° C. for 30 min. Purification by flash chromatography on silica gel using a gradient of ethyl acetate (10% to 40%) in heptane followed by purification by preparative HPLC (XBridge column; method 2) furnished 0.010 g (10%) of the desired compound as a white solid. ESI/APCI (+): 421, 423 (M+H). ESI/APCI(−): 419, 421 (M−H). $^1$H NMR (CDCl$_3$) δ 8.63 (1H, brs); 8.30 (1H, d); 7.95 (1H, d); 7.48-7.51 (2H, m); 7.21-7.37 (6H, m); 5.84-5.87 (3H, m); 5.66 (1H, s); 5.49 (1H, br s); 3.70 (6H, s).

Example 14: Preparation of 1-(1H-indol-3-yl)-2-((3-methoxy-5-(trifluoromethyl)phenyl)amino)-2-phenylethanone 1-(1H-Indol-3-yl)-2-((3-methoxy-5-(trifluoromethyl)phenyl)amino)-2-phenylethanone was prepared according to general procedure C from 2-chloro-1-(1H-indol-3-yl)-2-phenylethanone (0.109 g; 0.404 mmol), 3-methoxy-5-(trifluoromethyl)aniline (0.108 g; 0.565 mmol) and DIPEA (0.100 mL; 0.574 mmol) in ethanol (2 mL), irradiated in a microwave oven at 180° C. for 30 min. Purification by flash chromatography on silica gel using a gradient of ethyl acetate (10% to 40%) in heptane followed by purification by preparative HPLC (XBridge column; method 1) furnished 0.024 g (14%) of the desired compound as a white solid. ESI/APCI(+): 425 (M+H); 447 (M+Na). ESI/APCI(−): 423 (M−H). $^1$H NMR (CDCl$_3$) δ 8.63 (1H, br s); 8.41 (1H, m); 7.99 (1H, d); 7.50-7.52 (2H, m); 7.21-7.38 (6H, m); 6.54 (1H, s); 6.42 (1H, s); 6.33 (1H, s); 5.84 (1H, br s); 5.70 (1H, m); 3.74 (3H, s).

Example 15: Preparation of 2-((3-fluoro-5-methoxyphenyl)amino)-1-(1H-indol-3-yl)-2-phenylethanone 2-((3-Fluoro-5-methoxyphenyl)amino)-1-(1H-indol-3-yl)-2-phenylethanone was prepared according to general procedure C from 2-chloro-1-(1H-indol-3-yl)-2-phenylethanone (0.105 g; 0.389 mmol), 3-methoxy-5-fluoroaniline (0.100 mL; 0.849 mmol) and DIPEA (0.100 mL; 0.574 mmol) in ethanol (2 mL), irradiated in a microwave oven at 180° C. for 30 min. Purification by flash chromatography on silica gel using a gradient of ethyl acetate (10% to 40%) in heptane followed by purification by preparative HPLC (XBridge column; method 1) furnished 0.047 g (32%) of the desired compound as a white solid. ESI/APCI(+): 375 (M+H); 397 (M+Na). ESI/APCI(−): 373 (M−H). $^1$H NMR (CDCl$_3$) δ 8.61 (1H, br s); 8.41 (1H, m); 8.00 (1H, d); 7.50-7.52 (2H, m); 7.25-7.33 (6H, m); 5.95-6.02 (3H, m); 5.68 (2H, m); 3.70 (3H, s).

Example 16: Preparation of 1-(1H-indol-3-yl)-2-phenyl-2-(pyridin-3-ylamino)ethanone 1-(1H-Indol-3-yl)-2-phenyl-2-(pyridin-3-ylamino)ethanone was prepared according to general procedure D from 2-chloro-1-(1H-indol-3-yl)-2-phenylethanone (0.107 g; 0.397 mmol), 3-aminopyridine (0.099 g; 1.052 mmol) and PS-DIPEA (solid support 3.56 mmol/g; 0.300 g; 1.068 mmoL) in acetonitrile (2 mL). Purification by flash chromatography on silica gel using a gradient of methanol (0% to 20%) in dichloromethane followed by purification by preparative HPLC (XBridge column; method 2) furnished 0.004 g (3%) of the desired compound as a beige amorphous solid. ESI/APCI(+): 328 (M+H). ESI/APCI(−): 326 (M−H). $^1$H NMR (CDCl$_3$) δ 8.70 (1H, br s); 8.37 (1H, m); 8.11 (1H, d); 7.99 (1H, d); 7.89 (1H, d); 7.48-7.51 (2H, m); 7.35 (1H, m); 7.19-7.29 (5H, m); 6.93-6.99 (2H, m); 5.67-5.72 (2H, m).

Example 17: Preparation of 1-(1H-indol-3-yl)-2-phenyl-2-(pyridin-4-ylamino)ethanone 1-(1H-Indol-3-yl)-2-phenyl-2-(pyridin-4-ylamino)ethanone was prepared according to general procedure D from 2-chloro-1-(1H-indol-3-yl)-2-phenylethanone (0.103 g; 0.382 mmol), 4-aminopyridine (0.098 g; 1.041 mmol) and PS-DIPEA (solid support 3.56 mmol/g; 0.295 g; 1.050 mmol) in acetonitrile (2 mL). Purification by flash chromatography on silica gel using a gradient of methanol (0% to 20%) in dichloromethane followed by purification by preparative HPLC (XBridge column; method 5) furnished 0.022 g (18%) of the desired compound as a beige solid. ESI/APCI(+): 328 (M+H). ESI/APCI(−): 326 (M−H). $^1$H NMR (CDCl$_3$) δ 8.32 (1H, m); 8.22 (1H, m); 8.05 (1H, d); 7.3-7.55 (11H, m); 6.80 (1H, d).

Example 18: Preparation of 1-(1H-indol-3-yl)-2-((3-methoxyphenyl)(methyl)amino)-2-phenylethanone 1-(1H-Indol-3-yl)-2-((3-methoxyphenyl)(methyl)amino)-2-phenylethanone was prepared according to general procedure D from 2-chloro-1-(1H-indol-3-yl)-2-phenylethanone (0.101 g; 0.374 mmol), N-methyl-3-methoxyaniline (0.100 mL; 0.752 mmoL) and PS-DIPEA (solid support 3.56 mmol/g; 0.292 g; 1.040 mmol) in acetonitrile (2 mL). Purification by flash chromatography on silica gel using a gradient of ethyl acetate (10% to 40%) in heptane followed by purification by preparative HPLC (XBridge column; method 1) furnished 0.011 g (8%) of the desired compound as a beige solid. ESI/APCI(+): 371 (M+H); 393 (M+Na). ESI/APCI (−): 369 (M−H). $^1$H NMR (CDCl$_3$) δ 8.41 (1H, m); 7.73 (1H, s); 7.13-7.41 (7H, m); 6.26-6.50 (4H, m); 3.77 (3H, s); 2.93 (3H, s).

Example 19: Preparation of 1-(1H-indol-3-yl)-2-((3-methoxyphenyl)amino)-2-(pyridin-3-yl)ethanone Step 1: tert-Butyl 3-formyl-1H-indole-1-carboxylate was prepared according to general procedure F from 1H-indole-3-carbaldehyde (3.770 g; 25.97 mmol), di-tert-butyl dicarbonate (6.800 g; 31.16 mmol) and DMAP (0.317 g; 2.595 mmol) in acetonitrile (70 mL) to afford 6.100 g (96%) of the desired compound as a yellow solid. $^1$H NMR (DMSO-d$_6$) δ 10.09 (1H, s); 8.66 (1H, s); 8.15 (2H, dd); 7.32-7.53 (2H, m); 1.68 (9H, s).

Step 2: 3-Methoxy-N-(pyridin-3-ylmethylene)aniline was prepared quantitatively according to general procedure G from 3-pyridinyl carboxaldehyde (0.179 mL; 1.867 mmol), magnesium sulfate (0.300 g; 2.492 mmol) and 3-methoxyaniline (0.230 g; 1.867 mmol) in ethanol (1 mL).

Step 3: 1-(1H-Indol-3-yl)-2-((3-methoxyphenyl)amino)-2-(pyridin-3-yl)ethanone was prepared according to general procedure K from a mixture of 3-benzyl-5-(2-hydroxyethyl)-4-methylthiazol-3-ium chloride (0.101 g; 0.373 mmol) and triethylamine (0.052 mL; 0.373 mmol) in ethanol (1 mL), tert-butyl 3-formyl-1H-indole-1-carboxylate (0.549 g; 2.239 mmol) and a solution 3-methoxy-N-(pyridin-3-ylmethylene)aniline (1.867 mmol) in ethanol (1 mL), heated at 70° C. for 2 days. Purification by flash chromatography on silica gel using a gradient of ethyl acetate (20% to 100%) in heptane followed by precipitation from acetonitrile furnished 0.050 g (8%) of the desired compound as a white solid. ESI/APCI(+): 358 (M+H). ESI/APCI(−): 356 (M−H).

Example 20: Preparation of 1-(1H-indol-3-yl)-2-((3-methoxyphenyl)amino)-2-(pyridin-4-yl)ethanone Step 1: 3-Methoxy-N-(pyridin-4-ylmethylene)aniline was prepared quantitatively according to general procedure G from 4-pyridinyl carboxaldehyde (0.179 mL; 1.867 mmol), magnesium sulfate (0.300 g; 2.492 mmol) and 3-methoxyaniline (0.230 g; 1.867 mmol) in ethanol (1 mL).

Step 2: 1-(1H-Indol-3-yl)-2-((3-methoxyphenyl)amino)-2-(pyridin-4-yl)ethanone was prepared according to general procedure K from a mixture of 3-benzyl-5-(2-hydroxyethyl)-4-methylthiazol-3-ium chloride (0.101 g; 0.373 mmol) and triethylamine (0.052 mL; 0.373 mmol) in ethanol (1 mL), tert-butyl 3-formyl-1H-indole-1-carboxylate (0.549 g; 2.239 mmol) and a solution of 3-methoxy-N-(pyridin-4-ylmethylene)aniline (1.867 mmol) in ethanol (1 mL), heated at 70° C. for 2 days. Purification by flash chromatography on silica gel using a gradient of ethyl acetate (20% to 100%) in heptane followed by precipitation from dichloromethane furnished 0.074 g (11%) of the desired compound as a white solid. ESI/APCI(+): 358 (M+H). ESI/APCI(−): 356 (M−H).

Example 21: Preparation of 1-(1H-indol-3-yl)-2-((3-methoxyphenyl)amino)-2-(4-(methylsulfonyl)phenyl)ethanone Step 1: 3-Methoxy-N-(4-(methylsulfonyl)benzylidene)aniline was prepared quantitatively according to general procedure G from 4-(methylsulfonyl)benzaldehyde (0.748 g; 4.061 mmol), magnesium sulfate (0.600 g; 4.985 mmol) and 3-methoxyaniline (0.500 g; 4.060 mmol) in ethanol (5 mL). ESI/APCI(+): 290 (M+H).

Step 2: 1-(1H-Indol-3-yl)-2-((3-methoxyphenyl)amino)-2-(4-(methylsulfonyl)phenyl)ethanone was prepared according to general procedure K from a mixture of 3-benzyl-5-(2-hydroxyethyl)-4-methylthiazol-3-ium chloride (0.056 g; 0.207 mmol) and triethylamine (0.029 mL; 0.207 mmol) in ethanol (1 mL), tert-butyl 3-formyl-1H-indole-1-carboxylate (0.305 g; 1.244 mmol) and a solution of 3-methoxy-N-(4-(methylsulfonyl)benzylidene)aniline (1.037 mmol) in ethanol (1 mL) heated at 70° C. for 2 days. Purification by flash chromatography on silica gel using a gradient of ethyl acetate (20% to 100%) in heptane followed by precipitation from dichloromethane furnished 0.048 g (10%) of the desired compound as a white solid. ESI/APCI (+): 435 (M+H). ESI/APCI(−): 433 (M−H).

Example 22: Preparation of 1-(1H-indol-3-yl)-2-((5-methylisoxazol-3-yl)amino)-2-phenylethanone Step 1: N-Benzylidene-5-methylisoxazol-3-amine was prepared according to general procedure G from benzaldehyde (0.193 mL; 2.039 mmol), magnesium sulfate (0.300 g; 2.492 mmol) and 3-amino-5-methylisoxazole (0.200 g; 2.039 mmol) in ethanol (2 mL).

Step 2: 1-(1H-Indol-3-yl)-2-((5-methylisoxazol-3-yl)amino)-2-phenylethanone was prepared according to general procedure K from a mixture of 3-benzyl-5-(2-hydroxyethyl)-4-methylthiazol-3-ium chloride (0.056 g; 0.207 mmol) and triethylamine (0.029 mL; 0.207 mmol) in ethanol (1 mL), tert-butyl 3-formyl-1H-indole-1-carboxylate (0.308 g; 1.257 mmol) and a solution of N-benzylidene-5-methylisoxazol-3-amine (1.047 mmol) in ethanol (1 mL), heated at 70° C. for 2 days. Purification by flash chromatography on silica gel using a gradient of ethyl acetate (20% to 100%) in heptane followed by purification by preparative HPLC (XBridge column, method 2) furnished 0.060 g (16%) of the desired compound as a white powder. ESI/APCI(+): 332 (M+H). ESI/APCI(−): 330 (M−H).

Example 23: Preparation of 2-(furan-2-yl)-1-(1H-indol-3-yl)-2-((3-methoxyphenyl)amino)ethanone Step 1: N-(Furan-2-ylmethylene)-3-methoxyaniline was prepared quantitatively according to general procedure G from 2-furaldehyde (0.390 g; 4.059 mmol), magnesium sulfate (0.733 g; 6.090 mmol) and 3-methoxyaniline (0.500 g; 4.060 mmol) in ethanol (5 mL). $^1$H NMR (DMSO-$d_6$) δ 8.45 (1H, s); 7.95 (1H, s); 7.24-7.41 (1H, m); 7.16 (1H, d); 6.77-6.87 (3H, m); 6.72 (1H, dd); 3.79 (3H, s).

Step 2: 2-(Furan-2-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.046 g; 0.170 mmol) and triethylamine (0.024 mL; 0.170 mmol) in ethanol (1 mL), tert-butyl 3-formyl-1H-indole-1-carboxylate (0.250 g; 1.019 mmol) and a solution of N-(furan-2-ylmethylene)-3-methoxyaniline (0.849 mmol) in ethanol (1 mL), heated at 70° C. for 2 days. Purification by flash chromatography on silica gel using a gradient of ethyl acetate (20% to 100%) in heptane followed by purification by preparative HPLC (XBridge column; method 1) furnished 0.058 g (19%) of the desired compound as a white solid. ESI/APCI(+): 347 (M+H). ESI/APCI(−): 345 (M−H).

Example 24: Preparation of 1-(1H-indol-3-yl)-2-((3-methoxyphenyl)amino)-2-(thiophen-2-yl)ethanone Step 1: 3-Methoxy-N-(thiophen-2-ylmethylene)aniline was prepared quantitatively according to general procedure G from 2-thiophenecarboxaldehyde (0.455 g; 4.057 mmol), magnesium sulfate (0.733 g; 6.090 mmol) and 3-methoxyaniline (0.500 g; 4.060 mmol) in ethanol (5 mL).

Step 2: 1-(1H-Indol-3-yl)-2-((3-methoxyphenyl)amino)-2-(thiophen-2-yl)ethanone was prepared according to general procedure K from a mixture of 3-benzyl-5-(2-hydroxyethyl)-4-methylthiazol-3-ium chloride (0.046 g; 0.170 mmol) and triethylamine (0.024 mL; 0.170 mmol) in ethanol (1 mL), tert-butyl 3-formyl-1H-indole-1-carboxylate (0.250 g; 1.019 mmol) and a solution of 3-methoxy-N-(thiophen-2-ylmethylene)aniline (0.185 g; 0.849 mmol) in ethanol (1 mL), heated at 70° C. for 2 days. Purification by flash chromatography on silica gel using a gradient of ethyl acetate (0% to 100%) in heptane followed by purification by preparative HPLC (XBridge column; method 2) furnished 0.058 g (7%) of the desired compound as an oil. ESI/APCI (+): 363 (M+H). ESI/APCI(−): 361 (M−H).

Example 25: Preparation of 1-(1H-indol-3-yl)-2-((3-methoxyphenyl)amino)-2-(5-methylisoxazol-3-yl)ethanone Step 1: 3-Methoxy-N-((5-methylisoxazol-3-yl)methylene)aniline was prepared quantitatively according to general procedure I from 5-methylisoxazole-3-carbaldehyde (0.151 g; 1.359 mmol) and 3-methoxyaniline (0.152 mL; 1.353 mmol). $^1$H NMR (DMSO-$d_6$) δ 8.69 (1H, s); 7.35 (1H, t); 6.85-6.97 (3H, m); 6.69 (1H, s); 3.81 (3H, s); 2.50 (3H, s).

Step 2: 1-(1H-Indol-3-yl)-2-((3-methoxyphenyl)amino)-2-(5-methylisoxazol-3-yl)ethanone was prepared according to general procedure K from a mixture of 3-benzyl-5-(2-hydroxyethyl)-4-methylthiazolium chloride (0.180 g; 0.667 mmol) and triethylamine (0.095 mL; 0.676 mmol) in ethanol (1 mL), tert-butyl 3-formyl-1H-indole-1-carboxylate (0.400 g; 1.631 mmol) and a solution of 3-methoxy-N-((5-methylisoxazol-3-yl)methylene)aniline (1.353 mmol) in ethanol (1 mL), heated at 70° C. for 24 h. Purification by flash chromatography on silica gel using a gradient of ethyl acetate (0% to 100%) in heptane followed by precipitation from diethyl ether furnished 0.142 g (29%) of the desired compound as a white powder. ESI/APCI(+): 362 (M+H). ESI/APCI(−): 360 (M−H).

Example 26: Preparation of 1-(1H-indol-3-yl)-2-((3-methoxyphenyl)amino)-2-(1-methyl-1H-imidazol-2-yl)ethanone Step 1: 3-Methoxy-N-((1-methyl-1H-imidazol-2-yl)methylene)aniline was prepared quantitatively according to general procedure I from 1-methyl-1H-imidazole-2-carbaldehyde (0.098 g; 0.890 mmol) and 3-methoxyaniline (0.100 mL; 0.890 mmol).

Step 2: 1-(1H-Indol-3-yl)-2-((3-methoxyphenyl)amino)-2-(1-methyl-1H-imidazol-2-yl)ethanone was prepared according to general procedure K from a mixture of 3-benzyl-5-(2-hydroxyethyl)-4-methylthiazol-3-ium chloride (0.120 g; 0.445 mmol) and triethylamine (0.065 mL; 0.462 mmol) in ethanol (1 mL), tert-butyl 3-formyl-1H-indole-1-carboxylate (0.265 g; 1.080 mmol) and a solution of 3-methoxy-N-((1-methyl-1H-imidazol-2-yl)methylene)aniline (0.890 mmol) in ethanol (0.5 mL), heated at 70° C. for 3 days. Purification by flash chromatography on silica gel using a gradient of ethyl acetate (50% to 100%) in heptane followed by precipitation from diethyl ether furnished 0.065 g (22%) of the desired compound as a white powder. ESI/APCI(+): 361 (M+H). ESI/APCI(−): 359 (M−H).

Example 27: Preparation of 1-(1H-indol-3-yl)-2-((3-methoxyphenyl)amino)-2-(thiophen-3-yl)ethanone Step 1: 3-Methoxy-N-(thiophen-3-ylmethylene)aniline was prepared quantitatively according to general procedure I from thiophene-3-carbaldehyde (0.120 mL; 1.370 mmol) and 3-methoxyaniline (0.152 mL; 1.353 mmol).

Step 2: 1-(1H-Indol-3-yl)-2-((3-methoxyphenyl)amino)-2-(thiophen-3-yl)ethanone was prepared according to general procedure K from a mixture of 3-benzyl-5-(2-hydroxyethyl)-4-methylthiazol-3-ium chloride (0.180 g; 0.667 mmol) and triethylamine (0.095 mL; 0.676 mmol) in ethanol (1 mL), tert-butyl 3-formyl-1H-indole-1-carboxylate (0.400 g; 1.631 mmol) and 3-methoxy-N-(thiophen-3-ylmethylene)aniline (1.353 mmol) in ethanol (1 mL), heated at 70° C. for 24 h. Purification by flash chromatography on silica gel using a gradient of ethyl acetate (0% to 50%) in heptane followed by precipitation from diethyl ether furnished 0.076 g (15%) of the desired compound as a pale yellow powder. ESI/APCI(+): 363 (M+H). ESI/APCI(−): 361 (M−H).

Example 28: Preparation of 2-(1H-imidazol-2-yl)-1-(1H-indol-3-yl)-2-((3-methoxyphenyl)amino)ethanone Step 1: N-((1H-Imidazol-2-yl)methylene)-3-methoxyaniline was prepared according to general procedure I from 1H-imidazole-2-carbaldehyde (0.086 g; 0.895 mmol) and 3-methoxyaniline (0.100 mL; 0.890 mmol).

Step 2: 2-(1H-Imidazol-2-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.120 g; 0.445 mmol) and triethylamine (0.065 mL; 0.462 mmol) in ethanol (1 mL), tert-butyl 3-formyl-1H-indole-1-carboxylate (0.265 g; 1.080 mmol) and N-((1H-imidazol-2-yl)methylene)-3-methoxyaniline (0.890 mmol) in ethanol (0.5 mL), heated at 70° C. for 3 days. Purification by precipitation from methanol furnished 0.046 g (15%) of the desired compound as a pale brown solid. ESI/APCI(+): 347 (M+H). ESI/APCI(−): 345 (M−H).

Example 29: Preparation of 1-(1H-indol-3-yl)-2-((3-methoxyphenyl)amino)-2-(pyrimidin-5-yl)ethanone Step 1: 3-Methoxy-N-(pyrimidin-5-ylmethylene)aniline was prepared quantitatively according to general procedure I from pyrimidine-5-carboxaldehyde (0.115 g; 1.064 mmol) and 3-methoxyaniline (0.120 mL; 1.068 mmol).

Step 2: 1-(1H-Indol-3-yl)-2-((3-methoxyphenyl)amino)-2-(pyrimidin-5-yl)ethanone was prepared according to general procedure K from a mixture of 3-benzyl-5-(2-hydroxyethyl)-4-methylthiazol-3-ium chloride (0.144 g; 0.534 mmol) and triethylamine (0.100 mL; 0.712 mmol) in ethanol (1 mL), tert-butyl 3-formyl-1H-indole-1-carboxylate (0.295 g; 1.203 mmol) and a solution of 3-methoxy-N-(pyrimidin-5-ylmethylene)aniline (1.064 mmol) in ethanol (0.5 mL), heated at 70° C. for 24 h. Purification by flash chromatography on silica gel using a gradient of ethyl acetate (50% to 100%) in heptane followed by precipitation from diethyl ether furnished 0.065 g (17%) of the desired compound as a beige powder. ESI/APCI(+): 359 (M+H). ESI/APCI(−): 357 (M−H).

Example 30: Preparation of 2-(imidazo[1,2-a]pyridin-2-yl)-1-(1H-indol-3-yl)-2-((3-methoxyphenyl)amino)ethanone Step 1: N-(Imidazo[1,2-a]pyridin-2-ylmethylene)-3-methoxyaniline was prepared quantitatively according to general procedure I from imidazo[1,2-a]pyridine-2-carbaldehyde (0.156 g; 1.067 mmol) and 3-methoxyaniline (0.120 mL; 1.068 mmol).

Step 2: 2-(Imidazo[1,2-a]pyridin-2-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.144 g; 0.534 mmol) and triethylamine (0.100 mL; 0.712 mmol) in ethanol (1 mL), tert-butyl 3-formyl-1H-indole-1-carboxylate (0.295 g; 1.203 mmol) and a solution of N-(imidazo[1,2-a]pyridin-2-ylmethylene)-3-methoxyaniline (1.067 mmol) in ethanol (0.5 mL), heated at 70° C. for 24 h. Purification by flash chromatography on silica gel using a gradient of ethyl acetate (50% to 100%) in heptane followed by precipitation from diethyl ether furnished 0.111 g (28%) of the desired compound as a beige powder. ESI/APCI(+): 397 (M+H). ESI/APCI(−): 395 (M−H).

Example 31: Preparation of 2-((2-hydroxypyridin-4-yl)amino)-1-(1H-indol-3-yl)-2-phenylethanone A mixture of 2-chloro-1-(1H-indol-3-yl)-2-phenylethanone (0.104 g; 0.386 mmol), 2-methoxypyridin-4-amine (0.100 g; 0.806 mmol) and DIPEA (0.100 mL; 0.574 mmol) in acetonitrile (2 mL) was irradiated in a microwave oven at 120° C. for 60 min. The reaction mixture was concentrated under reduced pressure and the residue was purified by flash chromatography on silica gel using a gradient of methanol (2% to 20%) in dichloromethane. Further purification by recrystallization from dichloromethane furnished 0.017 g (13%) of 2-((2-hydroxypyridin-4-yl)amino)-1-(1H-indol-3-yl)-2-phenylethanone as a white solid. ESI/APCI(+): 344 (M+H); 366 (M+Na). ESI/APCI(−): 342 (M−H). $^1$H NMR (DMSO-$d_6$) δ 11.99 (1H, s); 8.27 (1H, s); 8.18 (1H, m); 7.2-7.5 (7H, m); 6.89 (1H, d); 6.09 (2H, s); 5.64 (1H, d); 5.29 (1H, s).

Example 32: Preparation of 1-(1H-indol-3-yl)-2-phenyl-2-((pyridin-2-ylmethyl)amino)ethanone 1-(1H-Indol-3-yl)-2-phenyl-2-((pyridin-2-ylmethyl)amino)ethanone was prepared according to general procedure C from 2-chloro-1-(1H-indol-3-yl)-2-phenylethanone (0.108 g; 0.400 mmol), pyridin-2-ylmethanamine (0.100 mL; 0.970 mmol) and DIPEA (0.100 mL; 0.574 mmol) in acetonitrile (2 mL), irradiated in a microwave oven at 200° C. for 30 min. Purification by flash chromatography on silica gel using a gradient of ethyl acetate (10% to 100%) in heptane followed by recrystallization from dichloromethane furnished 0.003 g (2%) of the desired compound as a solid. ESI/APCI(+): 342 (M+H). ESI/APCI(−): 340 (M−H). $^1$H NMR (MeOD) δ 8.46 (1H, m); 8.37 (1H, m); 7.91 (1H, s); 7.69 (1H, m); 7.20-7.46 (10H, m); 5.16 (1H, s); 3.90 (2H, m).

Example 33: Preparation of 1-(1H-indol-3-yl)-2-phenyl-2-((thiophen-2-ylmethyl)amino)ethanone 1-(1H-Indol-3-yl)-2-phenyl-2-((thiophen-2-ylmethyl)amino)ethanone was prepared according to general procedure C from 2-chloro-1-(1H-indol-3-yl)-2-phenylethanone (0.111 g; 0.412 mmol), thiophen-2-ylmethanamine (0.100 mL; 0.972 mmol) and DIPEA (0.200 mL; 1.148 mmol) in acetonitrile (2 mL), irradiated in a microwave oven at 200° C. for 30 min. Purification by flash chromatography on silica gel using a gradient of methanol (2% to 20%) in dichloromethane followed by recrystallization from dichloromethane furnished 0.021 g (15%) of the desired compound as a solid. ESI/APCI(+): 347 (M+H); 369 (M+Na). ESI/APCI(−): 345 (M−H). $^1$H NMR (DMSO-$d_6$) δ 12.01 (1H, br s); 8.50 (1H, s); 8.18 (1H, m); 7.14-7.58 (9H, m); 6.38 (1H, s); 6.24 (1H, s); 5.25 (1H, s); 3.67 (2H, s).

Example 34: Preparation of 2-((furan-2-ylmethyl)amino)-1-(1H-indol-3-yl)-2-phenylethanone 2-((Furan-2-ylmethyl)amino)-1-(1H-indol-3-yl)-2-phenylethanone was prepared according to general procedure C from 2-chloro-1-(1H-indol-3-yl)-2-phenylethanone (0.103 g; 0.382 mmol), furan-2-ylmethanamine (0.100 mL; 0.382 mmol) and DIPEA (0.200 mL; 1.148 mmol) in acetonitrile (2 mL) was irradiated in a microwave oven at 200° C. for 30 min. Purification by flash chromatography on silica gel using a gradient of methanol (2% to 20%) in dichloromethane followed by recrystallization from dichloromethane furnished 0.040 g (32%) of the desired compound as a solid. ESI/APCI(+): 331 (M+H); 353 (M+Na). ESI/APCI(−): 329 (M−H). $^1$H NMR (DMSO-$d_6$) δ 12.01 (1H, br s); 8.49 (1H, s); 8.20 (1H, m); 7.16-7.53 (9H, m); 6.89-6.93 (2H, m); 5.27 (1H, s); 3.80 (2H, s).

Example 35: Preparation of 3-((2-(1H-indol-3-yl)-2-oxo-1-phenylethyl)amino)benzonitrile 3-((2-(1H-Indol-3-yl)-2-oxo-1-phenylethyl)amino)benzonitrile was prepared according to general procedure C from 2-chloro-1-(1H-indol-3-yl)-2-phenylethanone (0.100 g; 0.371 mmol), 3-aminobenzonitrile (0.098 g; 0.830 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (5% to 40%) in heptane followed by recrystallization from dichloromethane furnished 0.007 g (5%) of the desired compound as a solid. ESI/APCI(+): 352 (M+H). ESI/APCI(−): 350 (M−H). $^1$H NMR (CDCl$_3$) δ 8.59 (1H, brs); 8.40 (1H, m); 8.01 (1H, s); 7.51 (2H, d); 7.17-7.41 (7H, m); 6.84-6.91 (3H, m); 5.70 (1H, s).

Example 36: Preparation of 4-(2-(1H-indol-3-yl)-1-((3-methoxyphenyl)amino)-2-oxoethyl)benzonitrile Step 1: 4-(((3-Methoxyphenyl)imino)methyl)benzonitrile was prepared quantitatively according to general procedure I from 4-formyl-benzonitrile (0.135 g; 1.030 mmol) and 3-methoxyaniline (0.116 mL; 1.030 mmol).

Step 2: 4-(2-(1H-Indol-3-yl)-1-((3-methoxyphenyl)amino)-2-oxoethyl)benzonitrile was prepared according to general procedure K from a mixture of 3-benzyl-5-(2-hydroxyethyl)-4-methylthiazolium chloride (0.144 g; 0.534 mmol) and triethylamine (0.100 mL; 0.717 mmol) in ethanol (1 mL), tert-butyl 3-formyl-1H-indole-1-carboxylate (0.252 g; 1.028 mmol) and a solution of 4-(((3-methoxyphenyl)imino)methyl)benzonitrile (1.030 mmol) in ethanol (0.5 mL), heated at 70° C. for 24 h. Purification by flash chromatography on silica gel using a gradient of ethyl acetate (5% to 60%) in heptane followed by precipitation from diethyl ether furnished 0.203 g (52%) of the desired compound as a pale yellow solid. ESI/APCI(+): 382 (M+H). ESI/APCI(−): 380 (M−H).

Example 37: Preparation of 1-(1H-indol-3-yl)-2-((3-methoxyphenyl)amino)-2-(quinoxalin-6-yl)ethanone Step 1: 3-Methoxy-N-(quinoxalin-6-ylmethylene)aniline was prepared quantitatively according to general procedure I from quinoxaline-6-carbaldehyde (0.100 g; 0.632 mmol) and 3-methoxyaniline (0.071 mL; 0.632 mmol).

Step 2: 1-(1H-Indol-3-yl)-2-((3-methoxyphenyl)amino)-2-(quinoxalin-6-yl)ethanone was prepared according to general procedure K from a mixture of 3-benzyl-5-(2-hydroxyethyl)-4-methylthiazol-3-ium chloride (0.135 g; 0.491 mmol) and triethylamine (0.055 mL; 0.397 mmol) in ethanol (0.7 mL), tert-butyl 3-formyl-1H-indole-1-carboxylate (0.155 g; 0.630 mmol) and a solution of 3-methoxy-N-(quinoxalin-6-ylmethylene)aniline (0.632 mmol) in ethanol (0.7 mL), heated at 70° C. for 18 h. Purification by flash chromatography on silica gel using a gradient of ethyl acetate (50% to 100%) in heptane followed by precipitation from methanol furnished 0.069 g (27%) of the desired compound as a yellow solid. ESI/APCI(+): 409 (M+H). ESI/APCI(−): 408 (M−H).

Example 38: Preparation of 1-(1H-indol-3-yl)-2-((2-methoxyphenyl)amino)-2-phenylethanone 1-(1H-Indol-3-yl)-2-((2-methoxyphenyl)amino)-2-phenylethanone was prepared according to general procedure C from 2-chloro-1-(1H-indol-3-yl)-2-phenylethanone (0.109 g; 0.404 mmol), 2-methoxyaniline (0.100 mL; 0.893 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (10% to 40%) in heptane followed by recrystallization from dichloromethane furnished 0.013 g (9%) of the desired compound as white crystals. ESI/APCI (+): 357 (M+H); 379 (M+Na). ESI/APCI(−): 355 (M−H). $^1$H NMR (CDCl$_3$) δ 8.55 (1H, br s); 8.42 (1H, m); 8.05 (1H, s); 7.54 (2H, d); 7.20-7.38 (6H, m); 6.57-6.78 (4H, m); 5.72 (1H, s); 3.88 (3H, s).

Example 39: Preparation of 2-((2,5-dimethoxyphenyl)amino)-1-(1H-indol-3-yl)-2-phenylethanone 2-((2,5-Dimethoxyphenyl)amino)-1-(1H-indol-3-yl)-2-phenylethanone was prepared according general procedure C from 2-chloro-1-(1H-indol-3-yl)-2-phenylethanone (0.110 g; 0.408 mmol), 2,5-dimethoxyaniline (0.102 g; 0.666 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (10% to 40%) in heptane followed by recrystallization from dichloromethane furnished 0.009 g (6%) of the desired compound as a white solid. ESI/APCI(+): 387 (M+H); 409 (M+Na). ESI/APCI (−): 385 (M−H). $^1$H NMR (CDCl$_3$) δ 8.62 (1H, br s); 8.41 (1H, m); 7.98 (1H, s); 7.52 (2H, d); 7.19-7.37 (5H, m); 6.66 (1H, d); 6.10-6.18 (2H, m); 5.67 (1H, s); 5.30 (1H, s); 3.84 (3H, s); 3.66 (3H, s).

Example 40: Preparation of 2-((2,3-dimethoxyphenyl)amino)-1-(1H-indol-3-yl)-2-phenylethanone 2-((2,3-Dimethoxyphenyl)amino)-1-(1H-indol-3-yl)-2-phenylethanone was prepared according general procedure C from 2-chloro-1-(1H-indol-3-yl)-2-phenylethanone (0.044 g; 0.163 mmol), 2,3-dimethoxyaniline (0.050 mL; 0.326 mmol) and DIPEA (0.100 mL; 0.574 mmol) in acetonitrile (2 mL), irradiated in a microwave oven at 200° C. for 30 min. Purification by flash chromatography on silica gel using a gradient of ethyl acetate (10% to 40%) in heptane followed by recrystallization from dichloromethane furnished 0.008 g (13%) of the desired compound as white crystals. ESI/APCI(+): 387 (M+H); 409 (M+Na). ESI/APCI (−): 385 (M−H). $^1$H NMR (CDCl$_3$) δ 8.54 (1H, br s); 8.42 (1H, m); 8.03 (1H, s); 7.52 (2H, d); 7.20-7.38 (6H, m); 6.81 (1H, m); 6.29 (2H, m); 5.75 (1H, s); 3.89 (3H, s); 3.82 (3H, s).

Example 41: Preparation of 3-(2-(1H-indol-3-yl)-1-((3-methoxyphenyl)amino)-2-oxoethyl)benzonitrile Step 1: 3-(((3-Methoxyphenyl)imino)methyl)benzonitrile was prepared quantitatively according to general procedure I from 3-formylbenzonitrile (0.135 g; 1.030 mmol) and 3-methoxyaniline (0.116 mL; 1.032 mmol).

Step 2: 3-(2-(1H-Indol-3-yl)-1-((3-methoxyphenyl)amino)-2-oxoethyl)benzonitrile was prepared according to general procedure L from a mixture of 3-benzyl-5-(2-hydroxyethyl)-4-methylthiazol-3-ium chloride (0.144 g; 0.534 mmol) and triethylamine (0.100 mL; 0.712 mmol) in ethanol (1 mL), tert-butyl 3-formyl-1H-indole-1-carboxylate (0.252 g; 1.028 mmol) and a solution of 3-(((3-methoxyphenyl)imino)methyl)benzonitrile (1.030 mmol) in ethanol (0.5 mL), heated at 70° C. for 3 days. Purification by flash chromatography on silica gel using a gradient of ethyl acetate (0% to 50%) in heptane followed by precipitation from diethyl ether furnished 0.077 g (20%) of the desired compound as a solid. ESI/APCI(+): 382 (M+H). ESI/APCI (−): 380 (M−H).

Example 42: Preparation of 1-(1H-indol-3-yl)-2-((3-methoxyphenyl)amino)-2-(1-methyl-1H-pyrazol-4-yl)ethanone Step 1: 3-Methoxy-N-((1-methyl-1H-pyrazol-4-yl)methylene)aniline was prepared quantitatively according to general procedure I from 1-methyl-1H-pyrazole-4-carbaldehyde (0.110 g; 0.999 mmol) and 3-methoxyaniline (0.112 mL; 0.999 mmol).

Step 2: 3-(2-(1H-Indol-3-yl)-1-((3-methoxyphenyl)amino)-2-oxoethyl)benzonitrile was prepared according to general procedure K from a mixture of 3-benzyl-5-(2- hydroxyethyl)-4-methylthiazol-3-ium chloride (0.135 g; 0.500 mmol) and triethylamine (0.100 mL; 0.712 mmol) in ethanol (1 mL), tert-butyl 3-formyl-1H-indole-1-carboxylate (0.245 g; 0.999 mmol) and a solution of 3-methoxy-N-((1-methyl-1H-pyrazol-4-yl)methylene)aniline (0.999 mmol) in ethanol (0.5 mL), heated at 70° C. for 24 h. After concentration of the reaction mixture under reduced pressure, purification by precipitation from dichloromethane furnished 0.219 g (61%) of the desired compound as a white solid. ESI/APCI(+): 361 (M+H). ESI/APCI(−): 359 (M−H).

Example 43: Preparation of 1-(1H-indol-3-yl)-2-((3-methoxyphenyl)amino)-2-(pyrazolo[1,5-a]pyridin-7-yl)ethanone Step 1: 3-Methoxy-N-(pyrazolo[1,5-a]pyridin-7-ylmethylene)aniline was prepared quantitatively according to general procedure I from pyrazolo[1,5-a]pyridine-7-carbaldehyde (0.100 g; 0.684 mmol) and 3-methoxyaniline (0.077 mL; 0.685 mmol). ESI/APCI (+): 252 (M+H).

Step 2: 1-(1H-Indol-3-yl)-2-((3-methoxyphenyl)amino)-2-(pyrazolo[1,5-a]pyridin-7-yl)ethanone was prepared according to general procedure K from a mixture of 3-benzyl-5-(2-hydroxyethyl)-4-methylthiazol-3-ium chloride (0.095 g; 0.352 mmol) and triethylamine (0.070 mL; 0.502 mmol) in ethanol (1 mL), tert-butyl 3-formyl-1H-indole-1-carboxylate (0.168 g; 0.684 mmol) and 3-methoxy-N-(pyrazolo[1,5-a]pyridin-7-ylmethylene)aniline (0.684 mmol) in ethanol (0.5 mL) heated at 50° C. for 3 days. After concentration of the reaction mixture under reduced pressure, methanol was added. The resulting precipitate was filtered. The filtrate was concentrated under reduced pressure. The residue was purified by flash chromatography on silica gel using a gradient of ethyl acetate (0% to 50%) in heptane followed by precipitation from diethyl ether furnished 0.095 g (35%) of the desired compound as a yellow solid. ESI/APCI(+): 397 (M+H). ESI/APCI(−): 395 (M−H).

Example 44: Preparation of 1-(1H-indol-3-yl)-2-((3-(methylsulfonyl)phenyl)amino)-2-phenylethanone 1-(1H-Indol-3-yl)-2-((3-(methylsulfonyl)phenyl)amino)-2-phenylethanone was prepared according general procedure C from 2-chloro-1-(1H-indol-3-yl)-2-phenylethanone (0.100 g; 0.371 mmol), 3-(methylsulfonyl)aniline hydrochloride (0.112 g; 0.539 mmol) and DIPEA (0.300 mL; 1.722 mmol) in acetonitrile (2 mL), irradiated in a microwave oven at 200° C. for 30 min. Purification by flash chromatography on silica gel using a gradient of ethyl acetate (30% to 100%) in heptane furnished 0.017 g (11%) of the desired compound as an amorphous crystals. ESI/APCI(+): 405 (M+H); 427 (M+Na); ESI/APCI(−): 403 (M−H).

Example 45: Preparation of 1-(1H-indol-3-yl)-2-((2-methoxypyridin-4-yl)amino)-2-phenylethanone Step 1: N-Benzylidene-2-methoxypyridin-4-amine was prepared quantitatively according to general procedure I from benzaldehyde (2.027 mL; 20.01 mmol) and 2-methoxypyridin-4-amine (2.483 g; 20.01 mmol).

Step 2: 1-(1H-Indol-3-yl)-2-((2-methoxypyridin-4-yl)amino)-2-phenylethanone was prepared according to general procedure L from a mixture of 3-benzyl-5-(2-hydroxyethyl)-4-methylthiazol-3-ium chloride (0.125 g; 0.463 mmol) and triethylamine (0.100 mL; 0,717 mmol) in ethanol (1 mL), tert-butyl 3-formyl-1H-indole-1-carboxylate (0.197 g; 0.803 mmol) and a solution of N-benzylidene-2-methoxypyridin-4-amine (0.803 mmol) in ethanol (2 mL), heated at 70° C. for 65 h. Purification by flash chromatography on silica gel using a gradient of ethyl acetate (30% to 100%) in heptane followed by recrystallization from dichloromethane furnished 0.015 g (5%) of the desired compound as a solid. ESI/APCI(+): 358 (M+H); 380 (M+Na). ESI/APCI(−): 356 (M−H). $^1$H NMR (CDCl$_3$) δ 9.39 (1H, brs); 8.42 (1H, d); 7.87 (2H, s); 7.48 (2H, d); 7.20-7.35 (4H, m); 6.40 (1H, d); 6.20 (1H, m); 6.01 (1H, s); 5.87 (1H, d); 5.29 (1H, s); 3.76 (3H, s).

Example 46: Preparation of 2-((3-ethylphenyl)amino)-1-(1H-indol-3-yl)-2-phenylethanone 2-((3-Ethylphenyl)amino)-1-(1H-indol-3-yl)-2-phenylethanone was prepared according to general procedure C from 2-chloro-1-(1H-indol-3-yl)-2-phenylethanone (0.106 g; 0.393 mmol), 3-ethylaniline (0.100 mL; 0.805 mmol) and DIPEA (0.200 mL; 1.148 mmol) in acetonitrile (2 mL) irradiated in a microwave oven at 200° C. for 30 min. Purification by flash chromatography on silica gel using a gradient of ethyl acetate (5% to 40%) in heptane followed by recrystallization from dichloromethane furnished 0.028 g (20%) of the desired compound as a solid. ESI/APCI(+): 355 (M+H); 377 (M+Na). ESI/APCI(−): 353 (M−H). $^1$H NMR (CDCl$_3$) δ 8.55 (1H, br s); 8.40 (1H, m); 8.02 (1H, s); 7.54 (2H, d); 7.20-7.40 (6H, m); 7.04 (1H, m); 6.51-6.55 (3H, m); 5.72 (1H, s); 5.46 (1H, brs); 2.57 (2H, q); 1.17 (3H, t).

Example 47: Preparation of 1-(1H-indol-3-yl)-2-(isoquinolin-5-yl)-2-((3-methoxyphenyl)amino)ethanone Step 1: N-(Isoquinolin-5-ylmethylene)-3-methoxyaniline was prepared quantitatively according to general procedure I from isoquinoline-5-carbaldehyde (0.119 g; 0.757 mmol) and 3-methoxyaniline (0.087 mL; 0.774 mmol).

Step 2: 1-(1H-Indol-3-yl)-2-(isoquinolin-5-yl)-2-((3-methoxyphenyl)amino)ethanone was prepared according to general procedure K from a mixture of 3-benzyl-5-(2-hydroxyethyl)-4-methylthiazol-3-ium chloride (0.100 g; 0.371 mmol) and triethylamine (0.080 mL; 0.574 mmol) in ethanol (1 mL), tert-butyl 3-formyl-1H-indole-1-carboxylate (0.186 g; 0.759 mmol) and a solution of N-(isoquinolin-5-ylmethylene)-3-methoxyaniline (0.757 mmol) in ethanol (0.5 mL), heated at 60° C. for 2 days. After concentration of the reaction mixture under reduced pressure, purification by precipitation from methanol furnished 0.093 g (30%) of the desired compound as a white powder. ESI/APCI (+): 408 (M+H). ESI/APCI (−): 406 (M−H).

Example 48: Preparation of 1-(1H-indol-3-yl)-2-((3-methoxyphenyl)amino)-2-(4-(pyrimidin-5-yl)phenyl)ethanone Step 1: 3-Methoxy-N-(4-(pyrimidin-5-yl)benzylidene)aniline was prepared quantitatively according to general procedure I from 5-(4-formylphenyl)pyrimidine (0.125 g; 0.679 mmol) and 3-methoxyaniline (0.076 mL; 0.679 mmol). ESI/APCI (+): 290 (M+H).

Step 2: 1-(1H-Indol-3-yl)-2-((3-methoxyphenyl)amino)-2-(4-(pyrimidin-5-yl)phenyl)ethanone was prepared according to general procedure L from a mixture of 3-benzyl-5-(2-hydroxyethyl)-4-methylthiazol-3-ium chloride (0.090 g; 0.334 mmol) and triethylamine (0.070 mL; 0.502 mmol) in ethanol (1 mL), tert-butyl 3-formyl-1H-indole-1-carboxylate (0.166 g; 0.677 mmol) and a solution of 3-methoxy-N-(4-(pyrimidin-5-yl)benzylidene)aniline (0.679 mmol) in ethanol (0.5 mL), heated at 75° C. for 3.5 days. Purification by flash chromatography on silica gel using a gradient of ethyl acetate (0% to 100%) in heptane followed by precipitation from diethyl ether and dichloromethane furnished 0.061 g (21%) of the desired compound as a pale yellow solid. ESI/APCI (+): 435 (M+H). ESI/APCI (−): 433 (M−H).

Example 49: Preparation of 2-((3-methoxyphenyl) amino)-1-(1-methyl-1H-indol-3-yl)-2-phenylethanone This compound has been prepared according to 2 different procedures described hereunder as method A and method B.

Method A:

Step 1: N-Benzylidene-3-methoxyaniline was prepared quantitatively according to general procedure G from benzaldehyde (3.030 mL; 29.98 mmol), 3-methoxyaniline (3.690 mL; 32.84 mmol) and magnesium sulfate (3.610 g; 29.99 mmol) in ethanol (15 mL). $^1$H NMR (DMSO-$d_6$) δ 8.63 (1H, s); 7.95 (2H, dd); 7.47-7.63 (3H, m); 7.32 (1H, t); 6.75-6.93 (3H, m); 3.80 (3H, s).

Step 2: 2-((3-Methoxyphenyl)amino)-1-(1-methyl-1H-indol-3-yl)-2-phenylethanone was prepared according to general procedure L from a mixture of 3-benzyl-5-(2-hydroxyethyl)-4-methylthiazol-3-ium chloride (0.169 g; 0.628 mmol) and triethylamine (0.088 mL; 0.628 mmol) in ethanol (2 mL), 1-methyl-1H-indole-3-carbaldehyde (0.200 g; 1.256 mmol) and a solution of N-benzylidene-3-methoxyaniline (1.256 mmol) in ethanol (1 mL), heated at 70° C. for 2 days. Purification by flash chromatography on silica gel using a gradient of ethyl acetate (0% to 100%) in heptane followed by purification by preparative HPLC (XBridge column; method 1) furnished 0.028 g (6%) of the desired compound as a white foam. ESI/APCI(+): 371 (M+H).

Method B:

Step 1: 2-Chloro-1-(1-methyl-1H-indol-3-yl)-2-phenylethanone was prepared according to general method M from 2-chloro-1-(1H-indol-3-yl)-2-phenylethanone (0.200 g; 0.741 mmol), methyliodide (0.166 mL; 2.573 mmol) and potassium carbonate (0.205 g; 1.476 mmol) in DMF (5 mL) The reaction mixture was stirred at room temperature for 3 h. Purification by flash chromatography on silica gel using a gradient of ethyl acetate (2% to 40%) in heptane furnished 0.140 g (66%) of the desired compound as a beige solid. ESI/APCI(+): 284, 286 (M+H); 306, 308 (M+Na).

Step 2: 2-((3-Methoxyphenyl)amino)-1-(1-methyl-1H-indol-3-yl)-2-phenylethanone was prepared according to general procedure C from 2-chloro-1-(1-methyl-1H-indol-3-yl)-2-phenylethanone (0.140 g; 0.493 mmol), 3-methoxyaniline (0.110 mL; 0.987 mmol) and DIPEA (0.169 mL; 0.987 mmol) in acetonitrile (1.5 mL), irradiated in a microwave oven at 200° C. for 1.5 h. After standing at room temperature for 24 h, the formed precipitate was filtered. The filtrate was concentrated under reduced pressure. The residue was purified by flash chromatography on silica gel using dichloromethane as eluent. Further purification by preparative TLC using dichloromethane as eluent furnished 0.011 g (6%) of the desired compound as a beige solid. ESI/APCI (+): 371 (M+H).

Example 50: Preparation of 1-(1H-indol-3-yl)-2-phenyl-2-(quinoxalin-6-ylamino)ethanone 1-(1H-Indol-3-yl)-2-phenyl-2-(quinoxalin-6-ylamino) ethanone was prepared according to general procedure C from 2-chloro-1-(1H-indol-3-yl)-2-phenylethanone (0.101 g; 0.374 mmol), quinoxalin-6-amine (0.094 g; 0.648 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (30% to 100%) in heptane, followed by purification by preparative HPLC (XBridge column; method 2) furnished 0.008 g (6%) of the desired compound as an orange solid. ESI/APCI(+): 379 (M+H). ESI/APCI(−): 377 (M−H).

Example 51: Preparation of 3-((2-(1H-indol-3-yl)-2-oxo-1-phenylethyl)amino)-N,N-dimethylbenzamide 3-((2-(1H-Indol-3-yl)-2-oxo-1-phenylethyl)amino)-N,N-dimethylbenzamide was prepared according to general procedure C from 2-chloro-1-(1H-indol-3-yl)-2-phenylethanone (0.099 g; 0.367 mmol), 3-amino-N,N-dimethylbenzamide (0.095 g; 0.579 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (30% to 100%) in heptane, followed by purification by preparative HPLC (XBridge column; method 2) furnished 0.028 g (19%) of the desired compound as a pink solid. ESI/APCI(+): 398 (M+H). ESI/APCI(−): 396 (M−H).

Example 52: Preparation of 3-((2-(1H-indol-3-yl)-2-oxo-1-phenylethyl)amino)-N-methylbenzenesulfonamide 3-((2-(1H-Indol-3-yl)-2-oxo-1-phenylethyl)amino)-N-methylbenzenesulfonamide was prepared according to general procedure C from 2-chloro-1-(1H-indol-3-yl)-2-phenylethanone (0.096 g; 0.356 mmol), 3-amino-N-methylbenzenesulfonamide hydrochloride (0.101 g; 0.454 mmol) and DIPEA (0.300 mL; 1.722 mmol) in acetonitrile (2 mL), irradiated in a microwave oven at 200° C. for 30 min. Purification by flash chromatography on silica gel using a gradient of ethyl acetate (30% to 100%) in heptane followed by purification by preparative HPLC (XBridge column; method 2) furnished 0.006 g (4%) of the desired compound as an orange solid. ESI/APCI(+): 420 (M+H). ESI/APCI(−): 418 (M−H).

Example 53: Preparation of 1-(4-chloro-1H-indol-3-yl)-2-((3-methoxyphenyl)amino)-2-phenylethanone Step 1: tert-Butyl 4-chloro-3-formyl-1H-indole-1-carboxylate was prepared according to general procedure F from 4-chloro-1H-indole-3-carbaldehyde (0.310 g; 1.726 mmol), di-tert-butyl dicarbonate (0.451 g; 2.066 mmol) and DMAP (0.021 g; 0.172 mmol) in acetonitrile (4 mL) to afford 0.431 g (89%) of the desired compound.

Step 2: 1-(4-Chloro-1H-indol-3-yl)-2-((3-methoxyphenyl)amino)-2-phenylethanone was prepared according to general procedure L from a mixture of 3-benzyl-5-(2-hydroxyethyl)-4-methylthiazol-3-ium chloride (0.232 g; 0.860 mmol) and triethylamine (0.120 mL; 0.860 mmol) in ethanol (3 mL), tert-butyl 4-chloro-3-formyl-1H-indole-1-carboxylate (0.481 g; 1.720 mmol) and a solution of N-benzylidene-3-methoxyaniline (1.718 mmol) in ethanol (1 mL), heated at 70° C. for 2 days. Purification by flash chromatography on silica gel using a gradient of ethyl acetate (0% to 100%) in heptane followed by purification by preparative HPLC (XBridge column; method 1) furnished 0.009 g (1%) of the desired compound as a white powder. ESI/APCI(+): 391, 393 (M+H). ESI/APCI(−): 389, 391 (M−H).

Example 54: Preparation of 1-(1H-indol-3-yl)-2-((3-methoxyphenyl)amino)-2-(3-(pyrimidin-5-yl)phenyl)ethanone Step 1: 3-Methoxy-N-(3-(pyrimidin-5-yl)benzylidene)aniline was prepared quantitatively according to general procedure I from 3-pyrimidin-5-ylbenzaldehyde (0.125 g; 0.679 mmol) and 3-methoxyaniline (0.076 mL; 0.679 mmol). ESI/APCI (+): 290 (M+H).
Step 2: 1-(1H-Indol-3-yl)-2-((3-methoxyphenyl)amino)-2-(3-(pyrimidin-5-yl)phenyl)ethanone was prepared according to general procedure L from a mixture of 3-benzyl-5-(2-hydroxyethyl)-4-methylthiazol-3-ium chloride (0.091 g; 0.337 mmol) and triethylamine (0.070 mL; 0.502 mmol) in ethanol (1 mL), tert-butyl 3-formyl-1H-indole-1-carboxylate (0.166 g; 0.677 mmol) and a solution of 3-methoxy-N-(3-(pyrimidin-5-yl)benzylidene)aniline (0.679 mmol) in ethanol (0.5 mL), heated at 65° C. for 5 days. Purification by flash chromatography on silica gel using a gradient of ethyl acetate (50% to 100%) in heptane followed by precipitation from diethyl ether furnished 0.066 g (22%) of the desired compound as a yellow solid. ESI/APCI (+): 435 (M+H). ESI/APCI (−): 433 (M−H).

Example 55: Preparation of 1-(1H-indol-3-yl)-2-((3-methoxyphenyl)amino)-2-(6-methoxypyridin-3-yl)ethanone Step 1: 3-Methoxy-N-((6-methoxypyridin-3-yl)methylene)aniline was prepared quantitatively according to general procedure I from 6-methoxynicotinaldehyde (0.140 g; 1.021 mmol) and 3-methoxyaniline (0.115 mL; 1.021 mmol). ESI/APCI (+): 243 (M+H).
Step 2: 1-(1H-Indol-3-yl)-2-((3-methoxyphenyl)amino)-2-(6-methoxypyridin-3-yl)ethanone was prepared according to general procedure L from a mixture of 3-benzyl-5-(2-hydroxyethyl)-4-methylthiazol-3-ium chloride (0.143 g; 0.530 mmol) and triethylamine (0.100 mL; 0.717 mmol) in ethanol (1 mL), tert-butyl 3-formyl-1H-indole-1-carboxylate (0.251 g; 1.020 mmol) and a solution of 3-methoxy-N-((6-methoxypyridin-3-yl)methylene)aniline (1.021 mmol) in ethanol (0.5 mL), heated at 65° C. for 5 days. Purification by flash chromatography on silica gel using a gradient of ethyl acetate (0% to 50%) in heptane followed by precipitation from diethyl ether furnished 0.097 g (25%) of the desired compound as a pale yellow solid. ESI/APCI (+): 388 (M+H). ESI/APCI (−): 386 (M−H).

Example 56: Preparation of 6-((2-(1H-indol-3-yl)-2-oxo-1-phenylethyl)amino)benzo[d]oxazol-2(3H)-one 6-((2-(1H-Indol-3-yl)-2-oxo-1-phenylethyl)amino)benzo[d]oxazol-2(3H)-one was prepared according to general procedure C from 2-chloro-1-(1H-indol-3-yl)-2-phenylethanone (0.102 g; 0.378 mmol), 6-aminobenzo[d]oxazol-2(3H)-one (0.104 g; 0.693 mmol) and DIPEA (0.200 mL; 1.148 mmol) in acetonitrile (2 mL), irradiated in a microwave oven at 200° C. for 30 minutes. Purification by flash chromatography on silica gel using a gradient of ethyl acetate (10% to 100%) in heptane followed by purification by preparative HPLC (XBridge column; method 2) furnished 0.023 g (16%) of the desired compound as an amorphous solid. ESI/APCI(+): 384 (M+H); 406 (M+Na). ESI/APCI(−): 382 (M−H).

Example 57: Preparation of 2-((3-(1H-1,2,4-triazol-1-yl)phenyl)amino)-1-(1H-indol-3-yl)-2-phenylethanone 2-((3-(1H-1,2,4-Triazol-1-yl)phenyl)amino)-1-(1H-indol-3-yl)-2-phenylethanone was prepared according to general procedure C from 2-chloro-1-(1H-indol-3-yl)-2-phenylethanone (0.104 g; 0.386 mmol), 3-(1H-1,2,4-triazol-1-yl)aniline (0.093 g; 0.581 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (10% to 100%) in heptane, followed by purification by preparative HPLC (XBridge column; method 2) furnished 0.009 g (6%) of the desired compound as an amorphous solid. ESI/APCI(+): 394 (M+H); 416 (M+Na). ESI/APCI(−): 392 (M−H).

Example 58: Preparation of 1-(1H-indol-3-yl)-2-((3-(oxazol-5-yl)phenyl)amino)-2-phenylethanone 1-(1H-Indol-3-yl)-2-((3-(oxazol-5-yl)phenyl)amino)-2-phenylethanone was prepared according to general procedure C from 2-chloro-1-(1H-indol-3-yl)-2-phenylethanone (0.101 g; 0.374 mmol), 3-(oxazol-5-yl)aniline (0.086 g; 0.537 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (10% to 100%) in heptane, followed by purification by preparative HPLC (XBridge column; method 1) furnished 0.008 g (5%) of the desired compound as an amorphous solid. ESI/APCI(+): 394 (M+H); 416 (M+Na). ESI/APCI(−): 392 (M−H).

Example 59: Preparation of 5-(2-(1H-indol-3-yl)-1-((3-methoxyphenyl)amino)-2-oxoethyl)-1,3-dimethyl-1H-benzo[d]imidazol-2(3H)-one Step 1: 5-(((3-Methoxyphenyl)imino)methyl)-1,3-dimethyl-1H-benzo[d]imidazol-2(3H)-one was prepared quantitatively according to general procedure I from 1,3-dimethyl-2-oxo-2,3-dihydro-1H-benzo[d]imidazole-5-carbaldehyde (0.109 g; 0.573 mmol) and 3-methoxyaniline (0.065 mL; 0.578 mmol). ESI/APCI (+): 296 (M+H).
Step 2: 5-(2-(1H-Indol-3-yl)-1-((3-methoxyphenyl)amino)-2-oxoethyl)-1,3-dimethyl-1H-benzo[d]imidazol-2(3H)-one was prepared according to general procedure L from a mixture of 3-benzyl-5-(2-hydroxyethyl)-4-methylthiazolium chloride (0.077 g; 0.285 mmol) and triethylamine (0.060 mL; 0.430 mmol) in ethanol (1 mL), tert-butyl 3-formyl-1H-indole-1-carboxylate (0.140 g; 0.572 mmol) and a solution of 5-(((3-methoxyphenyl)imino)methyl)-1,3-dimethyl-1H-benzo[d]imidazol-2(3H)-one (0.573 mmol) in ethanol (0.5 mL), heated at 65° C. for 3 days. After concentration of the reaction mixture under reduced pressure, precipitation from acetone and diethyl ether furnished 0.049 g (19%) of the desired compound as a pale yellow solid. ESI/APCI (+): 441 (M+H). ESI/APCI (−): 439 (M−H).

Example 60: Preparation of 4-(2-(1H-indol-3-yl)-1-((2-methoxypyridin-4-yl)amino)-2-oxoethyl)benzonitrile Step 1: 4-(((2-Methoxypyridin-4-yl)imino)methyl)benzonitrile was prepared quantitatively according to general procedure J from 4-formylbenzonitrile (0.131 g; 0.998 mmol), 2-methoxypyridin-4-amine (0.124 g; 0.999 mmol) and magnesium sulfate (0.100 g; 0.831 mmol) in ethanol (1 mL).

Step 2: 4-(2-(1H-Indol-3-yl)-1-((2-methoxypyridin-4-yl)amino)-2-oxoethyl)benzonitrile was prepared according to general procedure K from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 4-(((2-methoxypyridin-4-yl)imino)methyl)benzonitrile (0.999 mmol) in ethanol (1 mL), heated at 70° C. for 2 days. Purification by flash chromatography on silica gel using a gradient of ethyl acetate (0% to 100%) in heptane furnished 0.125 g (31%) of the desired compound as a white powder. ESI/APCI(+): 383 (M+H). ESI/APCI(−): 381 (M−H).

Example 61: Preparation of 1-(1H-indol-3-yl)-2-((4-methoxy-6-methylpyrimidin-2-yl)amino)-2-phenylethanone Step 1: N-Benzylidene-4-methoxy-6-methylpyrimidin-2-amine was prepared quantitatively according to general procedure J from benzaldehyde (0.100 mL; 0.987 mmol), 4-methoxy-6-methylpyrimidin-2-amine (0.132 g; 0.949 mmol) and magnesium sulfate (0.100 g; 0.831 mmol) in ethanol (1 mL). ESI/APCI(+): 228 (M+H).

Step 2: 1-(1H-Indol-3-yl)-2-((4-methoxy-6-methylpyrimidin-2-yl)amino)-2-phenylethanone was prepared according to general procedure L from a mixture of 3-benzyl-5-(2-hydroxyethyl)-4-methylthiazol-3-ium chloride (0.124 g; 0.460 mmol) and triethylamine (0.100 mL; 0.717 mmol) in ethanol (1 mL), tert-butyl 3-formyl-1H-indole-1-carboxylate (0.204 g; 0.832 mmol) and a solution of N-benzylidene-4-methoxy-6-methylpyrimidin-2-amine (0.949 mmol) in ethanol (2 mL), heated at 70° C. for 65 h. Purification by flash chromatography on silica gel using a gradient of ethyl acetate (30% to 100%) in heptane followed by recrystallization from dichloromethane furnished 0.001 g (1%) of the desired compound as a powder. ESI/APCI(+): 373 (M+H); 395 (M+Na). ESI/APCI(−): 371 (M−H).

Example 62: Preparation of 2-(6-hydroxypyridin-3-yl)-1-(1H-indol-3-yl)-2-((3-methoxyphenyl)amino)ethanone Step 1: 5-(((3-Methoxyphenyl)imino)methyl)pyridin-2-ol was prepared quantitatively according to general procedure I from 6-hydroxynicotinaldehyde (0.125 g; 1.015 mmol) and 3-methoxyaniline (0.115 mL; 1.023 mmol). ESI/APCI (+): 229 (M+H). ESI/APCI (−): 227 (M−H)

Step 2: 2-(6-Hydroxypyridin-3-yl)-1-(1H-indol-3-yl)-2-((3-methoxyphenyl)amino)ethanone was prepared according to general procedure L from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (1 mL), tert-butyl 3-formyl-1H-indole-1-carboxylate (0.249 g; 1.016 mmol) and a solution of 5-(((3-methoxyphenyl)imino)methyl)pyridin-2-ol (1.015 mmol) in ethanol (1 mL), heated at 65° C. for 4 days. The residue was purified by flash chromatography on silica gel using a gradient of ethyl acetate (50% to 100%) in heptane. Further purification by flash chromatography on silica gel using a gradient of methanol (0% to 5%) in dichloromethane followed purification by preparative HPLC (XBridge column; method 2) furnished 0.078 g (21%) of the desired compound as a yellow solid. ESI/APCI (+): 374 (M+H). ESI/APCI (−): 372 (M−H).

Example 63: Preparation of 2-(imidazo[1,2-a]pyridin-2-yl)-1-(1H-indol-3-yl)-2-((2-methoxypyridin-4-yl)amino)ethanone Step 1: N-(Imidazo[1,2-a]pyridin-2-ylmethylene)-2-methoxypyridin-4-amine has been prepared according to 2 different procedures described hereunder as method A and method B.

Method A: N-(Imidazo[1,2-a]pyridin-2-ylmethylene)-2-methoxypyridin-4-amine was prepared quantitatively according to general procedure H from imidazo[1,2-a]pyridine-2-carbaldehyde (0.150 g; 1.026 mmol), magnesium sulfate (0.200 g; 1.662 mmol) and 4-amino-2-methoxypyridine (0.129 g; 1.039 mmol) in ethanol (1 mL). ESI/APCI (+): 253 (M+H).

Method B: A mixture of imidazo[1,2-a]pyridine-2-carbaldehyde (0.250 g; 1.711 mmol) and 4-amino-2-methoxypyridine (0.215 g; 1.732 mmol) in 2-methyltetrahydrofuran (5 mL) was heated at reflux with a Dean-Stark apparatus. The solvent was evaporated under reduced pressure to give quantitatively N-(imidazo[1,2-a]pyridin-2-ylmethylene)-2-methoxypyridin-4-amine which was used in the next step without further purification. ESI/APCI (+): 253 (M+H).

Step 2: 2-(Imidazo[1,2-a]pyridin-2-yl)-1-(1H-indol-3-yl)-2-((2-methoxypyridin-4-yl)amino)ethanone was prepared according to general procedure L from a mixture of 3-benzyl-5-(2-hydroxyethyl)-4-methylthiazolium chloride (0.140 g; 0.519 mmol) and triethylamine (0.100 mL; 0.717 mmol) in ethanol (1 mL), tert-butyl 3-formyl-1H-indole-1-carboxylate (0.252 g; 1.027 mmol) and a solution of N-(imidazo[1,2-a]pyridin-2-ylmethylene)-2-methoxypyridine-4-amine (1.026 mmol) in ethanol (1 mL), heated at 65° C. for 4 days. Purification by flash chromatography on silica gel using a gradient of methanol (0% to 5%) in dichloromethane followed by purification by preparative HPLC (XBridge column; method 3) furnished 0.031 g (7%) of the desired compound as a yellow solid. ESI/APCI (+): 398 (M+H). ESI/APCI (−): 396 (M−H).

Example 64: Preparation of 3-((2-(1H-indol-3-yl)-2-oxo-1-phenylethyl)amino)benzamide 3-((2-(1H-Indol-3-yl)-2-oxo-1-phenylethyl)amino)benzamide was prepared according to general procedure C from 2-chloro-1-(1H-indol-3-yl)-2-phenylethanone (0.105 g; 0.389 mmol), 3-aminobenzamide (0.099 g; 0.727 mmol) and DIPEA (0.200 mL; 1.148 mmol) in acetonitrile (2 mL), irradiated in a microwave oven at 200° C. for 30 min. Purification by flash chromatography on silica gel using a gradient of ethyl acetate (10% to 100%) in heptane followed by purification by preparative HPLC (XBridge column; method 2) furnished 0.003 g (2%) of the desired compound as a solid. ESI/APCI(+): 370 (M+H); 392 (M+Na). ESI/APCI(−): 368 (M−H).

Example 65: Preparation of 1-(1H-indol-3-yl)-2-((4-methoxypyridin-2-yl)amino)-2-phenylethanone Step 1: N-Benzylidene-4-methoxypyridin-2-amine was prepared quantitatively according to general procedure J from benzaldehyde (0.100 mL; 0.987 mmol), 4-methoxypyridin-2-amine (0.124 g; 0.999 mmol) and magnesium sulfate (0.100 g; 0.831 mmol) in ethanol (1 mL). ESI/APCI (+): 213 (M+H).

Step 2: 1-(1H-Indol-3-yl)-2-((4-methoxypyridin-2-yl)amino)-2-phenylethanone was prepared according to general procedure L from a mixture of 3-benzyl-5-(2-hydroxyethyl)-4-methylthiazol-3-ium chloride (0.128 g; 0.474 mmol) and triethylamine (0.100 mL; 0.717 mmol) in ethanol (1 mL), tert-butyl 3-formyl-1H-indole-1-carboxylate (0.202 g; 0.824 mmol) and a solution of N-benzylidene-4-methoxypyridin-2-amine (0.999 mmol) in ethanol (2 mL), heated at 70° C. for 65 h. Purification by flash chromatography on silica gel using a gradient of ethyl acetate (30% to 100%) in heptane followed by purification by preparative HPLC (SunFire column; method 2) furnished 0.032 g (11%) of the desired compound as an amorphous solid. ESI/APCI(+): 358 (M+H). ESI/APCI(-): 356 (M-H).

Example 66: Preparation of 1-(1H-indol-3-yl)-2-((5-methoxypyridin-3-yl)amino)-2-phenylethanone Step 1: N-Benzylidene-5-methoxypyridin-3-amine was prepared quantitatively according to general procedure J from benzaldehyde (0.100 mL; 0.987 mmol), 5-methoxypyridin-3-amine (0.130 g; 1.047 mmol) and magnesium sulfate (0.100 g; 0.831 mmol) in ethanol (1 mL). ESI/APCI (+): 213 (M+H).

Step 2: 1-(1H-Indol-3-yl)-2-((5-methoxypyridin-3-yl)amino)-2-phenylethanone was prepared according to general procedure L from a mixture of 3-benzyl-5-(2-hydroxyethyl)-4-methylthiazol-3-ium chloride (0.124 g; 0.460 mmol) and triethylamine (0.100 mL; 0.717 mmol) in ethanol (1 mL), tert-butyl 3-formyl-1H-indole-1-carboxylate (0.203 g; 0.828 mmol) and a solution of N-benzylidene-5-methoxypyridin-3-amine (0.987 mmol) in ethanol (2 mL), heated at 70° C. for 65 h. Purification by flash chromatography on silica gel using a gradient of ethyl acetate (30% to 100%) in heptane followed by precipitation from diethyl ether furnished 0.033 g (11%) of the desired compound as a solid. ESI/APCI(+): 358 (M+H); 380 (M+Na). ESI/APCI(-): 356 (M-H). $^1$H NMR (DMSO-$d_6$): δ 12.19 (1H, br s); 8.91 (1H, m); 8.15 (1H, m); 7.83 (1H, m); 7.65 (2H, m); 7.48 (2H, m); 7.19-7.32 (4H, m); 6.68-6.81 (2H, m); 6.16 (1H, m); 3.70 (3H, s).

Example 67: Preparation of ethyl 3-((2-(1H-indol-3-yl)-2-oxo-1-phenylethyl)amino)benzoate Ethyl 3-((2-(1H-indol-3-yl)-2-oxo-1-phenylethyl)amino)benzoate was prepared according to general procedure C from 2-chloro-1-(1H-indol-3-yl)-2-phenylethanone (0.292 g; 1.083 mmol), ethyl 3-aminobenzoate (0.322 g; 1.949 mmol) and DIPEA (0.400 mL; 2.296 mmol) in acetonitrile (2 mL), irradiated in a microwave oven at 200° C. for 30 min. Purification by flash chromatography on silica gel using a gradient of ethyl acetate (10% to 40%) in heptane followed by precipitation from diethyl ether furnished 0.123 g (29%) of the desired compound as a solid. ESI/APCI(+): 399 (M+H); 421 (M+Na). ESI/APCI(-): 397 (M-H). $^1$H NMR (CDCl$_3$) δ 8.58 (1H, br s); 8.40 (1H, m); 8.02 (1H, m); 7.54 (2H, m); 7.18-7.38 (9H, m); 6.87 (1H, m); 5.77 (1H, s); 4.32 (2H, q); 1.36 (3H, t).

Example 68: Preparation of 1-(6-chloro-1H-indol-3-yl)-2-(imidazo[1,2-a]pyridin-2-yl)-2-((2-methoxypyridin-4-yl)amino)ethanone Step 1: tert-Butyl 6-chloro-3-formyl-1H-indole-1-carboxylate was prepared according to general procedure F from 6-chloro-1H-indole-3-carbaldehyde (0.500 g; 2.784 mmol), di-tert-butyl dicarbonate (0.740 g; 3.391 mmol) and DMAP (0.050 g; 0.409 mmol) in acetonitrile (9 mL) to afford 0.760 g (98%) of the desired compound as a brown solid. $^1$H NMR (DMSO-$d_6$) δ 10.07 (1H, s); 8.70 (1H, s); 8.13 (2H, m); 7.45 (1H, d); 1.67 (9H, s).

Step 2: 1-(6-Chloro-1H-indol-3-yl)-2-(imidazo[1,2-a]pyridin-2-yl)-2-((2-methoxypyridin-4-yl)amino)ethanone was prepared according to general procedure L from a mixture of 3-benzyl-5-(2-hydroxyethyl)-4-methylthiazol-3-ium chloride (0.141 g; 0.476 mmol) and triethylamine (0.085 mL; 0.611 mmol) in ethanol (1 mL), tert-butyl 6-chloro-3-formyl-1H-indole-1-carboxylate (0.240 g; 0.856 mmol) and a solution of N-(imidazo[1,2-a]pyridin-2-ylmethylene)-2-methoxypyridine-4-amine (0.856 mmol) in ethanol (2 mL), heated at 65° C. for 5 days. The residue was purified by flash chromatography on silica gel using a gradient of ethyl acetate (25% to 100%) in heptane. Further purification by preparative HPLC (XBridge column; method 3) followed by precipitation from acetone and heptane furnished 0.015 g (4%) of the desired compound as a beige solid. ESI/APCI (+): 432, 434 (M+H).

Example 69: Preparation of 1-(1H-indol-3-yl)-2-((5-methoxy-1,2,4-thiadiazol-3-yl)amino)-2-phenylethanone Step 1: N-Benzylidene-5-methoxy-1,2,4-thiadiazol-3-amine was prepared quantitatively according to general procedure J from benzaldehyde (0.100 mL; 0.987 mmol), 5-methoxy-1,2,4-thiadiazol-3-amine (0.157 g; 1.197 mmol) and magnesium sulfate (0.100 g; 0.831 mmol) in ethanol (1 mL). ESI/APCI(+): 220 (M+H).

Step 2: 1-(1H-Indol-3-yl)-2-((5-methoxy-1,2,4-thiadiazol-3-yl)amino)-2-phenylethanone was prepared according to general procedure L from a mixture of 3-benzyl-5-(2-hydroxyethyl)-4-methylthiazol-3-ium chloride (0.130 g; 0.482 mmol) and triethylamine (0.100 mL; 0.717 mmol) in ethanol (1 mL), tert-butyl 3-formyl-1H-indole-1-carboxylate (0.210 g; 0.856 mmol) and a solution of N-benzylidene-5-methoxy-1,2,4-thiadiazol-3-amine (0.987 mmol) in ethanol (2 mL), heated at 70° C. for 24 h. Purification by flash chromatography on silica gel using a gradient of ethyl acetate (20% to 80%) in heptane followed by recrystallization from diethyl ether furnished 0.002 g (1%) of the desired compound as a solid. ESI/APCI(+): 365 (M+H); 387 (M+Na). ESI/APCI(-): 363 (M-H).

Example 70: Preparation of 3-((2-(1H-indol-3-yl)-2-oxo-1-phenylethyl)amino)benzoic acid A mixture of ethyl 3-((2-(1H-indol-3-yl)-2-oxo-1-phenylethyl)amino)benzoate (0.067 g; 0.168 mmol) and lithium hydroxide (0.065 g; 2.714 mmol) in ethanol (2.5 mL) and water (2.5 mL) was stirred at room temperature for 3 days. The reaction mixture was concentrated under reduced pressure. The residue was partitioned between ethyl acetate and water. The phases were separated. The aqueous phase was acidified with a 1N hydrochloric acid solution and extracted with ethyl acetate. The phases were separated. The organic phase was dried over magnesium sulfate, filtered and concentrated under reduced pressure. Purification by recrystallization from diethyl ether furnished 0.010 g (16%) of the desired compound as a white solid. ESI/APCI(+): 371 (M+H). ESI/APCI(-): 369 (M-H).

Example 71: Preparation of 1-(1H-indol-3-yl)-2-((6-methoxypyrimidin-4-yl)amino)-2-phenylethanone Step 1: A solution of N-benzylidene-6-methoxypyrimidin-4-amine in methanol was prepared by heating a solution of benzaldehyde (0.100 mL; 0.987 mmol) and 6-methoxypyrimidin-4-amine (0.165 g; 1.319 mmol) in methanol (1 mL) at 70° C. for 18 h. The formation of the imine was quantitative and the solution was used without further purification. ESI/APCI(+): 214 (M+H).

Step 2: To a solution of 3-benzyl-5-(2-hydroxyethyl)-4-methylthiazol-3-ium chloride (0.147 g; 0.545 mmol) in ethanol (1 mL) was added triethylamine (0.100 mL; 0.717 mmol) and the mixture was stirred at 70° C. for 5 min. To the resulting yellow solution were added tert-butyl 3-formyl-1H-indole-1-carboxylate (0.208 g; 0.848 mmol) and a solution of N-benzylidene-6-methoxypyrimidin-4-amine (0.987 mmol) in methanol (1 mL). The reaction mixture was stirred in a sealed tube at 70° C. for 65 h. The reaction mixture was concentrated. Purification by flash chromatography on silica gel using a gradient of ethyl acetate (30% to 100%) in heptane furnished 0.015 g (5%) of 1-(1H-indol-3-yl)-2-((6-methoxypyrimidin-4-yl)amino)-2-phenylethanone as a white solid. ESI/APCI(+): 359 (M+H); 381 (M+Na). ESI/APCI(−): 357 (M−H).

Example 72: Preparation of 1-(6-chloro-1H-indol-3-yl)-2-((2-methoxypyridin-4-yl)amino)-2-phenylethanone 1-(6-Chloro-1H-indol-3-yl)-2-((2-methoxypyridin-4-yl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 6-chloro-3-formyl-1H-indole-1-carboxylate (0.280 g; 1.001 mmol) and a solution of N-benzylidene-2-methoxypyridin-4-amine (1.000 mmol) in ethanol (1 mL), heated at 70° C. for 3 days. Purification by flash chromatography on silica gel using a gradient of ethyl acetate (10% to 100%) in heptane followed by precipitation from diethyl ether furnished 0.094 g (23%) of the desired compound as a solid. ESI/APCI(+): 392, 394 (M+H). ESI/APCI(−): 390, 392 (M−H).

Example 73: Preparation of 1-(1H-indol-3-yl)-2-((2-methoxypyridin-4-yl)amino)-2-(pyridin-3-yl)ethanone Step 1: 2-Methoxy-N-(pyridin-3-ylmethylene)pyridin-4-amine was prepared quantitatively according to general procedure H from nicotinaldehyde (0.094 mL; 0.999 mmol), 2-methoxypyridin-4-amine (0.124 g; 0.999 mmol) and magnesium sulfate (0.100 g; 0.831 mmol) in ethanol (1 mL).

Step 2: 1-(1H-Indol-3-yl)-2-((2-methoxypyridin-4-yl)amino)-2-(pyridin-3-yl)ethanone was prepared according to general procedure K from a mixture of 3-benzyl-5-(2-hydroxyethyl)-4-methylthiazol-3-ium chloride (0.135 g; 0.555 mmol) and triethylamine (0.070 mL; 0.498 mmol) in ethanol (1 mL), tert-butyl 3-formyl-1H-indole-1-carboxylate (0.245 g; 0.999 mmol) and a solution of 2-methoxy-N-(pyridin-3-ylmethylene)pyridin-4-amine (0.999 mmol) in ethanol (1 mL), heated at 70° C. for 3 days. Purification by flash chromatography on silica gel using a gradient of ethyl acetate (10% to 100%) in heptane furnished 0.069 g (19%) of the desired compound. ESI/APCI(+): 359 (M+H). ESI/APCI(−): 357 (M−H).

Example 74: Preparation of 1-(6-fluoro-1H-indol-3-yl)-2-((2-methoxypyridin-4-yl)amino)-2-phenylethanone Step 1: tert-Butyl 6-fluoro-3-formyl-1H-indole-1-carboxylate was prepared according to general procedure F from 6-fluoro-1H-indole-3-carbaldehyde (0.653 g; 4.003 mmol), di-tert-butyl dicarbonate (1.048 g; 4.802 mmol) and DMAP (0.049 g; 0.401 mmol) in acetonitrile (10 mL) to afford 0.924 g (88%) of the desired compound as a white solid. ESI/APCI(+): 264 (M+H). $^1$H NMR (DMSO-$d_6$) δ10.06 (1H, s); 8.67 (1H, s); 8.14 (1H, t); 7.83 (1H, d); 7.28 (1H, t); 1.67 (9H, s).

Step 2: 1-(6-Fluoro-1H-indol-3-yl)-2-((2-methoxypyridin-4-yl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 6-fluoro-3-formyl-1H-indole-1-carboxylate (0.263 g; 0.999 mmol) and a solution of N-benzylidene-2-methoxypyridin-4-amine (0.999 mmol) in ethanol (1 mL), heated at 70° C. for 3 days. Purification by flash chromatography on silica gel using a gradient of ethyl acetate (0% to 100%) in heptane furnished 0.107 g (28%) of 1-(6-fluoro-1H-indol-3-yl)-2-((2-methoxypyridin-4-yl)amino)-2-phenylethanone. ESI/APCI(+): 376 (M+H). ESI/APCI(−): 374 (M−H).

Example 75: Preparation of 1-(6-methoxy-1H-indol-3-yl)-2-((2-methoxypyridin-4-yl)amino)-2-phenylethanone Step 1: tert-Butyl 3-formyl-6-methoxy-1H-indole-1-carboxylate was prepared according to general procedure F from 6-methoxy-1H-indole-3-carbaldehyde (0.466 g; 2.660 mmol), di-tert-butyl dicarbonate (0.697 g; 3.134 mmol) and DMAP (0.032 g; 0.266 mmol) in acetonitrile (4 mL) to afford 0.648 g (88%) of the desired compound as a white solid.

Step 2: 1-(6-Methoxy-1H-indol-3-yl)-2-((2-methoxypyridin-4-yl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-6-methoxy-1H-indole-1-carboxylate (0.275 g; 0.999 mmol) and a solution of N-benzylidene-2-methoxypyridin-4-amine (0.999 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.070 g (18%) of the desired compound as a solid. ESI/APCI(+): 388 (M+H). ESI/APCI(−): 386 (M−H).

Example 76: Preparation of 1-(6-methoxy-1H-indol-3-yl)-2-((3-methoxyphenyl)amino)-2-phenylethanone 1-(6-Methoxy-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-6-methoxy-1H-indole-1-carboxylate (0.275 g; 0.999 mmol) and a solution of N-benzylidene-3-methoxyaniline (0.999 mmol) in ethanol (1 mL), heated at 70° C. for 3 days. Purification by flash chromatography on silica gel using a gradient of ethyl acetate (0% to 100%) in heptane followed by precipitation from diethyl ether furnished 0.053 g (13%) of the desired compound as a solid. ESI/APCI(+): 387 (M+H). ESI/APCI(−): 385 (M−H).

Example 77: Preparation of 1-(5-methoxy-1H-indol-3-yl)-2-((2-methoxypyridin-4-yl)amino)-2-phenylethanone Step 1: tert-Butyl 3-formyl-5-methoxy-1H-indole-1-carboxylate was prepared according to general procedure F from 5-methoxy-1H-indole-3-carbaldehyde (0.701 g; 4.001 mmol), di-tert-butyl dicarbonate (1.048 g; 4.712 mmol) and DMAP (0.049 g; 0.4007 mmol) in acetonitrile (10 mL) to afford 0.934 g (85%) of the desired compound as a white solid. ESI/APCI(+): 276 (M+H).

Step 2: 1-(5-Methoxy-1H-indol-3-yl)-2-((2-methoxypyridin-4-yl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-5-methoxy-1H-indole-1-carboxylate (0.275 g; 0.999 mmol) and a solution of N-benzylidene-2-methoxypyridin-4-amine (0.999 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.085 g (21%) of the desired compound as a solid. ESI/APCI(+): 388 (M+H). ESI/APCI (−): 386 (M−H).

Example 78: Preparation of methyl 3-(2-((2-methoxypyridin-4-yl)amino)-2-phenylacetyl)-1H-indole-6-carboxylate Step 1: 1-tert-Butyl 6-methyl 3-formyl-1H-indole-1,6-dicarboxylate was prepared according to general procedure F from methyl 3-formyl-1H-indole-6-carboxylate (0.813 g; 4.001 mmol), di-tert-butyl dicarbonate (1.048 g; 4.712 mmol) and DMAP (0.049 g; 0.4007 mmol) in acetonitrile (10 mL) to afford 1.139 g (94%) of the desired compound as a white solid.

Step 2: Methyl 3-(2-((2-methoxypyridin-4-yl)amino)-2-phenylacetyl)-1H-indole-6-carboxylate was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), 1-tert-butyl 6-methyl 3-formyl-1H-indole-1,6-dicarboxylate (0.303 g; 0.999 mmol) and a solution of N-benzylidene-2-methoxypyridin-4-amine (0.999 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.055 g (13%) of the desired compound as a solid. ESI/APCI(+): 416 (M+H). ESI/APCI(−): 414 (M−H).

Example 79: Preparation of 2-(6,8-dihydro-5H-imidazo[2,1-c][1,4]oxazin-2-yl)-1-(1H-indol-3-yl)-2-((3-methoxyphenyl)amino)ethanone Step 1: N-((6,8-Dihydro-5H-imidazo[2,1-c]oxazin-2-yl)methylene)-3-methoxyaniline was prepared quantitatively according to general procedure I from 6,8-dihydro-5H-imidazo[2,1-c][1,4]oxazine-2-carbaldehyde (0.125 g; 0.999 mmol) and 3-methoxyaniline (0.115 mL; 1.023 mmol).

Step 2: 2-(6,8-Dihydro-5H-imidazo[2,1-c][1,4]oxazin-2-yl)-1-(1H-indol-3-yl)-2-((3-methoxyphenyl) amino)ethanone was prepared according to general procedure K from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (1 mL), tert-butyl 3-formyl-1H-indole-1-carboxylate (0.245 g; 0.999 mmol) and a solution of N-((6,8-dihydro-5H-imidazo[2,1-c]oxazin-2-yl)methylene)-3-methoxyaniline (0.999 mmol) in ethanol (1 mL), heated at 65° C. for 3 days and at 80° C. for 3 days. Purification by flash chromatography on silica gel using a gradient of ethyl acetate (50% to 100%) in heptane followed by precipitation from dichloromethane and diethyl ether furnished 0.036 g (9%) of the desired compound as a white solid. ESI/APCI(+): 403 (M+H). ESI/APCI(−): 401 (M−H).

Example 80: Preparation of 2-(5-fluoroimidazo[1,2-a]pyridin-2-yl)-1-(1H-indol-3-yl)-2-((2-methoxypyridin-4-yl)amino)ethanone Step 1: A solution of N-((5-fluoroimidazo[1,2-a]pyridin-2-yl)methylene)-2-methoxypyridin-4-amine in ethanol was prepared by heating a solution of 5-fluoroimidazo[1,2-a]pyridine-2-carbaldehyde (0.100 g; 0.609 mmol) and 6-methoxypyrimidin-4-amine (0.076 g; 0.609 mmol) in ethanol (1 mL) at 65° C. for 18 h. The formation of the imine was quantitative and the solution was used without further purification. ESI/APCI(+): 271 (M+H).

Step 2: 2-(5-Fluoroimidazo[1,2-a]pyridin-2-yl)-1-(1H-indol-3-yl)-2-((2-methoxypyridin-4-yl)amino)ethanone was prepared according to general procedure L from a mixture of 3-benzyl-5-(2-hydroxyethyl)-4-methylthiazol-3-ium chloride (0.080 g; 0.297 mmol) and triethylamine (0.065 mL; 0.466 mmol) in ethanol (1 mL), tert-butyl 3-formyl-1H-indole-1-carboxylate (0.215 g; 0.611 mmol) and a solution of N-((5-fluoroimidazo[1,2-a]pyridin-2-yl)methylene)-2-methoxypyridin-4-amine (0.609 mmol) in ethanol (1 mL), heated at 65° C. for 4 days. The residue was purified by flash chromatography on silica gel using a gradient of ethyl acetate (30% to 100%) in heptane and then methanol (25%) in dichloromethane as eluent. Further purification by preparative HPLC (XBridge column; method 3) furnished 0.063 g (25%) of the desired compound as a white solid. ESI/APCI(+): 416 (M+H). ESI/APCI(−): 414 (M−H).

Example 81: Preparation of 1-(1H-indol-3-yl)-2-((2-methoxypyridin-4-yl)amino)-2-(thiazol-4-yl)ethanone Step 1: A mixture of thiazole-4-carbaldehyde (0.115 g; 1.016 mmol) and 4-amino-2-methoxypyridine (0.126 g; 1.016 mmol) in ethanol (1 mL) was stirred at 65° C. for 16 h. The solvent was evaporated and the residue was dried under reduced pressure to give quantitatively 2-methoxy-N-(thiazol-4-ylmethylene)pyridin-4-amine which was used without further purification. ESI/APCI (+): 220 (M+H).

Step 2: 1-(1H-Indol-3-yl)-2-((2-methoxypyridin-4-yl) amino)-2-(thiazol-4-yl)ethanone was prepared according to general procedure K from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (1 mL), tert-butyl 3-formyl-1H-indole-1-carboxylate (0.249 g; 1.017 mmol) and a solution of 2-methoxy-N-(thiazol-4-ylmethylene)pyridin-4-amine (1.016 mmol) in ethanol (1 mL), heated at 65° C. for 6 days. Purification by flash chromatography on silica gel using a gradient of ethyl acetate (0% to 100%) in heptane followed by precipitation from diethyl ether furnished 0.044 g (12%) of the desired compound as a white solid. ESI/APCI(+): 365 (M+H). ESI/APCI(−): 363 (M−H).

Example 82: Preparation of 1-(1H-indol-3-yl)-2-((3-methoxyphenyl)amino)-2-(pyrazolo[1,5-a]pyridin-2-yl)ethanone Step 1: To a solution of pyrazolo[1,5-a]pyridine-2-carboxylic acid (0.202 g; 1.246 mmol) in dichloromethane (2 mL) were added HATU (0.472 g; 1.241 mmol) and DIPEA (0.450 mL; 2.577 mmol). After stirring for 5 min at room temperature, N,O-dimethylhydroxylamine hydrochloride (0.128 g; 1.312 mmol) was added and the reaction mixture was stirred at room temperature overnight. The reaction mixture was diluted with dichloromethane and washed with water. The phases were separated. The organic phase was washed with a 1N hydrochloric acid solution, a 1N sodium bicarbonate solution and brine, dried over magnesium sulfate, filtered and concentrated under reduced pressure to give N-methoxy-N-methylpyrazolo[1,5-a]pyridine-2-carboxamide which was used in the next step without further purification. ESI/APCI (+): 206 (M+H).

Step 2: To a solution of N-methoxy-N-methylpyrazolo[1,5-a]pyridine-2-carboxamide (1.246 mmol) in dry THF (3 mL) cooled at −15° C. (acetone/glace) was added lithium aluminum hydride (0.048 g; 1.257 mmol) and the solution was stirred for 3 h. A 1N Rochelle salt solution was added and the reaction mixture was stirred at room temperature for 10 min. The phases were separated. The aqueous phase was extracted with ether. The organic phases were combined, dried over magnesium sulfate, filtered and concentrated under reduced pressure. Purification by flash chromatography on silica using a gradient of ethyl acetate (0% to 30%) in heptane furnished 0.088 g (48% over 2 steps) of pyrazolo[1,5-a]pyridine-2-carbaldehyde as a white solid. ESI/APCI (+): 147 (M+H).

Step 3: 3-Methoxy-N-(pyrazolo[1,5-a]pyridin-2-ylmethylene)aniline was prepared quantitatively according to general procedure I from pyrazolo[1,5-a]pyridine-2-carbaldehyde (0.087 g; 0.595 mmol) and 3-methoxyaniline (0.070 mL; 0.623 mmol).

Step 4: 1-(1H-Indol-3-yl)-2-((3-methoxyphenyl)amino)-2-(pyrazolo[1,5-a]pyridin-2-yl)ethanone was prepared according to general procedure K from a mixture of 3-benzyl-5-(2-hydroxyethyl)-4-methylthiazol-3-ium chloride (0.082 g; 0.304 mmol) and triethylamine (0.060 mL; 0.430 mmol) in ethanol (0.7 mL), tert-butyl 3-formyl-1H-indole-1-carboxylate (0.151 g; 0.616 mmol) and a solution of 3-methoxy-N-(pyrazolo[1,5-a]pyridin-2-ylmethylene)aniline (0.623 mmol) in ethanol (0.7 mL), heated at 65° C. overnight. Purification by flash chromatography on silica gel using a gradient of ethyl acetate (10% to 60%) in heptane followed by precipitation from dichloromethane furnished 0.055 g (23%) of the desired compound as a yellow solid. ESI/APCI(+): 397 (M+H). ESI/APCI(−): 395 (M−H).

Example 83: Preparation of 1-(7-chloro-1H-indol-3-yl)-2-((3-methoxyphenyl)amino)-2-phenylethanone Step 1: tert-Butyl 7-chloro-3-formyl-1H-indole-1-carboxylate was prepared according to general procedure F from 7-chloro-1H-indole-3-carbaldehyde (0.718 g; 3.998 mmol), di-tert-butyl dicarbonate (1.048 g; 4.712 mmol) and DMAP (0.049 g; 0.401 mmol) in acetonitrile (10 mL) to afford 0.687 g (61%) of the desired compound as a white solid.

Step 2: 1-(7-Chloro-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 7-chloro-3-formyl-1H-indole-1-carboxylate (0.280 g; 1.001 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane followed by precipitation from acetonitrile furnished 0.058 g (14%) of the desired compound as a solid. ESI/APCI(+): 391 (M+H). ESI/APCI(−): 389 (M−H).

Example 84: Preparation of methyl 3-(2-((3-methoxyphenyl)amino)-2-phenylacetyl)-1H-indole-6-carboxylate Methyl 3-(2-((3-methoxyphenyl)amino)-2-phenylacetyl)-1H-indole-6-carboxylate was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), 1-tert-butyl 6-methyl 3-formyl-1H-indole-1,6-dicarboxylate (0.303 g; 0.999 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.038 g (9%) of the desired compound as a solid. ESI/APCI(+): 415 (M+H). ESI/APCI(−): 413 (M−H).

Example 85: Preparation of 1-(5-chloro-1H-indol-3-yl)-2-((3-methoxyphenyl)amino)-2-phenylethanone Step 1: tert-Butyl 5-chloro-3-formyl-1H-indole-1-carboxylate was prepared according to general procedure F from 5-chloro-1H-indole-3-carbaldehyde (0.718 g; 3.998 mmol), di-tert-butyl dicarbonate (1.048 g; 4.712 mmol) and DMAP (0.049 g; 0.401 mmol) in acetonitrile (10 mL) to afford 1.001 g (89%) of the desired compound as a white solid.

Step 2: 1-(5-Chloro-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 5-chloro-3-formyl-1H-indole-1-carboxylate (0.280 g; 1.001 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.011 g (3%) of the desired compound as a solid. ESI/APCI(+): 391 (M+H). ESI/APCI(−): 389 (M−H).

Example 86: Preparation of 2-((2,6-dimethoxypyrimidin-4-yl)amino)-1-(1H-indol-3-yl)-2-phenylethanone Step 1: A solution of N-benzylidene-2,6-dimethoxypyrimidin-4-amine in methanol was prepared by heating a solution of benzaldehyde (0.100 mL; 0.987 mmol) and 2,6-dimethoxypyrimidin-4-amine (0.136 g; 0.877 mmol) in methanol (1 mL) at 70° C. for 18 h. The formation of the imine was quantitative and the solution was used without further purification. ESI/APCI(+): 244 (M+H).

Step 2: To a solution of 3-benzyl-5-(2-hydroxyethyl)-4-methylthiazol-3-ium chloride (0.132 g; 0.489 mmol) in ethanol (1 mL) was added triethylamine (0.100 mL; 0.717 mmol) and the mixture was stirred at 70° C. for 5 min. To the resulting yellow solution were added a solution of N-benzylidene-2,6-dimethoxypyrimidin-4-amine (0.877 mmol) in methanol (1 mL) and tert-butyl 3-formyl-1H-indole-1-carboxylate (0.208 g; 0.848 mmol). The reaction mixture was stirred in a sealed tube at 70° C. for 24 h. The reaction mixture was concentrated. The residue was purified by flash chromatography on silica gel using a gradient of ethyl acetate (30% to 100%) in heptane. Further purification by preparative HPLC (XBridge column; method 2) furnished 0.005 g (2%) of the desired compound as a white solid. ESI/APCI(+): 389 (M+H); 411 (M+Na). ESI/APCI(−): 387 (M−H).

Example 87: Preparation of 1-(1H-indol-3-yl)-2-((3-methoxyphenyl)amino)-2-(8-methylimidazo[1,2-a]pyridin-2-yl)ethanone Step 1: A solution of 3-methoxy-N-((8-methylimidazo[1,2-a]pyridin-2-yl)methylene)aniline in ethanol was prepared by heating a solution of 8-methylimidazo[1,2-a]pyridine-2-carbaldehyde (0.162 g; 1.011 mmol) and 3-methoxyaniline (0.115 mL; 1.023 mmol) in ethanol (0.5 mL) at 65° C. for 24 h. The formation of the imine was quantitative and the solution was used without further purification. ESI/APCI(+): 266 (M+H); 288 (M+Na); 531 (2M+H); 553 (2M+Na).

Step 2: 1-(1H-Indol-3-yl)-2-((3-methoxyphenyl)amino)-2-(8-methylimidazo[1,2-a]pyridin-2-yl)ethanone was prepared according to general procedure K from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (1 mL), tert-butyl 3-formyl-1H-indole-1-carboxylate (0.270 g; 1.101 mmol) and a solution of 3-methoxy-N-((8-methylimidazo[1,2-a]pyridin-2-yl)methylene)aniline (1.011 mmol) in ethanol (1 mL), heated at 65° C. overnight. Purification by flash chromatography on silica gel using a gradient of ethyl acetate (20% to 70%) in heptane followed by precipitation from diethyl ether and dichloromethane furnished 0.022 g (5%) of the desired compound as a pale yellow solid. ESI/APCI(+): 411 (M+H). ESI/APCI(−): 409 (M−H).

Example 88: Preparation of 1-(1H-indol-3-yl)-2-((4-methoxypyrimidin-2-yl)amino)-2-phenylethanone Step 1: A solution of N-benzylidene-4-methoxypyrimidin-4-amine in methanol was prepared by heating a solution of benzaldehyde (0.100 mL; 0.987 mmol) and 4-methoxypyrimidin-2-amine (0.163 g; 1.303 mmol) in methanol (1 mL) at 70° C. for 18 h. The formation of the imine was quantitative and the solution was used without further purification. ESI/APCI(+): 214 (M+H).

Step 2: 1-(1H-Indol-3-yl)-2-((4-methoxypyrimidin-2-yl)amino)-2-phenylethanone was prepared according to general procedure L from a mixture of 3-benzyl-5-(2-hydroxyethyl)-4-methylthiazol-3-ium chloride (0.163 g; 0.604 mmol) and triethylamine (0.100 mL; 0.717 mmol) in ethanol (1 mL), tert-butyl 3-formyl-1H-indole-1-carboxylate (0.195 g; 0.795 mmol) and a solution of N-benzylidene-4-methoxypyrimidin-4-amine (0.987 mmol) in methanol (1 mL), heated at 70° C. for 24 h. Purification by flash chromatography on silica gel using a gradient of methanol (0% to 20%) in ethyl acetate followed by recrystallization from methanol furnished 0.020 g (7%) of the desired compound as a white solid. ESI/APCI(+): 359 (M+H); 381 (M+Na). ESI/APCI(−): 357 (M+H).

Example 89: Preparation of 2-(4-fluorophenyl)-1-(1H-indol-3-yl)-2-((2-methoxypyridin-4-yl)amino)ethanone Step 1: N-(4-Fluorobenzylidene)-2-methoxypyridin-4-amine was quantitatively prepared according to general procedure H from 4-fluorobenzaldehyde (0.106 mL; 1.004 mmol), magnesium sulfate (0.100 g; 0.831 mmol) and 2-methoxypyridin-4-amine (0.124 g; 0.999 mmol) in ethanol (1 mL).

Step 2: 2-(4-Fluorophenyl)-1-(1H-indol-3-yl)-2-((2-methoxypyridin-4-yl)amino)ethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-1H-indole-1-carboxylate (0.245 g; 0.999 mmol) and a solution of N-(4-fluorobenzylidene)-2-methoxypyridin-4-amine (0.999 mmol) in ethanol (1 mL), heated at 70° C. for 3 days. Purification by flash chromatography on silica gel using a gradient of ethyl acetate (0% to 100%) in heptane followed by purification by preparative HPLC (XBridge column; method 2) furnished 0.068 g (17%) of the desired compound. ESI/APCI(+): 376 (M+H). ESI/APCI(−): 374 (M−H).

Example 90: Preparation of 2-(3-fluorophenyl)-1-(1H-indol-3-yl)-2-((2-methoxypyridin-4-yl)amino)ethanone Step 1: N-(3-Fluorobenzylidene)-2-methoxypyridin-4-amine was quantitatively prepared according to general procedure H from 3-fluorobenzaldehyde (0.106 mL; 1.003 mmol), magnesium sulfate (0.100 g; 0.831 mmol) and 2-methoxypyridin-4-amine (0.124 g; 0.999 mmol) in ethanol (1 mL).

Step 2: 2-(3-Fluorophenyl)-1-(1H-indol-3-yl)-2-((2-methoxypyridin-4-yl)amino)ethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-1H-indole-1-carboxylate (0.245 g; 0.999 mmol) and a solution of N-(3-fluorobenzylidene)-2-methoxypyridin-4-amine (0.999 mmol) in ethanol (1 mL), heated at 70° C. for 3 days. Purification by flash chromatography on silica gel using a gradient of ethyl acetate (0% to 100%) in heptane followed by purification by preparative HPLC (XBridge column; method 5) furnished 0.093 g (24%) of the desired compound. ESI/APCI(+): 376 (M+H). ESI/APCI(−): 374 (M−H).

Example 91: Preparation of 1-(5-methoxy-1H-indol-3-yl)-2-((3-methoxyphenyl)amino)-2-phenylethanone 1-(5-Methoxy-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-5-methoxy-1H-indole-1-carboxylate (0.275 g; 0.999 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane furnished 0.085 g (22%) of the desired compound. ESI/APCI(+): 387 (M+H). ESI/APCI(−): 385 (M−H).

Example 92: Preparation of 3-(2-((2-methoxypyridin-4-yl)amino)-2-phenylacetyl)-1H-indole-6-carbonitrile Step 1: tert-Butyl 6-cyano-3-formyl-1H-indole-1-carboxylate was prepared according to general procedure F from 3-formyl-1H-indole-6-carbonitrile (0.511 g; 3.003 mmol), di-tert-butyl dicarbonate (0.786 g; 3.601 mmol) and DMAP (0.037 g; 0.303 mmol) in acetonitrile (7 mL) to afford 0.697 g (76%) of the desired compound as a white solid.

Step 2: 3-(2-((2-Methoxypyridin-4-yl)amino)-2-phenylacetyl)-1H-indole-6-carbonitrile was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 6-cyano-3-formyl-1H-indole-1-carboxylate (0.270 g; 0.999 mmol) and a solution of N-benzylidene-2-methoxypyridin-4-amine (0.999 mmol) in ethanol (1 mL), heated at 70° C. for 24 h. Purification by flash chromatography on silica gel using a gradient of ethyl acetate (0% to 100%) in heptane furnished 0.058 g (15%) of the desired compound. ESI/APCI(+): 383 (M+H). ESI/APCI (−): 381 (M−H).

Example 93: Preparation of 3-(2-((3-methoxyphenyl)amino)-2-phenylacetyl)-1H-indole-6-carbonitrile 3-(2-((3-Methoxyphenyl)amino)-2-phenylacetyl)-1H-indole-6-carbonitrile was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 6-cyano-3-formyl-1H-indole-1-carboxylate (0.270 g; 0.999 mmol) and a solution of N-benzylidene-3-methoxyaniline (0.999 mmol) in ethanol (1 mL), heated at 70° C. for 24 h. Purification by flash chromatography on silica gel using a gradient of ethyl acetate (0% to 100%) in heptane furnished 0.038 g (9%) of the desired compound. ESI/APCI(+): 382 (M+H). ESI/APCI(−): 380 (M−H).

Example 94: Preparation of 2-(6,8-dihydro-5H-imidazo[2,1-c][1,4]oxazin-2-yl)-1-(1H-indol-3-yl)-2-((2-methoxypyridin-4-yl)amino)ethanone Step 1: A mixture of 6,8-dihydro-5H-imidazo[2,1-c][1,4]oxazine-2-carbaldehyde (0.156 g; 1.025 mmol) and 4-amino-2-methoxypyridine (0.130 g; 1.047 mmol) in ethanol (1 mL) was stirred at 65° C. for 2.5 days. The solvent was evaporated and the residue was dried under reduced pressure to give quantitatively N-((6,8-dihydro-5H-imidazo[2,1-c][1,4]oxazin-2-yl)methylene)-2-methoxypyridin-4-amine which was used without further purification.

Step 2: 2-(6,8-Dihydro-5H-imidazo[2,1-c][1,4]oxazin-2-yl)-1-(1H-indol-3-yl)-2-((2-methoxypyridin-4-yl)amino)ethanone was prepared according to general procedure K from a mixture of 3-benzyl-5-(2-hydroxyethyl)-4-methylthiazol-3-ium chloride (0.133 g; 0.493 mmol) and triethylamine (0.100 mL; 0.717 mmol) in ethanol (1 mL), tert-butyl 3-formyl-1H-indole-1-carboxylate (0.252 g; 1.026 mmol) and a solution of N-((6,8-dihydro-5H-imidazo[2,1-c][1,4]oxazin-2-yl)methylene)-2-methoxypyridin-4-amine (1.025 mmol) in ethanol (1 mL), heated at 65° C. for 7 days. The residue was purified by flash chromatography on silica gel eluted first with ethyl acetate and then with methanol (30%) in dichloromethane. Further purification by preparative HPLC (XBridge column; method 2) furnished 0.131 g (32%) of the desired compound as a yellow oil. ESI/APCI (+): 404 (M+H). ESI/APCI(−): 402 (M−H).

Example 95: Preparation of 1-(1H-indol-3-yl)-2-((3-methoxyphenyl)amino)-2-(7-methylimidazo[1,2-a]pyridin-2-yl)ethanone Step 1: A solution of 3-methoxy-N-((7-methylimidazo[1,2-a]pyridin-2-yl)methylene)aniline in ethanol was prepared by heating a solution of 7-methylimidazo[1,2-a]pyridine-2-carbaldehyde (0.160 g; 0.999 mmol) and 3-methoxyaniline (0.113 mL; 1.009 mmol) in ethanol (0.5 mL) at 65° C. for 24 h. The formation of the imine was quantitative and the solution was used without further purification. ESI/APCI (+): 266 (M+H)

Step 2: 1-(1H-indol-3-yl)-2-((3-methoxyphenyl)amino)-2-(7-methylimidazo[1,2-a]pyridin-2-yl)ethanone was prepared according to general procedure K from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (0.7 mL), tert-butyl 3-formyl-1H-indole-1-carboxylate (0.270 g; 1.102 mmol) and a solution of 3-methoxy-N-((7-methylimidazo[1,2-a]pyridin-2-yl)methylene)aniline (0.999 mmol) in ethanol (1 mL), heated at 65° C. for 3 days. Purification by flash chromatography on silica gel using a gradient of ethyl acetate (30% to 100%) in heptane followed by precipitation from acetone furnished 0.050 g (12%) of the desired compound as a pale yellow solid. ESI/APCI(+): 411 (M+H). ESI/APCI(−): 409 (M−H).

Example 96: Preparation of 1-(1H-indol-3-yl)-2-(1H-indol-5-yl)-2-((2-methoxypyridin-4-yl)amino)ethanone Step 1: A solution of N-((1H-indol-5-yl)methylene)-2-methoxypyridin-4-amine in ethanol was prepared by heating a solution of 1H-indole-5-carbaldehyde (0.098 g; 0.675 mmol) and 2-methoxypyridin-4-amine (0.144 g; 1.160 mmol) in ethanol (1 mL) at 70° C. for 65 h. The formation of the imine was quantitative and the solution was used without further purification. ESI/APCI(+): 252 (M+H). ESI/APCI(−): 250 (M−H).

Step 2: 1-(1H-Indol-3-yl)-2-(1H-indol-5-yl)-2-((2-methoxypyridin-4-yl)amino)ethanone was prepared according to general procedure L from a mixture of 3-benzyl-5-(2-hydroxyethyl)-4-methylthiazol-3-ium chloride (0.156 g; 0.578 mmol) and triethylamine (0.100 mL; 0.717 mmol) in ethanol (1 mL), tert-butyl 3-formyl-1H-indole-1-carboxylate (0.214 g; 0.872 mmol) and a solution of N-((1H-indol-5-yl)methylene)-2-methoxypyridin-4-amine (0.675 mmol) in ethanol (1 mL), heated at 70° C. for 24 h. Purification by flash chromatography on silica gel using a gradient of ethyl acetate (30% to 100%) in heptane followed by purification by preparative HPLC (XBridge column; method 2) furnished 0.011 g (3%) of the desired compound as a white solid. ESI/APCI(+): 397 (M+H). ESI/APCI(−): 395 (M−H).

Example 97: Preparation of 1-(1H-indol-3-yl)-2-((3-methoxyphenyl)amino)-2-(6-methylimidazo[1,2-a]pyridin-2-yl)ethanone Step 1: A solution of 3-methoxy-N-((6-methylimidazo[1,2-a]pyridin-2-yl)methylene)aniline in ethanol was prepared by heating a solution of 6-methylimidazo[1,2-a]pyridine-2-carbaldehyde (0.160 g; 0.999 mmol) and 3-methoxyaniline (0.113 mL; 1.009 mmol) in ethanol (0.5 mL) at 65° C. for 24 h. The formation of the imine was quantitative and the solution was used without further purification. ESI/APCI (+): 266 (M+H).

Step 2: 1-(1H-Indol-3-yl)-2-((3-methoxyphenyl)amino)-2-(6-methylimidazo[1,2-a]pyridin-2-yl)ethanone was prepared according to general procedure K from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (0.7 mL), tert-butyl 3-formyl-1H-indole-1-carboxylate (0.270 g; 1.102 mmol) and a solution of 3-methoxy-N-((6-methylimidazo[1,2-a]pyridin-2-yl)methylene)aniline (0.999 mmol) in ethanol (1 mL), heated overnight at 65° C. Purification by flash chromatography on silica gel using a gradient of ethyl acetate (30% to 100%) in heptane followed by precipitation from acetone furnished 0.084 g (21%) of the desired compound as a white solid. ESI/APCI(+): 411 (M+H). ESI/APCI(−): 409 (M−H).

Example 98: Preparation of 1-(5-chloro-1H-indol-3-yl)-2-((2-methoxypyridin-4-yl)amino)-2-phenylethanone 1-(5-Chloro-1H-indol-3-yl)-2-((2-methoxypyridin-4-yl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 5-chloro-3-formyl-1H-indole-1-carboxylate (0.280 g; 1.001 mmol) and a solution of N-benzylidene-2-methoxypyridin-4-amine (0.999 mmol) in ethanol (1 mL), heating at 70° C. for 2 days. Purification by flash chromatography on silica gel using a gradient of ethyl acetate (0% to 100%) in heptane followed by precipitation from diethyl ether furnished 0.089 g (22%) of the desired compound. ESI/APCI(+): 392, 394 (M+H). ESI/APCI(−): 390, 392 (M−H).

Example 99: Preparation of 2-((2-methoxypyridin-4-yl)amino)-1-(1-methyl-1H-indol-3-yl)-2-phenylethanone 2-((2-Methoxypyridin-4-yl)amino)-1-(1-methyl-1H-indol-3-yl)-2-phenylethanone was prepared according to general procedure L from a mixture of 3-benzyl-5-(2-hydroxyethyl)-4-methylthiazol-3-ium chloride (0.169 g; 0.628 mmol) and triethylamine (0.088 mL; 0.628 mmol) in ethanol (2 mL), 1-methyl-1H-indole-3-carbaldehyde (0.200 g; 1.256 mmol) and a solution of N-benzylidene-2-methoxypyridin-4-amine (1.256 mmol) in ethanol (1 mL), heated at 70° C. for 2 days. Purification by flash chromatography on silica gel using a gradient of ethyl acetate (0% to 100%) in heptane followed by preparative HPLC (XBridge column; method 5) furnished 0.034 g (7%) of the desired compound. ESI/APCI (+): 372 (M+H). ESI/APCI(−): 370 (M−H).

Example 100: Preparation of 1-(7-chloro-1H-indol-3-yl)-2-((2-methoxypyridin-4-yl)amino)-2-phenylethanone 1-(7-Chloro-1H-indol-3-yl)-2-((2-methoxypyridin-4-yl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 7-chloro-3-formyl-1H-indole-1-carboxylate (0.280 g; 1.001 mmol) and a solution of N-benzylidene-2-methoxypyridin-4-amine (0.212 g; 0.999 mmol) in ethanol (1 mL), heated at 70° C. for 2 days. Purification by flash chromatography on silica gel using a gradient of ethyl acetate (0% to 100%) in heptane followed by purification by preparative HPLC (XBridge column; method 5) furnished 0.083 g (21%) of the desired compound. ESI/APCI(+): 392, 394 (M+H). ESI/APCI(−): 390, 392 (M−H).

Example 101: Preparation of 1-(1H-indol-3-yl)-2-((3-methoxyphenyl)amino)-2-(3-methylisoxazol-5-yl)ethanone Step 1: 3-Methoxy-N-((3-methylisoxazol-5-yl)methylene)aniline was prepared quantitatively according to general procedure I from 3-methylisoxazole-5-carbaldehyde (0.111 g; 1.000 mmol) and 3-methoxyaniline (0.113 mL; 1.000 mmol). ESI/APCI(+): 217 (M+H).

Step 2: 1-(1H-Indol-3-yl)-2-((3-methoxyphenyl)amino)-2-(3-methylisoxazol-5-yl)ethanone was prepared according to general procedure K from a mixture of 3-benzyl-5-(2-hydroxyethyl)-4-methylthiazolium chloride (0.135 g; 0.500 mmol) and triethylamine (0.069 mL; 0.497 mmol) in ethanol (0.7 mL), tert-butyl 3-formyl-1H-indole-1-carboxylate (0.294 g; 1.199 mmol) and a solution of 3-methoxy-N-((3-methylisoxazol-5-yl)methylene)aniline (1.000 mmol) in ethanol (0.7 mL), heated at 70° C. for 2 days. Purification by flash chromatography on silica gel using a gradient of ethyl acetate (0% to 100%) in heptane followed by recrystallization from ethyl acetate furnished 0.051 g (14%) of the desired compound as a white solid. ESI/APCI(+): 362 (M+H); 384 (M+Na); 745 (2M+Na). ESI/APCI(−): 360 (M−H).

Example 102: Preparation of 1-(1H-indol-3-yl)-2-((3-methoxyphenyl)amino)-2-(1-methyl-1H-imidazol-4-yl)ethanone Step 1: 3-Methoxy-N-((1-methyl-1H-imidazol-4-yl)methylene)aniline was prepared quantitatively according to general procedure I from 1-methyl-1H-imidazole-4-carbaldehyde (0.110 g; 0.999 mmol) and 3-methoxyaniline (0.113 mL; 1.000 mmol). ESI/APCI(+): 216 (M+H).

Step 2: 1-(1H-Indol-3-yl)-2-((3-methoxyphenyl)amino)-2-(1-methyl-1H-imidazol-4-yl)ethanone was prepared according to general procedure K from a mixture of 3-benzyl-5-(2-hydroxyethyl)-4-methylthiazolium chloride (0.135 g; 0.500 mmol) and triethylamine (0.069 mL; 0.497 mmol) in ethanol (0.7 mL), tert-butyl 3-formyl-1H-indole-1-carboxylate (0.294 g; 1.199 mmol) and a solution of 3-methoxy-N-((1-methyl-1H-imidazol-4-yl)methylene)aniline (0.999 mmol) in ethanol (0.7 mL), heated at 70° C. for 2 days. The residue was purified by flash chromatography on silica gel using a gradient of ethyl acetate (0% to 100%) in heptane. Further purification by flash chromatography on silica gel using a gradient of methanol (0% to 10%) in dichloromethane followed by precipitation from dichloromethane furnished 0.045 g (12%) of the desired compound as a beige powder. ESI/APCI(+): 361 (M+H); 383 (M+Na); 743 (2M+Na). ESI/APCI(−): 359 (M−H).

Example 103: Preparation of 1-(1-(2-hydroxyethyl)-1H-indol-3-yl)-2-((3-methoxyphenyl)amino)-2-phenylethanone Step 1: 2-Chloro-1-(1-(2-hydroxyethyl)-1H-indol-3-yl)-2-phenylethanone was prepared according to general method M from 2-chloro-1-(1H-indol-3-yl)-2-phenylethanone (0.150 g; 0.556 mmol), 2-bromoethanol (0.079 mL; 1.113 mmol) and potassium carbonate (0.115 g; 0.834 mmol) in DMF (3 mL). The reaction mixture was stirred at room temperature overnight.

Purification by flash chromatography on silica gel using a gradient of ethyl acetate (5% to 50%) in heptane furnished 0.020 g (11%) of the desired compound as a white solid. ESI/APCI(+): 314 (M+H); 336 (M+Na). ESI/APCI(−): 312 (M−H).

Step 2: 1-(1-(2-Hydroxyethyl)-1H-indol-3-yl)-2-((3-methoxyphenyl)amino)-2-phenylethanone was prepared according to general procedure C from 2-chloro-1-(1-(2-hydroxyethyl)-1H-indol-3-yl)-2-phenylethanone (0.020 g; 0.064 mmol), 3-methoxyaniline (0.014 mL; 0.127 mmol) and DIPEA (0.021 mL; 0.127 mmol) in acetonitrile (0.5 mL), irradiated in a microwave oven at 200° C. for 30 min. Purification by flash chromatography on silica gel using a gradient of ethyl acetate (2% to 20%) in dichloromethane furnished 0.006 g (25%) of the desired compound as a beige solid. ESI/APCI(+): 401 (M+H).

Example 104: Preparation of 1-(1-(2-aminoethyl)-1H-indol-3-yl)-2-((3-methoxyphenyl)amino)-2-phenylethanone and tert-butyl (2-(3-(2-((3-methoxyphenyl)amino)-2-phenylacetyl)-1H-indol-1-yl)ethyl) carbamate Step 1: tert-Butyl (2-(3-(2-chloro-2-phenylacetyl)-1H-indol-1-yl)ethyl)carbamate was prepared according to general method M from 2-chloro-1-(1H-indol-3-yl)-2-phenylethanone (0.150 g; 0.556 mmol), tert-butyl (2-bromoethyl)carbamate (0.249 g; 1.111 mmol) and potassium carbonate (0.154 g; 1.114 mmol) in DMF (3 mL). The reaction mixture was stirred at room temperature overnight. Purification by flash chromatography on silica gel using a gradient of ethyl acetate (5% to 50%) in heptane furnished 0.120 g (52%) of the desired compound as a pink solid. ESI/APCI(+): 413 (M+H); 435 (M+Na).

Step 2: tert-Butyl (2-(3-(2-((3-methoxyphenyl)amino)-2-phenylacetyl)-1H-indol-1-yl)ethyl)carbamate was prepared according to general procedure C from tert-butyl (2-(3-(2-chloro-2-phenylacetyl)-1H-indol-1-yl)ethyl)carbamate (0.120 g; 0.291 mmol), 3-methoxyaniline (0.065 mL; 0.581 mmol) and DIPEA (0.099 mL; 0.581 mmol) in acetonitrile (3 mL), irradiated in a microwave oven at 200° C. for 1.5 h. Purification by flash chromatography on silica gel using a gradient of ethyl acetate (1% to 10%) in dichloromethane furnished 0.066 g (45%) of the desired compound as an orange solid. ESI/APCI(+): 500 (M+H), 522 (M+Na).

Step 3: To a solution of tert-butyl (2-(3-(2-((3-methoxyphenyl)amino)-2-phenylacetyl)-1H-indol-1-yl)ethyl)carbamate (0.066 g; 0.132 mmol) in dichloromethane (6 mL) was added trifluoroacetic acid (3 mL) and the mixture was stirred at room temperature for 2 h. The reaction mixture was concentrated under reduced pressure. The residue was partitioned between dichloromethane and a saturated sodium bicarbonate solution. The phases were separated. The organic phase was dried over magnesium sulfate and concentrated under reduced pressure. The crude material was purified by flash chromatography on silica gel using a gradient of methanol (1% to 15%) in dichloromethane. Further purification by preparative TLC using 10% methanol in dichloromethane as eluent furnished 0.033 g (62%) of 1-(1-(2-aminoethyl)-1H-indol-3-yl)-2-((3-methoxyphenyl)amino)-2-phenylethanone as a beige solid. ESI/APCI(+): 400 (M+H); 422 (M+Na).

Example 105: Preparation of ethyl 2-(3-(2-((3-methoxyphenyl)amino)-2-phenylacetyl)-1H-indol-1-yl)acetate Step 1: Ethyl 2-(3-(2-chloro-2-phenylacetyl)-1H-indol-1-yl)acetate was prepared according to general procedure M from 2-chloro-1-(1H-indol-3-yl)-2-phenylethanone (0.400 g; 1.483 mmol), ethyl bromoacetate (0.329 mL; 2.974 mmol) and potassium carbonate (0.410 g; 2.967 mmol) in DMF (10 mL). The reaction mixture was stirred at room temperature for 1 h. Purification by precipitation followed by recrystallization from ethanol furnished 0.475 g (90%) of the desired compound as a beige solid. ESI/APCI(+): 356, 358 (M+H). ESI/APCI(−): 354, 356 (M−H).

Step 2: Ethyl 2-(3-(2-((3-methoxyphenyl)amino)-2-phenylacetyl)-1H-indol-1-yl)acetate was prepared according to general procedure C from ethyl 2-(3-(2-chloro-2-phenylacetyl)-1H-indol-1-yl)acetate (0.250 g; 0.703 mmol), 3-methoxyaniline (0.157 mL; 1.402 mmol) and DIPEA (0.240 mL; 1.402 mmol) in acetonitrile (3 mL), irradiated in a microwave oven at 200° C. for 1.5 h. The reaction mixture was concentrated under reduced pressure. The residue was purified by flash chromatography on silica gel using a gradient of ethyl acetate (2% to 40%) in heptane. Further purification by flash chromatography on silica gel eluting with dichloromethane followed by purification by preparative HPLC (XBridge column; method 1) furnished 0.058 g (19%) of the desired compound as a beige solid. ESI/APCI(+): 443 (M+H). ESI/APCI(−): 441 (M−H).

Example 106: Preparation of 2-(3-(2-((3-methoxyphenyl)amino)-2-phenylacetyl)-1H-indol-1-yl)acetic Acid To a solution of ethyl 2-(3-(2-((3-methoxyphenyl)amino)-2-phenylacetyl)-1H-indol-1-yl)acetate (0.040 g; 0.090 mmol) in ethanol (2 mL) was added a 1N sodium hydroxide solution (0.108 mL; 0.108 mmol) and the reaction mixture was stirred at room temperature for 3 h. Ethanol was evaporated under reduced pressure. The residue was diluted with water and extracted with dichloromethane. The phases were separated. The aqueous phase was acidified with a 1N hydrochloric acid solution to pH 2-3 and extracted with ethyl acetate. The organic phase was dried over magnesium sulfate and evaporated under reduced pressure to give 0.021 g (55%) of 2-(3-(2-((3-methoxyphenyl)amino)-2-phenylacetyl)-1H-indol-1-yl)acetic acid as a white solid. ESI/APCI(+): 415 (M+H). ESI/APCI(−): 413 (M−H).

Example 107: Preparation of 2-(1-ethyl-1H-pyrazol-5-yl)-1-(1H-indol-3-yl)-2-((3-methoxyphenyl)amino)ethanone Step 1: N-((1-Ethyl-1H-pyrazol-5-yl)methylene)-3-methoxyaniline was prepared quantitatively according to general procedure I from 1-ethyl-1H-pyrazole-5-carbaldehyde (0.254 g; 2.046 mmol) and 3-methoxyaniline (0.229 mL; 2.045 mmol). ESI/APCI(+): 230 (M+H).

Step 2: To a solution of 1H-indole-3-carbaldehyde (5.000 g; 34.45 mmol) in DMSO (35 mL) was added sodium hydride (60% dispersion in mineral oil; 1.520 g; 37.89 mmol) and the mixture was stirred at room temperature for 30 min. Ethyl chloroformate (3.520 mL; 37.89 mmol) was and the reaction mixture was stirred for 30 min. The reaction mixture was poured into a mixture ice-water. The resulting precipitate was filtered and dissolved in ethyl acetate. The organic phase was dried over magnesium sulfate, filtered and concentrated under reduced pressure. Purification by flash chromatography on silica gel using a gradient of ethyl acetate (2% to 40%) in heptane furnished 6.79 g (91%) of ethyl 3-formyl-1H-indole-1-carboxylate as a beige solid. ESI/APCI(+): 218 (M+H).

Step 3: 2-(1-Ethyl-1H-pyrazol-5-yl)-1-(1H-indol-3-yl)-2-((3-methoxyphenyl)amino)ethanone was prepared according to general procedure L from a mixture of 3-benzyl-5-(2-hydroxyethyl)-4-methylthiazolium chloride (0.124 g; 0.460 mmol) and triethylamine (0.064 mL; 0.462 mmol) in ethanol (2 mL), ethyl 3-formyl-1H-indole-1-carboxylate (0.200 g; 0.921 mmol) and a solution of N-((1-ethyl-1H-pyrazol-5-yl)methylene)-3-methoxyaniline (0.921 mmol) in ethanol (1 mL), heated overnight at 70° C. The residue was purified by flash chromatography on silica gel using a gradient of ethyl acetate (5% to 50%) in dichloromethane followed by precipitation from dichloromethane and diethyl ether furnished 0.008 g (2%) of the desired compound as a beige solid. ESI/APCI(+): 375 (M+H). ESI/APCI(−): 373 (M−H).

Example 108: Preparation of 1-(1H-indol-3-yl)-2-((2-methoxypyridin-4-yl)amino)-2-(5-methylisoxazol-3-yl)ethanone Step 1: 2-Methoxy-N-((5-methylisoxazol-3-yl)methylene)pyridin-4-amine was quantitatively prepared according to general procedure H from 5-methylisoxazole-3-carbaldehyde (0.111 g; 0.999 mmol), magnesium sulfate (0.100 g; 0.831 mmol) and 2-methoxypyridin-4-amine (0.124 g; 0.999 mmol) in ethanol (1 mL).

Step 2: 1-(1H-Indol-3-yl)-2-((2-methoxypyridin-4-yl)amino)-2-(5-methylisoxazol-3-yl)ethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-1H-indole-1-carboxylate (0.245 g; 0.999 mmol) and a solution of 2-methoxy-N-((5-methylisoxazol-3-yl)methylene)pyridin-4-amine (0.999 mmol) in ethanol (1 mL), heated at 70° C. for 2 days. The residue was purified by flash chromatography on silica gel using a gradient of ethyl acetate (0% to 100%) in heptane. Further purification by preparative HPLC (XBridge column; method 5) followed by purification by preparative TLC using 65% ethyl acetate in heptane as eluent furnished 0.021 g (6%) of the desired compound. ESI/APCI(+): 363 (M+H). ESI/APCI(−): 361 (M−H).

Example 109: Preparation of 2-(5-fluoroimidazo[1,2-a]pyridin-2-yl)-1-(1H-indol-3-yl)-2-((3-methoxyphenyl)amino)ethanone Step 1: A solution of 5-fluoroimidazo[1,2-a]pyridine-2-carbaldehyde (0.151 g; 0.920 mmol) and 3-methoxyaniline (0.105 mL; 0.934 mmol) in ethanol (1 mL) was stirred overnight at 60° C. The reaction mixture was evaporated and dried under reduced pressure to give quantitatively N-((5-fluoroimidazo[1,2-a]pyridin-2-yl)methylene)-3-methoxyaniline which was used without further purification. ESI/APCI (+): 270 (M+H)

Step 2: 2-(5-Fluoroimidazo[1,2-a]pyridin-2-yl)-1-(1H-indol-3-yl)-2-((3-methoxyphenyl)amino)-ethanone was prepared according to general procedure L from a mixture of 3-benzyl-5-(2-hydroxyethyl)-4-methylthiazol-3-ium chloride (0.125 g; 0.463 mmol) and triethylamine (0.100 mL; 0.717 mmol) in ethanol (0.7 mL), tert-butyl 3-formyl-1H-indole-1-carboxylate (0.270 g; 1.102 mmol) and a solution of N-((5-fluoroimidazo[1,2-a]pyridin-2-yl)methylene)-3-methoxyaniline (0.920 mmol) in ethanol (1 mL), heated at 60° C. for 3 days. Purification by flash chromatography on silica gel using a gradient of ethyl acetate (20% to 70%) in heptane followed by purification by preparative HPLC (XBridge column; method 5) furnished 0.072 g (19%) of the desired compound. ESI/APCI(+): 415 (M+H). ESI/APCI (−): 413 (M−H).

Example 110: Preparation of 2-(6-fluoroimidazo[1,2-a]pyridin-2-yl)-1-(1H-indol-3-yl)-2-((3-methoxyphenyl)amino)ethanone Step 1: A solution of N-((6-fluoroimidazo[1,2-a]pyridin-2-yl)methylene)-3-methoxyaniline in ethanol was prepared by heating a solution of 6-fluoroimidazo[1,2-a]pyridine-2-carbaldehyde (0.150 g; 0.914 mmol) and 3-methoxyaniline (0.113 mL; 1.009 mmol) in ethanol (0.5 mL) at 65° C. for 18 h. The formation of the imine was quantitative and the solution was used without further purification. ESI/APCI (+): 270 (M+H); 292 (M+Na).

Step 2: 2-(6-Fluoroimidazo[1,2-a]pyridin-2-yl)-1-(1H-indol-3-yl)-2-((3-methoxyphenyl)amino)-ethanone was prepared according to general procedure K from a mixture of 3-benzyl-5-(2-hydroxyethyl)-4-methylthiazol-3-ium chloride (0.130 g; 0.482 mmol) and triethylamine (0.090 mL; 0.646 mmol) in ethanol (0.7 mL), tert-butyl 3-formyl-1H-indole-1-carboxylate (0.275 g; 1.121 mmol) and a solution of N-((6-fluoroimidazo[1,2-a]pyridin-2-yl)methylene)-3-methoxyaniline (0.914 mmol) in ethanol (1 mL), heated at 65° C. for 3 days. Purification by flash chromatography on silica gel using a gradient of ethyl acetate (20% to 70%) in heptane furnished 0.078 g (21%) of the desired compound as a brown solid. ESI/APCI(+): 415 (M+H). ESI/APCI(−): 413 (M−H).

Example 111: Preparation of 2-((3-methoxyphenyl)amino)-1-(1-(methylsulfonyl)-1H-indol-3-yl)-2-phenylethanone Step 1: To a suspension of 1H-indole-3-carbaldehyde (0.214 g; 1.447 mmol) in dichloromethane (3 mL) were added methanesulfonyl chloride (0.200 mL; 2.578 mmol) and DIPEA (0.300 mL; 1.722 mmol). The reaction mixture was stirred at room temperature for 18 h. Water was added and the solution was stirred for 1 h. The phases were separated. The organic phase was washed with a saturated bicarbonate solution and water, dried over sodium sulfate, filtered and concentrated under reduced pressure. Purification by flash chromatography on silica gel using a gradient of ethyl acetate (10% to 40%) in heptane furnished 0.189 g (57%) of 1-(methylsulfonyl)-1H-indole-3-carbaldehyde as a beige solid. ESI/APCI(+): 224 (M+H).

Step 2: 2-((3-Methoxyphenyl)amino)-1-(1-(methylsulfonyl)-1H-indol-3-yl)-2-phenylethanone was prepared according to general procedure L from a mixture of 3-benzyl-5-(2-hydroxyethyl)-4-methylthiazol-3-ium chloride (0.157 g; 0.582 mmol) and triethylamine (0.100 ml; 0.717 mmol) in ethanol (1 mL), 1-(methylsulfonyl)-1H-indole-3-carbaldehyde (0.144 g; 0.645 mmol) and a solution of N-benzylidene-3-methoxyaniline (0.914 mmol) in ethanol (2 mL), heated at 70° C. for 24 h. Purification by flash chromatography on silica gel using a gradient of ethyl acetate (10% to 60%) in heptane followed by purification by preparative HPLC (XBridge column; method 2) furnished 0.041 g (15%) of the desired compound. ESI/APCI(+): 435 (M+H); 457 (M+Na). ESI/APCI(−): 433 (M−H).

Example 112: Preparation of 2-(4-(2-(dimethylamino)ethoxy)phenyl)-1-(1H-indol-3-yl)-2-((3-methoxyphenyl)amino)ethanone Step 1: N-(4-(2-(Dimethylamino)ethoxy)benzylidene)-3-methoxyaniline was prepared according to general procedure I from 4-(2-(dimethylamino)ethoxy)benzaldehyde (0.185 g; 0.943 mmol) and 3-methoxyaniline (0.108 mL; 0.965 mmol). ESI/APCI(+): 299 (M+H).

Step 2: 2-(4-(2-(dimethylamino)ethoxy)phenyl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.129 g; 0.478 mmol) and triethylamine (0.066 mL; 0.496 mmol) in ethanol (0.7 mL), tert-butyl 3-formyl-1H-indole-1-carboxylate (0.281 g; 1.146 mmol) and a solution of N-(4-(2-(dimethylamino)ethoxy)benzylidene)-3-methoxyaniline (0.943 mmol) in ethanol (0.7 mL), heated at 70° C. for 2 days. Purification by flash chromatography on silica gel using a gradient of methanol (0% to 30%) in dichloromethane followed by purification by preparative HPLC (XBridge column; method 5) furnished 0.087 g (20%) of the desired compound as a yellow solid. ESI/APCI(+): 444 (M+H). ESI/APCI(−): 442 (M−H).

Example 113: Preparation of 1-(1-(2-(dimethylamino)ethyl)-1H-indol-3-yl)-2-((3-methoxyphenyl)amino)-2-phenylethanone To a solution of 1-(1-(2-aminoethyl)-1H-indol-3-yl)-2-((3-methoxyphenyl)amino)-2-phenylethanone (0.020 g; 0.056 mmol) in a mixture of THF (1 mL) and acetonitrile (1 mL) was added a 37% formaldehyde solution in water (0.020 mL; 0.250 mmol) and sodium cyanoborohydride (0.004 g; 0.080 mmol). The reaction mixture was stirred at room temperature for 2 h. The reaction mixture was then diluted with dichloromethane and washed with a saturated sodium bicarbonate solution. The phases were separated. The organic phase was dried over magnesium sulfate, filtered and concentrated under reduced pressure. Purification by preparative TLC using 5% methanol in dichloromethane as eluent furnished 0.006 g (30%) of 1-(1-(2-(dimethylamino)ethyl)-1H-indol-3-yl)-2-((3-methoxyphenyl)amino)-2-phenylethanone as a beige solid. ESI/APCI(+): 428 (M+H). ESI/APCI(−): 426 (M−H).

Example 114: Preparation of N-(2-(1H-indol-3-yl)-2-oxo-1-phenylethyl)-2-(dimethylamino)-N-(3-methoxyphenyl)acetamide Step 1: To a solution of 1-(1H-indol-3-yl)-2-((3-methoxyphenyl)amino)-2-phenylethanone (0.050 g; 0.140 mmol) in dichloromethane (3 mL) cooled at 0° C. were added triethylamine (0.059 mL; 0.421 mmol) and chloroacetyl chloride (0.034 mL; 0.421 mmol). The reaction mixture was allowed to warm to room temperature over 15 min. The reaction mixture was diluted with dichloromethane and washed with a saturated sodium bicarbonate solution. The phases were separated. The organic layer was dried over magnesium sulfate and concentrated under reduced pressure. Purification by flash chromatography on silica gel using a gradient of ethyl acetate (5% to 50%) in heptane furnished 0.027 g (44%) of N-(2-(1H-indol-3-yl)-2-oxo-1-phenylethyl)-2-chloro-N-(3-methoxyphenyl)acetamide as a beige solid. ESI/APCI(+): 433, 435 (M+H). ESI/APCI(−): 431, 433 (M−H).

Step 2: To a solution of N-(2-(1H-indol-3-yl)-2-oxo-1-phenylethyl)-2-chloro-N-(3-methoxyphenyl)acetamide (0.027 g; 0.062 mmol) in dry THF (2 mL) cooled at 0° C. was added a 2M dimethylamine solution in THF (0.156 mL; 0.312 mmol). The reaction mixture was stirred at room temperature for 2 h and was then heated at 55° C. for 2 h. The reaction mixture was concentrated under reduced pressure. Purification by preparative TLC using 10% methanol in dichloromethane as eluent furnished 0.015 g (57%) of N-(2-(1H-indol-3-yl)-2-oxo-1-phenylethyl)-2-(dimethylamino)-N-(3-methoxyphenyl)acetamide as a beige solid. ESI/APCI(+): 442 (M+H). ESI/APCI(−): 440 (M−H).

Example 115: Preparation of 1-(6-chloro-1H-indol-3-yl)-2-((3-methoxyphenyl)amino)-2-(5-methylisoxazol-3-yl)ethanone 1-(6-Chloro-1H-indol-3-yl)-2-((3-methoxyphenyl)amino)-2-(5-methylisoxazol-3-yl)ethanone was prepared according to general procedure L from a mixture of 3-benzyl-5-(2-hydroxyethyl)-4-methylthiazolium chloride (0.135 g; 0.500 mmol) and triethylamine (0.070 mL; 0.498 mmol) in ethanol (1 mL), tert-butyl 6-chloro-3-formyl-1H-indole-1-carboxylate (0.280 g; 1.001 mmol) and a solution of 3-methoxy-N-((5-methylisoxazol-3-yl)methylene)aniline (0.999 mmol) in ethanol (1 mL), heated at 70° C. for 3 days. Purification by flash chromatography on silica gel using a gradient of ethyl acetate (0% to 100%) in heptane followed by purification by preparative HPLC (XBridge column; method 1) furnished 0.060 g (14%) of the desired compound. ESI/APCI (+): 396, 398 (M+H). ESI/APCI (−): 394, 396 (M−H).

Example 116: Preparation of 2-((3-methoxyphenyl)amino)-1-(1-methyl-1H-indol-3-yl)-2-(5-methylisoxazol-3-yl)ethanone 2-((3-Methoxyphenyl)amino)-1-(1-methyl-1H-indol-3-yl)-2-(5-methylisoxazol-3-yl)ethanone was prepared according to general procedure L from a mixture of 3-benzyl-5-(2-hydroxyethyl)-4-methylthiazolium chloride (0.135 g; 0.500 mmol) and triethylamine (0.070 mL; 0.498 mmol) in ethanol (1 mL), 1-methyl-1H-indole-3-carbaldehyde (0.159 g; 0.999 mmol) and a solution of 3-methoxy-N-((5-methylisoxazol-3-yl)methylene)aniline (0.999 mmol) in ethanol (1 mL), heated at 70° C. for 2 days. Purification by flash chromatography on silica gel using a gradient of ethyl acetate (0% to 100%) in heptane followed by purification by preparative HPLC (XBridge column; method 1) furnished 0.005 g (1%) of the desired compound. ESI/APCI (+): 376 (M+H).

Example 117: Preparation of 1-(6-chloro-1H-indol-3-yl)-2-((3-methoxyphenyl)amino)-2-phenylethanone 1-(6-Chloro-1H-indol-3-yl)-2-((3-methoxyphenyl)amino)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.498 mmol) in ethanol (1 mL), tert-butyl 6-chloro-3-formyl-1H-indole-1-carboxylate (0.280 g; 0.999 mmol) and a solution of N-benzylidene-3- methoxyaniline (0.999 mmol) in ethanol (1 mL), heated at 70° C. for 2 days. Purification by flash chromatography on silica gel using a gradient of ethyl acetate (0% to 100%) in heptane followed by recrystallization from ethyl acetate furnished 0.047 g (12%) of the desired compound as a solid. ESI/APCI (+): 391, 393 (M+H). ESI/APCI (−): 389, 391 (M−H).

Example 118: Preparation of 1-(5-fluoro-1H-indol-3-yl)-2-((3-methoxyphenyl)amino)-2-phenylethanone Step 1: tert-Butyl 5-fluoro-3-formyl-1H-indole-1-carboxylate was prepared according to general procedure F from 5-fluoro-1H-indole-3-carbaldehyde (0.454 g; 2.783 mmol), di-tert-butyl dicarbonate (0.728 g; 3.336 mmol) and DMAP (0.034 g; 0.278 mmol) in acetonitrile (7 mL) to afford 0.473 g (65%) of the desired compound as a solid. $^1$H NMR (DMSO-$d_6$) δ 10.07 (1H, s); 8.74 (1H, s); 8.12 (1H, dd); 7.82 (1H, dd); 7.33 (1H, dt); 1.66 (9H, s).

Step 2: 1-(5-Fluoro-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 5-fluoro-3-formyl-1H-indole-1-carboxylate (0.263 g; 0.999 mmol) and a solution of N-benzylidene-3-methoxyaniline (0.999 mmol) in ethanol (1 mL), heated at 70° C. for 3 days. Purification by flash chromatography on silica gel using a gradient of ethyl acetate (0% to 100%) in heptane followed by precipitation from diethyl ether furnished 0.043 g (11%) of the desired compound as a solid. ESI/APCI(+): 375 (M+H). ESI/APCI(−): 373 (M−H).

Example 119: Preparation of 4-(2-(7-chloro-1H-indol-3-yl)-1-((3-methoxyphenyl)amino)-2-oxoethyl)benzonitrile 4-(2-(7-Chloro-1H-indol-3-yl)-1-((3-methoxyphenyl)amino)-2-oxoethyl)benzonitrile was prepared according to general procedure K from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 7-chloro-3-formyl-1H-indole-1-carboxylate (0.280 g; 1.001 mmol) and a solution of 4-(((3-methoxyphenyl)imino)methyl)benzonitrile (0.999 mmol) in ethanol (1 mL), heated at 70° C. for 2 days. Purification by flash chromatography on silica gel using a gradient of ethyl acetate (0% to 100%) in heptane followed by recrystallization from ethyl acetate furnished 0.050 g (12%) of the desired compound as a solid. ESI/APCI(+): 416 (M+H). ESI/APCI(−): 414 (M−H).

Example 120: Preparation of 2-((2-methoxypyridin-4-yl)amino)-1-(1-(methylsulfonyl)-1H-indol-3-yl)-2-phenylethanone 2-((2-Methoxypyridin-4-yl)amino)-1-(1-(methylsulfonyl)-1H-indol-3-yl)-2-phenylethanone was prepared according to general procedure L from a mixture of 3-benzyl-5-(2-hydroxyethyl)-4-methylthiazol-3-ium chloride (0.166 g; 0.615 mmol) and triethylamine (0.100 mL; 0.717 mmol) in ethanol (1 mL), 1-(methylsulfonyl)-1H-indole-3-carbaldehyde (0.189 g; 0.847 mmol) and a solution of N-benzylidene-2-methoxypyridin-4-amine (0.909 mmol) in ethanol (2 mL), heated at 70° C. for 24 h. The reaction mixture was concentrated. The residue was purified by flash chromatography on silica gel using a gradient of methanol (0% to 10%) in ethyl acetate followed by purification by preparative HPLC (XBridge column; method 2) furnished 0.008 g (2%) of the desired compound. ESI/APCI(+): 436 (M+H). ESI/APCI(−): 434 (M−H).

Example 121: Preparation of 2-((3-methoxyphenyl)amino)-1-(6-methyl-1H-indol-3-yl)-2-phenylethanone Step 1: 2-Chloro-1-(6-methyl-1H-indol-3-yl)-2-phenylethanone was prepared according to general procedure A from 6-methyl-1H-indole (0.200 g; 1.525 mmol), pyridine (0.100 mL; 1.270 mmol) and α-chlorophenylacetyl chloride (0.240 mL; 1.530 mmol) in toluene (2.5 mL). Purification by precipitation furnished 0.200 g (46%) of the desired compound as a beige solid. ESI/APCI(+): 284, 286. ESI/APCI (−): 282, 284 (M−H).

Step 2: 2-((3-Methoxyphenyl)amino)-1-(6-methyl-1H-indol-3-yl)-2-phenylethanone was prepared according to general procedure C from 2-chloro-1-(6-methyl-1H-indol-3-yl)-2-phenylethanone (0.110 g; 0.388 mmol), 3-methoxypiridine (0.087 mL; 0.388 mmol), DIPEA (0.133 g; 0.775 mmol) and a catalytic amount of sodium iodide in acetonitrile (1.5 mL), irradiated in a microwave oven at 200° C. for 30 min. Purification by flash chromatography on silica gel eluting with dichloromethane followed by purification by preparative HPLC (XBridge column, method 5) furnished 0.006 g (4%) of the desired compound as a white solid. ESI/APCI(+): 371 (M+H). ESI/APCI(−): 369 (M−H).

Example 122: Preparation of 1-(6-fluoro-1H-indol-3-yl)-2-((3-methoxyphenyl)amino)-2-phenylethanone Step 1: 2-Chloro-1-(6-fluoro-1H-indol-3-yl)-2-phenylethanone was prepared according to general procedure A from 6-fluoro-1H-indole (0.250 g; 1.850 mmol), pyridine (0.120 mL; 1.518 mmol) and α-chlorophenylacetyl chloride (0.292 mL; 1.861 mmol) in toluene (3 mL). Purification by precipitation furnished 0.150 g (28%) of the desired compound as a beige solid. ESI/APCI(+): 288, 290 (M+H). ESI/APCI(−): 286, 288 (M−H).

Step 2: 1-(6-Fluoro-1H-indol-3-yl)-2-((3-methoxyphenyl)amino)-2-phenylethanone was prepared according to general procedure C from 2-chloro-1-(6-fluoro-1H-indol-3-yl)-2-phenylethanone (0.100 g; 0.348 mmol), 3-methoxyaniline (0.078 mL; 0.695 mmol), DIPEA (0.119 mL; 0.695 mmol) and a catalytic amount of sodium iodide in a mixture of dioxane (1 mL) and DMF (0.5 mL), irradiated in a microwave oven at 160° C. for 30 min. Purification by flash chromatography on silica gel eluting with dichloromethane followed by purification by preparative HPLC (XBridge column; method 5) furnished 0.012 g (9%) of the desired compound as a beige solid. ESI/APCI(+): 375 (M+H). ESI/APCI(−): 373 (M−H).

Example 123: Preparation of 2-(4-((dimethylamino)methyl)phenyl)-1-(1H-indol-3-yl)-2-((3-methoxyphenyl)amino)ethanone Step 1: A solution of N-(4-((dimethylamino)methyl)benzylidene)-3-methoxyaniline in ethanol was prepared by heating a solution of p-dimethylaminomethylbenzaldehyde (0.161 g; 0.986 mmol) and 3-methoxyaniline (0.113 mL; 1.000 mmol) in ethanol (0.5 mL) at 65° C. for 18 h. The formation of the imine was quantitative and the solution was used without further purification. ESI/APCI (+): 269 (M+H).

Step 2: 2-(4-((Dimethylamino)methyl)phenyl)-1-(1H-indol-3-yl)-2-((3-methoxyphenyl)amino)-ethanone was prepared according to general procedure K from a mixture of 3-benzyl-5-(2-hydroxyethyl)-4-methylthiazol-3-ium chloride (0.135 g; 0.500 mmol) and triethylamine (0.100 mL; 0.717 mmol) in ethanol (0.7 mL), tert-butyl 3-formyl-1H-indole-1-carboxylate (0.270 g; 1.101 mmol) and a solution of N-(4-((dimethylamino)methyl)benzylidene)-3-methoxyaniline (0.986 mmol) in ethanol (1.5 mL), heated overnight at 65° C. Purification by preparative HPLC (XBridge column; method 2) furnished 0.135 g (33%) of the desired compound as a brown solid. ESI/APCI(+): 414 (M+H). ESI/APCI(−): 412 (M−H).

Example 124: Preparation of 1-(1H-indol-3-yl)-2-((3-methoxyphenyl)amino)-2-(4-methyl-1H-imidazol-5-yl)ethanone Step 1: A solution of 3-methoxy-N-((4-methyl-1H-imidazol-5-yl)methylene)aniline in ethanol was prepared by heating a solution of 4-methyl-1H-imidazole-5-carbaldehyde (0.110 g; 0.999 mmol) and 3-methoxyaniline (0.115 mL; 1.023 mmol) in ethanol (0.7 mL) at 65° C. for 24 h. The formation of the imine was quantitative and the solution was used without further purification. ESI/APCI (+): 216 (M+H). ESI/APCI (−): 214 (M−H).

Step 2: 1-(1H-Indol-3-yl)-2-((3-methoxyphenyl)amino)-2-(4-methyl-1H-imidazol-5-yl)ethanone was prepared according to general procedure K from a mixture of 3-benzyl-5-(2-hydroxyethyl)-4-methylthiazol-3-ium chloride (0.134 g; 0.496 mmol) and triethylamine (0.100 mL; 0.717 mmol) in ethanol (0.7 mL), tert-butyl 3-formyl-1H-indole-1-carboxylate (0.270 g; 1.101 mmol) and a solution of 3-methoxy-N-((4-methyl-1H-imidazol-5-yl)methylene)aniline (0.999 mmol) in ethanol (1.5 mL), heated overnight at 65° C. The reaction mixture was concentrated under reduced pressure. The residue was purified by preparative HPLC (XBridge column, method 3). Further purification by preparative HPLC (SunFire column; method 3) furnished 0.043 g (12%) of the desired compound. ESI/APCI(+): 361 (M+H).

Example 125: Preparation of 3-(2-((3-methoxyphenyl)amino)-2-phenylacetyl)-1H-indole-5-carbonitrile Step 1: tert-Butyl 5-cyano-3-formyl-1H-indole-1-carboxylate was prepared according to general procedure F from 3-formyl-1H-indole-5-carbonitrile (0.340 g; 1.999 mmol), di-tert-butyl dicarbonate (0.524 g; 2.401 mmol) and DMAP (0.024 g; 0.197 mmol) in acetonitrile (7 mL) to afford 0.379 g (73%) of the desired compound as a solid. $^1$H NMR (DMSO-d$_6$) δ 10.11 (1H, s); 8.85 (1H, s); 8.50 (1H, s); 8.27 (1H, d); 7.87 (1H, dd); 1.68 (9H, s).

Step 2: 3-(2-((3-Methoxyphenyl)amino)-2-phenylacetyl)-1H-indole-5-carbonitrile was prepared according to general procedure L from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 5-cyano-3-formyl-1H-indole-1-carboxylate (0.270 g; 1.000 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane followed by recrystallization from ethyl acetate furnished 0.034 g (9%) of the desired compound as a white solid. ESI/APCI(+): 382 (M+H). ESI/APCI(−): 380 (M−H).

Example 126: Preparation of 2-(4-(hydroxymethyl)phenyl)-1-(1H-indol-3-yl)-2-((3-methoxyphenyl)amino)ethanone Step 1: ((4-Bromobenzyl)oxy)(tert-butyl)dimethylsilane was prepared according to general procedure N from 4-bromobenzyl alcohol (0.500 g; 2.673 mmol), DBU (0.408 mL; 2.734 mmol) and TBDMSCl (0.816 g; 5.414 mmol) in THF (10 mL). Purification by flash chromatography on silica gel using a gradient of ethyl acetate (20% to 50%) in heptane furnished 0.749 g (93%) of the desired compound as a colourless liquid.

Step 2: To a solution of ((4-bromobenzyl)oxy)(tert-butyl)dimethylsilane (0.500 g; 1.660 mmol) in THF (6 mL) cooled at −70° C., was added dropwise a 2.5 M n-butyllithium solution in hexane (0.800 mL; 2.000 mmol). After 30 min at −70° C., DMF (0.300 mL; 3.875 mmol) was added and the reaction mixture was allowed to warm to −5° C. over 4 h. The reaction was quenched by addition of a saturated ammonium chloride solution. After warming to room temperature, the reaction mixture was extracted with ethyl acetate. The organic phase was washed with water and brine, dried over sodium sulfate, filtered and concentrated under reduced pressure. The residue was purified by flash chromatography on silica gel using a gradient of dichloromethane (10% to 80%) in heptane to afford 0.382 g (92%) of 4-(((tert-butyldimethylsilyl)oxy)methyl)benzaldehyde as a colourless liquid. $^1$H NMR (DMSO-d$_6$) δ 9.89 (1H, s); 7.79 (2H, d); 7.44 (2H, d); 4.72 (2H, s); 0.82 (9H, s); 0.00 (6H, s).

Step 3: N-(4-(((tert-Butyldimethylsilyl)oxy)methyl)benzylidene)-3-methoxyaniline was prepared quantitatively according to general procedure I from 4-(((tert-butyldimethylsilyl)oxy)methyl)benzaldehyde (0.250 g; 0.998 mmol) and m-anisidine (0.113 mL; 1.000 mmol). ESI/APCI(+): 356 (M+H).

Step 4: 2-(4-(((tert-Butyldimethylsilyl)oxy)methyl)phenyl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.135 g; 0.500 mmol) and triethylamine (0.069 mL; 0.498 mmol) in ethanol (0.7 mL), tert-butyl 3-formyl-1H-indole-1-carboxylate (0.294 g; 1.199 mmol) and a solution of N-(4-(((tert-butyldimethylsilyl)oxy)methyl)benzylidene)-3-methoxyaniline (0.998 mmol) in ethanol (0.7 mL), heated at 70° C. for 2 days. The residue was purified by flash chromatography on silica gel using a gradient of ethyl acetate (20% to 50%) in heptane. Further purification by flash chromatography on silica gel using a gradient of ethyl acetate (20% to 50%) in heptane furnished 0.148 g (30%) of the desired compound as a yellow oil. ESI/APCI(+): 501 (M+H); 523 (M+Na). ESI/APCI(−): 499 (M−H).

Step 5: To a solution of 2-(4-(((tert-butyldimethylsilyl)oxy)methyl)phenyl)-1-(1H-indol-3-yl)-2-((3-methoxyphenyl)amino)ethanone (0.148 g; 0.296 mmol) in DMF (2.5 mL) was added cesium fluoride (0.221 g; 1.455 mmol). After 3 h at room temperature, the reaction mixture was concentrated. The residue was partitioned between ethyl acetate and a 1N hydrochloric acid solution. The phases were separated. The organic phase was washed with a saturated sodium hydrogencarbonate solution, water and brine, dried over sodium sulfate, filtered and concentrated. The residue was purified by flash chromatography on silica gel using a gradient of methanol (0% to 8%) in dichloromethane followed by recrystallization from ethyl acetate to give 0.027 g (24%) of 2-(4-(hydroxymethyl)phenyl)-1-(1H-indol-3-yl)-2-((3-methoxyphenyl)amino)ethanone as a white powder. ESI/APCI(+): 387 (M+H); 409 (M+Na). ESI/APCI(−): 385 (M−H).

Example 127: Preparation of 1-(1-(3-hydroxypropyl)-1H-indol-3-yl)-2-((3-methoxyphenyl)amino)-2-phenylethanone Step 1: 2-Chloro-1-(1-(3-hydroxypropyl)-1H-indol-3-yl)-2-phenylethanone was prepared according to general method M from 2-chloro-1-(1H-indol-3-yl)-2-phenylethanone (0.200 g; 0.741 mmol), 3-bromopropan-1-ol (0.206 g; 1.482 mmol) and potassium carbonate (0.205 g; 1.483 mmol) in DMF (3 mL). The reaction mixture was stirred at room temperature overnight. Purification by flash chromatography on silica gel using a gradient of ethyl acetate (15% to 70%) in heptane furnished 0.215 g (84%) of the desired compound as a red oil. ESI/APCI(+): 328, 330 (M+H). ESI/APCI(−): 326, 328 (M−H).

Step 2: 1-(1-(3-Hydroxypropyl)-1H-indol-3-yl)-2-((3-methoxyphenyl)amino)-2-phenylethanone was prepared according to general procedure E from 2-chloro-1-(1-(3-hydroxypropyl)-1H-indol-3-yl)-2-phenylethanone (0.070 g; 0.213 mmol), 3-methoxyaniline (0.478 mL; 4.270 mmol) in acetonitrile (1 mL), irradiated in a microwave oven at 150° C. for 30 min. Purification by flash chromatography on silica gel using a gradient of ethyl acetate (15% to 70%) in heptane followed by purification by preparative TLC using 10% ethyl acetate in dichloromethane as eluent furnished 0.027 g (30%) of the desired compound as a beige solid. ESI/APCI(+): 415 (M+H).

Example 128: Preparation of 3-(2-((3-methoxyphenyl)amino)-2-phenylacetyl)-N,N-dimethyl-1H-indole-5-sulfonamide Step 1: tert-Butyl 5-(N,N-dimethylsulfamoyl)-3-formyl-1H-indole-1-carboxylate was prepared according to general procedure F from 3-formyl-N,N-dimethyl-1H-indole-5-sulfonamide (0.505 g; 2.003 mmol), di-tert-butyl dicarbonate (0.524 g; 2.401 mmol) and DMAP (0.024 g; 0.197 mmol) in acetonitrile (5 mL) to afford of 0.602 g (85%) of the desired compound as a solid. $^1$H NMR (DMSO-$d_6$) δ 10.13 (1H, s); 8.87 (1H, s); 8.50 (1H, s); 8.36 (1H, d); 7.84 (1H, d); 2.62 (6H, s); 1.68 (9H, s).

Step 2: 3-(2-((3-Methoxyphenyl)amino)-2-phenylacetyl)-N,N-dimethyl-1H-indole-5-sulfonamide was prepared according to general procedure L from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 5-(N,N-dimethylsulfamoyl)-3-formyl-1H-indole-1-carboxylate (0.352 g; 0.999 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.047 g (9%) of the desired compound as a solid. ESI/APCI(+): 464 (M+H). ESI/APCI(−): 462 (M−H).

Example 129: Preparation of 2-((3-methoxyphenyl)amino)-1-(5-methyl-1H-indol-3-yl)-2-phenylethanone Step 1: tert-Butyl 3-formyl-5-methyl-1H-indole-1-carboxylate was prepared according to general procedure F from 5-methyl-1H-indole-3-carbaldehyde (0.478 g; 3.003 mmol), di-tert-butyl dicarbonate (0.524 g; 3.602 mmol) and DMAP (0.036 g; 0.295 mmol) in acetonitrile (8 mL) to afford 0.710 g (91%) of the desired compound as a solid. $^1$H NMR (DMSO-$d_6$) δ 10.06 (1H, s); 8.61 (1H, s); 7.91-8.03 (2H, m); 7.27 (1H, d); 2.43 (3H, s); 1.66 (9H, s).

Step 2: 2-((3-Methoxyphenyl)amino)-1-(5-methyl-1H-indol-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.498 mmol) in ethanol (1 mL), tert-butyl 3-formyl-5-methyl-1H-indole-1-carboxylate (0.259 g; 0.999 mmol) and a solution of N-benzylidene-3-methoxyaniline (0.999 mmol) in ethanol (1 mL), heated at 70° C. for 2 days. Purification by flash chromatography on silica gel using a gradient of ethyl acetate (0% to 100%) in heptane followed by precipitation from methyl tert-butyl ether furnished 0.053 g (14%) of the desired compound as a solid. ESI/APCI(+): 371 (M+H). ESI/APCI(−): 369 (M−H).

Example 130: Preparation of 2-((3,5-dimethoxyphenyl)amino)-1-(5-fluoro-1H-indol-3-yl)-2-phenylethanone Step 1: 2-Chloro-1-(5-fluoro-1H-indol-3-yl)-2-phenylethanone was prepared according to general procedure A from 5-fluoro-1H-indole (1.000 g; 7.400 mmol), pyridine (0.120 mL; 7.419 mmol) and α-chlorophenylacetyl chloride (1.100 mL; 7.390 mmol) in toluene (19 mL). Purification by precipitation furnished 0.978 g (46%) of the desired compound as a light yellow solid. ESI/APCI(+): 288, 290 (M+H); 310, 312 (M+Na). ESI/APCI(−): 286, 288 (M−H).

Step 2: 2-((3,5-Dimethoxyphenyl)amino)-1-(5-fluoro-1H-indol-3-yl)-2-phenylethanone was prepared according to general method E from 2-chloro-1-(5-fluoro-1H-indol-3-yl)-2-phenylethanone (0.100 g; 0.348 mmol) and 3,5-dimethoxyaniline (0.484 g; 3.160 mmol) in acetonitrile (1 mL), irradiated in a microwave oven at 150° C. for 15 min. Purification by flash chromatography on silica gel using a gradient of ethyl acetate (5% to 50%) in heptane furnished 0.045 g (32%) of the desired compound as a beige solid. ESI/APCI(+): 405 (M+H). ESI/APCI(−): 403 (M−H).

Example 131: Preparation of 4-(2-(1H-indol-3-yl)-1-((3-methoxyphenyl)amino)-2-oxoethyl)-2-fluorobenzonitrile Step 1: A solution of 2-fluoro-4-(((3-methoxyphenyl)imino)methyl)benzonitrile in ethanol was prepared by heating a solution of 2-fluoro-4-formylbenzonitrile (0.137 g; 0.919 mmol) and 3-methoxyaniline (0.107 mL; 0.952 mmol) in ethanol (1 mL) at 60° C. for 18 h. The formation of the imine was quantitative and the solution was used without further purification. ESI/APCI (+): 255 (M+H).

Step 2: 4-(2-(1H-Indol-3-yl)-1-((3-methoxyphenyl)amino)-2-oxoethyl)-2-fluorobenzonitrile was prepared according to general procedure K from a mixture of 3-benzyl-5-(2-hydroxyethyl)-4-methylthiazol-3-ium chloride (0.124 g; 0.460 mmol) and triethylamine (0.090 mL; 0.646 mmol) in ethanol (0.5 mL), tert-butyl 3-formyl-1H-indole-1-carboxylate (0.260 g; 1.060 mmol) and a solution of 2-fluoro-4-(((3-methoxyphenyl)-imino)methyl)benzonitrile (0.919 mmol) in ethanol (1.5 mL), heated at 60° C. for 3 days. Purification by flash chromatography on silica gel using a gradient of ethyl acetate (0% to 40%) in heptane furnished 0.154 g (42%) of the desired compound as a yellow foam. ESI/APCI(+): 400 (M+H). ESI/APCI(−): 398 (M−H).

Example 132: Preparation of 4-(2-(1H-indol-3-yl)-1-((3-methoxyphenyl)amino)-2-oxoethyl)-3,5-difluorobenzonitrile Step 1: A solution of 3,5-difluoro-4-(((3-methoxyphenyl)imino)methyl)benzonitrile in ethanol was prepared by heating a solution of 3,5-difluoro-4-formylbenzonitrile (0.151 g; 0.904 mmol) and 3-methoxyaniline (0.105 mL; 0.934 mmol) in ethanol (1 mL) at 60° C. for 24 h. The formation of the imine was quantitative and the solution was used without further purification. ESI/APCI (+): 273 (M+H).

Step 2: 4-(2-(1H-Indol-3-yl)-1-((3-methoxyphenyl)amino)-2-oxoethyl)-3,5-difluorobenzonitrile was prepared according to general procedure K from a mixture of 3-benzyl-5-(2-hydroxyethyl)-4-methylthiazol-3-ium chloride (0.124 g; 0.460 mmol) and triethylamine (0.090 mL; 0.646 mmol) in ethanol (0.5 mL), tert-butyl 3-formyl-1H-indole-1-carboxylate (0.260 g; 1.060 mmol) and a solution of 3,5-difluoro-4-(((3-methoxyphenyl)imino)methyl)benzonitrile (0.904 mmol) in ethanol (1.5 mL), heated at 60° C. for 3 days. Purification by flash chromatography on silica gel using a gradient of ethyl acetate (0% to 50%) in heptane furnished 0.214 g (58%) of the desired compound as a yellow oil. ESI/APCI(+): 418 (M+H).

Example 133: Preparation of 1-(6-hydroxy-1H-indol-3-yl)-2-((3-methoxyphenyl)amino)-2-phenylethanone Step 1:
6-((tert-Butyldimethylsilyl)oxy)-1H-indole was prepared according to general procedure N from 6-hydroxyindole (0.500 g; 3.755 mmol), DBU (0.573 mL; 3.839 mmol) and TBDMSCl (1.150 g; 7.630 mmol) in THE (13 mL). Purification by flash chromatography on silica gel using a gradient of ethyl acetate (20% to 50%) in heptane furnished 0.888 g (96%) of the desired compound as a white solid. ESI/APCI (+): 248 (M+H). ESI/APCI(−): 246 (M−H).

Step 2:
1-(6-((tert-Butyldimethylsilyl)oxy)-1H-indol-3-yl)-2-chloro-2-phenylethanone was prepared according to general procedure A from 6-((tert-butyldimethylsilyl)oxy)-1H-indole (0.785 g; 3.173 mmol), pyridine (0.275 mL; 3.276 mmol) and α-chlorophenylacetyl chloride (0.547 mL; 3.461 mmol) in toluene (8 mL). The residue obtained after extraction was purified by precipitation from ethyl acetate to give 0.669 g (53%) of the desired compound as a white solid. ESI/APCI(+): 400, 402 (M+H); 422, 424 (M+Na). ESI/APCI(−): 398, 400 (M−H).

Step 3:
1-(6-((tert-Butyldimethylsilyl)oxy)-1H-indol-3-yl)-2-((3-methoxyphenyl)amino)-2-phenylethanone was prepared according to general procedure E from 1-(6-((tert-butyldimethylsilyl)oxy)-1H-indol-3-yl)-2-chloro-2-phenylethanone (0.300 g; 0.750 mmol) and 3-methoxyaniline (1.680 mL; 15.02 mmol) in acetonitrile (3 mL), irradiated in a microwave oven at 150° C. for 30 min. Purification by flash chromatography on silica gel using a gradient of ethyl acetate (10% to 50%) in heptane furnished 0.200 g (55%) of the desired compound as a beige powder. ESI/APCI(+): 487 (M+H); 509 (M+Na). ESI/APCI(−): 485 (M−H).

Step 4:
To a solution of 1-(6-(((tert-butyldimethylsilyl)oxy)-1H-indol-3-yl)-2-((3-methoxyphenyl)amino)-2-phenylethanone (0.200 g; 0.411 mmol) in DMF (3.5 mL) was added cesium fluoride (0.312 g; 2.054 mmol). After 2.5 h at room temperature, the reaction mixture was concentrated. The residue was partitioned between ethyl acetate and a 1N hydrochloric acid solution. The phases were separated. The organic phase was washed with a saturated sodium hydrogencarbonate solution, water and brine, dried over sodium sulfate, filtered and concentrated. Purification by flash chromatography on silica gel using a gradient of methanol (0% to 10%) in dichloromethane followed by recrystallization from ethyl acetate and heptane furnished 0.020 g (13%) of 1-(6-hydroxy-1H-indol-3-yl)-2-((3-methoxyphenyl)amino)-2-phenylethanone as a grey powder. ESI/APCI(+): 373 (M+H); 395 (M+Na). ESI/APCI(−): 371 (M−H).

Example 134: Preparation of 3-(2-((3-methoxyphenyl)amino)-2-phenylacetyl)-1H-indole-6-carboxylic Acid To a solution of methyl 3-(2-((3-methoxyphenyl)amino)-2-phenylacetyl)-1H-indole-6-carboxylate (0.100 g; 0.241 mmol) in a mixture of THE (3 mL) and methanol (3 mL) was added a 6N sodium hydroxide solution (1.500 mL; 9.000 mmol) and the mixture was refluxed for 3 h. The reaction mixture was partially concentrated under reduced pressure. The remaining aqueous solution was acidified with a 1N hydrochloric acid solution to pH 2-3. The precipitate was filtered, washed with water and dried. Further purification of the precipitate by preparative HPLC (XBridge column; method 2) furnished 0.020 g (21%) of 3-(2-((3-methoxyphenyl)amino)-2-phenylacetyl)-1H-indole-6-carboxylic acid as a white solid. ESI/APCI(+): 401 (M+H). ESI/APCI(−): 399 (M−H).

Example 135: Preparation of 1-(1-(2-methoxyethyl)-1H-indol-3-yl)-2-((3-methoxyphenyl)amino)-2-phenylethanone Step 1: 2-Chloro-1-(1-(2-methoxyethyl)-1H-indol-3-yl)-2-phenylethanone was prepared according to general method M from 2-chloro-1-(1H-indol-3-yl)-2-phenylethanone (0.200 g; 0.741 mmol), 1-bromo-2-methoxyethane (0.206 g; 1.482 mmol) and potassium carbonate (0.205 g; 0.183 mmol) in DMF (3 mL). The reaction mixture was stirred at room temperature overnight. Purification by flash chromatography on silica gel using a gradient of ethyl acetate (5% to 50%) in heptane furnished 0.115 g (47%) of the desired compound as a beige solid. ESI/APCI(+): 350, 352 (M+Na). ESI/APCI(−): 326, 328 (M−H).

Step 2: 1-(1-(2-Methoxyethyl)-1H-indol-3-yl)-2-((3-methoxyphenyl)amino)-2-phenylethanone was prepared according to general procedure E from 2-chloro-1-(1-(3-hydroxypropyl)-1H-indol-3-yl)-2-phenylethanone (0.050 g; 0.153 mmol), 3-methoxyaniline (0.354 mL; 3.150 mmol) in acetonitrile (1 mL), irradiated in a microwave oven at 150° C. for 15 min. Purification by flash chromatography on silica gel using 5% ethyl acetate in dichloromethane as eluent followed by purification by preparative HPLC (XBridge column; method 1) furnished 0.025 g (39%) of the desired compound as a white solid. ESI/APCI(+): 415 (M+H). ESI/APCI(−): 413 (M−H). $^1$H NMR (DMSO-$d_6$) δ 8.95 (1H, s); 8.17 (1H, d); 7.57-7.68 (3H, m); 7.11-7.33 (5H, m); 6.92 (1H, t); 6.34-6.46 (3H, m); 6.11 (1H, d); 6.05 (1H, d); 4.45 (2H, br s); 3.73 (2H, m); 3.62 (3H, s); 3.23 (3H, s).

Example 136: Preparation of 1-(5-fluoro-1-methyl-1H-indol-3-yl)-2-((3-methoxyphenyl)amino)-2-phenylethanone Step 1: 2-Chloro-1-(5-fluoro-1-methyl-1H-indol-3-yl)-2-phenylethanone was prepared according to general method M from 2-chloro-1-(5-fluoro-1H-indol-3-yl)-2-phenylethanone (0.200 g; 0.695 mmol), iodomethane (0.216 mL; 3.470 mmol) and potassium carbonate (0.192 g; 1.389 mmol) in DMF (3 mL). The reaction mixture was stirred at room temperature overnight. Purification by flash chromatography on silica gel using a gradient of ethyl acetate (15% to 50%) in heptane furnished 0.076 g (36%) of the desired compound as a beige solid. ESI/APCI(+): 302, 304 (M+H); 324, 326 (M+Na). ESI/APCI(−): 300, 302 (M−H).

Step 2: 1-(5-Fluoro-1-methyl-1H-indol-3-yl)-2-((3-methoxyphenyl)amino)-2-phenylethanone was prepared according to general procedure E from 2-chloro-1-(5-fluoro-1-methyl-1H-indol-3-yl)-2-phenylethanone (0.070 g; 0.232 mmol), 3-methoxyaniline (0.519 mL; 4.619 mmol) in acetonitrile (1 mL), irradiated at 150° C. for 30 min. Purification by two flash chromatography on silica gel using first a gradient of ethyl acetate (5% to 50%) in heptane and then a gradient of dichloromethane (15% to 70%) in heptane followed by precipitation from tert-butyl methyl ether furnished 0.020 g (22%) of the desired compound as a beige solid. ESI/APCI(+): 389 (M+H). ESI/APCI(−): 387 (M−H). $^1$H NMR (DMSO-$d_6$) δ 8.99 (1H, s); 7.79-7.88 (1H, dd); 7.63 (2H, d); 7.54-7.61 (1H, m); 7.25-7.35 (2H, m); 7.10-7.24 (2H, m); 6.92 (1H, t); 6.33-6.44 (3H, m); 6.11 (1H, d); 5.99 (1H, d); 3.91 (3H, s); 3.62 (3H, s).

Example 137: Preparation of 1-(1H-indol-3-yl)-2-((3-methoxyphenyl)amino)-2-(m-tolyl)ethanone Step 1: A solution of 3-methoxy-N-(3-methylbenzylidene)aniline in ethanol was prepared by heating a solution of 3-methylbenzaldehyde (0.120 mL; 1.019 mmol) and 3-methoxyaniline (0.120 mL; 1.068 mmol) in ethanol (1 mL) at 60° C. for 18 h. The formation of the imine was quantitative and the solution was used without further purification. ESI/APCI (+): 226 (M+H).

Step 2: 1-(1H-Indol-3-yl)-2-((3-methoxyphenyl)amino)-2-(m-tolyl)ethanone was prepared according to general procedure K from a mixture of 3-benzyl-5-(2-hydroxyethyl)-4-methylthiazol-3-ium chloride (0.140 g; 0.519 mmol) and triethylamine (0.100 mL; 0.717 mmol) in ethanol (0.5 mL), tert-butyl 3-formyl-1H-indole-1-carboxylate (0.270 g; 1.101 mmol) and a solution of 3-methoxy-N-(3-methylbenzylidene)aniline (1.019 mmol) in ethanol (1.5 mL), heated 60° C. for 2 days. Purification by flash chromatography on silica gel using a gradient of ethyl acetate (0% to 30%) in heptane followed by preparative HPLC (XBridge column; method 1) furnished 0.085 g (23%) of the desired compound. ESI/APCI(+): 371 (M+H). ESI/APCI(−): 369 (M−H).

Example 138: Preparation of 1-(1H-indol-3-yl)-2-((3-methoxyphenyl)amino)-2-(p-tolyl)ethanone Step 1: A solution of 3-methoxy-N-(4-methylbenzylidene)aniline in ethanol was prepared by heating a solution of 4-methylbenzaldehyde (0.120 mL; 1.014 mmol) and 3-methoxyaniline (0.120 mL; 1.068 mmol) in ethanol (1 mL) at 60° C. for 18 h. The formation of the imine was quantitative and the solution was used without further purification. ESI/APCI (+): 226 (M+H).

Step 2: 1-(1H-Indol-3-yl)-2-((3-methoxyphenyl)amino)-2-(p-tolyl)ethanone was prepared according to general procedure K from a mixture of 3-benzyl-5-(2-hydroxyethyl)-4-methylthiazol-3-ium chloride (0.138 g; 0.512 mmol) and triethylamine (0.100 mL; 0.717 mmol) in ethanol (0.5 mL), tert-butyl 3-formyl-1H-indole-1-carboxylate (0.274 g; 1.117 mmol) and a solution of 3-methoxy-N-(4-methylbenzylidene)aniline (1.014 mmol) in ethanol (1.5 mL), heated at 60° C. for 24 h. Purification by flash chromatography on silica gel using a gradient of ethyl acetate (0% to 40%) in heptane followed by precipitation from acetone and heptane furnished 0.085 g (23%) of the desired compound as a beige solid. ESI/APCI(+): 371 (M+H). ESI/APCI(−): 369 (M−H).

Example 139: Preparation of 1-(6-(hydroxymethyl)-1H-indol-3-yl)-2-((3-methoxyphenyl)amino)-2-phenylethanone Step 1: To a suspension of lithium aluminium hydride (0.866 g; 22.82 mmol) in dry THF (30 mL) cooled at 0° C. was added a solution of methyl 1H-indole-6-carboxylate (2.000 g; 11.42 mmol) in THF (30 mL) under nitrogen atmosphere. The reaction mixture was stirred at room temperature overnight. The reaction was quenched by careful addition of a 1N Rochelle salt solution. The reaction mixture was stirred at room temperature for 2 h and was then extracted with dichloromethane. The phases were separated. The organic phase was dried over magnesium sulfate and evaporated under reduced pressure to afford 2.050 g of (1H-indolyl-6-yl)methanol as a yellow oil which was used in the next step without further purification. ESI/APCI(−): 146 (M−H).

Step 2: To a solution of (1H-indol-6-yl)methanol (0.500 g; 3.397 mmol) in dry THF (20 mL) cooled at 0° C. was added portionwise sodium hydride (60% in mineral oil; 0.271 g; 6.775 mmol). After stirring for 5 min, TBDMSCl (0.512 g; 3.397 mmol) was added. The resulting solution was stirred at room temperature for 1 h. The reaction mixture was diluted with dichloromethane and washed with a saturated sodium bicarbonate solution. The phases were separated. The aqueous phase was extracted with dichloromethane. The organic phases were combined, washed with water, dried over magnesium sulfate and concentrated under reduced pressure. Purification by flash chromatography on silica gel using a gradient of ethyl acetate (2% to 20%) in heptane furnished 0.482 g (46% over 2 steps) of 6-(((tert-butyldimethylsilyl)oxy)methyl)-1H-indole as a white solid. ESI/APCI(+): 262 (M+H). ESI/APCI(−): 260 (M−H).

Step 3: 2-Chloro-1-(6-(hydroxymethyl)-1H-indol-3-yl)-2-phenylethanone was prepared according to general procedure A from 6-(((tert-butyldimethylsilyl)oxy)methyl)-1H-indole (0.265 g; 1.014 mmol), pyridine (0.082 mL; 1.014 mmol) and α-chlorophenylacetyl chloride (0.151 mL; 1.014 mmol) in toluene (2.6 mL). Purification by flash chromatography on silica gel using a gradient of ethyl acetate (5% to 100%) in heptane furnished 0.064 g (21%) of the desired compound. ESI/APCI(+): 300, 302 (M+H); 322, 324 (M+Na). ESI/APCI(−): 298, 300 (M−H). $^1$H NMR (DMSO-$d_6$) δ 12.15 (1H, br s); 8.61 (1H, d); 8.09 (1H, d); 7.63 (2H, d); 7.25-7.48 (5H, m); 7.16 (1H, d); 6.73 (1H, s); 5.20 (1H, t); 4.58 (2H, d).

Step 4: 1-(6-(Hydroxymethyl)-1H-indol-3-yl)-2-((3-methoxyphenyl)amino)-2-phenylethanone was prepared according to general procedure E from 2-chloro-1-(6-(hydroxymethyl)-1H-indol-3-yl)-2-phenylethanone (0.060 g; 0.200 mmol) and 3-methoxyaniline (0.448 mL; 3.987 mmol) in acetonitrile (1 mL), irradiated in a microwave oven at 130° C. for 15 min. Purification by flash chromatography on silica gel using a gradient of ethyl acetate (5% to 50%) in dichloromethane and followed by another purification by flash chromatography on silica gel using a gradient of ethyl acetate (30% to 100%) in heptane furnished 0.021 g (27%) of the desired compound as a beige solid. ESI/APCI(+): 387 (M+H). ESI/APCI(−): 385 (M−H).

Example 140: Preparation of 1-(6-(2-hydroxyethoxy)-1H-indol-3-yl)-2-((3-methoxyphenyl)amino)-2-phenylethanone Step 1: To a solution of 6-hydroxyindole (0.645 g; 4.844 mmol) in acetone (25 mL) were added potassium carbonate (1.350 g; 9.768 mmol) and ethyl bromoacetate (1.000 mL; 9.018 mmol). The reaction mixture was refluxed overnight. After cooling to room temperature, the reaction mixture was diluted with ethyl acetate and washed with water. The phases were separated. The organic phase was washed with brine, dried over sodium sulfate, filtered and concentrated. Purification by flash chromatography on silica gel using a gradient of ethyl acetate (20% to 50%) in heptane furnished ethyl 2-((1H-indol-6-yl)oxy)acetate contaminated with the dialkylated product as a pink oil. This mixture was used in the next step without further purification. ESI/APCI(+): 220 (M+H); 242 (M+Na). ESI/APCI(−): 218 (M−H).

Step 2: To a suspension of lithium aluminium hydride (0.406 g; 10.97 mmol) in THF cooled at 0° C. was added dropwise a solution of ethyl 2-((1H-indol-6-yl)oxy)acetate (crude, 4.844 mmol) in THF (15 mL) over 25 min. After one night at room temperature, the reaction mixture was diluted with diethyl ether and cooled to 0° C. A 1M Rochelle salt solution was added and the reaction mixture was stirred at room temperature for 2 h. The phases were separated. The organic phase was washed with brine, dried over sodium sulfate, filtered and concentrated. Purification by flash chromatography on silica gel using a gradient of ethyl acetate (50% to 90%) in heptane furnished 0.586 g (68% over 2 steps) of 2-((1H-indol-6-yl)oxy)ethanol as a pink powder. ESI/APCI(+): 178 (M+H); 200 (M+Na). ESI/APCI(−): 176 (M−H). $^1$H NMR (DMSO-d$_6$) δ 10.84 (1H, s); 7.39 (1H, d); 7.18 (1H, s); 6.89 (1H, s); 6.66 (1H, d); 6.32 (1H, s), 4.85 (1H, m), 3.98 (2H, m); 3.73 (2H, m).

Step 3: 6-(2-((tert-Butyldimethylsilyl)oxy)ethoxy)-1H-indole was prepared according to general procedure N from 2-((1H-indol-6-yl)oxy)ethanol (0.581 g; 3.279 mmol), DBU (0.500 mL; 3.350 mmol) and TBDMSCl (1.000 g; 6.635 mmol) in THF (12 mL). Purification by flash chromatography on silica gel using a gradient of ethyl acetate (20% to 50%) in heptane furnished 0.757 g (79%) of the desired compound as a pink solid. ESI/APCI(+): 292 (M+H); 314 (M+Na). ESI/APCI(−): 290 (M−H).

Step 4: 1-(6-(2-((tert-Butyldimethylsilyl)oxy)ethoxy)-1H-indol-3-yl)-2-chloro-2-phenylethanone was prepared according to general procedure A from 6-(2-((tert-butyldimethylsilyl)oxy)ethoxy)-1H-indole (0.400 g; 1.372 mmol), pyridine (0.115 mL; 1.422 mmol) and α-chlorophenylacetyl chloride (0.240 mL; 1.536 mmol) in toluene (3.5 mL). The residue obtained after extraction was purified by precipitation from ethyl acetate and heptane. Further purification by recrystallization from ethyl acetate furnished 0.060 g (10%) of the desired compound as a beige powder. The filtrate of the recrystallization was purified by flash chromatography on silica gel using a gradient of ethyl acetate (20% to 80%) in heptane to give 0.066 g of the desired compound (11%) as a pink powder. ESI/APCI(+): 444, 446 (M+H); 466, 468 (M+Na). ESI/APCI(−): 442, 444 (M−H).

Step 5: 1-(6-(2-((tert-Butyldimethylsilyl)oxy)ethoxy)-1H-indol-3-yl)-2-((3-methoxyphenyl)amino)-2-phenylethanone was prepared according to general procedure E from 1-(6-(2-((tert-butyldimethylsilyl)oxy)ethoxy)-1H-indol-3-yl)-2-chloro-2-phenylethanone (0.242 g; 0.545 mmol) and 3-methoxyaniline (1.157 mL; 10.344 mmol) in acetonitrile (2.6 mL), irradiated in a microwave oven at 150° C. for 30 min. Purification by flash chromatography on silica gel using a gradient of ethyl acetate (20% to 50%) in heptane furnished 0.099 g (34%) of the desired compound as a beige powder. ESI/APCI(+): 487 (M+H); 509 (M+Na). ESI/APCI(−): 485 (M−H).

Step 6: To a solution of 1-(6-(2-((tert-butyldimethylsilyl)oxy)ethoxy)-1H-indol-3-yl)-2-((3-methoxyphenyl)amino)-2-phenylethanone (0.099 g; 0.186 mmol) in dichloromethane (2.75 mL) cooled to 0° C. was added a 4N hydrogen chloride solution in dioxane (0.645 mL; 2.580 mmol). After 2.5 h at room temperature, the reaction mixture was diluted with dichloromethane and basified with a 2N sodium hydroxide solution. The phases were separated. The organic phase was washed with water and brine, dried over sodium sulfate, filtered and concentrated. Purification by flash chromatography on silica gel using a gradient of ethyl acetate (50% to 95%) in heptane furnished 0.043 g (55%) of 1-(6-(2-hydroxyethoxy)-1H-indol-3-yl)-2-((3-methoxyphenyl)amino)-2-phenylethanone as a yellow oil. ESI/APCI(+): 417 (M+H); 439 (M+Na); 855 (2M+Na). ESI/APCI(−): 415 (M−H). $^1$H NMR (DMSO-d$_6$) δ 11.92 (1H, s); 8.75 (1H, s); 8.00 (1H, d); 7.63 (1H, d); 7.28 (2H, m); 7.19 (1H, m); 6.92 (3H, m); 6.08 (2H, m); 4.86 (1H, t); 3.98 (2H, t); 3.72 (2H, q); 3.62 (3H, s).

Example 141: Preparation of methyl 3-(2-((3-methoxyphenyl)amino)-2-phenylacetyl)-1H-indole-5-carboxylate Step 1: Methyl 3-(2-chloro-2-phenylacetyl)-1H-indole-5-carboxylate was prepared according to general procedure A from methyl 1H-indole-5-carboxylate (2.000 g; 11.42 mmol), pyridine (0.923 mL; 11.42 mmol) and α-chlorophenylacetyl chloride (1.676 mL; 11.42 mmol) in toluene (30 mL). Precipitation by precipitation furnished 0.324 g (9%) of the desired compound as a pink solid. ESI/APCI(+): 328, 330 (M+H). ESI/APCI(−): 326, 328 (M−H). $^1$H NMR (DMSO-d$_6$) δ 12.53 (1H, br. s); 8.87 (1H, s); 8.76 (1H, d); 7.87 (1H, dd); 7.54-7.69 (3H, m); 7.29-7.45 (3H, m); 6.79 (1H, s); 3.88 (3H, s).

Step 2: Methyl 3-(2-((3-methoxyphenyl)amino)-2-phenylacetyl)-1H-indole-5-carboxylate was prepared according to general procedure E from methyl 3-(2-chloro-2-phenylacetyl)-1H-indole-5-carboxylate (0.100 g; 0.305 mmol) and 3-methoxyaniline (0.683 mL; 6.101 mmol) in acetonitrile (1 mL), irradiated in a microwave oven at 150° C. for 30 min. Purification by flash chromatography on silica gel using a gradient of ethylacetate (0% to 100%) in heptane followed by precipitation from ethyl acetate furnished 0.040 g (32%) of the desired compound as a white solid. ESI/APCI(+): 415 (M+H). ESI/APCI(−): 413 (M−H)

Example 142: Preparation of methyl 3-(2-((3-methoxyphenyl)amino)-2-phenylacetyl)-1H-indole-5-carboxylate To a solution of methyl 3-(2-((3-methoxyphenyl)amino)-2-phenylacetyl)-1H-indole-5-carboxylate (0.028 g; 0.068 mmol) in a mixture of methanol (0.5 mL) and THF (0.5 mL) was added a 6N sodium hydroxide solution (0.250 mL;

1.500 mmol). The mixture was refluxed for 3 h and was concentrated under reduced pressure. The residue was dissolved in water and acidified with a 1N hydrochloric acid solution. The resulting precipitate was filtered and washed with water. Further purification by preparative HPLC (XBridge column; method 2) furnished 0.007 g (22%) of 3-(2-((3-methoxyphenyl)amino)-2-phenylacetyl)-1H-indole-5-carboxylic acid. ESI/APCI(+): 401 (M+H). ESI/APCI(−): 399 (M−H).

Example 143: Preparation of 2-(2-fluorophenyl)-1-(1H-indol-3-yl)-2-((3-methoxyphenyl)amino)ethanone Step 1: A solution of N-(2-fluorobenzylidene)-3-methoxyaniline was prepared by heating a solution of 2-fluorobenzaldehyde (0.105 mL; 0.998 mmol) and 3-methoxyaniline (0.120 mL; 1.068 mmol) in ethanol (1 mL) at 60° C. for 18 h. The formation of the imine was quantitative and the solution was used without further purification. ESI/APCI (+): 230 (M+H)

Step 2: 2-(2-Fluorophenyl)-1-(1H-indol-3-yl)-2-((3-methoxyphenyl)amino)ethanone was prepared according to general procedure L from a mixture of 3-benzyl-5-(2-hydroxyethyl)-4-methylthiazolium chloride (0.139 g; 0.515 mmol) and triethylamine (0.100 mL; 0.717 mmol), in ethanol (0.5 mL), tert-butyl 3-formyl-1H-indole-1-carboxylate (0.272 g; 1.109 mmol) and a solution of N-(2-fluorobenzylidene)-3-methoxyaniline (0.998 mmol) in ethanol (1.5 mL), heated at 60° C. for 2 days. Purification by flash chromatography on silica gel using a gradient of ethyl acetate (0% to 35%) in heptane followed by purification by preparative HPLC (XBridge column; method 1) furnished 0.037 g (10%) of the desired compound as a beige solid. ESI/APCI (+): 375 (M+H). ESI/APCI (−): 373 (M−H)

Example 144: Preparation of 1-(5-fluoro-1-(2-(methoxymethoxy)ethyl)-1H-indol-3-yl)-2-((3-methoxyphenyl)amino)-2-phenylethanone Step 1: 2-Chloro-1-(5-fluoro-1-(2-(methoxymethoxy)ethyl)-1H-indol-3-yl)-2-phenylethanone was prepared according to general procedure M from 2-chloro-1-(5-fluoro-1H-indol-3-yl)-2-phenylethanone (0.200 g; 0.695 mmol), 1-bromo-2-(methoxymethoxy)ethane (0.235 g; 1.390 mmol) and potassium carbonate (0.288 g; 2.084 mmol) in DMF (5 mL). The reaction mixture was stirred at room temperature for 4 h and was heated at 60° C. for 2 h. Purification by flash chromatography on silica gel using a gradient of ethyl acetate (5% to 50%) in heptane furnished 0.070 g (27%) of the desired compound as an oil. ESI/APCI (+): 376, 378 (M+H); 398, 400 (M+Na). ESI/APCI(−): 374, 376 (M−H).

Step 2: 1-(5-Fluoro-1-(2-(methoxymethoxy)ethyl)-1H-indol-3-yl)-2-((3-methoxyphenyl)amino)-2-phenylethanone was prepared according to general procedure E from 2-chloro-1-(5-fluoro-1-(2-(methoxymethoxy)ethyl)-1H-indol-3-yl)-2-phenylethanone (0.070 g; 0.186 mmol), 3-methoxyaniline (0.417 mL; 3.711 mmol) in acetonitrile (1 mL), irradiated in a microwave oven at 150° C. for 15 min. Purification by flash chromatography on silica gel using a gradient of ethyl acetate (5% to 50%) in heptane furnished 0.036 g (42%) of the desired compound as a red solid. ESI/APCI(+): 463 (M+H); 485 (M+H). ESI/APCI(−): 461 (M−H).

Example 145: Preparation of 1-(5-fluoro-1-(2-hydroxyethyl)-1H-indol-3-yl)-2-((3-methoxyphenyl)amino)-2-phenylethanone 1-(5-Fluoro-1-(2-(methoxymethoxy)ethyl)-1H-indol-3-yl)-2-((3-methoxyphenyl)amino)-2-phenylethanone (0.036 g; 0.078 mmol) was dissolved in a 4N hydrogen chloride solution in dioxane (3 mL; 12.00 mmol). The reaction mixture was stirred at room temperature for 4 h. The reaction mixture was neutralized with potassium carbonate, diluted with ethyl acetate and washed with water. The phases were separated. The organic layer was dried over magnesium sulfate, filtered and concentrated under reduced pressure. Purification by flash chromatography on silica gel using a gradient of ethyl acetate (5% to 50%) in dichloromethane followed by purification by preparative HPLC (XBridge column; method 1) furnished 0.015 g (45%) of 1-(5-fluoro-1-(2-hydroxyethyl)-1H-indol-3-yl)-2-((3-methoxyphenyl)amino)-2-phenylethanone as a white solid. ESI/APCI(+): 419 (M+H); 441 (M+Na). ESI/APCI(−): 417 (M−H).

Example 146: Preparation of 2-((3,5-dimethoxyphenyl)amino)-1-(1-(2-(methoxymethoxy)ethyl)-1H-indol-3-yl)-2-phenylethanone Step 1: 2-Chloro-1-(1-(2-(methoxymethoxy)ethyl)-1H-indol-3-yl)-2-phenylethanone was prepared according to general procedure M from 2-chloro-1-(1H-indol-3-yl)-2-phenylethanone (0.300 g; 1.112 mmol), 1-bromo-2-(methoxymethoxy)ethane (0.375 g; 2.218 mmol) and potassium carbonate (0.461 g; 3.336 mmol) in DMF (5 mL). The reaction mixture was stirred at room temperature for 4 h and was heated at 60° C. for 3 h. Purification by flash chromatography on silica gel using a gradient of ethyl acetate (15% to 70%) in heptane furnished 0.144 g (36%) of the desired compound as an oil. ESI/APCI(+): 358, 360 (M+H); 380, 382 (M+Na). ESI/APCI(−): 356, 358 (M−H).

Step 2: 2-((3,5-Dimethoxyphenyl)amino)-1-(1-(2-(methoxymethoxy)ethyl)-1H-indol-3-yl)-2-phenylethanone was prepared according to general procedure E from 2-chloro-1-(1-(2-(methoxymethoxy)ethyl)-1H-indol-3-yl)-2-phenylethanone (0.070 g; 0.196 mmol), 3,5-dimethoxyaniline (0.300 g; 1.958 mmol) in acetonitrile (1 mL), irradiated in a microwave oven at 130° C. for 15 min. Purification by flash chromatography on silica gel using a gradient of ethyl acetate (5% to 50%) in heptane furnished 0.038 g (41%) of the desired compound as a beige solid. ESI/APCI (+): 463 (M+H); 485 (M+H). ESI/APCI(−): 461 (M−H).

Example 147: Preparation of 2-((3,5-dimethoxyphenyl)amino)-1-(1-(2-hydroxyethyl)-1H-indol-3-yl)-2-phenylethanone 2-((3,5-Dimethoxyphenyl)amino)-1-(1-(2-(methoxymethoxy)ethyl)-1H-indol-3-yl)-2-phenylethanone (0.036 g; 0.079 mmol) was dissolved in a 4N hydrogen chloride solution in dioxane (3 mL; 12.00 mmol). The reaction mixture was stirred at room temperature for 4 h. The reaction mixture was neutralized with potassium carbonate, diluted with ethyl acetate and washed with water. The phases were separated. The organic layer was dried over magnesium sulfate, filtered and concentrated under reduced pressure. Purification by flash chromatography on silica gel using a gradient of ethyl acetate (2% to 40%) in dichloromethane followed by purification by preparative HPLC (XBridge column; method 1) furnished 0.005 g (15%) of 2-((3,5-dimethoxyphenyl)amino)-1-(1-(2-hydroxyethyl)-1H-indol-3-yl)-2-phenylethanone as a white solid. ESI/APCI(+): 431 (M+H).

Example 148: Preparation of 2-(4-fluorophenyl)-1-(1H-indol-3-yl)-2-((3-methoxyphenyl)amino)ethanone Step 1: A solution of N-(4-fluorobenzylidene)-3-methoxyaniline in ethanol was prepared by heating a solution of 4-fluorobenzaldehyde (0.156 g; 1.257 mmol) and 3-methoxyaniline (0.140 mL; 1.253 mmol) in ethanol (0.5 mL) at 60° C. for 18 h. The formation of the imine was quantitative and the solution was used without further purification. ESI/APCI (+): 230 (M+H).

Step 2: 2-(4-Fluorophenyl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.170 g; 0.630 mmol) and triethylamine (0.100 mL; 0.717 mmol) in ethanol (0.5 mL), tert-butyl 3-formyl-1H-indole-1-carboxylate (0.350 g; 1.136 mmol) and a solution of N-(4-fluorobenzylidene)-3-methoxyaniline (1.253 mmol) in ethanol (1.5 mL), heated at 60° C. for 4 days. Purification by flash chromatography on silica gel using a gradient of ethyl acetate (0% to 50%) in heptane furnished 0.120 g (26%) of the desired compound as a yellow solid. ESI/APCI(+): 375 (M+H).

Example 149: Preparation of 1-(6-chloro-1H-indol-3-yl)-2-(imidazo[1,2-a]pyridin-2-yl)-2-((3-methoxyphenyl)amino)ethanone 1-(6-Chloro-1H-indol-3-yl)-2-(imidazo[1,2-a]pyridin-2-yl)-2-((3-methoxyphenyl)amino)ethanone was prepared according to general procedure K from a mixture of 3-benzyl-5-(2-hydroxyethyl)-4-methylthiazol-3-ium chloride (0.156 g; 0.542 mmol) and triethylamine (0.100 mL; 0.717 mmol) in ethanol (0.5 mL), tert-butyl 6-chloro-3-formyl-1H-indole-1-carboxylate (0.319 g; 1.140 mmol) and a solution of N-(imidazo[1,2-a]pyridin-2-ylmethylene)-3-methoxyaniline (1.068 mmol) in ethanol (1.5 mL), heated at 60° C. for 18 h. Purification by flash chromatography on silica gel using a gradient of ethyl acetate (0% to 70%) in heptane followed by precipitation from ethyl acetate and heptane furnished 0.052 g (11%) of the desired compound as a white solid. ESI/APCI(+): 431, 433 (M+H). ESI/APCI(−): 429, 431 (M−H).

Example 150: Preparation of 1-(5-fluoro-1H-indol-3-yl)-2-((3-methoxyphenyl)amino)-2-(pyridin-3-yl)ethanone 1-(5-Fluoro-1H-indol-3-yl)-2-((3-methoxyphenyl)amino)-2-(pyridin-3-yl)ethanone was prepared according to general procedure K from a mixture of 3-benzyl-5-(2-hydroxyethyl)-4-methylthiazol-3-ium chloride (0.067 g; 0.248 mmol) and triethylamine (0.035 mL; 0.252 mmol) in ethanol (0.37 mL), tert-butyl 5-fluoro-3-formyl-1H-indole-1-carboxylate (0.158 g; 0.600 mmol) and a solution of 3-methoxy-N-(pyridin-3-ylmethylene)aniline (0.499 mmol) in ethanol (0.75 mL), heated at 70° C. for 20 h. Purification by flash chromatography on silica gel using a gradient of ethyl acetate (0% to 100%) in heptane followed by recrystallization from ethyl acetate and heptane furnished 0.036 g (19%) of the desired compound as a white solid. ESI/APCI(+): 376 (M+H); 398 (M+Na). ESI/APCI(−): 374 (M−H).

Example 151: Preparation of 1-(6-fluoro-1H-indol-3-yl)-2-((3-methoxyphenyl)amino)-2-(pyridin-3-yl)ethanone 1-(6-Fluoro-1H-indol-3-yl)-2-((3-methoxyphenyl)amino)-2-(pyridin-3-yl)ethanone was prepared according to general procedure K from a mixture of 3-benzyl-5-(2-hydroxyethyl)-4-methylthiazol-3-ium chloride (0.067 g; 0.248 mmol) and triethylamine (0.035 mL; 0.252 mmol) in ethanol (0.37 mL), tert-butyl 6-fluoro-3-formyl-1H-indole-1-carboxylate (0.158 g; 0.600 mmol) and a solution of 3-methoxy-N-(pyridin-3-ylmethylene)aniline (0.499 mmol) in ethanol (0.75 mL), heated at 70° C. for 20 h. Purification by flash chromatography on silica gel using a gradient of ethyl acetate (0% to 100%) in heptane followed by recrystallization from ethyl acetate and heptane furnished 0.045 g (24%) of the desired compound as a yellow solid. ESI/APCI(+): 376 (M+H); 398 (M+Na). ESI/APCI(−): 374 (M−H).

Example 152: Preparation of 1-(7-fluoro-1H-indol-3-yl)-2-((3-methoxyphenyl)amino)-2-(pyridin-3-yl)ethanone Step 1: The synthesis was performed as described in WO2009/015067. To a solution of DMF (0.600 mL; 7.749 mmol) in dichloromethane (2 mL) cooled at −15° C. was added dropwise phosphorus oxychloride (0.350 mL; 3.748 mmol). After 15 min at −15° C., 7-fluoroindole (0.497 g; 3.678 mmol) was added portionwise. The reaction mixture was then allowed to warm to room temperature and was stirred at room temperature overnight. The reaction mixture was basified with a 1N sodium hydroxide solution to pH 8 and extracted with ethyl acetate. The aqueous phase was extracted with ethyl acetate and with a mixture of methanol in dichloromethane. The organic phases were combined, washed with brine, dried over magnesium sulfate, filtered and concentrated under reduced pressure to yield 0.078 g of a yellow solid. After 24 h, the precipitate in the aqueous phase was filtered to yield 0.264 g of a white solid. The filtrate was basified with a 1N sodium hydroxide solution to pH 12 and was extracted with ethyl acetate. The organic phase was washed with brine, dried over magnesium sulfate, filtered and concentrated under reduced pressure to yield 0.290 g of a yellow solid. The three solids were mixed, adsorbed on silica gel and purified by flash chromatography on silica gel using 40% ethyl acetate in heptane as eluent to give 0.485 g (81%) of 7-fluoro-1H-indole-3-carbaldehyde as a pink solid. ESI/APCI(+): 164 (M+H). ESI/APCI(−): 162 (M−H).

Step 2: tert-Butyl 7-fluoro-3-formyl-1H-indole-1-carboxylate was prepared according to general procedure F from 7-fluoro-1H-indole-3-carbaldehyde (0.485 g; 2.973 mmol), di-tert-butyl dicarbonate (0.780 g; 3.574 mmol) and DMAP (0.046 g; 0.377 mmol) in acetonitrile (9 mL) to afford 0.687 g (88%) of the desired compound as a beige solid. $^1$H NMR (DMSO-$d_6$) δ 10.08 (1H, s); 8.77 (1H, s); 8.01 (1H, d); 7.25-7.43 (2H, m); 1.64 (9H, s).

Step 3: 1-(7-Fluoro-1H-indol-3-yl)-2-((3-methoxyphenyl)amino)-2-(pyridin-3-yl)ethanone was prepared according to general procedure K from a mixture of 3-benzyl-5-(2-hydroxyethyl)-4-methylthiazol-3-ium chloride (0.067 g; 0.248 mmol) and triethylamine (0.035 mL; 0.252 mmol) in ethanol (0.37 mL), tert-butyl 7-fluoro-3-formyl-1H-indole-1-carboxylate (0.158 g; 0.600 mmol) and a solution of 3-methoxy-N-(pyridin-3-ylmethylene)aniline (0.499 mmol) in ethanol (0.75 mL), heated at 70° C. for 20 h. Purification by flash chromatography on silica gel using a gradient of ethyl acetate (0% to 100%) in heptane followed by recrystallization from ethyl acetate and heptane furnished 0.033 g (18%) of the desired compound as a white powder. ESI/APCI(+): 376 (M+H); 398 (M+Na). ESI/APCI(−): 374 (M−H).

Example 153: Preparation of 1-(5-fluoro-1H-indol-3-yl)-2-((3-methoxyphenyl)amino)-2-(6-methoxypyridin-3-yl)ethanone 1-(5-Fluoro-1H-indol-3-yl)-2-((3-methoxyphenyl)amino)-2-(6-methoxypyridin-3-yl)ethanone was prepared according to general procedure K from a mixture of 3-benzyl-5-(2-hydroxyethyl)-4-methylthiazol-3-ium chloride (0.034 g; 0.125 mmol) and triethylamine (0.013 mL; 0.093 mmol) in ethanol (0.25 mL), tert-butyl 5-fluoro-3-formyl-1H-indole-1-carboxylate (0.066 g; 0.251 mmol) and a solution of 3-methoxy-N-((6-methoxypyridin-3-yl)methylene)aniline (0.248 mmol) in ethanol (0.25 mL), heated at 70° C. for 24 h. Purification by flash chromatography on silica gel using a gradient of ethyl acetate (0% to 100%) in heptane followed by recrystallization from ethyl acetate and heptane furnished 0.004 g (4%) of the desired compound as a beige solid. ESI/APCI(+): 406 (M+H). ESI/APCI(−): 404 (M−H).

Example 154: Preparation of 1-(7-fluoro-1H-indol-3-yl)-2-((3-methoxyphenyl)amino)-2-(6-methoxypyridin-3-yl)ethanone 1-(7-Fluoro-1H-indol-3-yl)-2-((3-methoxyphenyl)amino)-2-(6-methoxypyridin-3-yl)ethanone was prepared according to general procedure K from a mixture of 3-benzyl-5-(2-hydroxyethyl)-4-methylthiazol-3-ium chloride (0.034 g; 0.125 mmol) and triethylamine (0.013 mL; 0.093 mmol) in ethanol (0.25 mL), tert-butyl 7-fluoro-3-formyl-1H-indole-1-carboxylate (0.066 g; 0.251 mmol) and a solution of 3-methoxy-N-((6-methoxypyridin-3-yl)methylene)aniline (0.248 mmol) in ethanol (0.25 mL), heated at 70° C. for 24 h. Purification by flash chromatography on silica gel using a gradient of ethyl acetate (0% to 100%) in heptane followed by recrystallization from ethyl acetate and heptane furnished 0.005 g (5%) of the desired compound as a beige solid. ESI/APCI(+): 406 (M+H). ESI/APCI(−): 404 (M−H).

Example 155: Preparation of 2-((3,5-dimethoxyphenyl)amino)-1-(5-fluoro-1-(3-hydroxypropyl)-1H-indol-3-yl)-2-phenylethanone Step 1: 2-Chloro-1-(5-fluoro-1-(3-hydroxypropyl)-1H-indol-3-yl)-2-phenylethanone was prepared according to general method M from 2-chloro-1-(5-fluoro-1H-indol-3-yl)-2-phenylethanone (0.200 g; 0.695 mmol), 3-bromopropan-1-ol (0.193 g; 1.389 mmol) and potassium carbonate (0.192 g; 1.389 mmol) in DMF (5 mL). The reaction mixture was stirred at room temperature overnight. Purification by flash chromatography on silica gel using a gradient of ethyl acetate (2% to 40%) in dichloromethane furnished 0.219 g (91%) of the desired compound as a brown oil. ESI/APCI (+): 346, 348 (M+H); 368, 370 (M+Na).

Step 2: 2-((3,5-Dimethoxyphenyl)amino)-1-(5-fluoro-1-(3-hydroxypropyl)-1H-indol-3-yl)-2-phenylethanone was prepared according to general procedure E from 2-chloro-1-(5-fluoro-1-(3-hydroxypropyl)-1H-indol-3-yl)-2-phenylethanone (0.125 g; 0.361 mmol), 3,5-dimethoxyaniline (0.554 g; 3.617 mmol) in acetonitrile (1 mL), irradiated in a microwave oven at 130° C. for 15 min. Purification by flash chromatography on silica gel using a gradient of ethyl acetate (2% to 40%) in dichloromethane followed by a second purification by flash chromatography on silica gel using a gradient of ethyl acetate (30% to 100%) in heptane furnished 0.032 g (19%) of the desired product as a white solid. ESI/APCI(+): 463 (M+H).

Example 156: Preparation of 1-(6-fluoro-1H-indol-3-yl)-2-((5-methoxypyridin-3-yl)amino)-2-phenylethanone 1-(6-Fluoro-1H-indol-3-yl)-2-((5-methoxypyridin-3-yl)amino)-2-phenylethanone was prepared according to general procedure K from a mixture of 3-benzyl-5-(2-hydroxyethyl)-4-methylthiazol-3-ium chloride (0.067 g; 250 mmol) and triethylamine (0.035 mL; 0.250 mmol) in ethanol (1 mL), tert-butyl 6-fluoro-3-formyl-1H-indole-1-carboxylate (0.132 g; 0.500 mmol) and a solution of N-benzylidene-5-methoxypyridin-3-amine (0.500 mmol) in ethanol (1 mL), heated at 70° C. for 18 h. Purification by flash chromatography on silica gel using a gradient of methanol (1% to 10%) in dichloromethane followed by precipitation from dichloromethane furnished 0.017 g (9%) of the desired compound as a beige solid. ESI/APCI(+): 376 (M+H). ESI/APCI(−): 374 (M−H).

Example 157: Preparation of 1-(1H-indol-3-yl)-2-(6-methoxypyridin-3-yl)-2-((5-methoxypyridin-3-yl)amino)ethanone Step 1: A mixture of 6-methoxynicotinaldehyde (0.137 g; 0.999 mmol) and 5-methoxypyridin-3-amine (0.124 mg; 0.999 mmol) in ethanol (1.5 mL) was heated at 60° C. for 6 h. The reaction mixture was concentrated under reduced pressure and dried under vacuum over phosphorus(V) oxide to give quantitatively 5-methoxy-N-((6-methoxypyridin-3-yl)methylene)pyridine-3-amine which was used without further purification in the next step. ESI/APCI (+): 244 (M+H).

Step 2: 1-(1H-Indol-3-yl)-2-(6-methoxypyridin-3-yl)-2-((5-methoxypyridin-3-yl)amino)ethanone was prepared according to general procedure K from a mixture of 3-benzyl-5-(2-hydroxyethyl)-4-methylthiazol-3-ium chloride (0.134 g; 0.500 mmol) and triethylamine (0.069 mL; 0.496 mmol) in ethanol (2 mL), tert-butyl 3-formyl-1H-indole-1-carboxylate (0.245 g; 0.999 mmol) and a solution of 5-methoxy-N-((6-methoxypyridin-3-yl)methylene)pyridine-3-amine (0.999 mmol) in ethanol (1 mL), heated at 70° C. for 18 h. Purification by flash chromatography on silica gel using a gradient of methanol (1% to 15%) in dichloromethane followed by precipitations from diethyl ether and dichloromethane furnished 0.025 g (6%) of the desired compound as a beige solid. ESI/APCI(+): 389 (M+H). ESI/APCI(−): 387 (M−H).

Example 158: Preparation of 4-(2-(1H-indol-3-yl)-1-((5-methoxypyridin-3-yl)amino)-2-oxoethyl)benzonitrile Step 1: A mixture of 4-formylbenzonitrile (0.131 g; 0.999 mmol) and 5-methoxypyridin-3-amine (0.124 mg; 0.999 mmol) in ethanol (1.5 mL) was heated at 60° C. for 6 h. The reaction mixture was concentrated under reduced pressure and was dried under vacuum over phosphorus(V) oxide to give quantitatively 4-(((5-methoxypyridin-3-yl)imino)

methyl)benzonitrile which was used without further purification in the next step. ESI/APCI (+): 238 (M+H).

Step 2: 4-(2-(1H-Indol-3-yl)-1-((5-methoxypyridin-3-yl)amino)-2-oxoethyl)benzonitrile was prepared according to general procedure K from a mixture of 3-benzyl-5-(2-hydroxyethyl)-4-methylthiazol-3-ium chloride (0.134 g; 0.500 mmol) and triethylamine (0.069 mL; 0.496 mmol) in ethanol (2 mL), tert-butyl 3-formyl-1H-indole-1-carboxylate (0.245 g; 0.999 mmol) and a solution of 4-(((5-methoxypyridin-3-yl)imino)methyl)benzonitrile (0.999 mmol) in ethanol (1 mL), heated at 70° C. for 18 h. Purification by flash chromatography on silica gel using a gradient of methanol (1% to 7%) in dichloromethane followed by precipitation from diethyl ether furnished 0.132 g (34%) of the desired compound as a white solid. ESI/APCI(+): 383 (M+H). ESI/APCI(−): 381 (M−H).

Example 159: Preparation of 1-(benzo[b]thiophen-3-yl)-2-((3-methoxyphenyl)amino)-2-phenylethanone Step 1: To a solution of thianaphthene (0.300 g; 2.235 mmol) and phenylacetyl chloride (0.300 mL; 2.266 mmol) in dichloroethane (5 mL) cooled at 0° C. was added portionwise aluminum trichloride (0.894 g; 6.705 mmol) over 2 h. The reaction mixture was then stirred at room temperature overnight. A 1M Rochelle salt solution was added and the reaction mixture was stirred at room temperature for 1 h. The phases were separated. The organic phase was washed with water and brine, dried over sodium sulfate, filtered and concentrated under reduced pressure. Purification by flash chromatography on silica gel using a gradient of dichloromethane (30% to 90%) in heptane furnished 0.239 g (42%) of 1-(benzo[b]thiophen-3-yl)-2-phenylethanone as a white solid. ESI/APCI(+): 253 (M+H); 275 (M+Na). ESI/APCI(−): 251 (M−H). $^{1}$H NMR (CDCl$_{3}$) δ 8.78 (1H, d); 8.37 (1H, s); 7.85 (1H, d); 7.5-7.2 (7H, m); 4.30 (2H, s).

Step 2: 1-(Benzo[b]thiophen-3-yl)-2-bromo-2-phenylethanone has been prepared according to 2 different procedures described hereunder as method A and method B.

Method A.
To a solution of 1-(benzo[b]thiophen-3-yl)-2-phenylethanone (0.100 g; 0.396 mmol) in THF (4 mL) cooled to 0° C. was added dropwise a solution of phenyltrimethylammonium tribromide (0.171 g; 0.455 mmol) in THF (5 mL). The reaction mixture was stirred at 0° C. for 15 min and at room temperature for 1 h. The reaction mixture was filtered and the solid was washed with diethyl ether. The filtrate was concentrated under reduced pressure. The residue was dissolved in dichloromethane and was washed with water. The phases were separated. The organic phase was washed with water and brine, dried over sodium sulfate, filtered and concentrated under reduced pressure. Purification by flash chromatography on silica gel using a gradient of dichloromethane (20% to 80%) in heptane furnished 0.114 g of a mixture containing 1-(benzo[b]thiophen-3-yl)-2-bromo-2-phenylethanone as a brown oil. ESI/APCI(+): 331,333 (M+H). $^{1}$H NMR (DMSO-d$_{6}$) δ 9.27 (1H, s); 8.61 (1H, d); 8.11 (1H, d); 7.7-7.1 (7H, m); 7.17 (1H, s) (80% purity).

Method B.
To a solution of 1-(benzo[b]thiophen-3-yl)-2-phenylethanone (0.108 g; 0.428 mmol) in ethyl acetate (2 mL) was added copper(II) bromide (0.162 g; 0.725 mmol). The reaction mixture was refluxed for 2.5 h. After cooling to room temperature, the reaction mixture was diluted with ethyl acetate and washed with water. The phases were separated. The organic phase was washed with brine, dried over sodium sulfate, filtered and concentrated under reduced pressure. Purification by flash chromatography on silica gel using a gradient of dichloromethane (30% to 80%) in heptane furnished 0.102 g of a mixture containing 1-(benzo[b]thiophen-3-yl)-2-bromo-2-phenylethanone (same purity as in method A) as a brown oil.

Step 3: 1-(Benzo[b]thiophen-3-yl)-2-((3-methoxyphenyl)amino)-2-phenylethanone was prepared according to general procedure C from 1-(benzo[b]thiophen-3-yl)-2-bromo-2-phenylethanone (0.050 g; 0.151 mmol), DIPEA (0.052 mL; 0.298 mmol) and 3-methoxyaniline (0.034 mL; 0.303 mmol) in acetonitrile (2 mL), irradiated in a microwave oven at 200° C. for 30 min. Purification by flash chromatography on silica gel using a gradient of ethyl acetate (10% to 50%) in heptane followed by a second purification by flash chromatography on silica gel using a gradient of dichloromethane (20% to 90%) in heptane furnished 0.029 g (44% over two steps) of the desired product as a yellow oil. ESI/APCI (+): 374 (M+H); 396 (M+Na). ESI/APCI(−): 372 (M−H). $^{1}$H NMR (DMSO-d$_{6}$) δ 9.51 (1H, s); 8.53 (1H, d); 8.07 (1H, d); 7.6-7.2 (7H, m); 6.94 (1H, t); 6.42 (4H, m); 6.14 (1H, dd); 3.63 (3H, s).

Example 160: Preparation of 2-((3-methoxyphenyl)amino)-2-phenyl-1-(1H-pyrrolo[2,3-b]pyridin-3-yl)ethanone Step 1: tert-Butyl 3-formyl-1H-pyrrolo[2,3-b]pyridine-1-carboxylate was prepared according to general procedure F from 7-azaindole-3-carboxaldehyde (0.500 g; 3.421 mmol), di-tert-butyl dicarbonate (0.896 g; 4.105 mmol) and DMAP (0.042 g; 0.342 mmol) in acetonitrile (8 mL) to afford 0.779 g (92%) of the desired compound as a white solid. ESI/APCI(+): 269 (M+Na).

Step 2: 2-((3-Methoxyphenyl)amino)-2-phenyl-1-(1H-pyrrolo[2,3-b]pyridin-3-yl)ethanone was prepared according to general procedure L from a mixture of 3-benzyl-5-(2-hydroxyethyl)-4-methylthiazolium chloride (0.114 g; 0.423 mmol) and triethylamine (0.059 mL; 0.423 mmol) in ethanol (0.5 mL), tert-butyl 3-formyl-1H-pyrrolo[2,3-b]pyridine-1-carboxylate (0.250 g; 1.015 mmol) and a solution of N-benzylidene-3-methoxyaniline (0.846 mmol) in ethanol (0.5 mL), heated at 70° C. for 3 days. Purification by flash chromatography on silica gel using a gradient of ethyl acetate (0% to 100%) in heptane followed by a second purification by flash chromatography on silica gel using a gradient of ethyl acetate (20% to 100%) in heptane furnished 0.028 g (9%) of the desired compound as a solid. ESI/APCI (+): 358 (M+H). ESI/APCI(−): 356 (M−H).

Example 161: Preparation of 2-((3-methoxyphenyl)amino)-2-phenyl-1-(1H-pyrrolo[3,2-b]pyridin-3-yl)ethanone Step 1: A mixture of 4-azaindole (0.500 g; 4.223 mmol), hexamethylenetetramine (0.890 g; 6.348 mmol) and acetic acid (3.630 mL; 63.45 mmol) in water (9 mL) was refluxed for 4 h. The reaction mixture was cooled to room temperature and concentrated under reduced pressure. Purification by flash chromatography on silica gel using a gradient of methanol (2% to 4%) in dichloromethane furnished 0.550 g (89%) of 1H-pyrrolo[3,2-b]pyridine-3-carbaldehyde. ESI/APCI(+): 147 (M+H). ESI/APCI(−): 145 (M−H).

Step 2: tert-Butyl 3-formyl-1H-pyrrolo[3,2-b]pyridine-1-carboxylate was prepared according to general procedure F from 1H-pyrrolo[3,2-b]pyridine-3-carbaldehyde (0.550 g; 3.763 mmol), di-tert-butyl dicarbonate (0.986 g; 4.518 mmol) and DMAP (0.048 g; 0.376 mmol) in acetonitrile (8 mL) to afford 0.802 g (87%) of the desired compound as a white solid. ESI/APCI(+): 269 (M+Na).

Step 3: 2-((3-Methoxyphenyl)amino)-2-phenyl-1-(1H-pyrrolo[3,2-b]pyridin-3-yl)ethanone was prepared according to general procedure L from a mixture of 3-benzyl-5-(2-hydroxyethyl)-4-methylthiazolium chloride (0.137 g; 0.508 mmol) and triethylamine (0.071 mL; 0.508 mmol) in ethanol (0.5 mL), tert-butyl 3-formyl-1H-pyrrolo[3,2-b]pyridine-1-carboxylate (0.300 g; 1.218 mmol) and a solution of N-benzylidene-3-methoxyaniline (1.015 mmol) in ethanol (0.5 mL), heated at 70° C. for 3 days. Purification by flash chromatography on silica gel using a gradient of ethylacetate (20% to 100%) in heptane followed by precipitation from dichloromethane furnished 0.019 g (5%) of the desired compound as a solid. ESI/APCI(+): 358 (M+H). ESI/APCI(−): 356 (M−H).

Example 162: Preparation of 1-(imidazo[1,2-a]pyridin-3-yl)-2-((3-methoxyphenyl)amino)-2-phenylethanone 1-(Imidazo[1,2-a]pyridin-3-yl)-2-((3-methoxyphenyl)amino)-2-phenylethanone was prepared according to general procedure L from a mixture of 3-benzyl-5-(2-hydroxyethyl)-4-methylthiazolium chloride (0.135 g; 0.500 mmol) and triethylamine (0.070 mL; 0.505 mmol) in ethanol (1 mL), imidazo[1,2-a]pyridine-3-carbaldehyde (0.146 g; 0.999 mmol) and a solution of N-benzylidene-3-methoxyaniline (0.999 mmol) in ethanol (1 mL), heated at 70° C. for 3 days. Purification by flash chromatography on silica gel using a gradient of ethylacetate (0% to 100%) in heptane followed by precipitation from diethyl ether furnished 0.112 g (31%) of the desired compound as a solid. ESI/APCI(+): 358 (M+H). ESI/APCI(−): 356 (M−H).

Example 163: Preparation of 2-((3-methoxyphenyl)amino)-2-phenyl-1-(pyrazolo[1,5-a]pyridin-3-yl)ethanone Step 1: To a solution of ethyl pyrazolo[1,5-a]pyridine-3-carboxylate (0.400 g; 2.103 mmol) in dry dichloromethane (8 mL) cooled at −78° C. under a nitrogen atmosphere was added dropwise a 1M diisobutylaluminium hydride solution in dichloromethane (4.630 mL; 4.630 mmol). The reaction was stirred for 1.5 h at −78° C. after which it was allowed to warm to −15° C. for 30 min. The reaction was quenched by addition of a 1N Rochelle salt solution and the reaction mixture was vigorously stirred for 1 h. The phases were separated and the aqueous phase was extracted with dichloromethane. The organic phases were combined, washed with brine, dried over magnesium sulfate and concentrated under reduced pressure. Purification by flash chromatography on silica gel using a gradient of ethylacetate (20% to 100%) in heptane furnished 0.128 g (41%) of pyrazolo[1,5-a]pyridin-3-ylmethanol as a colourless oil. ESI/APCI(+): 149 (M+H).

Step 2: To a solution of pyrazolo[1,5-a]pyridin-3-ylmethanol (0.128 g; 0.864 mmol) in dichloromethane (10 mL) was added molecular sieves (4 Å) and pyridinium dichromate (0.488 g; 1.296 mmol). The reaction was stirred at room temperature overnight. Celite @ was added and the reaction mixture was stirred for 30 min. The red suspension was filtered. The filtrate was concentrated under reduced pressure. Purification by flash chromatography on silica gel using a gradient of ethylacetate (2% to 20%) in heptane furnished 0.064 g (51%) of pyrazolo[1,5-a]pyridine-3-carbaldehyde as a white solid. ESI/APCI(+): 147 (M+H).

Step 3: 2-((3-Methoxyphenyl)amino)-2-phenyl-1-(pyrazolo[1,5-a]pyridin-3-yl)ethanone was prepared according to general procedure L from a mixture of 3-benzyl-5-(2-hydroxyethyl)-4-methylthiazolium chloride (0.059 g; 0.219 mmol) and triethylamine (0.031 mL; 0.219 mmol) in ethanol (0.5 mL), pyrazolo[1,5-a]pyridine-3-carbaldehyde (0.093 g; 0.438 mmol) and a solution of N-benzylidene-3-methoxyaniline (0.438 mmol) in ethanol (0.5 mL), heated at 70° C. for 24 h. Purification by flash chromatography on silica gel using a gradient of ethylacetate (0% to 100%) in heptane followed by purification by preparative HPLC (XBridge column; method 2) furnished 0.020 g (13%) of the desired compound. ESI/APCI(+): 358 (M+H).

Example 164: Preparation of 1-(1H-indazol-3-yl)-2-((3-methoxyphenyl)amino)-2-phenylethanone Step 1: tert-Butyl 3-formyl-1H-indazole-1-carboxylate was prepared according to general procedure F from 1H-indazole-3-carboxaldehyde (0.500 g; 3.421 mmol), di-tert-butyl dicarbonate (0.896 g; 4.105 mmol) and DMAP (0.042 g; 0.342 mmol) in acetonitrile (8 mL). Purification by flash chromatography on silica gel using a gradient of ethylacetate (5% to 40%) in heptane furnished 0.318 g (38%) of the desired compound. ESI/APCI(+): 269 (M+Na).

Step 2: 1-(1H-Indazol-3-yl)-2-((3-methoxyphenyl)amino)-2-phenylethanone was prepared according to general procedure L from a mixture of 3-benzyl-5-(2-hydroxyethyl)-4-methylthiazolium chloride (0.174 g; 0.646 mmol) and triethylamine (0.091 mL; 0.646 mmol) in ethanol (1 mL), tert-butyl 3-formyl-1H-indazole-1-carboxylate (0.318 g; 1.291 mmol) and a solution of N-benzylidene-3-methoxyaniline (1.291 mmol) in ethanol (1 mL), heated at 70° C. for 2 days. Purification by flash chromatography on silica gel using a gradient of ethylacetate (0% to 100%) in heptane followed by purification by preparative HPLC (XBridge column; method 1) furnished 0.004 g (1%) of the desired compound. ESI/APCI(+): 358 (M+H). ESI/APCI(−): 356 (M−H).

Example 165: Preparation of 1-(benzo[b]thiophen-3-yl)-2-(imidazo[1,2-a]pyridin-2-yl)-2-((2-methoxypyridin-4-yl)amino)ethanone 1-(Benzo[b]thiophen-3-yl)-2-(imidazo[1,2-a]pyridin-2-yl)-2-((2-methoxypyridin-4-yl)amino)ethanone was prepared according to general procedure L from a mixture of 3-benzyl-5-(2-hydroxyethyl)-4-methylthiazolium chloride (0.110 g; 0.408 mmol) and triethylamine (0.080 mL; 0.574 mmol) in ethanol (0.5 mL), benzo[b]thiophene-3-carbaldehyde (0.140 g; 0.863 mmol) and a mixture of N-(imidazo[1,2-a]pyridin-2-ylmethylene)-2-methoxypyridin-4-amine (0.856 mmol) in ethanol (1 mL), heated at 65° C. for 3 days. Purification by flash chromatography on silica gel using a gradient of ethylacetate (50% to 100%) in heptane followed by precipitation from ethanol and heptane furnished 0.022 g (6%) of the desired compound as a pink solid. ESI/APCI(+): 415 (M+H).

Example 166: Preparation of 2-((3-methoxyphenyl)amino)-2-phenyl-1-(1H-pyrrolo[2,3-c]pyridin-3-yl)ethanone Step 1: To a solution of 1H-pyrrolo[2,3-c]pyridine (0.400 g; 3.386 mmol) in a mixture of 1,2-dichloroethane (10 mL) and nitromethane (10 mL) cooled at 0° C. under an argon atmosphere were added dichloro(methoxy)methane (1.544 mL; 16.92 mmol) and aluminum trichloride (1.500 g; 11.25 mmol) over 1 h. After the addition, the reaction was quenched by addition of water and of a saturated sodium bicarbonate solution. The reaction mixture was extracted with a solution of dichloromethane and ethanol (9/1, 6×100 mL). The combined organic layers were washed with brine, dried over magnesium sulfate, filtered and concentrated under reduced pressure to yield 0.295 g (60%) of 1H-pyrrolo[2,3-c]pyridine-3-carbaldehyde which was used without further purification. ESI/APCI(+): 147 (M+H). ESI/APCI(−): 145 (M−H). $^1$H NMR (DMSO-d$_6$) δ 10.01 (1H, s); 8.88 (1H, s); 8.50 (1H, s); 8.33 (1H, d); 8.00 (1H, d).

Step 2: tert-Butyl 3-formyl-1H-pyrrolo[2,3-c]pyridine-1-carboxylate was prepared according to general procedure F from 1H-pyrrolo[2,3-c]pyridine-3-carbaldehyde (0.295 g; 2.019 mmol), di-tert-butyl dicarbonate (0.529 g; 2.019 mmol) and DMAP (0.025 g; 0.202 mmol) in acetonitrile (5 mL) to afford 0.411 g (83%) of the desired compound as a solid. $^1$H NMR (DMSO-d$_6$) δ 10.13 (1H, s); 9.32 (1H, s); 8.86 (1H, s); 8.51 (1H, d); 8.07 (1H, d), 1.69 (9H, s).

Step 3: 2-((3-Methoxyphenyl)amino)-2-phenyl-1-(1H-pyrrolo[2,3-c]pyridin-3-yl)ethanone was prepared according to general procedure L from a mixture of 3-benzyl-5-(2-hydroxyethyl)-4-methylthiazolium chloride (0.135 g; 0.500 mmol) and triethylamine (0.070 mL; 0.505 mmol) in ethanol (1 mL), tert-butyl 3-formyl-1H-pyrrolo[2,3-c]pyridine-1-carboxylate (0.246 g; 0.999 mmol) and a solution of N-benzylidene-3-methoxyaniline (0.999 mmol) in ethanol (1 mL), heated at 70° C. for 2 days. Purification by flash chromatography on silica gel using a gradient of ethylacetate (0% to 100%) in heptane followed by a second purification by flash chromatography on silica gel using gradient of methanol (0% to 10%) in dichloromethane and a precipitation from diethyl ether furnished 0.055 g (14%) of the desired compound as a solid. ESI/APCI(+): 358 (M+H). ESI/APCI(−): 356 (M−H).

Example 167: Preparation of 2-((3-methoxyphenyl)amino)-2-phenyl-1-(1H-pyrrolo[3,2-c]pyridin-3-yl)ethanone Step 1: To a solution of 1H-pyrrolo[3,2-c]pyridine (0.400 g; 3.386 mmol) in a mixture of 1,2-dichloroethane (10 mL) and nitromethane (10 mL) cooled at 0° C. under an argon atmosphere were added dichloro(methoxy)methane (1.544 mL; 16.92 mmol) and aluminum trichloride (1.500 g; 11.25 mmol) over 1 h. After the addition, the reaction was quenched by addition of water and of a saturated sodium bicarbonate solution. The reaction mixture was extracted with a solution of dichloromethane and ethanol (9/1, 6×100 mL). The combined organic layers were washed with brine, dried over magnesium sulfate, filtered and concentrated under reduced pressure to yield 0.333 g (67%) of 1H-pyrrolo[3,2-c]pyridine-3-carbaldehyde which was used without further purification. ESI/APCI(+): 147 (M+H). ESI/APCI(−): 145 (M−H). $^1$H NMR (DMSO-d$_6$) δ 10.00 (1H, s); 9.29 (1H, s); 8.42 (1H, s); 8.35 (1H, d); 7.53 (1H, d).

Step 2: tert-Butyl 3-formyl-1H-pyrrolo[3,2-c]pyridine-1-carboxylate was prepared according to general procedure F from 1H-pyrrolo[3,2-c]pyridine-3-carbaldehyde (0.330 g; 2.258 mmol), di-tert-butyl dicarbonate (0.591 g; 2.708 mmol) and DMAP (0.027 g; 0.226 mmol) in acetonitrile (5 mL) to afford 0.374 g (67%) of the desired compound as a brown solid. $^1$H NMR (DMSO-d$_6$) δ 10.12 (1H, s); 9.33 (1H, s); 8.77 (1H, s); 8.57 (1H, d); 8.02 (1H, d); 1.63-1.74 (9H, m).

Step 3: 2-((3-Methoxyphenyl)amino)-2-phenyl-1-(1H-pyrrolo[3,2-c]pyridin-3-yl)ethanone was prepared according to general procedure L from a mixture of 3-benzyl-5-(2-hydroxyethyl)-4-methylthiazolium chloride (0.135 g; 0.500 mmol) and triethylamine (0.070 mL; 0.505 mmol) in ethanol (1 mL), tert-butyl 3-formyl-1H-pyrrolo[3,2-c]pyridine-1-carboxylate (0.246 g; 0.999 mmol) and a solution of N-benzylidene-3-methoxyaniline (0.999 mmol) in ethanol (1 mL), heated at 70° C. for 3 days. Purification by flash chromatography on silica gel using a gradient of ethylacetate (0% to 100%) in heptane followed by a second purification by flash chromatography on silica gel using gradient of methanol (0% to 10%) in dichloromethane and a precipitation from diethyl ether furnished 0.056 g (14%) of the desired compound as a solid. ESI/APCI(+): 358 (M+H). ESI/APCI(−): 356 (M−H).

Example 168: Preparation of 2-((3-methoxyphenyl)amino)-1-(6-methyl-4,5,6,7-tetrahydrothieno[2,3-c]pyridin-3-yl)-2-phenylethanone Step 1: To a suspension of ethyl 2-amino-6-methyl-4,5,6,7-tetrahydrothieno-[2,3-c]pyridine-3-carboxylate (1.000 g; 4.161 mmol) in dioxane (5 mL) was added a concentrated hydrochloric acid solution (3.200 mL; 38.40 mmol). After cooling to −5° C., a solution of sodium nitrite (0.316 g; 4.580 mmol) in water (0.5 mL) was added. The resulting black reaction mixture was stirred at −5° C. for 40 min and was then added portionwise to a mixture of a 50% orthophosphoric acid solution (9 mL) and diethyl ether (9 mL) cooled at 0° C. The reaction mixture was allowed to warm to room temperature and was stirred at room temperature overnight. The reaction mixture was carefully poured into a mixture ice/1N sodium hydroxide solution and extracted with dichloromethane. The organic phase was washed with water and brine, dried over sodium sulfate, filtered and concentrated under reduced pressure. Purification by flash chromatography on silica gel using a gradient of methanol (5% to 10%) in dichloromethane furnished 0.431 g (46%) of ethyl 6-methyl-4,5,6,7-tetrahydrothieno[2,3-c]pyridine-3-carboxylate as a brown oil. ESI/APCI(+): 226 (M+H). $^1$H NMR (DMSO-d$_6$) δ 8.12 (1H, s); 4.23 (2H, q); 3.53 (2H, s); 2.85 (2H, t); 2.61 (2H, t); 2.35 (3H, s); 1.28 (3H, s).

Step 2: A suspension of lithium aluminium hydride (0.110 g; 2.899 mmol) in diethyl ether (20 mL) was refluxed for 30 min. After cooling to room temperature, a solution of ethyl 6-methyl-4,5,6,7-tetrahydrothieno[2,3-c]pyridine-3-carboxylate (0.580 g; 2.574 mmol) in diethyl ether (6 mL) was added. The reaction mixture was refluxed for 5.5 h. After cooling to room temperature, the reaction mixture was diluted with ethyl acetate and washed with a 1N sodium hydroxide solution. The phases were separated. The aqueous phase was extracted twice with ethyl acetate. The organic phases were combined, washed with water and brine, dried over sodium sulfate, filtered and concentrated under reduced pressure to afford 0.415 g of (6-methyl-4,5,6,7-tetrahydrothieno[2,3-c]pyridin-3-yl)methanol which was used in the next step without further purification. ESI/APCI(+): 184 (M+H).

To a solution of (6-methyl-4,5,6,7-tetrahydrothieno[2,3-c]pyridin-3-yl)methanol (crude; 2.264 mmol) in dichloromethane (18 mL) was added a 15% Dess-Martin periodinane solution in dichloromethane (5.700 mL; 2.750 mmol). After 5 h at room temperature, a 15% Dess-Martin periodinane solution in dichloromethane (1.000 mL; 0.480 mmol) was added again and the reaction mixture was stirred at room temperature overnight. The reaction mixture was diluted with diethyl ether and a 1N sodium hydroxide solution was added. After 15 min at room temperature, the phases were separated. The organic phase was washed with a 1N sodium hydroxide solution, water and brine, dried over $Na_2SO_4$, filtered and concentrated under reduced pressure. Purification by flash chromatography on silica gel using a gradient of methanol (5% to 10%) in dichloromethane furnished 0.235 g (50% over two steps) of 6-methyl-4,5,6,7-tetrahydrothieno[2,3-c]pyridine-3-carbaldehyde as a brown solid. ESI/APCI(+): 182 (M+H). $^1$H NMR (DMSO-$d_6$) δ 9.87 (1H, s); 8.41 (1H, s); 3.55 (2H, s); 2.86 (2H, m); 2.51 (2H, t); 2.36 (3H, s).

Step 3: 2-((3-Methoxyphenyl)amino)-1-(6-methyl-4,5,6,7-tetrahydrothieno[2,3-c]pyridin-3-yl)-2-phenylethanone was prepared according to general procedure L from a mixture of 3-benzyl-5-(2-hydroxyethyl)-4-methylthiazolium chloride (0.117 g; 0.554 mmol) and triethylamine (0.039 mL; 0.281 mmol) in ethanol (1 mL), 6-methyl-4,5,6,7-tetrahydrothieno[2,3-c]pyridine-3-carbaldehyde (0.100 g; 0.552 mmol) and a mixture of N-benzylidene-3-methoxyaniline (0.117 g; 0.554 mmol) in ethanol (1 mL) heated at 70° C. for 24 h. The residue was purified by flash chromatography on silica gel using a gradient of methanol (0% to 10%) in methanol and by preparative TLC using 10% methanol in dichloromethane as eluent and by preparative HPLC (XBridge column; method 4) furnished 0.023 g (11%) of the desired compound as a yellow solid. ESI/APCI(+): 393 (M+H); 415 (M+Na). ESI/APCI(−): 391 (M−H).

Example 169: Preparation of 2-((3-methoxyphenyl)amino)-1-(1-methyl-1H-indazol-3-yl)-2-phenylethanone 2-((3-Methoxyphenyl)amino)-1-(1-methyl-1H-indazol-3-yl)-2-phenylethanone was prepared according to general procedure L from a mixture of 3-benzyl-5-(2-hydroxyethyl)-4-methylthiazolium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of N-benzylidene-3-methoxyaniline (1.000 mmol) in ethanol (1 mL), heated at 70° C. for 24 h. Purification by flash chromatography on silica gel using a gradient of ethyl acetate (0% to 100%) in heptane followed by precipitation from diethyl ether furnished 0.139 g (37%) of the desired compound as a white solid. ESI/APCI(+): 372 (M+H).

Example 170: Preparation of 1-(indolin-1-yl)-2-((3-methoxyphenyl)amino)-2-phenylethanone Step 1: To a solution of indoline (0.050 mL; 0.444 mmol) in dichloromethane (5 mL) were added potassium carbonate (0.262 g; 1.896 mmol) and α-chlorophenylacetyl chloride (0.150 mL; 0.952 mmol). The reaction mixture was stirred at room temperature for 2 h. The reaction mixture was filtered. The filtrate was concentrated under reduced pressure to give 2-chloro-1-(indolin-1-yl)-2-phenylethanone which was used in the next step without further purification. ESI/APCI(+): 272 (M+H); 294 (M+Na).

Step 2: A mixture of 2-chloro-1-(indolin-1-yl)-2-phenylethanone (crude; 0.444 mmol), 3-methoxyaniline (0.100 mL, 0.893 mmol) and DIPEA (0.100 mL, 0.514 mmol) in acetonitrile (2 mL) was irradiated in a microwave oven at 120° C. for 30 minutes. The reaction mixture was concentrated under reduced pressure. Purification by flash chromatography using a gradient of ethyl acetate (10% to 40%) in heptane followed by purification by preparative HPLC (XBridge column; method 1) furnished 0.043 g (27% over two steps) of the desired product as a white solid. ESI/APCI(+): 359 (M+H); 381 (M+Na). $^1$H NMR (CDCl$_3$): δ 8.26 (1H, m); 7.50 (1H, m); 7.17-7.36 (8H, m); 7.03 (1H, m); 6.21-6.27 (2H, m); 5.21 (1H, s); 4.26 (1H, m); 3.92 (1H, m); 3.73 (3H, s); 3.08-3.30 (2H, m).

Example 171: Preparation of 1-(7-fluoro-1H-indol-3-yl)-2-((3-methoxyphenyl)amino)-2-phenylethanone 1-(7-Fluoro-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.163 g; 0.604 mmol) and triethylamine (0.100 mL; 0.717 mmol) in ethanol, tert-butyl 7-fluoro-3-formyl-1H-indole-1-carboxylate (0.277 g; 1.052 mmol) and a solution of N-benzylidene-3-methoxyaniline (1.046 mmol) in ethanol (1.5 mL), heated at 60° C. for 48 h. The residue was purified by flash chromatography on silica gel using a gradient of ethyl acetate (0% to 40%) in heptane. Further purification by precipitation from diisopropyl ether and ethyl acetate furnished 0.042 g (11%) of the desired compound as a yellow solid. ESI/APCI(+): 375 (M+H). ESI/APCI(−): 373 (M−H).

Example 172: Preparation of 2-((3,5-dimethoxyphenyl)amino)-1-(5-fluoro-1H-indol-3-yl)-2-(6-methoxypyridin-3-yl)ethanone Step 1: A solution of 3,5-dimethoxy-N-((6-methoxypyridin-3-yl)methylene)aniline in ethanol was prepared by heating a solution of 6-methoxynicotinaldehyde (0.139 g; 1.014 mmol) and 3,5-dimethoxyaniline (0.158 g; 1.031 mmol) in ethanol (0.5 mL) at 60° C. for 18 h. The formation of the imine was quantitative and the solution was used without further purification. ESI/APCI(+): 273 (M+H).

Step 2: 2-((3,5-Dimethoxyphenyl)amino)-1-(5-fluoro-1H-indol-3-yl)-2-(6-methoxypyridin-3-yl)ethanone was prepared according to general procedure K from a mixture of 3-benzyl-5-(2-hydroxyethyl)-4-methylthiazol-3-ium chloride (0.160 g; 0.593 mmol) and triethylamine (0.100 mL; 0.717 mmol) in ethanol (0.5 mL), tert-butyl 5-fluoro-3-formyl-1H-indole-1-carboxylate (0.290 g; 1.102 mmol) and a solution of 3,5-dimethoxy-N-((6-methoxypyridin-3-yl)methylene)aniline (1.014 mmol) in ethanol (2 mL), heated at 60° C. for 24 h. Purification by flash chromatography on silica gel using a gradient of ethyl acetate (30% to 70%) in heptane followed by precipitation from dichloromethane furnished 0.043 g (9%) of the desired compound as a white solid. ESI/APCI(+): 436 (M+H). ESI/APCI(−): 434 (M−H).

Example 173: Preparation of 2-((2-fluoropyridin-4-yl)amino)-1-(1H-indol-3-yl)-2-phenylethanone Step 1: A solution of N-benzylidene-2-fluoropyridin-4-amine in ethanol was prepared by heating a solution of benzaldehyde (0.115 mL; 1.138 mmol) and 4-amino-2-fluoropyridine (0.130 g; 1.160 mmol) in ethanol (0.5 mL) at 60° C. for 18 h. The formation of the imine was quantitative and the solution was used without further purification. ESI/APCI(+): 201 (M+H).

Step 2: 2-((2-Fluoropyridin-4-yl)amino)-1-(1H-indol-3-yl)-2-phenylethanone was prepared according to general procedure L from a mixture of 3-benzyl-5-(2-hydroxyethyl)-4-methylthiazol-3-ium chloride (0.158 g; 0.586 mmol) and triethylamine (0.100 mL; 0.717 mmol) in ethanol (0.5 mL), tert-butyl 3-formyl-1H-indole-1-carboxylate (0.311 g; 1.268 mmol) and a solution of N-benzylidene-2-fluoropyridin-4-amine (1.138 mmol) in ethanol (1.5 mL), heated at 60° C. for 96 h. Purification by flash chromatography on silica gel using a gradient of ethyl acetate (0% to 50%) in heptane followed by purification by preparative HPLC (XBridge column; method 1) furnished 0.035 g (9%) of the desired compound as a white solid. ESI/APCI(+): 346 (M+H). ESI/APCI(−): 344 (M−H).

Example 174: Preparation of 2-((3-methoxyphenyl)amino)-2-phenyl-1-(1-((tetrahydrofuran-3-yl)sulfonyl)-1H-indol-3-yl)ethanone Step 1: To a solution of 2-chloro-1-(1H-indol-3-yl)-2-phenylethanone (0.200 g; 0.741 mmol) in DMF (5 mL) cooled to 0° C. was added sodium hydride (60% dispersion in mineral oil; 0.053 g; 1.333 mmol). The reaction mixture was stirred at room temperature for 0.5 h. Tetrahydrofuran-3-sulfonyl chloride (0.253 g; 1.483 mmol) and DMAP (0.005 g; 0.037 mmol) were added and the reaction mixture was stirred at room temperature for 3 h. Water was added and the reaction mixture was extracted with ethyl acetate. The organic phase was washed with brine, dried over sodium sulfate, filtered and concentrated under reduced pressure. Purification by flash chromatography on silica gel using a gradient of ethyl acetate (5% to 50%) in heptane furnished 0.299 g (100%) of 2-chloro-2-phenyl-1-(1-((tetrahydrofuran-3-yl)sulfonyl)-1H-indol-3-yl)ethanone as a solid. ESI/APCI(+): 404 (M+H). ESI/APCI(−): 402 (M−H).

Step 2: 2-((3-Methoxyphenyl)amino)-2-phenyl-1-(1-((tetrahydrofuran-3-yl)sulfonyl)-1H-indol-3-yl)ethanone was prepared according to general procedure E from 2-chloro-2-phenyl-1-(1-((tetrahydrofuran-3-yl)sulfonyl)-1H-indol-3-yl)ethanone (0.100 g; 0.248 mmol) and m-anisidine (0.277 mL; 2.474 mmol) in acetonitrile (1 mL), irradiated in a microwave oven at 100° C. for 30 min. Purification by flash chromatography on silica gel using a gradient of ethyl acetate (2% to 40%) in heptane followed by purification by preparative HPLC (XBridge column; method 1) furnished 0.058 g (48%) of the desired compound a beige solid. ESI/APCI(+): 491 (M+H). ESI/APCI(−): 489 (M−H).

Example 175: Preparation of 2-((3-methoxyphenyl)amino)-1-(1-((1-methyl-1H-imidazol-4-yl)sulfonyl)-1H-indol-3-yl)-2-phenylethanone Step 1: To a solution of 2-chloro-1-(1H-indol-3-yl)-2-phenylethanone (0.200 g; 0.741 mmol) in DMF (5 mL) cooled to 0° C. was added sodium hydride (60% dispersion in mineral oil; 0.053 g; 1.333 mmol). The reaction mixture was stirred at room temperature for 0.5 h. 1-Methyl-1H-imidazole-4-sulfonyl chloride (0.268 g; 1.484 mmol) and DMAP (0.005 g; 0.037 mmol) were added and the reaction mixture was stirred at room temperature for 3 h. Water was added and the reaction mixture was extracted with ethyl acetate. The organic phase was washed with brine, dried over sodium sulfate, filtered and concentrated under reduced pressure. Purification by flash chromatography on silica gel using a gradient of ethyl acetate (30% to 100%) in heptane furnished 0.301 g (98%) of 2-chloro-1-(1-((1-methyl-1H-imidazol-4-yl)sulfonyl)-1H-indol-3-yl)-2-phenylethanone as a solid. ESI/APCI(+): 414 (M+H); 436 (M+Na). ESI/APCI(−): 412 (M−H).

Step 2: 2-((3-Methoxyphenyl)amino)-1-(1-((1-methyl-1H-imidazol-4-yl)sulfonyl)-1H-indol-3-yl)-2-phenylethanone was prepared according to general procedure E from 2-chloro-1-(1-((1-methyl-1H-imidazol-4-yl)sulfonyl)-1H-indol-3-yl)-2-phenylethanone (0.166 g; 0.402 mmol) and m-anisidine (0.449 mL; 4.011 mmol) in acetonitrile (1.5 mL), irradiated in a microwave oven at 100° C. for 30 min. Purification by flash chromatography on silica gel using a gradient of ethyl acetate (30% to 100%) in heptane followed by purification by preparative HPLC (XBridge column; method 1) furnished 0.058 g (29%) of the desired compound a beige solid. ESI/APCI(+): 501 (M+H). ESI/APCI(−): 499 (M−H).

Example 176: Preparation of 2-((3,5-dimethoxyphenyl)amino)-1-(1-(3-hydroxypropyl)-1H-indol-3-yl)-2-phenylethanone 2-((3,5-Dimethoxyphenyl)amino)-1-(1-(3-hydroxypropyl)-1H-indol-3-yl)-2-phenylethanone was prepared according to general procedure E from 2-chloro-1-(1-(3-hydroxypropyl)-1H-indol-3-yl)-2-phenylethanone (0.125 g; 0.381 mmol) and 3,5-dimethoxyaniline (0.584 g; 3.813 mmol) in acetonitrile (1 mL), irradiated in a microwave oven at 130° C. for 15 min. The residue was purified by flash chromatography on silica gel using a gradient of ethyl acetate (2% to 20%) in dichloromethane. Further purification by flash chromatography on silica gel using a gradient of ethyl acetate (30% to 100%) in heptane followed by purification by preparative HPLC (XBridge column; method 1) furnished 0.022 g (13%) of the desired compound as a white solid. ESI/APCI(+): 445 (M+H).

Example 177: Preparation of 1-(1-(ethylsulfonyl)-1H-indol-3-yl)-2-((3-methoxyphenyl)amino)-2-phenylethanone Step 1: To a solution of 2-chloro-1-(1H-indol-3-yl)-2-phenylethanone (0.200 g; 0.741 mmol) in DMF (5 mL) cooled to 0° C. was added sodium hydride (60% dispersion in mineral oil; 0.053 g; 1.333 mmol). The reaction mixture was stirred at room temperature for 0.5 h. Ethane sulfonyl chloride (0.141 mL; 1.480 mmol) and DMAP (0.005 g; 0.037 mmol) were added and the reaction mixture was stirred at room temperature for 3 h. Water was added and the reaction mixture was extracted with ethyl acetate. The organic phase was washed with brine, dried over sodium sulfate, filtered and concentrated under reduced pressure. Purification by flash chromatography on silica gel using a gradient of ethyl acetate (2% to 40%) in heptane furnished 0.247 g (92%) of 2-chloro-1-(1-(ethylsulfonyl)-1H-indol-3-yl)-2-phenylethanone as a beige solid. ESI/APCI(+): 362 (M+H). ESI/APCI(−): 360 (M−H).

Step 2: 1-(1-(Ethylsulfonyl)-1H-indol-3-yl)-2-((3-methoxyphenyl)amino)-2-phenylethanone was prepared according to general procedure E from 2-chloro-1-(1-(ethylsulfonyl)-1H-indol-3-yl)-2-phenylethanone (0.130 g; 0.359 mmol) and m-anisidine (0.402 mL; 3.591 mmol) in acetonitrile (1.5 mL), irradiated in a microwave oven at 100° C. for 45 min. Purification by flash chromatography on silica gel using a gradient of dichloromethane (15% to 70%) in heptane furnished 0.039 g (25%) of the desired compound as a beige solid. ESI/APCI(+): 449 (M+H). ESI/APCI(−): 447 (M−H). $^1$H NMR (DMSO-d$_6$) δ 9.15 (1H, s); 8.23 (1H, d); 7.87 (1H, d); 7.62 (2H, d); 7.43 (2H, m); 7.25-7.35 (2H, m); 7.14-7.24 (1H, m); 6.89-6.98 (1H, m); 6.39-6.53 (3H, m); 6.28-6.38 (1H, m); 6.12 (1H, d); 3.68-3.87 (2H, m); 3.63 (3H, s); 1.03 (3H, t).

Example 178: Preparation of 1-(5-fluoro-1-(methylsulfonyl)-1H-indol-3-yl)-2-((3-methoxyphenyl)amino)-2-phenylethanone Step 1: To a solution of 2-chloro-1-(5-fluoro-1H-indol-3-yl)-2-phenylethanone (0.200 g; 0.695 mmol) in DMF (5 mL) cooled to 0° C. was added sodium hydride (60% dispersion in mineral oil; 0.053 g; 1.333 mmol). The reaction mixture was stirred at room temperature for 0.5 h. Mesyl chloride (0.108 mL; 1.395 mmol) and DMAP (0.005 g; 0.037 mmol) were added and the reaction mixture was stirred at room temperature for 3 h. Water was added and the reaction mixture was extracted with ethyl acetate. The organic phase was washed with brine, dried over sodium sulfate, filtered and concentrated under reduced pressure. Purification by flash chromatography on silica gel using a gradient of ethyl acetate (2% to 40%) in heptane furnished 0.219 g (86%) of 2-chloro-1-(5-fluoro-1-(methylsulfonyl)-1H-indol-3-yl)-2-phenylethanone as a solid. ESI/APCI(+): 366 (M+H). ESI/APCI(−): 364 (M−H).

Step 2: 1-(5-Fluoro-1-(methylsulfonyl)-1H-indol-3-yl)-2-((3-methoxyphenyl)amino)-2-phenylethanone was prepared according to general procedure E from 2-chloro-1-(5-fluoro-1-(methylsulfonyl)-1H-indol-3-yl)-2-phenylethanone (0.130 g; 0.355 mmol) and m-anisidine (0.398 mL; 3.555 mmol) in acetonitrile (1 mL), irradiated in a microwave oven at 100° C. for 45 min. The residue was purified by flash chromatography on silica gel using a gradient of dichloromethane (15% to 70%) in heptane. Further purification by flash chromatography on silica gel using a gradient of ethyl acetate (2% to 40%) in heptane furnished 0.030 g (18%) of the desired compound as a beige solid. ESI/APCI(+): 453 (M+H). ESI/APCI(−): 451 (M−H). $^1$H NMR (DMSO-$d_6$) δ9.22 (1H, s); 7.85-7.96 (2H, m); 7.62 (2H, d); 7.32 (3H, m); 7.15-7.26 (1H, m); 6.93 (1H, t); 6.39-6.50 (3H, m); 6.27-6.35 (1H, m); 6.13 (1H, d); 3.69 (3H, s); 3.63 (3H, s).

Example 179: Preparation of 1-(6-fluoro-1H-indol-3-yl)-2-((3-methoxyphenyl)amino)-2-(6-methoxypyridin-3-yl)ethanone 1-(6-Fluoro-1H-indol-3-yl)-2-((3-methoxyphenyl)amino)-2-(6-methoxypyridin-3-yl)ethanone was prepared according to general procedure L from a mixture of 3-benzyl-5-(2-hydroxyethyl)-4-methylthiazol-3-ium chloride (0.067 g; 0.248 mmol) and triethylamine (0.035 mL; 0.248 mmol) in ethanol (0.4 mL), tert-butyl 6-fluoro-3-formyl-1H-indole-1-carboxylate (0.158 g; 0.600 mmol) and a solution of 3-methoxy-N-((6-methoxypyridin-3-yl)methylene)aniline (0.503 mmol) in ethanol (0.735 mL), heated at 70° C. for 113 h. Purification by flash chromatography on silica gel using a gradient of ethyl acetate (0% to 100%) in heptane followed by purification by preparative TLC using methanol (5%) in dichloromethane as eluent furnished 0.032 g (16%) of the desired compound as a yellow solid. ESI/APCI(+): 406 (M+H); 428 (M+Na). ESI/APCI(−): 404 (M−H).

Example 180: Preparation of 2-(6-fluoropyridin-3-yl)-1-(1H-indol-3-yl)-2-((3-methoxyphenyl)amino)ethanone Step 1: A solution of N-((6-fluoropyridin-3-yl)methylene)-3-methoxyaniline in ethanol was prepared by heating a solution of 6-fluoronicotinaldehyde (0.131 g; 1.047 mmol) and 3-methoxyaniline (0.120 mL; 1.074 mmol) in ethanol (0.5 mL) at 60° C. for 4 h. The formation of the imine was quantitative and the solution was used without further purification. ESI/APCI(+): 231 (M+H).

Step 2: 2-(6-Fluoropyridin-3-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.160 g; 0.593 mmol) and triethylamine (0.100 mL; 0.717 mmol) in ethanol (0.5 mL), tert-butyl 3-formyl-1H-indole-1-carboxylate (0.281 g; 1.146 mmol) and a solution of N-((6-fluoropyridin-3-yl)methylene)-3-methoxyaniline (1.047 mmol) in ethanol (1.5 mL), heated at 60° C. for 16 h. Purification by flash chromatography on silica gel using a gradient of ethyl acetate (0% to 50%) in heptane followed by purification by preparative HPLC (XBridge column; method 1) furnished 0.123 g (31%) of the desired compound as a yellow solid. ESI/APCI(+): 376 (M+H). ESI/APCI(−): 374 (M−H).

Example 181: Preparation of 1-(1H-indol-3-yl)-2-((3-methoxyphenyl)amino)-2-(2-methoxypyridin-3-yl)ethanone Step 1: A solution of 3-methoxy-N-((2-methoxypyridin-3-yl)methylene)aniline in ethanol was prepared by heating a solution of 2-methoxynicotinaldehyde (0.141 g; 1.028 mmol) and 3-methoxyaniline (0.122 g; 1.088 mmol) in ethanol (0.5 mL) at 60° C. for 18 h. The formation of the imine was quantitative and the solution was used without further purification. ESI/APCI(+): 243 (M+H).

Step 2: 1-(1H-Indol-3-yl)-2-((3-methoxyphenyl)amino)-2-(2-methoxypyridin-3-yl)ethanone was prepared according to general procedure K from a mixture of 3-benzyl-5-(2-hydroxyethyl)-4-methylthiazol-3-ium chloride (0.156 g; 0.578 mmol) and triethylamine (0.100 mL; 0.717 mmol) in ethanol (0.5 mL), tert-butyl 3-formyl-1H-indole-1-carboxylate (0.294 g; 1.199 mmol) and a solution of 3-methoxy-N-((2-methoxypyridin-3-yl)methylene)aniline (1.028 mmol) in ethanol (1.5 mL), heated at 60° C. for 16 h. Purification by flash chromatography on silica gel using a gradient of ethyl acetate (0% to 50%) in heptane followed by purification by solid phase extraction on C18-reversed phase column using a gradient of acetonitrile (30% to 100%) in water furnished 0.105 g (26%) of the desired compound as a yellow foam. ESI/APCI(+): 388 (M+H). ESI/APCI(−): 386 (M−H).

Example 182: Preparation of 2-((3-methoxyphenyl)amino)-1-(1-(2-morpholinoethyl)-1H-indol-3-yl)-2-phenylethanone Step 1: To a solution of 2-chloro-1-(1H-indol-3-yl)-2-phenylethanone (0.200 g; 0.741 mmol) in DMF (5 mL) cooled to 0° C. was added sodium hydride (60% dispersion in mineral oil; 0.053 g; 1.333 mmol). The reaction mixture was stirred at room temperature for 0.5 h. 4-(2-bromoethyl)morpholine (0.287 g; 1.479 mmol) and DMAP (0.005 g; 0.037 mmol) were added and the reaction mixture was stirred at room temperature overnight. Water was added and the reaction mixture was extracted with ethyl acetate. The organic phase was washed with brine, dried over sodium sulfate, filtered and concentrated under reduced pressure. Purification by flash chromatography on silica gel using a gradient of methanol (1% to 5%) in dichloromethane furnished 0.198 g (70%) of 2-chloro-1-(1-(2-morpholinoethyl)-1H-indol-3-yl)-2-phenylethanone as an oil. ESI/APCI(+): 383 (M+H); 405 (M+Na). ESI/APCI(−): 381 (M−H).

Step 2: 2-((3-Methoxyphenyl)amino)-1-(1-(2-morpholinoethyl)-1H-indol-3-yl)-2-phenylethanone was prepared according to general procedure E from 2-chloro-1-(1-(2-morpholinoethyl)-1H-indol-3-yl)-2-phenylethanone (0.130 g; 0.261 mmol) and m-anisidine (0.402 mL; 3.591 mmol) in acetonitrile (1 mL), irradiated in a microwave oven at 150° C. for 15 min. The residue was purified by flash chromatography on silica gel using a gradient of methanol (1% to 10%) in dichloromethane. Further purification by flash chromatography on silica gel using a gradient of ethyl acetate (5% to 50%) in dichloromethane followed by purification by preparative HPLC (XBridge column; method 4) furnished 0.019 g (15%) of the desired product as a beige solid. ESI/APCI(+): 470 (M+H). ESI/APCI(−): 468 (M−H). $^1$H NMR (DMSO-d$_6$) δ 8.95 (1H, s); 8.17 (1H, d); 7.57 (3H, m); 7.15-7.35 (5H, m); 6.92 (1H, t); 6.32 (3H, m); 6.11 (1H, d); 6.02 (1H, d); 4.40 (2H, m); 3.62 (3H, s); 3.52 (4H, m); 3.37 (2H, m); 2.74 (2H, m); 2.40 (3H, m).

Example 183: Preparation of 2-((3-methoxyphenyl)amino)-2-phenyl-1-(1-(piperidin-4-ylsulfonyl)-1H-indol-3-yl)ethanone Step 1: To a solution of 2-chloro-1-(1H-indol-3-yl)-2-phenylethanone (0.200 g; 0.741 mmol) in DMF (5 mL) cooled to 0° C. was added sodium hydride (60% dispersion in mineral oil; 0.053 g; 1.333 mmol). The reaction mixture was stirred at room temperature for 0.5 h. Benzyl 4-(chlorosulfonyl)piperidine-1-carboxylate (0.471 g; 1.482 mmol) and DMAP (0.005 g; 0.037 mmol) were added and the reaction mixture was stirred at room temperature for 3 h. Water was added and the mixture was extracted with ethyl acetate. The organic phase was washed with brine, dried over sodium sulfate, filtered and concentrated under reduced pressure. Purification by flash chromatography on silica gel using a gradient of ethyl acetate (5% to 50%) in heptane furnished 0.320 g (78%) of benzyl 4-((3-(2-chloro-2-phenylacetyl)-1H-indol-1-yl)sulfonyl)piperidine-1-carboxylate as a white solid. ESI/APCI(+): 551 (M+H); 573 (M+Na). ESI/APCI(−): 549 (M−H).

Step 2: Benzyl 4-((3-(2-((3-methoxyphenyl)amino)-2-phenylacetyl)-1H-indol-1-yl)sulfonyl)piperidine-1-carboxylate was prepared according to general procedure E from benzyl 4-((3-(2-chloro-2-phenylacetyl)-1H-indol-1-yl)sulfonyl)piperidine-1-carboxylate (0.150 g; 0.272 mmol) and m-anisidine (0.304 mL; 2.724 mmol) in acetonitrile (1 mL), irradiated in a microwave oven at 150° C. for 15 min. Purification by flash chromatography on silica gel using a gradient of ethyl acetate (2% to 40%) in heptane furnished 0.068 g (39%) of the desired compound as a beige solid. ESI/APCI(+): 638 (M+H); 660 (M+Na). ESI/APCI(−): 636 (M−H). Step 3: A mixture of benzyl 4-((3-(2-((3-methoxyphenyl)amino)-2-phenylacetyl)-1H-indol-1-yl)sulfonyl)piperidine-1-carboxylate (0.135 g; 0.212 mmol), ammonium formate (0.047 g; 0.741 mmol) and palladium hydroxide (0.003 g; 0.021 mmol) in a mixture of methanol (1 mL) and THF (0.5 mL) was irradiated in a microwave oven at 100° C. for 10 min. The mixture was filtered through a pad of celite and the filtrate was concentrated under reduced pressure. Purification by flash chromatography on silica gel using a gradient of methanol (1% to 10%) in dichloromethane followed by purification by preparative HPLC (XBridge column; method 4) furnished 0.009 g (8%) of 2-((3-methoxyphenyl)amino)-2-phenyl-1-(1-(piperidin-4-ylsulfonyl)-1H-indol-3-yl)ethanone as a beige solid. ESI/APCI(+): 504 (M+H). ESI/APCI(−): 502 (M−H).

Example 184: Preparation of 4-((2-(1H-indol-3-yl)-2-oxo-1-phenylethyl)amino)-2-methoxybenzonitrile Step 1: 4-(Benzylideneamino)-2-methoxybenzonitrile was prepared quantitatively according to general procedure I from benzaldehyde (0.102 mL; 1.004 mmol) and 4-amino-2-methoxybenzonitrile (0.148 g; 0.999 mmol).

Step 2: 4-((2-(1H-Indol-3-yl)-2-oxo-1-phenylethyl)amino)-2-methoxybenzonitrile was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (2 mL), tert-butyl 3-formyl-1H-indole-1-carboxylate (0.245 g; 1.000 mmol) and a solution of 4-(benzylideneamino)-2-methoxybenzonitrile (0.999 mmol) in ethanol (1 mL), heated at 70° C. overnight. The residue was purified by flash chromatography on silica gel using a gradient of ethyl acetate (15% to 70%) in heptane. Further purification by flash chromatography on silica gel using a gradient of dichloromethane (30% to 100%) in heptane followed by purification by flash chromatography on silica gel using a gradient of ethyl acetate (1% to 10%) in dichloromethane furnished 0.100 g (26%) of the desired compound as a beige solid. ESI/APCI(+): 382 (M+H). ESI/APCI(−): 380 (M−H). $^1$H NMR (DMSO-d$_6$) δ 12.25 (1H, brs); 8.89 (1H, s); 8.17 (1H, d); 7.65 (2H, d); 7.46 (2H, t); 7.12-7.38 (6H, m); 6.63 (1H, br s); 6.49 (1H, d); 6.24 (1H, d); 3.76 (3H, s).

Example 185: Preparation of 1-(5-(hydroxymethyl)-1H-indol-3-yl)-2-((3-methoxyphenyl)amino)-2-phenylethanone Step 1: To a solution of (1H-indol-5-yl)methanol (0.253 g; 1.719 mmol), triethylamine (0.479 mL; 3.437 mmol) and DMAP (0.021 g; 0.172 mmol) in dichloromethane (4 mL) was added TBDMSCl (0.285 g; 1.891 mmol) and the reaction mixture was stirred at room temperature for 2 h. The reaction mixture was concentrated under reduced pressure and the residue was partitioned between ethyl acetate and a saturated sodium bicarbonate solution. The layers were separated and the aqueous layer was extracted with ethyl acetate. The organic phases were combined, washed with a 0.5N hydrochloric acid solution and brine, dried over sodium sulfate, filtered and concentrated under reduced pressure to furnish 0.370 g (82%) of 5-(((tert-butyldimethylsilyl)oxy)methyl)-1H-indole. $^1$H NMR (DMSO-d$_6$) δ 10.95 (1H, br s); 7.39 (1H, s); 7.20-7.31 (2H, m); 6.96 (1H, d); 6.32 (1H, s); 4.67 (2H, s); 3.27 (6H, s); 0.83 (9H, s).

Step 2: 1-(5-(((tert-Butyldimethylsilyl)oxy)methyl)-1H-indol-3-yl)-2-chloro-2-phenylethanone was prepared according to general procedure A from α-chlorophenylacetyl chloride (0.208 mL; 1.415 mmol), 5-(((tert-butyldimethylsilyl)oxy)methyl)-1H-indole (0.370 g; 1.415 mmol) and pyridine (0.114 mL; 1.415 mmol) in toluene (4 mL) at 55° C. The solid obtained after precipitation was recrystallized from acetonitrile to afford 0.183 g (31%) of the desired compound as a pink solid. ESI/APCI(−): 412, 414 (M−H).

Step 3: 1-(5-(Hydroxymethyl)-1H-indol-3-yl)-2-((3-methoxyphenyl)amino)-2-phenylethanone was prepared according to general procedure E from 1-(5-(((tert-butyldimethylsilyl)oxy)methyl)-1H-indol-3-yl)-2-chloro-2-phenylethanone (0.100 g; 0.242 mmol) and 3-methoxyaniline (0.541 mL; 4.832 mmol) in acetonitrile (1 mL), irradiated in a microwave oven at 150° C. for 30 min. Purification by flash chromatography on silica gel using a gradient of ethyl acetate (0% to 100%) in heptane followed by purification by preparative HPLC (XBridge column; method 5) furnished 0.002 g (2%) of the desired product. ESI/APCI(+): 387 (M+H). ESI/APCI(−): 385 (M−H).

Example 186: Preparation of tert-butyl 3-(2-((3-methoxyphenyl)amino)-2-phenylacetyl)-1-methyl-6,7-dihydro-1H-pyrazolo[4,3-c]pyridine-5(4H)-carboxylate tert-Butyl 3-(2-((3-methoxyphenyl)amino)-2-phenylacetyl)-1-methyl-6,7-dihydro-1H-pyrazolo[4,3-c]pyridine-5(4H)-carboxylate was prepared according to general procedure L from a mixture of 3-benzyl-5-(2-hydroxyethyl)-4-methylthiazol-3-ium chloride (0.117 g; 0.433 mmol) and triethylamine (0.061 mL; 0.433 mmol) in ethanol (1 mL), tert-butyl 3-formyl-1-methyl-6,7-dihydro-1H-pyrazolo[4,3-c]pyridine-5(4H)-carboxylate (0.230 g; 0.867 mmol) and a solution of N-benzylidene-3-methoxyaniline (0.867 mmol) in ethanol (1 mL), heated at 70° C. for 24 h. Purification by flash chromatography on silica gel using a gradient of ethyl acetate (0% to 80%) in heptane furnished 0.235 g (57%) of the desired compound. ESI/APCI(+): 477 (M+H).

Example 187: Preparation of 2-((3-methoxyphenyl)amino)-1-(1-methyl-4,5,6,7-tetrahydro-1H-pyrazolo[4,3-c]pyridin-3-yl)-2-phenylethanone hydrochloride To a solution of tert-butyl 3-(2-((3-methoxyphenyl)amino)-2-phenylacetyl)-1-methyl-6,7-dihydro-1H-pyrazolo[4,3-c]pyridine-5(4H)-carboxylate (0.235 g; 0.493 mmol) in dioxane (2 mL) cooled to 0° C. was added dropwise a 4N hydrogen chloride solution in dioxane (5.000 mL; 20.00 mmol). The reaction mixture was allowed to warm to room temperature and was stirred at room temperature for 30 min. The reaction mixture was concentrated under reduced pressure. The residue was triturated with diethylether and the resulting solid was filtered and dried under reduced pressure over phosphorus(V) oxide to afford 0.104 (48%) of 2-((3-methoxyphenyl)amino)-1-(1-methyl-4,5,6,7-tetrahydro-1H-pyrazolo[4,3-c]pyridin-3-yl)-2-phenylethanone hydrochloride as a green solid. ESI/APCI(+): 377 (M+H). ESI/APCI(−): 375 (M−H).

Example 188: Preparation of 1-(7-methoxy-1H-indol-3-yl)-2-((3-methoxyphenyl)amino)-2-phenylethanone Step 1: To a solution of DMF (0.600 mL; 7.749 mmol) in dichloromethane (2 mL) cooled to −15° C. was added dropwise phosphorus oxychloride (0.350 mL; 3.755 mmol). After 15 min at −15° C., a solution of 7-methoxy-1H-indole (0.498 g; 3.384 mmol) in dichloromethane (1.5 mL) was added. The reaction mixture was allowed to warm to room temperature and was stirred at room temperature overnight. The reaction mixture was basified with a 1M sodium hydroxide solution and extracted with dichloromethane. The organic phase was dried over magnesium sulfate, filtered and concentrated under reduced pressure. Purification by flash chromatography on silica gel using ethyl acetate (50%) in heptane as eluent furnished 0.346 g (58%) of 7-methoxy-1H-indole-3-carbaldehyde as a green solid. $^1$H NMR (DMSO-$d_6$) δ 12.31 (1H, br s); 9.92 (1H, s); 8.17 (1H, s); 7.65 (1H, d); 7.14 (1H, t); 6.84 (1H, d); 3.94 (3H, s).

tert-Butyl 3-formyl-7-methoxy-1H-indole-1-carboxylate was prepared according to general procedure F from 7-methoxy-1H-indole-3-carbaldehyde (0.346 g; 1.975 mmol), di-tert-butyl dicarboxylate (0.552 g; 2.529 mmol) and DMAP (0.032 g; 0.262 mmol) in acetonitrile (6 mL) to furnish 0.505 g (93%) of the desired product as an orange solid. ESI/APCI(+): 276 (M+H). $^1$H NMR (DMSO-$d_6$) δ 10.03 (1H, s); 8.59 (1H, s); 7.74 (1H, d); 7.73 (1H, t); 7.05 (1H, d); 3.92 (3H, s); 1.61 (9H, s).

Step 3: 1-(7-Methoxy-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.161 g; 0.597 mmol) and triethylamine (0.100 mL; 0.717 mmol) in ethanol, tert-butyl 3-formyl-7-methoxy-1H-indole-1-carboxylate (0.297 g; 1.079 mmol) and a solution of N-benzylidene-3-methoxyaniline (1.037 mmol) in ethanol (1.5 mL), heated at 60° C. for 16 h. Purification by flash chromatography on silica gel using a gradient of ethyl acetate (0% to 40%) in heptane followed by purification by preparative HPLC (XBridge column; method 2) furnished 0.018 g (4%) of the desired compound as a yellow solid. ESI/APCI(+): 387 (M+H). ESI/APCI(−): 385 (M−H).

Example 189: Preparation of 1-(1,5-dimethyl-4,5,6,7-tetrahydro-1H-pyrazolo[4,3-c]pyridin-3-yl)-2-((3-methoxyphenyl)amino)-2-phenylethanone To a stirred solution of 2-((3-methoxyphenyl)amino)-1-(1-methyl-4,5,6,7-tetrahydro-1H-pyrazolo[4,3-c]pyridin-3-yl)-2-phenylethanone hydrochloride (0.086 g; 0.208 mmol) in THF (2 mL) were added triethylamine (0.087 mL; 0.625 mmol), formaldehyde (0.047 mL; 0.625 mmol), sodium triacetoxyborohydride (0.132 g; 0.625 mmol) and a drop of acetic acid. The reaction mixture was stirred at room temperature for 16 h and was concentrated under reduced pressure. The residue was dissolved in dichloromethane and a mixture of methanol and a 25% ammonium hydroxide solution (9/1) was added. The precipitate was filtered and washed with dichloromethane. The filtrate was concentrated under reduced pressure. Purification by flash chromatography on silica gel using a gradient of methanol/25% ammonium hydroxide (911) (0% to 10%) in dichloromethane furnished 0.030 g (35%) of 1-(1,5-dimethyl-4,5,6,7-tetrahydro-1H-pyrazolo[4,3-c]pyridin-3-yl)-2-((3-methoxyphenyl)amino)-2-phenylethanone. ESI/APCI(+): 391 (M+H). $^1$H NMR (DMSO-$d_6$) δ 7.51 (2H, d); 7.27-7.36 (2H, m); 7.18-7.26 (1H, m); 6.92 (1H, t); 6.33-6.44 (1H, m); 6.18-6.32 (3H, m); 6.12 (1H, d); 3.84 (3H, s); 3.61 (3H, s); 3.37-3.51 (2H, m); 2.53-2.75 (4H, m); 2.32 (3H, s).

Example 190: Preparation of 2-((3-methoxyphenyl)amino)-1-(7-methyl-1H-indol-3-yl)-2-phenylethanone Step 1: tert-Butyl 3-formyl-7-methyl-1H-indole-1-carboxylate was prepared according to general procedure F from 7-methyl-1H-indole-3-carbaldehyde (0.500 g; 3.141 mmol), di-tert-butyl dicarboxylate (0.910 g; 4.170 mmol) and DMAP (0.057 g; 0.467 mmol) in acetonitrile (10 mL) to furnish 0.790 g (97%) of the desired product as a beige solid. ESI/APCI(+): 260 (M+H). $^1$H NMR (DMSO-$d_6$) δ 10.05 (1H, s); 8.65 (1H, s); 8.03 (1H, d); 7.28 (2H, m); 2.54 (3H, s); 1.64 (9H, s).

Step 2: 2-((3-Methoxyphenyl)amino)-1-(7-methyl-1H-indol-3-yl)-2-phenylethanone was prepared according to general procedure K from a mixture of 3-benzyl-5-(2-hydroxyethyl)-4-methylthiazol-3-ium chloride (0.145 g; 0.537 mmol) and triethylamine (0.100 mL; 0.717 mmol) in ethanol (0.5 mL), tert-butyl 3-formyl-7-methyl-1H-indole-1-carboxylate (0.280 g; 1.080 mmol) and a solution of N-benzylidene-3-methoxyaniline (0.989 mmol) in ethanol (1.5 mL), heated at 60° C. for 16 h. Purification by flash chromatography on silica gel using a gradient of ethyl acetate (20% to 50%) in heptane followed by precipitation from diethyl ether furnished 0.019 g (5%) of the desired compound as a yellow solid. ESI/APCI(+): 371 (M+H). ESI/APCI(−): 369 (M−H).

Example 191: Preparation of 2-((3-methoxyphenyl)amino)-1-(6-methyl-1H-pyrrolo[2,3-b]pyridin-3-yl)-2-phenylethanone Step 1: tert-Butyl 3-formyl-6-methyl-1H-pyrrolo[2,3-b]pyridine-1-carboxylate was prepared according to general procedure F from 6-methyl-1H-pyrrolo[2,3-b]pyridine-3-carbaldehyde (0.481 g; 3.003 mmol), di-tert-butyl dicarbonate (0.786 g; 3.601 mmol) and DMAP (0.037 g; 0.300 mmol) in acetonitrile (7.5 mL) to afford 0.753 g (96%) of the desired compound.

Step 2: 2-((3-Methoxyphenyl)amino)-1-(6-methyl-1H-pyrrolo[2,3-b]pyridin-3-yl)-2-phenylethanone was prepared according to general procedure L from a mixture of 3-benzyl-5-(2-hydroxyethyl)-4-methylthiazol-3-ium chloride (0.135 g; 0.556 mmol) and triethylamine (0.075 mL; 0.541 mmol) in ethanol (1 mL), tert-butyl 3-formyl-6-methyl-1H-pyrrolo[2,3-b]pyridine-1-carboxylate (0.260 g; 0.999 mmol) and a solution of N-benzylidene-3-methoxyaniline (0.999 mmol) in ethanol (1 mL), heated at 70° C. for 2 days. The residue was purified by flash chromatography on silica gel using a gradient of ethyl acetate (0% to 100%) in heptane. Further purification by flash chromatography on silica gel using ethyl acetate (55%) in heptane as eluent furnished 0.058 g (15%) of the desired compound as a white solid. ESI/APCI(+): 372 (M+H). ESI/APCI(−): 370 (M−H).

Example 192: Preparation of 1-(1H-indol-3-yl)-2-((3-methoxyphenyl)amino)-2-(6-methylpyridin-3-yl)ethanone Step 1: A solution of 3-methoxy-N-((6-methylpyridin-3-yl)methylene)aniline in ethanol was prepared by heating a solution of 6-methylnicotinaldehyde (0.126 g; 1.023 mmol) and 3-methoxyaniline (0.125 g; 1.131 mmol) in ethanol (0.5 mL) at 60° C. for 18 h. The formation of the imine was quantitative and the solution was used without further purification. ESI/APCI(+): 227 (M+H). ESI/APCI(−): 225 (M−H).

Step 2: 1-(1H-Indol-3-yl)-2-((3-methoxyphenyl)amino)-2-(6-methylpyridin-3-yl)ethanone was prepared according to general procedure K from a mixture of 3-benzyl-5-(2-hydroxyethyl)-4-methylthiazol-3-ium chloride (0.135 g; 0.500 mmol) and triethylamine (0.400 mL; 2.886 mmol) in ethanol (0.5 mL), tert-butyl 3-formyl-1H-indole-1-carboxylate (0.270 g; 1.101 mmol) and a solution of 3-methoxy-N-((6-methylpyridin-3-yl)methylene)aniline (1.023 mmol) in ethanol (1.5 mL), heated at 60° C. for 48 h. Purification by flash chromatography on silica gel using a gradient of ethyl acetate (20% to 70%) in heptane followed by precipitation from methanol furnished 0.021 g (6%) of the desired compound as a beige solid. ESI/APCI(+): 372 (M+H). ESI/APCI(−): 370 (M−H).

Example 193: Preparation of 1-(5-fluoro-1H-pyrrolo[2,3-b]pyridin-3-yl)-2-((3-methoxyphenyl)amino)-2-phenylethanone Step 1: To a solution of 5-fluoro-1H-pyrrolo[2,3-b]pyridine (0.545 g; 4.004 mmol) in a mixture of 1,2-dichloroethane (10 mL) and nitromethane (10 ml) cooled to 0° C. were added under an argon atmosphere dichloro(methoxy)methane (1.825 mL; 20.00 mmol) and aluminum trichloride (1.600 g; 12.00 mmol). The reaction mixture was stirred for 1 h. The reaction was quenched by the addition of water and a saturated sodium bicarbonate solution. The reaction mixture was extracted with a mixture of dichloromethane and ethanol (9/1). The organic layer was washed with brine, dried over magnesium sulfate, filtered and concentrated under reduced pressure to afford 0.503 g (77%) of 5-fluoro-1H-pyrrolo[2,3-b]pyridine-3-carbaldehyde as a brown solid. ESI/APCI(−): 163 (M−H). $^1$H NMR (DMSO-d$_6$) δ 12.88 (1H, br s); 9.94 (1H, s); 8.57 (1H, d); 8.37-8.42 (1H, m); 8.40 (1H, br s); 8.18 (1H, dd).

Step 2: tert-Butyl 5-fluoro-3-formyl-1H-pyrrolo[2,3-b]pyridine-1-carboxylate was prepared according to general procedure F from 5-fluoro-1H-pyrrolo[2,3-b]pyridine-3-carbaldehyde (0.497 g; 3.028 mmol), di-tert-butyl dicarbonate (0.793 g; 3.633 mmol) and DMAP (0.037 g; 0.303 mmol) in acetonitrile (7.5 mL) to afford 0.687 g (86%) of the desired compound as a brown solid. $^1$H NMR (DMSO-d$_6$) δ10.06 (1H, s); 8.89 (1H, s); 8.54 (1H, d); 8.25 (1H, dd); 1.66 (9H, s).

Step 3: 1-(5-Fluoro-1H-pyrrolo[2,3-b]pyridin-3-yl)-2-((3-methoxyphenyl)amino)-2-phenylethanone was prepared according to general procedure L from a mixture of 3-benzyl-5-(2-hydroxyethyl)-4-methylthiazol-3-ium chloride (0.135 g; 0.556 mmol) and triethylamine (0.070 mL; 0.505 mmol) in ethanol (1 mL), tert-butyl 5-fluoro-3-formyl-1H-pyrrolo[2,3-b]pyridine-1-carboxylate (0.264 g; 0.999 mmol) and a solution of N-benzylidene-3-methoxyaniline (0.998 mmol) in ethanol (1 mL), heated at 70° C. for 2 days. Purification by flash chromatography on silica gel using a gradient of ethyl acetate (0% to 80%) in heptane followed by precipitation from diethyl ether furnished 0.034 g (9%) of the desired compound as a white solid. ESI/APCI(+): 376 (M+H). ESI/APCI(−): 374 (M+H).

Example 194: Preparation of 1-(5-((dimethylamino)methyl)-1H-indol-3-yl)-2-((3-methoxyphenyl)amino)-2-phenylethanone Step 1: A solution of 1H-indole-5-carbaldehyde (1.000 g; 6.889 mmol), a 2M dimethylamine solution in THF (5.170 mL; 10.34 mmol), acetic acid (2.370 mL; 41.40 mmol) and sodium triacetoxyborohydride (3.650 g; 17.22 mmol) in THF (20 mL) was heated to 75° C. for 3 h. The reaction mixture was filtered and the filtrate was concentrated under reduced pressure. Purification by flash chromatography on silica gel using a gradient of methanol/25% ammonium hydroxide (9/1) (0% to 12%) in dichloromethane furnished 0.657 g (55%) of 1-(1H-indol-5-yl)-N,N-dimethylmethanamine. ESI/APCI(+): 175 (M+H).

Step 2: To DMF (2 mL) cooled to 0° C. was added dropwise phosphorus oxychloride (0.520 mL; 5.579 mmol) and the reaction mixture was stirred at 0° C. for 30 min. A solution of 1-(1H-indol-5-yl)-N,N-dimethylmethanamine (0.486 g; 2.789 mmol) in DMF (5 mL) was added dropwise to the cold Vilsmeier reagent and the reaction mixture was stirred at room temperature for 3 h. The suspension was poured into an ice/water mixture and neutralized with a 1N sodium hydroxide solution. The aqueous layer was extracted with a mixture of dichloromethane and ethanol (9/1) and with ethyl acetate. The organic phases were combined and concentrated under reduced pressure. Purification by flash chromatography on silica gel using a gradient of methanol (0% to 10%) in dichloromethane furnished 0.365 g (65%) of 5-((dimethylamino)methyl)-1H-indole-3-carbaldehyde. ESI/APCI(+): 203 (M+H).

Step 3: tert-Butyl 5-((dimethylamino)methyl)-3-formyl-1H-indole-1-carboxylate was prepared according to general procedure F from 5-((dimethylamino)methyl)-1H-indole-3-carbaldehyde (0.365 g; 1.805 mmol), di-tert-butyl dicarbonate (0.473 g; 2.166 mmol) and DMAP (0.022 g; 0.180 mmol) in acetonitrile (5 mL) to afford 0.112 g (21%) of the desired compound. ESI/APCI(+): 303 (M+H).

Step 5: 1-(5-((Dimethylamino)methyl)-1H-indol-3-yl)-2-((3-methoxyphenyl)amino)-2-phenylethanone was prepared according to general procedure L from a mixture of 3-benzyl-5-(2-hydroxyethyl)-4-methylthiazol-3-ium chloride (0.050 g; 0.185 mmol) and triethylamine (0.026 mL; 0.188 mmol) in ethanol (0.5 mL), tert-butyl 5-((dimethylamino)methyl)-3-formyl-1H-indole-1-carboxylate (0.112 g; 0.370 mmol) and a solution of N-benzylidene-3-methoxyaniline (0.369 mmol) in ethanol (0.5 mL), heated at 70° C. for 2 days. The residue was purified by flash chromatography on silica gel using a gradient of methanol/25% ammonium hydroxide (9/1) (0% to 10%) in dichloromethane followed by purification by preparative TLC using methanol (10%) in dichloromethane as eluent. Further purification by preparative HPLC (XBridge column; method 5) followed by purification by preparative TLC using methanol/25% ammonium hydroxide (911) (10%) in dichloromethane as eluent furnished 0.001 g (1%) of the desired compound. ESI/APCI (+): 414 (M+H). ESI/APCI(−): 412 (M−H).

Example 195: Preparation of 2-((3-methoxyphenyl)amino)-1-(5-(methylsulfonyl)-1H-indol-3-yl)-2-phenylethanone Step 1: To a solution of 5-(methylsulfonyl)indoline (0.450 g; 2.281 mmol) in dioxane (10 mL) was added 2,3-dichloro-5,6-dicyanobenzoquinone (0.777 g; 3.423 mmol). The reaction mixture was heated at 80° C. for 2 h. After cooling to room temperature, the reaction mixture was filtered. The filtrate was concentrated under reduced pressure. The residue was purified by flash chromatography on silica gel using a gradient of ethyl acetate (5% to 50%) in dichloromethane. Further purification by flash chromatography on silica gel using a gradient of ethyl acetate (15% to 70%) in heptane furnished 0.210 g (47%) of 5-methylsulfonyl-1H-indole as a white solid. ESI/APCI(+): 196 (M+H); 218 (M+Na). ESI/APCI(−): 194 (M−H).

Step 2: 5-(Methylsulfonyl)-1H-indole-3-carbaldehyde was prepared according to general procedure R from a solution of oxalyl chloride (0.107 mL; 1.231 mmol) in dichloromethane (8 mL), DMF (0.095 mL; 1.228 mmol) and 5-(methylsulfonyl)-1H-indole (0.200 g; 1.024 mmol). Purification by flash chromatography on silica gel using a gradient of ethyl acetate (15% to 70%) in dichloromethane furnished 0.155 g (84%) of the desired compound as a white solid. ESI/APCI(+): 224 (M+H); 246 (M+Na). ESI/APCI (−): 222 (M−H).

Step 3: To a solution of 5-(methylsulfonyl)-1H-indole-3-carbaldehyde (0.155 g; 0.694 mmol) in dichloromethane (10 mL) were added di-tert-butyl dicarbonate (0.182 g; 0.831 mmol), DMAP (0.017 g; 0.139 mmol) and triethylamine (0.116 mL; 0.833 mmol). After stirring for 15 min, the reaction mixture was diluted with a saturated ammonium chloride solution and extracted with dichloromethane. The organic phase was concentrated under reduced pressure. Purification by flash chromatography on silica gel using a gradient of ethyl acetate (15% to 100%) in heptane furnished 0.198 g (88%) of tert-butyl 3-formyl-5-(methylsulfonyl)-1H-indole-1-carboxylate as a white solid. ESI/APCI(+): 324 (M+H); 346 (M+Na).

Step 4: 2-((3-Methoxyphenyl)amino)-1-(5-(methylsulfonyl)-1H-indol-3-yl)-2-phenylethanone was prepared according to general method K from a mixture of 3-benzyl-5-(2-hydroxyethyl)-4-methylthiazolium chloride (0.093 g; 0.345 mmol) and triethylamine (0.042 mL; 0.313 mmol) in ethanol (2 mL), tert-butyl 3-formyl-5-(methylsulfonyl)-1H-indole-1-carboxylate (0.198 g; 0.612 mmol) and a solution of N-benzylidene-3-methoxyaniline (0.610 mmol) in ethanol (1 mL), heated at 70° C. overnight. Purification by flash chromatography on silica gel using a gradient of ethyl acetate (5% to 50%) in dichloromethane followed by precipitation from dichloromethane furnished 0.070 g (26%) of the desired compound as a yellowish solid. ESI/APCI(+): 435 (M+H). ESI/APCI(−): 433 (M−H). $^1$H NMR (DMSO-$d_6$) δ 9.11 (1H, s); 8.73 (1H, s); 7.70-7.81 (2H, m); 7.67 (2H, d); 7.27-7.38 (2H, m); 7.23 (1H, m); 6.95 (1H, t); 6.35-6.49 (3H, m); 6.16 (2H, m); 3.65 (3H, s); 3.17 (3H, s).

Example 196: Preparation of 1-(4-fluoro-1H-indol-3-yl)-2-((3-methoxy-phenyl)amino)-2-phenylethanone Step 1: To a solution DMF (0.670 mL; 8.653 mmol) in dichloromethane (2.5 mL) cooled to −15° C. was added dropwise phosphorus oxychloride (0.400 mL; 4.291 mmol). After 15 min at −15° C., a solution of 4-fluoro-1H-indole (0.500 g; 3.700 mmol) in dichloromethane (2 mL) was added. The reaction mixture was allowed to warm to room temperature and was stirred at room temperature overnight. A saturated sodium bicarbonate solution was added and the reaction mixture was extracted with dichloromethane. The organic phase was dried over magnesium sulfate, filtered and concentrated under reduced pressure. Purification by flash chromatography on silica gel using ethyl acetate (50%) in heptane as eluent furnished 0.144 g (24%) of 4-fluoro-1H-indole-3-carbaldehyde as a beige solid. ESI/APCI(+): 164. ESI/APCI(−): 162 (M−H).

Step 2: tert-Butyl 4-fluoro-3-formyl-1H-indole-1-carboxylate was prepared according to general procedure F from 4-fluoro-1H-indole-3-carbaldehyde (0.164 g; 1.005 mmol), di-tert-butyl dicarboxylate (0.301 g; 1.379 mmol) and DMAP (0.032 g; 0.261 mmol) in acetonitrile (3 mL) to furnish 0.230 g (87%) of the desired product as a beige solid. $^1$H NMR (DMSO-$d_6$) δ 10.08 (1H, s); 8.59 (1H, s); 8.00 (1H, d); 7.46 (1H, dt); 7.22 (1H, t); 1.66 (9H, s).

Step 3: 1-(4-Fluoro-1H-indol-3-yl)-2-((3-methoxyphenyl)amino)-2-phenylethanone was prepared according to general procedure L from a mixture of 3-benzyl-5-(2-hydroxyethyl)-4-methylthiazol-3-ium chloride (0.110 g; 0.408 mmol) and triethylamine (0.100 mL; 0.717 mmol) in ethanol (0.5 mL), tert-butyl 4-fluoro-3-formyl-1H-indole-1-carboxylate (0.230 g; 0.874 mmol) and a solution of N-benzylidene-3-methoxyaniline (0.809 mmol) in ethanol (1.5 mL), heated at 60° C. for 72 h. Purification by flash chromatography on silica gel using a gradient of ethyl acetate (0% to 50%) in heptane followed by purification by preparative HPLC (XBridge column; method 2) furnished 0.021 g (7%) of the desired compound as a beige solid. ESI/APCI(+): 375 (M+H). ESI/APCI(−): 373 (M−H).

Example 197: Preparation of 1-(4-methoxy-1H-indol-3-yl)-2-((3-methoxyphenyl)amino)-2-phenylethanone Step 1: tert-Butyl 3-formyl-4-methoxy-1H-indole-1-carboxylate was prepared according to general procedure F from 4-methoxy-1H-indole-3-carbaldehyde (0.400 g; 2.283 mmol), di-tert-butyl dicarboxylate (0.600 g; 2.749 mmol) and DMAP (0.030 g; 0.246 mmol) in acetonitrile (7 mL) to furnish 0.537 g (85%) of the desired product as a beige solid. APCI/ESCI(+): 276 (M+H). $^1$H NMR (DMSO-d$_6$) δ 10.43 (1H, s); 8.19 (1H, s); 7.77 (1H, d); 7.40 (1H, t); 7.00 (1H, d); 3.98 (3H, s); 1.66 (9H, s).

Step 2: 1-(4-Methoxy-1H-indol-3-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.115 g; 0.426 mmol) and triethylamine (0.085 mL; 0.610 mmol) in ethanol (0.5 mL), tert-butyl 3-formyl-4-methoxy-1H-indole-1-carboxylate (0.252 g; 0.915 mmol) and a solution of N-benzylidene-3-methoxyaniline (0.800 mmol) in ethanol (1.5 mL), heated at 60° C. for 16 h. Purification by flash chromatography on silica gel using a gradient of ethyl acetate (0% to 40%) in heptane followed by purification by preparative HPLC (XBridge column; method 2) furnished 0.031 g (10%) of the desired compound as a yellow foam. ESI/APCI(+): 387 (M+H). ESI/APCI(−): 385 (M−H).

Example 198: Preparation of 2-((3,5-dimethoxyphenyl)amino)-1-(6-methyl-1H-pyrrolo[2,3-b]pyridin-3-yl)-2-phenylethanone Step 1: N-Benzylidene-3,5-dimethoxyaniline was prepared quantitatively according to general procedure I from benzaldehyde (0.101 mL; 0.999 mmol) and 3,5-dimethoxyaniline (0.153 g; 0.999 mmol).

Step 2: 2-((3,5-Dimethoxyphenyl)amino)-1-(6-methyl-1H-pyrrolo[2,3-b]pyridin-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.504 mmol) in ethanol (1 mL), tert-butyl 3-formyl-6-methyl-1H-pyrrolo[2,3-b]pyridine-1-carboxylate (0.260 g; 0.999 mmol) and a solution of N-benzylidene-3,5-dimethoxyaniline (0.999 mmol) in ethanol (1 mL), heated at 70° C. for 4 days. The residue was purified by flash chromatography on silica gel using a gradient of ethyl acetate (0% to 80%) in heptane. Further purification by flash chromatography on silica gel using ethyl acetate (60%) in heptane as eluent followed by purification by preparative HPLC (XBridge column; method 5) furnished 0.016 g (4%) of the desired compound as a white solid. ESI/APCI(+): 402 (M+H). ESI/APCI(−): 400 (M−H).

Example 199: Preparation of 4-(1-((3,5-dimethoxyphenyl)amino)-2-(1H-indol-3-yl)-2-oxoethyl)benzonitrile Step 1: A solution of 4-(((3,5-dimethoxyphenyl)imino)methyl)benzonitrile in ethanol was prepared by heating a solution of 4-formylbenzonitrile (0.132 g; 1.007 mmol) and 3,5-dimethoxyaniline (0.166 g; 1.084 mmol) in ethanol (0.5 mL) at 60° C. for 18 h. The formation of the imine was quantitative and the solution was used without further purification. ESI/APCI(+): 267 (M+H). ESI/APCI(−): 265 (M−H).

Step 2: 4-(1-((3,5-Dimethoxyphenyl)amino)-2-(1H-indol-3-yl)-2-oxoethyl)benzonitrile was prepared according to general procedure K from a mixture of 3-benzyl-5-(2-hydroxyethyl)-4-methylthiazol-3-ium chloride (0.135 g; 0.500 mmol) and triethylamine (0.100 mL; 0.717 mmol) in ethanol (0.5 mL), tert-butyl 3-formyl-1H-indole-1-carboxylate (0.270 g; 1.101 mmol) and a solution of 4-(((3,5-dimethoxyphenyl)imino)methyl)benzonitrile (1.007 mmol) in ethanol (1.5 mL), heated at 60° C. for 16 h. Purification by flash chromatography on silica gel using a gradient of ethyl acetate (10% to 60%) in heptane followed by precipitation from methanol and water furnished 0.102 g (25%) of the desired compound as a yellow powder. ESI/APCI(+): 412 (M+H). ESI/APCI(−): 410 (M−H).

Example 200: Preparation of 2-((3,5-dimethoxyphenyl)amino)-1-(5-fluoro-1H-pyrrolo[2,3-b]pyridin-3-yl)-2-phenylethanone 2-((3,5-Dimethoxyphenyl)amino)-1-(5-fluoro-1H-pyrrolo[2,3-b]pyridin-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 5-fluoro-3-formyl-1H-pyrrolo[2,3-b]pyridine-1-carboxylate (0.264 g; 0.999 mmol) and a solution of N-benzylidene-3,5-dimethoxyaniline (0.999 mmol) in ethanol (1 mL), heated at 70° C. for 2 days. The residue was purified by flash chromatography on silica gel using a gradient of ethyl acetate (0% to 80%) in heptane. Further purification by flash chromatography on silica gel using ethyl acetate (55%) in heptane as eluent followed by purification by preparative HPLC (XBridge column; method 5) furnished 0.003 g (1%) of the desired compound as a white solid. ESI/APCI(+): 406 (M+H). ESI/APCI(−): 404 (M−H).

Example 201: Preparation of 2-((3,5-dimethoxyphenyl)amino)-2-(4-fluorophenyl)-1-(1H-indol-3-yl)ethanone Step 1: A solution of 4-fluorobenzaldehyde (0.124 g; 0.999 mmol) and 3,5-dimethoxyaniline (0.153 g; 0.999 mmol) in ethanol (1 mL) was heated at 60° C. overnight. The reaction mixture was concentrated under reduced pressure to give quantitatively N-(4-fluorobenzylidene)-3,5-dimethoxyaniline which was used in the next step without further purification.

Step 2: 2-((3,5-Dimethoxyphenyl)amino)-2-(4-fluorophenyl)-1-(1H-indol-3-yl)ethanone was prepared according to general procedure K from a mixture of 3-benzyl-5-(2-hydroxyethyl)-4-methylthiazolium chloride (0.135 g; 0.500 mmol) and triethylamine (0.069 mL; 0.498 mmol) in ethanol (2 mL), tert-butyl 3-formyl-1H-indole-1-carboxylate (0.245 g; 0.999 mmol) and a solution of N-(4-fluorobenzylidene)-3,5-dimethoxyaniline (0.999 mmol) in ethanol (1 mL), heated at 70° C. overnight. The residue was purified by flash chromatography on silica gel using a gradient of ethyl acetate (5% to 50%) in heptane. Further purification by flash chromatography on silica gel using a gradient of ethyl acetate (5% to 50%) in heptane followed by purification by preparative HPLC (XBridge column; method 1) furnished 0.008 g (2%) of the desired compound as a beige solid. ESI/APCI(+): 405 (M+H). ESI/APCI(−): 403 (M−H).

Example 202: Preparation of 2-((3,5-dimethoxyphenyl)amino)-1-(1H-indol-3-yl)-2-(pyridin-3-yl)ethanone 2-((3,5-Dimethoxyphenyl)amino)-1-(1H-indol-3-yl)-2-(pyridin-3-yl)ethanone has been prepared according to 2 different procedures described hereunder as method A and method B.

Method A:

Step 1: A solution of 3,5-dimethoxy-N-(pyridin-3-ylmethylene)aniline in ethanol was prepared by heating a solution of nicotinaldehyde (0.107 g; 0.999 mmol) and 3,5-dimethoxyaniline (0.153 g; 0.999 mmol) in ethanol (1.5 mL) at 60° C. for 6 h. The formation of the imine was quantitative and the solution was used without further purification.

Step 2: 2-((3,5-Dimethoxyphenyl)amino)-1-(1H-indol-3-yl)-2-(pyridin-3-yl)ethanone was prepared according to general procedure K from a mixture of 3-benzyl-5-(2-hydroxyethyl)-4-methylthiazolium chloride (0.135 g; 0.500 mmol) and triethylamine (0.069 mL; 0.498 mmol) in ethanol (1.5 mL), tert-butyl 3-formyl-1H-indole-1-carboxylate (0.245 g; 0.999 mmol) and a solution of 3,5-dimethoxy-N-(pyridin-3-ylmethylene)aniline (0.999 mmol) in a mixture of ethanol (1.5 mL) and dichloromethane (1.5 mL), heated at 70° C. for 2 days. Purification by flash chromatography on silica gel using a gradient of ethyl acetate (30% to 100%) in dichloromethane followed by purification by preparative HPLC (XBridge column; method 5) furnished 0.010 g (3%) of the desired compound as a white solid. ESI/APCI(+): 388 (M+H). ESI/APCI(−): 386 (M−H). $^1$H NMR (DMSO-$d_6$) δ12.21 (1H, br s); 8.94 (1H, d); 8.88 (1H, s); 8.40 (1H, d); 8.16 (1H, d); 7.96 (1H, d); 7.48 (1H, d); 7.32 (1H, dd); 7.12-7.27 (2H, m); 6.48 (1H, d); 6.17 (1H, d); 6.06 (2H, s); 5.74 (1H, s); 3.62 (6H, s).

Method B:

Step 1: A mixture of (pyridin-3-yl)acetic acid (1.850 g; 10.67 mmol) in acetic anhydride (1 mL) was heated in a sealed tube at 85° C. for 1 h and indole (1.250 g; 10.67 mmol) was added. The reaction mixture was heated at 85° C. for 20 min and at 105° C. for 30 min. After cooling to room temperature, the reaction mixture was basified (pH 8) with a saturated sodium bicarbonate solution and extracted with ethyl acetate. The organic phase was concentrated under reduced pressure. Purification by flash chromatography on silica gel using a gradient of methanol (1% to 10%) in dichloromethane furnished 0.674 g (27%) of 1-(1H-indol-3-yl)-2-(pyridin-3-yl)ethanone as a beige solid. ESI/APCI(+): 237 (M+H). ESI/APCI(−): 235 (M−H).

Step 2: 2-Bromo-1-(1H-indol-3-yl)-2-(pyridin-3-yl)ethanone was prepared according to general procedure P from a solution of 1-(1H-indol-3-yl)-2-(pyridin-3-yl)ethanone (0.570 g; 2.412 mmol) in THF (17 mL) and a solution of phenyltrimethylammonium tribromide (0.997 g; 2.652 mmol) in THF (22 mL). The reaction mixture was stirred at 0° C. for 1 h and at room temperature overnight. Purification by flash chromatography on silica gel using a gradient of methanol (1% to 10%) in dichloromethane furnished 0.275 g (36%) of the desired compound as a brown solid. ESI/APCI(+): 315, 317 (M+H).

Step 3: A mixture of 2-bromo-1-(1H-indol-3-yl)-2-(pyridin-3-yl)ethanone (0.050 g; 0.159 mmol) and 3,5-dimethoxyaniline (0.121 g; 0.793 mmol) in acetonitrile (1 mL) was irradiated in a microwave oven at 100° C. for 5 min. A saturated sodium bicarbonate solution was added and the reaction mixture was extracted with ethyl acetate. The organic phase was concentrated under reduced pressure. The residue was purified by flash chromatography on silica gel using a gradient of methanol (1% to 7%) in dichloromethane. Further purification by preparative HPLC (XBridge column; method 5) followed by precipitation from ethyl acetate furnished 0.019 g (31%) of 2-((3,5-dimethoxyphenyl)amino)-1-(1H-indol-3-yl)-2-(pyridin-3-yl)ethanone as a white solid. ESI/APCI(+): 388 (M+H). ESI/APCI(−): 386 (M−H).

Example 203: Preparation of 2-((3-methoxyphenyl)amino)-1-(6-morpholino-1H-indol-3-yl)-2-phenylethanone Step 1: To a solution of 6-nitroindole (0.800 g; 4.934 mmol) in pyridine (8 mL) cooled to 0° C. was added acetic anhydride (2.000 mL; 21.16 mmol). The reaction mixture was stirred at room temperature for 16 h. The reaction mixture was concentrated under reduced pressure. The residue was partitioned between ethyl acetate and brine. The phases were separated. The organic phase was dried over magnesium sulfate, filtered and concentrated under reduced pressure. The residue was dissolved in a mixture of methanol (40 mL) and THF (40 mL). 10% Palladium on carbon (0.080 g; 0.752 mmol) and ammonium formate (2.000 g; 31.72 mmol) were added. The reaction mixture was stirred at 60° C. for 2 h. After cooling to room temperature, the reaction mixture was filtered through a pad of celite and the filtrate was concentrated under reduced pressure. The residue was partitioned between ethyl acetate and brine. The phases were separated. The organic phase was dried over magnesium sulfate, filtered and concentrated under reduced pressure. Purification by flash chromatography on silica gel using a gradient of ethyl acetate (15% to 70%) in dichloromethane furnished 0.266 g (31%) of 1-(6-amino-1H-indol-1-yl)ethanone as a brown solid.

Step 2: A mixture of 1-(6-amino-1H-indol-1-yl)ethanone (0.260 g; 1.493 mmol), 1-bromo-2-(2-bromoethoxy)ethane (0.415 g; 1.789 mmol) and DIPEA (0.766 mL; 4.475 mmol) in DMF (8 mL) was stirred at 90° C. overnight. After cooling to room temperature, the reaction mixture was concentrated under reduced pressure. Purification by flash chromatography on silica gel using a gradient of ethyl acetate (15% to 70%) in heptane furnished 0.242 g (80%) of 4-(1H-indol-6-yl)morpholine as a white solid. ESI/APCI(+): 203 (M+H). ESI/APCI(−): 201 (M−H).

Step 3: 6-Morpholino-1H-indole-3-carbaldehyde was prepared according to general procedure R from a solution of oxalyl chloride (0.125 mL; 1.438 mmol) in dichloromethane (8 mL), DMF (0.111 mL; 1.435 mmol) and 4-(1H-indol-6-yl)morpholine (0.242 g; 1.197 mmol). Purification by flash chromatography on silica gel using a gradient of ethyl acetate (15% to 70%) in dichloromethane furnished 0.228 g (83%) of the desired compound as a white solid. ESI/APCI(+): 231 (M+H). ESI/APCI(−): 229 (M−H).

Step 4: To a solution of 6-morpholino-1H-indole-3-carbaldehyde (0.228 g; 0.990 mmol) in dichloromethane (15 mL) were added di-tert-butyl dicarbonate (0.259 g; 1.188 mmol), DMAP (0.024 g; 0.198 mmol) and triethylamine (0.165 mL; 1.190 mmol). After stirring for 30 min, the reaction mixture was washed with a saturated bicarbonate solution. The organic phase was washed with a saturated ammonium chloride solution, dried over magnesium sulfate, filtered and concentrated under reduced pressure to give 0.308 g (94%) of tert-butyl 3-formyl-6-morpholino-1H-indole-1-carboxylate as a white solid. ESI/APCI(+): 331 (M+H).

Step 5: 2-((3-Methoxyphenyl)amino)-1-(6-morpholino-1H-indol-3-yl)-2-phenylethanone was prepared according to general procedure K from a mixture of 3-benzyl-5-(2-hydroxyethyl)-4-methylthiazolium chloride (0.082 g; 0.304 mmol) and triethylamine (0.042 mL; 0.303 mmol) in ethanol (2 mL), tert-butyl 3-formyl-6-morpholino-1H-indole-1-carboxylate (0.200 g; 0.605 mmol) and a solution of N-benzylidene-3-methoxyaniline (0.605 mmol) in ethanol (1 mL), heated at 70° C. overnight. Purification by flash chromatography on silica gel using a gradient of ethyl acetate (5% to 50%) in dichloromethane followed by precipitation from diethyl ether furnished 0.059 g (22%) of the desired compound as a yellow solid. ESI/APCI(+): 442 (M+H). ESI/APCI(−): 440 (M−H). $^1$H NMR (DMSO-d$_6$) δ11.84 (1H, br s); 8.71 (1H, br s); 7.97 (1H, d); 7.62 (2H, d); 7.22 (2H, m); 7.19 (1H, d); 6.90 (2H, m); 6.86 (1H, br s); 6.35 (2H, m); 6.31 (1H, d); 6.10 (1H, d); 6.04 (1H, d); 3.75 (4H, br s); 3.62 (3H, s); 3.07 (4H, br s).

Example 204: Preparation of 2-(imidazo[1,2-b]pyridazin-2-yl)-1-(1H-indol-3-yl)-2-((3-methoxyphenyl)amino)ethanone Step 1: To a solution of imidazo[1,2-b]pyridazine-2-carboxylic acid (0.390 g; 2.391 mmol) in dichloromethane (7 mL) were added DIPEA (1.500 mL; 8.589 mmol), 1-ethyl-3-(3-dimethylaminopropyl)carbodiimide hydrochloride (0.505 g; 2.634 mmol) and hydroxybenzotriazole (0.406 g; 2.651 mmol). The solution was stirred at room temperature for 10 min and N,O-dimethylhydroxylamine hydrochloride (0.266 g; 2.727 mmol) was added. The reaction mixture was stirred at room temperature for 4 h. The reaction mixture was diluted with dichloromethane and washed with water. The aqueous phase was extracted with dichloromethane. The organic phases were combined, washed with a saturated ammonium chloride solution, a saturated sodium bicarbonate solution and brine, dried over magnesium sulfate, filtered and concentrated under reduced pressure to furnish 0.360 g (73%) of N-methoxy-N-methylimidazo[1,2-b]pyridazine-2-carboxamide as a yellow oil. ESI/APCI(+): 207 (M+H).

Step 2: To a solution of N-methoxy-N-methylimidazo[1,2-b]pyridazine-2-carboxamide (0.360 g; 1.746 mmol) in THF (10 mL) cooled to 0° C. was added lithium aluminium hydride (0.075 g; 1.976 mmol). The reaction mixture was stirred at room temperature for 1.5 h. A citric acid buffer (pH 5) solution was added and the reaction mixture was stirred at room temperature for 20 min. The reaction mixture was filtered through celite and the solid was washed with ethyl acetate. The phases were separated. The aqueous phase was extracted with ethyl acetate. The organic phases were combined, washed with brine, dried over magnesium sulfate, filtered and concentrated under reduced pressure to furnish 0.190 g (74%) of imidazo[1,2-b]pyridazine-2-carbaldehyde as a yellow solid. ESI/APCI(+): 148 (M+H). $^1$H NMR (DMSO-d$_6$) δ 10.09 (1H, s); 9.02 (1H, s); 8.69 (1H, s); 8.28 (1H, d); 7.39 (1H, d).

Step 3: A solution of N-(imidazo[1,2-b]pyridazin-2-ylmethylene)-3-methoxyaniline in ethanol was prepared by heating a solution of imidazo[1,2-b]pyridazine-2-carbaldehyde (0.124 g; 0.843 mmol) and 3-methoxyaniline (0.101 mL; 0.901 mmol) in ethanol (2 mL) at 60° C. for 20 h. The formation of the imine was quantitative and the solution was used without further purification. ESI/APCI(+): 253 (M+H).

Step 4: 2-(Imidazo[1,2-b]pyridazin-2-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.120 g; 0.445 mmol) and triethylamine (0.080 mL; 0.574 mmol) in ethanol (0.5 mL), tert-butyl 3-formyl-1H-indole-1-carboxylate (0.250 g; 1.019 mmol) and a solution of N-(imidazo[1,2-b]pyridazin-2-ylmethylene)-3-methoxyaniline (0.843 mmol) in ethanol (2.5 mL), heated at 60° C. for 72 h. Purification by flash chromatography on silica gel using a gradient of ethyl acetate (50% to 100%) in heptane followed by crystallization from ethyl acetate furnished 0.055 g (16%) of the desired compound as a white solid. ESI/APCI(+): 398 (M+H). ESI/APCI(−): 396 (M−H).

Example 205: Preparation of 2-(6-(dimethylamino)pyridin-3-yl)-1-(1H-indol-3-yl)-2-((3-methoxyphenyl)amino)ethanone Step 1: 5-(((3-Methoxyphenyl)imino)methyl)-N,N-dimethylpyridin-2-amine was prepared quantitatively according to general procedure I from 6-(dimethylamino)nicotinaldehyde (0.150 g; 0.999 mmol) and 3-methoxyaniline (0.112 mL; 1.001 mmol).

Step 2: 2-(6-(Dimethylamino)pyridin-3-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 5-(((3-methoxyphenyl)imino)methyl)-N,N-dimethylpyridin-2-amine (0.999 mmol) in ethanol (1 mL), heated at 70° C. for 2 days. Purification by flash chromatography on silica gel using a gradient of ethyl acetate (10% to 100%) in heptane followed by precipitation from ethyl acetate furnished 0.026 g (6%) of the desired compound as a white solid. ESI/APCI(+): 401 (M+H). ESI/APCI(−): 399 (M+H).

Example 206: Preparation of 1-(1H-indol-3-yl)-2-((3-methoxyphenyl)amino)-2-(2-methoxypyrimidin-5-yl)ethanone Step 1: 3-Methoxy-N-((2-methoxypyrimidin-5-yl)methylene)aniline was prepared quantitatively according to general procedure I from 2-methoxypyrimidine-5-carbaldehyde (0.138 g; 0.999 mmol) and 3-methoxyaniline (0.112 mL; 1.001 mmol).

Step 2: 1-(1H-Indol-3-yl)-2-((3-methoxyphenyl)amino)-2-(2-methoxypyrimidin-5-yl)ethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 3-methoxy-N-((2-methoxypyrimidin-5-yl)methylene)aniline (0.999 mmol) in ethanol (1 mL), heated at 70° C. for 2 days. Purification by flash chromatography on silica gel using a gradient of ethyl acetate (10% to 100%) in heptane followed by precipitation from ethyl acetate furnished 0.093 g (24%) of the desired compound as a white solid. ESI/APCI(+): 389 (M+H). ESI/APCI(−): 387 (M−H).

Example 207: Preparation of 1-(5-fluoro-1H-indol-3-yl)-2-(6-methoxypyridin-3-yl)-2-((5-methoxypyridin-3-yl)amino)ethanone Step 1: A solution of 5-methoxy-N-((6-methoxypyridin-3-yl)methylene)pyridin-3-amine in ethanol was prepared by heating a solution of 6-methoxynicotinaldehyde (0.137 g; 0.999 mmol) and 5-methoxypyridin-3-amine (0.124 g; 0.999 mmol) in ethanol (0.25 mL) at 45° C. for 24 h. The formation of the imine was quantitative and the solution was used without further purification. ESI/APCI(+): 244 (M+H); 487 (2M+H).

Step 2: 1-(5-Fluoro-1H-indol-3-yl)-2-(6-methoxypyridin-3-yl)-2-((5-methoxypyridin-3-yl)amino)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 5-fluoro-3-formyl-1H-indole-1-carboxylate (0.263 g; 0.999 mmol) and a solution of 5-methoxy-N-((6-methoxypyridin-3-yl)methylene)pyridin-3-amine (0.999 mmol) in ethanol (1 mL), heated at 70° C. for 4 days. Purification by flash chromatography on silica gel using a gradient of methanol (0% to 10%) in dichloromethane followed by precipitation from diethyl ether furnished 0.095 g (23%) of the desired compound as a white solid. ESI/APCI(+): 407 (M+H). ESI/APCI (−): 405 (M−H).

Example 208: Preparation of 1-(6-fluoro-1H-indol-3-yl)-2-(6-methoxypyridin-3-yl)-2-((5-methoxypyridin-3-yl)amino)ethanone 1-(6-Fluoro-1H-indol-3-yl)-2-(6-methoxypyridin-3-yl)-2-((5-methoxypyridin-3-yl)amino)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 6-fluoro-3-formyl-1H-indole-1-carboxylate (0.263 g; 0.999 mmol) and a solution of 5-methoxy-N-((6-methoxypyridin-3-yl)methylene)pyridin-3-amine (0.999 mmol) in ethanol (1 mL), heated at 70° C. for 4 days. Purification by flash chromatography on silica gel using a gradient of methanol (0% to 10%) in dichloromethane followed by precipitation from diethyl ether furnished 0.053 g (13%) of the desired compound as a white solid. ESI/APCI(+): 407 (M+H). ESI/APCI(−): 405 (M+H).

Example 209: Preparation of 2-((3-(2-(dimethylamino)ethoxy)-5-methoxyphenyl)amino)-1-(1H-indol-3-yl)-2-phenylethanone Step 1: To a solution of N,N-dimethylethanolamine (2.000 g; 22.44 mmol) in diethyl ether (100 mL) cooled to 0° C. was added dropwise methanesulfonyl chloride (1.910 mL; 24.68 mmol). The reaction mixture was stirred at room temperature for 65 h. The resulting white solid was filtered, washed with diethyl ether and dried under vacuum to give 4.460 g (97%) of 2-(dimethylamino)ethyl methanesulfonate hydrochloride.

Step 2: To a solution of 3,5-dimethoxyaniline (2.500 g; 16.32 mmol) in NMP (12 mL) was added sodium methanethiolate (2.290 g; 32.64 mmol) and the reaction mixture was heated to 140° C. overnight. After cooling to room temperature, the reaction mixture was poured into a saturated sodium phosphate monobasic solution and extracted with ethyl acetate. The organic phase was concentrated under reduced pressure. Purification by flash chromatography on silica gel using a gradient of ethyl acetate (15% to 70%) in heptane furnished 1.400 g (62%) of 3-amino-5-methoxyphenol as an orange oil. ESI/APCI(+): 140 (M+H).

Step 3: To a solution of 3-amino-5-methoxyphenol (0.500 g; 3.593 mmol) in DMF (25 mL) cooled to 0° C. was added portionwise sodium hydride (60% dispersion in mineral oil; 0.316 g; 7.925 mmol) followed by 2-(dimethylamino)ethyl methanesulfonate hydrochloride (0.731 g; 3.593 mmol). The reaction mixture was stirred at room temperature for 60 h. A saturated sodium bicarbonate solution was added and the reaction mixture was extracted with ethyl acetate. The organic phase was concentrated under reduced pressure. Purification by flash chromatography on silica gel using a gradient of methanol/25% ammonium hydroxide (9/1) (2% to 20%) in dichloromethane furnished 0.264 g (35%) of 3-(2-(dimethylamino)ethoxy)-5-methoxyaniline as a brown oil. ESI/APCI(+): 211 (M+H).

Step 4: A mixture of 2-chloro-1-(1H-indol-3-yl)-2-phenylethanone (0.150 g; 0.556 mmol) and 3-(2-(dimethylamino)ethoxy)-5-methoxyaniline (0.117 g; 0.556 mmol) in acetonitrile (1 mL) was irradiated in a microwave oven at 150° C. for 30 min. The reaction mixture was concentrated under reduced pressure. Purification by flash chromatography on silica gel using a gradient of methanol/25% ammonium hydroxide (9/1) (2% to 20%) in dichloromethane followed by purification by preparative TLC using methanol (10%) in dichloromethane as eluent furnished 0.005 g (18%) of 2-((3-(2-(dimethylamino)ethoxy)-5-methoxyphenyl) amino)-1-(1H-indol-3-yl)-2-phenylethanone as a beige solid. ESI/APCI(+): 444 (M+H). ESI/APCI(−): 442 (M−H). $^1$H NMR (DMSO-d$_6$) δ12.14 (1H, br s); 8.90 (1H, br s); 8.16 (1H, d); 7.63 (2H, d); 7.46 (1H, d); 7.27 (2H, m); 7.19 (3H, m); 6.33 (1H, d); 5.97-6.17 (3H, m); 5.71 (1H, br s); 3.89 (2H, m); 3.61 (3H, s); 2.55 (2H, m); 2.18 (6H, s).

Example 210: Preparation of 1-(1-(2-(tert-butoxy) ethyl)-6-fluoro-1H-indol-3-yl)-2-((3-methoxyphenyl)amino)-2-phenylethanone Step 1: To a solution of 2-(tert-butoxy)ethanol (2.220 mL; 16.92 mmol) in dichloromethane (50 mL) cooled to 0° C. were added triethylamine (2.820 mL; 20.31 mmol), tosyl chloride (3.870 g, 20.31 mmol) and DMAP (0.413 g; 3.381 mmol). The reaction mixture was allowed to warm to room temperature and was stirred overnight. The reaction mixture was diluted with dichloromethane and washed with a saturated ammonium chloride solution. The organic phase was concentrated under reduced pressure. Purification by flash chromatography on silica gel using a gradient of ethyl acetate (2% to 40%) in heptane furnished 3.930 g (85%) of 2-(tert-butoxy)ethyl 4-methylbenzenesulfonate as a colorless oil. ESI/APCI(+): 295 (M+Na).

Step 2: To a solution of 2-chloro-1-(6-fluoro-1H-indol-3-yl)-2-phenylethanone (0.139 g; 0.483 mmol) in THF (4 mL) cooled to 0° C. was added sodium hydride (60% dispersion in mineral oil; 0.035 g; 0.870 mmol). The mixture was stirred at room temperature for 30 min. 2-(tert-Butoxy)ethyl 4-methylbenzenesulfonate (0.263 g; 0.966 mmol) was added and the reaction mixture was stirred at room temperature for 60 h. The reaction mixture was partitioned between ethyl acetate and a saturated ammonium chloride solution. The organic phase was concentrated under reduced pressure. Purification by flash chromatography on silica gel using a gradient of ethyl acetate (5% to 50%) in heptane furnished 0.085 g (45%) of 1-(1-(2-(tert-butoxy)ethyl)-6-fluoro-1H-indol-3-yl)-2-chloro-2-phenylethanone as an orange oil. ESI/APCI(+): 388 (M+H). ESI/APCI(−): 386 (M−H).

Step 3: 1-(1-(2-(tert-Butoxy)ethyl)-6-fluoro-1H-indol-3-yl)-2-((3-methoxyphenyl)amino)-2-phenylethanone was prepared according to general procedure E from 1-(1-(2-(tert-butoxy)ethyl)-6-fluoro-1H-indol-3-yl)-2-chloro-2-phenylethanone (0.085 g; 0.219 mmol) and m-anisidine (0.245 mL; 2.188 mmol) in acetonitrile (1 mL), irradiated in a microwave oven at 150° C. for 15 min. Purification by flash chromatography on silica gel using a gradient of ethyl acetate (5% to 50%) in heptane furnished 0.066 g (64%) of 1-(1-(2-(tert-butoxy)ethyl)-6-fluoro-1H-indol-3-yl)-2-((3-methoxyphenyl)amino)-2-phenylethanone as an orange solid. ESI/APCI(+): 475 (M+H); 497 (M+Na). ESI/APCI (−): 473 (M−H).

Example 211: Preparation of 1-(6-fluoro-1-(2-hydroxyethyl)-1H-indol-3-yl)-2-((3-methoxyphenyl)amino)-2-phenylethanone 1-(1-(2-(tert-Butoxy)ethyl)-6-fluoro-1H-indol-3-yl)-2-((3-methoxyphenyl)amino)-2-phenylethanone (0.066 g; 0.139 mmol) was dissolved in a 4N hydrogen chloride solution in dioxane (3.000 mL; 12.00 mmol). The reaction mixture was stirred at room temperature overnight. The solution was neutralized with potassium carbonate and the reaction mixture was extracted with ethyl acetate. The organic phase was concentrated under reduced pressure. Purification by flash chromatography on silica gel using a gradient of ethyl acetate (15% to 70%) in heptane followed by purification by preparative HPLC (XBridge column; method 1) furnished 0.007 g (11%) of 1-(6-fluoro-1-(2-hydroxyethyl)-1H-indol-3-yl)-2-((3-methoxyphenyl)amino)-2-phenylethanone as a white solid. ESI/APCI(+): 419 (M+H). ESI/APCI(−): 417 (M−H). $^1$H NMR (DMSO-d$_6$) δ8.95 (1H, br s); 8.14 (1H, m); 7.63 (2H, d); 7.51 (1H, d); 7.23-7.35 (2H, m); 7.19 (1H, m); 7.07 (1H, t); 6.91 (1H, t); 6.31-6.46 (3H, m); 6.11 (1H, d); 6.04 (1H, d); 4.99 (1H, br s); 4.30 (2H, m); 3.78 (2H, m); 3.62 (3H, s).

Example 212: Preparation of 2-((5-ethoxypyridin-3-yl)amino)-1-(1H-indol-3-yl)-2-phenylethanone Step 1: To a suspension of sodium hydride (60% dispersion in mineral oil; 1.690 g; 42.21 mmol) in DMF (15 mL) cooled to 0° C. was added dropwise ethanol (2.460 mL; 42.21 mmol). The mixture was stirred at 0° C. for 30 min and 3,5-dibromopyridine (5.000 g; 21.11 mmol) was added. The reaction mixture was allowed to warm to room temperature and stirred at room temperature for 60 h. The reaction mixture was diluted with water and extracted with dichloromethane. The organic phase was concentrated under reduced pressure. Purification by flash chromatography on silica gel using a gradient of dichloromethane (30% to 100%) in heptane furnished 1.920 g (45%) of 3-bromo-5-ethoxypyridine as an oil. ESI/APCI(+): 202, 204 (M+H).

Step 2: A mixture of 3-bromo-5-ethoxypyridine (1.000 g; 4.949 mmol), copper(II) sulfate pentahydride (0.238 g; 0.990 mmol) and a 25% ammonium hydroxide solution (7.620 mL; 49.49 mmol) was placed in a sealed vessel and heated at 140° C. overnight. After cooling to room temperature, a 1N sodium hydroxide solution was added and the mixture was extracted with ethyl acetate. The organic phase was concentrated under reduced pressure. Purification by flash chromatography on silica gel using a gradient of ethyl acetate (30% to 100%) in dichloromethane furnished 0.357 g (52%) of 5-ethoxypyridin-3-amine as an orange oil. ESI/APCI(+): 139 (M+H). ESI/APCI(−): 137 (M−H).

Step 3: N-Benzylidene-5-ethoxypyridin-3-amine was prepared quantitatively according to general procedure I from benzaldehyde (0.102 mL; 1.004 mmol) and 5-ethoxypyridin-3-amine (0.138 g; 0.999 mmol).

Step 4: 2-((5-Ethoxypyridin-3-yl)amino)-1-(1H-indol-3-yl)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of N-benzylidene-5-ethoxypyridin-3-amine (0.999 mmol) in ethanol (1.5 mL), heated at 70° C. overnight. Purification by flash chromatography on silica gel using a gradient of ethyl acetate (30% to 100%) in dichloromethane followed by precipitation from ethyl acetate furnished 0.090 g (24%) of the desired compound as a green solid. ESI/APCI(+): 372 (M+H). ESI/APCI(−): 370 (M−H).

Example 213: Preparation of 1-(1H-indol-3-yl)-2-((5-isopropoxypyridin-3-yl)amino)-2-phenylethanone Step 1: To a suspension of sodium hydride (60% dispersion in mineral oil; 1.690 g; 42.21 mmol) in DMF (15 mL) cooled to 0° C. was added dropwise isopropanol (3.230 mL; 42.21 mmol). After 30 min at 0° C., 3,5-dibromopyridine (5.000 g; 21.11 mmol) was added. The reaction mixture was allowed to warm to room temperature and stirred at room temperature for 16 h. The reaction mixture was diluted with water and extracted with dichloromethane. The organic phase was concentrated under reduced pressure. Purification by flash chromatography on silica gel using a gradient of dichloromethane (15% to 70%) in heptane furnished 1.210 g (26%) of 3-bromo-5-isopropoxypyridine as an oil. ESI/APCI(+): 216, 218 (M+H).

Step 2: A mixture of 3-bromo-5-isopropoxypyridine (1.000 g; 4.628 mmol), copper(II) sulfate pentahydride (0.223 g; 0.926 mmol) and a 25% ammonium hydroxide solution (7.130 mL; 46.28 mmol) was placed in a sealed vessel and heated at 140° C. overnight. After cooling to room temperature, a 1N sodium hydroxide solution was added and the reaction mixture was extracted with ethyl acetate. The organic phase was concentrated under reduced pressure. Purification by flash chromatography on silica gel using a gradient of ethyl acetate (30% to 100%) in dichloromethane furnished 0.243 g (34%) of 5-isopropoxypyridin-3-amine as an orange oil. ESI/APCI(+): 153 (M+H).

Step 3: N-Benzylidene-5-isopropoxypyridin-3-amine was prepared quantitatively according to general procedure I from benzaldehyde (0.102 mL; 1.004 mmol) and 5-isopropoxypyridin-3-amine (0.152 g; 0.999 mmol).

Step 4: 1-(1H-Indol-3-yl)-2-((5-isopropoxypyridin-3-yl)amino)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of N-benzylidene-5-isopropoxypyridin-3-amine (0.999 mmol) in ethanol (1.5 mL), heated at 70° C. overnight. Purification by flash chromatography on silica gel using a gradient of ethyl acetate (30% to 100%) in dichloromethane followed by precipitation from ethyl acetate and heptane furnished 0.045 g (12%) of the desired compound as a beige solid. ESI/APCI(+): 386 (M+H). ESI/APCI(−): 384 (M−H).

Example 214: Preparation of 2-((5-ethylpyridin-3-yl)amino)-1-(1H-indol-3-yl)-2-phenylethanone Step 1: A solution of N-benzylidene-5-ethylpyridin-3-amine in ethanol was prepared by heating a solution of benzaldehyde (0.102 mL; 1.008 mmol) and 3-amino-5-ethylpyridine (0.117 g; 0.958 mmol) in ethanol (0.5 mL) at 60° C. for 16 h. The formation of the imine was quantitative and the solution was used without further purification. ESI/APCI (+): 211 (M+H).

Step 2: 2-((5-Ethylpyridin-3-yl)amino)-1-(1H-indol-3-yl)-2-phenylethanone was prepared according to general procedure K from a mixture of 3-benzyl-5-(2-hydroxyethyl)-4-methylthiazol-3-ium chloride (0.126 g; 0.467 mmol) and triethylamine (0.090 mL; 0.646 mmol) in ethanol (0.5 mL), tert-butyl 3-formyl-1H-indole-1-carboxylate (0.250 g; 1.019 mmol) and a solution of N-benzylidene-5-ethylpyridin-3-amine (0.958 mmol) in ethanol (1.5 mL), heated at 60° C. for 16 h. Purification by solid phase extraction on C18-reversed phase column using a gradient of acetonitrile (0% to 100%) in water furnished 0.051 g (15%) of the desired compound as a yellow solid. ESI/APCI(+): 356 (M+H). ESI/APCI(−): 354 (M−H).

Example 215: Preparation of 1-(1H-indol-3-yl)-2-((3-methoxyphenyl)amino)-2-(5-methoxypyrazin-2-yl)ethanone Step 1: 3-Methoxy-N-((5-methoxypyrazin-2-yl)methylene)aniline was prepared quantitatively according to general procedure I from 5-methoxypyrazine-2-carbaldehyde (0.138 g; 0.999 mmol) and 3-methoxyaniline (0.112 mL; 1.001 mmol).

Step 2: 1-(1H-Indol-3-yl)-2-((3-methoxyphenyl)amino)-2-(5-methoxypyrazin-2-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 3-methoxy-N-((5-methoxypyrazin-2-yl)methylene)aniline (0.999 mmol) in ethanol (1 mL), heated at 70° C. for 2 days. Purification by flash chromatography on silica gel using a gradient of ethyl acetate (0% to 100%) in heptane followed by precipitation from dichloromethane furnished 0.142 g (36%) of the desired compound as a white solid. ESI/APCI(+): 389 (M+H). ESI/APCI(−): 387 (M−H).

Example 216: Preparation of 2-(6-ethoxypyridin-3-yl)-1-(1H-indol-3-yl)-2-((3-methoxyphenyl)amino)ethanone Step 1: A solution of N-((6-ethoxypyridin-3-yl)methylene)-3-methoxyaniline in ethanol was prepared by heating a solution of 6-ethoxynicotinaldehyde (0.153 g; 1.012 mmol) and 3-methoxyaniline (0.114 mL; 1.012 mmol) in ethanol (0.5 mL) at 60° C. for 16 h. The formation of the imine was quantitative and the solution was used without further purification. ESI/APCI(+): 257 (M+H).

Step 2: 2-(6-Ethoxypyridin-3-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.143 g; 0.530 mmol) and triethylamine (0.100 mL; 0.717 mmol) in ethanol (0.5 mL), tert-butyl 3-formyl-1H-indole-1-carboxylate (0.273 g; 1.113 mmol) and a solution of N-((6-ethoxypyridin-3-yl)methylene)-3-methoxyaniline (1.012 mmol) in ethanol (1.5 mL), heated at 60° C. for 72 h. Purification by flash chromatography on silica gel using a gradient of ethyl acetate (0% to 45%) in heptane followed by purification by preparative HPLC (XBridge column; method 2) furnished 0.058 g (14%) of the desired compound as a white solid. ESI/APCI(+): 402 (M+H). ESI/APCI(−): 400 (M−H).

Example 217: Preparation of 2-((3-methoxyphenyl)amino)-1-(4-methyl-1H-indol-3-yl)-2-phenylethanone Step 1: tert-Butyl 3-formyl-4-methyl-1H-indole-1-carboxylate was prepared according to according to general procedure F from 4-methyl-1H-indole-3-carbaldehyde (0.250 g; 1.571 mmol), di-tert-butyl dicarbonate (0.445 g; 2.039 mmol) and DMAP (0.030 g; 0.246 mmol) in acetonitrile (4 mL) to yield 0.392 g (96%) of the desired compound as a yellow solid. $^1$H NMR (DMSO-d$_6$) δ 10.06 (1H, s); 8.59 (1H, s); 8.01 (1H, d); 7.33 (1H, t); 7.17 (1H, s); 2.76 (3H, s); 1.66 (9H, s).

Step 2: 2-((3-Methoxyphenyl)amino)-1-(4-methyl-1H-indol-3-yl)-2-phenylethanone was prepared according to general procedure K from a mixture of 3-benzyl-5-(2-hydroxyethyl)-4-methylthiazol-3-ium chloride (0.137 g; 0.508 mmol) and triethylamine (0.100 mL; 0.717 mmol) in ethanol (0.5 mL), tert-butyl 3-formyl-4-methyl-1H-indole-1-carboxylate (0.277 g; 1.068 mmol) and a solution of N-benzylidene-3-methoxyaniline (0.989 mmol) in ethanol (1.5 mL), heated at 60° C. for 48 h.

Purification by flash chromatography on silica gel using a gradient of ethyl acetate (0% to 50%) in heptane followed by purification by preparative HPLC (XBridge column; method 1) furnished 0.046 g (13%) of the desired compound as a white solid. ESI/APCI(+): 371 (M+H). ESI/APCI(−): 369 (M−H).

Example 218: Preparation of 1-(1H-indol-3-yl)-2-((6-methoxypyrazin-2-yl)amino)-2-phenylethanone Step 1: N-Benzylidene-6-methoxypyrazin-2-amine was prepared quantitatively according to general procedure I from benzaldehyde (0.102 mL; 1.004 mmol) and 6-methoxypyrazin-2-amine (0.125 g; 0.999 mmol).

Step 2: 1-(1H-Indol-3-yl)-2-((6-methoxypyrazin-2-yl)amino)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of N-benzylidene-6-methoxypyrazin-2-amine (0.999 mmol) in ethanol (1 mL), heated at 70° C. overnight. Purification by flash chromatography on silica gel using a gradient of ethyl acetate (5% to 50%) in dichloromethane followed by precipitation from diethyl ether furnished 0.048 g (13%) of the desired compound as a beige solid. ESI/APCI(+): 359 (M+H). ESI/APCI(−): 357 (M−H). $^1$H NMR (DMSO-d$_6$) δ12.02 (1H, br s); 8.72 (1H, s); 8.17 (1H, d); 7.78 (1H, d); 7.76 (1H, s); 7.67 (2H, d); 7.45 (1H, d); 7.31-7.38 (2H, m); 7.30 (1H, s); 7.13-7.28 (3H, m); 6.39 (1H, d); 3.60 (3H, s).

Example 219: Preparation of 2-((3-(2-(tert-butoxy)ethoxy)-5-methoxyphenyl)amino)-1-(1H-indol-3-yl)-2-phenylethanone AND 2-((3-ethoxy-5-methoxyphenyl)amino)-1-(1H-indol-3-yl)-2-phenylethanone Step 1: To a solution of 3-amino-5-methoxyphenol (0.447 g; 3.214 mmol) in DMF (20 mL) cooled to 0° C. was added portionwise sodium hydride (60% dispersion in mineral oil; 0.282 g; 7.050 mmol). After addition of a solution of 2-(tert-butoxy)ethyl 4-methylbenzenesulfonate (0.875 g; 3.213 mmol) in DMF (3 mL), the reaction mixture was stirred at room temperature for 20 h. Water was added and the reaction mixture was extracted with ethyl acetate. The organic phase was concentrated under reduced pressure. Purification by flash chromatography on silica gel using a gradient of ethyl acetate (5% to 50%) in heptane furnished 0.241 g of 3-(2-(tert-butoxy)ethoxy)-5-methoxyaniline (contaminated with 3-ethoxy-5-methoxyaniline) as a brown oil. ESI/APCI(+): 240 (M+H).

Step 2: 2-((3-(2-(tert-Butoxy)ethoxy)-5-methoxyphenyl)amino)-1-(1H-indol-3-yl)-2-phenylethanone was prepared according to general procedure C from 2-chloro-1-(1H-indol-3-yl)-2-phenylethanone (0.120 g; 0.445 mmol), 3-(2-(tert-butoxy)ethoxy)-5-methoxyaniline (0.106 g; 0.445 mmol) and triethylamine (0.124 mL; 0.890 mmol) in acetonitrile (0.5 mL), irradiated in a microwave oven at 150° C. for 30 min. Purification by flash chromatography on silica gel using dichloromethane as eluent furnished 0.054 g (26%) of 2-((3-(2-(tert-butoxy)ethoxy)-5-methoxyphenyl)amino)-1-(1H-indol-3-yl)-2-phenylethanone as a beige solid. ESI/APCI(+): 473 (M+H); 495 (M+Na). ESI/APCI (−): 471 (M−H). 2-((3-Ethoxy-5-methoxyphenyl)amino)-1-(1H-indol-3-yl)-2-phenylethanone was also isolated after the purification by flash column on silica gel described above. Further purification by preparative HPLC (XBridge column; method 5) furnished 0.008 g of pure compound as a white solid. ESI/APCI(+): 401 (M+H). ESI/APCI(−): 399 (M−H). $^1$H NMR (DMSO-$d_6$) δ12.14 (1H, br s); 8.90 (1H, s); 8.16 (1H, d); 7.63 (2H, d); 7.46 (1H, d); 7.25-7.35 (2H, m); 7.11-7.24 (3H, m); 6.32 (1H, d); 5.97-6.13 (3H, m); 5.69 (1H, s); 3.87 (2H, q); 3.60 (3H, s); 1.24 (4H, t).

Example 220: Preparation of 2-((3-(2-hydroxyethoxy)-5-methoxyphenyl)amino)-1-(1H-indol-3-yl)-2-phenylethanone 2-((3-(2-(tert-Butoxy)ethoxy)-5-methoxyphenyl)amino)-1-(1H-indol-3-yl)-2-phenylethanone (0.054 g; 0.114 mmol) was dissolved in a 4N hydrogen chloride solution in dioxane (3.000 mL; 12.00 mmol). The reaction mixture was stirred at room temperature for 6 h. The reaction mixture was poured into a mixture ice/water, neutralized with potassium carbonate and extracted with ethyl acetate. The organic phase was concentrated under reduced pressure. Purification by flash chromatography on silica gel using a gradient of ethyl acetate (5% to 50%) in dichloromethane followed by precipitation from diethyl ether furnished 0.009 g (19%) of 2-((3-(2-hydroxyethoxy)-5-methoxyphenyl)amino)-1-(1H-indol-3-yl)-2-phenylethanone as a beige solid. ESI/APCI (+): 417 (M+H). ESI/APCI(−): 415 (M−H). $^1$H NMR (DMSO-$d_6$) δ12.13 (1H, br s); 8.89 (1H, s); 8.17 (1H, d); 7.63 (2H, d); 7.47 (1H, d); 7.25-7.33 (2H, m); 7.14-7.25 (3H, m); 6.32 (1H, d); 6.07 (1H, d); 6.05 (2H, brs); 5.72 (1H, s); 4.77 (1H, t); 3.78-3.90 (2H, m); 3.63-3.69 (2H, m); 3.62 (3H, s).

Example 221: Preparation of 2-((5,6-dimethoxypyridin-3-yl)amino)-1-(1H-indol-3-yl)-2-phenylethanone Step 1: To a solution of sodium methoxide (0.215 g; 3.980 mmol) in methanol (13 mL) was added 2-chloro-3-methoxy-5-nitropyridine (0.500 g; 2.652 mmol). After 5.5 h at room temperature, sodium methoxide (0.215 g; 3.980 mmol) was added and the reaction mixture was stirred at room temperature overnight. Sodium methoxide (0.215 g; 3.980 mmol) was added again. After 4.5 h at room temperature, the reaction mixture was concentrated under reduced pressure. The residue was partitioned between ethyl acetate and water. The phases were separated. The organic phase was washed with brine, dried over sodium sulfate, filtered and concentrated under reduced pressure. Purification by flash chromatography on silica gel using a gradient of ethyl acetate (20% to 50%) in heptane furnished 0.467 g (96%) of 2,3-dimethoxy-5-nitropyridine as a yellow powder. ESI/APCI(+): 185 (M+H). $^1$H NMR (DMSO-$d_6$) δ 8.69 (1H, s); 7.94 (1H, s); 4.02 (3H, s); 3.93 (3H, s).

Step 2: To a suspension of 2,3-dimethoxy-5-nitropyridine (0.463 g; 2.514 mmol) in water (9 mL) was added acetic acid (0.500 mL; 8.734 mmol). After portionwise addition of sodium dithionite (1.670 g; 9.562 mmol), the suspension was stirred at room temperature for 4 h. The reaction mixture was poured into a mixture ice/1N sodium hydroxide solution and extracted with ethyl acetate. The organic phase was dried over sodium sulfate, filtered and concentrated under reduced pressure. Purification by flash chromatography on silica gel using a gradient of methanol (0% to 10%) in dichloromethane furnished 0.111 g (29%) of 5,6-dimethoxypyridin-3-amine as a pink solid. ESI/APCI(+): 155 (M+H). $^1$H NMR (DMSO-$d_6$) δ 7.03 (1H, s); 6.65 (1H, s); 4.72 (2H, br s); 3.70 (6H, m).

Step 3: A solution of N-benzylidene-5,6-dimethoxypyridin-3-amine in ethanol was prepared by heating a solution of benzaldehyde (0.067 mL; 0.661 mmol) and 5,6-dimethoxypyridin-3-amine (0.101 g; 0.655 mmol) in ethanol (1.3 mL) at 60° C. for 6 h. The formation of the imine was quantitative and the solution was used without further purification. ESI/APCI(+): 243 (M+H).

Step 4: 2-((5,6-Dimethoxypyridin-3-yl)amino)-1-(1H-indol-3-yl)-2-phenylethanone was prepared according to general procedure K from a mixture of 3-benzyl-5-(2-hydroxyethyl)-4-methylthiazol-3-ium chloride (0.090 g; 0.334 mmol) and triethylamine (0.045 mL; 0.325 mmol) in ethanol (0.5 mL), tert-butyl 3-formyl-1H-indole-1-carboxylate (0.193 g; 0.787 mmol) and a solution of N-benzylidene-5,6-dimethoxypyridin-3-amine (0.655 mmol) in ethanol (1.3 mL), heated at 70° C. for 65 h. The residue was purified by flash chromatography on silica gel using a gradient of methanol (0% to 10%) in dichloromethane. Further purification by preparative HPLC (XBridge column; method 5) followed by recrystallization from ethyl acetate and heptane furnished 0.006 g (2%) of the desired product as a pink powder. ESI/APCI(+): 388 (M+H); 410 (M+Na). ESI/APCI (−): 386 (M−H). $^1$H NMR (DMSO-$d_6$) δ 12.16 (1H, br s); 8.87 (1H, s); 8.16 (1H, d); 7.63 (2H, m); 7.30 (1H, d); 7.17-7.26 (6H, m); 7.05 (1H, s); 6.11 (2H, m); 3.67 (6H, d).

Example 222: Preparation of 2-((6-(dimethylamino)-5-methoxypyridin-3-yl)amino)-1-(1H-indol-3-yl)-2-phenylethanone Step 1: To a 2M dimethylamine solution in THF (6.250 mL; 12.50 mmol) was added 2-chloro-3-methoxy-5-nitropyridine (0.471 g; 2.500 mmol). The reaction mixture was stirred at 80° C. for 16 h and was concentrated under reduced pressure. The crude bright yellow residue was dissolved in methanol (20 mL). Palladium on carbon (0.030 g, 0.282 mmol) was added and the reaction mixture was stirred at room temperature for 16 h under hydrogen atmosphere. The reaction mixture was filtered over diatomaceous earth and the filter cake was washed with ethanol. The filtrate was concentrated under reduced pressure. Purification by flash chromatography on silica gel using a gradient of methanol (0% to 10%) in dichloromethane furnished 0.337 g (81%) of 3-methoxy-$N^2$,$N^2$-dimethylpyridine-2,5-diamine. ESI/APCI (+): 168 (M+H).

Step 2: A mixture of benzaldehyde (0.102 mL; 1.004 mmol) and 3-methoxy-$N^2$,$N^2$-dimethylpyridine-2,5-diamine (0.167 g; 0.999 mmol) in methanol (0.25 mL) was stirred at 45° C. for 24 h. The solvent was evaporated and the residue was dried under reduced pressure to give $N^5$-benzylidene-3-methoxy-$N^2$,$N^2$-dimethylpyridine-2,5-diamine quantitatively which was used without further purification. ESI/APCI (+): 256 (M+H).

Step 3: 2-((6-(Dimethylamino)-5-methoxypyridin-3-yl) amino)-1-(1H-indol-3-yl)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of $N^5$-benzylidene-3-methoxy-$N^2$,$N^2$-dimethylpyridine-2,5-diamine (0.999 mmol) in ethanol (1 mL), heated at 70° C. for 2 days. Purification by flash chromatography on silica gel using a gradient of ethyl acetate (0% to 100%) in heptane followed by crystallization from acetonitrile furnished 0.046 g (12%) of the desired compound as a light brown solid. ESI/APCI (+): 401 (M+H). ESI/APCI(−): 399 (M+H).

Example 223: Preparation of 2-((6-ethoxy-5-methoxypyridin-3-yl)amino)-1-(1H-indol-3-yl)-2-phenylethanone Step 1: To a 21% sodium ethoxide solution in ethanol (2.000 mL; 5.357 mmol) was added 2-chloro-3-methoxy-5-nitropyridine (0.500 g; 2.652 mmol). The reaction mixture was stirred at room temperature overnight and was concentrated under reduced pressure. The residue was partitioned between ethyl acetate and water. The phases were separated. The organic phase was washed with brine, dried over sodium sulfate, filtered and concentrated under reduced pressure to yield 0.476 g of 2-ethoxy-3-methoxy-5-nitropyridine as a brown foam which was used in the next step without further purification. ESI/APCI(+): 199 (M+H).

Step 2: To a suspension of 2-ethoxy-3-methoxy-5-nitropyridine (0.250 g; 1.261 mmol) in ethanol (8.5 mL) cooled to 0° C. was added a 2N hydrochloric acid solution (6.600 mL; 13.20 mmol).

After addition of zinc (1.800 g; 27.53 mmol), the reaction mixture was stirred at room temperature for 3 h. The reaction mixture was poured into a mixture ice/1N sodium hydroxide solution and was filtered through celite. The filtrate was extracted with ethyl acetate. The organic phase was washed with brine, dried over sodium sulfate, filtered and concentrated under reduced pressure. Purification by flash chromatography on silica gel using a gradient of methanol (0% to 10%) in dichloromethane furnished 0.168 g (72% over two steps) of 6-ethoxy-5-methoxypyridin-3-amine as a brown solid. ESI/APCI(+): 169 (M+H); 191 (M+Na). $^1$H NMR (DMSO-$d_6$) δ 7.02 (1H, s); 6.65 (1H, s); 4.68 (2H, br s); 4.15 (2H, q); 3.69 (3H, s); 1.25 (3H, t).

Step 3: A solution of N-benzylidene-6-ethoxy-5-methoxypyridin-3-amine in ethanol was prepared by heating a solution of benzaldehyde (0.100 mL; 0.942 mmol) and 6-ethoxy-5-methoxypyridin-3-amine (0.164 g; 0.975 mmol) in ethanol (2 mL) at 60° C. for 6 h. The formation of the imine was quantitative and the solution was used without further purification. ESI/APCI(+): 257 (M+H).

Step 4: 2-((6-Ethoxy-5-methoxypyridin-3-yl)amino)-1-(1H-indol-3-yl)-2-phenylethanone was prepared according to general procedure K from a mixture of 3-benzyl-5-(2-hydroxyethyl)-4-methylthiazol-3-ium chloride (0.134 g; 0.497 mmol) and triethylamine (0.067 mL; 0.483 mmol) in ethanol (0.7 mL), tert-butyl 3-formyl-1H-indole-1-carboxylate (0.287 g; 1.170 mmol) and a solution of N-benzylidene-6-ethoxy-5-methoxypyridin-3-amine (0.942 mmol) in ethanol (2 mL), heated at 70° C. for 65 h. Purification by flash chromatography on silica gel using a gradient of ethyl acetate (0% to 100%) in heptane followed by recrystallization from ethyl acetate and heptane furnished 0.018 g (5%) of the desired product as a pink powder. ESI/APCI(+): 402 (M+H); 424 (M+Na). ESI/APCI(−): 400 (M−H). $^1$H NMR (DMSO-$d_6$) δ 12.16 (1H, br s); 8.87 (1H, s); 8.15 (1H, d); 7.63 (2H, m); 7.46 (1H, d); 7.20-7.29 (6H, m); 7.04 (1H, s); 6.10 (2H, s); 4.09 (2H, q); 3.69 (3H, s); 1.22 (3H, t).

Example 224: Preparation of 2-((5-methoxypyridin-3-yl)amino)-1-(1-methyl-1H-indazol-3-yl)-2-phenylethanone 2-((5-Methoxypyridin-3-yl)amino)-1-(1-methyl-1H-indazol-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of N-benzylidene-5-methoxypyridin-3-amine (0.999 mmol) in ethanol (1 mL), heated at 70° C. for 24 h. Purification by flash chromatography on silica gel using a gradient of ethyl acetate (0% to 100%) in heptane followed by precipitation from ethanol and diethyl ether furnished 0.092 g (24%) of the desired compound as a white solid. ESI/APCI(+): 373 (M+H). ESI/APCI(−): 371 (M−H).

Example 225: Preparation of 4-(1-((3-methoxyphenyl)amino)-2-(1-methyl-1H-indazol-3-yl)-2-oxoethyl)benzonitrile 4-(1-((3-Methoxyphenyl)amino)-2-(1-methyl-1H-indazol-3-yl)-2-oxoethyl)benzonitrile was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of 4-(((3-methoxyphenyl)imino) methyl)benzonitrile (0.999 mmol) in ethanol (1 mL), heated at 70° C. for 2 days. Purification by flash chromatography on silica gel using a gradient of ethyl acetate (0% to 100%) in heptane followed by precipitation from ethanol furnished 0.176 g (43%) of the desired compound as a white solid. ESI/APCI(+): 397 (M+H). ESI/APCI(−): 395 (M−H).

Example 226: Preparation of 1-(1H-indol-3-yl)-2-((5-methoxy-6-(methylamino)pyridin-3-yl)amino)-2-phenylethanone Step 1:
To a 2M methylamine solution in THF (6.250 mL; 12.500 mmol) was added 2-chloro-3-methoxy-5-nitropyridine (0.471 g; 2.500 mmol). The reaction mixture was stirred at 80° C. for 16 h and was concentrated under reduced pressure. The crude bright yellow residue was dissolved in methanol (20 mL) and palladium on carbon (0.030 g, 0.282 mmol) was added. The reaction mixture was stirred at room temperature for 16 h under hydrogen atmosphere. The reaction mixture was filtered over diatomaceous earth and the filter cake was washed with ethanol. The filtrate was concentrated under reduced pressure. Purification by flash chromatography on silica gel using a gradient of methanol (1% to 10%) in dichloromethane furnished 0.172 g (45%) of 3-methoxy-$N^2$-methylpyridine-2,5-diamine. ESI/APCI(+): 154 (M+H).

Step 2: A mixture of benzaldehyde (0.114 mL; 1.123 mmol) and 3-methoxy-$N^2$-methylpyridine-2,5-diamine (0.172 g; 1.123 mmol) in methanol (0.25 mL) was stirred at 45° C. for 24 h. The reaction mixture was concentrated under reduced pressure to give quantitatively N-benzylidene-3-methoxy-N-methylpyridine-2,5-diamine which was used without further purification. ESI/APCI (+): 242 (M+H).

Step 3: 1-(1H-Indol-3-yl)-2-((5-methoxy-6-(methylamino)pyridin-3-yl)amino)-2-phenylethanone was prepared according to general procedure L from a mixture of 3-benzyl-5-(2-hydroxyethyl)-4-methylthiazol-3-ium chloride (0.151 g; 0.562 mmol) and triethylamine (0.079 mL; 0.562 mmol) in ethanol (1 mL), tert-butyl 3-formyl-1H-indole-1-carboxylate (0.275 g; 1.121 mmol) and a solution of N-benzylidene-3-methoxy-N-methylpyridine-2,5-diamine (1.123 mmol) in ethanol (1 mL), heated at 70° C. for 3 days. Purification by flash chromatography on silica gel using a gradient of ethyl acetate (0% to 100%) in heptane followed by crystallization from acetonitrile furnished 0.008 g (2%) of the desired compound as a white solid. ESI/APCI(+): 387 (M+H). ESI/APCI(−): 385 (M−H).

Example 227: Preparation of 2-((3-(hydroxymethyl)-5-methoxyphenyl)amino)-1-(1H-indol-3-yl)-2-phenylethanone Step 1: To a solution of the 3-amino-5-methoxybenzoic acid (2.500 g; 14.96 mmol) in ethanol (30 mL) cooled to 0° C., was added dropwise thionyl chloride (1.500 mL; 20.68 mmol) over 15 min. The resulting suspension was stirred at room temperature for 1 h and refluxed for 2 h. The reaction mixture was concentrated under reduced pressure. The residue was partitioned between dichloromethane and a saturated sodium bicarbonate solution. The phases were separated. The organic phase was dried over magnesium sulfate, filtered and concentrated under reduced pressure to yield crude ethyl 5-amino-2-chlorobenzoate as brown oil. To a suspension of lithium aluminium hydride (2.200 g; 57.99 mmol) in THF (15 mL) cooled to 0° C. was slowly added a solution of ethyl 5-amino-2-chlorobenzoate (14.50 mmol) in THF (30 mL). The reaction mixture was stirred at 0° C. for 30 min and at room temperature for 2 h. After cooling to 0° C., the reaction was quenched by slow addition of a 1N Rochelle salt solution. The reaction mixture was stirred for 2 h and extracted with dichloromethane. The organic phase was concentrated under reduced pressure. Purification by flash chromatography on silica gel using a gradient of ethyl acetate (15% to 70%) in dichloromethane furnished 1.670 g (75%) of (3-amino-5-methoxyphenyl)methanol as a white solid. ESI/APCI(+): 154 (M+H).

Step 2: A solution of 3-(benzylideneamino)-5-methoxyphenyl)methanol in ethanol was prepared by heating a solution of benzaldehyde (0.102 mL; 1.004 mmol) and (3-amino-5-methoxyphenyl)methanol (0.153 g; 0.999 mmol) in ethanol (1 mL) at 60° C. overnight. The formation of the imine was quantitative and the solution was used without further purification. ESI/APCI(+): 342 (M+H).

Step 3: 2-((3-(Hydroxymethyl)-5-methoxyphenyl)amino)-1-(1H-indol-3-yl)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of (3-(benzylideneamino)-5-methoxyphenyl)methanol (0.999 mmol) in ethanol (1 mL), heated at 70° C. overnight. Purification by flash chromatography on silica gel using a gradient of ethyl acetate (5% to 50%) in dichloromethane followed by precipitation from dichloromethane furnished 0.060 g (15%) of the desired compound as a white solid. ESI/APCI(+): 387 (M+H). ESI/APCI(−): 385 (M−H). $^1$H NMR (DMSO-d$_6$) δ12.10 (1H, br s); 8.87 (1H, s); 8.17 (1H, d); 7.64 (2H, d); 7.47 (1H, d); 7.29 (2H, t); 7.12-7.25 (3H, m); 6.41 (1H, s); 6.22-6.32 (2H, m); 6.12 (1H, s); 6.09 (1H, d); 4.97 (1H, br s); 4.30 (2H, d); 3.63 (3H, s).

Example 228: Preparation of 2-((3-((dimethylamino)methyl)-5-methoxyphenyl)amino)-1-(1H-indol-3-yl)-2-phenylethanone Step 1: To a solution of (3-amino-5-methoxyphenyl)methanol (0.500 g; 3.264 mmol) in dichloromethane (30 mL) was added triethylamine (0.635 mL; 4.581 mmol) followed by mesyl chloride (0.278 mL, 3.592 mmol). The mixture was stirred at room temperature for 2 h. A 2M dimethylamine solution in THF (2.000 mL; 4.000 mmol) was added and the mixture was stirred at room temperature overnight. The reaction mixture was diluted with dichloromethane and washed with water. The organic phase was concentrated under reduced pressure. Purification by flash chromatography on silica gel using a gradient of methanol/25% ammonium hydroxide (911) (2% to 15%) in dichloromethane furnished 0.192 g (32%) of 3-((dimethylamino)methyl)-5-methoxyaniline as an oil. ESI/APCI(+): 180 (M+H).

Step 2: A mixture of 2-chloro-1-(1H-indol-3-yl)-2-phenylethanone (0.170 g; 0.630 mmol) and 3-((dimethylamino)methyl)-5-methoxyaniline (0.102 g; 0.567 mmol) in acetonitrile (1 mL) was irradiated in a microwave oven at 150° C. for 15 min. The reaction mixture was concentrated under reduced pressure. Purification by flash chromatography on silica gel using a gradient of methanol/25% ammonium hydroxide (9/1) (2% to 20%) in dichloromethane furnished 0.032 g (13%) of 2-((3-((dimethylamino)methyl)-5-methoxyphenyl)amino)-1-(1H-indol-3-yl)-2-phenylethanone as a white solid. ESI/APCI(+): 414 (M+H). ESI/APCI(−): 412 (M−H). $^1$H NMR (DMSO-d$_6$) δ12.14 (1H, br s); 8.89 (1H, d); 8.16 (1H, d); 7.64 (2H, d); 7.46 (1H, d); 7.24-7.24 (5H, m); 6.39 (1H, s); 6.24-6.34 (2H, m); 6.03-6.13 (2H, m); 3.61 (3H, s); 3.21 (2H, s); 2.09 (6H, s).

Example 229: Preparation of 2-((3-methoxyphenyl)amino)-2-(6-methoxypyridin-3-yl)-1-(1-methyl-1H-indazol-3-yl)ethanone 2-((3-Methoxyphenyl)amino)-2-(6-methoxypyridin-3-yl)-1-(1-methyl-1H-indazol-3-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of 3-methoxy-N-((6-methoxypyridin-3-yl)methylene)aniline (0.999 mmol) in ethanol (1 mL), heated at 70° C. for 24 h. The precipitate was filtered, washed with ethanol and dried under reduced pressure to furnish 0.249 g (61%) of the desired compound as a white solid. ESI/APCI(+): 403 (M+H). ESI/APCI(−): 401 (M−H).

Example 230: Preparation of 2-((3,5-dimethoxyphenyl)amino)-1-(1-methyl-1H-indazol-3-yl)-2-phenylethanone 2-((3,5-Dimethoxyphenyl)amino)-1-(1-methyl-1H-indazol-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of N-benzylidene-3,5-dimethoxyaniline (0.999 mmol) in ethanol (1 mL), heated at 70° C. for 2 days. The residue was purified by flash chromatography on silica gel using a gradient of ethyl acetate (0% to 80%) in heptane followed by purification by solid phase extraction on C18-reversed phase column using a gradient of acetonitrile (30% to 100%) in water. Further purification by crystallization from acetonitrile furnished 0.008 g (2%) of the desired compound as clear crystals. ESI/APCI(+): 402 (M+H).

Example 231: Preparation of 1-(6-methoxy-1-methyl-1H-indazol-3-yl)-2-((3-methoxyphenyl)amino)-2-phenylethanone Step 1: To a solution of 6-methoxy-1H-indazole-3-carbaldehyde (0.088 g; 0.500 mmol) and cesium carbonate (0.652 g; 2.000 mmol) in DMSO (2.5 mL) was added iodomethane (0.062 mL; 1.000 mmol) and the reaction mixture was stirred at room temperature for 3 h. The reaction mixture was diluted with water until a precipitate formed. The solid was filtered, washed with water and dried under reduced pressure over phosphorus(V) oxide to furnish 0.063 g (66%) of 6-methoxy-1-methyl-1H-indazole-3-carbaldehyde as a grey solid. ESI/APCI(+): 191 (M+H). $^1$H NMR (DMSO-d$_6$) δ 10.07 (1H, s); 7.97 (1H, d); 7.29 (1H, s); 7.01 (1H, d); 4.17 (3H, s); 3.89 (3H, s).

Step 2: 1-(6-Methoxy-1-methyl-1H-indazol-3-yl)-2-((3-methoxyphenyl)amino)-2-phenylethanone was prepared according to general procedure L from a mixture of 3-benzyl-5-(2-hydroxyethyl)-4-methylthiazol-3-ium chloride (0.042 g; 0.158 mmol) and triethylamine (0.022 mL; 0.158 mmol) in ethanol (0.35 mL), 6-methoxy-1-methyl-1H-indazole-3-carbaldehyde (0.060 g; 0.315 mmol) and a solution of N-benzylidene-3-methoxyaniline (0.315 mmol) in ethanol (0.35 mL), heated at 70° C. for 24 h. Purification by flash chromatography on silica gel using a gradient of ethyl acetate (0% to 80%) in heptane followed by precipitation from diethyl ether furnished 0.042 g (32%) of the desired compound as a white solid. ESI/APCI(+): 402 (M+H).

Example 232: Preparation of 2-(1,5-dimethyl-1H-pyrazol-3-yl)-1-(1H-indol-3-yl)-2-((3-methoxyphenyl)amino)ethanone Step 1: A solution of N-((1,5-dimethyl-1H-pyrazol-3-yl)methylene)-3-methoxyaniline in ethanol was prepared by heating a solution of 1,5-dimethyl-1H-pyrazole-3-carbaldehyde (0.127 g; 1.023 mmol) and 3-methoxyaniline (0.119 mL; 1.056 mmol) in ethanol (0.5 mL) at 60° C. for 18 h. The formation of the imine was quantitative and the solution was used without further purification. ESI/APCI (+): 230 (M+H); 252 (M+Na); 481 (2M+Na).

Step 2: 2-(1,5-Dimethyl-1H-pyrazol-3-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.141 g; 0.523 mmol) and triethylamine (0.100 mL; 0.717 mmol) in ethanol (0.5 mL), tert-butyl 3-formyl-1H-indole-1-carboxylate (0.263 g; 1.072 mmol) and a solution of N-((1,5-dimethyl-1H-pyrazol-3-yl)methylene)-3-methoxyaniline (1.023 mmol) in ethanol (1.5 mL), heated at 60° C. for 24 h. The residue was purified by flash chromatography on silica gel using a gradient of ethyl acetate (50% to 100%) in heptane. Further purification by precipitation from ethyl acetate followed by precipitation from a mixture of acetonitrile, water and DMF furnished 0.085 g (22%) of the desired compound as a white solid. ESI/APCI(+): 375 (M+H). ESI/APCI(−): 373 (M−H).

Example 233: Preparation of 1-(1H-indol-3-yl)-2-(6-isopropoxypyridin-3-yl)-2-((3-methoxyphenyl)amino)ethanone Step 1: A solution of N-((6-isopropoxypyridin-3-yl)methylene)-3-methoxyaniline in ethanol was prepared by heating a solution of 6-isopropoxynicotinaldehyde (0.156 g; 0.944 mmol) and 3-methoxyaniline (0.109 mL; 0.966 mmol) in ethanol (0.5 mL) at 60° C. for 18 h. The formation of the imine was quantitative and the solution was used without further purification.

Step 2: 1-(1H-Indol-3-yl)-2-(6-isopropoxypyridin-3-yl)-2-((3-methoxyphenyl)amino)ethanone was prepared according to general protocol K from a mixture of 3-benzyl-5-(2-hydroxyethyl)-4-methylthiazol-3-ium chloride (0.136 g; 0.504 mmol) and triethylamine (0.100 mL; 0.717 mmol) in ethanol (0.5 mL), tert-butyl 3-formyl-1H-indole-1-carboxylate (0.267 g; 1.089 mmol) and a solution of N-((6-isopropoxypyridin-3-yl)methylene)-3-methoxyaniline (0.944 mmol) in ethanol (1.5 mL), heated at 60° C. for 120 h. Purification by flash chromatography on silica gel using a gradient of ethyl acetate (10% to 60%) in heptane followed by purification by preparative HPLC (XBridge column; method 2) furnished 0.084 g (21%) of the desired compound as a yellow solid. ESI/APCI(+): 416 (M+H). ESI/APCI(−): 414 (M−H).

Example 234: Preparation of 2-((5-(difluoromethoxy)pyridin-3-yl)amino)-1-(1H-indol-3-yl)-2-phenylethanone Step 1: A mixture of 6-bromopyridinol (2.000 g; 11.49 mmol), sodium chlorodifluoroacetate (2.630 g; 17.24 mmol) and potassium carbonate (3.180 g; 22.99 mmol) in acetonitrile (50 mL) was placed in a sealed tube and heated at 110° C. overnight. After cooling to room temperature, the reaction mixture was diluted with diethyl ether and washed with a saturated sodium bicarbonate solution. The organic phase was concentrated under reduced pressure. Purification by flash chromatography on silica gel using dichloromethane as eluent furnished 0.393 g (15%) of 3-bromo-5-(difluoromethoxy)pyridine as a yellow oil. ESI/APCI(+): 224,226 (M+H).

Step 2: A mixture of 3-bromo-5-(difluoromethoxy)pyridine (0.500 g; 2.232 mmol), copper(II) sulfate pentahydride (0.107 g; 0.446 mmol) and a 25% ammonium hydroxide solution (3.440 mL; 22.32 mmol) was placed in sealed tube and heated at 150° C. overnight. After cooling to room temperature, a 1N sodium hydroxide solution was added and the reaction mixture was extracted with ethyl acetate. The organic phase was concentrated under reduced pressure. Purification by flash chromatography on silica gel using a gradient of ethyl acetate (15% to 70%) in dichloromethane furnished 0.291 g (81%) of 5-(difluoromethoxy)pyridin-3-amine as a brown solid. ESI/APCI(+): 161 (M+H). ESI/APCI(−): 159 (M−H).

Step 3: A solution of N-benzylidene-5-(difluoromethoxy)pyridin-3-amine in ethanol was prepared by heating a solution of benzaldehyde (0.102 mL; 1.004 mmol) and 5-(difluoromethoxy)pyridin-3-amine (0.160 g; 0.999 mmol) in ethanol (1 mL) at 60° C. for 6 h. The formation of the imine was quantitative and the solution was used without further purification.

Step 4: 2-((5-(Difluoromethoxy)pyridin-3-yl)amino)-1-(1H-indol-3-yl)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of N-benzylidene-5-(difluoromethoxy)pyridin-3-amine (0.999 mmol) in ethanol (1 mL), heated at 70° C. overnight. The residue was purified by flash chromatography on silica gel using a gradient of ethyl acetate (15% to 70%) in dichloromethane. Further purification by flash chromatography on silica gel using a gradient of methanol (1% to 7%) in dichloromethane followed by precipitation from dichloromethane furnished 0.018 g (6%) of the desired compound as a white solid. ESI/APCI(+): 394 (M+H). ESI/APCI(−): 392 (M−H). $^1$H NMR (DMSO-d$_6$) δ12.20 (1H, brs); 8.89 (1H, s); 8.17 (1H, d); 8.11 (1H, d); 7.65 (3H, d); 7.48 (1H, d); 7.41 (1H, t); 7.26-7.37 (2H, m); 7.17-7.26 (3H, m); 7.08 (1H, d); 7.02 (1H, s); 6.21 (1H, d).

Example 235: Preparation of 1-(5-fluoro-1-methyl-1H-indazol-3-yl)-2-((3-methoxyphenyl)amino)-2-phenylethanone Step 1: A mixture of 5-fluoro-1H-indazole-3-carbaldehyde (0.050 g; 0.305 mmol), cesium carbonate (0.397 g; 1.218 mmol) and methyl iodide (0.038 mL; 0.609 mmol) in DMSO (2.5 mL) was stirred at room temperature for 2 h. Water was added. The resulting precipitate was filtered, washed with water and dried to give 0.027 g (50%) of 5-fluoro-1-methyl-1H-indazole-3-carbaldehyde as a beige solid. ESI/APCI(+): 179 (M+H).
Step 2: 1-(5-Fluoro-1-methyl-1H-indazol-3-yl)-2-((3-methoxyphenyl)amino)-2-phenylethanone was prepared according to general procedure L from a mixture of 3-benzyl-5-(2-hydroxyethyl)-4-methylthiazolium chloride (0.020 g; 0.076 mmol) and triethylamine (0.011 mL; 0.076 mmol) in ethanol (0.5 mL), 5-fluoro-1-methyl-1H-indazole-3-carbaldehyde (0.027 g; 0.152 mmol) and a solution of N-benzylidene-3-methoxyaniline (0.152 mmol) in ethanol (0.5 mL), heated at 70° C. for 60 h. Purification by flash chromatography on silica gel using a gradient of ethyl acetate (5% to 50%) in heptane followed by precipitation from acetonitrile furnished 0.010 g (17%) of the desired compound as a yellow solid. ESI/APCI(+): 390 (M+H). $^1$H NMR (DMSO-d$_6$) (7.92 (1H, dd); 7.80 (1H, d); 7.61 (2H, d); 7.42-7.52 (1H, m); 7.29-7.39 (2H, m); 7.18-7.29 (1H, m); 6.95 (1H, t); 6.52-6.60 (1H, m); 6.39-6.48 (1H, m); 6.34 (2H, br s); 6.15 (1H, d); 4.29 (3H, s); 3.56 (3H, s).

Example 236: Preparation of 1-(1H-indol-3-yl)-2-((3-methoxyphenyl)amino)-2-(6-(methylamino)pyridin-3-yl)ethanone Step 1: 5-(((3-Methoxyphenyl)imino)methyl)-N-methylpyridin-2-amine was prepared quantitatively according to general procedure I from 6-(methylamino)nicotinaldehyde (0.136 g; 0.999 mmol) and 3-methoxyaniline (0.112 mL; 1.001 mmol).
Step 2: 1-(1H-Indol-3-yl)-2-((3-methoxyphenyl)amino)-2-(6-(methylamino)pyridin-3-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 5-(((3-methoxyphenyl)imino)methyl)-N-methylpyridin-2-amine (0.999 mmol) in ethanol (1 mL), heated at 70° C. for 4 days. The residue was purified by flash chromatography on silica gel using a gradient of methanol (0% to 12%) in dichloromethane. Further purification by flash chromatography on silica gel using a gradient of methanol (0% to 12%) in dichloromethane followed by precipitation from ethanol furnished 0.006 g (2%) of the desired compound. ESI/APCI (+): 387 (M+H). ESI/APCI(−): 385 (M−H).

Example 237: Preparation of 2-((3-methoxyphenyl)amino)-2-(5-methoxypyrazin-2-yl)-1-(1-methyl-1H-indazol-3-yl)ethanone 2-((3-Methoxyphenyl)amino)-2-(5-methoxypyrazin-2-yl)-1-(1-methyl-1H-indazol-3-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of 3-methoxy-N-((5-methoxypyrazin-2-yl)methylene)aniline (0.999 mmol) in ethanol (1 mL), heated at 70° C. for 24 h. The precipitate was filtered, washed with ethanol and dried to furnish 0.312 g (76%) of the desired compound as a white solid. ESI/APCI(+): 404 (M+H). $^1$H NMR (DMSO-d$_6$) δ 8.55 (1H, s); 8.21 (1H, s); 8.15 (1H, d); 7.81 (1H, d); 7.53 (1H, t); 7.33-7.43 (1H, m); 6.96 (1H, t); 6.62 (1H, d); 6.46 (1H, d); 6.33-6.42 (2H, m); 6.14-6.22 (1H, m); 4.22 (3H, s); 3.87 (3H, s); 3.63 (3H, s).

Example 238: Preparation of 2-((3-methoxyphenyl)amino)-1-(1-methyl-1H-indazol-3-yl)-2-(pyrazolo[1,5-a]pyridin-2-yl)ethanone 2-((3-Methoxyphenyl)amino)-1-(1-methyl-1H-indazol-3-yl)-2-(pyrazolo[1,5-a]pyridin-2-yl)ethanone was prepared according to general procedure L from a mixture of 3-benzyl-5-(2-hydroxyethyl)-4-methylthiazol-3-ium chloride (0.118 g; 0.438 mmol) and triethylamine (0.062 mL; 0.438 mmol) in ethanol (1 mL), 1-methyl-1H-indazole-3-carbaldehyde (0.140 g; 0.874 mmol) and a solution of 3-methoxy-N-(pyrazolo[1,5-a]pyridin-2-ylmethylene)aniline (0.876 mmol) in ethanol (1 mL) heated at 70° C. for 24 h. Purification by flash chromatography on silica gel using a gradient of ethyl acetate (0% to 80%) in heptane followed by precipitation from diethyl ether furnished 0.209 g (56%) of the desired compound as a white solid. ESI/APCI(+): 412 (M+H).

Example 239: Preparation of 1-(1H-indol-3-yl)-2-((3-methoxyphenyl)amino)-2-(pyrazin-2-yl)ethanone Step 1: 3-Methoxy-N-(pyrazin-2-ylmethylene)aniline was prepared quantitatively according to general procedure I from pyrazine-2-carbaldehyde (0.108 g; 0.999 mmol) and 3-methoxyaniline (0.112 mL; 1.001 mmol). ESI/APCI(+): 214 (M+H).
Step 2: 1-(1H-Indol-3-yl)-2-((3-methoxyphenyl)amino)-2-(pyrazin-2-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 3-methoxy-N-(pyrazin-2-ylmethylene)aniline (0.999 mmol) in ethanol (1 mL), heated at 70° C. for 24 h. Purification by flash chromatography on silica gel using a gradient of ethyl acetate (0% to 80%) in heptane followed by precipitation from diethyl ether furnished 0.046 g (13%) of the desired compound as a white solid. ESI/APCI(+): 359 (M+H). ESI/APCI(−): 357 (M−H).

Example 240: Preparation of 3-(2-((3-methoxyphenyl)amino)-2-phenylacetyl)-1-methyl-1H-indazole-5-carbonitrile Step 1: To a solution of 3-formyl-1H-imidazole-5-carbonitrile (0.100 g; 0.584 mmol) in DMSO (3 mL) were added potassium carbonate (0.330 g; 2.388 mmol) and methyl iodide (0.073 mL; 1.167 mmol). The reaction mixture was stirred at room temperature for 18 h. Water was added and the precipitate was filtered. The pink solid was dissolved in dichloromethane and washed with brine. The organic phase was dried over sodium sulfate, filtered and concentrated under reduced pressure to furnish 0.083 g (77%) of 3-formyl-1-methyl-1H-indazole-5-carbonitrile as an orange solid. ESI/APCI(+): 186 (M+H).

Step 2: 3-(2-((3-Methoxyphenyl)amino)-2-phenylacetyl)-1-methyl-1H-indazole-5-carbonitrile was prepared according to general procedure L from a mixture of 3-benzyl-5-(2-hydroxyethyl)-4-methylthiazol-3-ium chloride (0.133 g; 0.493 mmol) and triethylamine (0.100 mL; 0.717 mmol) in ethanol (0.7 mL), 3-formyl-1-methyl-1H-indazole-5-carbonitrile (0.179 g; 0.987 mmol) and a solution of N-benzylidene-3-methoxyaniline (0.985 mmol) in ethanol (1 mL), heated at 60° C. for 24 h. The precipitate formed during the reaction was filtered. The solid was recrystallized from diethyl ether and washed with methanol to furnish 0.230 g (59%) of the desired compound as a bright yellow solid. ESI/APCI(+): 397 (M+H). ESI/APCI(−): 395 (M−H).

Example 241: Preparation of 2-((6-methoxypyrazin-2-yl)amino)-1-(1-methyl-1H-indazol-3-yl)-2-phenylethanone 2-((6-Methoxypyrazin-2-yl)amino)-1-(1-methyl-1H-indazol-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of N-benzylidene-6-methoxypyrazin-2-amine (0.999 mmol) in ethanol (1 mL), heated at 70° C. for 24 h. Purification by flash chromatography on silica gel using a gradient of ethyl acetate (0% to 80%) in heptane followed by precipitation from diethyl ether furnished 0.049 g (13%) of the desired compound as a white solid. ESI/APCI(+): 374 (M+H).

Example 242: Preparation of 1-(1H-indol-3-yl)-2-((6-methoxypyridin-2-yl)amino)-2-phenylethanone 1-(1H-Indol-3-yl)-2-((6-methoxypyridin-2-yl)amino)-2-phenylethanone was prepared according to general procedure E from 2-bromo-1-(1H-indol-3-yl)-2-phenylethanone (0.045 g; 0.143 mmol) and 2-amino-6-methoxypyridine (0.089 g; 0.717 mmol) in acetonitrile (0.6 mL), irradiated in a microwave oven at 120° C. for 20 min. Purification by flash chromatography on silica gel using a gradient of ethyl acetate (20% to 60%) in heptane followed by recrystallization from ethyl acetate and heptane furnished 0.020 g (39%) of the desired product as a white powder. ESI/APCI(+): 358 (M+H); 380 (M+Na). ESI/APCI(−): 356 (M−H). $^1$H NMR (DMSO-d$_6$) δ 11.99 (1H, br s); 8.71 (1H, s); 8.17 (1H, d); 7.65 (2H, m); 7.44 (1H, d); 7.1-7.35 (7H, m); 6.41 (1H, d); 6.30 (1H, d); 5.86 (1H, d); 3.54 (3H, s).

Example 243: Preparation of 2-((3-(hydroxymethyl)-5-methoxyphenyl)amino)-1-(1-methyl-1H-indazol-3-yl)-2-phenylethanone 2-((3-(Hydroxymethyl)-5-methoxyphenyl)amino)-1-(1-methyl-1H-indazol-3-yl)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of (3-(benzylideneamino)-5-methoxyphenyl)methanol (0.999 mmol) in ethanol (1 mL), heated at 70° C. for 24 h. Purification by flash chromatography on silica gel using a gradient of ethyl acetate (10% to 100%) in heptane followed by precipitation from diethyl ether furnished 0.187 g (45%) of the desired compound as a light yellow solid. ESI/APCI(+): 402 (M+H).

Example 244: Preparation of 2-((3,5-dimethoxyphenyl)amino)-1-(1-methyl-1H-indazol-3-yl)-2-(pyridin-3-yl)ethanone 2-((3,5-Dimethoxyphenyl)amino)-1-(1-methyl-1H-indazol-3-yl)-2-(pyridin-3-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), 1-methyl-1H-indazole-3-carbaldehyde (0.160 g; 0.999 mmol) and a solution of 3,5-dimethoxy-N-(pyridin-3-ylmethylene)aniline (0.999 mmol) in ethanol (1 mL), heated at 70° C. for 24 h. Purification by flash chromatography on silica gel using a gradient of ethyl acetate (20% to 100%) in heptane followed by precipitation from diethyl ether furnished 0.077 g (18%) of the desired compound as a white solid. ESI/APCI(+): 403 (M+H). ESI/APCI(−): 401 (M−H). $^1$H NMR (DMSO-d$_6$) δ 8.83 (1H, d); 8.38-8.50 (1H, m); 8.14 (1H, d); 7.96 (1H, d); 7.82 (1H, d); 7.53 (1H, t); 7.30-7.44 (2H, m); 6.68 (1H, d); 6.49 (1H, d); 5.97 (2H, d); 5.77 (1H, s); 4.26 (3H, s); 3.60 (6H, s).

Example 245: Preparation of 1-(1H-indol-3-yl)-2-((6-methoxypyrazin-2-yl)amino)-2-(pyridin-3-yl)ethanone Step 1: A solution of 6-methoxy-N-(pyridin-3-ylmethylene)pyrazin-2-amine in ethanol was prepared by heating a solution of nicotinaldehyde (0.107 g; 0.999 mmol) and 6-methoxypyrazin-2-amine (0.125 g; 0.999 mmol) in ethanol (1 mL) at 60° C. for 6 h. The formation of the imine was quantitative and the solution was used without further purification.

Step 2: 1-(1H-Indol-3-yl)-2-((6-methoxypyrazin-2-yl)amino)-2-(pyridin-3-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of 6-methoxy-N-(pyridin-3-ylmethylene)pyrazin-2-amine (0.999 mmol) in ethanol (1 mL), heated at 70° C. overnight. Purification by flash chromatography on silica gel using a gradient of methanol (1% to 10%) in dichloromethane followed by purification by preparative HPLC (XBridge column; method 5) furnished 0.005 g (1%) of the desired compound as a yellow solid. ESI/APCI(+): 360 (M+H). ESI/APCI(-): 358 (M-H).

Example 246: Preparation of 1-(6-fluoro-1-methyl-1H-indazol-3-yl)-2-((3-methoxyphenyl)amino)-2-phenylethanone Step 1: To a suspension of lithium aluminum hydride (0.210 g; 5.553 mmol) in THF (20 mL) cooled to 0° C. was added dropwise a solution of 6-fluoro-1H-indazole-3-carboxylic acid (0.500 g; 2.776 mmol) in THF (5 mL). The reaction mixture was stirred at room temperature for 2 h. After cooling to 0° C., a saturated Rochelle salt solution was added. The reaction mixture was vigorously stirred and was extracted with ethyl acetate. The organic phase was dried over magnesium sulfate, filtered and concentrated under reduced pressure to furnish crude (6-fluoro-1H-indazol-3-yl)methanol as a white solid. ESI/APCI(+): 167 (M+H).

To a solution of (6-fluoro-1H-indazol-3-yl)methanol (0.207 g; 1.25 mmol) in dichloromethane (15 mL) was manganese(IV) oxide (1.080 g; 12.46 mmol). The resulting suspension was stirred at room temperature for 3 h and filtered through a pad of celite. The solid was washed with dichloromethane. The filtrate was concentrated under reduced pressure. Purification by flash chromatography on silica gel using a gradient of ethyl acetate (15% to 70%) in heptane furnished 0.153 g (34% over the two steps) of 6-fluoro-1H-indazole-3-carbaldehyde as a white solid. ESI/APCI(+): 165 (M+H). ESI/APCI(-): 163 (M-H).

Step 2: A mixture of 6-fluoro-1H-indazole-3-carbaldehyde (0.150 g; 0.914 mmol), cesium carbonate (1.190 g; 3.652 mmol) and methyl iodide (0.114 mL; 1.831 mmol) in DMSO (7.5 mL) was stirred at room temperature for 2 h. Water was added and the precipitate was filtered, washed with water and dried to afford 0.105 g (65%) of 6-fluoro-1-methyl-1H-indazole-3-carbaldehyde as a beige solid. ESI/APCI(+): 179 (M+H).

Step 3: 1-(6-Fluoro-1-methyl-1H-indazol-3-yl)-2-((3-methoxyphenyl)amino)-2-phenylethanone was prepared according to general procedure L from a mixture of 3-benzyl-5-(2-hydroxyethyl)-4-methylthiazolium chloride (0.079 g; 0.295 mmol) and triethylamine (0.041 mL; 0.295 mmol) in ethanol (1 mL), 6-fluoro-1-methyl-1H-indazole-3-carbaldehyde (0.105 g; 0.589 mmol) and a solution of N-benzylidene-3-methoxyaniline (0.589 mmol) in ethanol (1 mL), heated at 70° C. for 2 days. Purification by flash chromatography on silica gel using a gradient of ethyl acetate (2% to 40%) in heptane followed by precipitation from acetonitrile furnished 0.054 g (23%) of the desired compound as a yellow solid. ESI/APCI(+): 390 (M+H). ESI/APCI(-): 388 (M-H). $^1$H NMR (DMSO-d$_6$) δ8.13 (1H, dd); 7.74 (1H, d); 7.59 (2H, d); 7.18-7.40 (4H, m); 6.93 (1H, t); 6.49-6.60 (1H, m); 6.42 (1H, d); 6.26-6.37 (2H, m); 6.14 (1H, d); 4.22 (3H, s); 3.61 (3H, s).

Example 247: Preparation of 2-((3-(hydroxymethyl)-5-methoxyphenyl)amino)-1-(1H-indol-3-yl)-2-(pyridin-3-yl)ethanone Step 1: A solution of (3-methoxy-5-((pyridin-3-ylmethylene)amino)phenyl)methanol in ethanol was prepared by heating a solution of nicotinaldehyde (0.107 g; 0.999 mmol) and (3-amino-5-methoxyphenyl)methanol (0.153 g; 0.999 mmol) in ethanol (1 mL) at 60° C. for 6 h. The formation of the imine was quantitative and the solution was used without further purification.

Step 2: 2-((3-(Hydroxymethyl)-5-methoxyphenyl)amino)-1-(1H-indol-3-yl)-2-(pyridin-3-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of (3-methoxy-5-((pyridin-3-ylmethylene)amino)phenyl)methanol (0.999 mmol) in ethanol (1 mL), heated at 70° C. overnight. Purification by flash chromatography on silica gel using a gradient of methanol (1% to 10%) in dichloromethane followed by precipitation from diethyl ether and dichloromethane furnished 0.150 g (39%) of the desired compound as a yellow solid. ESI/APCI(+): 388 (M+H). ESI/APCI(-): 386 (M-H). $^1$H NMR (DMSO-d$_6$) δ12.23 (1H, br s); 8.85-8.98 (2H, m); 8.41 (1H, d); 8.18 (1H, d); 7.98 (1H, d); 7.50 (1H, d); 7.34 (1H, dd); 7.15-7.29 (2H, m); 6.38-6.50 (2H, m); 6.31 (1H, br s); 6.20 (1H, d); 6.16 (1H, s); 5.02 (1H, t); 4.32 (2H, d); 3.65 (3H, s).

Example 248: Preparation of 2-((3-(hydroxymethyl)-5-methoxyphenyl)amino)-1-(1H-indol-3-yl)-2-(6-methoxypyridin-3-yl)ethanone Step 1: A solution of (3-methoxy-5-(((6-methoxypyridin-3-yl)methylene)amino)phenyl)-methanol in ethanol was prepared by heating a solution of 6-methoxynicotinaldehyde (0.137 g; 0.999 mmol) and (3-amino-5-methoxyphenyl)methanol (0.153 g; 0.999 mmol) in ethanol (1 mL) at 60° C. for 6 h. The formation of the imine was quantitative and the solution was used without further purification.

Step 2: 2-((3-(Hydroxymethyl)-5-methoxyphenyl)amino)-1-(1H-indol-3-yl)-2-(6-methoxypyridin-3-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of (3-methoxy-5-(((6-methoxypyridin-3-yl)methylene)amino)phenyl)methanol (0.999 mmol) in ethanol (1 mL), heated at 70° C. overnight. Purification by flash chromatography on silica gel using a gradient methanol (1% to 7%) in dichloromethane followed by precipitation from diethyl ether furnished 0.081 g (19%) of the desired compound as a yellow solid. ESI/APCI(+): 418 (M+H). ESI/APCI(-): 416 (M-H). $^1$H NMR (DMSO-d$_6$) δ12.17 (1H, br s); 8.88 (1H, s); 8.47 (1H, s); 8.16 (1H, d); 7.85 (1H, dd); 7.48 (1H, d); 7.20 (2H, m); 6.74 (1H, d); 6.41 (1H, s); 6.23-6.37 (2H, m); 6.05-6.18 (2H, m); 5.00 (1H, t); 4.31 (2H, d); 3.77 (3H, s); 3.63 (3H, s).

Example 249: Preparation of 1-(1H-indol-3-yl)-2-((6-methoxypyrazin-2-yl)amino)-2-(6-methoxypyridin-3-yl)ethanone Step 1: A solution of 6-methoxy-N-((6-methoxypyridin-3-yl)methylene)pyrazin-2-amine in ethanol was prepared by heating a solution of 6-methoxynicotinaldehyde (0.137 g; 0.999 mmol) and 6-methoxypyrazin-2-amine (0.125 g; 0.999 mmol) in ethanol (1 mL) at 60° C. for 6 h. The formation of the imine was quantitative and the solution was used without further purification. ESI/APCI(+): 245 (M+H).

Step 1: 1-(1H-Indol-3-yl)-2-((6-methoxypyrazin-2-yl)amino)-2-(6-methoxypyridin-3-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol)

in ethanol (1.5 mL), tert-butyl 3-formyl-1H-indole-1-carboxylate (0.245 g; 0.999 mmol) and a solution of 6-methoxy-N-((6-methoxypyridin-3-yl)methylene)pyrazin-2-amine (0.999 mmol) in ethanol (1 mL), heated at 70° C. overnight. Purification by flash chromatography on silica gel using a gradient of ethyl acetate (30% to 100%) in dichloromethane followed by precipitation from dichloromethane furnished 0.137 g (30%) of the desired compound as a white solid. ESI/APCI(+): 390 (M+H). $^1$H NMR (DMSO-d$_6$) δ12.08 (1H, br s); 8.76 (1H, s); 8.50 (1H, d); 8.17 (1H, d); 7.80-7.94 (2H, m); 7.73 (1H, s); 7.46 (1H, d); 7.32 (1H, s); 7.12-7.26 (2H, m); 6.80 (1H, d); 6.39 (1H, d); 3.79 (3H, s); 3.60 (3H, s).

Example 250: Preparation of 1-(6-fluoro-1H-indol-3-yl)-2-((3-(hydroxymethyl)-5-methoxyphenyl)amino)-2-phenylethanone 1-(6-Fluoro-1H-indol-3-yl)-2-((3-(hydroxymethyl)-5-methoxyphenyl)amino)-2-phenylethanone was prepared according to general procedure K from a mixture of 3-benzyl-5-(2-hydroxyethyl)-4-methylthiazol-3-ium chloride (0.132 g; 0.489 mmol) and triethylamine (0.100 mL; 0.717 mmol) in ethanol (1 mL), tert-butyl 6-fluoro-3-formyl-1H-indole-1-carboxylate (0.262 g; 0.995 mmol) and a solution of (3-(benzylideneamino)-5-methoxyphenyl)methanol (0.974 mmol) in ethanol (1 mL), heated at 60° C. for 16 h. The residue was purified by flash chromatography on silica gel using a gradient of ethyl acetate (20% to 70%) in heptane. Further purification by flash chromatography on silica gel using a gradient of ethyl acetate (40% to 80%) in heptane followed by purification by solid phase extraction on C18-reversed phase column using a gradient of acetonitrile (0% to 90%) in water furnished 0.032 g (8%) of the desired compound as a yellow solid. ESI/APCI(+): 405 (M+H). ESI/APCI(−): 403 (M−H).

Example 251: Preparation of 3-(2-((3-methoxyphenyl)amino)-2-phenylacetyl)-1-methyl-1H-indazole-6-carbonitrile Step 1: To a solution of 3-formyl-1H-imidazole-6-carbonitrile (0.250 g; 1.461 mmol) in DMSO (7 mL) were added potassium carbonate (0.817 g; 5.911 mmol) and methyl iodide (0.185 mL; 2.958 mmol). The reaction mixture was stirred at room temperature for 18 h. Water was added and the precipitate was filtered. The pink solid was dissolved in dichloromethane and washed with brine. The organic phase was dried over sodium sulfate, filtered and concentrated under reduced pressure to furnish 0.247 g of crude 3-formyl-1-methyl-1H-indazole-6-carbonitrile (contaminated with 3-formyl-2-methyl-2H-indazole-6-carbonitrile). ESI/APCI (+): 186 (M+H).

Step 2: 3-(2-((3-Methoxyphenyl)amino)-2-phenylacetyl)-1-methyl-1H-indazole-6-carbonitrile was prepared according to general procedure L from a mixture of 3-benzyl-5-(2-hydroxyethyl)-4-methylthiazol-3-ium chloride (0.070 g; 0.259 mmol) and triethylamine (0.050 mL; 0.359 mmol) in ethanol (0.3 mL), 3-formyl-1-methyl-1H-indazole-6-carbonitrile (0.095 g; crude) and a solution of N-benzylidene-3-methoxyaniline (0.488 mmol) in ethanol (0.5 mL), heated at 60° C. for 16 h. The precipitate formed during the reaction was filtered, washed with ethanol and water and dried. The solid was purified by preparative HPLC (XBridge column; method 2) to furnish 0.064 g (11% over the two steps) of the desired compound as a yellow solid. ESI/APCI(+): 397 (M+H). ESI/APCI(−): 395 (M−H).

Example 252: Preparation of 1-(6-fluoro-1H-indol-3-yl)-2-((6-methoxypyrazin-2-yl)amino)-2-phenylethanone 1-(6-Fluoro-1H-indol-3-yl)-2-((6-methoxypyrazin-2-yl)amino)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.100 mL; 0.717 mmol) in ethanol (1 mL), tert-butyl 6-fluoro-3-formyl-1H-indole-1-carboxylate (0.268 g; 1.018 mmol) and a solution of N-benzylidene-6-methoxypyrazin-2-amine (0.999 mmol) in ethanol (1 mL), heated at 60° C. for 72 h. Purification by flash chromatography on silica gel using a gradient of ethyl acetate (20% to 80%) in heptane followed by purification by preparative HPLC (XBridge column; method 2) furnished 0.056 g (15%) of the desired compound as a pink solid. ESI/APCI(+): 377 (M+H). ESI/APCI(−): 375 (M−H).

Example 253: Preparation of 2-((3-(hydroxymethyl)-5-methoxyphenyl)amino)-1-(1H-indol-3-yl)-2-(5-methoxypyrazin-2-yl)ethanone Step 1: A solution of (3-methoxy-5-(((5-methoxypyrazin-2-yl)methylene)amino)phenyl)methanol in ethanol was prepared by heating a solution of 5-methoxypyrazine-2-carbaldehyde (0.138 g; 0.999 mmol) and (3-amino-5-methoxyphenyl)methanol (0.153 g; 0.999 mmol) in ethanol (1 mL) at 60° C. for 6 h. The formation of the imine was quantitative and the solution was used without further purification.

Step 2: 2-((3-(Hydroxymethyl)-5-methoxyphenyl)amino)-1-(1H-indol-3-yl)-2-(5-methoxypyrazin-2-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of (3-methoxy-5-(((5-methoxypyrazin-2-yl)methylene)amino)phenyl)methanol (0.999 mmol) in ethanol (1 mL), heated at 70° C. overnight. The residue was purified by flash chromatography on silica gel using a gradient of methanol (1% to 7%) in dichloromethane. Further purification by flash chromatography on silica gel using a gradient of ethyl acetate (15% to 70%) in dichloromethane followed by purification by preparative HPLC (XBridge column; method 5) furnished 0.089 g (21%) of the desired compound as a white solid. ESI/APCI(+): 419 (M+H). ESI/APCI(−): 417 (M−H). $^1$H NMR (DMSO-d$_6$) δ12.14 (1H, br s); 8.75 (1H, s); 8.49 (1H, s); 8.23 (1H, s); 8.15 (1H, d); 7.47 (1H, d); 7.12-7.28 (2H, m); 6.40 (1H, s); 6.26-6.36 (2H, m); 6.18-6.25 (1H, m); 6.15 (1H, s); 5.01 (1H, t); 4.31 (2H, d); 3.84 (3H, s); 3.64 (3H, s).

Example 254: Preparation of 2-((3-(hydroxymethyl)-5-methoxyphenyl)amino)-1-(1H-indol-3-yl)-2-(pyrazolo[1,5-a]pyridin-2-yl)ethanone Step 1: A mixture of pyrazolo[1,5-a]pyridine-2-carbaldehyde (0.066 g; 0.452 mmol) and (3-amino-5-methoxyphenyl)methanol (0.069 g; 0.451 mmol) in ethanol (0.4 mL) was heated at 60° C. overnight. The reaction mixture was concentrated under reduced pressure and the residue was dried under reduced pressure over phosphorus(V) oxide to give quantitatively 3-methoxy-5-((pyrazolo[1,5-a]pyridin-2-ylmethylene)amino)phenyl)methanol which was used without further purification.

Step 2: 2-((3-(Hydroxymethyl)-5-methoxyphenyl)amino)-1-(1H-indol-3-yl)-2-(pyrazolo[1,5-a]pyridin-2-yl)ethanone was prepared according to general procedure L from a mixture of 3-benzyl-5-(2-hydroxyethyl)-4-methylthiazol-3-ium chloride (0.061 g; 0.226 mmol) and triethylamine (0.032 mL; 0.231 mmol) in ethanol (0.5 mL), tert-butyl 3-formyl-1H-indole-1-carboxylate (0.111 g; 0.453 mmol) and a solution of (3-methoxy-5-((pyrazolo[1,5-a]pyridin-2-ylmethylene)amino)phenyl)methanol (0.451 mmol) in ethanol (0.5 mL), heated at 70° C. for 4 days. Purification by flash chromatography on silica gel using a gradient of ethyl acetate (20% to 100%) in heptane followed by a gradient of methanol (0% to 10%) in dichloromethane furnished 0.019 g (10%) of the desired compound as a white solid. ESI/APCI(+): 427 (M+H). ESI/APCI(−): 425 (M−H).

Example 255: Preparation of 1-(1H-indol-3-yl)-2-((6-methoxypyrazin-2-yl)amino)-2-(pyrazolo[1,5-a]pyridin-2-yl)ethanone Step 1: A mixture of pyrazolo[1,5-a]pyridine-2-carbaldehyde (0.066 g; 0.452 mmol) and 6-methoxypyrazin-2-amine (0.057 g; 0.456 mmol) in ethanol (0.4 mL) was heated at 60° C. overnight. The reaction mixture was concentrated under reduced pressure and the residue was dried under reduced pressure over phosphorus(V) oxide to give quantitatively 6-methoxy-N-(pyrazolo[1,5-a]pyridin-2-ylmethylene)pyrazin-2-amine which was used without further purification.

Step 2: 1-(1H-Indol-3-yl)-2-((6-methoxypyrazin-2-yl)amino)-2-(pyrazolo[1,5-a]pyridin-2-yl)ethanone was prepared according to general procedure L from a mixture of 3-benzyl-5-(2-hydroxyethyl)-4-methylthiazol-3-ium chloride (0.061 g; 0.226 mmol) and triethylamine (0.032 mL; 0.231 mmol) in ethanol (1 mL), tert-butyl 3-formyl-1H-indole-1-carboxylate (0.111 g; 0.453 mmol) and a solution of 6-methoxy-N-(pyrazolo[1,5-a]pyridin-2-ylmethylene)pyrazin-2-amine (0.452 mmol) in ethanol (1 mL), heated at 70° C. for 4 days. The residue was purified by flash chromatography on silica gel using a gradient of ethyl acetate (20% to 100%) in heptane followed by a gradient of methanol (0% to 12%) in dichloromethane. Further purification by flash chromatography on silica gel using a gradient of ethyl acetate (20% to 100%) in heptane furnished 0.004 g (2%) of the desired compound as a white solid. ESI/APCI(+): 399 (M+H). ESI/APCI(−): 397 (M−H).

Example 256: Preparation of 2-((3-(2-hydroxyethoxy)-5-methoxyphenyl)amino)-1-(1H-indol-3-yl)-2-(6-methoxypyridin-3-yl)ethanone Step 1: A mixture of 3-amino-5-methoxyphenol (1.860 g; 13.37 mmol), cesium carbonate (8.710 g; 26.73 mmol) and 2-bromoethanol (1.040 mL; 14.70 mmol) in DMF (40 mL) was stirred at 60° C. for 3 days. After cooling to room temperature, the reaction mixture was diluted with ethyl acetate and washed with a saturated sodium bicarbonate solution. The organic phase was concentrated under reduced pressure. Purification by flash chromatography on silica gel using a gradient of ethyl acetate (15% to 100%) in dichloromethane furnished 0.749 g (30%) of 2-(3-amino-5-methoxyphenoxy)ethanol as a brown solid. ESI/APCI(+): 184 (M+H).

Step 2: 2-(3-Methoxy-5-(((6-methoxypyridin-3-yl)methylene)amino)phenoxy)ethanol was prepared quantitatively according to general procedure I from 6-methoxynicotinaldehyde (0.069 g; 0.503 mmol) and 2-(3-amino-5-methoxyphenoxy)ethanol (0.092 g; 0.502 mmol).

Step 3: 2-((3-(2-Hydroxyethoxy)-5-methoxyphenyl)amino)-1-(1H-indol-3-yl)-2-(6-methoxypyridin-3-yl)ethanone was prepared according to general procedure K from a mixture of 3-benzyl-5-(2-hydroxyethyl)-4-methylthiazolium chloride (0.067 g; 0.248 mmol) and triethylamine (0.035 mL; 0.252 mmol) in ethanol (1 mL), tert-butyl 3-formyl-1H-indole-1-carboxylate (0.123 g; 0.501 mmol) and a solution of 2-(3-methoxy-5-(((6-methoxypyridin-3-yl)methylene)amino)phenoxy)ethanol (0.502 mmol) in ethanol (1 mL), heated at 70° C. overnight. Purification by flash chromatography on silica gel using a gradient of ethyl acetate (30% to 100%) in dichloromethane followed by purification by preparative HPLC (XBridge column; method 5) furnished 0.011 g (5%) the desired compound as a white solid. ESI/APCI(+): 448 (M+H). ESI/APCI(−): 446 (M−H). $^1$H NMR (DMSO-$d_6$) δ 12.17 (1H, br s); 8.90 (1H, s); 8.46 (1H, s); 8.16 (1H, d); 7.84 (1H, d); 7.47 (1H, d); 7.13-7.28 (2H, m); 6.75 (1H, d); 6.37 (1H, d); 6.09 (1H, d); 6.05 (2H, br s); 5.73 (1H, s); 4.79 (1H, t); 3.84 (2H, br s); 3.77 (3H, s); 3.65 (2H, br s); 3.62 (3H, s).

Example 257: Preparation of 2-((3-(2-hydroxyethoxy)-5-methoxyphenyl)amino)-1-(1H-indol-3-yl)-2-(5-methoxypyrazin-2-yl)ethanone Step 1: 2-(3-Methoxy-5-(((5-methoxypyrazin-2-yl)methylene)amino)phenoxy)ethanol was prepared quantitatively according to general procedure I from 5-methoxypyrazine-2-carbaldehyde (0.069 g; 0.500 mmol) and 2-(3-amino-5-methoxyphenoxy)ethanol (0.092 g; 0.502 mmol).

Step 2: 2-((3-(2-Hydroxyethoxy)-5-methoxyphenyl)amino)-1-(1H-indol-3-yl)-2-(5-methoxypyrazin-2-yl)ethanone was prepared according to general procedure K from a mixture of 3-benzyl-5-(2-hydroxyethyl)-4-methylthiazolium chloride (0.067 g; 0.248 mmol) and triethylamine (0.035 mL; 0.252 mmol) in ethanol (1 mL), tert-butyl 3-formyl-1H-indole-1-carboxylate (0.123 g; 0.501 mmol) and a solution of 2-(3-methoxy-5-(((5-methoxypyrazin-2-yl)methylene)amino)phenoxy)ethanol (0.500 mmol) in ethanol (1 mL), heated at 70° C. for 2 days. The residue was purified by flash chromatography on silica gel using a gradient of methanol (1% to 7%) in dichloromethane. Further purification by flash chromatography on silica gel using a gradient of ethyl acetate (15% to 70%) in dichloromethane followed by purification by preparative HPLC (XBridge column; method 5) furnished 0.008 g (3%) of the desired compound as a beige solid. ESI/APCI(+): 449 (M+H). ESI/APCI(−): 447 (M−H). $^1$H NMR (DMSO-$d_6$) δ12.14 (1H, br s); 8.76 (1H, s); 8.48 (1H, s); 8.23 (1H, s); 8.15 (1H, d); 7.47 (1H, d); 7.20 (2H, br s); 6.36 (1H, d); 6.21 (1H, d); 6.05 (2H, br s); 5.75 (1H, s); 4.79 (1H, t); 3.84 (5H, m); 3.55-3.71 (5H, m).

Example 258: Preparation of 2-((3,5-dimethoxyphenyl)amino)-1-(1H-indol-3-yl)-2-(pyrazolo[1,5-a]pyridin-2-yl)ethanone Step 1: A mixture of pyrazolo[1,5-a]pyridine-2-carbaldehyde (0.066 g; 0.452 mmol) and 3,5-dimethoxyaniline (0.069 g; 0.450 mmol) in ethanol (0.4 mL) was heated at 60° C. overnight. The reaction mixture was concentrated under reduced pressure and the residue was dried under reduced pressure over phosphorus(V) oxide to give quantitatively 3,5-dimethoxy-N-(pyrazolo[1,5-a]pyridin-2-ylmethylene) aniline which was used without further purification.

Step 2: 2-((3,5-Dimethoxyphenyl)amino)-1-(1H-indol-3-yl)-2-(pyrazolo[1,5-a]pyridin-2-yl)ethanone was prepared according to general procedure L from a mixture of 3-benzyl-5-(2-hydroxyethyl)-4-methylthiazol-3-ium chloride (0.061 g; 0.226 mmol) and triethylamine (0.032 mL; 0.231 mmol) in ethanol (1 mL), tert-butyl 3-formyl-1H-indole-1-carboxylate (0.111 g; 0.453 mmol) and a solution of 3,5-dimethoxy-N-(pyrazolo[1,5-a]pyridin-2-ylmethylene)aniline (0.450 mmol) in ethanol (1 mL), heated at 70° C. for 4 days. The residue was purified by flash chromatography on silica gel using a gradient of ethyl acetate (20% to 100%) in heptane. Further purification by flash chromatography on silica gel using a gradient of methanol (0% to 10%) in dichloromethane followed by purification by preparative HPLC (XBridge column; method 4) furnished 0.003 g (1%) of the desired compound. ESI/APCI(+): 427 (M+H). ESI/APCI(−): 425 (M−H).

Example 259: Preparation of 2-((3,5-dimethoxyphenyl)amino)-1-(1H-indol-3-yl)-2-(5-methoxypyrazin-2-yl)ethanone Step 1: A mixture of 5-methoxypyrazine-2-carbaldehyde (0.138 g; 0.999 mmol) and 3,5-dimethoxyaniline (0.153 g; 0.999 mmol) in ethanol (1 mL) was heated at 60° C. overnight. The reaction mixture was concentrated under reduced pressure and the residue was dried under reduced pressure over phosphorus(V) oxide to give quantitatively 3,5-dimethoxy-N-((5-methoxypyrazin-2-yl)methylene)aniline which was used without further purification.

Step 2: 2-((3,5-Dimethoxyphenyl)amino)-1-(1H-indol-3-yl)-2-(5-methoxypyrazin-2-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 3,5-dimethoxy-N-((5-methoxypyrazin-2-yl)methylene)aniline (0.999 mmol) in ethanol (1 mL), heated at 70° C. for 4 days. The residue was purified by flash chromatography on silica gel using a gradient of ethyl acetate (25% to 100%) in heptane. Further purification by flash chromatography on silica gel using ethyl acetate/dichloromethane/heptane (3/3/4) as eluent followed by purification by preparative HPLC (XBridge column; method 4) furnished 0.009 g (2%) of the desired compound. ESI/APCI(+): 419 (M+H). ESI/APCI(−): 417 (M−H).

Example 260: Preparation of 1-(5-fluoro-1H-indol-3-yl)-2-((3-methoxyphenyl)amino)-2-(5-methoxypyrazin-2-yl)ethanone 1-(5-Fluoro-1H-indol-3-yl)-2-((3-methoxyphenyl)amino)-2-(5-methoxypyrazin-2-yl)ethanone was prepared according to general procedure L from a mixture of 3-benzyl-5-(2-hydroxyethyl)-4-methylthiazol-3-ium chloride (0.101 g; 0.374 mmol) and triethylamine (0.070 mL; 0.502 mmol) in ethanol (0.5 mL), tert-butyl 5-fluoro-3-formyl-1H-indole-1-carboxylate (0.194 g; 0.737 mmol) and a solution of 3-methoxy-N-((5-methoxypyrazin-2-yl)methylene)aniline (0.724 mmol) in ethanol (1 mL), heated at 60° C. for 96 h. Purification by flash chromatography on silica gel using a gradient of ethyl acetate (0% to 50%) in heptane followed by purification by preparative HPLC (XBridge column; method 2) furnished 0.120 g (41%) of the desired compound as a yellow solid. ESI/APCI(+): 407 (M+H). ESI/APCI(−): 405 (M−H).

Example 261: Preparation of 1-(5-fluoro-1H-indol-3-yl)-2-((3-(hydroxymethyl)-5-methoxyphenyl)amino)-2-phenylethanone 1-(5-Fluoro-1H-indol-3-yl)-2-((3-(hydroxymethyl)-5-methoxyphenyl)amino)-2-phenylethanone was prepared according to general procedure L from a mixture of 3-benzyl-5-(2-hydroxyethyl)-4-methylthiazol-3-ium chloride (0.084 g; 0.311 mmol) and triethylamine (0.065 mL; 0.466 mmol) in ethanol (0.5 mL), tert-butyl 5-fluoro-3-formyl-1H-indole-1-carboxylate (0.177 g; 0.672 mmol) and a solution of (3-(benzylideneamino)-5-methoxyphenyl)methanol (0.655 mmol) in ethanol (1 mL), heated at 60° C. for 96 h. Purification by flash chromatography on silica gel using a gradient of ethyl acetate (0% to 50%) in heptane followed by purification by solid phase extraction on C18-reversed phase column using a gradient of acetonitrile (20% to 80%) in water furnished 0.053 g (20%) of the desired compound as a brown solid. ESI/APCI(+): 405 (M+H). ESI/APCI(−): 403 (M−H). $^1$H NMR (DMSO-$d_6$) δ 12.25 (1H, br s); 8.93 (1H, s); 7.82 (1H, dd); 7.63 (1H, d); 7.48 (1H, dd); 7.29 (1H, t); 7.16 (1H, t); 7.05 (1H, dt); 6.40 (1H, s); 6.29 (1H, d); 6.26 (1H, s); 6.11 (1H, s); 6.07 (1H, d); 4.98 (1H, t); 4.29 (2H, d); 3.62 (3H, s).

Example 262: Preparation of 1-(6-fluoro-1H-indol-3-yl)-2-((3-methoxyphenyl)amino)-2-(5-methoxypyrazin-2-yl)ethanone 1-(6-Fluoro-1H-indol-3-yl)-2-((3-methoxyphenyl)amino)-2-(5-methoxypyrazin-2-yl)ethanone was prepared according to general procedure L from a mixture of 3-benzyl-5-(2-hydroxyethyl)-4-methylthiazol-3-ium chloride (0.133 g; 0.493 mmol) and triethylamine (0.100 mL; 0.717 mmol) in ethanol (0.5 mL), tert-butyl 6-fluoro-3-formyl-1H-indole-1-carboxylate (0.253 g; 0.961 mmol) and a solution of 3-methoxy-N-((5-methoxypyrazin-2-yl)methylene)aniline (0.933 mmol) in ethanol (1 mL), heated at 60° C. for 96 h. Purification by flash chromatography on silica gel using a gradient of ethyl acetate (0% to 40%) in heptane followed by precipitation from diethyl ether furnished 0.146 g (39%) of the desired compound as a white solid. ESI/APCI(+): 407 (M+H). ESI/APCI(−): 405 (M−H).

Example 263: Preparation of 2-((3-(2-hydroxyethoxy)-5-methoxyphenyl)amino)-1-(1-methyl-1H-indazol-3-yl)-2-phenylethanone Step 1: 2-(3-(Benzylideneamino)-5-methoxyphenoxy)ethanol was prepared quantitatively according to general procedure I from benzaldehyde (0.102 mL; 1.004 mmol) and 2-(3-amino-5-methoxyphenoxy)ethanol (0.183 g; 0.999 mmol).

Step 2: 2-((3-(2-Hydroxyethoxy)-5-methoxyphenyl)amino)-1-(1-methyl-1H-indazol-3-yl)-2-phenylethanone was prepared according to general procedure L from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), 1-methyl-1H-indazole-3-carbaldehyde (0.160 g; 0.999 mmol) and a solution of 2-(3-(benzylideneamino)-5-methoxyphenoxy)ethanol (0.999 mmol) in ethanol (1.5 mL), heated at 70° C. overnight. Purification by flash chromatography on silica gel using a gradient of ethyl acetate (2% to 40%) in dichloromethane followed by purification by preparative HPLC (XBridge column; method 1) furnished 0.031 g (7%) of the desired compound as a beige solid. ESI/APCI(+): 432 (M+H). $^1$H NMR (DMSO-d$_6$) δ 8.14 (1H, d); 7.82 (1H, d); 7.59 (2H, d); 7.46-7.56 (1H, m); 7.16-7.43 (5H, m); 6.54 (1H, d); 6.44 (1H, d); 5.95 (2H, br s); 5.74 (1H, s); 4.78 (1H, br s); 4.27 (3H, s); 3.81 (2H, m); 3.53-3.70 (5H, m).

Example 264: Enantiomers separation of 1-(1H-indol-3-yl)-2-((5-methoxypyridin-3-yl)amino)-2-phenylethanone leading to (−)-1-(1H-indol-3-yl)-2-((5-methoxypyridin-3-yl)amino)-2-phenylethanone and (+)-1-(1H-indol-3-yl)-2-((5-methoxypyridin-3-yl)amino)-2-phenylethanone 1-(1H-Indol-3-yl)-2-((5-methoxypyridin-3-yl)amino)-2-phenylethanone (0.054 g) was separated into its enantiomers and purified by preparative HPLC (ChiralPak column; method 6). Under these conditions, 0.021 g of the faster eluting enantiomer (t$_r$=6.7 min; ee>98%) and 0.020 g of the slower eluting enantiomer (t$_r$=12.1 min; ee=96%) were obtained.

Example 265: Preparation of 1-(1H-indol-3-yl)-2-((3-methoxyphenyl)amino)-2-(pyridin-2-yl)ethanone Step 1: 3-Methoxy-N-(pyridin-2-ylmethylene)aniline was prepared quantitatively according to general procedure I from picolinaldehyde (0.107 g; 0.999 mmol) and 3-methoxyaniline (0.112 mL; 1.001 mmol).
Step 2: 1-(1H-Indol-3-yl)-2-((3-methoxyphenyl)amino)-2-(pyridin-2-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 3-methoxy-N-(pyridin-2-ylmethylene)aniline (0.999 mmol) in ethanol (1 mL), heated at 70° C. for 3 days. Purification by flash chromatography on silica gel using a gradient of ethyl acetate (0% to 100%) in heptane followed by crystallization from acetonitrile furnished 0.013 g (4%) of the desired compound as a white solid. ESI/APCI (+): 358 (M+H). ESI/APCI(−): 356 (M−H).

Example 266: Preparation of 1-(1H-indol-4-yl)-2-((3-methoxyphenyl)amino)-2-phenylethanone Step 1: tert-butyl 4-Formyl-1H-indole-1-carboxylate was prepared according to general procedure F from 1H-indole-4-carbaldehyde (0.435 g; 2.997 mmol), di-tert-butyl dicarbonate (0.786 g; 3.601 mmol) and DMAP (0.037 g; 0.303 mmol) in acetonitrile (7.5 mL) to afford 0.654 g (89%) of the desired compound as a brown oil. $^1$H NMR (DMSO-d$_6$) 10.26 (1H, s); 8.41 (1H, d); 7.92 (1H, d); 7.88 (1H, d); 7.57 (1H, t); 7.34 (1H, d); 1.65 (9H, s).
Step 2: 1-(1H-Indol-4-yl)-2-((3-methoxyphenyl)amino)-2-phenylethanone was prepared according to general procedure K from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 4-formyl-1H-indole-1-carboxylate (0.245 g; 0.999 mmol) and a solution of N-benzylidene-3-methoxyaniline (0.999 mmol) in ethanol (1 mL), heated at 70° C. for 3 days. Purification by flash chromatography on silica gel using a gradient of ethyl acetate (0% to 100%) in heptane followed by purification by preparative HPLC (XBridge column; method 4) furnished 0.051 g (14%) of the desired compound. ESI/APCI(+): 357 (M+H). ESI/APCI(−): 355 (M−H).

Example 267: Preparation of 1-(1-(2-hydroxyethyl)-1H-indazol-3-yl)-2-((3-methoxyphenyl)amino)-2-phenylethanone Step 1: To a solution of 1H-indazole-3-carbaldehyde (0.201 g; 1.375 mmol), potassium carbonate (0.218 g; 1.577 mmol) and lithium iodide (0.095 g; 0.710 mmol) in NMP (3 mL) was added 2-(2-chloroethoxy)tetrahydro-2H-pyran (0.210 mL; 1.422 mmol). The reaction mixture was stirred at 80° C. for 20 h. After cooling to room temperature, water was added and the reaction mixture was extracted with ethyl acetate. The organic phase was washed with brine, dried over magnesium sulfate, filtered and concentrated under reduced pressure. Purification by flash chromatography on silica gel using a gradient of ethyl acetate (0% to 35%) in heptane furnished 0.145 g (38%) of 1-(2-((tetrahydro-2H-pyran-2-yl)oxy)ethyl)-1H-indazole-3-carbaldehyde as a pale yellow oil.
Step 2: 2-((3-Methoxyphenyl)amino)-2-phenyl-1-(1-(2-((tetrahydro-2H-pyran-2-yl)oxy)ethyl)-1H-indazol-3-yl)ethanone was prepared according to general procedure L from a mixture of 3-benzyl-5-(2-hydroxyethyl)-4-methylthiazol-3-ium chloride (0.067 g; 0.248 mmol) and triethylamine (0.050 mL; 0.359 mmol) in ethanol (0.7 mL), 1-(2-((tetrahydro-2H-pyran-2-yl)oxy)ethyl)-1H-indazole-3-carbaldehyde (0.145 g; 0.529 mmol) and a solution of N-benzylidene-3-methoxyaniline (0.483 mmol) in ethanol (1.2 mL), heated at 60° C. for 16 h. Purification by flash chromatography on silica gel using a gradient of ethyl acetate (0% to 30%) in heptane furnished 0.138 g (59%) of the desired product as a yellow oil (80% purity). ESI/APCI (+): 486 (M+H).
Step 2: To a solution of 2-((3-methoxyphenyl)amino)-2-phenyl-1-(1-(2-((tetrahydro-2H-pyran-2-yl)oxy)ethyl)-1H-indazol-3-yl)ethanone (0.138 g; 0.284 mmol) in acetonitrile (3 mL) was added a 1N hydrochloric acid solution (0.150 mL; 0.150 mmol). The reaction mixture was stirred at room temperature for 24 h. The reaction mixture was concentrated under reduced pressure. Purification by preparative HPLC (XBridge column; method 2) furnished 0.022 g (36%) of the desired compound as a yellow oil. ESI/APCI(+): 402 (M+H).

Example 268: Preparation of 2-((3-(2-(tert-butoxy)ethoxy)-5-methoxyphenyl)amino)-1-(1-methyl-1H-indol-3-yl)-2-phenylethanone 2-((3-(2-(tert-Butoxy)ethoxy)-5-methoxyphenyl)amino)-1-(1-methyl-1H-indol-3-yl)-2-phenylethanone was prepared according to general procedure C from 2-chloro-1-(1-methyl-1H-indol-3-yl)-2-phenylethanone (0.100 g; 0.352 mmol), triethylamine (0.057 mL; 0.423 mmol) and 3-(2-(tert-butoxy)ethoxy)-5-methoxyaniline (0.107 g; 0.423 mmol) in acetonitrile (1 mL), irradiated in a microwave oven at 130° C. for 15 min and at 150° C. for 1 h. Purification by flash chromatography on silica gel using a gradient of ethyl acetate (5% to 50%) in heptane furnished 0.151 g (88%) of the desired compound as an oil. ESI/APCI(+): 487 (M+H), 509 (M+Na). ESI/APCI(−): 485 (M−H).

Example 269: Preparation of 2-((3-(2-hydroxyethoxy)-5-methoxyphenyl)amino)-1-(1-methyl-1H-indol-3-yl)-2-phenylethanone 2-((3-(2-(tert-Butoxy)ethoxy)-5-methoxyphenyl)amino)-1-(1-methyl-1H-indol-3-yl)-2-phenylethanone (0.150 g;

0.308 mmol) was dissolved in a 4N hydrogen chloride solution in dioxane (10.00 mL; 40.00 mmol). The reaction mixture was stirred at room temperature for 6 h and was concentrated under reduced pressure. The residue was partitioned between dichloromethane and a saturated sodium bicarbonate solution. The phases were separated. The organic phase was concentrated under reduced pressure. The residue was purified by flash chromatography on silica gel using a gradient of ethyl acetate (30% to 100%) in heptane. Further purification by flash chromatography on silica gel using a gradient of ethyl acetate (2% to 40%) in dichloromethane furnished 0.032 g (24%) of 2-((3-(2-hydroxyethoxy)-5-methoxyphenyl)amino)-1-(1-methyl-1H-indol-3-yl)-2-phenylethanone as a white solid. ESI/APCI(+): 431 (M+H). $^1$H NMR (DMSO-$d_6$) δ8.94 (1H, br s); 8.17 (1H, d); 7.63 (2H, d); 7.55 (1H, d); 7.11-7.37 (5H, m); 6.35 (1H, d); 5.91-6.08 (3H, m); 5.72 (1H, br s); 4.79 (1H, br s); 3.90 (3H, s); 3.83 (2H, m); 3.61 (5H, m).

Example 270: Preparation of 3-methoxy-5-((2-(1-methyl-1H-indol-3-yl)-2-oxo-1-phenylethyl)amino) benzyl acetate Step 1: To a solution of (3-amino-5-methoxyphenyl) methanol (0.300 g; 1.958 mmol), triethylamine (0.817 mL; 5.894 mmol) and DMAP (0.024 g; 0.196 mmol) in dichloromethane (10 ml) was added dropwise acetic anhydride (0.184 mL; 1.965 mmol). The reaction mixture was stirred at room temperature for 1.5 h and the reaction mixture was concentrated under reduced pressure. Purification by flash chromatography on silica gel using a gradient of ethyl acetate (15% to 70%) in heptane furnished 0.314 g (82%) of 3-amino-5-methoxybenzyl acetate as an oil. ESI/APCI(+): 196 (M+H).

Step 2: 3-Methoxy-5-((2-(1-methyl-1H-indol-3-yl)-2-oxo-1-phenylethyl)amino)benzyl acetate was prepared according to general procedure C from 2-chloro-1-(1-methyl-1H-indol-3-yl)-2-phenylethanone (0.080 g; 0.282 mmol), triethylamine (0.078 mL; 0.564 mmol) and 3-amino-5-methoxybenzyl acetate (0.110 g; 0.564 mmol) in acetonitrile (1 mL), irradiated in a microwave oven at 150° C. for 1 h. Purification by flash chromatography on silica gel using a gradient of ethyl acetate (5% to 50%) in heptane furnished 0.057 g (46%) of the desired compound as an orange solid. ESI/APCI(+): 443 (M+H); 465 (M+Na).

Example 271: Preparation of 2-((3-(hydroxymethyl)-5-methoxyphenyl)amino)-1-(1-methyl-1H-indol-3-yl)-2-phenylethanone To a solution of 3-methoxy-5-((2-(1-methyl-1H-indol-3-yl)-2-oxo-1-phenylethyl)amino)benzyl acetate (0.057 g; 0.129 mmol) in a mixture of THF (1.5 mL) and methanol (1.5 mL) was added potassium carbonate (0.036 g; 0.258 mmol). After stirring at room temperature for 3 h, the reaction mixture was diluted with dichloromethane and filtered through a plug of celite. The filtrate was concentrated under reduced pressure. Purification by flash chromatography on silica gel using a gradient of ethyl acetate (30% to 100%) in heptane followed by precipitation from diethyl ether furnished 0.020 g (38%) of 2-((3-(hydroxymethyl)-5-methoxyphenyl)amino)-1-(1-methyl-1H-indol-3-yl)-2-phenylethanone as a beige solid. ESI/APCI(+): 401 (M+H). ESI/APCI(−): 399 (M−H). $^1$H NMR (DMSO-$d_6$) δ8.92 (1H, s); 8.17 (1H, d); 7.63 (2H, d); 7.54 (1H, d); 7.11-7.35 (5H, m); 6.39 (1H, s); 6.29 (1H, d); 6.24 (1H, s); 6.12 (1H, s); 5.99 (1H, d); 4.99 (1H, t); 4.29 (2H, d); 3.90 (3H, s); 3.62 (3H, s).

Example 272: Preparation of 1-(isoquinolin-4-yl)-2-((3-methoxyphenyl)amino)-2-phenylethanone 1-(Isoquinolin-4-yl)-2-((3-methoxyphenyl)amino)-2-phenylethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), isoquinoline-4-carbaldehyde (0.157 g, 0.999 mmol) and a solution of N-benzylidene-3-methoxyaniline (0.999 mmol) in ethanol (1 mL), heated at 70° C. for 24 h. Purification by flash chromatography on silica gel using a gradient of ethyl acetate (20% to 100%) in heptane followed by precipitation from diethyl ether furnished 0.002 g (1%) of the desired compound as a white solid. ESI/APCI(+): 369 (M+H). ESI/APCI(−): 367 (M−H).

Example 273: Preparation of 1-(1H-indol-3-yl)-2-((3-methoxyphenyl)amino)-2-(5-methylpyridin-3-yl) ethanone Step 1: A solution of 3-methoxy-N-((5-methylpyridin-3-yl)methylene)aniline in ethanol was prepared by heating a solution of 5-methylnicotinaldehyde (0.105 g; 0.867 mmol) and 3-methoxyaniline (0.111 mL; 0.983 mmol) in ethanol (0.5 mL) at 60° C. for 24 h. The formation of the imine was quantitative and the solution was used without further purification.

Step 2: 1-(1H-Indol-3-yl)-2-((3-methoxyphenyl)amino)-2-(5-methylpyridin-3-yl)ethanone was prepared according to general procedure K from a mixture of 3-benzyl-5-(2-hydroxyethyl)-4-methylthiazol-3-ium chloride (0.130 g; 0.482 mmol) and triethylamine (0.100 mL; 0.717 mmol) in ethanol (0.5 mL), tert-butyl 3-formyl-1H-indole-1-carboxylate (0.230 g; 0.938 mmol) and a solution of 3-methoxy-N-((5-methylpyridin-3-yl)methylene)aniline (0.867 mmol) in ethanol (1 mL), heated at 60° C. for 96 h. Purification by flash chromatography on silica gel using a gradient of ethyl acetate (50% to 100%) in heptane followed by precipitation from diethyl ether furnished 0.029 g (9%) of the desired compound as a white solid. ESI/APCI(+): 372 (M+H). ESI/APCI(−): 370 (M−H).

Example 274: Preparation of 1-(1H-indol-3-yl)-2-((3-methoxyphenyl)amino)-2-(5-methoxypyridin-2-yl)ethanone Step 1: A solution of 3-methoxy-N-((5-methoxypyridin-2-yl)methylene)aniline in ethanol was prepared by heating a solution of 5-methoxypicolinaldehyde (0.137 g; 0.999 mmol) and m-anisidine (0.112 mL; 1.000 mmol) in ethanol (1 mL) at 60° C. overnight. The formation of the imine was quantitative and the solution was used without further purification. ESI/APCI(+): 243 (M+H); 265 (M+Na).

Step 2: 1-(1H-Indol-3-yl)-2-((3-methoxyphenyl)amino)-2-(5-methoxypyridin-2-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of 3-methoxy-N-((5-methoxypyridin-2-yl)methylene)aniline (0.999 mmol) in ethanol (1 mL), heated at 70° C. overnight. The residue was purified by flash chromatography on silica gel using a gradient of ethyl acetate (5% to 50%) in dichloromethane. Further purification by flash chromatography on silica gel using a gradient of ethyl acetate (30% to 100%) in heptane followed by precipitation from diethyl ether and heptane furnished 0.139 g (36%) of the desired compound as a beige solid. ESI/APCI(+): 388 (M+H). ESI/APCI(−): 386 (M−H). $^1$H NMR (DMSO-d$_6$) δ12.07 (1H, br s); 8.71 (1H, d); 8.22 (1H, d); 8.15 (1H, d); 7.53 (1H, d); 7.46 (1H, d); 7.33 (1H, dd); 7.12-7.25 (2H, m); 6.92 (1H, t); 6.28-6.45 (3H, m); 6.01-6.17 (2H, m); 3.75 (3H, s); 3.63 (3H, s).

Example 275: Preparation of 2-(6,7-dihydro-4H-pyrazolo[5,1-c][1,4]oxazin-2-yl)-1-(1H-indol-3-yl)-2-((3-methoxyphenyl)amino)ethanone Step 1: To a solution of morpholine-3-carboxylic acid hydrochloride (1.000 g; 5.967 mmol) in water (3 mL) cooled to 0° C. was added portionwise sodium nitrite (0.553 g; 8.015 mmol). The reaction mixture was stirred at 0° C. for 1 h. The reaction mixture was concentrated under reduced pressure. The residue was taken up in acetone. The solid was filtered. The filtrate was concentrated under reduced pressure. The residue was coevaporated with THF to furnish 4-nitrosomorpholine-3-carboxylic acid as a pale yellow foam which was used in the next step without further purification. ESI/APCI(−): 159 (M−H).

Step 2: To solution of 4-nitrosomorpholine-3-carboxylic acid (5.967 mmol) in THF (25 mL) cooled to 0° C. was added dropwise a solution of trifluoroacetic anhydride (0.850 mL; 6.018 mmol) in THF (2 mL). The reaction mixture was stirred at 0° C. for 5 h and at room temperature overnight. The reaction mixture was concentrated under reduced pressure. The residue was dissolved in ethyl acetate (25 mL) and stirred with potassium carbonate. The solid was filtered through cellite. The filtrate was concentrated under reduced pressure to furnish 6,7-dihydro-4H-[1,2,3]oxadiazolo[4,3-c][1,4]oxazin-8-ium-3-olate as a pale brown wax which was used in the next step without purification. ESI/APCI (+): 143 (M+H).

Step 3: To a solution of 6,7-dihydro-4H-[1,2,3]oxadiazolo[4,3-c][1,4]oxazin-8-ium-3-olate (5.967 mmol) in xylene (20 mL) was added ethyl propiolate (0.650 mL; 6.414 mmol). The reaction mixture was heated at 140° C. for 5 h. Ethyl propiolate (0.500 mL, 4.934 mmol) was added again and the reaction mixture was heated at 140° C. for 16 h. After cooling to room temperature, the reaction mixture was concentrated under reduced pressure. Purification by flash chromatography on silica gel using ethyl acetate (50%) in heptane as eluent furnished 0.638 g (55% over 3 steps) of ethyl 6,7-dihydro-4H-pyrazolo[5,1-c][1,4]oxazine-2-carboxylate as a yellow solid. ESI/APCI (+): 197 (M+H). $^1$H NMR (DMSO-d$_6$) δ 6.55 (1H, s); 4.80 (1H, s), 4.28 (2H, q); 4.18 (1H, t); 4.08 (2H, t); 1.27 (3H, t).

Step 4: To a solution of ethyl 6,7-dihydro-4H-pyrazolo[5,1-c][1,4]oxazine-2-carboxylate (0.327 g; 1.667 mmol) in THF (5 mL) cooled to −78° C. was added lithium aluminium hydride (0.100 g; 2.635 mmol). The reaction mixture was allowed to warm to room temperature and was stirred at room temperature overnight. Water was added and the reaction mixture was stirred for 10 min. After addition of magnesium sulfate, stirring was continued for 5 min. The reaction mixture was filtered and the solid was washed with ethyl acetate. The filtrate was concentrated under reduced pressure to furnish 0.245 g (95%) of (6,7-dihydro-4H-pyrazolo[5,1-c][1,4]oxazin-2-yl)methanol as a yellow oil. ESI/APCI (+): 155 (M+H). $^1$H NMR (DMSO-d$_6$) δ 5.97 (1H, s); 4.99 (1H, t); 4.75 (2H, s); 4.36 (1H, d); 4.02 (4H, s).

Step 5: To a solution of (6,7-dihydro-4H-pyrazolo[5,1-c][1,4]oxazin-2-yl)methanol (0.237 g; 1.537 mmol) in dichloroethane (12 mL) was added manganese dioxide (1.210 g; 13.92 mmol). The reaction mixture was stirred at 60° C. for 1 h and at room temperature for 18 h. The reaction mixture was filtered through celite. The solid was washed with dichloromethane and ethyl acetate. The filtrate was concentrated under reduced pressure to furnish 0.201 g (86%) of 6,7-dihydro-4H-pyrazolo[5,1-c][1,4]oxazine-2-carbaldehyde as an orange solid. ESI/APCI (+): 153 (M+H).

Step 6: A solution of N-((6,7-dihydro-4H-pyrazolo[5,1-c][1,4]oxazin-2-yl)methylene)-3-methoxyaniline in ethanol was prepared by heating a solution of 6,7-dihydro-4H-pyrazolo[5,1-c][1,4]oxazine-2-carbaldehyde (0.102 g; 0.670 mmol) and 3-methoxyaniline (0.078 mL; 0.690 mmol) in ethanol (0.5 mL) at 60° C. for 18 h. The formation of the imine was quantitative and the solution was used without further purification.

Step 7: 2-(6,7-Dihydro-4H-pyrazolo[5,1-c][1,4]oxazin-2-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.089 g; 0.330 mmol) and triethylamine (0.070 mL; 0.502 mmol) in ethanol (0.5 mL), tert-butyl 3-formyl-1H-indole-1-carboxylate (0.193 g; 0.787 mmol) and a solution of N-((6,7-dihydro-4H-pyrazolo[5,1-c][1,4]oxazin-2-yl)methylene)-3-methoxyaniline (0.670 mmol) in ethanol (1 mL), heated at 60° C. for 24 h. Purification by flash chromatography on silica gel using a gradient of ethyl acetate (20% to 100%) in heptane followed by precipitation from diethyl ether furnished 0.087 g (32%) of the desired compound as a white solid. ESI/APCI(+): 403 (M+H). ESI/APCI(−): 401 (M−H).

Example 276: Preparation of 1-(1H-indol-3-yl)-2-((3-methoxyphenyl)amino)-2-(5-methoxypyridin-3-yl)ethanone Step 1: A solution of 3-methoxy-N-((5-methoxypyridin-3-yl)methylene)aniline in ethanol was prepared by heating a solution of 5-methoxynicotinaldehyde (0.137 g; 0.999 mmol) and 3-methoxyaniline (0.119 mL; 1.056 mmol) in ethanol (1 mL) at 60° C. for 18 h. The formation of the imine was quantitative and the solution was used without further purification. ESI/APCI (+): 243 (M+H).

Step 2: 1-(1H-Indol-3-yl)-2-((3-methoxyphenyl)amino)-2-(5-methoxypyridin-3-yl)ethanone was prepared according to general procedure K from a mixture of 3-benzyl-5-(2-hydroxyethyl)-4-methylthiazol-3-ium chloride (0.138 g; 0.512 mmol) and triethylamine (0.100 mL; 0.717 mmol) in ethanol (0.5 mL), tert-butyl 3-formyl-1H-indole-1-carboxylate (0.260 g; 1.060 mmol) and a solution of 3-methoxy-N-((5-methoxypyridin-3-yl)methylene)aniline (0.999 mmol) in ethanol (1 mL), heated at 60° C. for 24 h. Purification by flash chromatography on silica gel using a gradient of ethyl acetate (50% to 100%) in heptane followed by precipitation from methanol furnished 0.065 g (17%) of the desired compound as a white solid. ESI/APCI(+): 388 (M+H). ESI/APCI(−): 386 (M−H).

Example 277: Preparation of 2-(4-fluorophenyl)-2-((3-(hydroxymethyl)-5-methoxyphenyl)amino)-1-(1H-indol-3-yl)ethanone Step 1: A solution of (3-((4-fluorobenzylidene)amino)-5-methoxyphenyl)methanol in ethanol was prepared by heating a solution of 4-fluorobenzaldehyde (0.114 g; 0.919 mmol) and (3-amino-5-methoxyphenyl)methanol (0.130 g; 0.849 mmol) in ethanol (0.5 mL) at 60° C. for 18 h. The formation of the imine was quantitative and the solution was used without further purification. ESI/APCI (+): 260 (M+H).

Step 2: 2-(4-Fluorophenyl)-2-((3-(hydroxymethyl)-5-methoxyphenyl)amino)-1-(1H-indol-3-yl)ethanone was prepared according to general procedure K from a mixture of 3-benzyl-5-(2-hydroxyethyl)-4-methylthiazol-3-ium chloride (0.130 g; 0.482 mmol) and triethylamine (0.085 mL; 0.610 mmol) in ethanol (0.5 mL), tert-butyl 3-formyl-1H-indole-1-carboxylate (0.220 g; 0.897 mmol) and a solution of (3-((4-fluorobenzylidene)amino)-5-methoxyphenyl)methanol (0.849 mmol) in ethanol (1 mL), heated at 60° C. for 24 h. The residue was purified by flash chromatography on silica gel using a gradient of ethyl acetate (40% to 100%) in heptane. Further purification by flash chromatography on silica gel using isopropanol (2.5%) in dichloromethane as eluent furnished 0.051 g (15%) of the desired compound as a yellow foam. ESI/APCI(+): 405 (M+H). ESI/APCI(−): 403 (M−H).

Example 278: Preparation of 5-(2-(1H-indol-3-yl)-1-((3-methoxyphenyl)amino)-2-oxoethyl)picolinonitrile Step 1: To a solution of 6-bromonicotinaldehyde (0.500 g; 2.688 mmol) in DMF (5 mL) was added copper(I) cyanide (0.361 g; 4.031 mmol) and the mixture was heated to 120° C. After cooling to room temperature, the reaction mixture was diluted with ethyl acetate and filtered over a pad of celite. The organic phase was washed with water and brine, dried over magnesium sulfate, filtered and concentrated under reduced pressure. The residue was purified by flash chromatography on silica gel using a gradient of ethyl acetate (0% to 80%) in heptane to yield 0.161 g (45%) of 5-formylpicolinonitrile as a pink solid. $^1$H NMR (CDCl$_3$) δ 10.21 (1H, s); 9.19 (1H, s); 8.33 (1H, dd); 7.90 (1H, d); 7.27 (1H, s).

Step 2: 5-(((3-Methoxyphenyl)imino)methyl)picolinonitrile was prepared quantitatively according to general procedure I from 5-formylpicolinonitrile (0.132 g; 0.999 mmol) and 3-methoxyaniline (0.112 mL; 1.001 mmol).

Step 3: 5-(2-(1H-Indol-3-yl)-1-((3-methoxyphenyl)amino)-2-oxoethyl)picolinonitrile was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 5-(((3-methoxyphenyl)imino)methyl)picolinonitrile (0.999 mmol) in ethanol (1 mL), heated at 70° C. for 3 days. The residue was purified by flash chromatography on silica gel using a gradient of ethyl acetate (0% to 100%) in heptane. Further purification by flash chromatography on silica gel using ethyl acetate (42%) in heptane as eluent furnished 0.049 g (12%) of the desired compound as a yellow solid. ESI/APCI (+): 383 (M+H). ESI/APCI(−): 381 (M−H).

Example 279: Preparation of 1-(1H-indol-3-yl)-2-((3-methoxyphenyl)amino)-2-(6-(trifluoromethyl)pyridin-3-yl)ethanone Step 1: A solution of 3-methoxy-N-((6-(trifluoromethyl)pyridin-3-yl)methylene)aniline in ethanol was prepared by heating a solution of 6-(trifluoromethyl)nicotinaldehyde (0.175 g; 0.999 mmol) and m-anisidine (0.112 mL; 1.000 mmol) in ethanol (1 mL) at 60° C. overnight. The formation of the imine was quantitative and the solution was used without further purification. ESI/APCI(+):281 (M+H).

Step 2: 1-(1H-Indol-3-yl)-2-((3-methoxyphenyl)amino)-2-(6-(trifluoromethyl)pyridin-3-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of 3-methoxy-N-((6-(trifluoromethyl)pyridin-3-yl)methylene)aniline (0.999 mmol) in ethanol (1 mL), heated at 70° C. overnight. Purification by flash chromatography on silica gel using a gradient of ethyl acetate (15% to 70%) in heptane followed by precipitation from dichloromethane and heptane furnished 0.125 g (29%) of the desired compound as a beige solid. ESI/APCI(+): 426 (M+H). ESI/APCI(−): 424 (M−H). $^1$H NMR (DMSO-d$_6$) δ12.28 (1H, br s); 9.07 (1H, s); 8.96 (1H, s); 8.27 (1H, d); 8.17 (1H, d); 7.89 (1H, d); 7.50 (1H, d); 7.16-7.29 (2H, m); 6.96 (1H, t); 6.67 (1H, d); 6.41-6.52 (2H, m); 6.36 (1H, d); 6.16 (1H, d); 3.65 (3H, s).

Example 280: Preparation of 1-(6-fluoro-1H-indol-3-yl)-2-((3-(2-hydroxyethoxy)-5-methoxyphenyl)amino)-2-phenylethanone 1-(6-Fluoro-1H-indol-3-yl)-2-((3-(2-hydroxyethoxy)-5-methoxyphenyl)amino)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 6-fluoro-3-formyl-1H-indole-1-carboxylate (0.263 g; 0.999 mmol) and a solution of 2-(3-(benzylideneamino)-5-methoxyphenoxy)ethanol (0.999 mmol) in ethanol (1 mL), heated at 70° C. overnight. Purification by flash chromatography on silica gel using a gradient of ethyl acetate (5% to 50%) in dichloromethane followed by precipitation from diethyl ether furnished 0.025 g (6%) of the desired compound as a beige solid. ESI/APCI (+): 435 (M+H). ESI/APCI(−): 433 (M−H). $^1$H NMR (DMSO-d$_6$) δ12.19 (1H, br s); 8.90 (1H, s); 8.13 (1H, dd); 7.62 (2H, d); 7.12-7.35 (5H, m); 7.05 (1H, t); 6.34 (1H, d); 5.96-6.11 (3H, m); 5.71 (1H, s); 4.78 (1H, t); 3.83 (2H, m); 3.64 (2H, m); 3.60 (3H, s).

Example 281: Preparation of 1-(1H-indol-3-yl)-2-((3-methoxyphenyl)amino)-2-(pyridazin-3-yl)ethanone Step 1: A mixture of 3-methylpyridazine (1.830 mL; 20.03 mmol), benzaldehyde (4.080 mL; 40.08 mmol)) and zinc chloride (0.546 g; 4.006 mmol) was heated at 150 C for 2.5 h in a sealed tube. After cooling to room temperature, the reaction mixture was diluted with dichloromethane and was washed with a 1N sodium hydroxide solution. The organic phase concentrated under reduced pressure. Purification by flash chromatography on silica gel using a gradient of ethyl acetate (15% to 70%) in dichloromethane furnished 2.820 g (77%) of 3-styrylpyridazine as a pale brown solid. ESI/APCI(+): 183 (M+H).

Step 2: A mixture of 3-styrylpyridazine (0.600 g; 3.293 mmol), sodium periodate (1.410 g; 6.592 mmol) and a 2.5% osmium tetraoxide solution in tert-butanol (4.500 mL; 0.494 mmol) in a mixture of acetone (6 mL), tert-butanol (6 mL) and water (6 mL) was stirred at room temperature for 2 days. The reaction mixture was filtered and the filtrate was concentrated under reduced pressure. Purification by flash chromatography on silica gel using a gradient of ethyl acetate (15% to 70%) in dichloromethane furnished 0.264 g (74%) of pyridazine-3-carbaldehyde as a light brown solid. ESI/APCI(+): 109 (M+H).

Step 3: A solution of 3-methoxy-N-(pyridazin-3-ylmethylene)aniline in ethanol was prepared by heating a solution of pyridazine-3-carbaldehyde (0.108 g; 0.999 mmol) and m-anisidine (0.112 mL; 1.000 mmol) in ethanol (1 mL) at 60° C. overnight. The formation of the imine was quantitative and the solution was used without further purification. ESI/APCI(+):214 (M+H).

Step 4: 1-(1H-Indol-3-yl)-2-((3-methoxyphenyl)amino)-2-(pyridazin-3-yl)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of 3-methoxy-N-(pyridazin-3-ylmethylene)aniline (0.999 mmol) in ethanol (1 mL), heated at 70° C. overnight. Purification by flash chromatography on silica gel using a gradient of ethyl acetate (15% to 70%) in dichloromethane followed by precipitation from ethyl acetate furnished 0.080 g (22%) of the desired compound as a beige solid. ESI/APCI(+): 359 (M+H). $^1$H NMR (DMSO-$d_6$) δ12.22 (1H, br s); 9.11 (1H, d); 8.83 (1H, s); 8.12 (1H, m); 7.78 (1H, m); 7.66 (1H, dd); 7.50 (1H, d); 7.16-7.30 (2H, m); 6.96 (1H, t); 6.68 (1H, d); 6.39 (3H, m); 6.17 (1H, d); 3.65 (3H, s).

Example 282: Preparation of 2-((3-(hydroxymethyl)-5-methoxyphenyl)amino)-1-(7-methyl-1H-indol-3-yl)-2-phenylethanone 2-((3-(Hydroxymethyl)-5-methoxyphenyl)amino)-1-(7-methyl-1H-indol-3-yl)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-7-methyl-1H-indole-1-carboxylate (0.259 g; 0.999 mmol) and a solution of (3-(benzylideneamino)-5-methoxyphenyl)methanol (0.999 mmol) in ethanol (1 mL), heated at 70° C. overnight. Purification by flash chromatography on silica gel using a gradient of ethyl acetate (5% to 50%) in dichloromethane followed by precipitation from ethyl acetate furnished 0.080 g (20%) of the desired compound as a beige solid. ESI/APCI(+): 401 (M+H). ESI/APCI(−): 399 (M−H). $^1$H NMR (DMSO-$d_6$) δ12.08 (1H, br s); 8.87 (1H, d); 7.98 (1H, d); 7.63 (2H, d); 7.22-7.33 (2H, m); 7.12-7.22 (1H, m); 7.03-7.11 (1H, m); 6.96-7.03 (1H, m); 6.41 (1H, s); 6.22-6.32 (2H, m); 6.07-6.17 (2H, m); 4.97 (1H, t); 4.30 (2H, d); 3.62 (3H, s); 2.47 (3H, s).

Example 283: Preparation of 2-((2,6-dimethoxypyridin-4-yl)amino)-1-(1H-indol-3-yl)-2-phenylethanone 2-((2,6-Dimethoxypyridin-4-yl)amino)-1-(1H-indol-3-yl)-2-phenylethanone was prepared according to general procedure E from 2-bromo-1-(1H-indol-3-yl)-2-phenylethanone (0.042 g; 0.134 mmol) and 2,6-dimethoxy-4-pyridinamine (0.103 g; 0.668 mmol) in acetonitrile (0.6 mL), irradiated in a microwave oven at 100° C. for 30 min, at 120° C. for 15 min and at 130° C. for 35 min. Purification by flash chromatography on silica gel using a gradient of ethyl acetate (20% to 60%) in heptane furnished 0.021 g (41%) of the desired product as a white powder. ESI/APCI(+): 388 (M+H). ESI/APCI(−): 386 (M−H). $^1$H NMR (DMSO-$d_6$) δ 12.16 (1H, br s); 8.88 (1H, d); 8.15 (1H, d); 7.61 (2H, m); 7.45 (1H, d); 7.1-7.35 (7H, m); 6.13 (1H, d); 5.85 (2H, s); 3.69 (6H, s).

Example 284: Preparation of 2-((3-(hydroxymethyl)-5-methoxyphenyl)amino)-1-(1H-indol-3-yl)-2-(6-methylpyridin-3-yl)ethanone Step 1: A solution of (3-methoxy-5-(((6-methylpyridin-3-yl)methylene)amino)phenyl)methanol in ethanol was prepared by heating a solution of 6-fluoronicotinaldehyde (0.098 g; 0.809 mmol) and (3-amino-5-methoxyphenyl)methanol (0.124 g; 0.810 mmol) in ethanol (0.7 mL) at 60° C. for 24 h. The formation of the imine was quantitative and the solution was used without further purification. ESI/APCI (+): 257 (M+H).

Step 2: 2-((3-(Hydroxymethyl)-5-methoxyphenyl)amino)-1-(1H-indol-3-yl)-2-(6-methylpyridin-3-yl)ethanone was prepared according to general procedure K from a mixture of 3-benzyl-5-(2-hydroxyethyl)-4-methylthiazol-3-ium chloride (0.110 g; 0.408 mmol) and triethylamine (0.080 mL; 0.574 mmol) in ethanol (0.5 mL), tert-butyl 3-formyl-1H-indole-1-carboxylate (0.210 g; 0.856 mmol) and a solution of (3-methoxy-5-(((6-methylpyridin-3-yl)methylene)amino)phenyl)methanol (0.809 mmol) in ethanol (1 mL), heated at 60° C. for 96 h. The residue was purified by flash chromatography on silica gel using a gradient of methanol (1% to 15%) in ethyl acetate. Further purification by flash chromatography on silica gel using a gradient of methanol (0% to 5%) in ethyl acetate furnished 0.056 g (17%) of the desired compound. ESI/APCI(+): 402 (M+H). ESI/APCI(−): 400 (M−H).

Example 285: Preparation of 2-(5-fluoropyridin-3-yl)-1-(1H-indol-3-yl)-2-((3-methoxyphenyl)amino)ethanone Step 1: A solution of N-((5-fluoropyridin-3-yl)methylene)-3-methoxyaniline in ethanol was prepared by heating a solution of 5-fluoronicotinaldehyde (0.125 g; 0.999 mmol) and m-anisidine (0.112 mL; 1.000 mmol) in ethanol (1 mL) at 60° C. overnight. The formation of the imine was quantitative and the solution was used without further purification. ESI/APCI(+):231 (M+H).

Step 2: 2-(5-Fluoropyridin-3-yl)-1-(1H-indol-3-yl)-2-((3-methoxyphenyl)amino)ethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-1H-indole-1-carboxylate (0.245 g; 0.999 mmol) and a solution of N-((5-fluoropyridin-3-yl)methylene)-3-methoxyaniline (0.999 mmol) in ethanol (1 mL), heated at 70° C. overnight. Purification by flash chromatography on silica gel using a gradient of ethyl acetate (15% to 70%) in dichloromethane followed by precipitation from diethyl ether furnished 0.161 g (43%) of the desired compound as a beige solid. ESI/APCI(+): 376 (M+H). ESI/APCI(−): 374 (M−H). $^1$H NMR (DMSO-$d_6$) δ12.26 (1H, br s); 8.95 (1H, d); 8.78 (1H, s); 8.43 (1H, d); 8.17 (1H, d); 7.91 (1H, d); 7.50 (1H, d); 7.15-7.29 (2H, m); 6.96 (1H, t); 6.58 (1H, d); 6.40-6.50 (2H, m); 6.27 (1H, d); 6.16 (1H, d); 3.65 (3H, s).

Example 286: Enantiomers separation of 1-(5-fluoro-1H-indol-3-yl)-2-(6-methoxypyridin-3-yl)-2-((5-methoxypyridin-3-yl)amino)ethanone leading to (−)-1-(5-fluoro-1H-indol-3-yl)-2-(6-methoxypyridin-3-yl)-2-((5-methoxypyridin-3-yl)amino)ethanone and (+)-1-(5-fluoro-1H-indol-3-yl)-2-(6-methoxypyridin-3-yl)-2-((5-methoxypyridin-3-yl)amino)ethanone 1-(5-Fluoro-1H-indol-3-yl)-2-(6-methoxypyridin-3-yl)-2-((5-methoxypyridin-3-yl)amino)ethanone (0.064 g) was separated into its enantiomers and purified by preparative HPLC (ChiralPak column; method 6). Under these conditions, 0.015 g of the faster eluting enantiomer ($t_r$=9.7 min; ee=90%) and 0.013 g of the slower eluting enantiomer ($t_r$=12.5 min; ee=96%) were obtained.

Example 287: Enantiomers separation of 1-(1H-indol-3-yl)-2-((3-methoxyphenyl)amino)-2-(pyrazolo[1,5-a]pyridin-2-yl)ethanone leading to (−)-1-(1H-indol-3-yl)-2-((3-methoxyphenyl)amino)-2-(pyrazolo[1,5-a]pyridin-2-yl)ethanone and (+)-1-(1H-indol-3-yl)-2-((3-methoxyphenyl)amino)-2-(pyrazolo[1,5-a]pyridin-2-yl)ethanone 1-(1H-Indol-3-yl)-2-((3-methoxyphenyl)amino)-2-(pyrazolo[1,5-a]pyridin-2-yl)ethanone (0.029 g) was separated into its enantiomers and purified by preparative HPLC (ChiralPak column; method 7). Under these conditions, 0.008 g of the faster eluting enantiomer ($t_r$=9.3 min; ee=98%) and 0.008 g of the slower eluting enantiomer ($t_r$=12.9 min; ee=94%) were obtained.

Example 288: Enantiomers separation of 2-((3,5-dimethoxyphenyl)amino)-1-(1H-indol-3-yl)-2-phenylethanone leading to (−)-2-((3,5-dimethoxyphenyl)amino)-1-(1H-indol-3-yl)-2-phenylethanone and (+)-2-((3,5-dimethoxyphenyl)amino)-1-(1H-indol-3-yl)-2-phenylethanone 2-((3,5-Dimethoxyphenyl)amino)-1-(1H-indol-3-yl)-2-phenylethanone (0.050 g) was separated into its enantiomers and purified by preparative HPLC (ChiralPak column; method 7). Under these conditions, 0.016 g of the faster eluting enantiomer ($t_r$=8.1 min; ee=96%) and 0.012 g of the slower eluting enantiomer ($t_r$=17.9 min; ee=96%) were obtained.

Example 289: Preparation of 2-(benzo[d]oxazol-2-yl)-1-(1H-indol-3-yl)-2-((3-methoxyphenyl)amino)ethanone Step 1: A solution of 2-methylbenzo[d]oxazole (1.020 g; 7.661 mmol) and N,N-dimethylformamide dimethyl acetal (1.230 g; 10.32 mmol) in DMF (8 mL) was heated at 140° C. for 18 h. The reaction mixture was concentrated under reduced pressure to furnish 1.170 g (81%) of 2-(benzo[d]oxazol-2-yl)-N,N-dimethylethenamine as a brown solid. ESI/APCI (+): 189 (M+H). $^1$H NMR (DMSO-$d_6$) δ 7.64 (1H, d); 7.42 (1H, d); 7.38 (1H, d); 7.19 (1H, t); 7.09 (1H, t); 5.00 (1H, d); 2.95 (6H, s).

Step 2: To a solution of 2-(benzo[d]oxazol-2-yl)-N,N-dimethylethenamine (0.233 g; 1.238 mmol) in THF (3.8 mL) heated at 45° C. was added a 1M sodium periodate solution in water (3.800 mL; 3.800 mmol). The reaction mixture was stirred at 45° C. for 1 h. After cooling to room temperature, the precipitate was filtered and was washed with ethyl acetate. The filtrate was washed with a 1M sodium bicarbonate solution. The organic phase was dried over magnesium sulfate, filtered and concentrated under reduced pressure. Purification by flash chromatography on silica gel using a gradient of ethyl acetate (0% to 25%) in heptane furnished 0.079 g (43%) of benzo[d]oxazole-2-carbaldehyde as a yellow oil ESI/APCI (+): 148 (M+H). $^1$H NMR (DMSO-$d_6$) δ 9.92 (1H, s); 8.02 (1H, d); 7.93 (1H, d); 7.67 (1H, t); 7.56 (1H, t).

Step 3: A solution of N-(benzo[d]oxazol-2-ylmethylene)-3-methoxyaniline in ethanol was prepared by heating a solution of benzo[d]oxazole-2-carbaldehyde (0.100 g; 0.680 mmol) and 3-methoxyaniline (0.078 mL; 0.698 mmol) in ethanol (0.5 mL) at 60° C. for 5 h. The formation of the imine was quantitative and the solution was used without further purification. ESI/APCI (+): 253 (M+H).

Step 4: 2-(Benzo[d]oxazol-2-yl)-1-(1H-indol-3-yl)-2-((3-methoxyphenyl)amino)ethanone was prepared according to general procedure K from a mixture of 3-benzyl-5-(2-hydroxyethyl)-4-methylthiazol-3-ium chloride (0.095 g; 0.352 mmol) and triethylamine (0.070 mL; 0.502 mmol) in ethanol (0.5 mL), tert-butyl 3-formyl-1H-indole-1-carboxylate (0.189 g; 0.771 mmol) and a solution of N-(benzo[d]oxazol-2-ylmethylene)-3-methoxyaniline (0.680 mmol) in ethanol (1 mL), heated at 60° C. for 16 h. Purification by flash chromatography on silica gel using a gradient of ethyl acetate (50% to 100%) in heptane followed by precipitation from methanol furnished 0.028 g (10%) of the desired compound as a yellow solid. ESI/APCI(+): 398 (M+H). ESI/APCI(−): 396 (M−H).

Example 290: Preparation of 2-((3-methoxyphenyl)amino)-1-(7-methyl-1H-indol-3-yl)-2-(pyrazolo[1,5-a]pyridin-2-yl)ethanone 2-((3-Methoxyphenyl)amino)-1-(7-methyl-1H-indol-3-yl)-2-(pyrazolo[1,5-a]pyridin-2-yl)ethanone was prepared according to general procedure K from a mixture of 3-benzyl-5-(2-hydroxyethyl)-4-methylthiazol-3-ium chloride (0.095 g; 0.352 mmol) and triethylamine (0.070 mL; 0.502 mmol) in ethanol (0.5 mL), tert-butyl 3-formyl-7-methyl-1H-indole-1-carboxylate (0.195 g; 0.752 mmol) and a solution of 3-methoxy-N-(pyrazolo[1,5-a]pyridin-2-ylmethylene)aniline (0.704 mmol) in ethanol (1 mL), heated at 60° C. for 16 h. Purification by flash chromatography on silica gel using a gradient of ethyl acetate (10% to 60%) in heptane furnished 0.034 g (12%) of the desired compound as a yellow oil. ESI/APCI(+): 411 (M+H). ESI/APCI(−): 409 (M−H).

Example 291: Preparation of 1-(benzo[d]isoxazol-3-yl)-2-((3-methoxyphenyl)amino)-2-phenylethanone Step 1: To a solution of benzo[d]isoxazole-3-carboxylic acid (0.500 g; 3.065 mmol) in THF (20 mL) was added N,O-dimethylhydroxylamine hydrochloride (0.359 g; 3.680 mmol), 1-(3-dimethylaminopropyl)-3-ethylcarbodiimide hydrochloride (1.180 g; 6.155 mmol) and pyridine (0.500 mL; 6.195 mmol). The reaction mixture was stirred at room temperature overnight. And was concentrated under reduced pressure. The residue was partitioned between ethyl acetate. The phases were separated. The organic phase was concentrated under reduced pressure. Purification by flash chromatography on silica gel using a gradient of ethyl acetate (5% to 50%) in heptane furnished 0.225 g (36%) of N-methoxy-N-methylbenzo[d]isoxazole-3-carboxamide as a white solid. ESI/APCI(+): 207 (M+H).

Step 2: To a solution of N-methoxy-N-methylbenzo[d]isoxazole-3-carboxamide (0.100 g; 0.485 mmol) in THF (5 mL) cooled to 0° C. was added a 1M benzylmagnesium chloride solution in THF (1.450 mL; 1.450 mmol). The reaction mixture was stirred at 0° C. for 2 h and at room temperature overnight. After cooling to 0° C., the reaction was quenched by addition of water. The reaction mixture was extracted with ethyl acetate. The organic phase was concentrated under reduced pressure. Purification by flash chromatography on silica gel using a gradient of ethyl acetate (2% to 20%) in heptane furnished 0.052 g (45%) of 1-(benzo[d]isoxazol-3-yl)-2-phenylethanone as a beige solid. ESI/APCI(+): 238 (M+H). ESI/APCI(+): 236 (M−H).

Step 3: 1-(Benzo[d]isoxazol-3-yl)-2-bromo-2-phenylethanone was prepared according to general procedure P from a solution of 1-(benzo[d]isoxazol-3-yl)-2-phenylethanone (0.080 g; 0.337 mmol) in THF (3.5 mL) and a solution of phenyltrimethylammonium tribromide (0.140 g; 0.371 mmol) in THF (4.5 mL). The reaction mixture was stirred at 0° C. for 1 h and at room temperature overnight. Purification by flash chromatography on silica gel using a gradient of ethyl acetate (2% to 20%) in heptane furnished 0.092 g (86%) of 1-(benzo[d]isoxazol-3-yl)-2-bromo-2-phenylethanone as a yellow solid.

Step 4: 1-(Benzo[d]isoxazol-3-yl)-2-((3-methoxyphenyl)amino)-2-phenylethanone was prepared according to general procedure E from 1-(benzo[d]isoxazol-3-yl)-2-bromo-2-phenylethanone (0.044 g; 0.114 mmol) and m-anisidine (0.127 mL; 1.134 mmol) in acetonitrile (0.5 mL), irradiated in a microwave oven at 100° C. for 15 min. Purification by flash chromatography on silica gel using a gradient of ethyl acetate (2% to 40%) in heptane followed by purification by preparative HPLC (XBridge column; method 1) furnished 0.004 g (9%) of the desired compound as a yellow solid. ESI/APCI(+): 359 (M+H).

Example 292: Preparation of 2-((3-(2-hydroxyethoxy)-5-methoxyphenyl)amino)-1-(7-methyl-1H-indol-3-yl)-2-phenylethanone 2-((3-(2-Hydroxyethoxy)-5-methoxyphenyl)amino)-1-(7-methyl-1H-indol-3-yl)-2-phenylethanone was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 3-formyl-7-methyl-1H-indole-1-carboxylate (0.259 g; 0.999 mmol) and a solution of 2-(3-(benzylideneamino)-5-methoxyphenoxy)ethanol (0.999 mmol) in ethanol (1 mL), heated at 70° C. overnight. The residue was purified by flash chromatography on silica gel using a gradient of ethyl acetate (5% to 50%) in dichloromethane. Further purification by flash chromatography on silica gel using a gradient of ethyl acetate (30% to 100%) in heptane followed by purification by preparative HPLC (XBridge column; method 1) furnished 0.012 g (3%) of the desired compound as a white solid. ESI/APCI(+): 431 (M+H). ESI/APCI(−): 429 (M−H). $^1$H NMR (DMSO-$d_6$) δ12.09 (1H, br s); 8.89 (1H, d); 7.98 (1H, d); 7.62 (2H, d); 7.22-7.36 (2H, m); 7.13-7.22 (1H, m); 7.03-7.11 (1H, m); 6.95-7.03 (1H, m); 6.32 (1H, d); 6.10 (1H, d); 6.05 (2H, br s); 5.71 (1H, s); 4.78 (1H, t); 3.83 (2H, m); 3.62-3.71 (2H, m); 3.61 (3H, s); 2.48 (3H, s).

Example 293: Preparation of 2-((3-methoxyphenyl)amino)-2-(6-methoxypyridin-3-yl)-1-(7-methyl-1H-indol-3-yl)ethanone 2-((3-Methoxyphenyl)amino)-2-(6-methoxypyridin-3-yl)-1-(7-methyl-1H-indol-3-yl)ethanone was prepared according to general procedure K from a mixture of 3-benzyl-5-(2-hydroxyethyl)-4-methylthiazol-3-ium chloride (0.126 g; 0.467 mmol) and triethylamine (0.090 mL; 0.646 mmol) in ethanol (0.5 mL), tert-butyl 3-formyl-7-methyl-1H-indole-1-carboxylate (0.241 g; 0.929 mmol) and a solution of 3-methoxy-N-((6-methoxypyridin-3-yl)methylene)aniline (0.875 mmol) in ethanol (1 mL), heated at 60° C. for 98 h. Purification by flash chromatography on silica gel using a gradient of ethyl acetate (0% to 50%) in heptane furnished 0.055 g (16%) of the desired compound as a white solid. ESI/APCI(+): 402 (M+H). ESI/APCI(−): 400 (M−H).

Example 294: Preparation of 2-(6-fluoropyridin-3-yl)-2-((3-(hydroxymethyl)-5-methoxyphenyl)amino)-1-(1H-indol-3-yl)ethanone Step 1: A solution of (3-(((6-fluoropyridin-3-yl)methylene)amino)-5-methoxyphenyl)methanol in ethanol was prepared by heating a solution of 6-fluoronicotinaldehyde (0.110 g; 0.879 mmol) and (3-amino-5-methoxyphenyl)methanol (0.140 g; 0.914 mmol) in ethanol (0.5 mL) at 60° C. for 5 h. The formation of the imine was quantitative and the solution was used without further purification. ESI/APCI (+): 261 (M+H).

Step 2: 2-(6-Fluoropyridin-3-yl)-2-((3-(hydroxymethyl)-5-methoxyphenyl)amino)-1-(1H-indol-3-yl)ethanone was prepared according to general procedure K from a mixture of 3-benzyl-5-(2-hydroxyethyl)-4-methylthiazol-3-ium chloride (0.121 g; 0.448 mmol) and triethylamine (0.090 mL; 0.646 mmol) in ethanol (0.5 mL), tert-butyl 3-formyl-1H-indole-1-carboxylate (0.235 g; 0.958 mmol) and a solution of (3-(((6-fluoropyridin-3-yl)methylene)amino)-5-methoxyphenyl)methanol (0.879 mmol) in ethanol (1 mL), heated at 60° C. for 16 h. The residue was purified by flash chromatography on silica gel using a gradient of ethyl acetate (0% to 100%) in heptane. Further purification by flash chromatography on silica gel using a gradient of methanol (0% to 4%) in dichloromethane furnished 0.038 g (11%) of the desired compound as a yellow oil. ESI/APCI (+): 406 (M+H). ESI/APCI(−): 404 (M−H).

Example 295: Preparation of 1-(5-fluoro-1H-indol-3-yl)-2-((3-(hydroxymethyl)-5-methoxyphenyl)amino)-2-(pyridin-3-yl)ethanone 1-(5-Fluoro-1H-indol-3-yl)-2-((3-(hydroxymethyl)-5-methoxyphenyl)amino)-2-(pyridin-3-yl)ethanone was prepared according to general procedure L from a mixture of 3-benzyl-5-(2-hydroxyethyl)-4-methylthiazol-3-ium chloride (0.126 g; 0.467 mmol) and triethylamine (0.100 mL; 0.717 mmol) in ethanol (0.5 mL), tert-butyl 5-fluoro-3-formyl-1H-indole-1-carboxylate (0.259 g; 0.984 mmol) and a solution of (3-methoxy-5-((pyridin-3-ylmethylene)amino)phenyl)methanol (0.953 mmol) in ethanol (1 mL), heated at 60° C. for 96 h. Purification by flash chromatography on silica gel using a gradient of methanol (0% to 7%) in dichloromethane followed by precipitation from dichloromethane furnished 0.100 g (26%) of the desired compound as a white solid. ESI/APCI(+): 406 (M+H). ESI/APCI (−): 404 (M−H).

Example 296: Preparation of 2-((3,5-dimethoxyphenyl)amino)-1-(1H-indol-3-yl)-2-(6-methoxypyridin-3-yl)ethanone 2-((3,5-Dimethoxyphenyl)amino)-1-(1H-indol-3-yl)-2-(6-methoxypyridin-3-yl)ethanone was prepared according to general procedure K from a mixture of 3-benzyl-5-(2-hydroxyethyl)-4-methylthiazol-3-ium chloride (0.125 g; 0.463 mmol) and triethylamine (0.090 mL; 0.646 mmol) in ethanol (0.5 mL), tert-butyl 3-formyl-1H-indole-1-carboxylate (0.260 g; 1.060 mmol) and a solution of 3,5-dimethoxy-N-((6-methoxypyridin-3-yl)methylene)aniline (0.912 mmol) in ethanol (1 mL), heated at 60° C. for 16 h. tert-Butyl 3-formyl-1H-indole-1-carboxylate (0.127 g; 0.518 mmol) was added and the reaction mixture was heated at 60° C. for 24 h. Purification by flash chromatography on silica gel using a gradient of ethyl acetate (10% to 60%) in heptane followed by purification by preparative HPLC (XBridge column; method 2) furnished 0.008 g (2%) of the desired compound as a brown solid. ESI/APCI(+): 418 (M+H). ESI/APCI(−): 416 (M−H).

Example 297: Preparation of 2-((3-(2-hydroxyethoxy)-5-methoxyphenyl)amino)-1-(1H-indol-3-yl)-2-(pyrazolo[1,5-a]pyridin-2-yl)ethanone Step 1: A solution of 2-(3-methoxy-5-((pyrazolo[1,5-a]pyridin-2-ylmethylene)amino)phenoxy)ethanol in ethanol was prepared by heating a solution of pyrazolo[1,5-a]pyridine-2-carbaldehyde (0.073 g; 0.499 mmol) and 2-(3-amino-5-methoxyphenoxy)ethanol (0.092 g; 0.502 mmol) in ethanol (1 mL) at 60° C. for 6 h. The formation of the imine was quantitative and the solution was used without further purification. ESI/APCI(+):312 (M+H).

Step 2: 2-((3-(2-Hydroxyethoxy)-5-methoxyphenyl)amino)-1-(1H-indol-3-yl)-2-(pyrazolo[1,5-a]pyridin-2-yl)ethanone was prepared according to general procedure K from a mixture of 3-benzyl-5-(2-hydroxyethyl)-4-methylthiazolium chloride (0.067 g; 0.248 mmol) and triethylamine (0.035 mL; 0.252 mmol) in ethanol (1 mL), tert-butyl 3-formyl-1H-indole-1-carboxylate (0.123 g; 0.501 mmol) and a solution of 2-(3-methoxy-5-((pyrazolo[1,5-a]pyridin-2-ylmethylene)amino)phenoxy)ethanol (0.499 mmol) in ethanol (0.5 mL), heated at 70° C. overnight. The residue was purified by flash chromatography on silica gel using a gradient of methanol (1% to 10%) in dichloromethane. Further purification by preparative HPLC (XBridge column; method 5) followed by precipitation from diethyl ether furnished 0.010 g (4%) of the desired compound as a light brown solid. ESI/APCI(+): 457 (M+H). ESI/APCI(−): 455 (M−H). $^1$H NMR (DMSO-d$_6$) δ12.10 (1H, br s); 8.80 (1H, br s); 8.61 (1H, d); 8.19 (1H, d); 7.61 (1H, d); 7.48 (1H, d); 7.08-7.29 (3H, m); 6.82 (1H, d); 6.65 (1H, s); 6.29 (2H, s); 6.10 (2H, s); 5.75 (1H, s); 4.81 (1H, t); 3.85 (2H, m); 3.67 (2H, m); 3.63 (3H, s).

Example 298: Preparation of 2-((3,5-dimethoxyphenyl)amino)-1-(7-methyl-1H-indol-3-yl)-2-phenylethanone Step 1: 1-(7-Methyl-1H-indol-3-yl)-2-phenylethanone was prepared according to general procedure O from a solution of 7-methylindole (0.500 g; 3.811 mmol) in dichloromethane (16 mL), a 1M diethylaluminium chloride solution in hexane (5.790 mL; 5.790 mmol) and a solution of phenylacetyl chloride (0.762 mL; 5.718 mmol) in dichloromethane (16 mL). Purification by flash chromatography on silica gel using a gradient of ethyl acetate (5% to 50%) in heptane furnished 0.320 g (34%) of the desired compound as a beige solid. ESI/APCI(+): 250 (M+H). ESI/APCI(−): 248 (M−H).

Step 2: 2-Bromo-1-(7-methyl-1H-indol-3-yl)-2-phenylethanone was prepared according to general procedure P from a solution of 1-(7-methyl-1H-indol-3-yl)-2-phenylethanone (0.200 g; 0.802 mmol) in THF (5.5 mL) and a solution of phenyltrimethylammonium tribromide (0.332 g; 0.882 mmol) in THF (7 mL). The reaction mixture was stirred at 0° C. for 1 h and at room temperature overnight. Purification by flash chromatography on silica gel using a gradient of ethyl acetate (5% to 50%) in heptane furnished 0.314 g (99%) of the desired compound as a brown solid. ESI/APCI (+): 328, 330 (M+H). ESI/APCI(−): 326, 328 (M−H).

Step 3: 2-((3,5-Dimethoxyphenyl)amino)-1-(7-methyl-1H-indol-3-yl)-2-phenylethanone was prepared according to general procedure E from 2-bromo-1-(7-methyl-1H-indol-3-yl)-2-phenylethanone (0.120 g; 0.366 mmol) and 3,5-dimethoxyaniline (0.280 g; 1.828 mmol) in acetonitrile (1.5 mL), irradiated in a microwave oven at 100° C. for 5 min. Purification by flash chromatography on silica gel using a gradient of ethyl acetate (5% to 50%) in heptane furnished 0.042 g (29%) of 2-((3,5-dimethoxyphenyl)amino)-1-(7-methyl-1H-indol-3-yl)-2-phenylethanone as a white solid. ESI/APCI(+): 401 (M+Na). ESI/APCI(−): 399 (M−H). $^1$H NMR (DMSO-d$_6$) δ12.08 (1H, br s); 8.88 (1H, d); 7.98 (1H, d); 7.63 (2H, d); 7.23-7.34 (2H, m); 7.18 (1H, d); 7.03-7.12 (1H, m); 6.96-7.03 (1H, m); 6.34 (1H, d); 6.10 (1H, d); 6.06 (2H, d); 5.71 (1H, m); 3.61 (6H, s); 2.48 (3H, s).

Example 299: Preparation of 2-((3,5-dimethoxyphenyl)amino)-1-(1-methyl-1H-indol-3-yl)-2-phenylethanone Step 1: To a solution of phenylacetic acid (0.500 g; 3.672 mmol) in dichloromethane (7 mL) was added a solution of 1H-benzotriazole (1.360 g; 11.42 mmol) and thionyl chloride (0.294 mL; 4.053 mmol) in dichloromethane (7 mL). The reaction mixture was stirred at room temperature for 1 h. The white precipitate was filtered and the filtrate was concentrated under reduced pressure. The residue was partitioned between dichloromethane and a saturated sodium carbonate solution. The phases were separated. The organic phase was washed with a saturated sodium carbonate solution, water and brine, dried over sodium sulfate, filtered and concentrated under reduced pressure to yield 0.812 g (93%) of 1-(1H-benzo[d][1,2,3]triazol-1-yl)-2-phenylethanone as a yellow solid. $^1$H NMR (CDCl$_3$) δ 8.27 (1H, d); 8.12 (1H, d); 7.65 (1H, t); 7.25-7.5 (6H, m); 4.74 (2H, s).

Step 2: 1-(1-Methyl-1H-indol-3-yl)-2-phenylethanone has been prepared according to 2 different procedures described hereunder as method A and method B.

Method A: To a solution of N-methylindole (0.300 g; 2.287 mmol) and 1-(1H-benzo[d][1,2,3]triazol-1-yl)-2-phenylethanone (0.434 g; 1.829 mmol) in dichloromethane (19 mL) cooled to 0° C. was added portionwise aluminum trichloride (0.381 g; 2.857 mmol). The reaction mixture was stirred at room temperature for 3 h. Methanol was added and the reaction mixture was concentrated under reduced pressure. The residue was partitioned between dichloromethane and a saturated sodium carbonate solution. The phases were separated. The organic phase was washed with a saturated sodium carbonate solution, water and brine, dried over sodium sulfate, filtered and concentrated under reduced pressure. Purification of by flash chromatography on silica gel using a gradient of ethyl acetate (20% to 70%) in heptane furnished 0.266 g (58%) of 1-(1-methyl-1H-indol-3-yl)-2-phenylethanone as a pink oil. ESI/APCI(+): 250 (M+H); 272 (M+Na). $^1$H NMR (DMSO-d$_6$) δ 8.56 (1H, s); 8.18 (1H, d); 7.54 (1H, d); 7.2-7.4 (7H, m); 4.11 (2H, s); 3.89 (3H, s).

Method B: 1-(1-Methyl-1H-indol-3-yl)-2-phenylethanone was prepared according to general procedure O from a solution of N-methylindole (0.300 g; 2.287 mmol) in dichloromethane (11.5 mL), a 1M diethylaluminium chloride solution in hexane (3.960 mL; 3.960 mmol) and a solution of phenylacetyl chloride (0.518 mL; 3.887 mmol) in dichloromethane (11.5 mL). Purification by flash chromatography on silica gel using a gradient of ethyl acetate (20% to 60%) in heptane furnished 0.350 g (76%) of the desired product as pink powder.

Step 3: 2-Bromo-1-(1-methyl-1H-indol-3-yl)-2-phenylethanone was prepared according to general procedure P from a solution of 1-(1-methyl-1H-indol-3-yl)-2-phenylethanone (0.256 g; 1.027 mmol) in THF (11 mL) and a solution of phenyltrimethylammonium tribromide (0.448 g; 1.192 mmol) in THF (13.5 mL). The reaction mixture was stirred at 0° C. for 1 h and at room temperature for 2 h. Purification by flash chromatography on silica gel using a gradient of ethyl acetate (20% to 50%) in heptane furnished 0.302 g (90%) of the desired product as a pink solid. ESI/APCI(+): 328, 330 (M+H). $^1$H NMR (DMSO-d$_6$) δ 8.69 (1H, s); 8.20 (1H, d); 7.67 (2H, m); 7.57 (1H, d); 7.0-7.4 (5H, m); 6.73 (1H, s); 3.88 (3H, s).

Step 4: 2-((3,5-Dimethoxyphenyl)amino)-1-(1-methyl-1H-indol-3-yl)-2-phenylethanone was prepared according to general procedure E from 2-bromo-1-(1-methyl-1H-indol-3-yl)-2-phenylethanone (0.050 g; 0.152 mmol) and 3,5-dimethoxyaniline (0.116 g; 0.757 mmol) in acetonitrile (0.7 mL), irradiated in a microwave oven at 100° C. for 10 min. Purification by flash chromatography on silica gel using a gradient of ethyl acetate (20% to 60%) in heptane furnished 0.051 g (84%) of the desired product as a white powder. ESI/APCI(+): 401 (M+H); 423 (M+Na). ESI/APCI(-): 399 (M-H). $^1$H NMR (DMSO-d$_6$) δ 8.93 (1H, s); 8.17 (1H, d); 7.61 (2H, m); 7.55 (1H, d); 7.1-7.3 (4H, m); 6.36 (1H, d); 3.88 (3H, s).

Example 300: Preparation of 2-((3,5-dimethoxyphenyl)amino)-1-(7-(2-hydroxyethyl)-1H-indol-3-yl)-2-phenylethanone Step 1: To a suspension of 1H-indole-7-carboxaldehyde (1.000 g; 6.889 mmol) and methyltriphenylphosphonium bromide (2.960 g; 8.286 mmol) in THF (40 mL) cooled to 0° C. was added dropwise a solution of potassium tert-butoxide (1.170 g; 10.43 mmol) in THF (10 mL). The reaction mixture was stirred overnight at room temperature. The reaction mixture was poured into a mixture ice/water and was extracted with ethyl acetate. The organic phase was washed with brine, dried over sodium sulfate, filtered and concentrated under reduced pressure. Purification by flash chromatography on silica gel using a gradient of ethyl acetate (10% to 50%) in heptane furnished 0.914 g of 7-vinyl-1H-indole as a pink oil. ESI/APCI(+): 144 (M+H).

Step 2: To a solution of 7-vinyl-1H-indole (0.914 g; 6.383 mmol) in THF (37 mL) cooled to 0° C. was added dropwise a 1M borane-tetrahydrofuran complex solution in THF (6.400 mL; 6.400 mmol). The reaction mixture was stirred at room temperature for 2.5 h. A 10% sodium hydroxide solution (3.100 mL; 7.750 mmol) was added dropwise followed by the addition of a 30% hydrogen peroxide solution in water (0.869 mL; 9.837 mmol). The reaction mixture was stirred at room temperature for 4 h. A saturated ammonium chloride solution was added. After 5 min at room temperature, the reaction mixture was extracted with ethyl acetate. The organic phase was washed with water and brine, dried over sodium sulfate, filtered and concentrated under reduced pressure. Purification by flash chromatography on silica gel using a gradient of ethyl acetate (20% to 70%) in heptane furnished 0.490 g (44% over two steps) of 2-(1H-indol-7-yl)ethanol as a brown oil. ESI/APCI(+): 162 (M+H). ESI/APCI(-): 160 (M-H). $^1$H NMR (DMSO-d$_6$) δ 11.00 (1H, br s); 7.35 (1H, m); 7.28 (1H, t); 6.90 (2H, m); 6.40 (1H, m); 4.67 (1H, t); 3.70 (2H, q); 2.98 (2H, t).

Step 3: 7-(2-((tert-Butyldimethylsilyl)oxy)ethyl)-1H-indole was prepared according to general procedure N from 2-(1H-indol-7-yl)ethanol (0.200 g; 1.241 mmol), DBU (0.280 mL; 1.876 mmol) and TBDMSCl (0.412 g; 2.734 mmol) in THF (4.6 mL). Purification by flash chromatography on silica gel using a gradient of ethyl acetate (20% to 80%) in heptane furnished 0.288 g (84%) of the desired product as an orange oil. ESI/APCI(+): 276 (M+H). $^1$H NMR (DMSO-d$_6$) δ 11.12 (1H, br s); 7.48 (1H, m); 7.39 (1H, t); 7.00 (2H, m); 6.51 (1H, m); 3.97 (2H, t); 3.14 (2H, t); 0.91 (9H, s); 0.00 (6H, s).

Step 3: 1-(7-(2-((tert-Butyldimethylsilyl)oxy)ethyl)-1H-indol-3-yl)-2-phenylethanone was prepared according to general procedure O from a solution of 7-(2-((tert-butyldimethylsilyl)oxy)ethyl)-1H-indole (0.193 g; 0.701 mmol) in dichloromethane (3.5 mL), a 1M diethylaluminium chloride solution in hexane (1.200 mL; 1.200 mmol) and a solution of phenylacetyl chloride (0.156 mL; 1.171 mmol) in dichloromethane (3.5 mL). Purification by flash chromatography on silica gel using a gradient of ethyl acetate (10% to 70%) in heptane furnished 0.179 g (65%) of the desired product as pink powder. ESI/APCI(+): 394 (M+H); 416 (M+Na). ESI/APCI(-): 392 (M-H). $^1$H NMR (DMSO-d$_6$) δ 12.11 (1H, br s); 8.64 (1H, s); 8.17 (1H, d); 7.3-7.5 (5H, m); 7.17-7.26 (2H, m); 4.30 (2H, s); 4.01 (2H, t); 3.21 (2H, t); 0.93 (9H, s); 0.00 (6H, s).

Step 4: 2-Bromo-1-(7-(2-hydroxyethyl)-1H-indol-3-yl)-2-phenylethanone was prepared according to general procedure P from a solution of 1-(7-(2-((tert-butyldimethylsilyl)oxy)ethyl)-1H-indol-3-yl)-2-phenylethanone (0.064 g; 0.163 mmol) in THF (2 mL) and a solution of phenyltrimethylammonium tribromide (0.074 g; 0.197 mmol) in THF (2.4 mL). The reaction mixture was stirred at 0° C. for 1 h and at room temperature for 3 h. Purification by flash chromatography on silica gel using a gradient of methanol (0% to 10%) in dichloromethane furnished 0.045 g (77%) of the desired product as a beige solid. ESI/APCI(+): 358, 360 (M+H). ESI/APCI(-): 356, 358 (M-H).

Step 5: 2-((3,5-Dimethoxyphenyl)amino)-1-(7-(2-hydroxyethyl)-1H-indol-3-yl)-2-phenylethanone was prepared according to general procedure E from 2-bromo-1-(7-(2-hydroxyethyl)-1H-indol-3-yl)-2-phenylethanone (0.045 g; 0.126 mmol) and 3,5-dimethoxyaniline (0.194 g; 1.266 mmol) in acetonitrile (0.8 mL), irradiated in a microwave oven at 100° C. for 5 min. Purification by flash chromatography on silica gel using a gradient of methanol (0% to 10%) in dichloromethane furnished 0.033 g (61%) of the desired product as a green powder. ESI/APCI(+): 431 (M+H); 453 (M+Na). ESI/APCI(-): 429 (M-H). $^1$H NMR (DMSO-d$_6$) δ 12.06 (1H, br s); 8.86 (1H, s); 8.01 (1H, d); 7.63 (2H, m); 7.28 (2H, m); 7.0-7.2 (3H, m); 6.33 (1H, d); 6.10 (1H, d); 6.05 (2H, d); 5.71 (1H, s); 4.69 (1H, brs); 3.69 (2H, t); 3.61 (6H, s); 3.00 (2H, t).

Example 301: Preparation of 2-((3,5-dimethoxyphenyl)amino)-2-(4-fluorophenyl)-1-(1-methyl-1H-indazol-3-yl)ethanone 2-((3,5-Dimethoxyphenyl)amino)-2-(4-fluorophenyl)-1-(1-methyl-1H-indazol-3-yl)ethanone was prepared according to general procedure L from a mixture of 3-benzyl-5-(2-hydroxyethyl)-4-methylthiazol-3-ium chloride (0.135 g;

0.500 mmol) and triethylamine (0.070 mL; 0.505 mmol) in ethanol (1 mL), 1-methyl-1H-indazole-3-carbaldehyde (0.160 g; 0.999 mmol) and a solution of N-(4-fluorobenzylidene)-3,5-dimethoxyaniline (0.999 mmol) in ethanol (1 mL), heated at 70° C. for 24 h. Purification by flash chromatography on silica gel using a gradient of ethyl acetate (0% to 100%) in heptane followed by crystallization from dichloromethane furnished 0.062 g (15%) of the desired compound as a white solid. ESI/APCI(+): 420 (M+H). ESI/APCI(−): 418 (M−H). $^1$H NMR (DMSO-$d_6$) δ 8.14 (1H, d); 7.82 (1H, d); 7.63 (2H, dd); 7.53 (1H, t); 7.33-7.44 (1H, m); 7.16 (2H, t); 6.57 (1H, d); 6.43 (1H, d); 5.95 (2H, br s); 5.75 (1H, s); 4.26 (3H, s); 3.60 (6H, s).

Example 302: Preparation of 2-((3,5-dimethoxyphenyl)amino)-2-(4-fluorophenyl)-1-(7-methyl-1H-indol-3-yl)ethanone Step 1: To a solution of 2-(4-fluorophenyl)acetic acid (0.500 g; 3.244 mmol) in dichloromethane (5 mL) were added oxalylchloride (0.550 mL; 6.282 mmol) and DMF (1 drop). The reaction mixture was stirred at room temperature for 2 h and was concentrated under reduced pressure. The residue was coevaporated with toluene to give quantitatively 2-(4-fluorophenyl)acetyl chloride which was used in the next step without further purification.

Step 2: 2-(4-Fluorophenyl)-1-(7-methyl-1H-indol-3-yl) ethanone was prepared according to general procedure O from a solution of 7-methyl-1H-indole (0.280 g; 2.135 mmol) in dichloromethane (8.5 mL), a 1M diethylaluminium chloride solution in hexane (4.300 mL; 4.300 mmol) and a solution of 4-(2-fluorophenyl)acetyl chloride (3.244 mmol) in dichloromethane (8.5 mL). Purification by precipitation from diethyl ether furnished 0.188 g (33%) of the desired compound as a beige solid. ESI/APCI(+): 268 (M+H). ESI/APCI(−): 266 (M−H).

Step 3: 2-Bromo-2-(4-fluorophenyl)-1-(7-methyl-1H-indol-3-yl)ethanone was prepared according to general procedure P from a solution of 2-(4-fluorophenyl)-1-(7-methyl-1-H-indol-3-yl)ethanone (0.186 g; 0.696 mmol) in THF (5 mL) and a solution of phenyltrimethylammonium tribromide (0.296 g; 0.787 mmol) in THF (6 mL). The reaction mixture was stirred at 0° C. for 1 h and at room temperature for 4 h. Purification by flash chromatography on silica gel using a gradient of ethyl acetate (0% to 30%) in heptane furnished 0.225 g (93%) of the desired compound as a brown solid. ESI/APCI (+): 346, 348 (M+H). ESI/APCI (−): 344, 346 (M−H).

Step 4: A mixture of 2-bromo-2-(4-fluorophenyl)-1-(7-methyl-1H-indol-3-yl)ethanone (0.050 g; 0.144 mmol) and 3,5-dimethoxyaniline (0.047 g; 0.307 mmol) in acetonitrile (1 mL) was stirred at room temperature for 72 h. The reaction mixture was diluted with ethyl acetate and washed with a 1M sodium bicarbonate solution. The organic phase was dried over magnesium sulfate, filtered and concentrated under reduced pressure. Purification by flash chromatography on silica gel using a gradient of ethyl acetate (0% to 40%) in heptane furnished 0.054 g (89%) of 2-((3,5-dimethoxyphenyl)amino)-2-(4-fluorophenyl)-1-(7-methyl-1H-indol-3-yl)ethanone as a white solid. ESI/APCI (+): 419 (M+H). ESI/APCI (−): 417 (M−H).

Example 303: Preparation of 2-((3-(2-(tert-butoxy) ethoxy)-5-methoxyphenyl)amino)-1-(1H-indol-3-yl)-2-(pyridin-3-yl)ethanone Step 1: A mixture of (pyridin-3-yl)acetic acid hydrochloride (1.850 g; 10.67 mmol) and acetic anhydride (1.000 mL; 10.68 mmol) was heated in a sealed tube at 85° C. for 1 hour. Indole (1.250 g; 10.7 mmol) was added. The reaction mixture was heated at 85° C. for 20 min and at 105° C. for 30 min. After cooling to room temperature, the reaction mixture was basified with a saturated sodium bicarbonate solution and extracted with ethyl acetate. The organic phase was concentrated under reduced pressure. Purification by flash chromatography on silica gel using a gradient of methanol (1% to 10%) in dichloromethane furnished 0.674 g (27%) of 1-(1H-indol-3-yl)-2-(pyridin-3-yl)ethanone as a beige solid. ESI/APCI(+): 237 (M+H). ESI/APCI(−): 235 (M−H).

Step 2: 2-Bromo-1-(1H-indol-3-yl)-2-(pyridin-3-yl)ethanone was prepared according to general procedure P from a solution of 1-(1H-indol-3-yl)-2-(pyridin-3-yl)ethanone (0.570 g; 2.412 mmol) in THF (17 mL) and a solution of phenyltrimethylammonium tribromide (0.997 g; 2.652 mmol) in THF (22 mL). The reaction mixture was stirred at room temperature overnight. Purification by flash chromatography on silica gel using a gradient of methanol (1% to 10%) in dichloromethane furnished 0.275 g (36%) of the desired compound as a brown solid. ESI/APCI(+): 315, 317 (M+H).

Step 3: A mixture of 2-bromo-1-(1H-indol-3-yl)-2-(pyridin-3-yl)ethanone (0.060 g; 0.190 mmol) and 3-(2-(tert-butoxy)ethoxy)-5-methoxyaniline (0.091 g; 0.381 mmol) in acetonitrile (1 mL) was stirred at room temperature for 24 h. The reaction mixture was diluted with a saturated sodium bicarbonate solution and extracted with ethyl acetate. The organic phase was concentrated under reduced pressure. Purification by flash chromatography on silica gel using a gradient of methanol (1% to 10%) in dichloromethane furnished 0.041 g of 2-((3-(2-(tert-butoxy)ethoxy)-5-methoxyphenyl)amino)-1-(1H-indol-3-yl)-2-(pyridin-3-yl) ethanone as a beige solid. ESI/APCI(+): 474 (M+H), 496 (M+Na). ESI/APCI(−): 472 (M−H).

Example 304: Preparation of 2-((3-(2-hydroxyethoxy)-5-methoxyphenyl)amino)-1-(1H-indol-3-yl)-2-(pyridin-3-yl)ethanone 2-((3-(2-(tert-Butoxy)ethoxy)-5-methoxyphenyl)amino)-1-(1H-indol-3-yl)-2-(pyridin-3-yl)ethanone (0.040 g; 0.084 mmol) was dissolved in a 4N hydrogen chloride solution in dioxane (3.000 mL; 12.00 mmol). The reaction mixture was stirred at room temperature for 6 h and was partially concentrated under reduced pressure. The residue was partitioned dichloromethane and a saturated sodium bicarbonate solution. The phases were separated. The organic phase was concentrated under reduced pressure. Purification by flash chromatography on silica gel using a gradient of methanol (1% to 15%) in dichloromethane followed by purification by preparative HPLC (XBridge column; method 5) furnished 0.015 g (42%) of 2-((3-(2-hydroxyethoxy)-5-methoxyphenyl)amino)-1-(1H-indol-3-yl)-2-(pyridin-3-yl) ethanone as a beige solid. ESI/APCI(+): 418 (M+H). ESI/APCI(−): 416 (M−H). $^1$H NMR (DMSO-$d_6$) δ12.22 (1H, br s); 8.94 (1H, s); 8.87 (1H, s); 8.40 (1H, d); 8.16 (1H, d); 7.95 (1H, d); 7.48 (1H, d); 7.32 (1H, dd); 7.14-7.27 (2H, m); 6.47 (1H, d); 6.17 (1H, d); 6.06 (2H, s); 5.70-5.79 (1H, m); 4.79 (1H, t); 3.76-3.93 (2H, m); 3.62-3.71 (2H, m); 3.61 (3H, s).

Example 305: Preparation of 1-(6-fluoro-1H-indol-3-yl)-2-((3-(hydroxymethyl)-5-methoxyphenyl) amino)-2-(pyridin-3-yl)ethanone 1-(6-Fluoro-1H-indol-3-yl)-2-((3-(hydroxymethyl)-5-methoxyphenyl)amino)-2-(pyridin-3-yl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 6-fluoro-3-formyl-1H-indole-1-carboxylate (0.263 g; 0.999 mmol) and a solution of (3-methoxy-5-((pyridin-3-ylmethylene)amino) phenyl)methanol (0.999 mmol) in ethanol (1 mL), heated at 70° C. for 4 days. Purification by flash chromatography on silica gel using a gradient of methanol (0% to 12%) in dichloromethane followed by purification by preparative TLC using methanol (10%) in dichloromethane as eluent furnished 0.029 g (7%) of the desired compound. ESI/APCI (+): 406 (M+H). ESI/APCI(−): 404 (M−H).

Example 306: Preparation of 2-((2-fluoro-3,5-dimethoxyphenyl)amino)-1-(1H-indol-3-yl)-2-phenylethanone Step 1: To a solution of 3,5-dimethoxyaniline (0.200 g; 1.306 mmol) in dichloromethane (5 mL) was added N-fluoro-2,4,6-trimethylpyridinium triflate (0.377 g; 1.303 mmol) and the reaction mixture was heated at 100° C. overnight. After cooling to room temperature, water was added and the reaction mixture was extracted with ethyl acetate. The organic phase was concentrated under reduced pressure. Purification by flash chromatography on silica gel using a gradient of ethyl acetate (15% to 70%) in heptane furnished 0.068 g (30%) of 2-fluoro-3,5-dimethoxyaniline as a white solid. ESI/APCI(+): 172 (M+Na). $^1$H NMR (DMSO-$d_6$) δ5.94 (1H, dd); 5.89 (1H, dd); 3.73 (3H, s); 3.63 (3H, s).
Step 2: 2-((2-Fluoro-3,5-dimethoxyphenyl)amino)-1-(1H-indol-3-yl)-2-phenylethanone was prepared according to general procedure C from 2-bromo-1-(1H-indol-3-yl)-2-phenylethanone (0.120 g; 0.382 mmol), 2-fluoro-3,5-dimethoxyaniline (0.065 g; 0.382 mmol) and triethylamine (0.106 mL; 0.764 mmol) in acetonitrile (0.5 mL), irradiated in a microwave oven at 100° C. for 15 min and at 120° C. for 10 min. Purification by flash chromatography on silica gel using a gradient of ethyl acetate (15% to 70%) in heptane followed by purification by preparative HPLC (XBridge column; method 2) furnished 0.058 g (37%) of the desired compound as a white solid. ESI/APCI(+): 405 (M+H). ESI/APCI(−): 403 (M−H). $^1$H NMR (DMSO-$d_6$) δ12.20 (1H, br s); 8.87 (1H, s); 8.15 (1H, d); 7.62 (2H, d); 7.47 (1H, d); 7.24-7.34 (2H, m); 7.13-7.23 (3H, m); 6.21 (1H, d); 6.13 (1H, dd); 5.98 (1H, dd); 5.72-5.81 (1H, m); 3.75 (3H, s); 3.63 (3H, s).

Example 307: Preparation of 2-((3,5-dimethoxyphenyl)amino)-1-(1H-indol-3-yl)-2-(6-methylpyridin-3-yl)ethanone Step 1: A mixture of 2-(6-methylpyridin-3-yl)acetic acid (0.150 g; 0.992 mmol) in acetic anhydride (0.094 mL; 0.996 mmol) was irradiated at 85° C. for 1 h in a microwave oven. 1H-Indole (0.116 g; 0.990 mmol) was added and the reaction mixture was irradiated at 85° C. for 60 min in a microwave oven. The reaction mixture was diluted with ethyl acetate and washed with a 1M sodium bicarbonate solution. The organic phase was washed with brine, dried over magnesium sulfate, filtered and concentrated under reduced pressure. Purification by flash chromatography on silica gel using a gradient of methanol (0% to 7%) in dichloromethane furnished 0.057 g (23%) of 1-(1H-indol-3-yl)-2-(6-methylpyridin-3-yl)ethanone as a beige solid. ESI/APCI(+): 251 (M+H). ESI/APCI (−): 249 (M−H).

Step 2: 2-Bromo-1-(1H-indol-3-yl)-2-(6-methylpyridin-3-yl)ethanone was prepared according to general procedure P from a solution of 1-(1H-indol-3-yl)-2-(6-methylpyridin-3-yl)ethanone (0.084 g; 0.336 mmol) in THF (5 mL) and a solution of phenyltrimethylammonium tribromide (0.145 g; 0.386 mmol) in THF (2 mL). The reaction mixture was stirred at 0° C. for 1 h and at room temperature for 4 h. Purification by flash chromatography on silica gel using a gradient of methanol (0% to 5%) in dichloromethane furnished 0.039 g (35%) of the desired compound. ESI/APCI (+): 329, 331 (M+H). ESI/APCI(−): 327, 329 (M−H).
Step 3: A mixture of 2-bromo-1-(1H-indol-3-yl)-2-(6-methylpyridin-3-yl)ethanone (0.038 g; 0.115 mmol) and 3,5-dimethoxyaniline (0.036 g; 0.235 mmol) in acetonitrile (0.8 mL) was stirred at room temperature for 96 h. The reaction mixture was concentrated under reduced pressure. Purification by flash chromatography on silica gel using a gradient of methanol (0% to 5%) in dichloromethane followed by purification by preparative HPLC (XBridge column; method 2) furnished 0.020 g (43%) of 2-((3,5-dimethoxyphenyl)amino)-1-(1H-indol-3-yl)-2-(6-methylpyridin-3-yl)ethanone as a yellow solid. ESI/APCI(+): 402 (M+H). ESI/APCI(−): 400 (M−H).

Example 308: Preparation of 2-((4,6-dimethoxypyrimidin-2-yl)amino)-1-(1H-indol-3-yl)-2-phenylethanone To a solution of 2-bromo-1-(1H-indol-3-yl)-2-phenylethanone (0.050 g; 0.159 mmol) in acetonitrile (0.5 mL) was added 4,6-dimethoxypyrimidin-2-amine (0.123 g; 0.793 mmol) and the mixture was irradiated to 130° C. for 20 min in a microwave oven. The reaction mixture was concentrated under reduced pressure and the residue was purified by flash chromatography on silica gel using a gradient of ethyl acetate (0% to 70%) in heptane. Further purification by solid phase extraction on C18-reversed phase column using a gradient of acetonitrile (30% to 100%) in water furnished 0.010 g (16%) of 2-((4,6-dimethoxypyrimidin-2-yl)amino)-1-(1H-indol-3-yl)-2-phenylethanone. ESI/APCI(+): 389 (M+H). ESI/APCI(−): 387 (M−H).

Example 309: Preparation of 1-(1H-indol-3-yl)-2-((3-methoxyphenyl)amino)-2-(o-tolyl)ethanone Step 1: 3-Methoxy-N-(2-methylbenzylidene)aniline was prepared quantitatively according to general procedure I from 2-methylbenzaldehyde (0.116 mL; 1.003 mmol) and 3-methoxyaniline (0.112 mL; 1.001 mmol). ESI/APCI(+): 226 (M+H).
Step 2: 1-(1H-Indol-3-yl)-2-((3-methoxyphenyl)amino)-2-(o-tolyl)ethanone was prepared according to general procedure L from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 3-formyl-1H-indole-1-carboxylate (0.245 g; 0.999 mmol) and a solution of 3-methoxy-N-(2-methylbenzylidene)aniline (1.001 mmol) in ethanol (1 mL), heated at 70° C. for 2 days. Purification by flash chromatography on silica gel using a gradient of ethyl acetate (0% to 100%) in heptane followed by precipitation from diethyl ether furnished 0.056 g (15%) of the desired compound as a white solid. ESI/APCI(+): 371 (M+H). ESI/APCI(−): 369 (M−H).

Example 310: Preparation of 2-((3-(2-(tert-butoxy) ethoxy)-5-methoxyphenyl)amino)-2-(4-fluorophenyl)-1-(1H-indol-3-yl)ethanone Step 1: 2-(4-Fluorophenyl)-1-(1H-indol-3-yl)ethanone was prepared according to general procedure O from a solution of 1H-indole (0.234 g; 1.997 mmol) in dichloromethane (10 mL), a 1M diethylaluminum chloride solution in hexane (3.000 mL; 3.000 mmol) and a solution of 2-(4-fluorophenyl)acetyl chloride (0.411 mL; 3.001 mmol) in dichloromethane (1 mL). Purification by flash chromatography on silica gel using a gradient of ethyl acetate (10% to 80%) in heptane furnished 0.324 g (64%) of the desired product. ESI/APCI(+): 254 (M+H). ESI/APCI(−): 252 (M−H).

Step 2: 2-Bromo-2-(4-fluorophenyl)-1-(1H-indol-3-yl)ethanone was prepared according to general procedure P from a solution of 2-(4-fluorophenyl)-1-(1H-indol-3-yl)ethanone (0.320 g; 1.263 mmol) in THF (8.5 mL) and a solution of phenyltrimethylammonium tribromide (0.522 g; 1.389 mmol) in THF (5 mL). The reaction mixture was stirred at 0° C. for 1 h and at room temperature overnight. Purification by flash chromatography on silica gel using a gradient of ethyl acetate (0% to 80%) in heptane furnished quantitatively the desired product as a crude brown solid. ESI/APCI(−): 330, 332 (M−H).

Step 3: 2-((3-(2-(tert-Butoxy)ethoxy)-5-methoxyphenyl)amino)-2-(4-fluorophenyl)-1-(1H-indol-3-yl)ethanone was prepared according to general procedure C from 2-bromo-2-(4-fluorophenyl)-1-(1H-indol-3-yl)ethanone (0.200 g; 0.602 mmol), 3-(2-(tert-butoxy)ethoxy)-5-methoxyaniline (0.200 g; 0.836 mmol) and triethylamine (0.168 mL; 1.212 mmol) in acetonitrile (1 mL), irradiated in a microwave oven at 100° C. for 15 min. Purification by flash chromatography on silica gel using a gradient of ethyl acetate (10% to 100%) in heptane furnished 0.153 g (52%) of the desired compound as a brown solid. ESI/APCI(+): 491 (M+H). ESI/APCI(−): 489 (M−H).

Example 311: Preparation of 2-(4-fluorophenyl)-2-((3-(2-hydroxyethoxy)-5-methoxyphenyl)amino)-1-(1H-indol-3-yl)ethanone 2-((3-(2-(tert-Butoxy)ethoxy)-5-methoxyphenyl)amino)-2-(4-fluorophenyl)-1-(1H-indol-3-yl)ethanone (0.150 g; 0.306 mmol) was dissolved in a 4N hydrogen chloride solution in dioxane (3.000 mL; 12.00 mmol) was stirred at room temperature for 16 h. The reaction was quenched by addition of a saturated sodium bicarbonate solution. The reaction mixture was extracted with ethyl acetate. The organic phase was washed with brine, dried over magnesium sulfate, filtered and concentrated under reduced pressure. Purification by flash chromatography on silica gel using a gradient of ethyl acetate (30% to 100%) in heptane furnished 0.052 g (39%) of 2-(4-fluorophenyl)-2-((3-(2-hydroxyethoxy)-5-methoxyphenyl)amino)-1-(1H-indol-3-yl)ethanone. ESI/APCI(+): 435 (M+H). ESI/APCI(−): 433 (M−H).

Example 312: Preparation of 2-((3,5-dimethoxyphenyl)amino)-1-(5-(hydroxymethyl)-1H-indol-3-yl)-2-phenylethanone Step 1: 5-(((tert-Butyldimethylsilyl)oxy)methyl)-1H-indole was prepared according to general procedure N from (1H-indol-5-yl)methanol (1.000 g; 6.785 mmol), DBU (1.520 mL; 10.18 mmol) and TBDMSCl (2.250 g; 14.93 mmol) in THF (25 mL). Purification by flash chromatography on silica gel using a gradient of dichloromethane (5% to 50%) in heptane furnished 1.540 g (86%) of the desired compound as a beige solid.

Step 2: 1-(5-(((tert-Butyldimethylsilyl)oxy)methyl)-1H-indol-3-yl)-2-chloro-2-phenylethanone was prepared according to general procedure A from 5-(((tert-butyldimethylsilyl)oxy)methyl)-1H-indole (0.700 g; 2.675 mmol), pyridine (0.210 mL; 2.602 mmol) and α-chlorophenylacetyl chloride (0.386 mL; 2.678 mmol) in toluene (2 mL). The residue obtained after extraction was purified by flash chromatography on silica gel using a gradient of ethyl acetate (15% to 100%) in heptane to give 0.550 g (50%) of the desired compound as a white solid.

Step 3: 2-((3,5-Dimethoxyphenyl)amino)-1-(5-(hydroxymethyl)-1H-indol-3-yl)-2-phenylethanone was prepared according to general procedure E from 1-(5-(((tert-butyldimethylsilyl)oxy)methyl)-1H-indol-3-yl)-2-chloro-2-phenylethanone (0.300 g; 0.724 mmol) and 3,5-dimethoxyaniline (1.110 g; 7.246 mmol) in acetonitrile (3 mL), irradiated in a microwave oven at 130° C. for 30 min. The residue was purified by flash chromatography on silica gel using a gradient of ethyl acetate (15% to 100%) in heptane. Further purification by flash chromatography on silica gel using a gradient of ethyl acetate (5% to 50%) in dichloromethane followed by purification by preparative HPLC (XBridge column; method 2) furnished 0.019 g (5%) of the desired compound as a white solid. ESI/APCI(+): 417 (M+H). ESI/APCI(−): 415 (M−H). $^1$H NMR (DMSO-$d_6$) δ12.08 (1H, br s); 8.87 (1H, s); 8.15 (1H, s); 7.64 (2H, d); 7.41 (1H, d); 7.25-7.35 (2H, m); 7.12-7.24 (2H, m); 6.33 (1H, d); 5.98-6.15 (3H, m); 5.73 (1H, s); 5.11 (1H, t); 4.56 (2H, d); 3.63 (6H, s).

Example 313: Preparation of 2-((3,5-dimethoxyphenyl)amino)-1-(4-(hydroxymethyl)-1H-indol-3-yl)-2-phenylethanone Step 1: 4-(((tert-Butyldimethylsilyl)oxy)methyl)-1H-indole was prepared according to general procedure N from (1H-indol-4-yl)methanol (1.000 g; 6.785 mmol), DBU (1.520 mL; 10.18 mmol) and TBDMSCl (2.250 g; 14.93 mmol) in THF (25 mL). Purification by flash chromatography on silica gel using a gradient of dichloromethane (15% to 70%) in heptane furnished 1.650 g (93%) of the desired compound as a white solid.

Step 2: To a solution of 4-(((tert-butyldimethylsilyl)oxy)methyl)-1H-indole (1.000 g; 3.825 mmol) and pyridine (0.300 mL; 3.717 mmol) in toluene (10 mL) heated at 55° C. was added dropwise α-chlorophenylacetyl chloride (0.552 mL; 3.825 mmol). The reaction mixture was heated at 55° C. for 1 h. After cooling to room temperature, water and methanol were added. The reaction mixture was stirred at room temperature for 1 h. The reaction mixture was extracted with ethyl acetate. The organic layer was washed with brine, dried over magnesium sulfate, filtered and concentrated under reduced pressure. Purification by flash chromatography on silica gel using a gradient of ethyl acetate (15% to 70%) in heptane furnished 0.648 g (41%) of 1-(4-(((tert-butyldimethylsilyl)oxy)methyl)-1H-indol-3-yl)-2-chloro-2-phenylethanone as a brown oil and 0.317 g (28%) of 2-chloro-1-(4-(hydroxymethyl)-1H-indol-3-yl)-2-phenylethanone.

Step 3: 2-((3,5-Dimethoxyphenyl)amino)-1-(4-(hydroxymethyl)-1H-indol-3-yl)-2-phenylethanone was prepared according to general procedure E from 2-chloro-1-(4-(hydroxymethyl)-1H-indol-3-yl)-2-phenylethanone (0.150 g; 0.500 mmol) and 3,5-dimethoxyaniline (0.767 g; 5.007 mmol) in acetonitrile (3 mL), irradiated in a microwave oven at 130° C. for 15 min. The residue was purified by flash chromatography on silica gel using a gradient of ethyl acetate (2% to 40%) in heptane. Further purification by preparative HPLC (XBridge column; method 2) followed by precipitation from dichloromethane furnished 0.028 g (14%)

of the desired compound as a white solid. ESI/APCI(+): 417 (M+H). ESI/APCI(−): 415 (M−H). $^1$H NMR (DMSO-d$_6$) δ12.24 (1H, br s); 8.96 (1H, s); 7.60 (3H, d); 7.25-7.43 (4H, m); 7.20 (2H, m); 6.36 (1H, d); 6.17 (1H, d); 6.08 (2H, s); 4.94-5.15 (2H, m); 4.65 (1H, dd); 3.64 (6H, s).

Example 314: Preparation of 2-((3,5-dimethoxyphenyl)amino)-1-(5-(3-hydroxypropyl)-1H-indol-3-yl)-2-phenylethanone Step 1: To a mixture of 1H-indole-5-carboxaldehyde (4.790 g; 33.00 mmol) and potassium carbonate (11.40 g; 82.48 mmol) in THF (90 mL) was added methyl diethylphosphonoacetate (8.700 mL; 47.40 mmol). The reaction mixture was heated under reflux for 24 h and concentrated under reduced pressure. The residue was taken up in water, a 1N hydrochloric acid solution and diethyl ether. The orange precipitate was filtered. The phases of the filtrate were separated. The organic phase was dried over magnesium sulfate, filtered and concentrated under reduced pressure. Purification by flash chromatography on silica gel using a gradient of ethyl acetate (0% to 40%) in heptane furnished 2.350 g (35%) of methyl 3-(1H-indol-5-yl)acrylate as a white solid. ESI/APCI(−): 200 (M−H). $^1$HNMR (DMSO-d$_6$) δ 8.32 (1H, br s); 7.85 (1H, d); 7.81 (1H, s); 7.43 (1H, dd); 7.38 (1H, d); 7.24 (1H, t); 6.59 (1H, br s); 6.42 (1H, d); 3.81 (3H, s).

Step 2: To a solution of methyl 3-(1H-indol-5-yl)acrylate (2.000 g; 9.939 mmol) in methanol (20 mL) was added 10% palladium on carbon (0.530 g; 0.489 mmol). The suspension was stirred at room temperature under hydrogen atmosphere for 24 h. The reaction mixture was filtered through a pad of celite and the filtrate was concentrated under reduced pressure to give 1.820 g (90%) of methyl 3-(1H-indol-5-yl)propanoate as a white solid. ESI/APCI(+): 204 (M+H).

Step 3: To a solution of methyl 3-(1H-indol-5-yl)propanoate (1.820 g; 8.955 mmol) in a mixture of THF (30 mL) and ethanol (7.5 mL) was added a 4M lithium borohydride solution in THF (5.000 mL; 20.00 mmol). The reaction mixture was stirred at room temperature overnight. After cooling to 0° C., the reaction was quenched by addition of a saturated ammonium chloride solution. The reaction mixture was extracted with ethyl acetate. The organic phase was dried over magnesium sulfate and concentrated under reduced pressure. Purification by flash chromatography on silica gel using a gradient of ethyl acetate (0% to 40%) in heptane furnished 1.400 g (89%) of 3-(1H-indol-5-yl)propan-1-ol as a colorless oil. ESI/APCI(+): 176 (M+H).

Step 4: 5-(3-((tert-Butyldimethylsilyl)oxy)propyl)-1H-indole was prepared according to general procedure N from 3-(1H-indol-5-yl)propan-1-ol (0.200 g; 1.141 mmol), DBU (0.255 mL; 1.708 mmol) and TBDMSCl (0.378 g; 2.508 mmol) in THF (4 mL). Purification by flash chromatography on silica gel using a gradient of dichloromethane (15% to 70%) in heptane furnished 0.313 g (95%) of the desired compound as an oil. ESI/APCI(+): 290 (M+H).

Step 5: To a solution of 5-(3-((tert-butyldimethylsilyl)oxy)propyl)-1H-indole (0.310 g; 1.071 mmol) in dichloromethane (4 mL) cooled to 0° C. was added a 1M diethylaluminium chloride solution in THF (1.630 mL; 1.630 mmol). The mixture was stirred at 0° C. for 30 min and a solution of phenylacetyl chloride (0.214 mL; 1.606 mmol) in dichloromethane (4 mL) was added dropwise. The resulting solution was stirred at 0° C. for 2 h. The reaction was quenched by addition of a mixture of water and a saturated sodium bicarbonate solution. The reaction mixture was extracted with ethyl acetate. The organic phase was concentrated under reduced pressure. Purification by flash chromatography on silica gel using a gradient of ethyl acetate (2% to 100%) in heptane furnished 0.071 g (23%) of 1-(5-(3-hydroxypropyl)-1H-indol-3-yl)-2-phenylethanone as a white solid. ESI/APCI(+): 294 (M+H); 316 (M+Na). ESI/APCI(−): 292 (M−H).

Step 6: 2-Bromo-1-(5-(3-hydroxypropyl)-1H-indol-3-yl)-2-phenylethanone was prepared according to general procedure P from a solution of 1-(5-(3-hydroxypropyl)-1H-indol-3-yl)-2-phenylethanone (0.088 g; 0.300 mmol) in THF (2.5 mL) and a solution of phenyltrimethylammonium tribromide (0.124 g; 0.330 mmol) in THF (2.5 mL). The reaction mixture was stirred at 0° C. for 1 h and at room temperature overnight. The organic phase was concentrated under reduced pressure. Purification by flash chromatography on silica gel using a gradient of ethyl acetate (5% to 50%) in dichloromethane furnished 0.096 g (86%) of the desired compound as a beige solid. ESI/APCI(+): 372, 374 (M+H); 394, 396 (M+Na). ESI/APCI(−): 370, 372 (M−H).

Step 7: A mixture of 2-bromo-1-(5-(3-hydroxypropyl)-1H-indol-3-yl)-2-phenylethanone (0.100 g; 0.269 mmol), 3,5-dimethoxyaniline (0.205 g; 1.345 mmol) and triethylamine (0.075 mL; 0.541 mmol) in acetonitrile (2 mL) was stirred at room temperature for 2 days. A 1N hydrochloric acid solution was added and the reaction mixture was extracted with ethyl acetate. The organic phase was concentrated under reduced pressure. Purification by flash chromatography on silica gel using a gradient of ethyl acetate (5% to 50%) in dichloromethane furnished 0.071 g (59%) of 2-((3,5-dimethoxyphenyl)amino)-1-(5-(3-hydroxypropyl)-1H-indol-3-yl)-2-phenylethanone as a beige solid. ESI/APCI(+): 445 (M+Na). ESI/APCI(−): 443 (M−H). $^1$H NMR (DMSO-d$_6$) δ12.06 (1H, br s); 8.86 (1H, br s); 8.01 (1H, s); 7.65 (2H, d); 7.38 (1H, d); 7.31 (2H, t); 7.16-7.25 (1H, m); 7.08 (1H, d); 6.32 (1H, br s); 6.06 (3H, br s); 5.74 (1H, br s); 4.45 (1H, br s); 3.63 (6H, s); 3.43 (2H, m); 2.69 (2H, t); 1.65-1.85 (2H, m).

Example 315: Preparation of 2-((3-(2-(tert-butoxy)ethoxy)-5-methoxyphenyl)amino)-1-(5-fluoro-1H-indol-3-yl)-2-phenylethanone Step 1: 1-(5-Fluoro-1H-indol-3-yl)-2-phenylethanone was prepared according to general procedure O from a solution of 5-fluoro-1H-indole (0.680 g; 5.032 mmol) in dichloromethane (20 mL), a 1M diethylaluminium chloride solution in hexane (7.600 mL; 7.600 mmol) and a solution of phenylacetyl chloride (1.000 mL; 7.504 mmol) in dichloromethane (20 mL). Purification by precipitation from ethyl acetate furnished 0.820 g (64%) of the desired compound as a white solid. ESI/APCI(+): 254 (M+H). ESI/APCI(−): 252 (M−H).

Step 2: 2-Bromo-1-(5-fluoro-1H-indol-3-yl)-2-phenylethanone was prepared according to general procedure P from a solution of 1-(5-fluoro-1H-indol-3-yl)-2-phenylethanone (0.800 g; 3.159 mmol) in THF (22 mL) and a solution of phenyltrimethylammonium tribromide (1.310 g; 3.485 mmol) in THF (25 mL). The reaction mixture was stirred at 0° C. for 1 h and at room temperature for 4 h. Purification by flash chromatography on silica gel using a gradient of ethyl acetate (0% to 70%) in heptane furnished 1.040 g (99%) of the desired compound as a white solid. ESI/APCI (+): 332, 334 (M+H). ESI/APCI (−): 330, 332 (M−H).

Step 3: A solution of 2-bromo-1-(5-fluoro-1H-indol-3-yl)-2-phenylethanone (0.100 g; 0.301 mmol), 3-(2-(tert-butoxy)ethoxy)-5-methoxyaniline (0.075 g; 0.313 mmol) and triethylamine (0.085 mL; 0.610 mmol) in acetonitrile (0.45 mL)

was stirred at room temperature for 7 days. The reaction mixture was concentrated under reduced pressure. Purification by flash chromatography on silica gel using a gradient of ethyl acetate (0% to 50%) in heptane furnished 0.101 g (68%) of 2-((3-(2-(tert-butoxy)ethoxy)-5-methoxyphenyl)amino)-1-(5-fluoro-1H-indol-3-yl)-2-phenylethanone as an oil. ESI/APCI(+): 491 (M+H). ESI/APCI(−): 489 (M−H).

Example 316: Preparation of 1-(5-fluoro-1H-indol-3-yl)-2-((3-(2-hydroxyethoxy)-5-methoxyphenyl)amino)-2-phenylethanone 2-((3-(2-tert-Butoxy)ethoxy)-5-methoxyphenyl)amino)-1-(5-fluoro-1H-indol-3-yl)-2-phenylethanone (0.101 g; 0.206 mmol) was dissolved in a 4N hydrogen chloride solution in dioxane (2.000 mL; 8.000 mmol). The reaction mixture was stirred at room temperature for 16 h and was concentrated under reduced pressure. The residue was partitioned between ethyl acetate and a 1M sodium bicarbonate solution. The phases were separated. The organic phase was dried over magnesium sulfate, filtered and concentrated under reduced pressure. Purification by flash chromatography on silica gel using a gradient of ethyl acetate (50% to 100%) in heptane furnished 0.060 g (67%) of 1-(5-fluoro-1H-indol-3-yl)-2-((3-(2-hydroxyethoxy)-5-methoxyphenyl)amino)-2-phenylethanone as a solid. ESI/APCI(+): 435 (M+H). ESI/APCI (−): 433 (M−H).

Example 317: Preparation of 2-((4-fluoro-3-methoxyphenyl)amino)-1-(1H-indol-3-yl)-2-phenylethanone A solution of 2-bromo-1-(1H-indol-3-yl)-2-phenylethanone (0.048 g; 0.153 mmol), 4-fluoro-3-methoxyaniline (0.026 g; 0.184 mmol) and triethylamine (0.030 mL; 0.215 mmol) in acetonitrile (0.5 mL) was stirred at 50° C. for 16 h and at room temperature for 96 h. The reaction mixture was concentrated under reduced pressure. Purification by flash chromatography on silica gel using a gradient of ethyl acetate (0% to 40%) in heptane furnished 0.054 g (94%) of 2-((4-fluoro-3-methoxyphenyl)amino)-1-(1H-indol-3-yl)-2-phenylethanone as a beige foam. ESI/APCI(+): 375 (M+H). ESI/APCI(−): 373 (M−H).

Example 318: Preparation of 2-((3,5-dimethoxyphenyl)amino)-1-(4-(3-hydroxypropyl)-1H-indol-3-yl)-2-phenylethanone Step 1: To a solution of 1H-indole-4-carbaldehyde (1.000 g; 6.889 mmol) and methyl 2-(diethoxyphosphoryl)acetate (1.511 mL; 8.268 mmol) in THF (15 mL) was added potassium carbonate (2.380 g; 17.22 mmol). The reaction mixture was heated under reflux for 16 h. The reaction mixture was concentrated under reduced pressure. The residue was partitioned between diethyl ether and water. The phases were separated. The organic phase was washed with brine, dried over magnesium sulfate, filtered and concentrated under reduced pressure. Purification by flash chromatography on silica gel using a gradient of ethyl acetate (0% to 60%) in heptane furnished 1.059 g (76%) of methyl 3-(1H-indol-4-yl)acrylate as an oil. ESI/APCI(−): 200 (M−H).

Step 2: To a solution of methyl 3-(1H-indol-4-yl)acrylate (1.059 g; 5.263 mmol) in methanol was added 10% palladium on carbon (0.560 g; 5.262 mmol). The suspension was stirred under a hydrogen atmosphere at room temperature for 16 h. The reaction mixture was filtered over a plug of celite. The solid was washed with ethanol and the filtrate was concentrated under reduced pressure. Purification by flash chromatography on silica gel using a gradient of ethyl acetate (0% to 60%) in heptane furnished 0.936 g (88%) of methyl 3-(1H-indol-4-yl)propanoate. ESI/APCI(+): 204 (M+H).

Step 3: To a solution of methyl 3-(1H-indol-4-yl)propanoate (0.935 g; 4.601 mmol) in a mixture of THF (15 mL) and ethanol (4 mL) was added lithium borohydride (0.230 g; 10.58 mmol). The reaction mixture was stirred at room temperature for 16 h. The reaction was quenched by addition of a saturated ammonium chloride solution and the reaction mixture was extracted with ethyl acetate. The organic phase was washed with brine, dried over magnesium sulfate, filtered and concentrated under reduced pressure to furnish 0.730 g (91%) of 3-(1H-indol-4-yl)propan-1-ol as a milky oil. ESI/APCI(+): 176 (M+H). ESI/APCI(−): 174 (M−H).

Step 4: 4-(3-((tert-Butyldimethylsilyl)oxy)propyl)-1H-indole was prepared according to general procedure N from 3-(1H-indol-4-yl)propan-1-ol (0.300 g; 1.712 mmol), TBDMSCl (0.568 g; 3.769 mmol) and DBU (0.387 mL; 2.568 mmol) in THF (6 mL). Purification by flash chromatography on silica gel using a gradient of ethyl acetate (0% to 60%) in heptane furnished 0.388 g (78%) of the desired compound. ESI/APCI(+): 290 (M+H). ESI/APCI(−): 288 (M−H).

Step 5: 1-(4-(3-((tert-Butyldimethylsilyl)oxy)propyl)-1H-indol-3-yl)-2-phenylethanone was prepared according to general procedure O from a solution of 4-(3-((tert-butyldimethylsilyl)oxy)propyl)-1H-indole (0.385 g; 1.330 mmol) in dichloromethane (7 mL), a 1M diethylaluminum chloride solution in hexane (1.995 mL; 1.995 mmol) and phenylacetyl chloride (0.266 mL; 1.996 mmol). Purification by flash chromatography on silica gel using a gradient of ethyl acetate (0% to 60%) in heptane furnished 0.090 g (17%) of the desired product as a white solid. ESI/APCI(+): 408 (M+H); 430 (M+Na). ESI/APCI(−): 406 (M−H).

Step 6: 2-Bromo-1-(4-(3-hydroxypropyl)-1H-indol-3-yl)-2-phenylethanone was prepared according to general procedure P from a solution of 1-(4-(3-((tert-butyldimethylsilyl)oxy)propyl)-1H-indol-3-yl)-2-phenylethanone (0.090 g; 0.221 mmol) in THF (2 mL) and a solution of phenyltrimethylammonium tribromide (0.091 g; 0.243 mmol) in THF (2 mL). The reaction mixture was stirred at 0° C. for 1 h and at room temperature overnight. Purification by flash chromatography on silica gel using a gradient of ethyl acetate (0% to 100%) in heptane furnished 0.040 g (49%) the desired product. ESI/APCI(+): 372, 374 (M+H). ESI/APCI (−): 370, 372 (M−H).

Step 7: To a solution of 2-bromo-1-(4-(3-hydroxypropyl)-1H-indol-3-yl)-2-phenylethanone (0.040 g; 0.107 mmol) in acetonitrile (0.5 mL) was added 3,5-dimethoxyaniline (0.049 g; 0.322 mmol) and the mixture was stirred at room temperature for 2 days. The reaction mixture was concentrated under reduced pressure and the residue was purified by flash chromatography on silica gel using a gradient of ethyl acetate (10% to 80%) in heptane. Further purification by preparative HPLC (XBridge column; method 2) furnished 0.009 g (18%) of 2-((3,5-dimethoxyphenyl)amino)-1-(4-(3-hydroxypropyl)-1H-indol-3-yl)-2-phenylethanone as a white amorphous solid. ESI/APCI(+): 445 (M+H). ESI/APCI(−): 443 (M−H).

Example 319: Preparation of 2-((3,5-dimethoxyphenyl)amino)-1-(7-(2-hydroxyethyl)-1-methyl-1H-indol-3-yl)-2-phenylethanone Step 1: 2-(1H-Indol-7-yl)ethyl acetate was prepared according to general procedure Q from 2-(1H-indol-7-yl)

ethanol (0.200 g; 1.241 mmol), DMAP (0.310 g; 2.537 mmol) and acetic anhydride (0.310 mL; 3.285 mmol) in dichloromethane (30 mL). Purification by flash chromatography on silica gel using a gradient of ethyl acetate (20% to 80%) in heptane furnished 0.218 g (86%) of the desired product as a colourless oil. ESI/APCI(+): 204 (M+H); 226 (M+Na). $^1$H NMR (DMSO-d$_6$) δ 11.11 (1H, br s); 7.41 (1H, m); 7.33 (1H, t); 6.93 (2H, m); 6.43 (1H, m); 4.29 (2H, t); 3.16 (2H, t); 1.97 (3H, s).

Step 2: To a solution of 2-(1H-indol-7-yl)ethyl acetate (0.118 g; 0.581 mmol) in DMF (4 mL) were added cesium carbonate (0.483 g; 2.965 mmol) and methyl iodide (0.055 mL; 1.767 mmol). After 7 h at room temperature, cesium carbonate (0.483 g; 2.965 mmol) and methyl iodide (0.055 mL; 1.767 mmol) were added again. The reaction mixture was stirred overnight at room temperature. Water was added and the reaction mixture was extracted with ethyl acetate. The organic phase was washed with water and brine, dried over sodium sulfate, filtered and concentrated under reduced pressure. Purification by flash chromatography on silica gel using a gradient of ethyl acetate (20% to 60%) in heptane furnished 0.094 g (75%) of 2-(1-methyl-1H-indol-7-yl)ethyl acetate as a yellow oil. ESI/APCI(+): 218 (M+H); 240 (M+Na). $^1$H NMR (DMSO-d$_6$) δ 7.44 (1H, m); 7.24 (1H, t); 6.95 (2H, m); 6.40 (1H, m); 4.30 (2H, t); 4.04 (3H, s); 3.38 (2H, t); 2.02 (3H, s).

Step 3: 2-(1-Methyl-3-(2-phenylacetyl)-1H-indol-7-yl)ethyl acetate was prepared according to general procedure O from a solution of 2-(1-methyl-1H-indol-7-yl)ethyl acetate (0.094 g; 0.433 mmol) in dichloromethane (2.2 mL), a 1M diethylaluminium chloride solution in hexane (0.750 mL; 0.750 mmol) and a solution of phenylacetyl chloride (0.098 mL; 0.735 mmol) in dichloromethane (2.2 mL). Purification by flash chromatography on silica gel using a gradient of ethyl acetate (20% to 80%) in heptane furnished 0.071 g (49%) of the desired product as purple powder. ESI/APCI (+): 336 (M+H); 358 (M+Na). $^1$H NMR (DMSO-d$_6$) δ 8.53 (1H, m); 8.15 (1H, d); 7.1-7.4 (7H, m); 4.31 (2H, t); 4.15 (3H, s); 4.11 (2H, s); 3.40 (2H, t); 2.00 (3H, s).

Step 4: To a suspension of 2-(1-methyl-3-(2-phenylacetyl)-1H-indol-7-yl)ethyl acetate (0.090 g; 0.268 mmol) in a mixture of dioxane (1.4 mL) and water (1.4 mL) was added a 1N lithium oxide solution. The reaction mixture was stirred at room temperature for 2 h. The reaction mixture was extracted with ethyl acetate. The organic phase was washed with a 1N hydrochloric acid solution, water and brine, dried over sodium sulfate, filtered and concentrated under reduced pressure. Purification by flash chromatography on silica gel using a gradient of methanol (0% to 10%) in dichloromethane furnished 0.069 g (88%) of 1-(7-(2-hydroxyethyl)-1-methyl-1H-indol-3-yl)-2-phenylethanone as a white foam. ESI/APCI(+): 294 (M+H); 316 (M+Na).

Step 4: 2-Bromo-1-(7-(2-hydroxyethyl)-1-methyl-1H-indol-3-yl)-2-phenylethanone was prepared according to general procedure P from a solution of 1-(7-(2-hydroxyethyl)-1-methyl-1H-indol-3-yl)-2-phenylethanone (0.069 g; 0.235 mmol) in THF (2.9 mL) and a solution of phenyltrimethylammonium tribromide (0.131 g; 0.348 mmol) in THF (3.5 mL). The reaction mixture was stirred at 0° C. for 1 h and at room temperature for 3 h. Purification by flash chromatography on silica gel using a gradient of methanol (0% to 10%) in dichloromethane furnished 0.057 g (65%) of the desired product as a yellow oil. ESI/APCI(+): 372, 374 (M+H). $^1$H NMR (DMSO-d$_6$) δ 8.62 (1H, m); 8.12 (1H, d); 7.67 (2H, m); 7.35 (3H, m); 7.16 (1H, m); 7.08 (1H, m); 6.70 (1H, s); 4.11 (3H, s); 3.67 (2H, t); 3.19 (2H, t).

Step 5: 2-((3,5-Dimethoxyphenyl)amino)-1-(7-(2-hydroxyethyl)-1-methyl-1H-indol-3-yl)-2-phenylethanone was prepared according to general procedure E from 2-bromo-1-(7-(2-hydroxyethyl)-1-methyl-1H-indol-3-yl)-2-phenylethanone (0.052 g; 0.140 mmol) and 3,5-dimethoxyaniline (0.216 g; 1.410 mmol) in acetonitrile (0.8 mL), irradiated in a microwave oven at 100° C. for 10 min. The residue was purified by flash chromatography on silica gel using a gradient of methanol (0% to 10%) in dichloromethane. Further purification by flash chromatography on silica gel using a gradient of ethyl acetate (40% to 95%) in heptane furnished 0.042 g (68%) of the desired product as a beige powder. ESI/APCI(+): 445 (M+H); 467 (M+Na). ESI/APCI (−): 443 (M−H). $^1$H NMR (DMSO-d$_6$) δ 8.85 (1H, s); 8.09 (1H, d); 7.62 (2H, m); 7.29 (2H, m); 7.0-7.2 (3H, m); 6.34 (1H, d); 6.01 (1H, s); 5.96 (2H, d); 5.72 (1H, s); 4.80 (1H, t); 4.15 (3H, s); 3.68 (2H, q); 3.61 (6H, s); 3.20 (2H, m).

Example 320: Preparation of 2-((3-hydroxy-5-methoxyphenyl)amino)-1-(1H-indol-3-yl)-2-phenylethanone A mixture of 2-bromo-1-(1H-indol-3-yl)-2-phenylethanone (0.065 g; 0.207 mmol), 3-amino-5-methoxyphenol (0.115 g; 0.828 mmol) and triethylamine (0.058 mL; 0.418 mmol) in acetonitrile (0.75 mL) was stirred at room temperature for 65 h. A 1N hydrochloric acid solution was added and the reaction mixture was extracted with ethyl acetate. The organic phase was concentrated under reduced pressure. The residue was purified by flash chromatography on silica gel using a gradient of ethyl acetate (15% to 70%) in heptane. Further purification by flash chromatography on silica gel using a gradient of ethyl acetate (2% to 20%) in dichloromethane furnished 0.033 g (43%) of 2-((3-hydroxy-5-methoxyphenyl)amino)-1-(1H-indol-3-yl)-2-phenylethanone as a white solid. ESI/APCI(+): 373 (M+H). ESI/APCI (−): 371 (M−H). $^1$H NMR (DMSO-d$_6$) δ12.12 (1H, br s); 8.93 (1H, br s); 8.85 (1H, s); 8.15 (1H, d); 7.61 (2H, d); 7.46 (1H, d); 7.24-7.35 (2H, m); 7.19 (3H, m); 6.17 (1H, d); 6.00 (1H, d); 5.90 (1H, s); 5.84 (1H, s); 5.58 (1H, s); 3.56 (3H, s).

Example 321: Preparation of 2-((3,5-dimethoxyphenyl)amino)-1-(1-methyl-1H-indol-3-yl)-2-(pyridin-3-yl)ethanone Step 1: To a solution of 3-acetylindole (2.000 g; 12.56 mmol) in DMF (26 mL) cooled to 0° C. was added portionwise sodium hydride (60% dispersion in mineral oil; 0.552 g; 13.80 mmol). After 10 min at 0° C., methyl iodide (0.939 mL; 15.08 mmol) was added and the reaction mixture was stirred at room temperature for 23 h. The reaction mixture was poured into a mixture ice/water and extracted ethyl acetate. The organic phase was washed with brine, dried over sodium sulfate, filtered and concentrated under reduced pressure. Purification by flash chromatography on silica gel using a gradient of ethyl acetate (10% to 50%) in heptane furnished 1.732 g (80%) of 1-(1-methyl-1H-indol-3-yl)ethanone as a white powder. ESI/APCI(+): 174 (M+H); 196 (M+Na).

Step 2: A mixture of tris(dibenzylideneacetone)dipalladium (0.030 g; 0.033 mmol), (±) 2,2'-bis(diphenylphosphino)binaphthyl (0.051 g: 0.082 mmol) and sodium tert-butoxide (0.211 g; 2.300 mmol) in THF (3.9 mL) was degassed for 15 min with argon. 1-(1-Methyl-1H-indol-3-yl)ethanone (0.200 g; 1.155 mmol), 3-bromopyridine (0.094 mL; 0.862 mmol) and THF (1.9 mL) were added. The reaction mixture was heated at 80° C. for 39 h. After cooling to room temperature, the reaction mixture was diluted with ethyl acetate and washed with water. The organic phase was washed with a 1N hydrochloric acid solution. The aqueous phase was basified with a 2N sodium hydroxide solution and extracted with ethyl acetate. The organic phase was washed with water and brine, dried over sodium sulfate, filtered and concentrated under reduced pressure. Purification by flash chromatography on silica gel using a gradient of methanol (0% to 10%) in dichloromethane furnished 0.093 g (39%) of 1-(1-methyl-1H-indol-3-yl)-2-(pyridin-3-yl)ethanone. ESI/APCI(+): 251 (M+H); 273 (M+Na). $^1$H NMR (DMSO-$d_6$) δ 8.60 (1H, s); 8.55 (1H, d); 8.44 (1H, dd); 8.17 (1H, d); 7.74 (1H, d); 7.56 (1H, d); 7.2-7.35 (3H, m); 4.20 (2H, s); 3.91 (3H, s).

Step 3: To a solution of 1-(1-methyl-1H-indol-3-yl)-2-(pyridin-3-yl)ethanone (0.051 g; 0.204 mmol) in THF (5 mL) was added pyridinium tribromide (0.130 g; 0.406 mmol). The reaction mixture was heated at 60° C. for 6 h. 3,5-Dimethoxyaniline (0.312 g; 2.037 mmol) was added and the reaction mixture was refluxed for 2 h. After cooling to room temperature, the reaction mixture was filtered and the solid was washed with ethyl acetate. The filtrate was concentrated under reduced pressure. The residue was partitioned between ethyl acetate and a saturated sodium bicarbonate solution. The phases were separated. The organic phase was washed with water and brine, dried over sodium sulfate, filtered and concentrated under reduced pressure. Purification by flash chromatography on silica gel using a gradient of ethyl acetate (10% to 90%) in heptane furnished 0.043 g (53%) of 2-((3,5-dimethoxyphenyl)amino)-1-(1-methyl-1H-indol-3-yl)-2-(pyridin-3-yl)ethanone as a yellow solid. ESI/APCI(+): 402 (M+H); 424 (M+Na). ESI/APCI(−): 400 (M−H). $^1$H NMR (DMSO-$d_6$) δ 9.02 (1H, s); 8.94 (1H, d); 8.46 (1H, dd); 8.22 (1H, d); 8.02 (1H, d); 7.62 (1H, d); 7.27-7.41 (3H, m); 6.55 (1H, d); 6.14 (1H, d); 6.10 (2H, d); 5.80 (1H, s); 3.97 (3H, s); 3.68 (6H, s).

Example 322: Preparation of 2-((3-(3-hydroxypropoxy)-5-methoxyphenyl)amino)-1-(1H-indol-3-yl)-2-phenylethanone Step 1: To a mixture of 3-amino-5-methoxyphenol (1.000 g; 7.186 mmol) and cesium carbonate (4.680 g; 14.37 mmol) in DMF (24 mL) was added 3-bromopropan-1-ol (1.100 g; 7.914 mmol).

The reaction mixture was stirred at 60° C. for 20 h. After cooling to 0° C., a saturated sodium bicarbonate solution was added and the reaction mixture was extracted with ethyl acetate. The organic phase was concentrated under reduced pressure. Purification by flash chromatography on silica gel using a gradient of ethyl acetate (15% to 100%) in heptane furnished 0.758 g (53%) of 3-(3-amino-5-methoxyphenoxy)propan-1-ol as an oil. ESI/APCI(+): 198 (M+H).

Step 2: A mixture of 2-bromo-1-(1H-indol-3-yl)-2-phenylethanone (0.100 g; 0.318 mmol), 3-(3-amino-5-methoxyphenoxy)propan-1-ol (0.063 g; 0.319 mmol) and triethylamine (0.088 mL; 0.635 mmol) in acetonitrile (2 mL) was stirred at room temperature for 2 days. 3-(3-Amino-5-methoxyphenoxy)propan-1-ol (0.063 g; 0.319 mmol) was added again and stirring was continued at room temperature for 2 days. The mixture was diluted with ethyl acetate and washed with a 1N hydrochloric acid solution. The organic phase was concentrated under reduced pressure. Purification by flash chromatography on silica gel using a gradient of ethyl acetate (5% to 50%) in dichloromethane followed by purification by preparative HPLC (XBridge column; method 5) furnished 0.036 g (26%) of 2-((3-(3-hydroxypropoxy)-5-methoxyphenyl)amino)-1-(1H-indol-3-yl)-2-phenylethanone as a white solid. ESI/APCI(+): 431 (M+H). ESI/APCI(−): 429 (M−H). $^1$H NMR (DMSO-$d_6$) δ12.14 (1H, br s); 8.90 (1H, s); 8.16 (1H, d); 7.63 (2H, d); 7.46 (1H, d); 7.07-7.36 (5H, m); 6.32 (1H, d); 5.93-6.15 (3H, m); 5.71 (1H, s); 4.51 (1H, t); 3.89 (2H, t); 3.61 (3H, s); 3.51 (2H, m); 1.78 (2H, m).

Example 323: Preparation of 2-((3,5-dimethoxyphenyl)amino)-1-(7-(hydroxymethyl)-1H-indol-3-yl)-2-phenylethanone Step 1: A solution of (1H-indol-7-yl)methanol (0.251 g; 1.705 mmol), imidazole (0.287 g; 4.216 mmol) and TBDMSCl (0.300 g; 1.990 mmol) in THF (8 mL) was stirred at room temperature for 4 days. The solid was filtered and the filtrate was concentrated under reduced pressure. Purification by flash chromatography on silica gel using a gradient of ethyl acetate (0% to 10%) in heptane furnished 0.344 g (77%) of 7-(((tert-butyldimethylsilyl)oxy)methyl)-1H-indole a colorless oil. $^1$H NMR (DMSO-$d_6$) δ 10.83 (1H, s); 7.35 (1H, d); 7.23 (1H, t); 7.01 (1H, d); 6.89 (1H, t); 6.35 (1H, dd); 4.91 (2H, s); 0.83 (9H, s); 0.00 (6H, s).

Step 2: 1-(7-(((tert-Butyldimethylsilyl)oxy)methyl)-1H-indol-3-yl)-2-chloro-2-phenylethanone was prepared according to general procedure A from 7-(((tert-butyldimethylsilyl)oxy)methyl)-1H-indole (0.173 g; 0.662 mmol), pyridine (0.060 mL; 0.742 mmol) and α-chlorophenylacetyl chloride (0.095 mL; 0.662 mmol) in toluene (1.5 mL). The residue obtained after extraction was purified by flash chromatography on silica gel using a gradient ethyl acetate (0% to 25%) in heptane to furnish 0.060 g (22%) of the desired compound as a red-brown solid. ESI/APCI(+): 414, 416 (M+H). ESI/APCI(−): 412, 414 (M−H).

Step 3: 2-((3,5-Dimethoxyphenyl)amino)-1-(7-(hydroxymethyl)-1H-indol-3-yl)-2-phenylethanone was prepared according to general procedure E from 1-(7-(((tert-butyldimethylsilyl)oxy)methyl)-1H-indol-3-yl)-2-chloro-2-phenylethanone (0.060 g; 0.145 mmol) and 3,5-dimethoxyaniline (0.220 g; 1.436 mmol) in acetonitrile (0.5 mL), irradiated at 100° C. for 15 min and at 150° C. for 15 min. Purification by preparative HPLC (XBridge column; method 2) furnished 0.006 g (10%) of the desired compound as a beige solid. ESI/APCI(+): 417 (M+H). ESI/APCI(−): 415 (M−H).

Example 324: Preparation of 2-(3-(2-((5-methoxypyridin-3-yl)amino)-2-phenylacetyl)-1H-indol-7-yl) ethyl acetate Step 1: 2-(3-Formyl-1H-indol-7-yl)ethyl acetate was prepared according to general procedure R from a solution of oxalyl chloride (0.806 mL; 9.207 mmol) in dichloromethane (30 mL), DMF (0.773 mL; 9.984 mmol) and a solution of 2-(1H-indol-7-yl)ethyl acetate (1.560 g; 7.676 mmol) in dichloromethane (5 mL). The residue obtained after concentration of the organic phase under reduced pressure was dried to give crude 2-(3-formyl-1H-indol-7-yl)ethyl acetate as a beige solid which was used without further purification. ESI/APCI(+): 232 (M+H). ESI/APCI(−): 230 (M−H).

Step 2: tert-Butyl 7-(2-acetoxyethyl)-3-formyl-1H-indole-1-carboxylate was prepared according to general procedure F from 2-(3-formyl-1H-indol-7-yl)ethyl acetate (1.776 g; 7.680 mmol), di-tert-butyl dicarbonate (2.011 g; 9.214 mmol) and DMAP (0.094 g; 0.768 mmol) in acetonitrile (40 mL). Purification by flash chromatography on silica gel using a gradient of ethyl acetate (10% to 60%) in heptane furnished 1.770 g (70%) of the desired compound as a yellow solid.

Step 3: 2-(3-(2-((5-Methoxypyridin-3-yl)amino)-2-phenylacetyl)-1H-indol-7-yl)ethyl acetate was prepared according to general procedure K from a mixture of 3-benzyl-5-(2-hydroxyethyl)-4-methylthiazol-3-ium chloride (0.120 g; 0.445 mmol) and triethylamine (0.090 mL; 0.646 mmol) in ethanol (0.5 mL), tert-butyl 7-(2-acetoxyethyl)-3-formyl-1H-indole-1-carboxylate (0.273 g; 0.824 mmol) and a solution of N-benzylidene-5-methoxypyridin-3-amine (0.857 mmol) in ethanol (1 mL), heated at 60° C. for 72 h. Purification by flash chromatography on silica gel using a gradient of ethyl acetate (20% to 100%) in heptane furnished 0.148 g (41%) of the desired compound as a yellow oil. ESI/APCI(+): 444 (M+H). ESI/APCI(−): 442 (M−H).

Example 325: Preparation of 1-(7-(2-hydroxyethyl)-1H-indol-3-yl)-2-((5-methoxypyridin-3-yl)amino)-2-phenylethanone 1-(7-(2-Hydroxyethyl)-1H-indol-3-yl)-2-((5-methoxypyridin-3-yl)amino)-2-phenylethanone was prepared according to general procedure S from a solution of 2-(3-(2-((5-methoxypyridin-3-yl)amino)-2-phenylacetyl)-1H-indol-7-yl)ethyl acetate (0.148 g; 0.334 mmol) in a mixture of THE (2 mL) and methanol (2 mL) and potassium carbonate (0.095 g; 0.689 mmol). The reaction mixture was stirred at room temperature for 3 h. Purification by flash chromatography on silica gel using a gradient of methanol (0% to 6%) in dichloromethane followed by precipitation from dichloromethane furnished 0.037 g (28%) of the desired compound as a brown powder. ESI/APCI(+): 402 (M+H).

Example 326: Preparation of 2-((3,5-dimethoxyphenyl)amino)-1-(7-(2-(dimethylamino)ethyl)-1H-indol-3-yl)-2-phenylethanone Step 1: To a solution of 1-(7-(2-((tert-butyldimethylsilyl)oxy)ethyl)-1H-indol-3-yl)-2-phenylethanone (0.178 g; 0.452 mmol) in dichloromethane (7 mL) was added a 4N hydrogen chloride solution in dioxane (1.600 mL; 6.400 mmol). The reaction mixture was stirred at room temperature for 2 h. The reaction mixture was diluted with dichloromethane and washed with water. The organic phase was washed with a saturated sodium bicarbonate solution, water and brine, dried over sodium sulfate, filtered and concentrated under reduced pressure. Purification by flash chromatography on silica gel using a gradient of ethyl acetate (40% to 80%) in heptane furnished 0.102 g (81%) of 1-(7-(2-hydroxyethyl)-1H-indol-3-yl)-2-phenylethanone. ESI/APCI(+): 280 (M+H); 302 (M+Na). ESI/APCI(−): 278 (M−H).

Step 2: To a suspension of 1-(7-(2-hydroxyethyl)-1H-indol-3-yl)-2-phenylethanone (0.102 g; 0.365 mmol) in dichloromethane (4.9 mL) were added triethylamine (0.074 mL; 0.534 mmol) and mesyl chloride (0.032 mL; 0.413 mmol). The reaction mixture was stirred at room temperature for 4 h. A 2N dimethylamine solution in THE (2.100 mL; 4.200 mmol) was gradually added over 4 days at room temperature. The reaction mixture was then partially concentrated under reduced pressure to remove dichloromethane. A 2N dimethylamine solution in THE (1.000 mL; 2.000 mmol) was added and the reaction mixture was heated at 60° C. for 6 h. A 2N dimethylamine solution in THE (1.000 mL; 2.000 mmol) was added and the reaction mixture was stirred overnight at room temperature. The reaction mixture was concentrated under reduced pressure. The residue was partitioned between ethyl acetate and a saturated sodium bicarbonate solution. The phases were separated. The organic phase was washed several times with a 2N hydrochloric acid solution. The acidic aqueous phases were combined, basified with a 2N sodium hydroxide solution and extracted with ethyl acetate. The organic phase was washed with water and brine, dried over sodium sulfate, filtered and concentrated under reduced pressure to yield 0.064 g (57%) of 1-(7-(2-(dimethylamino)ethyl)-1H-indol-3-yl)-2-phenylethanone as an orange oil which was used in the next step without further purification. ESI/APCI(+): 307 (M+H); 329 (M+Na). ESI/APCI(−): 305 (M−H).

Step 3: To a solution of 1-(7-(2-(dimethylamino)ethyl)-1H-indol-3-yl)-2-phenylethanone (0.063 g; 0.206 mmol) in THE (2.5 mL) cooled to 0° C. was added a solution of phenyltrimethylammonium tribromide (0.110 g; 0.292 mmol) in THE (3 mL). The reaction mixture was stirred at 0° C. for 1 h and at room temperature for 5 h. 3,5-Dimethoxyaniline (0.154 g; 1.005 mmol) was added. The reaction mixture was refluxed for 2 h and was stirred overnight at room temperature. 3,5-Dimethoxyaniline (0.051 g; 0.553 mmol) was added and the reaction mixture was stirred at room temperature for 65 h. The reaction mixture was concentrated under reduced pressure. The residue was partitioned between ethyl acetate and a saturated sodium bicarbonate solution. The phases were separated. The organic phase was washed with water and brine, dried over sodium sulfate, filtered and concentrated under reduced pressure. Purification by flash chromatography on silica gel using a gradient of methanol (2% to 10%) in dichloromethane followed by purification by preparative TLC using methanol (10%) in dichloromethane as eluent furnished 0.029 g (31%) of 2-((3,5-dimethoxyphenyl)amino)-1-(7-(2-(dimethylamino)ethyl)-1H-indol-3-yl)-2-phenylethanone as a beige powder. ESI/APCI(+): 458 (M+H). ESI/APCI(−): 456 (M−H). $^1$H NMR (DMSO-d$_6$) δ 12.24 (1H, br s); 8.89 (1H, s); 8.04 (1H, d); 7.64 (2H, m); 7.29 (1H, t); 7.05-7.2 (4H, m); 6.34 (1H, d); 6.10 (1H, d); 6.06 (2H, d); 5.72 (1H, s); 3.68 (6H, s); 3.08 (2H, m); 2.79 (2H, m); 2.43 (6H, m).

Example 327: Preparation of 2-((3-hydroxyphenyl)amino)-1-(1H-indol-3-yl)-2-phenylethanone A suspension of 2-bromo-1-(1H-indol-3-yl)-2-phenylethanone (0.098 g; 0.312 mmol) and 3-aminophenol (0.068 g; 0.623 mmol) in acetonitrile (1 mL) was stirred at room temperature for 24 h. The reaction mixture was concentrated under reduced pressure. Purification by flash chromatography on silica gel using a gradient of ethyl acetate (0% to 50%) in heptane furnished 0.065 g (61%) of 2-((3-hydroxyphenyl)amino)-1-(1H-indol-3-yl)-2-phenylethanone as a beige solid. ESI/APCI(+): 343 (M+H). ESI/APCI(−): 341 (M−H).

Example 328: Preparation of ethyl 4-(3-((2-(1H-indol-3-yl)-2-oxo-1-phenylethyl)amino)-5-methoxyphenoxy)butanoate Step 1: To a solution of 3-amino-5-methoxyphenol (0.500 g; 3.593 mmol) in THE (10 mL) was added di-tert-butyl dicarbonate (0.863 g, 3.954 mmol) in THF (2 mL). The reaction mixture was refluxed overnight. After cooling to room temperature, the reaction mixture was diluted with ethyl acetate and washed with a saturated sodium bicarbonate solution. The organic phase was concentrated under reduced pressure. Purification by flash chromatography on silica gel using a gradient of ethyl acetate (5% to 50%) in heptane furnished 0.427 g (50%) of tert-butyl (3-hydroxy-5-methoxyphenyl)carbamate as an oil. ESI/APCI(+): 240 (M+H).

Step 2: A mixture of tert-butyl (3-hydroxy-5-methoxyphenyl)carbamate (0.200 g; 0.836 mmol), potassium carbonate (0.231 g; 1.671 mmol), ethyl 4-bromobutyrate (0.245 g; 1.256 mmol) and potassium iodide (0.014 g; 0.084 mmol) in acetone (5 mL) was stirred at 60° C. for 65 h. After cooling to room temperature, water was added and the reaction mixture was extracted with ethyl acetate. The organic phase was concentrated under reduced pressure. Purification by flash chromatography on silica gel using a gradient of ethyl acetate (2% to 40%) in heptane furnished 0.189 g (64%) of ethyl 4-(3-((tert-butoxycarbonyl)amino)-5-methoxyphenoxy)butanoate as an oil. ESI/APCI(+): 354 (M+H); 376 (M+Na).

Step 3: Ethyl 4-(3-((tert-butoxycarbonyl)amino)-5-methoxyphenoxy)butanoate (0.104 g; 0.294 mmol) was dissolved in a 4N hydrogen chloride solution in dioxane (3.000 mL; 12.00 mmol). The reaction mixture was stirred at room temperature overnight. The reaction mixture was partially concentrated. The residue was partitioned between ethyl acetate and a saturated sodium bicarbonate solution. The phases were separated. The organic phase was concentrated under reduced pressure. Purification by flash chromatography on silica gel using a gradient of ethyl acetate (15% to 70%) in heptane furnished 0.054 g (72%) of ethyl 4-(3-amino-5-methoxyphenoxy)butanoate as an orange oil.

Step 3: Ethyl 4-(3-((2-(1H-indol-3-yl)-2-oxo-1-phenylethyl)amino)-5-methoxyphenoxy)butanoate was prepared according to general procedure C from 2-bromo-1-(1H-indol-3-yl)-2-phenylethanone (0.102 g; 0.324 mmol), ethyl 4-(3-amino-5-methoxyphenoxy)butanoate (0.082 g; 0.324 mmol) and triethylamine (0.090 mL; 0.647 mmol) in acetonitrile (2 mL), irradiated in a microwave oven at 100° C. for 20 min. Purification by flash chromatography on silica gel using a gradient of ethyl acetate (5% to 50%) in heptane followed by precipitation from diethyl ether furnished 0.057 g (36%) of the desired compound as a white solid. ESI/APCI(+): 487 (M+H). ESI/APCI(−): 485 (M−H).

Example 329: Preparation of 2-((3-(2-(tert-butoxy)ethoxy)-5-methoxyphenyl)amino)-1-(1H-indol-3-yl)-2-(p-tolyl)ethanone Step 1: 1-(1H-Indol-3-yl)-2-(p-tolyl)ethanone was prepared according to general procedure O from a solution of 1H-indole (0.350 g; 2.988 mmol) in dichloromethane(15 mL), a 1M diethylaluminum chloride solution in hexane (3.880 mL; 3.880 mmol) and a solution of 2-(p-tolyl)acetyl chloride (0.655 g; 3.884 mmol) in dichloromethane (2 mL). The residue obtained after extraction was purified by precipitation from dichloromethane to give 0.417 g (56%) of the desired compound as a white solid. ESI/APCI(+): 250 (M+H). ESI/APCI(−): 248 (M−H)

Step 2: 2-Bromo-1-(1H-indol-3-yl)-2-(p-tolyl)ethanone was prepared according to general procedure P from a solution of 1-(1H-indol-3-yl)-2-(p-tolyl)ethanone (0.417 g; 1.673 mmol) in THF (11 mL) and phenyltrimethylammonium tribromide (0.692 g; 1.840 mmol). The reaction mixture was stirred at room temperature overnight. Purification by flash chromatography on silica gel using a gradient of ethyl acetate (5% to 80%) in heptane furnished 0.642 g of crude 2-bromo-1-(1H-indol-3-yl)-2-(p-tolyl)ethanone as a pink solid which was used in the next step without further purification. ESI/APCI(+): 328, 330 (M+H). ESI/APCI(−): 326, 328 (M−H)

Step 3: 2-((3-(2-(tert-Butoxy)ethoxy)-5-methoxyphenyl)amino)-1-(1H-indol-3-yl)-2-(p-tolyl)ethanone was prepared according to general procedure C from 2-bromo-1-(1H-indol-3-yl)-2-(p-tolyl)ethanone (0.075 g; 0.228 mmol), 3-(2-(tert-butoxy)ethoxy)-5-methoxyaniline (0.060 g; 0.251 mmol) and triethylamine (0.064 mL; 0.456 mmol) in acetonitrile (0.5 mL), irradiated in a microwave oven at 100° C. for 15 min. Purification by flash chromatography on silica gel using a gradient of ethyl acetate (10 to 80%) in heptane furnished 0.058 g (52%) of the desired compound as a brown solid. ESI/APCI(+): 487 (M+H). ESI/APCI(−): 485 (M−H)

Example 330: Preparation of 2-((3-(2-hydroxyethoxy)-5-methoxyphenyl)amino)-1-(1H-indol-3-yl)-2-(p-tolyl)ethanone 2-((3-(2-(tert-Butoxy)ethoxy)-5-methoxyphenyl)amino)-1-(1H-indol-3-yl)-2-(p-tolyl)ethanone (0.058 g; 0.119 mmol) was dissolved in a 4N hydrogen chloride solution in dioxane (1.5 mL; 6.000 mmol). The reaction mixture was stirred at room temperature for 16 h. The reaction mixture was neutralized with a saturated sodium bicarbonate solution and was extracted with ethyl acetate. The organic phase was washed with brine, dried over magnesium sulfate, filtered and concentrated under reduced pressure. Purification by flash chromatography on silica gel using a gradient of ethyl acetate (50% to 100%) in heptane furnished 0.030 g (58%) of 2-((3-(2-hydroxyethoxy)-5-methoxyphenyl)amino)-1-(1H-indol-3-yl)-2-(p-tolyl)ethanone as a solid. ESI/APCI(+): 431 (M+H). ESI/APCI(−): 429 (M−H). $^1$H NMR (DMSO-$d_6$) δ 8.85 (1H, s); 8.15 (1H, d); 7.40-7.56 (3H, m); 7.12-7.27 (2H, m); 7.08 (2H, d); 6.27 (1H, d); 6.03 (3H, br s); 5.70 (1H, s); 4.79 (1H, t); 3.83 (2H, d); 3.58-3.68 (5H, m); 2.20 (3H, s).

Example 331: Preparation of 2-((3,5-dimethoxyphenyl)amino)-1-(5-(2-hydroxyethyl)-1H-indol-3-yl)-2-phenylethanone Step 1: To a solution of 1H-indole-5-carbaldehyde (5.000 g; 34.45 mmol) in THF (200 mL) cooled to 0° C. were added methyltriphenylphosphonium bromide (14.77 g; 41.33 mmol) and a solution of potassium tert-butoxide (5.800 g; 51.67 mmol) in THF (50 mL). The reaction mixture was stirred at room temperature for 24 h. The reaction mixture was partially concentrated under reduced pressure. The residue was poured into a mixture ice/water and extracted with ethyl acetate. The organic phase was concentrated under reduced pressure. Purification by flash chromatography on silica gel using a gradient of ethyl acetate (5% to 50%) in heptane furnished 3.110 g (63%) of 5-vinyl-1H-indole as a beige solid. ESI/APCI(+): 144 (M+H). ESI/APCI(−): 142 (M−H).

Step 2: To a solution of 5-vinyl-1H-indole (2.960 g; 20.67 mmol) in THF (100 mL) was added dropwise a 1M borane-tetrahydrofuran complex solution in THF (20.70 mL; 20.70 mmol) and the reaction mixture was stirred for 2.5 h. A 10% sodium hydroxide solution (8.240 mL; 24.83 mmol) and a 30% hydrogen peroxide solution (2.350 mL; 24.83 mmol) were added sequentially and the reaction mixture was stirred at room temperature for 3.5 h. The reaction was quenched by addition of a saturated ammonium chloride solution. The reaction mixture was stirred vigorously for 5 min and partitioned between ethyl acetate and water. The phases were separated. The organic phase was washed with brine and concentrated under reduced pressure. Purification by flash chromatography on silica gel using a gradient of ethyl acetate (30% to 100%) in heptane furnished 2.310 g (66%) of 2-(1H-indol-5-yl)ethanol as an oil. ESI/APCI(+):162 (M+H); 184 (M+Na).

Step 3: 5-(2-((tert-Butyldimethylsilyl)oxy)ethyl)-1H-indole was prepared according to general procedure N from 2-(1H-indol-5-yl)ethanol (0.464 g; 2.878 mmol), TBDMSCl (0.954 g; 6.330 mmol) and DBU (0.651 mL; 4.319 mmol) in THF (10 mL). Purification by flash chromatography on silica gel using a gradient of ethyl acetate (10% to 16%) in heptane furnished 0.582 g (73%) of the desired compound as a yellow oil. ESI/APCI(+): 276 (M+H).

Step 4: 1-(5-(2-((tert-Butyldimethylsilyl)oxy)ethyl)-1H-indol-3-yl)-2-phenylethanone was prepared according to general procedure O from a solution of 5-(2-((tert-butyldimethylsilyl)oxy)ethyl)-1H-indole (0.580 g; 2.106 mmol) in dichloromethane (15 mL), a 1M diethylaluminum chloride solution in hexane (2.740 mL; 2.740 mmol) and a solution of phenylacetyl chloride (0.365 mL; 2.739 mmol) in dichloromethane (2 mL). Purification by flash chromatography on silica gel using a gradient of ethyl acetate (10% to 80%) in heptane furnished 0.182 (22%) of the desired compound. ESI/APCI(+): 394 (M+H). ESI/APCI(−): 392 (M−H) Step 5: 2-Bromo-1-(5-(2-hydroxyethyl)-1H-indol-3-yl)-2-phenylethanone was prepared according to general procedure P from a solution of 1-(5-(2-((tert-butyldimethylsilyl)oxy)ethyl)-1H-indol-3-yl)-2-phenylethanone (0.182 g; 0.462 mmol) in THF (3 mL) and phenyltrimethylammonium tribromide (0.191 g; 0.509 mmol). The reaction mixture was stirred at room temperature overnight. Purification by flash chromatography on silica gel using a gradient of ethyl acetate (20% to 100%) in heptane furnished 0.083 g (50%) of the desired compound as a brown solid. ESI/APCI(+): 358, 360 (M+H). ESI/APCI(−): 356, 358 (M−H).

Step 6: 2-((3,5-Dimethoxyphenyl)amino)-1-(5-(2-hydroxyethyl)-1H-indol-3-yl)-2-phenylethanone was prepared according to general procedure E from 2-bromo-1-(5-(2-hydroxyethyl)-1H-indol-3-yl)-2-phenylethanone (0.040 g; 0.112 mmol) and 3,5-dimethoxyaniline (0.086 g; 0.558 mmol) in acetonitrile (0.5 mL), irradiated in a microwave oven at 100° C. for 15 min. Purification by flash chromatography on silica gel using a gradient of ethyl acetate (10% to 100%) in heptane furnished 0.032 g (65%) of the desired compound as a grey solid. ESI/APCI(+): 431 (M+H). ESI/APCI(−): 429 (M−H)

Example 332: Preparation of 2-((3,5-dimethoxyphenyl)amino)-2-(4-fluorophenyl)-1-(7-(2-hydroxyethyl)-1H-indol-3-yl)ethanone Step 1: 1-(7-(2-((tert-Butyldimethylsilyl)oxy)ethyl)-1H-indol-3-yl)-2-(4-fluorophenyl)ethanone was prepared according to general procedure O from a solution of 7-(2-((tert-butyldimethylsilyl)oxy)ethyl)-1H-indole (0.434 g, 1.576 mmol) in dichloromethane (9 mL), a 1M diethylaluminum chloride solution in hexane (2.048 mL; 2.048 mmol) and 2-(4-fluorophenyl)acetyl chloride (0.353 g, 2.048 mmol) in dichloromethane (1 mL). Purification by flash chromatography on silica gel using a gradient of ethyl acetate (10% to 100%) in heptane furnished 0.149 g (23%) of the desired compound. ESI/APCI(+): 412 (M+H). ESI/APCI(−): 410 (M−H). 0.137 g (29%) of 2-(4-fluorophenyl)-1-(7-(2-hydroxyethyl)-1H-indol-3-yl)ethanone was also isolated.

Step 2: 2-Bromo-2-(4-fluorophenyl)-1-(7-(2-hydroxyethyl)-1H-indol-3-yl)ethanone was prepared according to general procedure P from a solution of 2-(4-fluorophenyl)-1-(7-(2-hydroxyethyl)-1H-indol-3-yl)ethanone (0.137 g; 0.461 mmol) in THF (3 mL) and phenyltrimethylammonium tribromide (0.203 g; 0.540 mmol). The reaction mixture was stirred at room temperature overnight. Purification by flash chromatography on silica gel using a gradient of ethyl acetate (30% to 100%) in heptane furnished 0.097 g (56%) of the desired compound. ESI/APCI(+): 376, 378 (M+H). ESI/APCI(−): 374, 376 (M−H).

Step 3: 2-((3,5-Dimethoxyphenyl)amino)-2-(4-fluorophenyl)-1-(7-(2-hydroxyethyl)-1H-indol-3-yl)ethanone was prepared according to general procedure E from 2-bromo-2-(4-fluorophenyl)-1-(7-(2-hydroxyethyl)-1H-indol-3-yl)ethanone (0.050 g; 0.133 mmol) and 3,5-dimethoxyaniline (0.102 g; 0.665 mmol) in acetonitrile (0.5 mL), irradiated in a microwave oven at 100° C. for 15 min. Purification by flash chromatography on silica gel using a gradient of ethyl acetate (20% to 100%) in heptane furnished 0.036 g (58%) of the desired compound as a solid. ESI/APCI(+): 449 (M+H). ESI/APCI(−): 447 (M−H). $^1$H NMR (DMSO-$d_6$) δ 8.86 (1H, s); 8.01 (1H, d); 7.66 (2H, dd); 6.99-7.20 (4H, m); 6.35 (1H, d); 6.12 (1H, d); 6.05 (2H, d); 5.72 (1H, s); 3.69 (2H, t); 3.62 (6H, s); 3.02 (2H, t).

Example 333: Preparation of 3-(3-(2-((5-methoxypyridin-3-yl)amino)-2-phenylacetyl)-1H-indol-5-yl)propyl acetate Step 1: 3-(1H-Indol-5-yl)propyl acetate was prepared according to general procedure Q from 3-(1H-indol-5-yl)propan-1-ol (1.400 g; 7.989 mmol), DMAP (0.976 g; 8.185 mmol) and acetic anhydride (1.900 mL; 20.14 mmol) in dichloromethane (150 mL). Purification by flash chromatography on silica gel using dichloromethane as eluent furnished 1.590 g (92%) of the desired compound as a colorless oil. ESI/APCI(+): 218 (M+H)

Step 2: 3-(3-Formyl-1H-indol-5-yl)propyl acetate was prepared according to general procedure R from a solution of oxalyl chloride (0.800 mL; 9.139 mmol) in dichloromethane (40 mL), DMF (0.750 mL; 9.687 mmol) and a solution of 3-(1H-indol-5-yl)propyl acetate (1.590 g; 7.318 mmol) in dichloromethane (15 mL). The residue obtained after concentration of the organic phase under reduced pressure was dried to give 1.700 g (95%) of the desired compound as a beige solid which was used without further purification. ESI/APCI(+): 246 (M+H). ESI/APCI(−): 244 (M−H).

Step 3: tert-Butyl 5-(3-acetoxypropyl)-3-formyl-1H-indole-1-carboxylate was prepared according to general procedure F from 3-(3-formyl-1H-indol-5-yl)propyl acetate (1.710 g; 6.931 mmol), di-tert-butyl dicarboxylate (1.820 g; 8.339 mmol) and DMAP (0.090 g; 0.737 mmol) in acetonitrile (35 mL) to furnish 2.350 g (98%) of the desired product as a pale yellow solid. ESI/APCI(+): 346 (M+H). H NMR (DMSO-$d_6$) δ 10.06 (1H, s); 8.63 (1H, s); 8.02 (1H, d); 7.98 (1H, s); 7.31 (1H, dd); 3.99 (2H, t); 2.76 (2H, t); 2.01 (3H, s); 1.92 (2H, m); 1.66 (9H, s).

Step 4: 3-(3-(2-((5-Methoxypyridin-3-yl)amino)-2-phenylacetyl)-1H-indol-5-yl)propyl acetate was prepared according to general procedure K from a mixture of 3-benzyl-5-(2-hydroxyethyl)-4-methylthiazol-3-ium chloride (0.132 g; 0.489 mmol) and triethylamine (0.100 mL; 0.717 mmol) in ethanol (0.5 mL), tert-butyl 5-(3-acetoxypropyl)-3-formyl-1H-indole-1-carboxylate (0.340 g; 0.984 mmol) and a solution of N-benzylidene-5-methoxypyridin-3-amine (0.980 mmol) in ethanol (1 mL), heated at 60° C. for 72 h. Purification by flash chromatography on silica gel using a gradient of methanol (0% to 5%) in dichloromethane fur-

Example 334: Preparation of 1-(5-(3-hydroxypropyl)-1H-indol-3-yl)-2-((5-methoxypyridin-3-yl)amino)-2-phenylethanone 1-(5-(3-Hydroxypropyl)-1H-indol-3-yl)-2-((5-methoxypyridin-3-yl)amino)-2-phenylethanone was prepared according to general procedure S from a solution of 3-(3-(2-(5-methoxypiridin-3-yl)amino)-2-phenylacetyl)-1H-indol-5-yl)propyl acetate (0.224 g; 0.490 mmol) in THF (3 mL) and methanol (3 mL) and potassium carbonate (0.135 g; 0.977 mmol). The reaction mixture was heated at 45° C. for 3 h. Purification by flash chromatography on silica gel using a gradient of methanol (0% to 7%) in dichloromethane followed by precipitation from dichloromethane furnished 0.072 g (35%) of the desired compound as a white solid. ESI/APCI(+): 416 (M+H). ESI/APCI(−): 414 (M−H)

Example 335: Preparation of 2-(3-fluorophenyl)-2-((3-(2-hydroxyethoxy)-5-methoxyphenyl)amino)-1-(1H-indol-3-yl)ethanone Step 1: 2-(3-Fluorophenyl)-1-(1H-indol-3-yl)ethanone was prepared according to general procedure O from a solution of 1H-indole (0.292 g; 2.492 mmol) in dichloromethane (15 mL), a 1M diethylaluminum chloride solution in hexane (3.240 mL; 3.240 mmol) and a solution of 2-(3-fluorophenyl)acetyl chloride (0.559 g; 3.184 mmol) in dichloromethane (2 mL). Purification by flash chromatography on silica gel using a gradient of ethyl acetate (10% to 80%) in heptane furnished 0.459 g (73%) of the desired compound as a solid. ESI/APCI(+): 254 (M+H). ESI/APCI(−): 252 (M−H).

Step 2: 2-Bromo-2-(3-fluorophenyl)-1-(1H-indol-3-yl)ethanone was prepared according to general procedure P from a solution of 2-(3-fluorophenyl)-1-(1H-indol-3-yl)ethanone (0.459 g; 1.812 mmol) in THF (12 mL) and phenyltrimethylammonium tribromide (0.749 g; 1.994 mmol). Purification by flash chromatography on silica gel using a gradient of ethyl acetate (10% to 80%) in heptane furnished 0.466 g (77%) of the desired compound as a brown solid. ESI/APCI(+): 332, 334 (M+H). ESI/APCI(−): 330, 332 (M−H).

Step 3: To a solution of 2-bromo-2-(3-fluorophenyl)-1-(1H-indol-3-yl)ethanone (0.054 g, 0.164 mmol) and triethylamine (0.046 mL, 0.328 mmol) in acetonitrile (0.3 mL) was added 2-(3-amino-5-methoxyphenoxy)ethanol (0.030 g, 0.164 mmol). The reaction mixture was stirred at room temperature for 4 days and concentrated under reduced pressure. The residue was purified by flash chromatography on silica gel using a gradient of ethyl acetate (10% to 100%) in heptane. Further purification by flash chromatography on silica gel using a gradient of methanol (2% to 8%) in dichloromethane furnished 0.030 g (42%) of 2-(3-fluorophenyl)-2-((3-(2-hydroxyethoxy)-5-methoxyphenyl)amino)-1-(1H-indol-3-yl)ethanone as a yellow solid. ESI/APCI(+): 435 (M+H). ESI/APCI(−): 433 (M−H).

Example 336: Preparation of 2-(3-(2-(5-methoxypyrazin-2-yl)-2-((5-methoxypyridin-3-yl)amino)acetyl)-1H-indol-7-yl)ethyl acetate Step 1: A solution of 5-methoxy-N-((5-methoxypyrazin-2-yl)methylene)pyridin-3-amine in ethanol was prepared by heating a solution of 5-methoxypyrazine-2-carbaldehyde (0.130 g; 0.941 mmol) and 5-methoxypyridin-3-amine (0.133 g; 1.071 mmol) in ethanol (0.5 mL) at 60° C. for 16 h. The formation of the imine was quantitative and the solution was used without further purification. ESI/APCI(+): 245 (M+H).

Step 2: 2-(3-(2-(5-Methoxypyrazin-2-yl)-2-((5-methoxypyridin-3-yl)amino)acetyl)-1H-indol-7-yl)ethyl acetate was prepared according to general procedure L from a mixture of 3-benzyl-5-(2-hydroxyethyl)-4-methylthiazol-3-ium chloride (0.135 g; 0.500 mmol) and triethylamine (0.717 mL; 0.500 mmol) in ethanol (1 mL), tert-butyl 7-(2-acetoxyethyl)-3-formyl-1H-indole-1-carboxylate (0.331 g; 0.998 mmol) and a solution of 5-methoxy-N-((5-methoxypyrazin-2-yl)methylene)pyridin-3-amine (0.999 mmol) in ethanol (1 mL), heated at 70° C. for 2 days. Purification by flash chromatography on silica gel using a gradient of methanol (0% to 7%) in dichloromethane furnished 0.281 g (59%) of the desired compound as a beige solid. ESI/APCI(+): 476 (M+H). ESI/APCI(−): 474 (M−H).

Example 337: Preparation of 1-(7-(2-hydroxyethyl)-1H-indol-3-yl)-2-(5-methoxypyrazin-2-yl)-2-((5-methoxypyridin-3-yl)amino)ethanone 1-(7-(2-Hydroxyethyl)-1H-indol-3-yl)-2-(5-methoxypyrazin-2-yl)-2-((5-methoxypyridin-3-yl)amino)ethanone was prepared according to general procedure S from a solution of 2-(3-(2-(5-methoxypyrazin-2-yl)-2-((5-methoxypyridin-3-yl)amino)acetyl)-1H-indol-7-yl)ethyl acetate (0.280 g; 0.589 mmol) in a mixture of THF (4 mL) and methanol (4 mL) and potassium carbonate (0.163 g; 1.178 mmol). The reaction mixture was stirred at room temperature for 16 h. Purification by flash chromatography on silica gel using a gradient of methanol (1% to 10%) in dichloromethane furnished 0.084 g (33%) of the desired compound as a solid. ESI/APCI(+): 434 (M+H). ESI/APCI(−): 432 (M−H). $^1$H NMR (DMSO-$d_6$) δ 8.76 (1H, s); 8.53 (1H, s); 8.26 (1H, s); 8.02 (1H, d); 7.87 (1H, d); 7.55 (1H, d); 7.04-7.19 (2H, m); 6.85 (1H, s); 6.69 (1H, d); 6.37 (1H, d); 3.86 (3H, s); 3.66-3.77 (5H, m); 3.03 (2H, t).

Example 338: Preparation of 2-(3-(2-((5-methoxypyridin-3-yl)amino)-2-(pyrazolo[1,5-a]pyridin-2-yl)acetyl)-1H-indol-7-yl)ethyl acetate Step 1: A solution of 5-methoxy-N-(pyrazolo[1,5-a]pyridin-2-ylmethylene)pyridin-3-amine in ethanol was prepared by heating a solution of pyrazolo[1,5-a]pyridine-2-carbaldehyde (0.139 g; 0.951 mmol) and 5-methoxypyridin-3-amine (0.121 g; 0.975 mmol) in ethanol (0.5 mL) at 60° C. for 5.5 h. The formation of the imine was quantitative and the solution was used without further purification. ESI/APCI (+): 253 (M+H).

Step 2: 2-(3-(2-((5-Methoxypyridin-3-yl)amino)-2-(pyrazolo[1,5-a]pyridin-2-yl)acetyl)-1H-indol-7-yl)ethyl acetate was prepared according to general procedure K from a mixture of 3-benzyl-5-(2-hydroxyethyl)-4-methylthiazol-3-ium chloride (0.135 g; 0.500 mmol) and triethylamine (0.070 mL; 0.550 mmol) in ethanol (1 mL), tert-butyl 7-(2-acetoxyethyl)-3-formyl-1H-indole-1-carboxylate (0.331 g; 0.998 mmol) and a solution of 5-methoxy-N-(pyrazolo[1,5-a]pyridin-2-ylmethylene)pyridin-3-amine (0.999 mmol) in ethanol (1 mL), heated at 70° C. for 2 days. Purification by flash chromatography on silica gel using a gradient of methanol (0% to 7%) in dichloromethane furnished 0.130 g (27%) of the desired compound as a red oil. ESI/APCI(+): 484 (M+H). ESI/APCI(-): 482 (M-H)

Example 339: Preparation of 1-(7-(2-hydroxyethyl)-1H-indol-3-yl)-2-((5-methoxypyridin-3-yl)amino)-2-(pyrazolo[1,5-a]pyridin-2-yl)ethanone 1-(7-(2-Hydroxyethyl)-1H-indol-3-yl)-2-((5-methoxypyridin-3-yl)amino)-2-(pyrazolo[1,5-a]pyridin-2-yl)ethanone was prepared according to general procedure S from a solution 2-(3-(2-((5-methoxypyridin-3-yl)amino)-2-(pyrazolo[1,5-a]pyridin-2-yl)acetyl)-1H-indol-7-yl)ethyl acetate (0.130 g, 0.269 mmol) in THF (2 mL) and methanol (2 mL) and potassium carbonate (0.074 g, 0.538 mmol). The reaction mixture was stirred at room temperature for 16 h. Purification by flash chromatography on silica gel using a gradient of methanol (1% to 10%) in dichloromethane furnished 0.053 g (44%) of the desired compound as a solid. ESI/APCI(+): 442 (M+H). ESI/APCI(-): 440 (M-H). $^1$H NMR (DMSO-d$_6$) δ 12.05 (1H, br s); 8.77 (1H, s); 8.60 (1H, d); 8.03 (1H, d); 7.89 (1H, d); 7.59 (1H, d); 7.51 (1H, d); 7.00-7.23 (3H, m); 6.76-6.91 (2H, m); 6.55-6.68 (2H, m); 6.42 (1H, d); 4.70 (1H, br s); 3.61-3.79 (5H, m); 3.01 (2H, t).

Example 340: Preparation of 2-(3-(2-(5-fluoropyridin-3-yl)-2-((5-methoxypyridin-3-yl)amino)acetyl)-1H-indol-7-yl)ethyl acetate Step 1: A solution of N-((5-fluoropyridin-3-yl)methylene)-5-methoxypyridin-3-amine in ethanol was prepared by heating a solution of 5-fluoronicotinaldehyde (0.125 g; 0.999 mmol) and 5-methoxypyridin-3-amine (0.124 g; 0.999 mmol) in ethanol (0.5 mL) at 60° C. for 4 h. The formation of the imine was quantitative and the solution was used without further purification.

Step 2: 2-(3-(2-(5-Fluoropyridin-3-yl)-2-((5-methoxypyridin-3-yl)amino)acetyl)-1H-indol-7-yl)ethyl acetate was prepared according to general procedure K from a mixture of 3-benzyl-5-(2-hydroxyethyl)-4-methylthiazol-3-ium chloride (0.135 g; 0.500 mmol) and triethylamine (0.070 mL; 0.500 mmol) in ethanol (1 mL), tert-butyl 7-(2-acetoxyethyl)-3-formyl-1H-indole-1-carboxylate (0.331 g; 0.998 mmol) and a solution of N-((5-fluoropyridin-3-yl)methylene)-5-methoxypyridin-3-amine (0.999 mmol) in ethanol (1 mL), heated at 70° C. for 2 days. Purification by precipitation from dichloromethane furnished 0.254 g (55%) of the desired compound as a white solid. ESI/APCI(+): 463 (M+H). ESI/APCI(-): 461 (M-H).

Example 341: Preparation of 2-(5-fluoropyridin-3-yl)-1-(7-(2-hydroxyethyl)-1H-indol-3-yl)-2-((5-methoxypyridin-3-yl)amino)ethanone 2-(5-Fluoropyridin-3-yl)-1-(7-(2-hydroxyethyl)-1H-indol-3-yl)-2-((5-methoxypyridin-3-yl)amino)ethanone was prepared according to general procedure S from a solution of 2-(3-(2-(5-fluoropyridin-3-yl)-2-((5-methoxypyridin-3-yl)amino)acetyl)-1H-indol-7-yl)ethyl acetate (0.190 g; 0.411 mmol) in a mixture of THF (3 mL) and methanol (3 mL) and potassium carbonate (0.114 g; 0.822 mmol). The reaction mixture was stirred at room temperature for 16 h. Purification by flash chromatography on silica gel using a gradient of methanol (1% to 10%) in dichloromethane furnished 0.074 g (43%) of the desired compound as a white solid. ESI/APCI(+): 421 (M+H). ESI/APCI(-): 419 (M-H). $^1$H NMR (DMSO-d$_6$) δ 8.93 (1H, s); 8.79 (1H, s); 8.44 (1H, d); 8.02 (1H, d); 7.83-7.96 (2H, m); 7.55 (1H, d); 7.03-7.21 (2H, m); 6.79-6.93 (2H, m); 6.36 (1H, d); 3.65-3.79 (5H, m); 3.03 (2H, t).

Example 342: Preparation of 2-(3-(2-((5-methoxypyridin-3-yl)amino)-2-phenylacetyl)-1H-indol-5-yl)ethyl acetate Step 1: 2-(1H-Indol-5-yl)ethyl acetate was prepared according to general procedure Q from 2-(1H-indol-5-yl)ethanol 2.310 g; 14.33 mmol), DMAP (3.500 g; 28.66 mmol) and acetic anhydride (3.500 mL; 37.26 mmol) in dichloromethane (250 mL). Purification by flash chromatography on silica gel using a gradient of ethyl acetate (15% to 70%) in heptane furnished 2.580 g (89%) of the desired compound as an oil.

Step 2: 2-(3-Formyl-1H-indol-5-yl)ethyl acetate was prepared according to general procedure R from a solution of oxalyl chloride (1.330 mL; 15.23 mmol) in dichloromethane (8 mL), DMF (1.180 mL; 15.23 mmol) and a solution of 2-(1H-indol-5-yl)ethyl acetate (2.580 g; 12.69 mmol) in dichloromethane (20 mL). Purification by flash chromatography on silica gel using a gradient of ethyl acetate (30% to 100%) in heptane furnished 2.780 g (95%) of the desired compound as a beige solid. ESI/APCI(+): 232 (M+H); 254 (M+Na). ESI/APCI(-): 230 (M-H).

Step 3: tert-Butyl 5-(2-acetoxyethyl)-3-formyl-1H-indole-1-carboxylate was prepared according to general procedure F from 2-(3-formyl-1H-indol-5-yl)ethyl acetate (2.780 g; 12.02 mmol), di-tert-butyl dicarbonate (2.150 g; 14.43 mmol) and DMAP (0.294 g; 2.406 mmol) in acetonitrile (50 mL). Purification by flash chromatography on silica gel using a gradient of ethyl acetate (5% to 50%) in heptane furnished 3.940 (99%) of the desired compound as a beige solid. ESI/APCI(+): 354 (M+Na).

Step 4: 2-(3-(2-((5-Methoxypyridin-3-yl)amino)-2-phenylacetyl)-1H-indol-5-yl)ethyl acetate was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 5-(2-acetoxyethyl)-3-formyl-1H-indole-1-carboxylate (0.331 g; 0.999 mmol) and a solution of N-benzylidene-5-methoxypyridin-3-amine (0.996 mmol) in ethanol (1 mL), heated at 70° C. overnight. Purification by flash chromatography on silica gel using a gradient of methanol (1% to 10%) in dichloromethane furnished 0.216 g (49%) the desired compound as a solid. ESI/APCI(+): 444 (M+H). ESI/APCI(-): 442 (M-H).

Example 343: Preparation of 1-(5-(2-hydroxyethyl)-1H-indol-3-yl)-2-((5-methoxypyridin-3-yl)amino)-2-phenylethanone 1-(5-(2-Hydroxyethyl)-1H-indol-3-yl)-2-((5-methoxypyridin-3-yl)amino)-2-phenylethanone was prepared according to general procedure S from a solution of 2-(3-(2-((5-methoxypyridin-3-yl)amino)-2-phenylacetyl)-1H-indol-5-yl)ethyl acetate (0.216 g; 0.487 mmol) in THF (5 mL) and methanol (5 mL) and potassium carbonate (0.135 g; 0.977 mmol). The reaction mixture was stirred at room temperature for 3 h. Purification by flash chromatography on silica gel using a gradient of methanol (1% to 10%) in dichloromethane followed by precipitation from acetonitrile furnished 0.075 g (38%) of as a beige solid. ESI/APCI(+): 402 (M+H). ESI/APCI(-): 400 (M-H). $^1$H NMR (DMSO-d$_6$) δ12.10 (1H, br s); 8.86 (1H, s); 8.02 (1H, s); 7.85 (1H, d); 7.66 (2H, d); 7.51 (1H, d); 7.38 (1H, d); 7.26-7.35 (2H, m); 7.17-7.25 (1H, m); 7.09 (1H, d); 6.79 (1H, s); 6.68 (1H, d); 6.17 (1H, d); 4.62 (1H, t); 3.72 (3H, s); 3.54-3.66 (2H, m); 2.80 (2H, t).

Example 344: Preparation of 2-(3-(2-(5-methoxypyrazin-2-yl)-2-((5-methoxypyridin-3-yl)amino)acetyl)-1H-indol-5-yl)ethyl acetate 2-(3-(2-(5-Methoxypyrazin-2-yl)-2-((5-methoxypyridin-3-yl)amino)acetyl)-1H-indol-5-yl)ethyl acetate was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 5-(2-acetoxyethyl)-3-formyl-1H-indole-1-carboxylate (0.331 g; 0.999 mmol) and a solution of 5-methoxy-N-((5-methoxypyrazin-2-yl)methylene)pyridin-3-amine (0.999 mmol) in ethanol (1 mL), heated at 70° C. overnight. Purification by flash chromatography on silica gel using a gradient of methanol (1% to 10%) in dichloromethane furnished 0.311 g (65%) of the desired compound as a solid. ESI/APCI(+): 476 (M+H). ESI/APCI(−): 474 (M−H).

Example 345: Preparation of 1-(5-(2-hydroxyethyl)-1H-indol-3-yl)-2-(5-methoxypyrazin-2-yl)-2-((5-methoxypyridin-3-yl)amino)ethanone 1-(5-(2-Hydroxyethyl)-1H-indol-3-yl)-2-(5-methoxypyrazin-2-yl)-2-((5-methoxypyridin-3-yl)amino)ethanone was prepared according to general procedure S from a solution of 2-(3-(2-(5-methoxypyrazin-2-yl)-2-((5-methoxypyridin-3-yl)amino)acetyl)-1H-indol-5-yl)ethyl acetate (0.311 g; 0.654 mmol) in THF (7.5 mL) and methanol (7.5 mL) and potassium carbonate (0.181 g; 1.210 mmol). The reaction mixture was stirred at room temperature for 3 h. Purification by flash chromatography on silica gel using a gradient of methanol (1% to 10%) in dichloromethane followed by precipitation from acetonitrile furnished 0.165 g (58%) the desired compound as a beige solid. ESI/APCI(+): 434 (M+H). ESI/APCI(−): 432 (M−H). $^1$H NMR (DMSO-$d_6$) δ12.10 (1H, br s); 8.75 (1H, s); 8.52 (1H, s); 8.26 (1H, s); 8.01 (1H, s); 7.86 (1H, d); 7.56 (1H, d); 7.40 (1H, d); 7.11 (1H, d); 6.84 (1H, br s); 6.68 (1H, d); 6.33 (1H, d); 4.64 (1H, t); 3.86 (3H, s); 3.74 (3H, s); 3.55-3.67 (2H, m); 2.81 (2H, t).

Example 346: Preparation of 2-(3-(2-((5-methoxypyridin-3-yl)amino)-2-(pyrazolo[1,5-a]pyridin-2-yl)acetyl)-1H-indol-5-yl)ethyl acetate 2-(3-(2-((5-Methoxypyridin-3-yl)amino)-2-(pyrazolo[1,5-a]pyridin-2-yl)acetyl)-1H-indol-5-yl)ethyl acetate was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 5-(2-acetoxyethyl)-3-formyl-1H-indole-1-carboxylate (0.331 g; 0.999 mmol) and a solution of 5-methoxy-N-(pyrazolo[1,5-a]pyridin-2-ylmethylene)pyridin-3-amine (0.999 mmol) in ethanol (1 mL), heated at 70° C. overnight. Purification by flash chromatography on silica gel using a gradient of methanol (1% to 10%) in dichloromethane furnished 0.218 g (45%) of the desired compound as a solid. ESI/APCI(+): 484 (M+H). ESI/APCI(−): 482 (M−H).

Example 347: Preparation of 1-(5-(2-hydroxyethyl)-1H-indol-3-yl)-2-((5-methoxypyridin-3-yl)amino)-2-(pyrazolo[1,5-a]pyridin-2-yl)ethanone 1-(5-(2-Hydroxyethyl)-1H-indol-3-yl)-2-((5-methoxypyridin-3-yl)amino)-2-(pyrazolo[1,5-a]pyridin-2-yl)ethanone was prepared according to general procedure S from a solution of 2-(3-(2-((5-methoxypyridin-3-yl)amino)-2-(pyrazolo[1,5-a]pyridin-2-yl)acetyl)-1H-indol-5-yl)ethyl acetate (0.218 g; 0.451 mmol) in THF (5 mL) and methanol (5 mL) and potassium carbonate (0.124 g; 0.904 mmol). The reaction mixture was stirred at room temperature for 3 h. Purification by flash chromatography on silica gel using a gradient of methanol (1% to 10%) in dichloromethane followed by precipitation from ethanol furnished 0.077 g (39%) of the desired compound as a pink solid. ESI/APCI (+): 442 (M+H). ESI/APCI(−): 440 (M−H). $^1$H NMR (DMSO-$d_6$) δ11.95 (1H, br s); 8.68 (1H, s); 8.52 (1H, d); 7.94 (1H, s); 7.81 (1H, d); 7.52 (1H, d); 7.44 (1H, d); 7.29 (1H, d); 7.04-7.15 (1H, m); 7.01 (1H, d); 6.68-6.83 (2H, m); 6.58 (1H, s); 6.52 (1H, d); 6.31 (1H, d); 4.55 (1H, t); 3.64 (3H, s); 3.46-3.58 (2H, m); 2.72 (2H, t),

Example 348: Preparation of 2-(3-(2-(4-fluorophenyl)-2-((5-methoxypyridin-3-yl)amino)acetyl)-1H-indol-7-yl)ethyl acetate Step 1: A solution of N-(4-fluorobenzylidene)-5-methoxypyridin-3-amine in ethanol was prepared by heating a solution of 4-fluorobenzaldehyde (0.120 g; 0.967 mmol) and 5-methoxypyridin-3-amine (0.121 g; 0.975 mmol) in ethanol (0.5 mL) at 60° C. for 20 h. The formation of the imine was quantitative and the solution was used without further purification.

Step 2: 2-(3-(2-(4-Fluorophenyl)-2-((5-methoxypyridin-3-yl)amino)acetyl)-1H-indol-7-yl)ethyl acetate was prepared according to general procedure K from a mixture of 3-benzyl-5-(2-hydroxyethyl)-4-methylthiazol-3-ium chloride (0.135 g; 0.500 mmol) and triethylamine (0.070 mL; 0.505 mmol) in ethanol (1 mL), tert-butyl 7-(2-acetoxyethyl)-3-formyl-1H-indole-1-carboxylate (0.331 g; 0.998 mmol) and a solution of N-(4-fluorobenzylidene)-5-methoxypyridin-3-amine (0.999 mmol) in ethanol (1 mL), heated at 70° C. for 2 days. Purification by flash chromatography on silica gel using a gradient of methanol (0% to 7%) in dichloromethane furnished 0.191 g (41%) of the desired compound as a beige solid. ESI/APCI(+): 462 (M+H). ESI/APCI(−): 460 (M−H).

Example 349: Preparation of 2-(4-fluorophenyl)-1-(7-(2-hydroxyethyl)-1H-indol-3-yl)-2-((5-methoxypyridin-3-yl)amino)ethanone 2-(4-Fluorophenyl)-1-(7-(2-hydroxyethyl)-1H-indol-3-yl)-2-((5-methoxypyridin-3-yl)amino)ethanone was prepared according to general procedure S from a solution of 2-(3-(2-(4-fluorophenyl)-2-((5-methoxypyridin-3-yl)amino)acetyl)-1H-indol-7-yl)ethyl acetate (0.190 g; 0.412 mmol) in a mixture of THF (3 mL) and methanol (3 mL) and potassium carbonate (0.114 g; 0.823 mmol). The reaction mixture was stirred at room temperature for 16 h. Purification by flash chromatography on silica gel using a gradient of methanol (1% to 10%) in dichloromethane followed by purification by preparative HPLC (XBridge column; method 5) furnished 0.038 g (22%) of the desired compound as a yellow powder. ESI/APCI(+): 420 (M+H). ESI/APCI(−): 418 (M−H).

Example 350: Preparation of 4-(3-((2-(1H-indol-3-yl)-2-oxo-1-phenylethyl)amino)-5-methoxyphenoxy)butanoic Acid To a solution of ethyl 4-(3-((2-(1H-indol-3-yl)-2-oxo-1-phenylethyl)amino)-5-methoxyphenoxy)butanoate (0.050 g;

0.103 mmol) in dioxane (3 mL) was added a 1N sodium hydroxide solution (0.308 mL; 0.308 mmol). The reaction mixture was stirred at room temperature for 4 days. A 1N hydrochloric acid solution was added and the reaction mixture was extracted with ethyl acetate. The organic phase was concentrated under reduced pressure. Purification by preparative HPLC (Xbridge column; method 2) followed by purification by flash chromatography on silica gel using a gradient of methanol (1% to 7%) in dichloromethane furnished 0.009 g (19%) of 4-(3-((2-(1H-indol-3-yl)-2-oxo-1-phenylethyl)amino)-5-methoxyphenoxy)butanoic acid as a beige solid. ESI/APCI(+): 459 (M+H). ESI/APCI(−): 457 (M−H). $^1$H NMR (DMSO-d$_6$) δ12.14 (1H, brs); 8.89 (1H, s); 8.16 (1H, d); 7.63 (2H, d); 7.46 (1H, d); 7.25-7.35 (2H, m); 7.12-7.24 (3H, m); 6.31 (1H, d); 5.99-6.12 (3H, m); 5.71 (1H, s); 3.84 (2H, t); 3.61 (3H, s); 2.73 (1H, br s); 2.32 (2H, t); 1.86 (2H, m).

Example 351: Preparation of 2-(3-(2-((3,5-dimethoxyphenyl)amino)-2-(pyrazolo[1,5-a]pyridin-2-yl)acetyl)-1H-indol-5-yl)ethyl acetate 2-(3-(2-((3,5-Dimethoxyphenyl)amino)-2-(pyrazolo[1,5-a]pyridin-2-yl)acetyl)-1H-indol-5-yl)ethyl acetate was prepared according to general procedure K from a mixture of 3-benzyl-5-(2-hydroxyethyl)-4-methylthiazolium chloride (0.135 g; 0.500 mmol) and triethylamine (0.070 mL; 0.505 mmol) in ethanol (1.5 mL), tert-butyl 5-(2-acetoxyethyl)-3-formyl-1H-indole-1-carboxylate (0.331 g; 0.999 mmol) and a solution of 3,5-dimethoxy-N-(pyrazolo[1,5-a]pyridin-2-ylmethylene)aniline (0.999 mmol) in ethanol (1 mL), heated at 70° C. overnight. Purification by flash chromatography on silica gel using a gradient of ethyl acetate (5% to 50%) in dichloromethane furnished 0.250 g (50%) of the desired compound as an oil. ESI/APCI(+): 513 (M+H). ESI/APCI(−): 511 (M−H).

Example 352: Preparation of 2-((3,5-dimethoxyphenyl)amino)-1-(5-(2-hydroxyethyl)-1H-indol-3-yl)-2-(pyrazolo[1,5-a]pyridin-2-yl)ethanone 2-((3,5-Dimethoxyphenyl)amino)-1-(5-(2-hydroxyethyl)-1H-indol-3-yl)-2-(pyrazolo[1,5-a]pyridin-2-yl)ethanone was prepared according to general procedure S from a solution of 2-(3-(2-((3,5-dimethoxyphenyl)amino)-2-(pyrazolo[1,5-a]pyridin-2-yl)acetyl)-1H-indol-5-yl)ethyl acetate (0.250 g; 0.488 mmol) in THF (5 mL) and methanol (5 mL) and potassium carbonate (0.135 g; 0.977 mmol). The reaction mixture was stirred at room temperature for 3 h. Purification by flash chromatography on silica gel using a gradient of ethyl acetate (15% to 70%) in dichloromethane followed by precipitation from ethanol furnished 0.086 g (37%) of the desired compound as a beige solid. ESI/APCI (+): 471 (M+H). ESI/APCI(−): 469 (M−H). $^1$H NMR (DMSO-d$_6$) δ11.99 (1H, brs); 8.74 (1H, s); 8.58 (1H, d); 8.01 (1H, s); 7.59 (1H, d); 7.36 (1H, d); 7.00-7.20 (2H, m); 6.80 (1H, t); 6.64 (1H, s); 6.26 (2H, s); 6.09 (2H, s); 5.74 (1H, s); 4.62 (1H, t); 3.62 (6H, s); 3.58 (2H, m); 2.79 (2H, t).

Example 353: Preparation of 3-(3-(2-((5-methoxypyridin-3-yl)amino)-2-(pyrazolo[1,5-a]pyridin-2-yl)acetyl)-1H-indol-5-yl)propyl acetate 3-(3-(2-((5-Methoxypyridin-3-yl)amino)-2-(pyrazolo[1,5-a]pyridin-2-yl)acetyl)-1H-indol-5-yl)propyl acetate was prepared according to general procedure K from a mixture of 3-benzyl-5-(2-hydroxyethyl)-4-methylthiazol-3-ium chloride (0.135 g; 0.500 mmol) and triethylamine (0.100 mL; 0.717 mmol) in ethanol (0.5 mL), tert-butyl 5-(3-acetoxypropyl)-3-formyl-1H-indole-1-carboxylate (0.353 g; 1.022 mmol) and a solution of 5-methoxy-N-(pyrazolo[1,5-a]pyridin-2-ylmethylene)pyridin-3-amine (0.951 mmol) in ethanol (2 mL), heated at 60° C. for 72 h. Purification by flash chromatography on silica gel using a gradient of methanol (0% to 5%) in dichloromethane furnished 0.233 g (46%) of the desired compound as a brown solid. ESI/APCI (+): 498 (M+H). ESI/APCI(−): 496 (M−H).

Example 354: Preparation of 1-(5-(3-hydroxypropyl)-1H-indol-3-yl)-2-((5-methoxypyridin-3-yl)amino)-2-(pyrazolo[1,5-a]pyridin-2-yl)ethanone To solution of 3-(3-(2-((5-methoxypyridin-3-yl)amino)-2-(pyrazolo[1,5-a]pyridin-2-yl)acetyl)-1H-indol-5-yl)propyl acetate (0.233 g; 0.468 mmol) in a mixture of methanol (3 mL), THF (3 mL) and water (0.5 mL) was added potassium carbonate (0.135 g; 0.977 mmol). The reaction mixture was stirred at room temperature for 3 h. The reaction mixture was filtered through celite and the filtrate was concentrated under reduced pressure. The residue was dissolved in ethyl acetate and washed with a citric acid buffer (pH 5) solution. The organic phase was dried over magnesium sulfate, filtered and concentrated under reduced pressure. Purification by flash chromatography on silica gel using a gradient of methanol (0% to 7%) in dichloromethane followed by purification by preparative HPLC (XBridge column; method 3) furnished 0.040 g (19%) of 1-(5-(3-hydroxypropyl)-1H-indol-3-yl)-2-((5-methoxypyridin-3-yl)amino)-2-(pyrazolo[1,5-a]pyridin-2-yl)ethanone as a beige solid. ESI/APCI(+): 456 (M+H). ESI/APCI(−): 454 (M−H).

Example 355: Preparation of 3-(3-(2-(5-methoxypyrazin-2-yl)-2-((5-methoxypyridin-3-yl)amino)acetyl)-1H-indol-5-yl)propyl acetate 3-(3-(2-(5-Methoxypyrazin-2-yl)-2-((5-methoxypyridin-3-yl)amino)acetyl)-1H-indol-5-yl)propyl acetate was prepared according to general procedure K from a mixture of 3-benzyl-5-(2-hydroxyethyl)-4-methylthiazol-3-ium chloride (0.135 g; 0.500 mmol) and triethylamine (0.100 mL; 0.717 mmol) in ethanol (0.5 mL), tert-butyl 5-(3-acetoxypropyl)-3-formyl-1H-indole-1-carboxylate (0.340 g; 0.984 mmol) and a solution of 5-methoxy-N-((5-methoxypyrazin-2-yl)methylene)pyridin-3-amine (0.941 mmol) in ethanol (1 mL), heated at 60° C. for 48 h. Purification by flash chromatography on silica gel using a gradient of methanol (0% to 5%) in dichloromethane furnished 0.397 g (64%) of the desired compound as a brown solid. ESI/APCI(+): 490 (M+H). ESI/APCI(−): 488 (M−H).

Example 356: Preparation of 1-(5-(3-hydroxypropyl)-1H-indol-3-yl)-2-(5-methoxypyrazin-2-yl)-2-((5-methoxypyridin-3-yl)amino)ethanone 1-(5-(3-Hydroxypropyl)-1H-indol-3-yl)-2-(5-methoxypyrazin-2-yl)-2-((5-methoxypyridin-3-yl)amino)ethanone was prepared according to general procedure S from a solution of 3-(3-(2-(5-methoxypyrazin-2-yl)-2-((5-methoxypyridin-3-yl)amino)acetyl)-1H-indol-5-yl)propyl acetate (0.297 g; 0.607 mmol) in THF (4 mL) and methanol (4 mL) and potassium carbonate (0.171 g; 1.237 mmol). The reaction mixture was heated at 45° C. for 5 h. Purification by flash chromatography on silica gel using a gradient of methanol (0% to 10%) in dichloromethane furnished 0.090 g (33%) of the desired product as a pale yellow solid. ESI/APCI(+): 448 (M+H).

Example 357: Preparation of 2-((3,5-dimethoxyphenyl)amino)-1-(7-(2-(methylsulfonyl)ethyl)-1H-indol-3-yl)-2-phenylethanone Step 1: To a suspension of 1-(7-(2-hydroxyethyl)-1H-indol-3-yl)-2-phenylethanone (0.089 g; 0.319 mmol) in dichloromethane (4.3 mL) were added triethylamine (0.065 mL; 0.498 mmol) and mesyl chloride (0.028 mL; 0.468 mmol). The reaction mixture was stirred at room temperature for 5 h. Water was added and the phases were separated. The organic phase was washed with water and brine, dried over sodium sulfate, filtered and concentrated under reduced pressure to give quantitatively 2-(3-(2-phenylacetyl)-1H-indol-7-yl)ethyl methanesulfonate which was used without further purification. ESI/APCI(+): 358 (M+H). To a solution of 2-(3-(2-phenylacetyl)-1H-indol-7-yl)ethyl methanesulfonate (0.319 mmol) in methanol (3.6 mL) was added sodium thiomethoxide (0.045 g; 0.642 mmol). After 18 h at room temperature, sodium thiomethoxide (0.045 g; 0.642 mmol) was added again. The reaction mixture was stirred at room temperature for 8.5 h. After addition of sodium thiomethoxide (0.018 g; 0.257 mmol), stirring at room temperature was continued for 18 h. The reaction mixture was partitioned between ethyl acetate and water. The phases were separated. The organic phase was washed with brine, dried over sodium sulfate, filtered and concentrated under reduced pressure. Purification by flash chromatography on silica gel using a gradient of ethyl acetate (15% to 50%) in heptane furnished 0.041 g (42%) of 1-(7-(2-(methylthio)ethyl)-1H-indol-3-yl)-2-phenylethanone as a white powder. ESI/APCI(+): 310 (M+H). ESI/APCI(−): 308 (M−H).

Step 2: To a solution of 1-(7-(2-(methylthio)ethyl)-1H-indol-3-yl)-2-phenylethanone (0.087 g; 0.236 mmol) in dichloromethane (1 mL) cooled to 0° C. was added portionwise 3-chloroperoxybenzoic acid (0.125 g; 0.507 mmol). After 2 h at room temperature, 3-chloroperoxybenzoic acid (0.040 g; 0.174 mmol) was added. The reaction mixture was stirred at room temperature for 2 h. The reaction mixture was diluted with dichloromethane and washed with a saturated sodium bicarbonate solution. The organic phase was washed with water and brine, dried over sodium sulfate, filtered and concentrated under reduced pressure. Purification by flash chromatography on silica gel using a gradient of ethyl acetate (40% to 90%) in heptane furnished 0.037 g (46%) of 1-(7-(2-(methylsulfonyl)ethyl)-1H-indol-3-yl)-2-phenylethanone as a white powder. ESI/APCI(+): 342 (M+H); 364 (M+Na). ESI/APCI(−): 340 (M−H).

Step 3: To a solution of 1-(7-(2-(methylsulfonyl)ethyl)-1H-indol-3-yl)-2-phenylethanone (0.037 g; 0.108 mmol) in THF (1.3 mL) cooled to 0° C. was added a solution of phenyltrimethylammonium tribromide (0.058 g; 0.154 mmol) in THF (1.6 mL). The reaction mixture was stirred at 0° C. for 1 h and at room temperature for 4 h. 3,5-Dimethoxyaniline (0.167 g; 1.090 mmol) was added. The reaction mixture was refluxed for 3 h and was stirred overnight at room temperature. The reaction mixture was filtered and the solid was washed with ethyl acetate. The filtrate was concentrated under reduced pressure. The residue was partitioned between ethyl acetate and a 1N hydrochloric acid solution. The phases were separated. The organic phase was washed with a saturated sodium bicarbonate solution, water and brine, dried over sodium sulfate, filtered and concentrated under reduced pressure. Purification by flash chromatography on silica gel using of ethyl acetate (40% to 90%) in heptane furnished 0.035 g (66%) of 2-((3,5-dimethoxyphenyl)amino)-1-(7-(2-(methylsulfonyl)ethyl)-1H-indol-3-yl)-2-phenylethanone as a beige powder. ESI/APCI(+): 493 (M+H); 515 (M+Na). ESI/APCI(−): 491 (M−H). $^1$H NMR (DMSO-d$_6$) δ 12.22 (1H, br s); 8.93 (1H, s); 8.06 (1H, t); 7.63 (2H, m); 7.26 (2H, m); 7.13-7.20 (3H, m); 6.35 (1H, d); 6.11 (1H, d); 6.06 (2H, s); 5.71 (1H, s); 3.61 (6H, s); 3.47 (2H, m); 3.33 (2H, m); 3.02 (3H, s).

Example 358: Preparation of 2-((3,5-dimethoxyphenyl)amino)-2-(4-fluorophenyl)-1-(5-(3-hydroxypropyl)-1H-indol-3-yl)ethanone Step 1: 1-(5-(3-((tert-Butyldimethylsilyl)oxy)propyl)-1H-indol-3-yl)-2-(4-fluorophenyl)ethanone was prepared according to general procedure O from a solution of 5-(3-((tert-butyldimethylsilyl)oxy)propyl)-1H-indole (0.130 g; 0.449 mmol) in dichloromethane (2.5 mL), a 1M diethylaluminum chloride solution in hexane (0.584 mL; 0.584 mmol) and a solution of 2-(4-fluorophenyl)acetyl chloride (0.101 g; 0.584 mmol) in dichloromethane (1 mL). Purification by flash chromatography on silica gel using a gradient of ethyl acetate (5% to 100%) in heptane furnished 0.042 g (22%) of the desired compound. ESI/APCI(+): 426 (M+H). ESI/APCI(−): 424 (M−H).

Step 2: 2-Bromo-2-(4-fluorophenyl)-1-(5-(3-hydroxypropyl)-1H-indol-3-yl)ethanone was prepared according to general procedure P from a solution of 1-(5-(3-((tert-butyldimethylsilyl)oxy)propyl)-1H-indol-3-yl)-2-(4-fluorophenyl) ethanone (0.042 g; 0.099 mmol) in THF (1 mL) and phenyltrimethylammonium tribromide (0.045 g; 0.118 mmol). Purification by flash chromatography on silica gel using a gradient of methanol (1% to 10%) in dichloromethane furnished 0.020 g (52%) of the desired compound. ESI/APCI(+): 390, 392 (M+H). ESI/APCI(−): 388, 390 (M−H).

Step 3: 2-((3,5-Dimethoxyphenyl)amino)-2-(4-fluorophenyl)-1-(5-(3-hydroxypropyl)-1H-indol-3-yl)ethanone was prepared according to general procedure E from 2-bromo-2-(4-fluorophenyl)-1-(5-(3-hydroxypropyl)-1H-indol-3-yl) ethanone (0.020 g; 0.051 mmol) and 3,5-dimethoxyaniline (0.039 g; 0.256 mmol) in acetonitrile (0.5 mL), irradiated in a microwave oven at 100° C. for 15 min. Purification by flash chromatography on silica gel using a gradient of ethyl acetate (20% to 100%) in heptane furnished 0.008 g (34%) of the desired compound as a solid. ESI/APCI(+): 463 (M+H). ESI/APCI(−): 461 (M−H).

Example 359: Preparation of 3-(3-(2-(4-fluorophenyl)-2-((5-methoxypyridin-3-yl)amino)acetyl)-1H-indol-5-yl)propyl acetate 3-(3-(2-(4-Fluorophenyl)-2-((5-methoxypyridin-3-yl) amino)acetyl)-1H-indol-5-yl)propyl acetate was prepared according to general procedure K from a mixture of 3-benzyl-5-(2-hydroxyethyl)-4-methylthiazol-3-ium chloride (0.133 g; 0.486 mmol) and triethylamine (0.100 mL; 0.717 mmol) in ethanol (0.5 mL), tert-butyl 5-(3-acetoxypropyl)-3-formyl-1H-indole-1-carboxylate (0.350 g; 1.013 mmol) and a solution of N-(4-fluorobenzylidene)-5-methoxypyridin-3-amine (0.967 mmol) in ethanol (1 mL), heated at 60° C. for 24 h. Purification by flash chromatography on silica gel using a gradient of methanol (0% to 5%) in dichloromethane furnished 0.193 g (40%) of the desired compound as a brown oil. ESI/APCI(+): 476 (M+H). ESI/APCI(−): 474 (M−H).

Example 360: Preparation of 2-(4-fluorophenyl)-1-(5-(3-hydroxypropyl)-1H-indol-3-yl)-2-((5-methoxypyridin-3-yl)amino)ethanone 2-(4-Fluorophenyl)-1-(5-(3-hydroxypropyl)-1H-indol-3-yl)-2-((5-methoxypyridin-3-yl)amino)ethanone was prepared according to general procedure S from a 3-(3-(2-(4-fluorophenyl)-2-((5-methoxypyridin-3-yl)amino)acetyl)-1H-indol-5-yl)propyl acetate (0.193 g; 0.406 mmol) in a mixture of THF (3 mL) and methanol (3 mL) and potassium carbonate (0.117 g; 0.847 mmol). The reaction mixture was heated at 45° C. for 5 h. Purification by flash chromatography on silica gel using a gradient of methanol (0% to 5%) in dichloromethane followed by precipitation from dichloromethane furnished 0.027 g (15%) of the desired product as a white solid. ESI/APCI(+): 434 (M+H). ESI/APCI(−): 432 (M−H).

Example 361: Preparation of 2-((3,5-dimethoxyphenyl)amino)-2-(4-fluorophenyl)-1-(5-(2-hydroxyethyl)-1H-indol-3-yl)ethanone Step 1: 2-(4-Fluorophenyl)-1-(5-(2-hydroxyethyl)-1H-indol-3-yl)ethanone was prepared according to general procedure O from 5-(2-((tert-butyldimethylsilyl)oxy)ethyl)-1H-indole (0.430 g; 1.561 mmol) in dichloromethane (5 mL), a 1M diethylaluminium chloride solution in hexane (0.322 mL; 0.322 mmol) and a solution of 2-(4-fluorophenyl)acetyl chloride (0.322 mL; 2.351 mmol) in dichloromethane (5 mL). Purification by flash chromatography on silica gel using a gradient of ethyl acetate (2% to 70%) in heptane furnished 0.062 (13%) the desired compound. ESI/APCI(+): 298 (M+H). ESI/APCI(−): 296 (M−H).

Step 2: To a solution of 2-(4-fluorophenyl)-1-(5-(2-hydroxyethyl)-1H-indol-3-yl)ethanone (0.060 g; 0.202 mmol) in THF (2.5 mL) cooled to 0° C. was added a solution of phenyltrimethylammonium tribromide (0.106 g; 0.282 mmol) in THF (2.5 mL). The reaction mixture was stirred at 0° C. for 1 h and at room temperature for 5 h. 3,5-Dimethoxyaniline (0.309 g; 2.021 mmol) was added and the reaction mixture was refluxed for 2 h. After cooling to room temperature, a 1N hydrochloric acid solution was added and the reaction mixture was extracted with ethyl acetate. The organic phase was concentrated under reduced pressure. Purification by flash chromatography on silica gel using a gradient of ethyl acetate (5% to 50%) in dichloromethane followed by purification by preparative HPLC (XBridge column; method 2) furnished 0.025 g (28%) of 2-((3,5-dimethoxyphenyl)amino)-2-(4-fluorophenyl)-1-(5-(2-hydroxyethyl)-1H-indol-3-yl)ethanone as a white solid. ESI/APCI(+): 449 (M+H). ESI/APCI(−): 447 (M−H). $^1$H NMR (DMSO-$d_6$) δ 12.07 (1H, br s); 8.84 (1H, d); 7.99 (1H, s); 7.59-7.72 (2H, m); 7.36 (1H, d); 7.02-7.19 (3H, m); 5.98-6.13 (3H, m); 5.74 (1H, s); 3.62 (6H, s); 3.52-3.60 (2H, m); 2.78 (2H, t).

Without being limiting, some more examples of compounds of the present invention which can be prepared by using similar protocols as described herein are the following:

4-(3-((1-(4,6-dimethylpyridin-3-yl)-2-(1H-indol-3-yl)-2-oxoethyl)amino)-5-methoxyphenyl)butanoic acid;

2-(6-(hydroxymethyl)pyridin-3-yl)-1-(1H-indol-3-yl)-2-((3-methoxy-5-(2-(methylsulfonyl)ethyl)phenyl)amino)ethanone;

2-((3,5-dimethoxyphenyl)amino)-1-(5-fluoro-7-(2-hydroxyethyl)-1H-indol-3-yl)-2-(tetrahydrofuran-3-yl)ethanone;

2-((3,5-dimethoxyphenyl)amino)-1-(5-((methylsulfonyl)methyl)-1H-indol-3-yl)-2-(tetrahydro-2H-pyran-4-yl)ethanone;

2-((3,5-dimethoxyphenyl)amino)-1-(5-(3-(dimethylamino)propyl)-1H-indol-3-yl)-2-(3,5-dimethylisoxazol-4-yl)ethanone;

2-([1,2,4]triazolo[1,5-a]pyridin-7-yl)-1-(7-(3-aminopropyl)-1H-indol-3-yl)-2-((3,5-dimethoxyphenyl)amino)ethanone;

2-(benzo[d]isoxazol-3-yl)-2-((3,5-dimethoxyphenyl)amino)-1-(7-(3-hydroxypropyl)-1H-indol-3-yl)ethanone;

3-(3-(2-((3,5-dimethoxyphenyl)amino)-2-(5-phenylisoxazol-3-yl)acetyl)-1H-indol-5-yl)propanoic acid;

1-(5-(2-aminoethyl)-1H-indol-3-yl)-2-((3,5-dimethoxyphenyl)amino)-2-(5-methyl-1-phenyl-1H-pyrazol-3-yl)ethanone;

1-methyl-4-((2-(5-(2-(methylsulfonyl)ethyl)-1H-indol-3-yl)-2-oxo-1-phenylethyl)amino)pyrrolidin-2-one;

1-(1H-indol-3-yl)-2-((3-methoxy-5-((methylamino)methyl)phenyl)amino)-2-(3-methyl-3H-imidazo[4,5-b]pyridin-2-yl)ethanone;

2-(6,7-dihydro-4H-pyrano[3,4-d]thiazol-2-yl)-2-((3-(2-hydroxyethyl)-5-methoxyphenyl)amino)-1-(1H-indol-3-yl)ethanone;

2-((3-(2-aminoethoxy)-5-methoxyphenyl)amino)-1-(1H-indol-3-yl)-2-(1-methyl-1H-benzo[d]imidazol-2-yl)ethanone;

2-(benzo[d]thiazol-2-yl)-1-(1H-indol-3-yl)-2-((3-methoxy-5-(2-(pyrrolidin-1-yl)ethoxy)phenyl)amino)ethanone;

2-((3-(difluoromethoxy)phenyl)amino)-1-(1H-indol-3-yl)-2-(thiazolo[4,5-b]pyrazin-2-yl)ethanone;

2-(3-((1-(benzo[b]thiophen-2-yl)-2-(1H-indol-3-yl)-2-oxoethyl)amino)-5-methoxyphenyl)acetic acid;

2-((3-(3-aminopropoxy)-5-methoxyphenyl)amino)-1-(1H-indol-3-yl)-2-(thieno[2,3-b]pyridin-2-yl)ethanone;

1-(5-(aminomethyl)-1H-indol-3-yl)-2-((3,5-dimethoxyphenyl)amino)-2-(thiazolo[5,4-c]pyridin-2-yl)ethanone;

1-(7-(aminomethyl)-1H-indol-3-yl)-2-((3,5-dimethoxyphenyl)amino)-2-(thiazolo[4,5-c]pyridin-2-yl)ethanone;

1-(5-(2-aminoethyl)-1H-indol-3-yl)-2-((3,5-dimethoxyphenyl)amino)-2-(thiazolo[4,5-b]pyridin-2-yl)ethanone;

1-(1H-indol-3-yl)-2-((3-methoxy-5-(2-(methylsulfonyl)ethoxy)phenyl)amino)-2-(5-methyl-4,5,6,7-tetrahydropyrazolo[1,5-a]pyrazin-2-yl)ethanone;

2-((3,5-dimethoxyphenyl)amino)-1-(1H-indol-3-yl)-2-(5-methyl-4,5,6,7-tetrahydrothiazolo[4,5-c]pyridin-2-yl)ethanone;

2-((3,5-dimethoxyphenyl)amino)-1-(7-(2-hydroxyethyl)-1H-indol-3-yl)-2-(p-tolyl)ethanone;

2-(4-fluorophenyl)-2-((3-(2-hydroxyethoxy)-5-methoxyphenyl)amino)-1-(7-(2-hydroxyethyl)-1H-indol-3-yl)ethanone;

2-((3-(2-hydroxyethoxy)-5-methoxyphenyl)amino)-1-(5-(2-hydroxyethyl)-1H-indol-3-yl)-2-phenylethanone;

2-((3,5-dimethoxyphenyl)amino)-1-(5-(2-(dimethylamino)ethyl)-1H-indol-3-yl)-2-(4-fluorophenyl)ethanone;

2-((3,5-dimethoxyphenyl)amino)-2-(4-fluorophenyl)-1-(5-(2-hydroxyethyl)-1-methyl-1H-indazol-3-yl)ethanone;

2-(4-fluorophenyl)-2-((3-(2-hydroxyethoxy)-5-methoxyphenyl)amino)-1-(1-methyl-1H-indazol-3-yl)ethanone;

2-((3,5-dimethoxyphenyl)amino)-1-(5-(2-hydroxyethyl)-1-methyl-1H-indazol-3-yl)-2-(pyrazolo[1,5-a]pyridin-2-yl)ethanone;

2-(4-fluorophenyl)-1-(1H-indol-3-yl)-2-((3-methoxy-5-((methylsulfonyl)methyl)phenyl)amino)ethanone;

2-((3,5-dimethoxyphenyl)amino)-2-(3-methylpyridin-2-yl)-1-(7-((methylsulfonyl)methyl)-1H-indol-3-yl)ethanone; and 3-(3-(2-(6-cyanopyridin-2-yl)-2-((3,5-dimethoxyphenyl)amino)acetyl)-1H-indol-5-yl)propanoic acid.

Part B

Example 362: Antiviral Activity of the Compounds of the Invention

For Dengue virus: Vero-B cells ($5 \times 10^4$) were seeded in 96-well plates. One day later, culture medium was replaced with 100 μL assay medium containing a 2× serial dilution of the compound (concentration range: 50 μg/mL-0.004 μg/mL) and 100 μL of dengue virus inoculum (DENV). Following a 2 hour incubation period, the cell monolayer was washed 3 times with assay medium to remove residual, non-adsorbed virus and cultures were further incubated for either 4 days (DENV-2 NGC), 5 days (DENV-4 strain Dak HD 34 460) or 7 or 8 days (DENV-1 Djibouti strain D1/H/IMTSSA/98/606 and DENV-3 strain H87 prototype) in the presence of the inhibitor. Supernatant was harvested and viral RNA load was determined by real-time quantitative RT-PCR. The 50% effective concentration ($EC_{50}$), which is defined as the compound concentration that is required to inhibit viral RNA replication by 50%, was determined using logarithmic interpolation.

The antiviral activity of the compounds against DENV-2 NGC was also tested in adenocarcinomic human alveolar basal epithelial cells (A549 cells), using the above described protocol with the difference that less cells/well were seeded ($2 \times 10^4$ cells/well).

For the yellow fever virus: Vero-B cells ($5 \times 10^4$) were seeded in 96-well plates. One day later, culture medium was replaced with 100 μL assay medium containing a 2× serial dilution of the compound (concentration range 50 μg/mL-0.004 μg/mL) and 100 μL of yellow fever virus inoculum (YFV-17D). Following a 2 hour incubation period, the cell monolayer was washed 3 times with assay medium to remove residual, non-adsorbed virus and cultures were further incubated for 4 days in the presence of the inhibitor. Supernatant was harvested and viral RNA load was determined by real-time quantitative RT-PCR. The 50% effective concentration ($EC_{50}$), which is defined as the compound concentration that is required to inhibit viral RNA replication by 50%, was determined using logarithmic interpolation.

Quantitative reverse transcriptase-PCR (RT-qPCR) RNA was isolated from 100 μL (or in some circumstances 150 μL) supernatant with the NucleoSpin 96 Virus kit (Macherey-Nagel, Düren, Germany) as described by the manufacturer. The sequences of the TaqMan primers (DENV-For, DENV-Rev, YFV-For, YFV-Rev; Table 2) and TaqMan probes (DENV-Probe and YFV-Probe; Table 2) were selected from non-structural gene 3 (NS3) or NS5, of the respective flaviviruses using Primer Express software (version 2.0; Applied Biosystems, Lennik, Belgium). The TaqMan probe was fluorescently labelled with 6-carboxyfluorescein (FAM) at the 5' end as the reporter dye, and with minor groove binder (MGB) at the 3' end as the quencher (Table 2). One-step, quantitative RT-PCR was performed in a total volume of 25 μL, containing 13.9375 μL $H_2O$, 6.25 μL master mix (Eurogentec, Seraing, Belgium), 0.375 μL forward primer, 0.375 μL reverse primer, 1 μL probe, 0.0625 μL reverse transcriptase (Eurogentec) and 3 μL sample. RT-PCR was performed using the ABI 7500 Fast Real-Time PCR System (Applied Biosystems, Branchburg, New Jersey, USA) using the following conditions: 30 min at 48° C. and 10 min at 95° C., followed by 40 cycles of 15 s at 95° C. and 1 min at 60° C. The data was analyzed using the ABI PRISM 7500 SDS software (version 1.3.1; Applied Biosystems). For absolute quantification, standard curves were generated using 10-fold dilutions of template preparations of known concentrations.

TABLE 2

Primers and probes used for real-time, quantitative RT-PCR.

| Primer/Probe | Sequence (5' → 3')[a] | Source[b] | Target |
| --- | --- | --- | --- |
| DENV-For | TCGGAGCCGGAGTTTACAAA (SEQ ID N. 1) | DENV 2 NGC | NS3 |
| DENV-Rev | TCTTAACGTCCGCCCATGAT (SEQ ID N. 2) | | |
| DENV-Probe | *FAM*-ATTCCACACAATGTGGCAT-*MGB* (SEQ ID N. 3) | | |
| DenS | GGATAGACCAGAGATCCTGCTGT (SEQ ID N. 4) | DENV-1, -3, -4 | NS5 |
| DenAS1-3 | CATTCCATTTTCTGGCGTTC (SEQ ID N. 5) | DENV-1, -3 | |
| DenAS4 | CAATCCATCTTGCGGCGCTC (SEQ ID N. 6) | DENV-4 | |
| DEN_1-3 probe | *FAM*-CAGCATCATTCCAGGCACAG-*MGB* (SEQ ID N. 7) | DENV-1, -3 | |
| DEN_4 probe | *FAM*-CAACATCAATCCAGGCACAG-*MGB* (SEQ ID N. 8) | DENV-4 | |

TABLE 2-continued

Primers and probes used for real-time, quantitative RT-PCR.

| Primer/Probe | Sequence (5' → 3')[a] | Source[b] | Target |
|---|---|---|---|
| YFV-For | TGGCATATTCCAGTCAACCTTCT (SEQ ID N. 9) | YFV-17D | NS3 |
| YFV-Rev | GAAGCCCAAGATGGAATCAACT (SEQ ID N. 10) | | |
| YFV-Probe | *FAM*-TTCCACACAATGTGGCATG-*MGB* (SEQ ID N. 11) | | |

[a] Reporter dye (FAM) and quencher (MGB/TAMRA) elements are indicated in bold and italics.
[b] The nucleotide sequence and position of the primers and probes within the genome were deduced from the nucleotide sequence of DENV 2 NGC (GenBank accession no. M29095; Irie et al., 1989), dengue virus serotype 1 Djibouti strain D1/H/IMTSSA/98/606 (Genbank Accession Number AF298808), dengue virus serotype 3 strain H87 prototype (c93130), dengue virus serotype 4 strain Dak HD 34 460 (only partial, unpublished sequences available) and YFV-17D (GenBank accession no. X03700; Rice et al., 1985).

Cytotoxic Assay

Potential cytotoxic effects of the compounds were evaluated in uninfected quiescent Vero-B cells. Cells were seeded at $5 \times 10^4$ cells/well in a 96-well plate in the presence of two-fold serial dilutions (ranging from 50 µg/mL-0.004 µg/mL) of compound and incubated for 4 days. Culture medium was discarded and 100 µL 3-(4,5-dimethylthiazol-2-yl)-5-(3-carboxymethoxyphenyl)-2-(4-sulfophenyl)-2H-tetrazolium/phenazinemethosulfate (MTS/PMS; Promega, Leiden, The Netherlands) in PBS was added to each well. Following a 2-hour incubation period at 37° C., the optical density was determined at 498 nm. Cytotoxic activity was calculated using the following formula: % cell viability=$100 \times (OD_{Compound}/OD_{CC})$, where $OD_{Compound}$ and $OD_{CC}$ correspond to the optical density at 498 nm of the uninfected cell cultures treated with compound and that of uninfected, untreated cell cultures, respectively. The 50% cytotoxic concentration (i.e., the concentration that reduces the total cell number with 50%; $CC_{50}$) was calculated using linear interpolation.

A similar protocol was used to assess cytotoxicity in A549 cells with the difference that cells were seeded at $2 \times 10^4$ cells/well.

Table 3 shows the activity against DENV-2 in Vero-B cells and the cytotoxicity of some example compounds of the invention.

| Code | $EC_{50}$ (µM) | $CC_{50}$ (µM) | SI |
|---|---|---|---|
| CPD-001 | 0.08 | 29 | 380 |
| CPD-002 | 0.01 | 16 | 2307 |
| CPD-003 | 0.11 | 13 | 114 |
| CPD-004 | 0.19 | 11 | 57 |
| CPD-005 | 0.93 | 5 | 6 |
| CPD-006 | 0.75 | 6 | 8 |
| CPD-007 | 2.53 | 5 | 2 |
| CPD-008 | 2.42 | 12 | 5 |
| CPD-009 | 0.66 | 4 | 7 |
| CPD-010 | 0.07 | 18 | 244 |
| CPD-011 | 1.66 | 23 | 14 |
| CPD-012 | 0.05 | 14 | 297 |
| CPD-013 | 0.002 | 9 | 5726 |
| CPD-014 | 0.02 | 8 | 354 |
| CPD-015 | 0.02 | 22 | 1065 |
| CPD-016 | 5.01 | 54 | 11 |
| CPD-018 | 0.37 | 19 | 52 |
| CPD-019 | 0.14 | 71 | 514 |
| CPD-020 | 0.14 | 16 | 114 |
| CPD-021 | 1.62 | >115 | >70 |
| CPD-022 | 12.80 | 77 | 6 |
| CPD-023 | 0.30 | 16 | 53 |
| CPD-024 | 0.50 | 14 | 27 |

-continued

| Code | $EC_{50}$ (µM) | $CC_{50}$ (µM) | SI |
|---|---|---|---|
| CPD-025 | 0.68 | 48 | 69 |
| CPD-026 | 17.19 | >138 | >8 |
| CPD-027 | 0.13 | 15 | 111 |
| CPD-028 | 135.17 | >144 | >1 |
| CPD-029 | 0.84 | 65 | 78 |
| CPD-030 | 0.09 | >126 | >1412 |
| CPD-031 | 50.19 | >145 | >2 |
| CPD-032 | 55.53 | >146 | >2 |
| CPD-033 | 9.15 | 71 | 8 |
| CPD-034 | 46.49 | >151 | >3 |
| CPD-035 | 2.11 | 14 | 7 |
| CPD-036 | 0.04 | 14 | 333 |
| CPD-037 | 1.20 | 19 | 16 |
| CPD-039 | 2.48 | 15 | 6 |
| CPD-040 | 4.24 | >129 | >30 |
| CPD-041 | 0.50 | 14 | 29 |
| CPD-042 | 12.51 | >138 | >11 |
| CPD-043 | 0.29 | >126 | >440 |
| CPD-044 | 6.48 | 65 | 10 |
| CPD-045 | 0.06 | >139 | >2183 |
| CPD-046 | 0.65 | 17 | 26 |
| CPD-047 | 0.42 | 16 | 39 |
| CPD-048 | 2.09 | >115 | >54 |
| CPD-049 | 0.08 | >134 | >1642 |
| CPD-050 | 2.40 | 87 | 36 |
| CPD-051 | 2.47 | >125 | >51 |
| CPD-052 | 3.72 | 52 | 14 |
| CPD-053 | 0.02 | 18 | 774 |
| CPD-054 | 2.09 | >115 | >54 |
| CPD-055 | 0.07 | 50 | 759 |
| CPD-056 | 0.45 | >139 | >312 |
| CPD-057 | 6.05 | 15 | 2 |
| CPD-058 | 2.85 | 64 | 22 |
| CPD-059 | 1.25 | 16 | 13 |
| CPD-060 | 10.33 | >113 | >10 |
| CPD-061 | 1.71 | 59 | 34 |
| CPD-062 | 0.58 | >134 | >230 |
| CPD-063 | 14.33 | >134 | >9 |
| CPD-064 | 8.75 | 72 | 8 |
| CPD-065 | 12.10 | 90 | 7 |
| CPD-066 | 6.32 | 95 | 15 |
| CPD-067 | 0.04 | 20 | 546 |
| CPD-068 | 1.32 | 12 | 9 |
| CPD-069 | 2.13 | 71 | 33 |
| CPD-070 | 3.27 | 90 | 27 |
| CPD-071 | 60.85 | 135 | 2 |
| CPD-072 | 6.84 | 68 | 10 |
| CPD-073 | 2.35 | 76 | 32 |
| CPD-074 | 0.81 | 77 | 95 |
| CPD-075 | 1.52 | 102 | 67 |
| CPD-076 | 3.77 | 115 | 31 |
| CPD-077 | 0.04 | 13 | 313 |
| CPD-078 | 11.64 | 109 | 9 |
| CPD-080 | 0.99 | >124 | >125 |
| CPD-081 | 10.76 | 50 | 5 |
| CPD-082 | 61.85 | 109 | 2 |

| Code | EC$_{50}$ (μM) | CC$_{50}$ (μM) | SI |
|---|---|---|---|
| CPD-083 | 0.03 | 26 | 941 |
| CPD-084 | 0.03 | >127 | >4185 |
| CPD-085 | 0.07 | 16 | 227 |
| CPD-086 | 0.04 | 12 | 329 |
| CPD-087 | 0.80 | >128 | >161 |
| CPD-088 | 2.53 | >121 | >48 |
| CPD-089 | 0.67 | >139 | >208 |
| CPD-090 | 2.90 | 13 | 5 |
| CPD-092 | 0.10 | 19 | 184 |
| CPD-093 | 16.79 | 87 | 5 |
| CPD-094 | 0.14 | 11 | 77 |
| CPD-096 | 2.90 | >121 | >42 |
| CPD-097 | 2.32 | 12 | 5 |
| CPD-098 | 10.69 | >121 | >11 |
| CPD-099 | 1.76 | 12 | 7 |
| CPD-100 | 12.03 | 42 | 3 |
| CPD-101 | 4.90 | 11 | 2 |
| CPD-102 | 0.62 | 65 | 105 |
| CPD-103 | 12.43 | >138 | >11 |
| CPD-104 | 0.35 | 65 | 186 |
| CPD-105 | 1.23 | 14 | 11 |
| CPD-106 | 8.93 | >120 | >13 |
| CPD-107 | 7.88 | 20 | 3 |
| CPD-109 | 0.53 | 84 | 159 |
| CPD-110 | 0.58 | 73 | 127 |
| CPD-111 | 0.44 | >115 | >263 |
| CPD-112 | 3.27 | 12 | 4 |
| CPD-113 | 0.49 | >112 | >232 |
| CPD-114 | 1.10 | 52 | 48 |
| CPD-115 | 10.58 | 49 | 5 |
| CPD-116 | 0.14 | 13 | 88 |
| CPD-117 | 3.57 | >133 | >37 |
| CPD-118 | 0.01 | 13 | 943 |
| CPD-119 | 0.03 | 13 | 372 |
| CPD-120 | 0.02 | 11 | 674 |
| CPD-121 | 5.76 | 60 | 10 |
| CPD-122 | 0.02 | 16 | 785 |
| CPD-123 | 0.05 | 15 | 337 |
| CPD-124 | 0.56 | 3 | 5 |
| CPD-125 | 7.19 | >138 | >19 |
| CPD-126 | 0.07 | 16 | 241 |
| CPD-127 | 2.15 | 72 | 33 |
| CPD-128 | 0.56 | 63 | 113 |
| CPD-129 | 1.09 | >108 | >99 |
| CPD-130 | 0.03 | 15 | 749 |
| CPD-131 | 0.01 | 13 | 1779 |
| CPD-132 | 0.05 | 12 | 235 |
| CPD-133 | 0.04 | 19 | 499 |
| CPD-134 | 0.46 | 49 | 106 |
| CPD-135 | 40.66 | >124 | >3 |
| CPD-136 | 0.22 | >120 | >545 |
| CPD-137 | 0.05 | >128 | >2762 |
| CPD-138 | 0.27 | 20 | 74 |
| CPD-139 | 0.02 | 20 | 915 |
| CPD-140 | 2.15 | 53 | 24 |
| CPD-141 | 1.63 | 44 | 27 |
| CPD-142 | 0.10 | 13 | 137 |
| CPD-144 | 0.06 | 20 | 320 |
| CPD-146 | 0.05 | 25 | 498 |
| CPD-148 | 0.07 | 44 | 594 |
| CPD-149 | 0.03 | 14 | 554 |
| CPD-150 | 0.03 | 105 | 3956 |
| CPD-151 | 0.09 | >133 | >1443 |
| CPD-152 | 0.09 | 75 | 814 |
| CPD-153 | 0.29 | >133 | >454 |
| CPD-154 | 0.06 | 44 | 778 |
| CPD-155 | 0.08 | 15 | 191 |
| CPD-156 | 0.02 | 11 | 665 |
| CPD-157 | 0.05 | 15 | 299 |
| CPD-158 | 0.09 | 63 | 746 |
| CPD-159 | 0.11 | 67 | 624 |
| CPD-170 | 0.44 | 26 | 58 |
| CPD-173 | 0.02 | 69 | 3693 |
| CPD-174 | 10.07 | 61 | 6 |
| CPD-179 | 5.30 | 135 | 26 |
| CPD-180 | 56.97 | >145 | >2 |
| CPD-181 | 4.22 | >122 | >28 |
| CPD-182 | 3.01 | 12 | 4 |
| CPD-183 | 15.20 | 86 | 6 |
| CPD-184 | 22.42 | 70 | 3 |
| CPD-186 | 4.35 | 40 | 9 |
| CPD-187 | 3.18 | 58 | 18 |
| CPD-189 | 0.93 | >145 | >156 |
| CPD-190 | 1.71 | 11 | 7 |
| CPD-191 | 2.58 | 13 | 5 |
| CPD-192 | 5.62 | 50 | 9 |
| CPD-193 | 0.72 | >133 | >185 |
| CPD-194 | 0.94 | 61 | 65 |
| CPD-195 | 12.73 | 65 | 5 |
| CPD-196 | 62.56 | >139 | >2 |
| CPD-197 | 3.30 | >139 | >42 |
| CPD-198 | 0.14 | 16 | 119 |
| CPD-199 | 24.90 | >120 | >4 |
| CPD-200 | 2.24 | 54 | 24 |
| CPD-201 | 12.23 | 74 | 6 |
| CPD-202 | 8.33 | 104 | 12 |
| CPD-203 | 0.73 | >134 | >185 |
| CPD-205 | 0.06 | 14 | 244 |
| CPD-206 | 0.02 | 12 | 625 |
| CPD-207 | 3.83 | 16 | 4 |
| CPD-208 | 0.37 | >102 | >279 |
| CPD-209 | 1.12 | >100 | >89 |
| CPD-210 | 0.20 | 13 | 68 |
| CPD-211 | 2.83 | >111 | >39 |
| CPD-212 | 0.42 | >110 | >260 |
| CPD-213 | 0.06 | 15 | 256 |
| CPD-214 | 0.03 | 16 | 469 |
| CPD-215 | 0.16 | 14 | 90 |
| CPD-216 | 0.84 | >106 | >127 |
| CPD-217 | 0.25 | 11 | 44 |
| CPD-218 | 2.39 | 13 | 6 |
| CPD-219 | 0.52 | 86 | 166 |
| CPD-221 | 29.28 | 80 | 3 |
| CPD-222 | 0.13 | >129 | >1003 |
| CPD-223 | 57.95 | >128 | >2 |
| CPD-224 | 0.05 | >134 | >2622 |
| CPD-225 | 0.38 | >134 | >357 |
| CPD-226 | 0.07 | 73 | 1005 |
| CPD-227 | 0.27 | >124 | >454 |
| CPD-228 | 1.62 | 13 | 8 |
| CPD-229 | 2.40 | >115 | >48 |
| CPD-230 | 0.12 | 21 | 176 |
| CPD-231 | 1.22 | 18 | 15 |
| CPD-232 | 0.10 | >125 | >1206 |
| CPD-233 | 0.01 | 11 | 817 |
| CPD-234 | 0.05 | 15 | 319 |
| CPD-235 | 0.004 | 13 | 3701 |
| CPD-236 | 0.02 | 69 | 4562 |
| CPD-237 | 1.35 | >113 | >84 |
| CPD-238 | 0.04 | >125 | >3548 |
| CPD-239 | 22.65 | >125 | >6 |
| CPD-240 | 0.11 | 63 | 578 |
| CPD-241 | 0.04 | 58 | 1531 |
| CPD-242 | 0.04 | 59 | 1340 |
| CPD-243 | 1.69 | 13 | 8 |
| CPD-245 | 0.08 | 16 | 192 |
| CPD-246 | 0.32 | 16 | 51 |
| CPD-247 | 0.42 | 15 | 37 |
| CPD-248 | 0.56 | 15 | 27 |
| CPD-249 | 0.10 | 53 | 553 |
| CPD-250 | 0.22 | 15 | 65 |
| CPD-251 | 0.07 | 14 | 195 |
| CPD-252 | 0.48 | 68 | 140 |
| CPD-254 | 0.02 | 13 | 743 |
| CPD-255 | 0.04 | 63 | 1535 |
| CPD-256 | 0.19 | 83 | 433 |
| CPD-257 | 0.45 | 17 | 37 |
| CPD-258 | 1.47 | 72 | 49 |
| CPD-259 | 0.54 | 14 | 26 |
| CPD-260 | 0.08 | >126 | >1681 |
| CPD-261 | 0.39 | 15 | 40 |
| CPD-262 | 0.06 | 71 | 1099 |
| CPD-263 | 2.18 | 13 | 6 |
| CPD-264 | 0.51 | >124 | >244 |

-continued

| Code | EC$_{50}$ (μM) | CC$_{50}$ (μM) | SI |
|---|---|---|---|
| CPD-265 | 0.02 | >124 | >5616 |
| CPD-266 | 0.06 | >124 | >2222 |
| CPD-267 | 1.30 | 79 | 61 |
| CPD-268 | 0.46 | 15 | 34 |
| CPD-269 | 0.48 | 13 | 28 |
| CPD-270 | 0.13 | >128 | >1001 |
| CPD-272 | 0.47 | >124 | >263 |
| CPD-273 | 0.32 | >122 | >382 |
| CPD-274 | 0.39 | 100 | 257 |
| CPD-275 | 9.96 | >126 | >13 |
| CPD-276 | 2.62 | 23 | 9 |
| CPD-277 | 0.29 | 16 | 54 |
| CPD-278 | 0.27 | >125 | >455 |
| CPD-279 | 0.18 | >124 | >682 |
| CPD-280 | 0.78 | >139 | >179 |
| CPD-281 | 0.21 | >128 | >612 |
| CPD-282 | 0.26 | >128 | >490 |
| CPD-283 | 0.17 | 56 | 323 |
| CPD-284 | 0.62 | 74 | 120 |
| CPD-285 | 0.04 | 50 | 1327 |
| CPD-286 | 1.05 | >126 | >120 |
| CPD-287 | 0.44 | >132 | >303 |
| CPD-288 | 0.12 | 77 | 620 |
| CPD-289 | 0.06 | 68 | 1150 |
| CPD-290 | 0.88 | >125 | >142 |
| CPD-291 | 0.06 | 53 | 872 |
| CPD-292 | 0.06 | 68 | 1043 |
| CPD-293 | 0.001 | 65 | 50498 |
| CPD-294 | 0.02 | 41 | 2598 |
| CPD-295 | 0.03 | 18 | 679 |
| CPD-296 | 0.05 | 31 | 605 |
| CPD-297 | 0.03 | 22 | 668 |
| CPD-298 | 0.42 | >116 | >278 |
| CPD-299 | 0.02 | 62 | 3136 |
| CPD-300 | 1.29 | 50 | 39 |
| CPD-301 | 0.08 | 89 | 1097 |
| CPD-302 | 0.65 | 15 | 23 |
| CPD-303 | 0.52 | 71 | 135 |
| CPD-305 | 0.09 | >116 | >1263 |
| CPD-307 | 0.18 | >124 | >702 |
| CPD-309 | 0.54 | 74 | 138 |
| CPD-310 | 0.06 | 25 | 454 |
| CPD-311 | 2.58 | 77 | 30 |
| CPD-312 | 4.67 | 69 | 15 |
| CPD-313 | 0.04 | 58 | 1464 |
| CPD-314 | 0.21 | 50 | 240 |
| CPD-315 | 0.05 | 13 | 265 |
| CPD-316 | 0.02 | 29 | 1180 |
| CPD-317 | 0.58 | 88 | 153 |
| CPD-318 | 0.06 | 54 | 967 |
| CPD-319 | 0.12 | 20 | 172 |
| CPD-320 | 0.07 | >124 | >1781 |
| CPD-321 | 0.11 | 33 | 310 |
| CPD-322 | 0.02 | 51 | 2855 |
| CPD-323 | 0.35 | 58 | 166 |
| CPD-324 | 0.01 | 30 | 3306 |
| CPD-325 | 0.09 | 68 | 731 |
| CPD-326 | 0.001 | 13 | 9127 |
| CPD-327 | 0.35 | 11 | 33 |
| CPD-328 | 0.01 | 13 | 1231 |
| CPD-329 | 0.01 | 41 | 2980 |
| CPD-330 | 4.63 | >139 | >30 |
| CPD-331 | 0.02 | 14 | 736 |
| CPD-332 | 0.04 | 20 | 527 |
| CPD-333 | 0.04 | 90 | 2078 |
| CPD-334 | 0.07 | 122 | 1746 |
| CPD-335 | 0.02 | 18 | 909 |
| CPD-336 | 0.01 | >123 | >8498 |
| CPD-337 | 0.005 | 15 | 3237 |
| CPD-338 | 0.01 | >124 | >16618 |
| CPD-339 | 0.09 | 19 | 205 |
| CPD-340 | 0.02 | >119 | >6223 |
| CPD-341 | 0.002 | 12 | 6121 |
| CPD-343 | 0.19 | >119 | >637 |
| CPD-344 | 0.09 | 94 | 1054 |
| CPD-345 | 0.21 | 106 | 493 |
| CPD-346 | 0.01 | 54 | 9945 |
| CPD-347 | 0.98 | 6 | 6 |
| CPD-348 | 0.10 | 14 | 151 |
| CPD-350 | 0.01 | 46 | 3462 |
| CPD-351 | 0.11 | 65 | 605 |
| CPD-352 | 0.29 | 71 | 247 |
| CPD-353 | 0.10 | 56 | 582 |
| CPD-355 | 0.03 | 44 | 1511 |
| CPD-356 | 0.12 | 13 | 113 |
| CPD-357 | 1.35 | 55 | 40 |
| CPD-358 | 0.18 | 63 | 345 |
| CPD-359 | 0.10 | 52 | 501 |
| CPD-360 | 0.04 | >124 | >3541 |
| CPD-361 | 0.09 | 50 | 586 |
| CPD-362 | 0.09 | 41 | 470 |
| CPD-364 | 1.12 | 62 | 55 |
| CPD-365 | 2.03 | 12 | 6 |
| CPD-366 | 0.26 | 78 | 293 |
| CPD-367 | 0.04 | >103 | >2863 |
| CPD-369 | 0.01 | 11 | 1306 |
| CPD-370 | 0.06 | 66 | 1152 |
| CPD-371 | 0.03 | 12 | 389 |

Table 4 shows the effect against DENV-1, DENV-3 and DENV-4 in Vero-B cells of some example compounds of the invention.

| Code | DENV-1 EC$_{50}$ (μM) | DENV-3 EC$_{50}$ (μM) | DENV-4 EC$_{50}$ (μM) |
|---|---|---|---|
| CPD-001 | 1.60 | 29.40 | 4.45 |
| CPD-002 | 0.54 | <0.5 | 27.20 |
| CPD-004 | 4.53 | 8.55 | ND |
| CPD-010 | 1.29 | 3.54 | 5.43 |
| CPD-012 | 4.42 | <0.5 | ND |
| CPD-013 | 0.09 | <0.5 | 1.81 |
| CPD-019 | 0.67 | 2.18 | 8.38 |
| CPD-020 | 15.08 | ND | ND |
| CPD-025 | 7.89 | 12.95 | 11.76 |
| CPD-027 | 2.10 | 9.90 | 3.70 |
| CPD-029 | 2.82 | ND | ND |
| CPD-030 | 4.80 | 6.24 | 13.15 |
| CPD-036 | 2.43 | 3.42 | 5.85 |
| CPD-043 | 3.38 | 5.88 | 4.76 |
| CPD-045 | 0.64 | 0.87 | 11.05 |
| CPD-049 | 2.21 | 10.54 | 2.27 |
| CPD-051 | 5.76 | 24.23 | 32.63 |
| CPD-053 | 1.64 | 11.18 | 7.11 |
| CPD-055 | 1.86 | 3.38 | 4.44 |
| CPD-056 | 10.57 | 69.18 | 5.92 |
| CPD-067 | <0.5 | 1.20 | ND |
| CPD-077 | 1.42 | 2.07 | 4.27 |
| CPD-083 | 0.54 | 0.71 | 2.52 |
| CPD-084 | <0.5 | 2.38 | 3.09 |
| CPD-086 | 0.97 | 1.05 | 3.57 |
| CPD-087 | 6.05 | ND | ND |
| CPD-092 | ND | 0.93 | 6.73 |
| CPD-104 | 3.85 | 24.02 | 14.88 |
| CPD-116 | 4.19 | 9.30 | ND |
| CPD-118 | 0.44 | 3.68 | ND |
| CPD-119 | 0.69 | 1.74 | 2.91 |
| CPD-120 | 2.31 | 5.18 | ND |
| CPD-122 | 3.64 | 8.25 | ND |
| CPD-123 | 1.60 | 2.56 | 2.64 |
| CPD-126 | 2.99 | 8.50 | 6.29 |
| CPD-128 | 7.50 | 18.37 | ND |
| CPD-130 | 0.35 | 1.70 | 7.42 |
| CPD-131 | 0.25 | 0.68 | 4.77 |
| CBD-132 | 2.45 | 3.47 | ND |
| CPD-133 | 2.25 | 4.17 | ND |
| CPD-137 | 0.67 | 3.81 | 2.78 |
| CPD-138 | 3.21 | 6.52 | ND |
| CPD-139 | 0.65 | 0.46 | 3.81 |
| CPD-142 | 1.71 | 3.97 | ND |
| CPD-144 | 2.89 | 3.08 | ND |
| CPD-146 | 0.69 | 2.72 | 4.25 |

| Code | DENV-1 EC$_{50}$ (μM) | DENV-3 EC$_{50}$ (μM) | DENV-4 EC$_{50}$ (μM) |
|---|---|---|---|
| CPD-148 | 1.65 | 5.54 | 2.87 |
| CPD-149 | 2.88 | 4.01 | 5.72 |
| CPD-150 | 1.28 | 1.07 | 8.87 |
| CPD-151 | 0.53 | 2.10 | 4.87 |
| CPD-152 | 2.05 | 0.99 | 5.62 |
| CPD-153 | 6.26 | 2.26 | 3.68 |
| CPD-154 | 3.92 | 4.40 | 9.87 |
| CPD-155 | 2.94 | ND | ND |
| CPD-156 | 0.61 | 2.12 | 3.37 |
| CPD-157 | 1.31 | 0.85 | 5.10 |
| CPD-158 | 2.50 | 2.19 | 7.20 |
| CPD-159 | 1.48 | 3.16 | 6.86 |
| CPD-173 | 30.71 | ND | ND |
| CPD-193 | 23.67 | 18.93 | 5.44 |
| CPD-194 | ND | ND | 18.69 |
| CPD-203 | 5.09 | 5.06 | 5.32 |
| CPD-206 | 0.37 | 0.67 | 1.52 |
| CPD-208 | ND | 6.65 | 6.95 |
| CPD-210 | 1.03 | ND | ND |
| CPD-212 | ND | 5.90 | 2.64 |
| CPD-213 | 0.81 | 2.54 | 2.85 |
| CPD-214 | 0.15 | 0.99 | 4.16 |
| CPD-219 | ND | 22.07 | ND |
| CPD-222 | 1.81 | 3.27 | 3.14 |
| CPD-225 | ND | 2.99 | 1.16 |
| CPD-226 | 0.92 | 0.81 | 8.64 |
| CPD-227 | ND | 2.91 | 7.45 |
| CPD-229 | 2.81 | 42.99 | 7.55 |
| CPD-230 | 0.35 | 3.53 | 2.56 |
| CPD-232 | 0.85 | 2.69 | 1.15 |
| CPD-233 | 0.22 | 1.29 | 3.09 |
| CPD-234 | 0.76 | 2.00 | 4.19 |
| CPD-235 | 0.09 | 0.27 | 3.02 |
| CPD-236 | 0.17 | 0.31 | 2.45 |
| CPD-237 | ND | ND | 8.31 |
| CPD-238 | 0.54 | 1.65 | 10.17 |
| CPD-240 | 1.20 | 2.38 | 8.73 |
| CPD-241 | 0.62 | 0.62 | 5.69 |
| CPD-242 | 0.40 | 0.57 | 7.87 |
| CPD-245 | 0.70 | 2.38 | 3.01 |
| CPD-249 | 1.13 | 4.57 | 1.98 |
| CPD-252 | ND | 12.56 | 2.29 |
| CPD-254 | 0.67 | 0.80 | 1.15 |
| CPD-255 | 0.75 | 1.66 | 3.36 |
| CPD-256 | 6.76 | 4.49 | 19.90 |
| CPD-258 | ND | ND | 9.42 |
| CPD-260 | 6.63 | 22.63 | 5.44 |
| CPD-262 | 2.33 | 6.73 | 8.49 |
| CPD-265 | 0.29 | 1.64 | 4.88 |
| CPD-266 | 0.70 | 4.32 | 3.51 |
| CPD-270 | 1.57 | 1.87 | ND |
| CPD-273 | 0.58 | 7.66 | 8.41 |
| CPD-278 | 2.84 | 13.20 | 5.80 |
| CPD-279 | 0.62 | 0.89 | 8.66 |
| CPD-281 | 0.85 | 5.57 | 1.12 |
| CPD-282 | 1.24 | 3.12 | 13.13 |
| CPD-283 | 2.83 | 7.14 | 7.89 |
| CPD-285 | 0.84 | 2.20 | 2.31 |
| CPD-288 | 1.90 | 2.70 | 6.33 |
| CPD-289 | 0.80 | 0.91 | 10.22 |
| CPD-291 | 0.80 | 0.80 | 8.67 |
| CPD-292 | 0.83 | 1.11 | 7.08 |
| CPD-293 | 0.06 | 0.04 | 1.15 |
| CPD-294 | 0.23 | 0.67 | 7.21 |
| CPD-295 | 0.34 | 1.38 | 6.29 |
| CPD-296 | 0.99 | 1.83 | 3.31 |
| CPD-297 | ND | 0.57 | 6.68 |
| CPD-298 | 2.02 | 5.79 | 4.52 |
| CPD-299 | 0.50 | 0.78 | 3.65 |
| CPD-300 | 5.29 | 21.12 | 4.13 |
| CPD-301 | 1.12 | 0.50 | 4.25 |
| CPD-303 | 3.26 | ND | ND |
| CPD-305 | 0.44 | 1.02 | 2.56 |
| CPD-307 | 2.43 | ND | 11.49 |
| CPD-309 | 0.62 | 0.70 | 2.80 |
| CPD-310 | 1.11 | 0.65 | 9.37 |
| CPD-313 | 0.72 | 1.11 | 5.84 |
| CPD-314 | 1.70 | 2.80 | 8.76 |
| CPD-315 | 0.38 | 1.01 | 1.97 |
| CPD-316 | 0.39 | 0.32 | 4.42 |
| CPD-317 | 4.13 | 12.84 | 10.63 |
| CPD-318 | 0.22 | 2.32 | 10.84 |
| CPD-319 | 2.84 | 1.70 | 2.27 |
| CPD-320 | 0.96 | 1.17 | 9.44 |
| CPD-321 | 0.40 | 0.32 | 2.74 |
| CPD-322 | 0.30 | 0.32 | 3.00 |
| CPD-323 | 3.62 | 4.99 | ND |
| CPD-324 | 0.27 | 0.19 | 5.32 |
| CPD-325 | 0.87 | 1.84 | 7.16 |
| CPD-326 | 0.05 | 0.09 | 1.89 |
| CPD-327 | 1.42 | 4.61 | 2.25 |
| CPD-328 | 0.20 | 0.13 | 2.84 |
| CPD-329 | 0.27 | 0.32 | 2.92 |
| CPD-331 | 0.39 | 0.39 | 3.28 |
| CPD-332 | 0.72 | 1.35 | 2.84 |
| CPD-333 | 0.39 | 0.49 | 5.92 |
| CPD-334 | 1.29 | 0.81 | 16.77 |
| CPD-335 | 0.32 | 0.42 | 2.38 |
| CPD-336 | 0.26 | 0.35 | 5.77 |
| CPD-337 | 0.09 | 0.23 | 0.95 |
| CPD-338 | 0.35 | 0.25 | 1.82 |
| CPD-339 | 0.81 | 0.82 | 2.93 |
| CPD-340 | 0.18 | 0.24 | 6.39 |
| CPD-341 | ND | 0.05 | 3.36 |
| CPD-343 | ND | 3.11 | ND |
| CPD-344 | ND | 0.79 | 25.90 |
| CPD-345 | ND | 1.73 | 2.94 |
| CPD-346 | ND | 0.04 | 1.27 |
| CPD-348 | ND | ND | 3.75 |
| CPD-350 | ND | 0.28 | 3.11 |
| CPD-351 | ND | 2.02 | 9.58 |
| CPD-352 | ND | 3.03 | 8.60 |
| CPD-353 | ND | 0.17 | 7.18 |
| CPD-355 | ND | 0.30 | 6.17 |
| CPD-359 | ND | ND | 5.48 |
| CPD-360 | ND | ND | 5.78 |

ND: not determined

Table 5 shows the effect against YFV in Vero-B cells of some example compounds of the invention.

| Code | EC$_{50}$ (μM) | CC$_{50}$ (μM) | SI |
|---|---|---|---|
| CPD-001 | 9.16 | 43 | 5 |
| CPD-002 | 2.81 | 25 | 9 |
| CPD-010 | <0.6 | 12 | >22 |
| CPD-012 | <0.5 | 12 | >23 |
| CPD-013 | 0.52 | 11 | 20 |
| CPD-019 | 6.18 | 56 | 9 |
| CPD-193 | <0.5 | >133 | >250 |

Table 6 shows the effect against DENV-2 in A549 cells of some example compounds of the invention.

| Code | EC$_{50}$ (μM) | CC$_{50}$ (μM) | SI |
|---|---|---|---|
| CPD-010 | 0.066 | 16 | 242 |
| CPD-131 | 0.008 | 11 | 1447 |
| CPD-236 | 0.019 | 65 | 3428 |
| CPD-242 | 0.010 | 47 | 4642 |
| CPD-255 | 0.029 | 59 | 2030 |
| CPD-293 | 0.003 | >117 | >43103 |
| CPD-294 | 0.015 | 61 | 4048 |
| CPD-320 | 0.006 | >124 | >22522 |
| CPD-328 | 0.006 | 12 | 2140 |
| CPD-334 | 0.024 | 85 | 3536 |
| CPD-336 | 0.005 | >123 | >22523 |

-continued

| Code | EC$_{50}$ (µM) | CC$_{50}$ (µM) | SI |
|---|---|---|---|
| CPD-338 | 0.026 | >124 | >4808 |
| CPD-340 | 0.027 | >119 | >4425 |
| CPD-346 | 0.008 | 60 | 7559 |
| CPD-350 | 0.008 | 63 | 7758 |
| CPD-360 | 0.027 | >124 | >4630 |

Example 363: In Vivo Activity of the Compounds of the Invention Against Dengue Infection A dengue viremia model in mice as described in Schul W, Liu W, Xu H Y, Flamand M, Vasudevan S G. J. Infect Dis. 2007; 95(5):665-74) (included herein by reference) can be used to examine the in vivo efficacy of compounds. In this model, AG129 mice (lacking alpha/beta interferon and gamma interferon receptors) are intraperitoneally inoculated with 2×10$^6$ plaque-forming units (PFU) of DENV-2 (strain TSV01) on day 0. The infected mice (6 or 8 animals per group) are immediately treated with the compound to test at one or more selected doses via IP, IV or SC injection or via oral administration and the vehicle as a control for three consecutive days. On day 4, blood samples are taken, and viral titers are determined using a plaque assay. A dengue mortality model in AG129 mice (lacking alpha/beta interferon and gamma interferon receptors) as described in Tan et al (PLoS Negl Trop Dis 2010; 4(4) and Ann Acad Med Singapore 2011; 40:523-32) (included herein by reference) was established to examine the in vivo efficacy of compound CPD-242. Female AG129 mice (B&K Universal, UK), 7-9 weeks old, were divided randomly in 3 test groups (n=4 or 5 per group): 1 infected group that only received vehicle and 2 infected groups that were treated either with the test compound CPD-242 (60 mg/kg/day, sc, twice daily, dissolved in a 10% DMSO, 5% Solutol in Saline (0.9%)) or with the reference compound Celgosivir (100 mg/kg/day; ip, twice daily, dissolved in 0.9% NaCl). The mice were subcutaneously inoculated on day 0 with 1×10$^7$ plaque-forming units (PFU) of the non-mouse-adapted DENV-2 strain D2Y98P, a highly infectious strain in AG129 mice, which results in severe disease and eventually death within 2 weeks. The infected mice were subsequently treated BID for 17 consecutive days with either vehicle, Celgosivir or CPD-242. Mice were euthanized as soon as they had signs of virus-induced paralysis and/or had lost >=30% bodyweight. The results obtained in this in vivo experiment are shown in FIG. 1 and clearly indicate that treatment of dengue infected AG129 mice with CPD-242 led to a highly significant delay (p: 0.0017) in virus-induced morbidity (day of euthanasia is presented).

The invention claimed is:

1. A method of treatment of Dengue virus or yellow fever virus, by the administration of an effective amount of a compound of formula B:

(B)

[structure]

or a pharmaceutically acceptable salt thereof, optionally in combination with one or more other medicines, to a human patient in need thereof, wherein the moiety

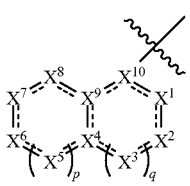

is

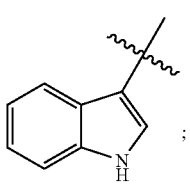 [SMILES: *c1c[nH]c2ccccc12]

;

wherein the wavy line (⌇) indicates the point of attachment to the carbonyl of the main formula (B); wherein said moiety is substituted with one or more $Z^1$;
cycle B is

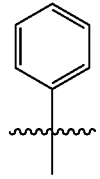

wherein the wavy line (⌇) indicates the point of attachment to the carbon atom of the main formula (B), and wherein the depicted cycles are substituted with one, two, or three $Z^{1a}$;
$R^1$ is phenyl; wherein said phenyl is substituted with one, two, or three $Z^{1b}$;
$R^2$ is hydrogen;
each $Z^1$ and $Z^{1a}$ is independently selected from the group consisting of halogen, hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O)$OZ^2$, —C(=O)$NZ^4Z^5$, $C_{1-6}$alkyl, hetero$C_{1-6}$alkyl, aryl, heterocycle, and heterocycle-$C_{1-6}$alkyl;
and wherein said $C_{1-6}$alkyl, hetero$C_{1-6}$alkyl, aryl, heterocycle, and heterocycle-$C_{1-6}$alkyl, are optionally substituted with one, two, or three substituents selected from hydroxyl, =O, halogen, trifluoromethyl, —$OCF_3$, —O—C(O)Me, cyano, nitro, —C(O)OH, —C(O)OC$_{1-6}$alkyl, —$NH_2$, —$NHCH_3$; —$N(CH_3)_2$, —NH—C(=O)O—C$_{1-4}$alkyl, —S(O)$_2$C$_{1-4}$alkyl, and —O—C$_{1-6}$alkyl;
each $Z^{1b}$ is independently selected from the group consisting of hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O)$OZ^2$, —C(=O)$NZ^4Z^5$, $C_{3-6}$alkyl, hetero$C_{1-6}$alkyl, aryl, heterocycle, and heterocycle-$C_{1-6}$alkyl;
and wherein said $C_{3-6}$alkyl, hetero$C_{1-6}$alkyl, aryl, heterocycle, and heterocycle-$C_{1-6}$alkyl, are optionally substituted with one, two, or three substituents selected from hydroxyl, =O, halogen, trifluoromethyl, —$OCF_3$, —O—C(O)Me, cyano, nitro, —C(O)OH, —C(O)OC$_{1-6}$alkyl, —$NH_2$, —$NHCH_3$; —$N(CH_3)_2$, —NH—C(=O)O—C$_{1-4}$alkyl, —S(O)$_2$C$_{1-4}$alkyl, and —O—C$_{1-6}$alkyl;
each $Z^2$ is independently selected from $C_{1-6}$alkyl, aryl, heterocycle, and heterocycle-$C_1$-6alkyl;
wherein said $C_{1-6}$alkyl, aryl, heterocycle, and heterocycle-$C_{1-6}$alkyl, are optionally substituted with one, two, or three substituents selected from hydroxyl, =O, halogen, trifluoromethyl, difluoromethyl, —O—$C_{1-6}$alkyl, —$OCF_3$, —S(=O)$_2$C$_{1-4}$alkyl, cyano, —C(O)OH, —C(=O)O—$C_{1-4}$alkyl, —$NH_2$, —$N(CH_3)_2$, pyrrolidinyl, piperidinyl, and piperazinyl, wherein said $C_{1-6}$alkyl is not substituted with hydroxyl;

each $Z^3$ is independently selected from hydroxyl, aryl, and heterocycle;
wherein said aryl and heterocycle are optionally substituted with one, two, or three substituents selected from $C_{1-6}$alkyl and —$N(CH_3)_2$;
each $Z^4$ and $Z^5$ is independently selected from hydrogen, $C_{1-6}$alkyl, aryl, $C_{3-7}$cycloalkyl, and heterocycle;
or an isomer thereof, or a solvate thereof, or a salt thereof, or a prodrug thereof;
wherein the term "heterocycle" means a saturated, unsaturated, or aromatic ring system of 3 to 18 atoms including at least one N, O, S, or P.

2. The method of claim 1, wherein
each $Z^1$ and $Z^{1a}$ is independently selected from the group consisting of halogen, hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O)$OZ^2$, —C(=O)$NZ^4Z^5$, $C_{1-6}$alkyl, hetero$C_{1-6}$alkyl, aryl, heterocycle, and heterocycle-$C_{1-6}$alkyl;
and wherein said $C_{1-6}$alkyl, hetero$C_{1-6}$alkyl, aryl, heterocycle, and heterocycle-$C_{1-6}$alkyl, are optionally substituted with one, two, or three substituents selected from hydroxyl, =O, —O—C(O)Me, cyano, —C(O)OH, —C(O)OC$_{1-6}$alkyl, —$NH_2$, —$NHCH_3$; —$N(CH_3)_2$, —NH—C(=O)O—$C_{1-4}$alkyl, —S(O)$_2$C$_{1-4}$alkyl, and —O—$C_{1-6}$alkyl;
each $Z^{1b}$ is independently selected from the group consisting of hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O)$OZ^2$, —C(=O)$NZ^4Z^5$, $C_{3-6}$alkyl, hetero$C_{1-6}$alkyl, aryl, heterocycle, and heterocycle-$C_{1-6}$alkyl;
and wherein said $C_{3-6}$alkyl, hetero$C_{1-6}$alkyl, aryl, heterocycle, and heterocycle-$C_{1-6}$alkyl, are optionally substituted with one, two, or three substituents selected from hydroxyl, =O, —O—C(O)Me, cyano, —C(O)OH, —C(O)OC$_{1-6}$alkyl, —$NH_2$, —$NHCH_3$, —$N(CH_3)_2$, —NH—C(=O)O—$C_{1-4}$alkyl; —S(O)$_2$C$_{1-4}$alkyl, and —O—$C_{1-6}$alkyl;
each $Z^2$ is independently selected from $C_{1-6}$alkyl, aryl, and heterocycle-$C_{1-6}$alkyl;
wherein said $C_{1-6}$alkyl and aryl, are optionally substituted with one, two, or three substituents selected from hydroxyl, halogen, difluoromethyl, —O—$C_{1-6}$alkyl, —S(=O)$_2$C$_{1-4}$alkyl, —C(=O)OH, —C(=O)O—$C_{1-4}$alkyl, —$NH_2$, —$N(CH_3)_2$, pyrrolidinyl, piperidinyl, and piperazinyl, wherein said $C_{1-6}$alkyl is not substituted with hydroxyl;
each $Z^3$ is independently selected from hydroxyl and heterocycle;
wherein said heterocycle are optionally substituted with one, two, or three substituents selected from $C_{1-6}$alkyl and —$N(CH_3)_2$; and
each $Z^4$ and $Z^5$ is independently selected from hydrogen, $C_{1-6}$alkyl, and $C_{3-7}$cycloalkyl.

3. The method of claim 1, wherein
each $Z^{1b}$ is independently selected from the group consisting of hydroxyl, —$OZ^2$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, cyano, —C(=O)$Z^3$, —C(=O)$OZ^2$, —C(=O)$NZ^4Z^5$, $C_{3-6}$alkyl, aryl, and heterocycle;
and wherein said $C_{3-6}$alkyl, aryl, and heterocycle, are optionally substituted with one, two, or three substituents selected from hydroxyl, =O, —O—C(O)

Me, cyano, —C(O)OH, —NHCH₃, —N(CH₃)₂, —S(O)₂C₁₋₄alkyl, and —O—C₁₋₆alkyl;

R² is hydrogen;

each Z¹ and Z^{1a} is independently selected from the group consisting of halogen, hydroxyl, —OZ², —O—C(=O)Z³, =O, —S(=O)₂Z³, —S(=O)₂NZ⁴Z⁵, trifluoromethyl, trifluoromethoxy, —NZ⁴Z⁵, —NZ⁴C(=O)Z², —NZ⁴C(=O)OZ², cyano, —C(=O)Z³, —C(=O)OZ², —C(=O)NZ⁴Z⁵, C₁₋₆alkyl, heteroC₁₋₆alkyl, aryl, heterocycle, and heterocycle-C₁₋₆alkyl;

and wherein said C₁₋₆alkyl, aryl, and heterocycle, are optionally substituted with one, two, or three substituents selected from hydroxyl, =O, —O—C(O)Me, cyano, —C(O)OH, —C(O)OC₁₋₆alkyl, —NH₂, —NHCH₃, —N(CH₃)₂, —NH—C(=O)O—C₁₋₄alkyl, —S(O)₂C₁₋₄alkyl, and —O—C₁₋₆alkyl;

each Z² is independently selected from C₁₋₆alkyl, aryl, and heterocycle-C₁₋₆alkyl;

wherein said C₁₋₆alkyl and aryl, are optionally substituted with one, two, or three substituents selected from hydroxyl, halogen, difluoromethyl, —O—C₁₋₆alkyl, —S(=O)₂C₁₋₄alkyl, —C(=O)OH, —C(=O)O—C₁₋₄alkyl, —NH₂, —N(CH₃)₂, pyrrolidinyl, piperidinyl, and piperazinyl, wherein said C₁₋₆alkyl is not substituted with hydroxyl;

each Z³ is independently selected from hydroxyl and heterocycle;

wherein said heterocycle are optionally substituted with one, two, or three substituents selected from C₁₋₆alkyl and —N(CH₃)₂; and each Z⁴ and Z⁵ is independently selected from hydrogen, C₁₋₆alkyl, and C₃₋₇cycloalkyl.

4. The method of claim 1, wherein the compound has the structure of Formula (G),

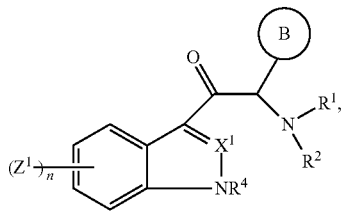

wherein
X¹ is CH; and
n is 1, 2, or 3.

5. The method of claim 1, wherein the compound has the structure of Formula (H),

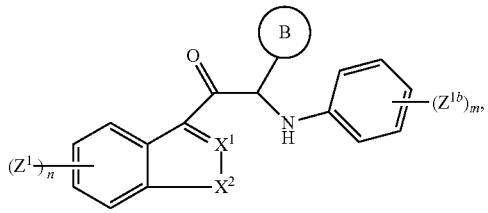

wherein
m is 1, 2, or 3;
n is 1, 2, or 3; and
X² is NH and X¹ is CH.

6. The method of claim 1, wherein the compound has the structure of Formula (I),

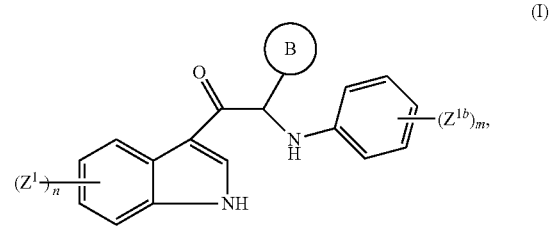

wherein cycle B is phenyl, wherein said phenyl is substituted with one or more groups selected from halogen, C₁₋₄alkyl, and C₁₋₄alkoxy;

m is 1, 2, or 3; and n is 1, 2, or 3.

7. The method of claim 1, wherein the carbon atom substituted with cycle B is in the R configuration.

8. The method of claim 1, wherein the carbon atom substituted with cycle B is in the S configuration.

9. The method of claim 1, wherein the compound of Formula (B) is administered in combination with one or more other medicines.

10. A method of inhibiting Dengue virus or yellow fever virus replication, by the administration of an effective amount of a compound of formula B:

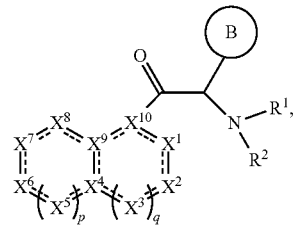

or a pharmaceutically acceptable salt thereof, optionally in combination with one or more other medicines, to a human patient in need thereof, wherein
the moiety

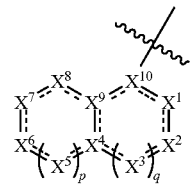

is

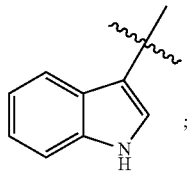 [SMILES: *c1c[nH]c2ccccc12]

wherein the wavy line (⁓)
indicates the point of attachment to the carbonyl of the main formula (B); wherein said moiety is substituted with one or more $Z^1$;
cycle B is

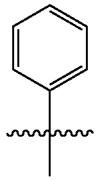

wherein the wavy line (⁓) indicates the point of attachment to the carbon atom of the main formula (B), and wherein the depicted cycles are substituted with one, two, or three $Z^{1a}$;

$R^1$ is phenyl; wherein said phenyl is substituted with one, two, or three $Z^{1b}$;

$R^2$ is hydrogen;

each $Z^1$ and $Z^{1a}$ is independently selected from the group consisting of halogen, hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O)$OZ^2$, —C(=O)$NZ^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, hetero$C_{1-6}$alkyl, aryl, heterocycle, and heterocycle-$C_{1-6}$alkyl, are optionally substituted with one, two, or three substituents selected from hydroxyl, =O, halogen, trifluoromethyl, —$OCF_3$, —O—C(O)Me, cyano, nitro, —C(O)OH, —C(O)O$C_{1-6}$alkyl, —$NH_2$, —$NHCH_3$; —$N(CH_3)_2$, —NH—C(=O)O—$C_{1-4}$alkyl, —S(O)$_2C_{1-4}$alkyl, and —O—$C_{1-6}$alkyl;

each $Z^{1b}$ is independently selected from the group consisting of hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O) $OZ^2$, —C(=O)$NZ^4Z^5$, $C_{3-6}$alkyl, hetero$C_{1-6}$alkyl, aryl, heterocycle, and heterocycle-$C_{1-6}$alkyl;

and wherein said $C_{3-6}$alkyl, hetero$C_{1-6}$alkyl, aryl, heterocycle, and heterocycle-$C_{1-6}$alkyl, are optionally substituted with one, two, or three substituents selected from hydroxyl, =O, halogen, trifluoromethyl, —$OCF_3$, —O—C(O)Me, cyano, nitro, —C(O)OH, —C(O)O$C_{1-6}$alkyl, —$NH_2$, —$NHCH_3$; —$N(CH_3)_2$, —NH—C(=O) O—$C_{1-4}$alkyl, —S(O)$_2C_{1-4}$alkyl, and —O—$C_{1-6}$alkyl;

each $Z^2$ is independently selected from $C_{1-6}$alkyl, aryl, heterocycle, and heterocycle-$C_1$-6alkyl;

wherein said $C_{1-6}$alkyl, aryl, heterocycle, and heterocycle-$C_{1-6}$alkyl, are optionally substituted with one, two, or three substituents selected from hydroxyl, =O, halogen, trifluoromethyl, difluoromethyl, —O—$C_{1-6}$alkyl, —$OCF_3$, —S(=O)$_2C_{1-4}$alkyl, cyano, —C(=O)OH, —C(=O)O—$C_{1-4}$alkyl, —$NH_2$, —$N(CH_3)_2$, pyrrolidinyl, piperidinyl, and piperazinyl, wherein said $C_{1-6}$alkyl is not substituted with hydroxyl;

each $Z^3$ is independently selected from hydroxyl, aryl, and heterocycle;

wherein said and heterocycle are optionally substituted with one, two, or three substituents selected from $C_{1-6}$alkyl and —$N(CH_3)_2$;

each $Z^4$ and $Z^5$ is independently selected from hydrogen, $C_{1-6}$alkyl, aryl, $C_{3-7}$cycloalkyl, and heterocycle;

or an isomer thereof, or a solvate thereof, or a salt thereof, or a prodrug thereof;

wherein the term "heterocycle" means a saturated, unsaturated, or aromatic ring system of 3 to 18 atoms including at least one N, O, S, or P.

11. The method of claim 10, wherein each $Z^1$ and $Z^{1a}$ is independently selected from the group consisting of halogen, hydroxyl, —$OZ^2$, —O—C(=O) $Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C(=O)$OZ^2$, cyano, —C(=O)$Z^3$, —C(=O) $OZ^2$, —C(=O)$NZ^4Z^5$, $C_{1-6}$alkyl, hetero$C_{1-6}$alkyl, aryl, heterocycle, and heterocycle-$C_{1-6}$alkyl;

and wherein said $C_{1-6}$alkyl, hetero$C_{1-6}$alkyl, aryl, heterocycle, and heterocycle-$C_{1-6}$alkyl, are optionally substituted with one, two, or three substituents selected from hydroxyl, =O, —O—C(O)Me, cyano, —C(O)OH, —C(O)O$C_{1-6}$alkyl, —$NH_2$, —$NHCH_3$; —$N(CH_3)_2$, —NH—C(=O)O—$C_{1-4}$alkyl, —S(O)$_2C_{1-4}$alkyl, and —O—$C_{1-6}$alkyl;

each $Z^{1b}$ is independently selected from the group consisting of hydroxyl, —$OZ^2$, —O—C(=O)$Z^3$, =O, —S(=O)$_2Z^3$, —S(=O)$_2NZ^4Z^5$, trifluoromethyl, trifluoromethoxy, —$NZ^4Z^5$, —$NZ^4$C(=O)$Z^2$, —$NZ^4$C (=O)$OZ^2$, cyano, —C(=O)$Z^3$, —C(=O)$OZ^2$, —C(=O)$NZ^4Z^5$, $C_{3-6}$alkyl, hetero$C_{1-6}$alkyl, aryl, heterocycle, and heterocycle-$C_{1-6}$alkyl;

and wherein said $C_{3-6}$alkyl, hetero$C_{1-6}$alkyl, aryl, heterocycle, and heterocycle-$C_{1-6}$alkyl, are optionally substituted with one, two, or three substituents selected from hydroxyl, =O, —O—C(O)Me, cyano, —C(O)OH, —C(O)O$C_{1-6}$alkyl, —$NH_2$, —$NHCH_3$, —$N(CH_3)_2$, —NH—C(=O)O—$C_{1-4}$alkyl; —S(O)$_2C_{1-4}$alkyl, and —O—$C_{1-6}$alkyl;

each $Z^2$ is independently selected from $C_{1-6}$alkyl, aryl, and heterocycle-$C_{1-6}$alkyl;

wherein said $C_{1-6}$alkyl and aryl, are optionally substituted with one, two, or three substituents selected from hydroxyl, halogen, difluoromethyl, —O—$C_{1-6}$alkyl, —S(=O)$_2C_{1-4}$alkyl, —C(=O) OH, —C(=O)O—$C_{1-4}$alkyl, —$NH_2$, —$N(CH_3)_2$, pyrrolidinyl, piperidinyl, and piperazinyl, wherein said $C_{1-6}$alkyl is not substituted with hydroxyl;

each $Z^3$ is independently selected from hydroxyl and heterocycle;

wherein said heterocycle are optionally substituted with one, two, or three substituents selected from $C_{1-6}$alkyl and —$N(CH_3)_2$; and each $Z^4$ and $Z^5$ is independently selected from hydrogen, $C_{1-6}$alkyl, and $C_{3-7}$cycloalkyl.

12. The method of claim 10, wherein
each $Z^{1b}$ is independently selected from the group consisting of hydroxyl, —$OZ^2$ =O, —$S(=O)_2Z^3$, —$S(=O)_2NZ^4Z^5$, trifluoromethyl, trifluoromethoxy, —$NZ^4Z^5$, —$NZ^4C(=O)Z^2$, cyano, —$C(=O)Z^3$, —$C(=O)OZ^2$, —$C(=O)NZ^4Z^5$, $C_{3-6}$alkyl, aryl, and heterocycle;
and wherein said $C_{3-6}$alkyl, aryl, and heterocycle, are optionally substituted with one, two, or three substituents selected from hydroxyl, =O, —O—C(O)Me, cyano, —C(O)OH, —NHCH$_3$, —N(CH$_3$)$_2$, —S(O)$_2$C$_{1-4}$alkyl, and —O—C$_{1-6}$alkyl;
$R^2$ is hydrogen;
each $Z^1$ and $Z^{1a}$ is independently selected from the group consisting of halogen, hydroxyl, —$OZ^2$, —O—C(=O)$Z^3$, =O, —$S(=O)_2Z^3$, —$S(=O)_2NZ^4Z^5$, trifluoromethyl, trifluoromethoxy, —$NZ^4Z^5$, —$NZ^4C(=O)Z^2$, —$NZ^4C(=O)OZ^2$, cyano, —$C(=O)Z^3$, —$C(=O)OZ^2$, —$C(=O)NZ^4Z^5$, $C_{1-6}$alkyl, hetero$C_{1-6}$alkyl, aryl, heterocycle, and heterocycle-$C_{1-6}$alkyl;
and wherein said $C_{1-6}$alkyl, aryl, and heterocycle, are optionally substituted with one, two, or three substituents selected from hydroxyl, =O, —O—C(O)Me, cyano, —C(O)OH, —C(O)OC$_{1-6}$alkyl, —NH$_2$, —NHCH$_3$, —N(CH$_3$)$_2$, —NH—C(=O)O—C$_{1-4}$alkyl, —S(O)$_2$C$_{1-4}$alkyl, and —O—C$_{1-6}$alkyl;
each $Z^2$ is independently selected from $C_{1-6}$alkyl, aryl, and heterocycle-$C_{1-6}$alkyl;
wherein said $C_{1-6}$alkyl and aryl, are optionally substituted with one, two, or three substituents selected from hydroxyl, halogen, difluoromethyl, —O—C$_{1-6}$alkyl, —S(=O)$_2$C$_{1-4}$alkyl, —C(=O)OH, —C(=O)O—C$_{1-4}$alkyl, —NH$_2$, —N(CH$_3$)$_2$, pyrrolidinyl, piperidinyl, and piperazinyl, wherein said $C_{1-6}$alkyl is not substituted with hydroxyl;
each $Z^3$ is independently selected from hydroxyl and heterocycle;
wherein said heterocycle are optionally substituted with one, two, or three substituents selected from $C_{1-6}$alkyl and —N(CH$_3$)$_2$; and
each $Z^4$ and $Z^5$ is independently selected from hydrogen, $C_{1-6}$alkyl, and $C_{3-7}$cycloalkyl.

13. The method of claim 10, wherein the compound has the structure of Formula (G),

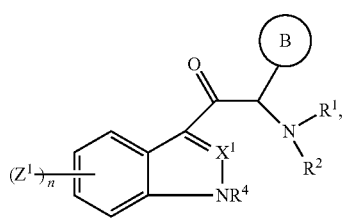

(G)

wherein
$X^1$ is CH; and
n is 1, 2, or 3.

14. The method of claim 10, wherein the compound has the structure of Formula (H),

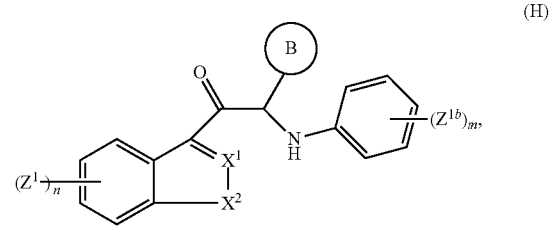

(H)

wherein
m is 1, 2, or 3;
n is 1, 2, or 3;
$X^2$ is NH and $X^1$ is CH.

15. The method of claim 10, wherein the compound has the structure of Formula (I),

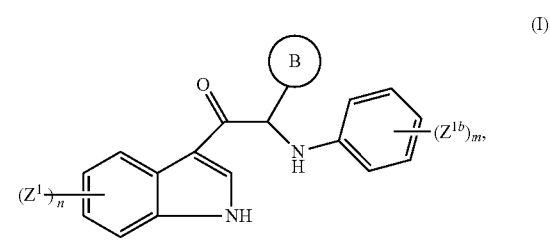

(I)

wherein cycle B is phenyl, wherein said phenyl is substituted with one or more groups selected from halogen, $C_{1-4}$alkyl, and $C_{1-4}$alkoxy;
m is 1, 2, or 3; and
n is 1, 2, or 3.

16. The method of claim 10, wherein the carbon atom substituted with cycle B is in the R configuration.

17. The method of claim 10, wherein the carbon atom substituted with cycle B is in the S configuration.

18. The method of claim 10, wherein the compound of Formula (B) is administered in combination with one or more other medicines.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tcggagccgg agtttacaaa                                          20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tcttaacgtc cgcccatgat                                          20

<210> SEQ ID NO 3
<211> LENGTH: 19
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (19)..(19)
<223> OTHER INFORMATION: minor groove binder

<400> SEQUENCE: 3
attccacaca atgtggcat                                           19

```
<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
ggatagacca gagatcctgc tgt                                              23

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cattccattt tctggcgttc                                                  20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
caatccatct tgcggcgctc                                                  20

<210> SEQ ID NO 7
<211> LENGTH: 20
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (20)..(20)
<223> OTHER INFORMATION: minor groove binder

<400> SEQUENCE: 7
cagcatcatt ccaggcacag                                                  20

<210> SEQ ID NO 8
<211> LENGTH: 20
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (20)..(20)
<223> OTHER INFORMATION: minor groove binder

<400> SEQUENCE: 8
caacatcaat ccaggcacag                                                  20

<210> SEQ ID NO 9
<211> LENGTH: 23
```

```
<212> TYPE: DNA
<213> ORGANISM: Artificial Sequence
<220> FEATURE:
<223> OTHER INFORMATION: primer

<400> SEQUENCE: 9
tggcatattc cagtcaacct tct                                              23

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gaagcccaag atggaatcaa ct                                               22

<210> SEQ ID NO 11
<211> LENGTH: 19
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(1)
<223> OTHER INFORMATION: 6-carboxyfluorescein
<220> FEATURE:
<221> NAME/KEY: misc_feature
<222> LOCATION: (19)..(19)
<223> OTHER INFORMATION: minor groove binder

<400> SEQUENCE: 11
ttccacacaa tgtggcatg                                                   19
```